United States Patent
Gitman et al.

(10) Patent No.: US 11,963,933 B2
(45) Date of Patent: Apr. 23, 2024

(54) TORQUE ENHANCER DEVICE FOR GRASPING AND TOOLING, AND ASSEMBLIES AND USES THEREOF

(71) Applicant: ScalPal, LLC, Baltimore, MD (US)

(72) Inventors: Eliot Robert Gitman, Jerusalem (IL); Tuvia Gitman, Jerusalem (IL)

(73) Assignee: SCALPAL LLC, Wilmington, DE (US)

( * ) Notice: Subject to any disclaimer, the term of this patent is extended or adjusted under 35 U.S.C. 154(b) by 0 days.

(21) Appl. No.: 17/821,357

(22) Filed: Aug. 22, 2022

(65) Prior Publication Data

US 2023/0053731 A1     Feb. 23, 2023

Related U.S. Application Data

(63) Continuation of application No. 15/977,431, filed on May 11, 2018, now Pat. No. 11,458,071.

(Continued)

(51) Int. Cl.
    *F16B 23/00*     (2006.01)
    *A61J 1/16*     (2023.01)
    (Continued)

(52) U.S. Cl.
    CPC .............. *A61J 1/2055* (2015.05); *A61J 1/16* (2013.01); *A61J 1/2065* (2015.05); *A61J 1/2096* (2013.01);
    (Continued)

(58) Field of Classification Search
    CPC .... F16B 37/16; F16B 41/005; F16B 23/0092; F16B 35/04; F16B 23/0061; F16B 5/0258; B25B 13/483
    See application file for complete search history.

(56) References Cited

U.S. PATENT DOCUMENTS

| | | |
|---|---|---|
| 135,809 A | 2/1873 | Hubbard |
| 181,716 A | 8/1876 | Pickles |

(Continued)

FOREIGN PATENT DOCUMENTS

| | | |
|---|---|---|
| CN | 2010/23742 Y | 2/2008 |
| DE | 296 06 408 U1 | 6/1996 |

(Continued)

OTHER PUBLICATIONS

Engineer Edge, ANSI Inch Wing Nut Specification Chart, Mar. 2015, p. 1 (Year: 2015).*

(Continued)

*Primary Examiner* — Michael W Hotchkiss
(74) *Attorney, Agent, or Firm* — Smith, Gambrell & Russell, LLP

(57) ABSTRACT

A torque enhancement device having torque enhancement member(s) with each having an exterior (preferably bi-symmetric or essentially bi-symmetric) surface configuration with parallel, longer side walls extending in a Y-axis direction and shorter side walls extending in an X-axis direction and corner recesses positioned between ends of adjacent longer and shorter side walls, and with some embodiments of the invention featuring a torque enhancement device having a hole extending in a Z-axis direction. A fastener assembly is also provided that includes one or more torque enhancement devices as well as methods for utilization of the torque enhancement device or utilization or assemblage of an assembly including a torque enhancement device. The surface configuration includes arrangements where there is a torque differential in one direction or the other as well as arrangements that are adapted to handle both standard fastener configurations and torque enhancement configurations with a common torque enhancement device.

28 Claims, 169 Drawing Sheets

Related U.S. Application Data

(60) Provisional application No. 62/505,034, filed on May 11, 2017.

(51) Int. Cl.
*A61J 1/20* (2006.01)
*B25B 13/46* (2006.01)
*B25B 15/00* (2006.01)
*B25B 21/00* (2006.01)
*F16B 35/06* (2006.01)
*F16B 37/16* (2006.01)

(52) U.S. Cl.
CPC .............. *B25B 13/46* (2013.01); *B25B 21/00* (2013.01); *F16B 23/0061* (2013.01); *F16B 37/16* (2013.01); *A61M 2209/08* (2013.01); *A61M 2209/088* (2013.01); *B25B 15/005* (2013.01); *F16B 23/0023* (2013.01); *F16B 23/0092* (2013.01); *F16B 35/06* (2013.01)

(56) References Cited

U.S. PATENT DOCUMENTS

| | | | |
|---|---|---|---|
| 225,121 A | 3/1880 | Hackman et al. | |
| 244,379 A * | 7/1881 | Coulter et al. | F16B 37/16 411/918 |
| 331,169 A | 11/1885 | Thomas | |
| 332,540 A | 12/1885 | Law | |
| 367,196 A | 7/1887 | Deblieux | |
| 779,751 A | 1/1905 | Waitt | |
| 975,285 A | 11/1910 | Robertson | |
| 1,289,450 A * | 12/1918 | Holaday | F16B 35/06 411/409 |
| 1,320,259 A | 10/1919 | Martens | |
| 1,467,824 A * | 9/1923 | Ahlers | F16B 39/36 411/932 |
| 1,632,227 A | 6/1927 | Halsey | |
| 1,764,990 A | 6/1930 | Schultz | |
| 1,773,146 A * | 8/1930 | Kellogg | F16B 37/16 411/435 |
| 1,798,944 A | 3/1931 | Jackman | |
| 1,875,930 A | 9/1932 | Martin | |
| 1,919,728 A * | 7/1933 | Kellogg | F16B 37/16 411/435 |
| 2,083,045 A | 6/1937 | Vaurs | |
| 2,116,775 A | 5/1938 | Blackburn | |
| 2,140,449 A | 12/1938 | Brown | |
| 2,173,707 A | 9/1939 | Brown | |
| 2,216,381 A * | 10/1940 | West | F16B 23/0023 81/460 |
| 2,259,425 A | 10/1941 | Murphy | |
| 2,305,427 A * | 12/1942 | Joachim | F16B 37/16 411/409 |
| 2,317,319 A * | 4/1943 | West | B25B 15/007 81/438 |
| 2,335,205 A | 11/1943 | Zepp | |
| 2,361,814 A * | 10/1944 | Berry | F16B 39/36 411/270 |
| 2,383,670 A * | 8/1945 | Moss | F16B 37/16 411/409 |
| 2,397,238 A * | 3/1946 | Brose | F16B 37/02 411/526 |
| 2,400,684 A * | 5/1946 | Clark | F16B 23/0092 411/404 |
| 2,402,342 A * | 6/1946 | Phillips | F16B 23/0023 411/404 |
| 2,538,350 A | 1/1951 | Baule | |
| 2,639,622 A * | 5/1953 | Ginder | F16G 5/16 411/964 |
| 2,742,939 A * | 4/1956 | Larson | F16B 39/284 411/277 |
| 2,752,814 A | 7/1956 | Iaia | |
| 2,764,197 A * | 9/1956 | Torresen | B25B 15/005 411/404 |
| 2,800,829 A | 7/1957 | West | |
| 2,930,424 A | 3/1960 | Van Buren, Jr. | |
| 3,086,414 A * | 4/1963 | Nardi | F16B 37/16 81/176.1 |
| 3,123,120 A * | 3/1964 | Grimm et al. | F16B 37/044 411/965 |
| 3,171,459 A | 3/1965 | Storch | |
| 3,175,454 A | 3/1965 | Morse | |
| 3,208,494 A | 9/1965 | Skidmore | |
| 3,242,775 A | 3/1966 | Hinkle | |
| 3,304,109 A | 2/1967 | Schuster | |
| 3,319,509 A * | 5/1967 | Romeo | F16B 37/16 411/435 |
| 3,340,920 A | 9/1967 | Johnson | |
| 3,409,058 A * | 11/1968 | La Pointe | B25B 15/005 81/460 |
| 3,412,772 A | 11/1968 | Meyfarth et al. | |
| 3,422,721 A | 1/1969 | Yonkers | |
| 3,463,209 A | 8/1969 | Podolsky | |
| 3,466,956 A | 9/1969 | Bowers | |
| 3,474,009 A | 10/1969 | Wang | |
| 3,584,531 A | 6/1971 | Greenleaf et al. | |
| 3,584,667 A | 6/1971 | Reiland | |
| 3,628,584 A | 12/1971 | Gutshall | |
| 3,675,694 A * | 7/1972 | Barlow | B25B 15/007 81/460 |
| 3,695,324 A * | 10/1972 | Gulistan | B23P 11/00 411/111 |
| 3,854,372 A | 12/1974 | Gutshall | |
| 3,856,066 A | 12/1974 | Reynolds | |
| 3,931,749 A | 1/1976 | Evans | |
| 3,985,170 A * | 10/1976 | Iskra | B25B 15/007 81/460 |
| 4,027,572 A * | 6/1977 | Burge | B25B 13/485 81/461 |
| 4,084,478 A | 4/1978 | Simmons | |
| 4,089,357 A | 5/1978 | Gill | |
| 4,202,244 A | 5/1980 | Gutshall | |
| 4,227,561 A * | 10/1980 | Molina | F16B 37/044 411/103 |
| 4,246,811 A | 1/1981 | Bondhus et al. | |
| 4,291,737 A | 9/1981 | McMurray et al. | |
| 4,292,007 A | 9/1981 | Wagner | |
| 4,293,262 A | 10/1981 | Holmes | |
| 4,355,552 A | 10/1982 | Gutshall | |
| 4,378,187 A * | 3/1983 | Fullerton | F16B 39/36 411/303 |
| 4,459,074 A | 7/1984 | Capuano | |
| 4,462,731 A * | 7/1984 | Rovinsky | F16B 37/0892 411/433 |
| 4,512,220 A | 4/1985 | Barnhill, III et al. | |
| 4,569,259 A * | 2/1986 | Rubin | F16B 23/0061 81/460 |
| 4,580,322 A | 4/1986 | Wright et al. | |
| 4,581,957 A | 4/1986 | Dossier | |
| 4,598,616 A | 7/1986 | Colvin | |
| 4,600,344 A * | 7/1986 | Sutenbach | F16B 37/0842 411/908 |
| 4,646,594 A | 3/1987 | Tien | |
| 4,701,088 A | 10/1987 | Crull | |
| 4,712,957 A * | 12/1987 | Edwards | F16B 13/141 411/258 |
| 4,729,703 A * | 3/1988 | Sato | F16B 39/12 411/238 |
| 4,882,957 A | 11/1989 | Wright et al. | |
| 4,895,484 A | 1/1990 | Wilcox | |
| 4,970,922 A | 11/1990 | Krivec | |
| 5,067,750 A | 11/1991 | Minneman | |
| 5,131,312 A | 7/1992 | Macor | |
| 5,139,380 A | 8/1992 | Reynolds | |
| 5,146,668 A * | 9/1992 | Gulistan | B21K 1/70 72/356 |
| 5,251,521 A | 10/1993 | Burda et al. | |
| 5,279,190 A | 1/1994 | Goss et al. | |
| 5,340,252 A * | 8/1994 | Weddendorf | F16B 37/0864 411/433 |

(56) References Cited

U.S. PATENT DOCUMENTS

| | | | |
|---|---|---|---|
| 5,358,368 A | 10/1994 | Conlan et al. | |
| 5,364,212 A * | 11/1994 | Gill | F16B 23/0007 |
| | | | 411/404 |
| 5,370,021 A | 12/1994 | Shigematsu | |
| 5,378,101 A | 1/1995 | Olson et al. | |
| 5,386,749 A | 2/1995 | Kim | |
| 5,528,966 A * | 6/1996 | Coppejans | B25B 15/005 |
| | | | 81/439 |
| 5,553,983 A | 9/1996 | Shinjo | |
| 5,575,602 A * | 11/1996 | Savage | F16B 23/0061 |
| | | | 411/405 |
| 5,577,871 A | 11/1996 | Brugola | |
| 5,578,050 A | 11/1996 | Webb | |
| 5,674,036 A * | 10/1997 | Hsieh | F16B 23/0092 |
| | | | 411/410 |
| 5,674,037 A | 10/1997 | Lu | |
| 5,709,356 A * | 1/1998 | Avenet | F16B 35/04 |
| | | | 244/1 A |
| 5,762,457 A * | 6/1998 | Lide | B25B 15/02 |
| | | | 411/405 |
| 5,827,027 A | 10/1998 | Wakabayashi | |
| 5,868,049 A | 2/1999 | Kanwal | |
| 5,873,290 A | 2/1999 | Chaconas | |
| 5,919,019 A * | 7/1999 | Fischer | F16B 37/043 |
| | | | 411/177 |
| 5,931,618 A | 8/1999 | Wallace et al. | |
| 6,032,556 A | 3/2000 | Hu | |
| D427,053 S | 6/2000 | Nelson | |
| 6,089,807 A * | 7/2000 | Larsson | A47K 13/26 |
| | | | 411/433 |
| 6,109,849 A | 8/2000 | Nagayama | |
| 6,128,983 A | 10/2000 | Arnn | |
| 6,129,493 A * | 10/2000 | Leistner | F16B 37/065 |
| | | | 411/179 |
| 6,227,784 B1 | 5/2001 | Antoine et al. | |
| 6,238,372 B1 | 5/2001 | Zinger et al. | |
| 6,283,689 B1 * | 9/2001 | Roytberg | F16B 37/0842 |
| | | | 411/61 |
| 6,289,772 B1 | 9/2001 | Ying-Wen | |
| 6,293,745 B1 | 9/2001 | Lu | |
| 6,295,900 B1 | 10/2001 | Julicher et al. | |
| 6,314,840 B2 * | 11/2001 | Bozonnet | F16D 1/101 |
| | | | 81/436 |
| 6,321,625 B1 | 11/2001 | Fernandez | |
| 6,341,546 B1 | 1/2002 | Totsu | |
| 6,511,274 B1 * | 1/2003 | Nagayama | F16B 37/065 |
| | | | 411/181 |
| 6,572,316 B2 | 6/2003 | Toyooka | |
| 6,575,061 B2 | 6/2003 | Wagner | |
| 6,585,695 B1 | 7/2003 | Adair et al. | |
| 6,626,067 B1 | 9/2003 | Iwinski et al. | |
| 6,715,384 B1 | 4/2004 | Kozak | |
| 6,725,746 B1 | 4/2004 | Wright | |
| 6,755,748 B2 | 6/2004 | Brooks | |
| 6,761,089 B2 | 7/2004 | Bergamo | |
| 6,792,838 B2 | 9/2004 | Brooks et al. | |
| 6,854,943 B2 * | 2/2005 | Nagayama | F16B 37/065 |
| | | | 411/429 |
| 6,889,580 B1 | 5/2005 | Tseng | |
| 6,890,139 B2 * | 5/2005 | Hughes | B25B 15/005 |
| | | | 411/410 |
| 6,904,833 B2 | 6/2005 | Wright | |
| 6,918,725 B2 * | 7/2005 | Gauron | F16B 37/043 |
| | | | 411/112 |
| 6,951,158 B1 | 10/2005 | Edland | |
| 6,988,432 B2 * | 1/2006 | Brooks | B25B 15/008 |
| | | | 411/407 |
| D514,405 S | 2/2006 | Chaconas | |
| 6,997,085 B2 | 2/2006 | Yamamoto | |
| 7,021,875 B2 * | 4/2006 | Yake | F16B 33/06 |
| | | | 411/111 |
| 7,059,816 B2 * | 6/2006 | Toosky | B23P 9/025 |
| | | | 411/181 |
| 7,107,879 B1 | 9/2006 | Cheng | |
| 7,156,598 B2 * | 1/2007 | Tibbenham | F16B 35/06 |
| | | | 411/187 |
| 7,228,764 B1 | 6/2007 | Macor | |
| 7,231,851 B2 | 6/2007 | Tuan-mu | |
| 7,255,522 B2 | 8/2007 | Dilling | |
| 7,322,265 B2 * | 1/2008 | Chen | B25B 15/005 |
| | | | 81/436 |
| 7,325,470 B2 | 2/2008 | Kay et al. | |
| 7,340,983 B2 | 3/2008 | Ling et al. | |
| D568,731 S | 5/2008 | Campbell | |
| 7,373,709 B2 | 5/2008 | Fernando et al. | |
| 7,437,975 B1 | 10/2008 | De Anfrasio | |
| 7,438,513 B2 * | 10/2008 | Craven | F16B 23/0038 |
| | | | 411/408 |
| 7,452,361 B2 * | 11/2008 | Kreidler | B25B 15/007 |
| | | | 606/305 |
| 7,462,007 B2 | 12/2008 | Sullivan et al. | |
| 7,478,986 B2 | 1/2009 | Bushell et al. | |
| 7,568,872 B2 | 8/2009 | Schultz | |
| 7,628,772 B2 | 12/2009 | McConnell et al. | |
| 7,674,081 B2 | 3/2010 | Selle | |
| 7,730,812 B2 | 6/2010 | Edland | |
| 7,771,459 B2 | 8/2010 | von Oepen | |
| D624,796 S | 10/2010 | Taylor, Jr. | |
| 7,955,036 B2 | 6/2011 | Palm | |
| 7,988,683 B2 | 8/2011 | Adair et al. | |
| 8,065,940 B2 | 11/2011 | Wilson et al. | |
| 8,083,082 B2 | 12/2011 | Sasaki | |
| 8,206,071 B1 | 6/2012 | Johnson | |
| 8,210,786 B2 | 7/2012 | Okada et al. | |
| 8,257,004 B2 * | 9/2012 | Smith | F16B 37/0857 |
| | | | 403/109.5 |
| 8,273,061 B2 | 9/2012 | McConnell et al. | |
| 8,342,061 B2 | 1/2013 | Super | |
| 8,347,761 B2 | 1/2013 | Goss | |
| 8,353,230 B2 | 1/2013 | Cole | |
| 8,506,578 B2 | 8/2013 | Smith | |
| 8,545,156 B2 | 10/2013 | Kageyama et al. | |
| 8,562,582 B2 | 10/2013 | Tuckwell et al. | |
| 8,640,575 B2 | 2/2014 | Huang | |
| 8,647,035 B2 | 2/2014 | Bakken et al. | |
| 8,696,275 B2 | 4/2014 | Wallace et al. | |
| 8,739,660 B2 | 6/2014 | Edland et al. | |
| 8,740,533 B2 | 6/2014 | Gaillard | |
| 8,745,825 B2 | 6/2014 | Gitman et al. | |
| 8,757,950 B2 * | 6/2014 | Ogawa | F16B 23/0061 |
| | | | 411/404 |
| 8,794,113 B2 | 8/2014 | Maury | |
| 8,850,662 B2 | 10/2014 | Gitman et al. | |
| 8,864,725 B2 | 10/2014 | Ranalletta et al. | |
| 8,944,736 B2 | 2/2015 | Figge et al. | |
| 8,955,417 B2 | 2/2015 | Stiebitz et al. | |
| 8,973,471 B2 | 3/2015 | Hsieh | |
| 9,039,673 B2 | 5/2015 | Weitzel et al. | |
| 9,044,843 B1 | 6/2015 | Kokhtee | |
| D741,159 S | 10/2015 | Campbell | |
| 9,283,324 B2 | 3/2016 | Lev et al. | |
| 9,316,245 B2 * | 4/2016 | Dvorak | F16B 37/0892 |
| 9,422,965 B2 | 8/2016 | Campbell, II | |
| 9,522,457 B2 | 12/2016 | Huang | |
| 9,587,688 B2 | 3/2017 | Zdeb et al. | |
| 9,624,962 B2 | 4/2017 | Unseld et al. | |
| 9,637,893 B2 * | 5/2017 | Lin | E03C 1/0401 |
| 9,638,234 B2 | 5/2017 | Campbell | |
| 9,651,078 B2 | 5/2017 | Santiago-Anadon | |
| 9,664,225 B2 | 5/2017 | Szczukowski et al. | |
| 9,687,968 B2 | 6/2017 | Doroslovac et al. | |
| D794,405 S | 8/2017 | Doroslovac et al. | |
| D798,682 S | 10/2017 | Doroslovac et al. | |
| 9,795,536 B2 | 10/2017 | Lev et al. | |
| 9,829,020 B2 * | 11/2017 | Ortega Dona | F16B 5/0283 |
| 9,839,580 B2 | 12/2017 | Lev et al. | |
| 9,840,002 B2 * | 12/2017 | Schon | B25B 23/0007 |
| 9,907,729 B2 | 3/2018 | Nord et al. | |
| 9,943,463 B2 | 4/2018 | Marks et al. | |
| 10,022,298 B2 | 7/2018 | Marici et al. | |
| D829,088 S | 9/2018 | Campbell, II | |
| 10,081,094 B2 | 9/2018 | Doroslovac et al. | |

(56) References Cited

U.S. PATENT DOCUMENTS

| | | | |
|---|---|---|---|
| 10,197,088 B2 | 2/2019 | Dang | |
| 10,215,217 B2* | 2/2019 | Hess | A61B 17/7032 |
| 10,286,201 B2 | 5/2019 | McKinnon et al. | |
| 10,731,692 B2 | 8/2020 | Goss | |
| 10,882,162 B2 | 1/2021 | Kukucka et al. | |
| 10,926,384 B2 | 2/2021 | Norton | |
| 10,960,520 B2 | 3/2021 | Schulz | |
| 10,995,788 B2 | 5/2021 | Dilling | |
| 11,028,870 B2 | 6/2021 | Tomaszewski et al. | |
| 11,154,969 B2 | 10/2021 | Kukucka et al. | |
| 11,173,589 B2 | 11/2021 | Campbell, II | |
| 11,215,215 B2 | 1/2022 | Lukes | |
| 11,234,899 B2 | 2/2022 | Gitman et al. | |
| 11,337,892 B2 | 5/2022 | Gitman | |
| 11,413,730 B2 | 8/2022 | Doroslovac et al. | |
| 11,458,071 B2 | 10/2022 | Gitman et al. | |
| 11,554,467 B2* | 1/2023 | Lin | B25B 15/008 |
| 11,572,914 B2 | 2/2023 | Chen | |
| 11,592,054 B1* | 2/2023 | Kemeny | F16B 5/0241 |
| D980,707 S | 3/2023 | Lee | |
| 11,602,828 B2 | 3/2023 | Kukucka et al. | |
| 2002/0016595 A1 | 2/2002 | Michelson | |
| 2002/0141847 A1* | 10/2002 | Oh | F16B 23/0092 |
| | | | 411/402 |
| 2004/0100097 A1 | 5/2004 | Fukano et al. | |
| 2005/0047891 A1 | 3/2005 | Toyooka et al. | |
| 2005/0126349 A1* | 6/2005 | Trank | B25B 13/485 |
| | | | 81/460 |
| 2005/0129488 A1* | 6/2005 | Weinstein | F16B 41/005 |
| | | | 411/533 |
| 2005/0137523 A1 | 6/2005 | Wyatt et al. | |
| 2005/0216015 A1 | 9/2005 | Kreidler | |
| 2005/0254921 A1* | 11/2005 | Leblanc | F16B 23/00 |
| | | | 411/409 |
| 2006/0002781 A1 | 1/2006 | Mangapora | |
| 2006/0089601 A1 | 4/2006 | Dionigi | |
| 2006/0116644 A1 | 6/2006 | Norton | |
| 2006/0162505 A1 | 7/2006 | Choi et al. | |
| 2006/0233626 A1* | 10/2006 | Lin | F16B 23/0092 |
| | | | 411/304 |
| 2007/0043379 A1 | 2/2007 | Sullivan, Jr. et al. | |
| 2007/0060904 A1 | 3/2007 | Vedrine et al. | |
| 2007/0079894 A1 | 4/2007 | Kraus et al. | |
| 2007/0183865 A1* | 8/2007 | Severns | F16B 5/0275 |
| | | | 411/387.1 |
| 2007/0245863 A1 | 10/2007 | Edland | |
| 2008/0009789 A1 | 1/2008 | Zinger et al. | |
| 2008/0172024 A1 | 7/2008 | Yow | |
| 2008/0179353 A1 | 7/2008 | Maymon | |
| 2008/0249479 A1 | 10/2008 | Zinger et al. | |
| 2008/0287914 A1 | 11/2008 | Wyatt et al. | |
| 2009/0043282 A1 | 2/2009 | Hughes et al. | |
| 2009/0092462 A1* | 4/2009 | Pratt | F16B 35/06 |
| | | | 411/383 |
| 2009/0220321 A1* | 9/2009 | Sakamura | F16B 23/003 |
| | | | 411/410 |
| 2010/0030282 A1 | 2/2010 | Ciccone et al. | |
| 2010/0095487 A1 | 4/2010 | Gitman et al. | |
| 2010/0140431 A1 | 6/2010 | Van Horne | |
| 2010/0192344 A1* | 8/2010 | Zollmann | B25B 13/48 |
| | | | 411/407 |
| 2010/0192736 A1 | 8/2010 | Burch et al. | |
| 2011/0044784 A1* | 2/2011 | Da Fonseca | F16B 41/005 |
| | | | 411/366.1 |
| 2011/0172719 A1 | 7/2011 | Gorhan et al. | |
| 2011/0264037 A1 | 10/2011 | Foshee et al. | |
| 2011/0271800 A1 | 11/2011 | Lin | |
| 2011/0314768 A1 | 12/2011 | Johnson | |
| 2012/0155988 A1* | 6/2012 | Schumacher | F16B 31/02 |
| | | | 411/369 |
| 2012/0241332 A1 | 9/2012 | Crossman | |
| 2013/0030476 A1 | 1/2013 | Shimko et al. | |
| 2013/0097848 A1* | 4/2013 | Inaba | F16B 43/001 |
| | | | 411/371.1 |
| 2013/0144248 A1 | 6/2013 | Putter et al. | |
| 2013/0213193 A1 | 8/2013 | Lukes | |
| 2013/0226100 A1 | 8/2013 | Lev | |
| 2013/0282019 A1 | 10/2013 | Bouliane | |
| 2014/0066945 A1 | 3/2014 | Humphreys et al. | |
| 2014/0217099 A1 | 8/2014 | Browne | |
| 2015/0104269 A1 | 4/2015 | Gillis et al. | |
| 2015/0265500 A1 | 9/2015 | Russo et al. | |
| 2016/0061246 A1 | 3/2016 | Campbell | |
| 2016/0167838 A1 | 6/2016 | Dong et al. | |
| 2016/0193722 A1 | 7/2016 | Cunningham | |
| 2017/0128948 A1 | 5/2017 | Anger | |
| 2017/0175798 A1* | 6/2017 | Arndt | F16B 41/005 |
| 2017/0252905 A1 | 9/2017 | Doroslovac et al. | |
| 2017/0312897 A1 | 11/2017 | Doroslovac et al. | |
| 2018/0003241 A1 | 1/2018 | Goss | |
| 2018/0106286 A1 | 4/2018 | Cone, III et al. | |
| 2018/0128301 A1* | 5/2018 | Rosén | F16B 19/02 |
| 2018/0156257 A1 | 6/2018 | Rühl et al. | |
| 2018/0280067 A1 | 10/2018 | Bjork et al. | |
| 2018/0313395 A1* | 11/2018 | Rajewski | F16B 41/005 |
| 2018/0347612 A1 | 12/2018 | Falkenstein et al. | |
| 2020/0180123 A1 | 6/2020 | Lukes et al. | |
| 2020/0269398 A1 | 8/2020 | Donovan et al. | |
| 2021/0148395 A1 | 5/2021 | Kukucka et al. | |
| 2022/0192925 A1 | 6/2022 | Gitman et al. | |
| 2022/0281085 A1 | 9/2022 | Kukucka et al. | |
| 2022/0402105 A1 | 12/2022 | Gitman et al. | |

FOREIGN PATENT DOCUMENTS

| | | |
|---|---|---|
| EP | 2278175 A2 | 1/2011 |
| FR | 2945437 A1 | 11/2010 |
| GB | 1 032 144 | 6/1966 |
| GB | 1 205 445 | 9/1970 |
| GB | 1 360 644 | 7/1974 |
| GB | 1 398 180 | 6/1975 |
| GB | 2 141 803 | 1/1985 |
| GB | 2 153 033 | 8/1985 |
| GB | 2 271 738 | 4/1994 |
| GB | 2 413 296 | 10/2005 |
| KR | 101276303 B1 | 6/2013 |
| RU | 2 160 396 C1 | 12/2000 |
| WO | 2010/037250 A1 | 4/2010 |
| WO | 2015/118521 A1 | 8/2015 |
| WO | 2018/073153 A1 | 4/2018 |
| WO | 2018/167321 A2 | 9/2018 |

OTHER PUBLICATIONS

Polyvinyl chloride, Wikipedia, Website, Accessed May 12, 2017, 19 pages, https://en.wikipedia.org/wiki/Polyvinyl_chloride.

Thermoplastic Elastomer, Wikipedia, Website, Accessed May 12, 2017, 4 pages, https://en.wikipedia.org/wiki/Thermoplastic_elasomer.

TPR: Thermpoplastic Rubber—S&E Specialty Polymers, Website, Accessed May 12, 2017, 2 pages, http://www.sespoly.com/products/tpr-thermoplastic-rubber/.

(1/4"-3/8"-1/2") Drive Finger Ratchet Head with Quick Release 72 Teethe Gears (GS-4343BH-BK). Accessed Oct. 20, 2021 (3 pages). https://www.alibaba.com/product-detail/-1-4-3-8-1_1700001046437.html.

TE-5003-9-3, Plastic Thumb Nut, set of 4. Accessed Oct. 20, 2021 (3 pages). https://tisch-env.com/product/te-5003-9-3-plastic-thumb-nut-set-of-4/.

(1/4"-3/8"-1/2") Drive Finger Ratchet Head CR-V Steel (GS-4343BE-BG). Accessed Oct. 22, 2021 (3 pages). https://golconda-source.en.alibaba.com/product/1700000997430-813579114/_1_4_3_8_1_2_DRIVE_FINGER_RATCHET_HEAD_CR_V_STEEL_GS_4343BE_BG_.html.

1/4"-3/8"-1/2") Drive Finger Ratchet Head with 72 Teeth Gears (GS-4343BB- BD) Accessed Oct. 22, 2021 (3 pages). https://golconda-source.en.alibaba.com/product/1700001028449-813579114/_1_4_3_8_1_2_DRIVE_FINGER_RATCHET_HEAD_WITH_72_TEETH_GEARS_GS_4343BB_BD_.html.

(56) References Cited

OTHER PUBLICATIONS

PAGOW 2pcs Power Wing Nut Driver Set, Wing Nut Drill Bit Socket Wrench Tool Set, 1/4" Hex Shank for Panel Nuts, Screws Eye, C Hook Bolt, Q-Hanger. https://www.amazon.com/PAGOW-2-Pack-Hurricane-Wing-Driver/dp/B075XBG8LB?th=1 Accessed Oct. 22, 2021 (8 pages).
Theengineeringtoolbox, Wrench Conversion Chart, May 9, 2017, p. 1 (Year:2017) 2 Pages.
Stanley Engineered Fastening. TORX Plus® Drive System. 16 pages. Accessed Apr. 25, 2023.https://pdf.directindustry.com/pdf/stanley-engineered-fastening/torx-plus/22234-645055.html.
OSG System Products. Qua Stix®. 6 pages. Accessed Apr. 25, 2023. https://www.j-osp.com/_userdata/pdf/neji/catalog/2-QuaStix.pdf.
Eccles, Bill. Self-loosening of threaded fasteners. Bolt Science. 2 pages. Accessed Apr. 25, 2023. https://www.boltscience.com/pages/self-loosening-of-threaded-fasteners.pdf.
Mountz. What is Torque? 6 pages. Accessed Apr. 25, 2023. https://www.mountztorque.com/What-is-Torque_3.
Eccles, Bill. The basics of bolted joints. Bolt Science. 2011. 2 pages. Accessed Apr. 25, 2023. https://www.boltscience.com/pages/the-basics-of-bolted-joints.pdf.
Eccles, Bill. The loosening of prevailing torque nuts. Bolt Science. 2009. 2 pages. Accessed Apr. 25, 2023. https://www.boltscience.com/pages/the-loosening-of-prevailing-torque-nuts.pdf.
APM Hexseal. Bolting failure analysis. 2015. 8 pages. Accessed Apr. 25, 2023. https://www.fastenerandfixing.com/application-technology/bolting-failure-analysis/.
HILTI. Fastening Technology Manual: Dynamic Design for Anchors. p. 43. Accessed Apr. 25, 2023. https://www.hilti.co.uk/medias/sys_master/documents/h81/h73/9484926484510/Dynamic-design-of-anchors-Brochure-ASSET-DOC-LOC-2521843.pdf.
Stanley Engineered Fastening. 2020 Selection and Configuration Guide. pp. 128-132. Accessed Apr. 25, 2023. https://www.stanleyengineeredfastening.com/-/media/Web/SEF/Resources/Docs/STANLEY-Assembly-Technologies/2020_STANLEY_Catalog_A4.pdf.
SPS Technologies Aerospace Fasteners Group. Preload Indicating Washers: Maximize bolted joint strength by controlling clamp force. 12 pages. Accessed Apr. 25, 2023. https://www.pccfasteners.com/assets/local/documents/product-literature/pli_brochure.pdf.
Wikipedia. Circular motion. 10 Pages. Accessed Apr. 26, 2023. https://en.wikipedia.org/wiki/Circular_motion#.
DeWalt Anchors and Fasteners. General Information: Woodknocker®II+ and Pan-Knocker®II+. 13 pages. Accessed Apr. 25, 2023. https://anchors.dewalt.com/anchors/_documents/uploads/DWANF_WKII_PKII_TP_revJ.pdf?1682534413.
DeWalt Anchors and Fasteners. Cast-In-Place Concrete Inserts. Bang-it®+ and Wood-KnockerRII +. 8 pages. Accessed Apr. 25, 2023. https://anchors.dewalt.com/anchors/_documents/uploads/DWANF_WDKBANGR_BR_r01.pdf?1622227270.
The FreeDictionary. Torque. 10 pages. Accessed Apr. 25, 2023. https://encyclopedia.thefreedictionary.com/Torque.
The FreeDictionary. Dampening. 5 pages. Accessed Apr. 25, 2023. https://encyclopedia.thefreedictionary.com/dampening.
The FreeDictionary. Non-uniform circular motion. 9 pages. Accessed Apr. 25, 2023. https://encyclopedia.thefreedictionary.com/non-uniform+circular+motion.
Wikipedia. Torque. 11 pages. Accessed Apr. 25, 2023. https://en.wikipedia.org/wiki/Torque.
University of Guelph. Torque and Rotational Motion Tutorial. 8 pages. Accessed Apr. 25, 2023. https://www.physics.uoguelph.ca/torque-and-rotational-motion-tutorial.
Spencer, Kevin R., et al. Screw Head Design: An Experimental Study to Assess the Influence of Design on Performance. Journal of Oral and Maxillofacial Surgery. 2004. vol. 62. pp. 473-478. https://www.joms.org/article/S0278-2391(03)01270-9/fulltext.
Lin, Chen-Huei, et al. Improving socket design to prevent difficult removal of locking screws. Injury. 2018. vol. 49. pp. 585-592. https://www.sciencedirect.com/science/article/pii/S0020138318300561.
Borowski, Larry. Inspecting Combination Screw Drive Systems. Fastener World. 170. May/Jun. 2018. p. 302. Accessed Apr. 25, 2023. https://www.fastener-world.com/data/pdf_download/FW_170_E.pdf.
Bosch. Drilling and Fastening. p. 169. Accessed Apr. 25, 2023. https://www.scribd.com/document/444711224/bosch-20182019-catalog-drillingfastening-1-pdf#.
Torx Plus® drive system exclusives. p. 9. Accessed Apr. 25, 2023. https://www.yumpu.com/en/document/read/1355808/licensed-products-acument-global-technologies.
Celo Screws Technology. Catalogue V. 02. pp. 95, 99, 101 and 102. Accessed Apr. 25, 2023. https://www.celofixings.es/import/catalogue_celo_industry.pdf.
Böllhoff. Hexalobular / TORX®. Efficient Assembly. pp. 16. Accessed Apr. 25, 2023. https://eshop.boellhoff.de/out/media/pdf/prospekte/hexalobular-torx 8200_en.pdf.
SPS Technologies Aerospace Fasteners Group. SPS MP98T Fasteners. 4 pages. Accessed Apr. 25, 2023. https://www.nittoseiko.co.jp/dcms_media/other/F-J-IE.pdf.
Nitto Seiko. Co., LTD. Tough Cross. 2 pages. Accessed Apr. 25, 2023. https://www.nittoseiko.co.jp/dcms_media/other/F-J-IE.pdf.
Würth. Tools & Shop Supplies. p. 5. Accessed Apr. 25, 2023. https://catalogs.wurthusa.com/WurthUSACatalog/Section8Tools/.
PROTOR®. Aviation Hand Tools & Storage solutions. Torqueplus™ For Impact Sockets. p. 96. Accessed Apr. 25, 2023. https://www.protoindustrial.com/literatures/Brand/Proto/MKT-2870_ICPRAEROCAT_proto%20Aviation%20Catalog.pdf.
Atlas Copco. Pocket Guide to Tightening Technique. 28 pages. Accessed Apr. 25, 2023. https://www.atlascopco.com/content/dam/atlas-copco/industrial-technique/general/documents/pocketguides/9833864801_L.pdf.
OSG System Products., Ltd. Excellent torque transmission No Cam-out design. 9 pages. Accessed Apr. 25, 2023. https://www.j-osp.com/en/neji/index.html.
The Difference Between Torque and Clamp. Video runtime of 8:11. Screenshots from Youtube. 6 pages. Accessed Apr. 26, 2023. https://www.youtube.com/watch?v=ZDDrtIL7SQ4.
Multifunctional Wedge-Lock Washers | Nord-Lock X-series™. Screenshot from Youtube. Video runtime of 8:18. Screenshot from Youtube. 1 page. Accessed Apr. 27, 2023. https://www.youtube.com/watch?v=cDlmbMV9ICU.
Non Final Office Action dated Sep. 6, 2023 for U.S. Appl. No. 17/821,714 (23 Pages).

* cited by examiner

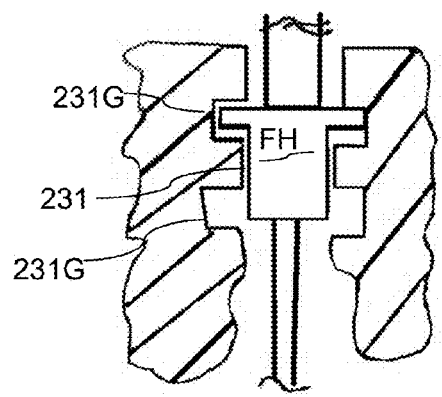
FIG. 38A
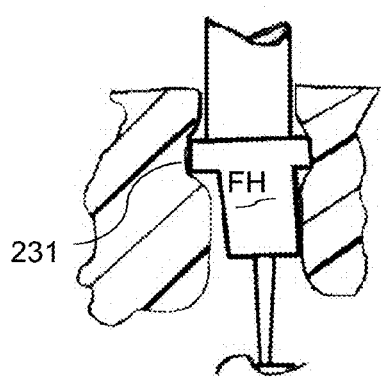
FIG. 38B
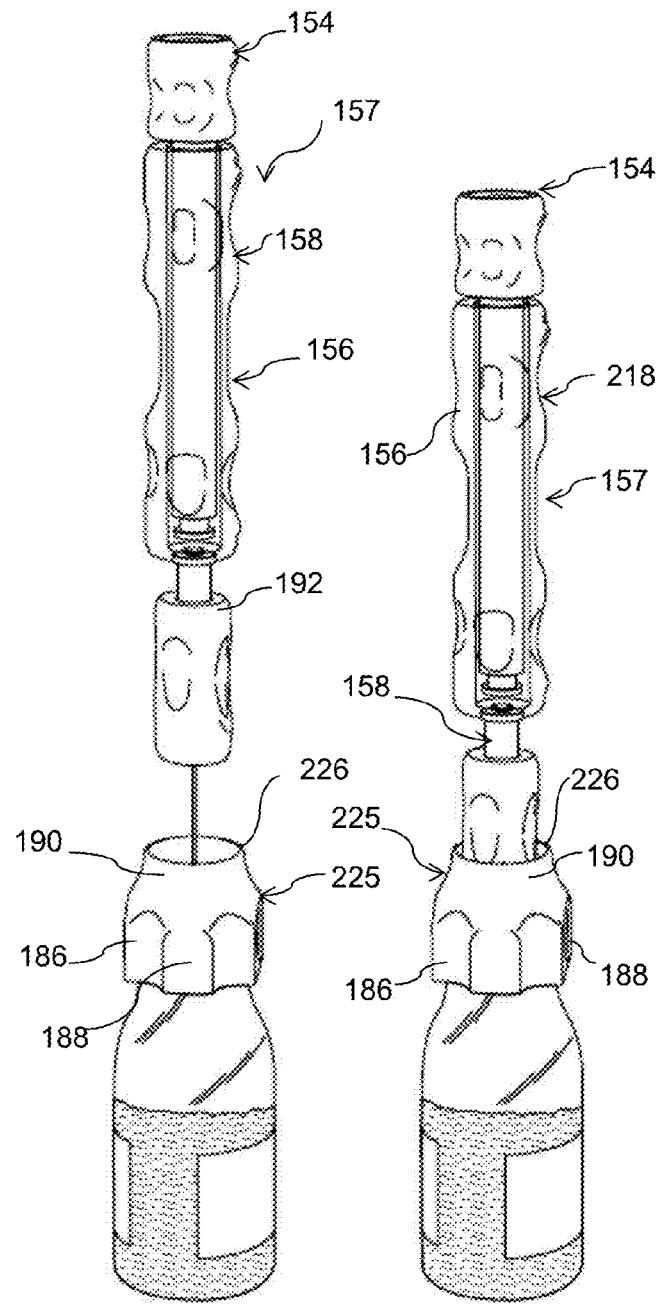
FIG. 39  FIG. 40

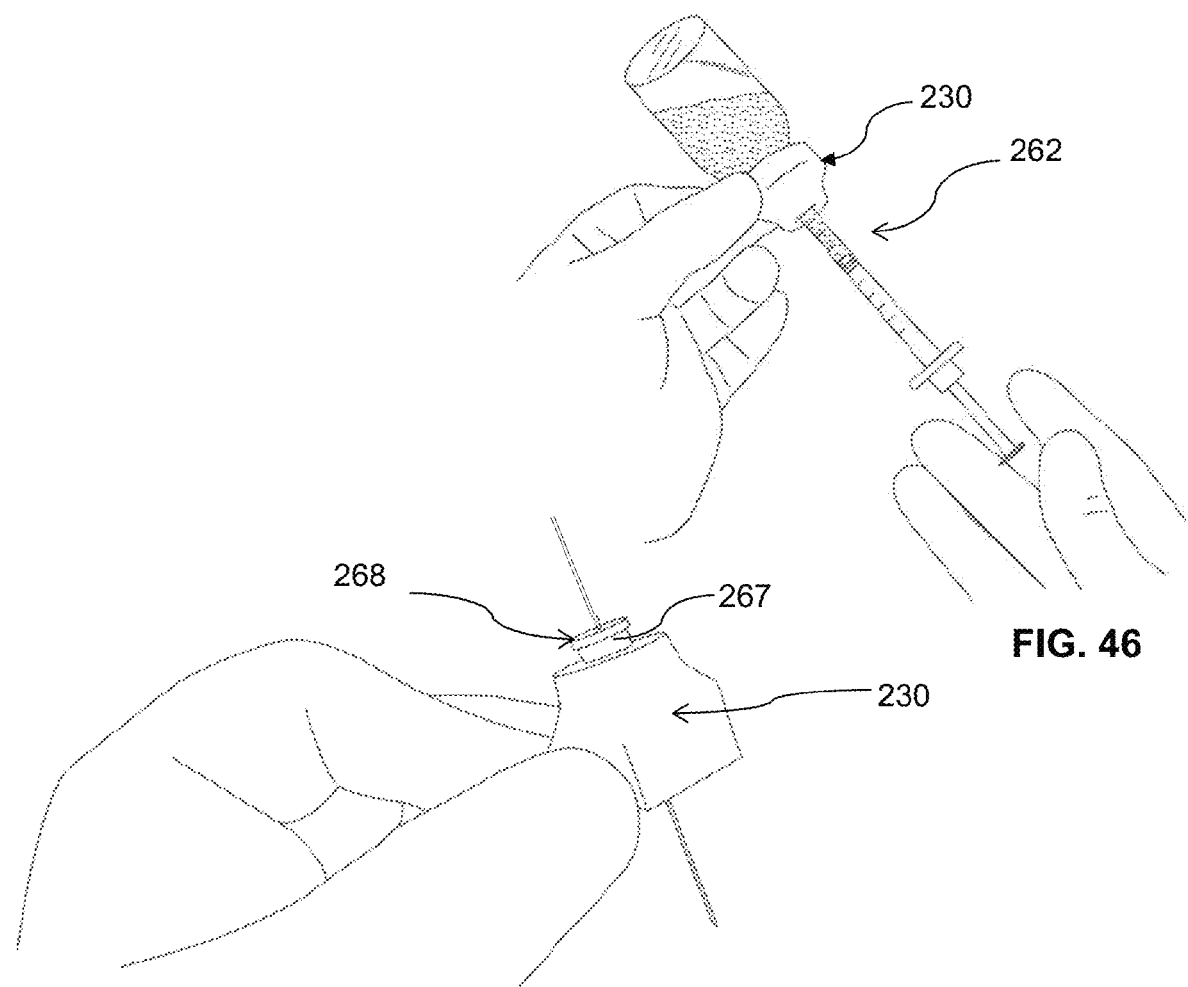
FIG. 46
FIG. 47
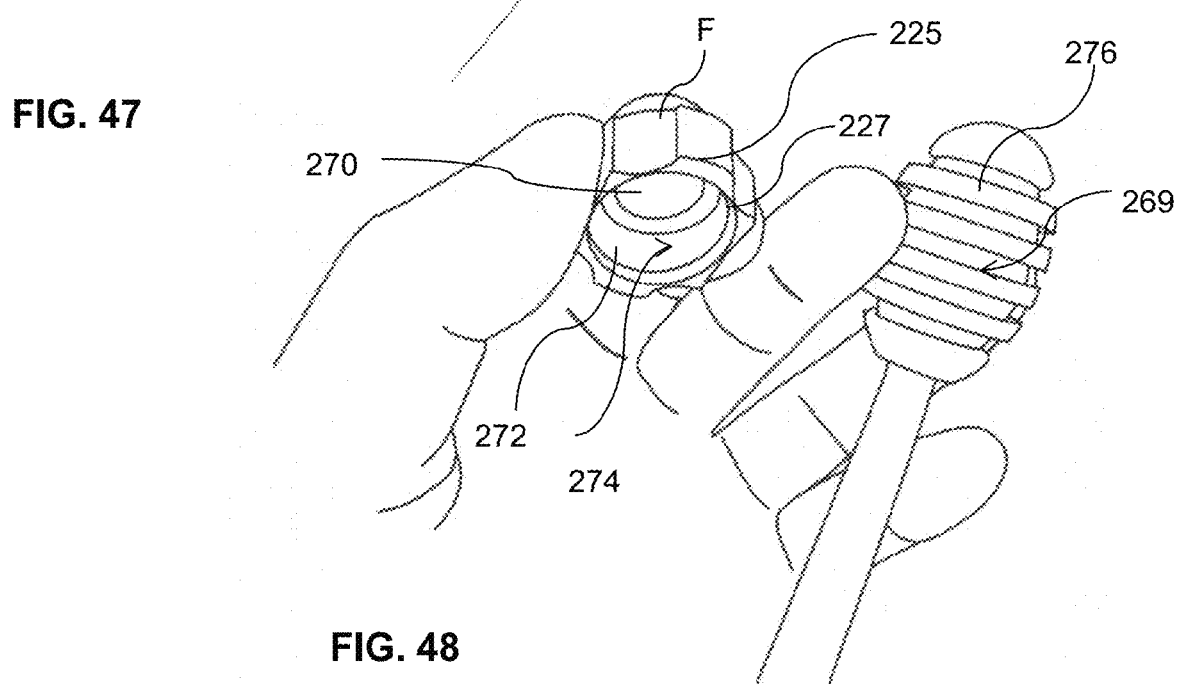
FIG. 48

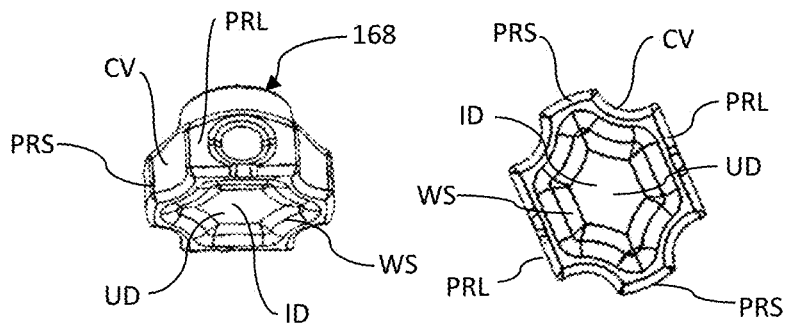
FIG. 54
FIG. 55
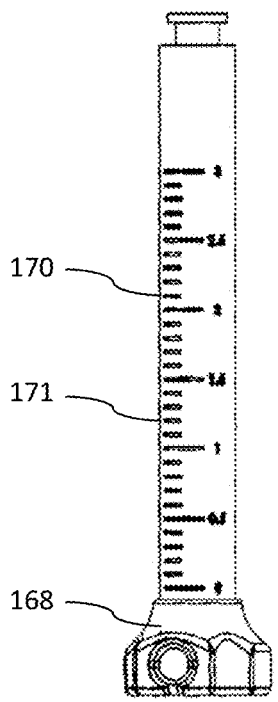
FIG. 53
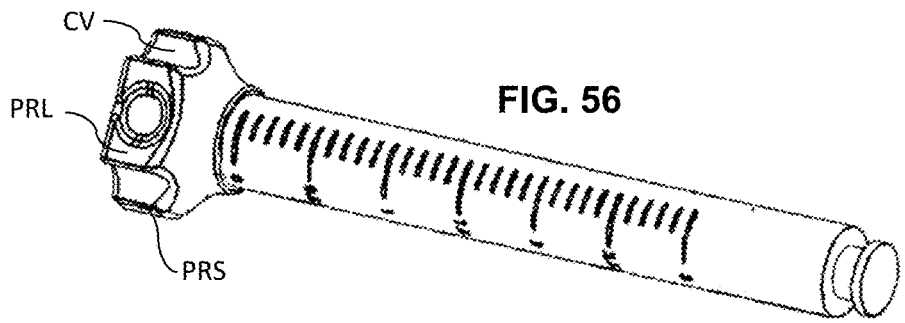
FIG. 56
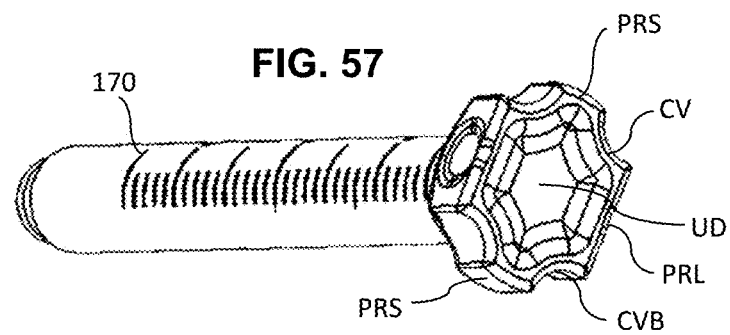
FIG. 57

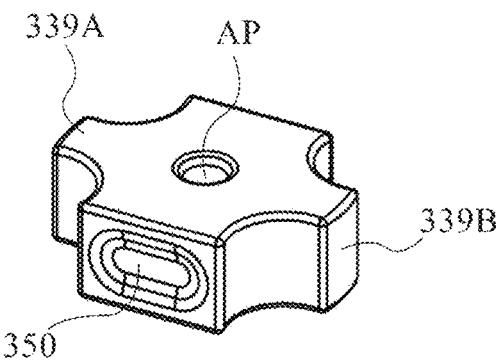
FIG. 77I  FIG. 77J
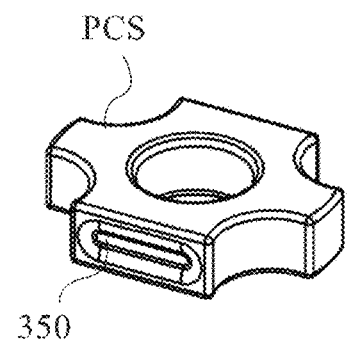
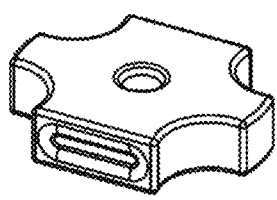
FIG. 77K
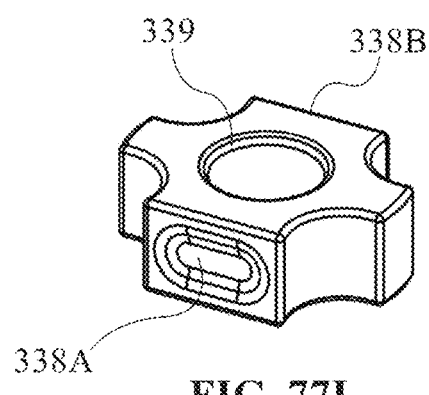
FIG. 77L
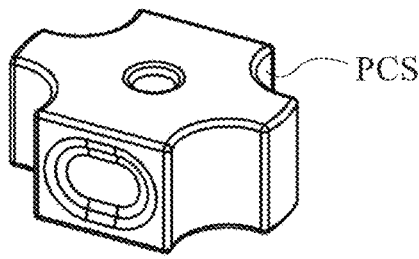
FIG. 77M
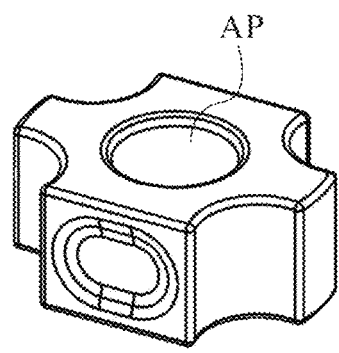
FIG. 77N

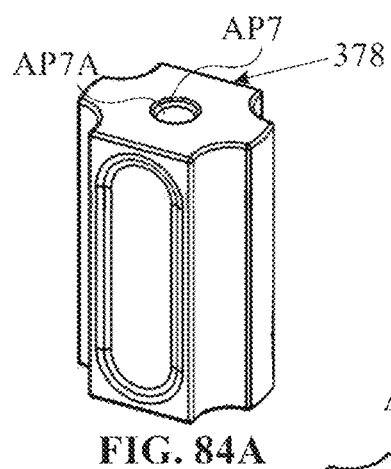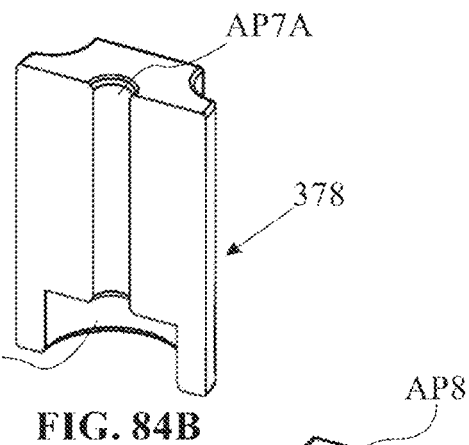
FIG. 84A  FIG. 84B
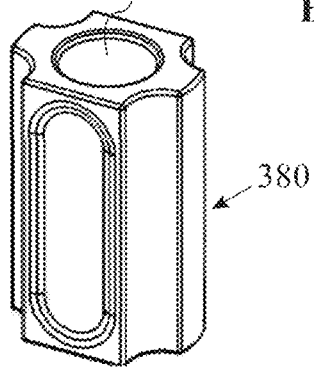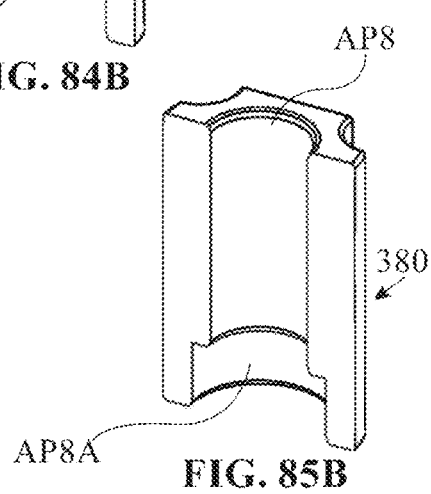
FIG. 85A  FIG. 85B
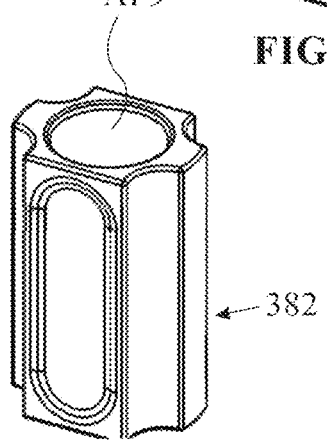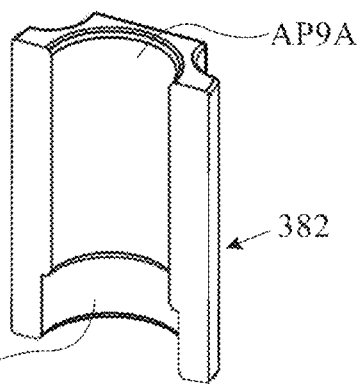
FIG. 86A  FIG. 86B
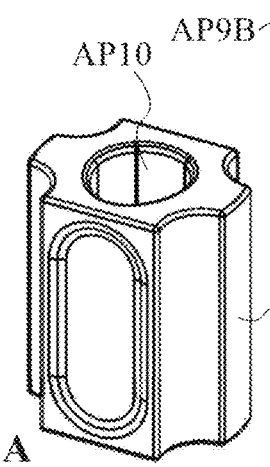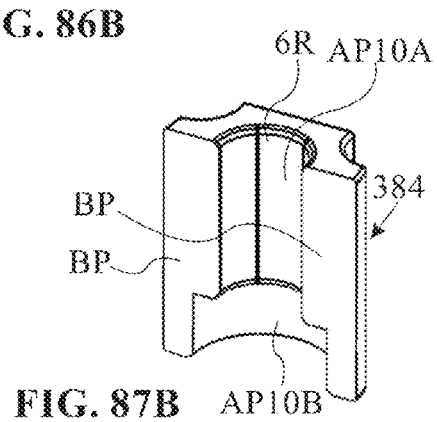
FIG. 87A  FIG. 87B

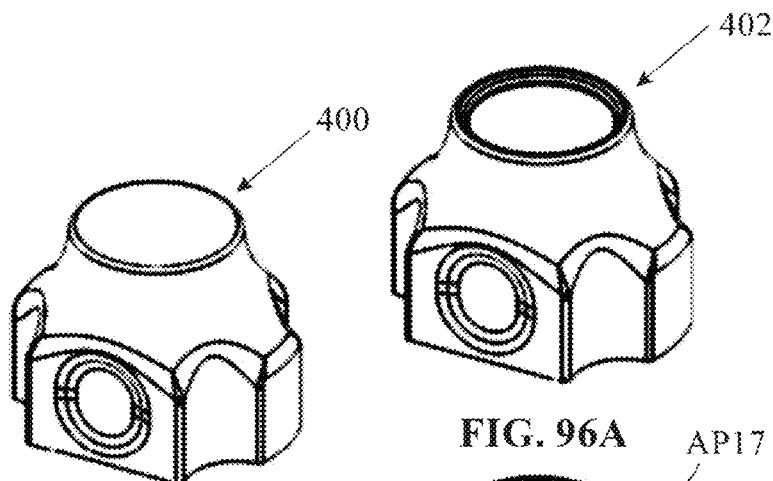
FIG. 95A
FIG. 96A
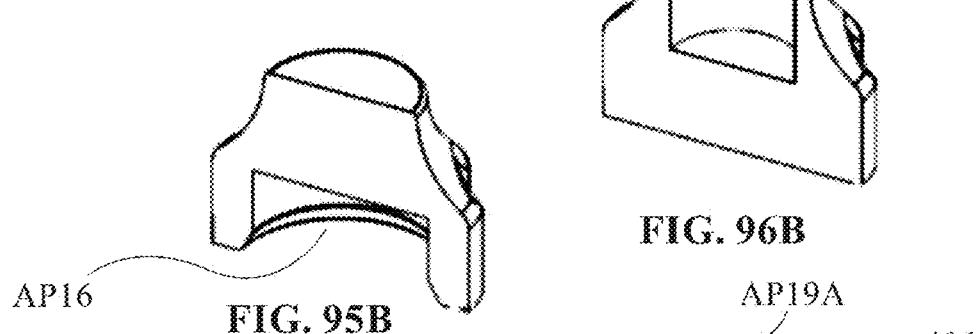
FIG. 95B
FIG. 96B
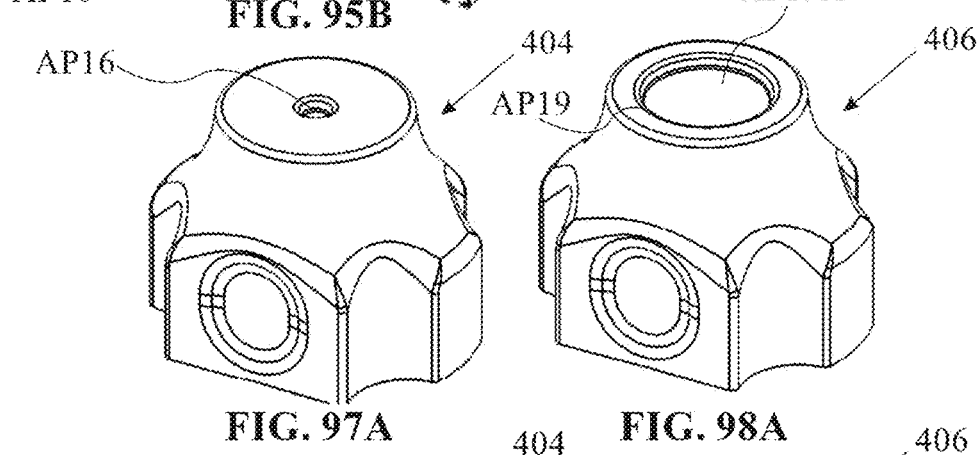
FIG. 97A
FIG. 98A
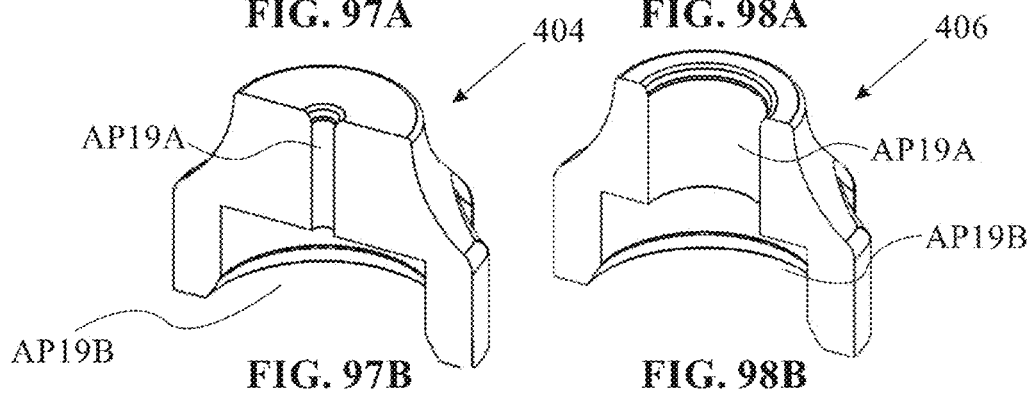
FIG. 97B
FIG. 98B

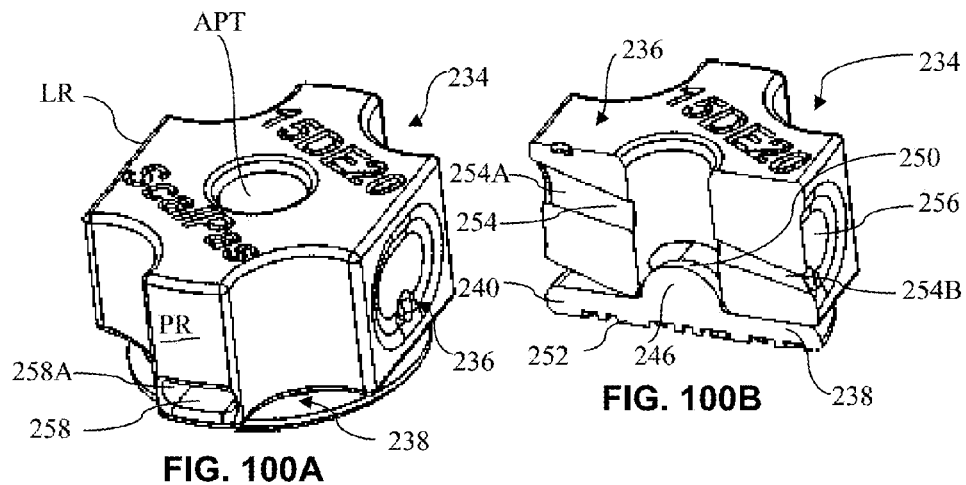
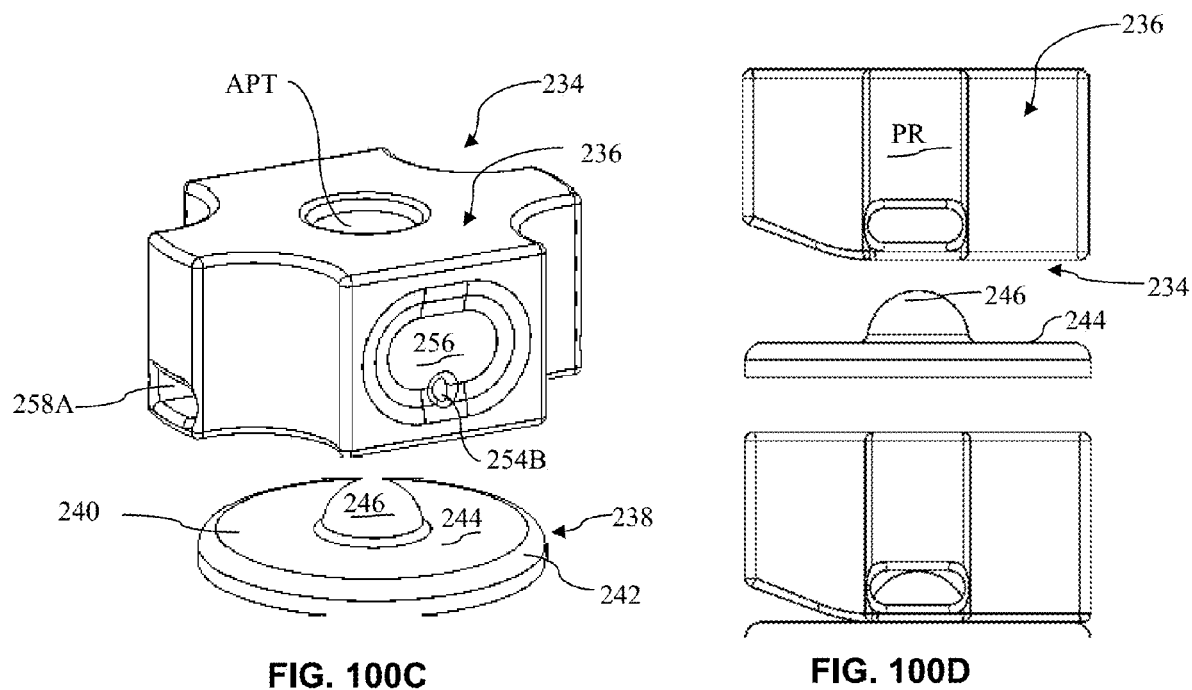

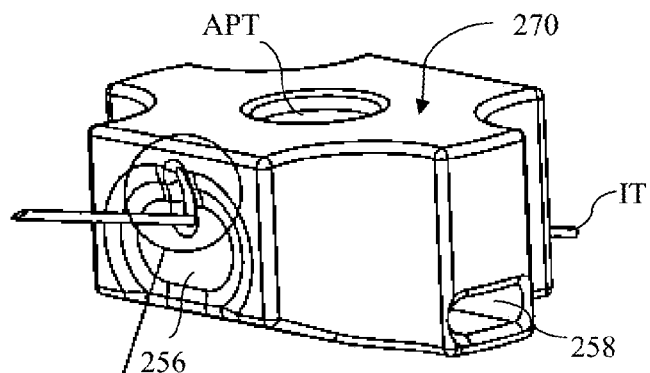
FIG. 102
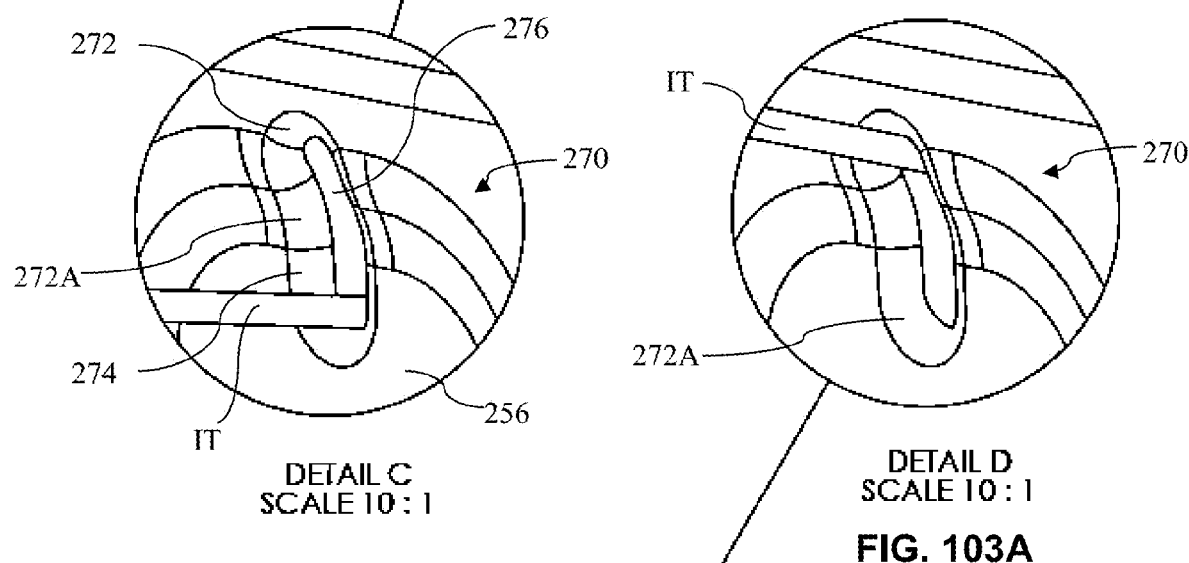
DETAIL C
SCALE 10 : 1
FIG. 102A
DETAIL D
SCALE 10 : 1
FIG. 103A
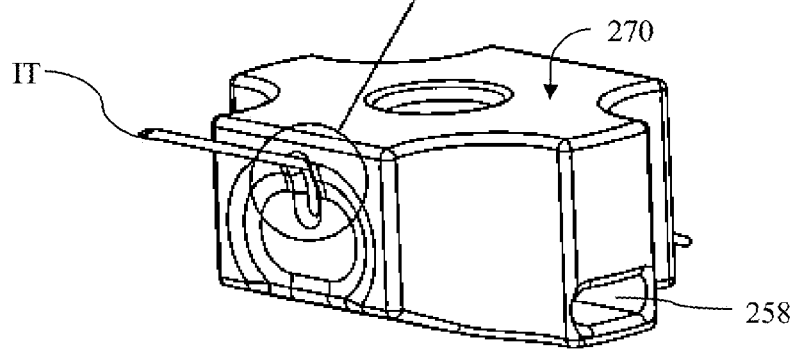
FIG. 103

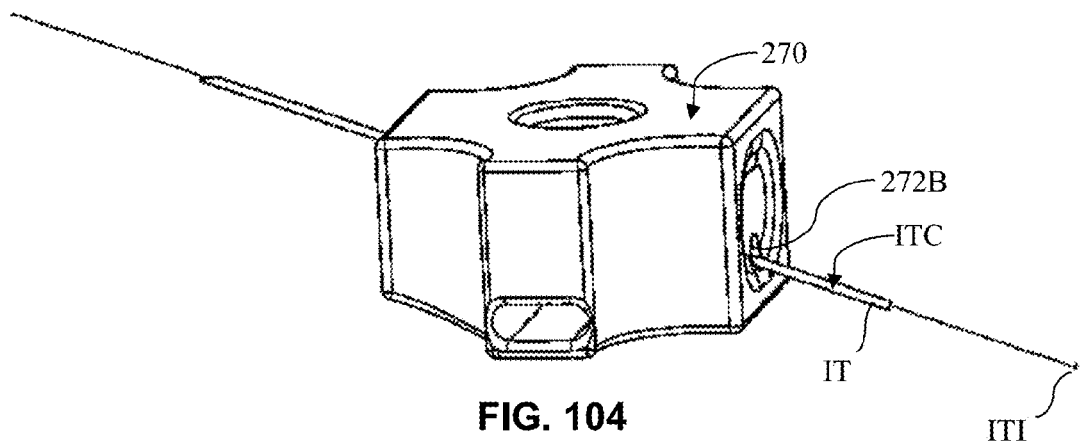
FIG. 104
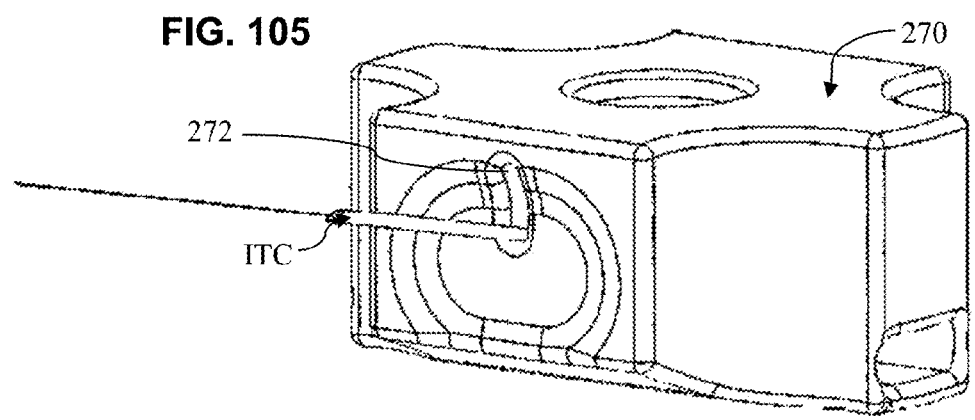
FIG. 105
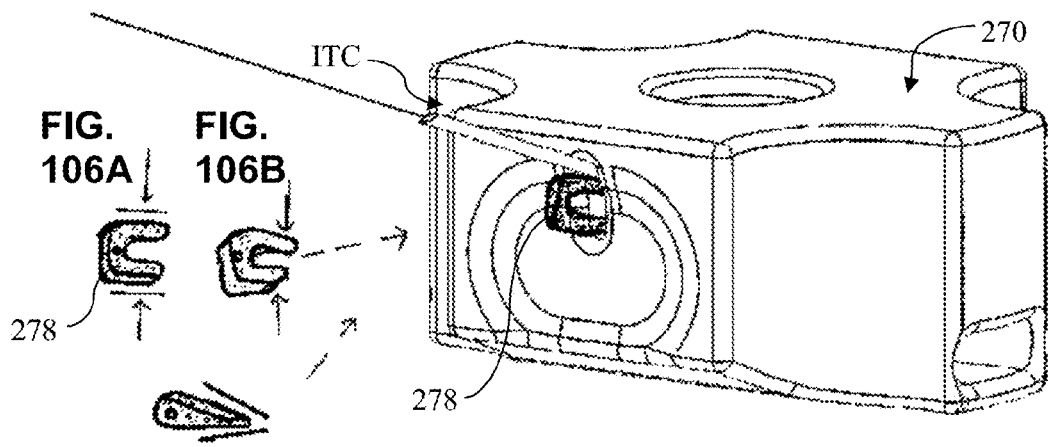
FIG. 106A  FIG. 106B
FIG. 106C
FIG. 106

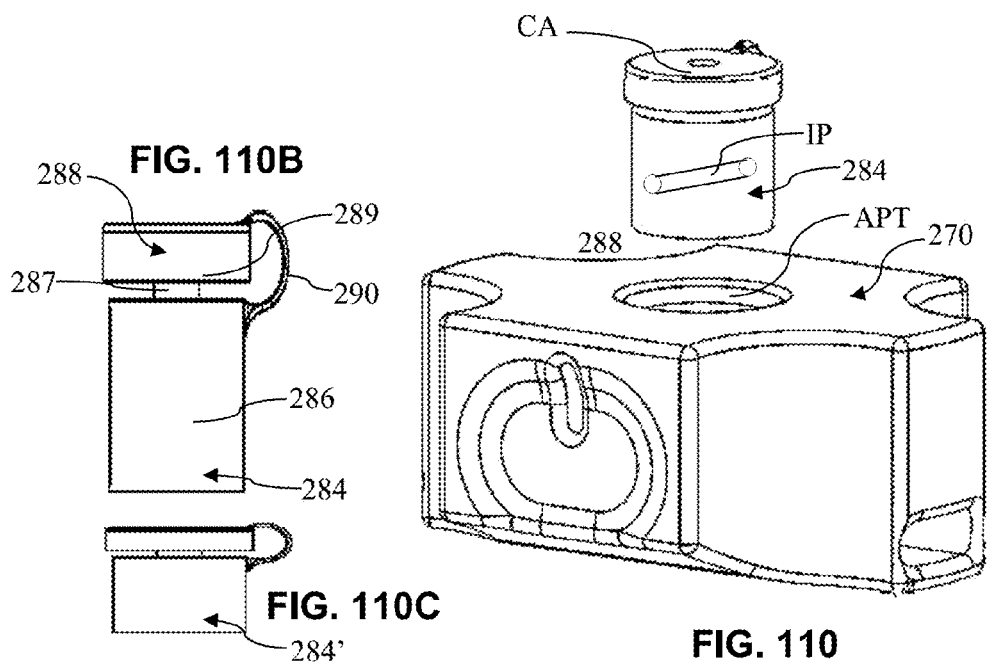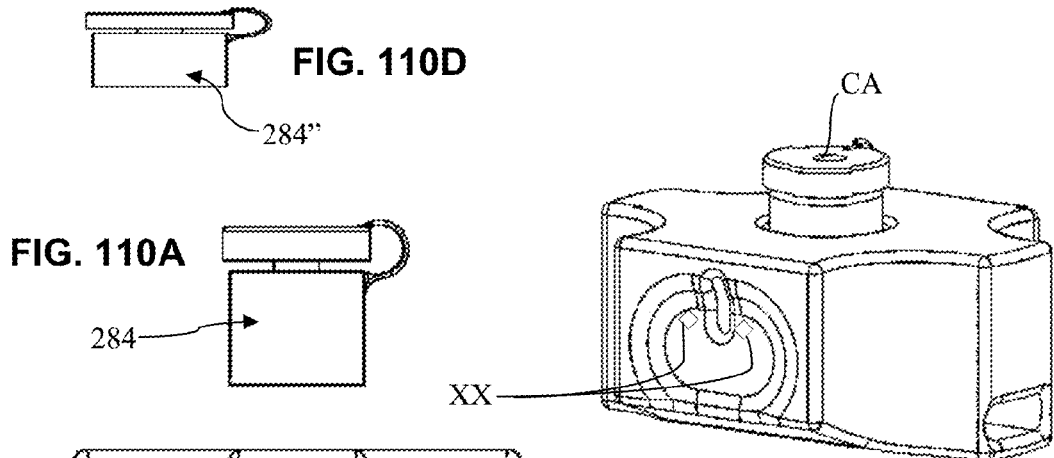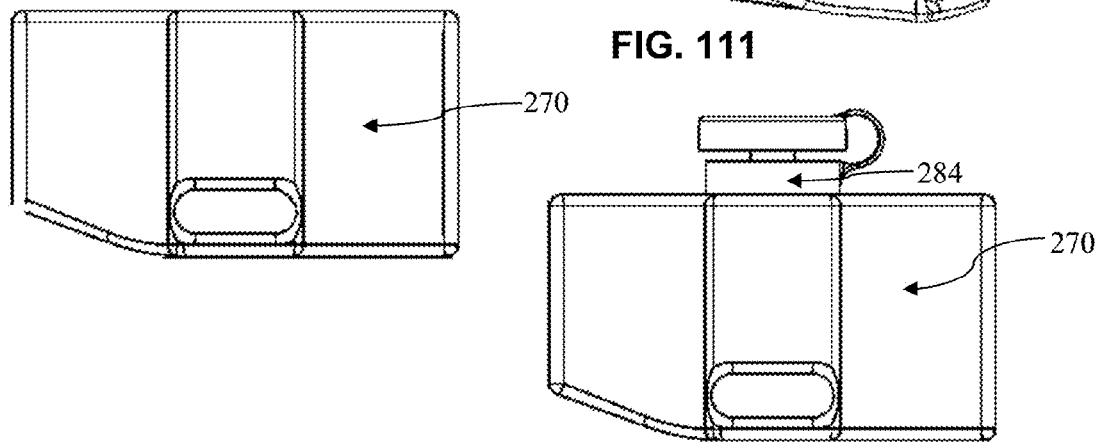

FIG. 121
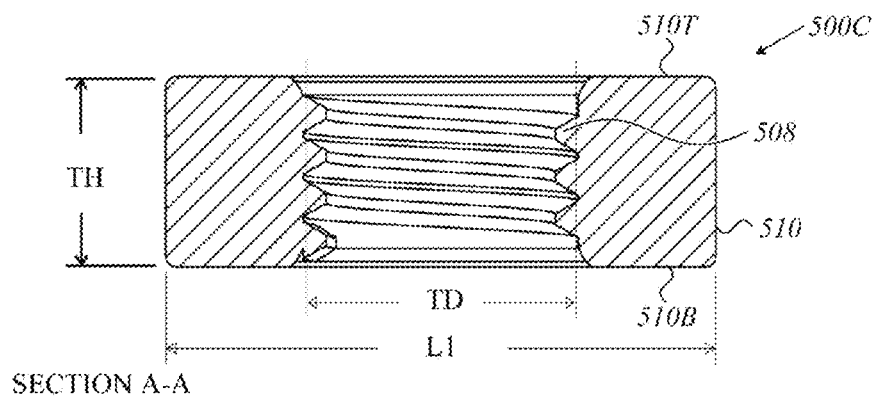
SECTION A-A
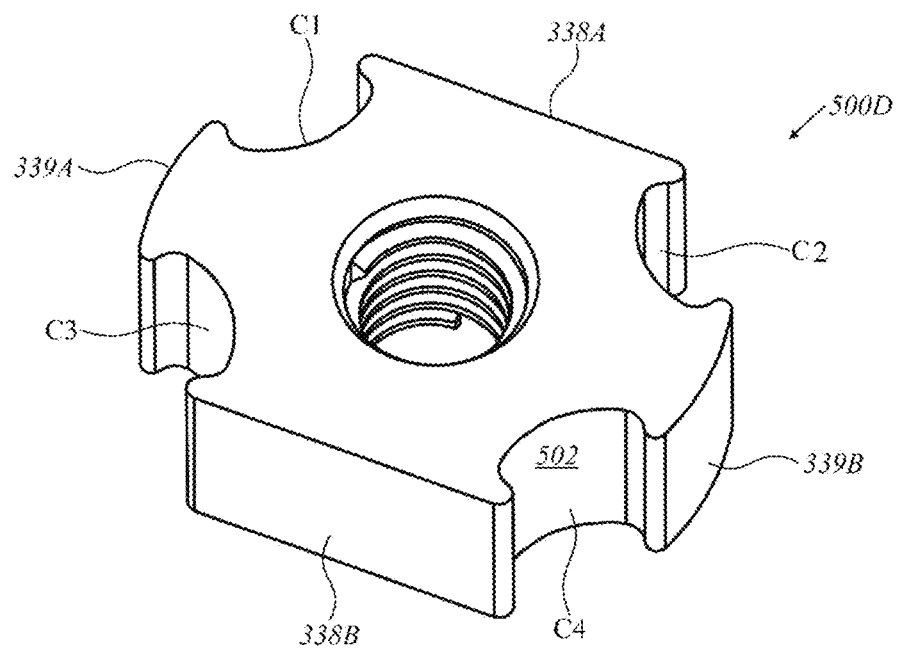
FIG. 122

FIG. 126
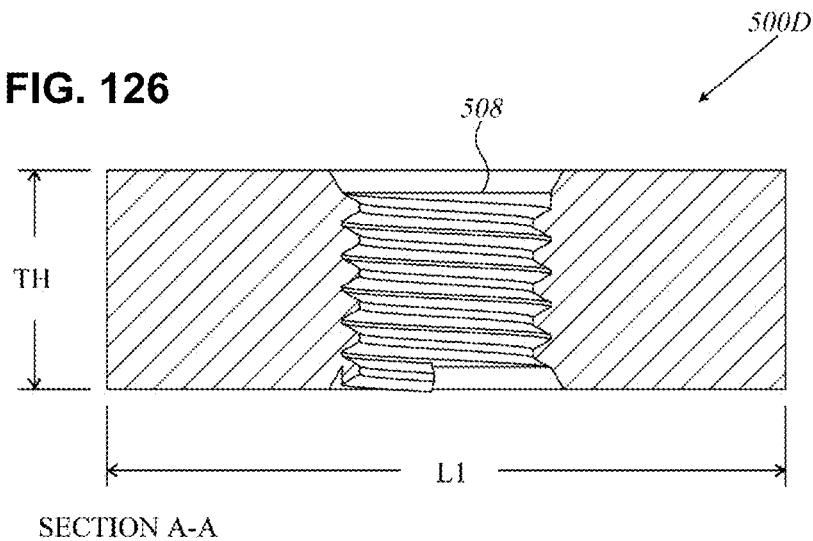
SECTION A-A
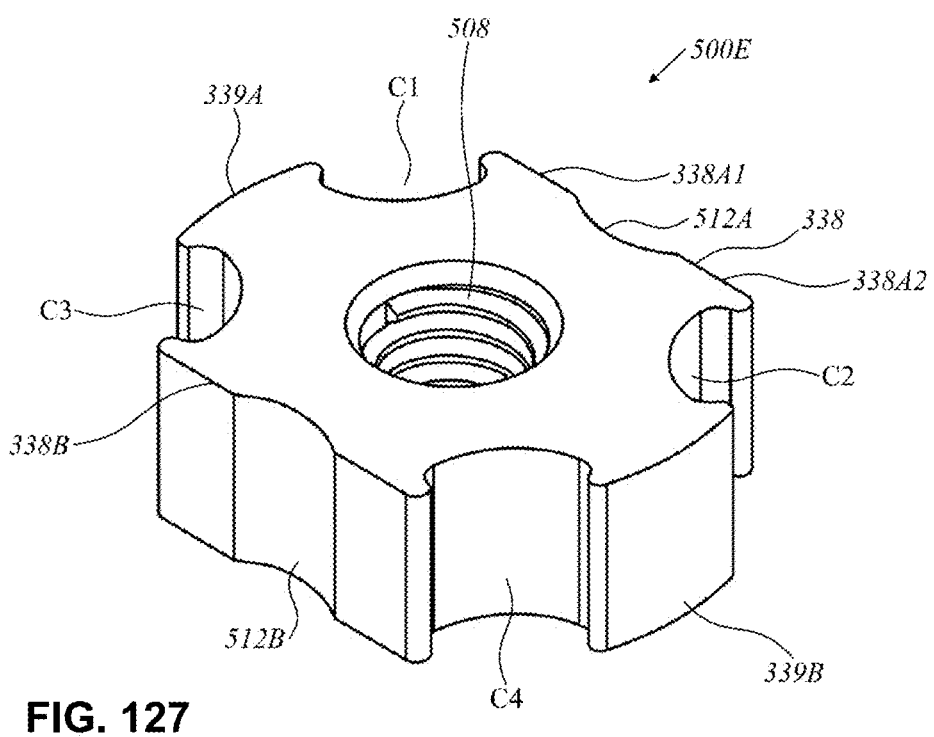
FIG. 127

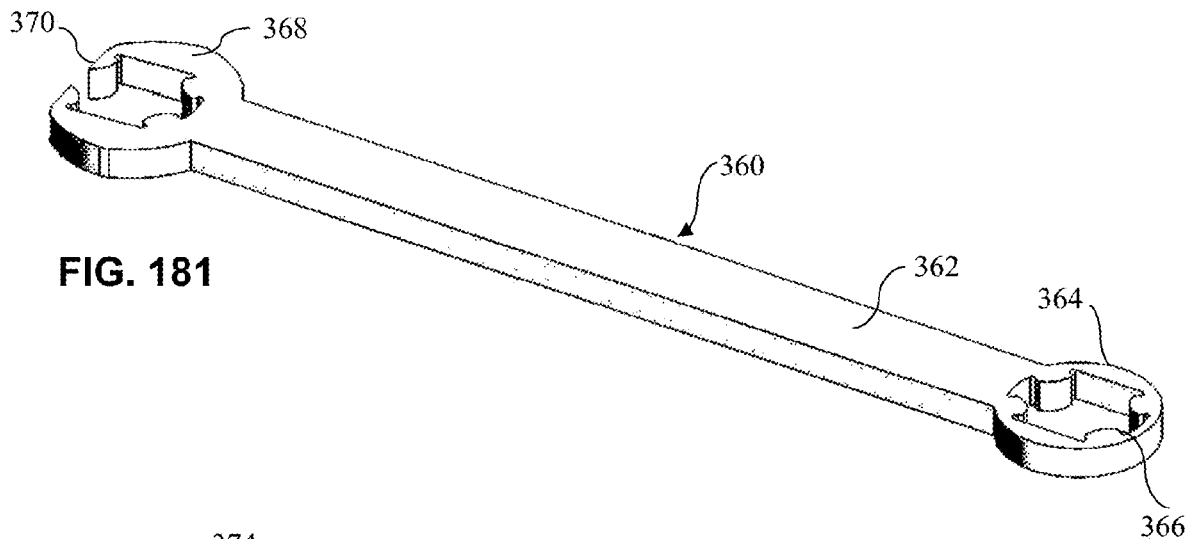
FIG. 181
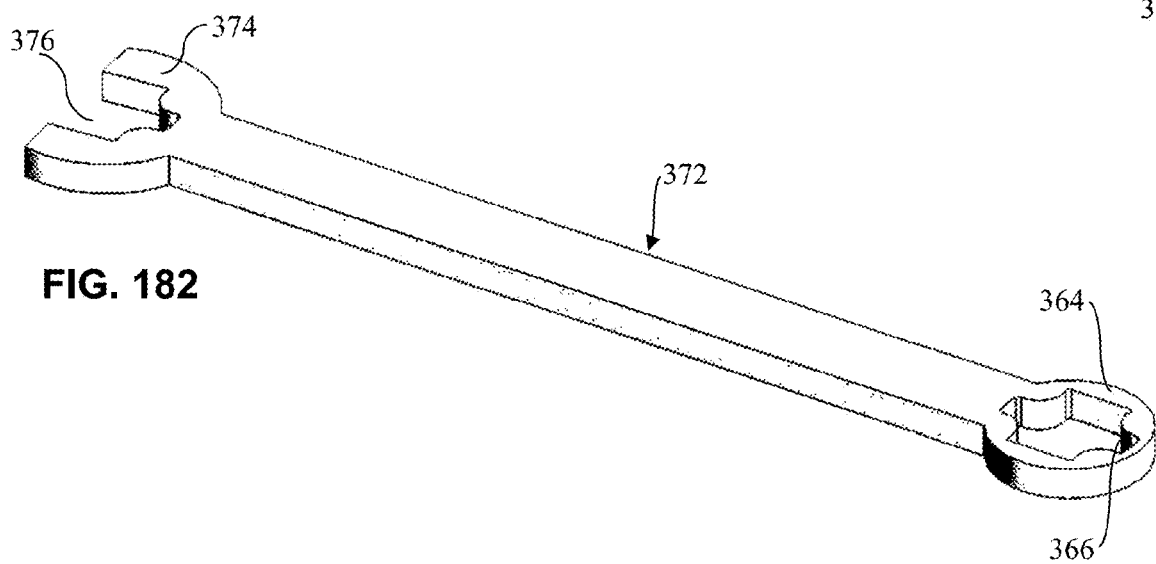
FIG. 182
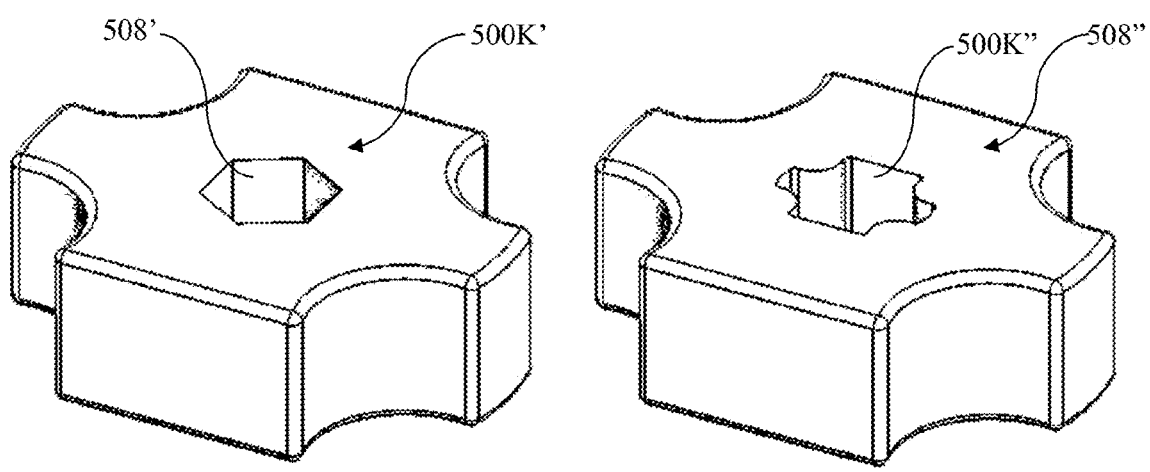
FIG. 183
FIG. 184

FIG. 190B
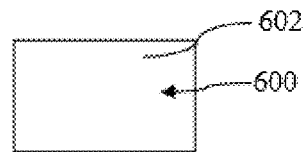
FIG. 191B
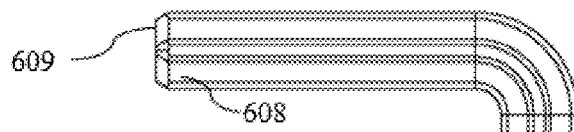
FIG. 190A
FIG. 190C
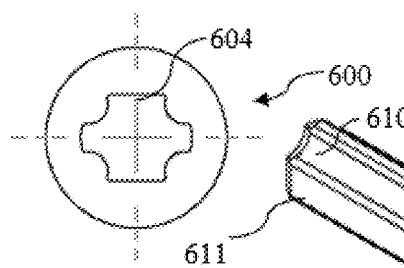
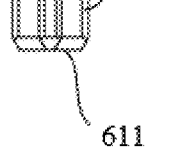
FIG. 191A
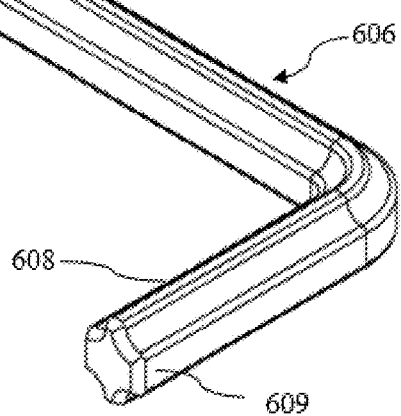

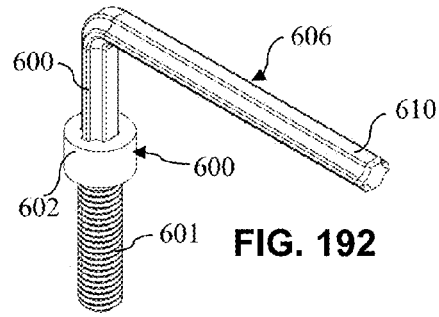
FIG. 192
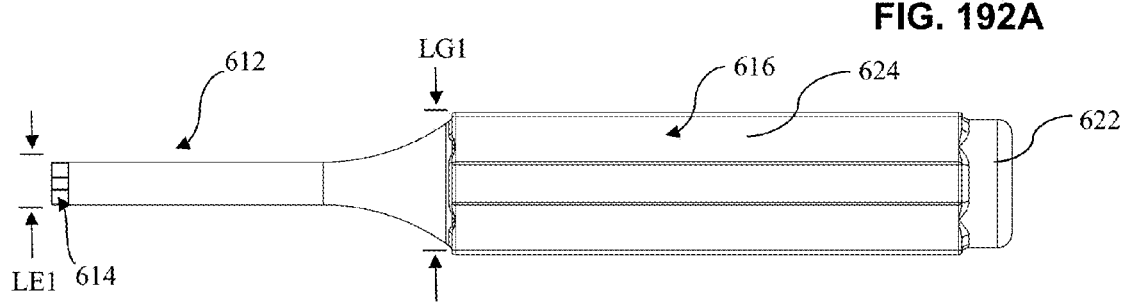
FIG. 192A
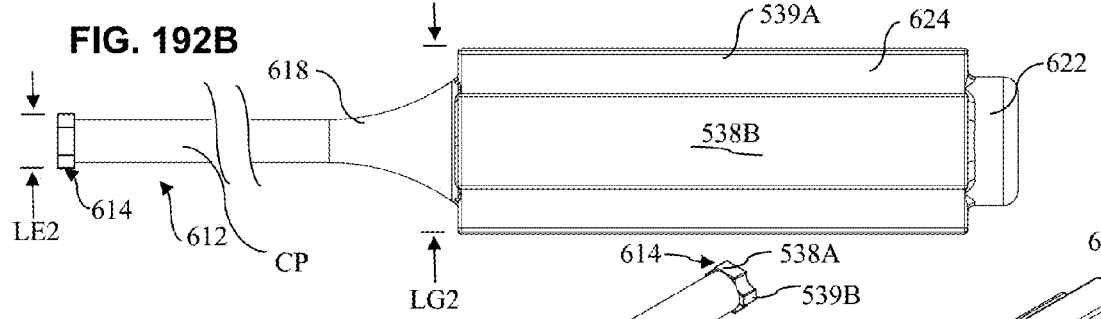
FIG. 192B
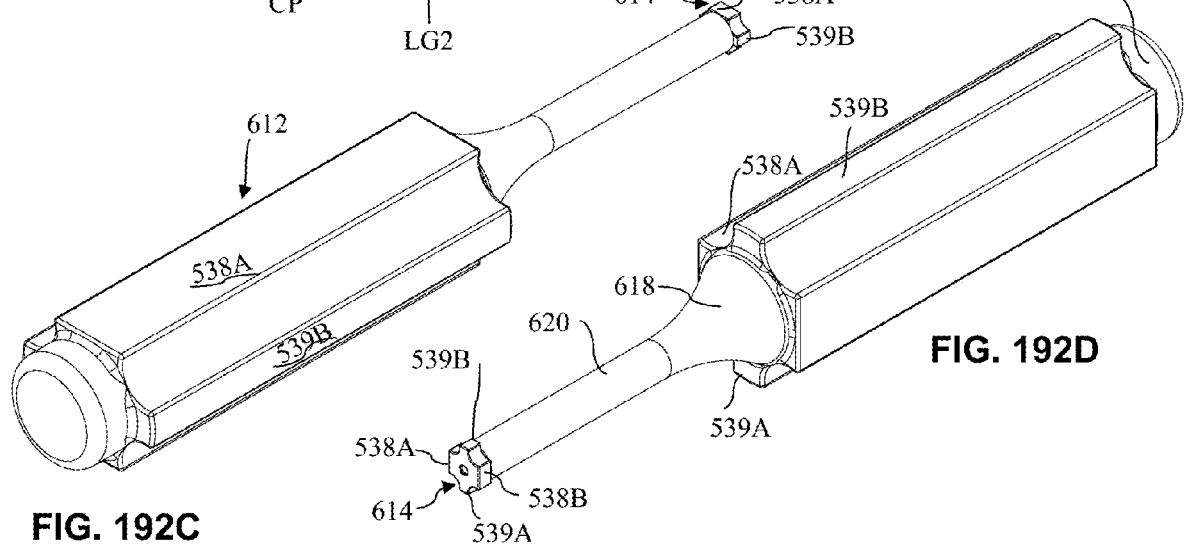
FIG. 192C
FIG. 192D

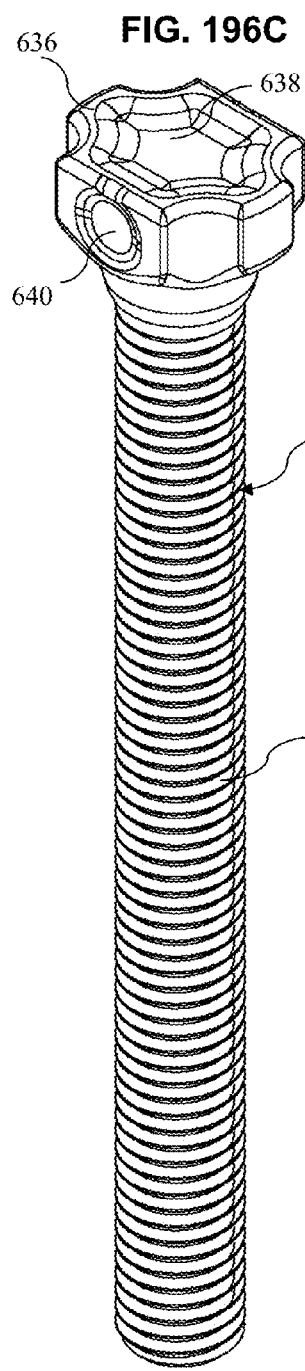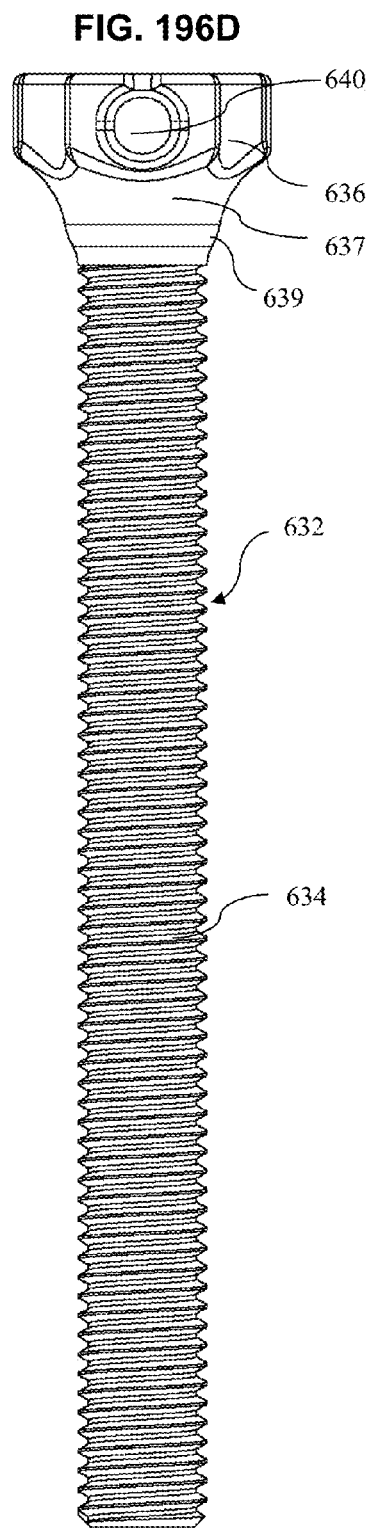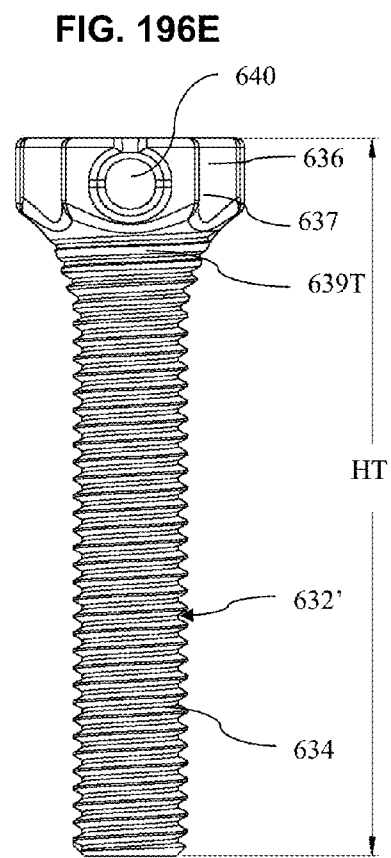

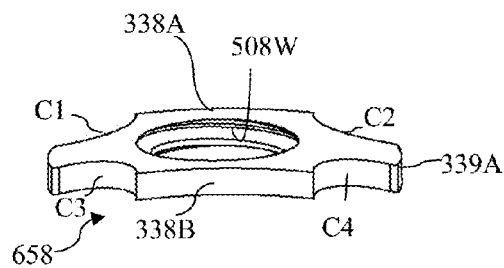
FIG. 199B
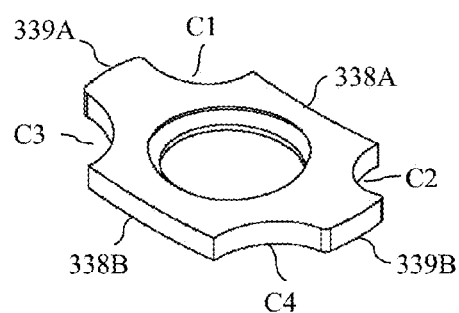
FIG. 199A
FIG. 199D
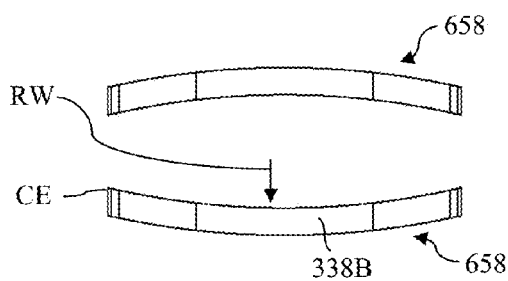
FIG. 199C
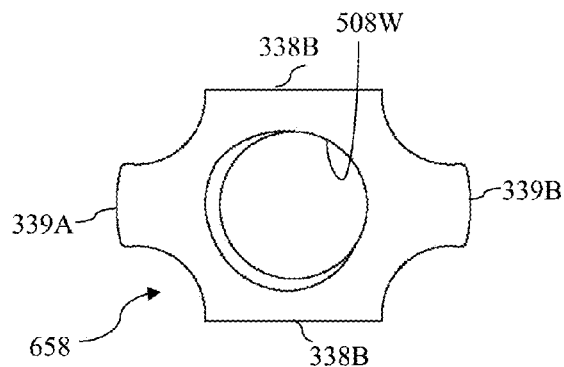
FIG. 199E
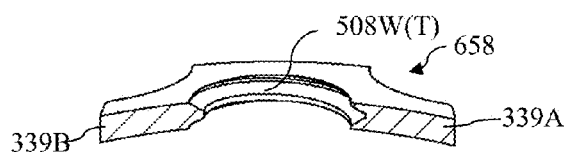
FIG. 199F

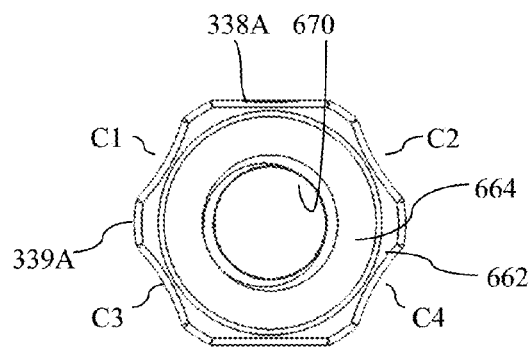
FIG. 200D
FIG. 200B
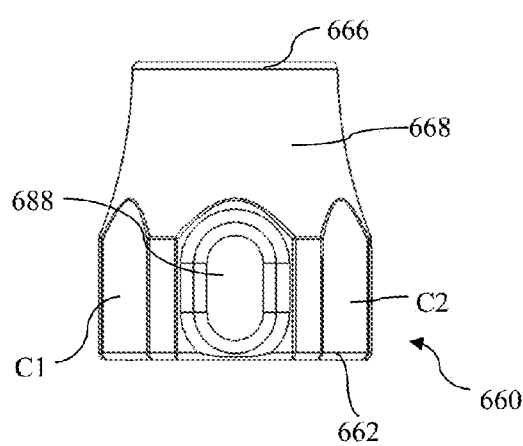
FIG. 200C
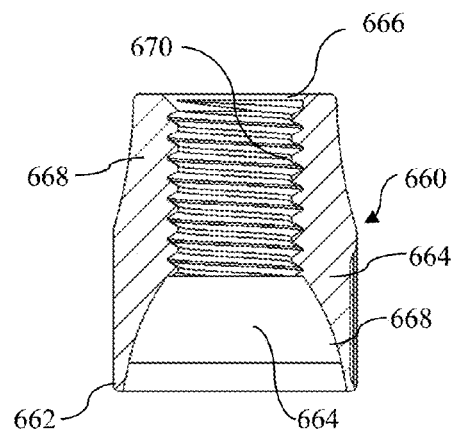
FIG. 200E
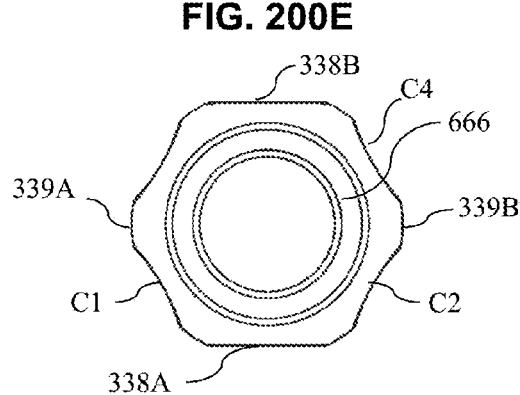
FIG. 200A
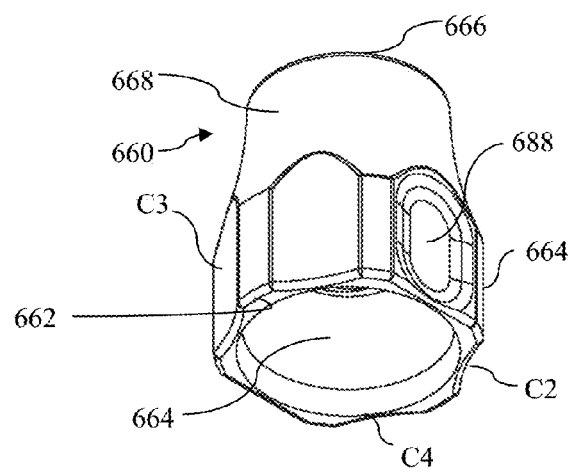

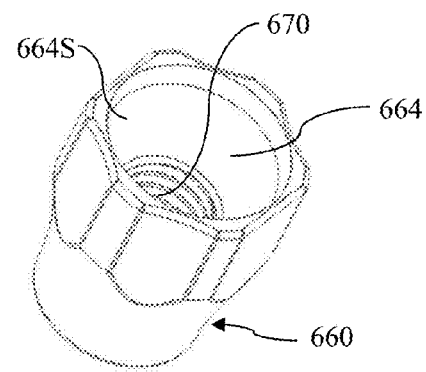
FIG. 200F
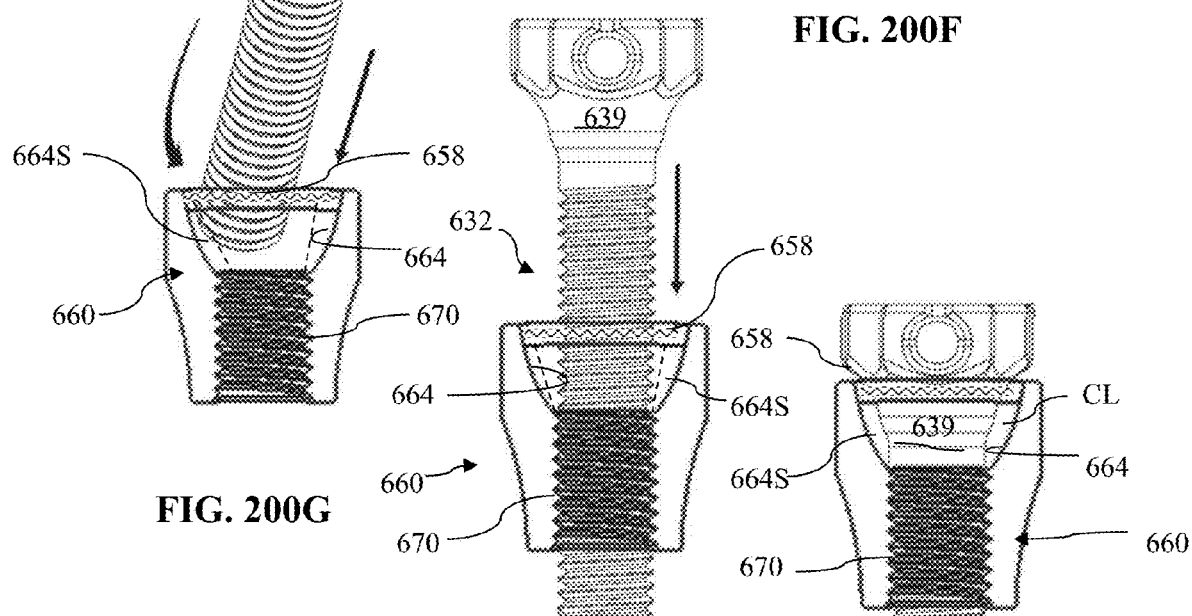
FIG. 200G
FIG. 200H
FIG. 200I

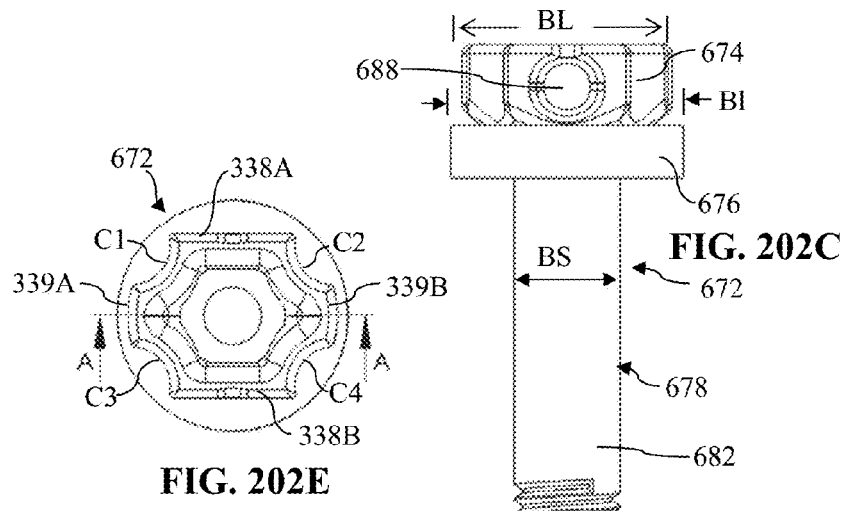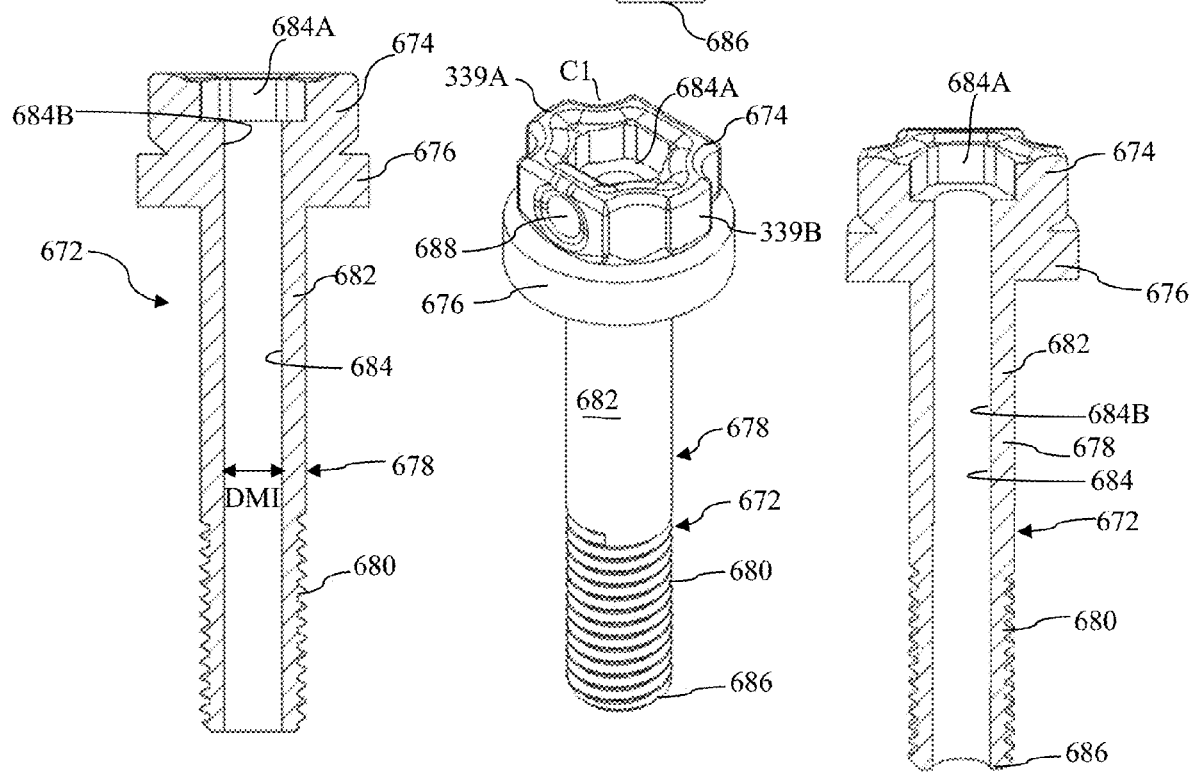
FIG. 202D  FIG. 202A  FIG. 202B

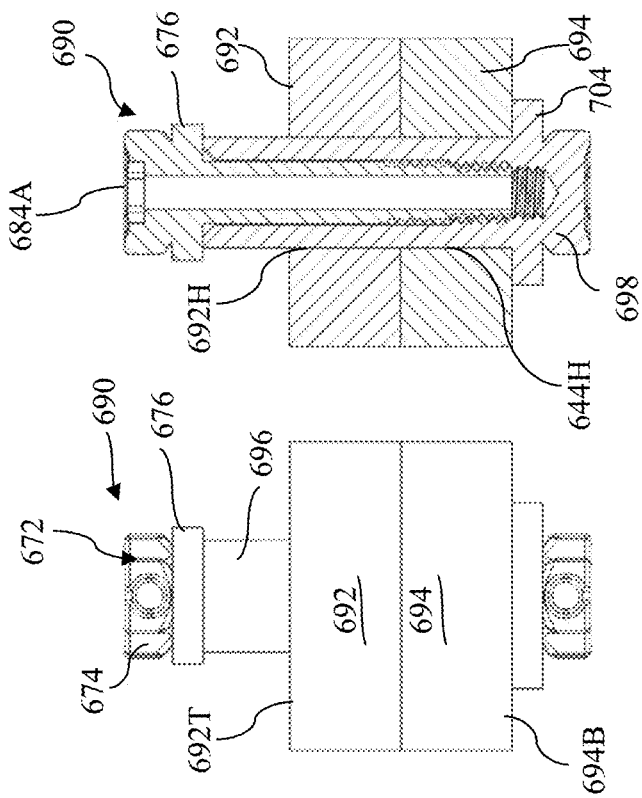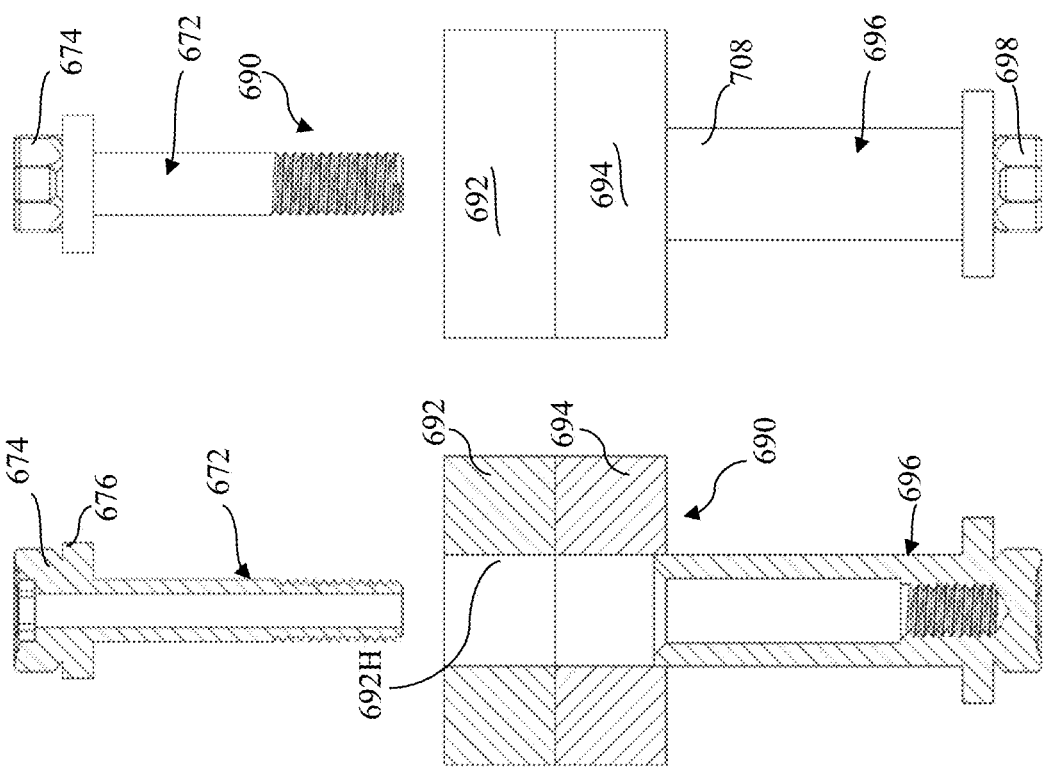

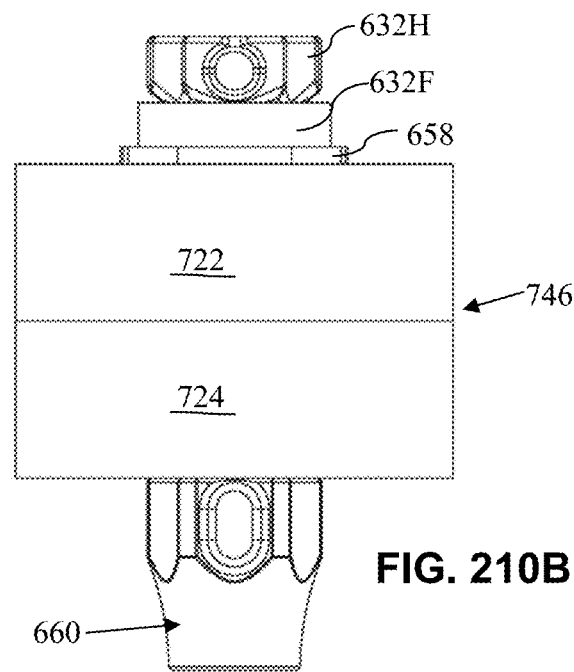
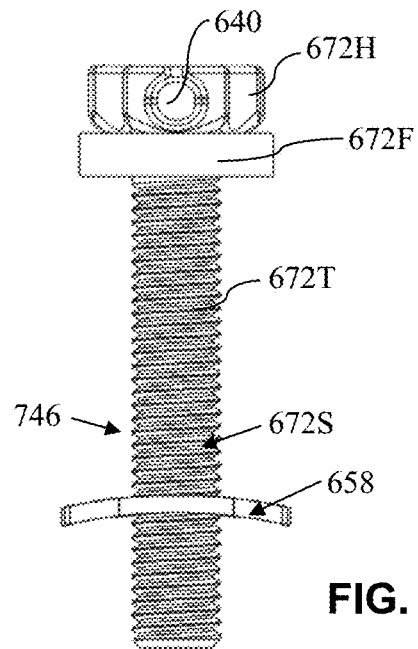
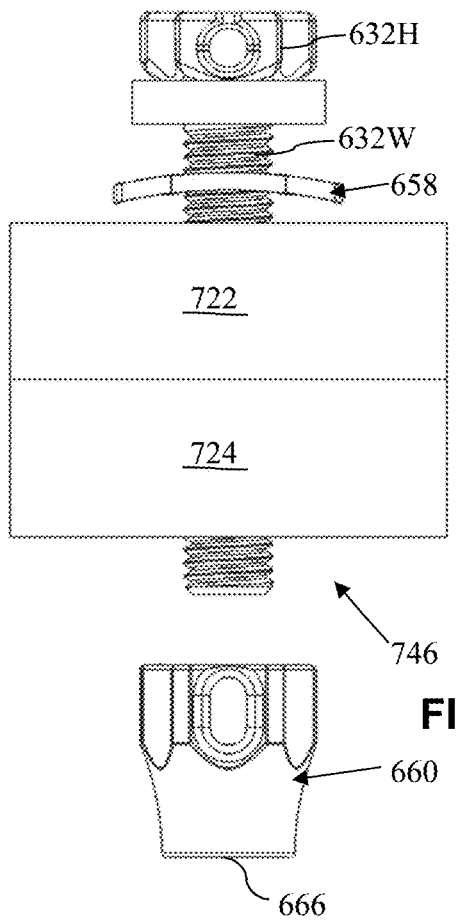
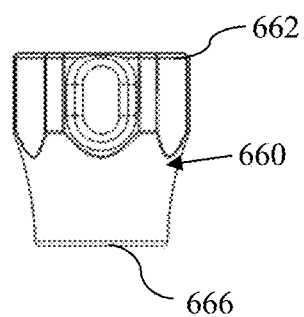
FIG. 210B
FIG. 210A
FIG. 210C

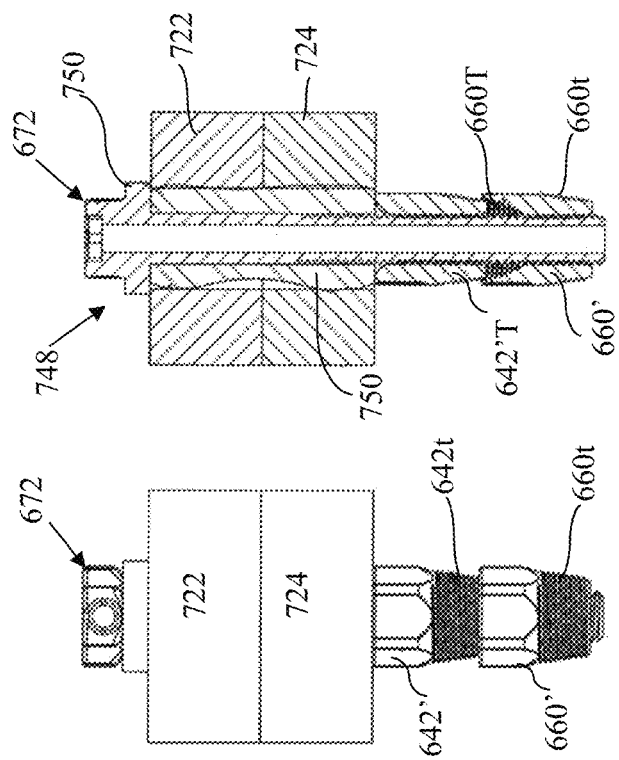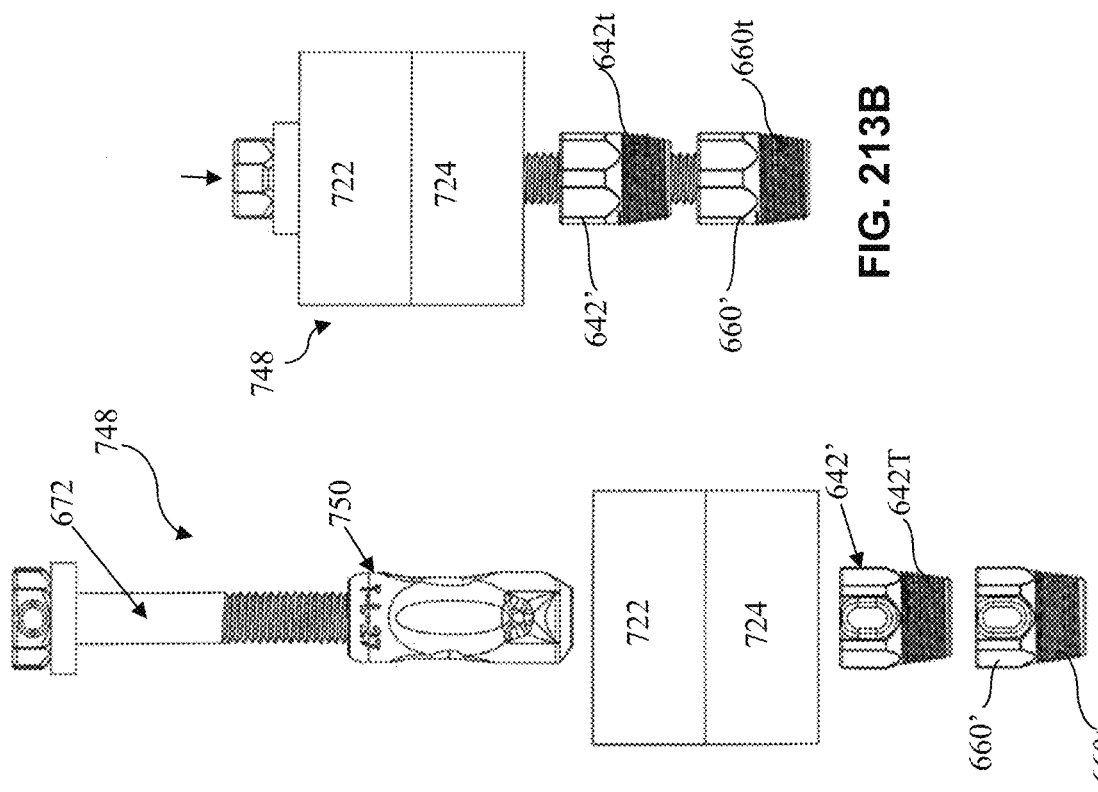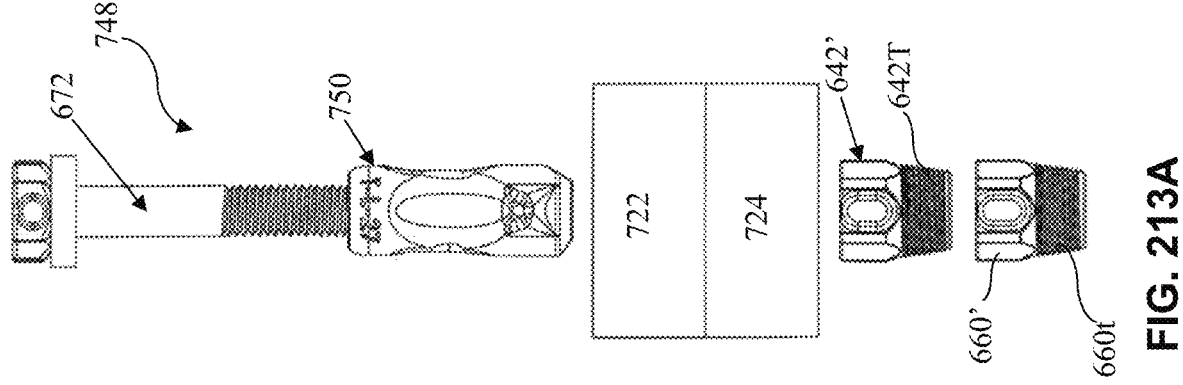

FIG. 216A
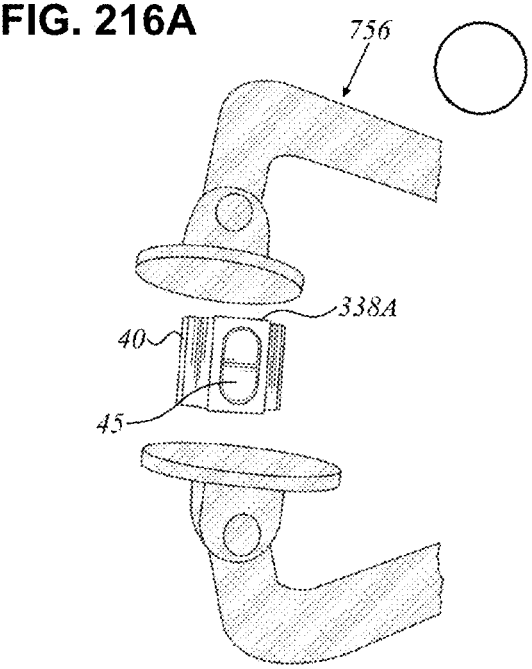
FIG. 216B
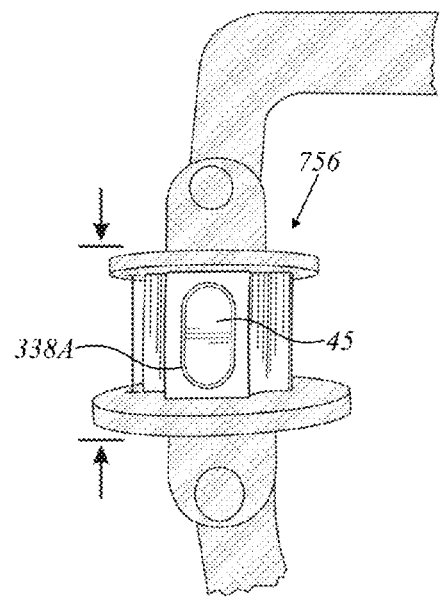
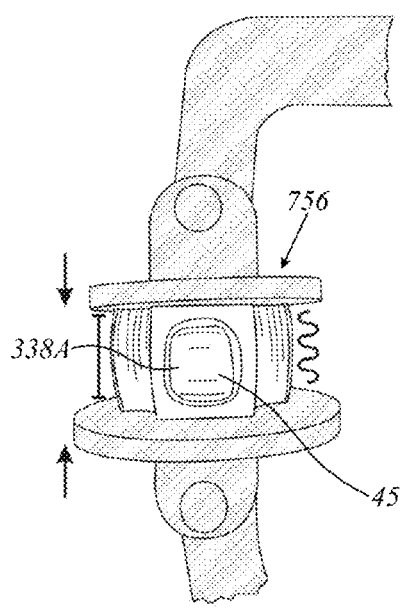
FIG. 216C

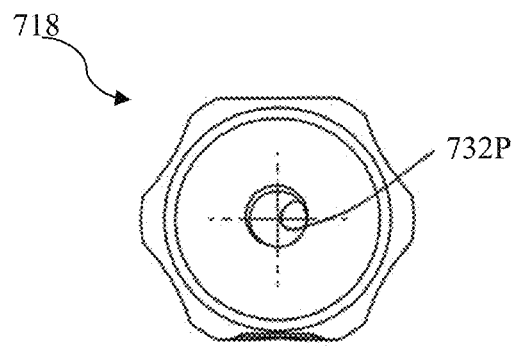
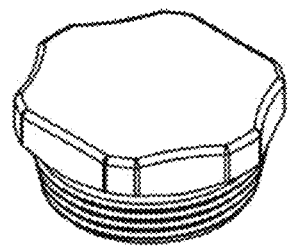
FIG. 227C          FIG. 227D
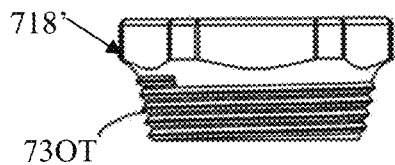
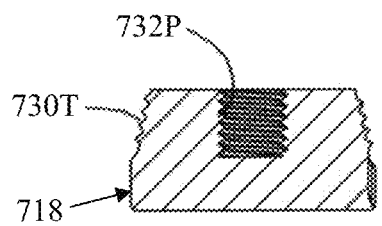
FIG. 227E          FIG. 227B
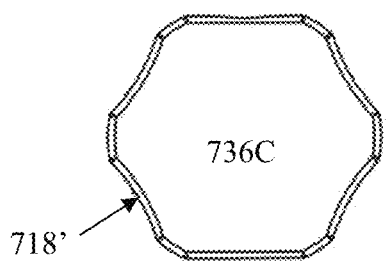
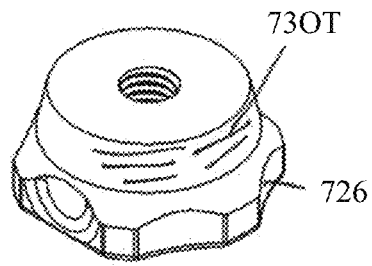
FIG. 227F          FIG. 227A

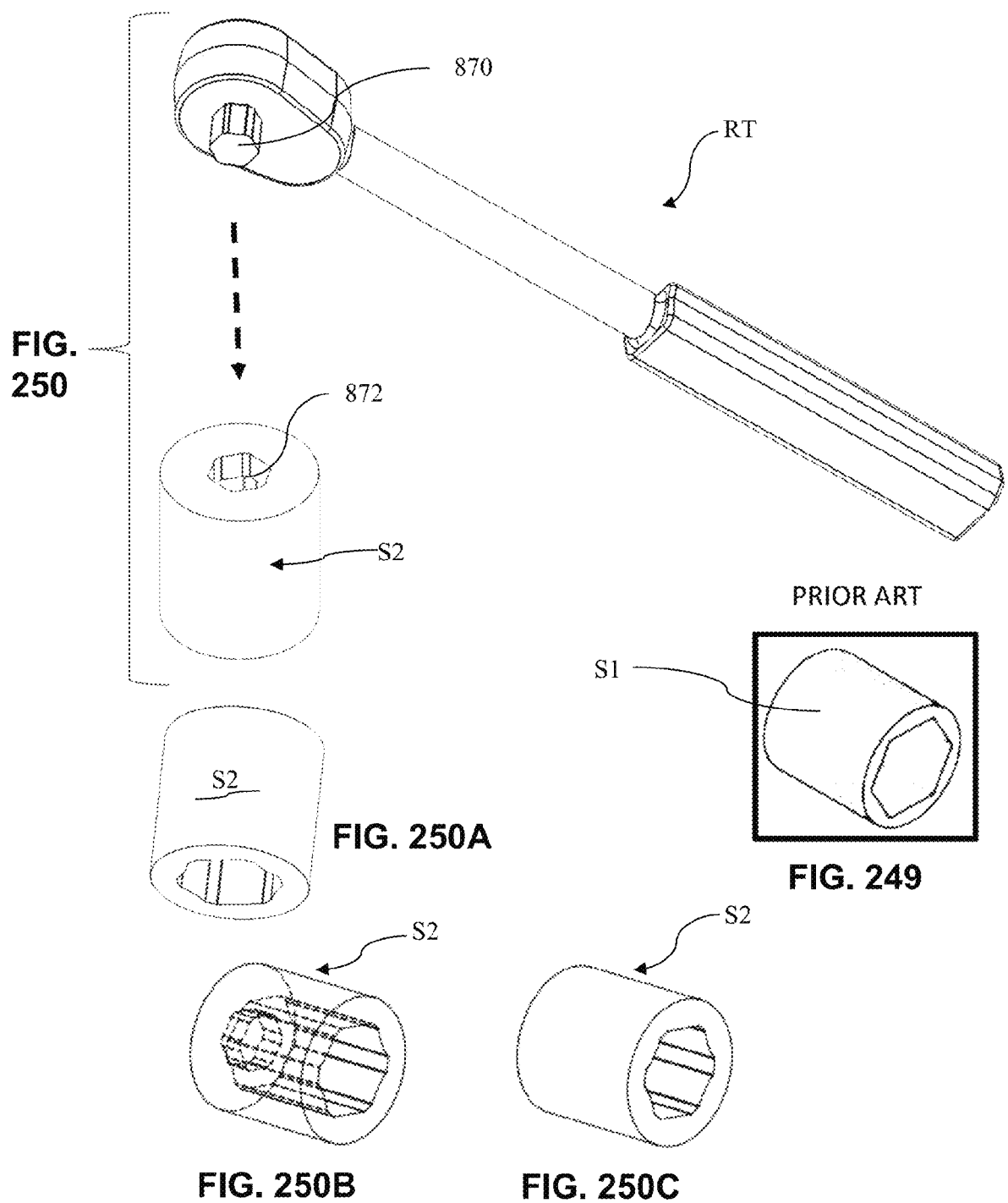

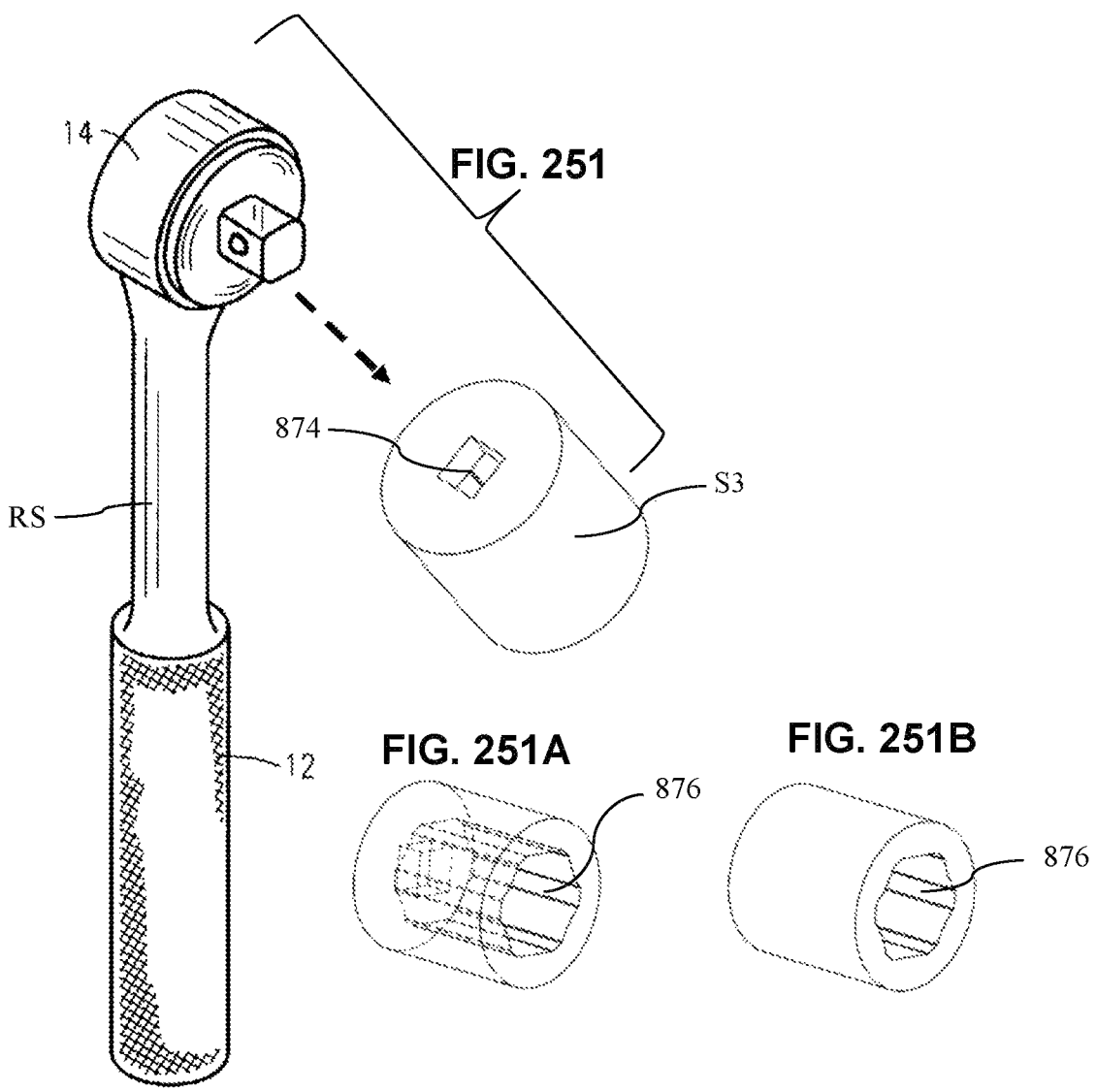

TORQUE ENHANCER DEVICE FOR GRASPING AND TOOLING, AND ASSEMBLIES AND USES THEREOF

PRIORITY

The present invention is a continuation of U.S. patent application Ser. No. 15/977,431 filed May 11, 2018, which claims priority to U.S. Provisional Patent Application Ser. No. 62/505,034; filed May 11, 2017, which is incorporated herein by reference in its entirety.

BACKGROUND OF THE INVENTION

There is a wide assortment of devices and tools geared toward fastening or removing fastened members that utilize a variety of different configurations. Examples of some standard torque engagement configurations are found in FIG. 148 in the present application. However, the prior art is considered not to provide a geometry that beneficially treats the need for torque generation at the same time as other needs as in easy grasping and/or providing stability.

SUMMARY OF THE INVENTION

The present invention is directed at providing a torque enhancement device that is adaptable to a wide variety of uses and is considered to provide a geometry that beneficially treats the need for torque generation at the same time as meeting other needs (e.g., providing stability, avoiding cam-out or axial separation between a fastener and tool, etc.). As such, the present invention is directed at providing a torque enhancement device having a geometry that is considered to provide a synergistic relationship between the need for torque generation while maintaining stability. The present invention is inclusive of a variety of embodiments of torque enhancer devices with each having a configuration rendering it well suited for grasping and usage with (and/or as) tooling. The present invention is also inclusive of assemblies involving one or more of the torque enhancer devices in an assembly. The present invention is also inclusive of methods associated with the torque enhancement members of the present invention inclusive of their use in fastening assemblies and the fastening of structural components therewith.

An aspect of an embodiment of the torque enhancement device of the present application is the providing of a geometric shape that is readily integrated into standard shapes and tooling, for example, and provides the potential for magnifying torque, a replacement for a failed fastener or the like, a means for removing of an existing geometric shape that is bound in place when greater torque is needed (as in insertion on a hexagonal fastener head).

An aspect of an embodiment of the torque enhancement device of the present application is the stacking of multiple members inclusive of one or more torque enhancement members of the present invention with the stacked arrangement reinforcing existing clamping assemblies after loosening and stretching has occurred without removing those preexisting fasteners.

An aspect of an embodiment of the torque enhancement device of the present application is the providing of a geometry that is considered to present contact points that facilitate controlling torque rotation, as in relative to force coiling for a rotating element; with the geometry being designed to harness the circumferential forces that arise while also trapping or capping those forces at different points of contact. Thus, the general geometric configuration of the torque enhancement member embodiments is considered to facilitate a balanced and high torque potential approach to fastening attachment and removal even when the spin increases (e.g., the general geometry is considered to help unify the leverage and momentum that develops in such situations). The result is a more readily determined torque or fastening measure, as when reviewing the torque level imposed on a fastener or the like, such as in industrial settings where inspection of such imposed initial torque levels on fasteners (e.g., I-beam bolts and nut assemblies) is made easier and more assured.

A first embodiment of the invention features a torque enhancement device having a torque enhancement member that has an interior and/or exterior (preferably bi-symmetric or essentially bi-symmetric) configuration with parallel, longer side walls extending in a Y-axis direction and shorter side walls extending in an X-axis direction, and corner recesses positioned between ends of adjacent longer and shorter side walls, and with some embodiments of the invention featuring a torque enhancement device having a hole extending in a Z-axis direction.

A first aspect of the torque enhancement device of the first embodiment includes having a ratio of the shorter side wall length to the longer side wall length of 50% to 95% and more preferably, 65% to 90%, with 75% to 81% being an exemplary range.

A second aspect of the torque enhancement device of the first embodiment and first aspect includes having all four corner recesses of a common configuration and size and wherein the four corner recesses include having one of a semi-circular recess configuration, a U-shaped recess, an opposing stepped side wall configuration, or an open rectangle recess in each of the corner recesses.

A third aspect of the torque enhancement device of the first embodiment and first and second aspects includes having the shorter side walls extending in the X-axis direction with curved outer surfaces.

A fourth aspect of the torque enhancement device of the first embodiment and any one of the first to third aspects includes having one or more notched recesses formed in each of the longer side walls, or each of the shorter side walls, or in each of the longer and shorter side walls with the notches maintaining a bi-symmetric configuration.

A fifth aspect includes having the one or more notched recesses of the fourth aspect with different sloped defining notch side walls.

A sixth aspect of the torque enhancement device of the first embodiment and any one of the first to fifth aspects includes having a hole that is centrally positioned in the body and has a stepped or tapered configuration along the Z-axis.

A seventh aspect of the torque enhancement device according to the sixth aspect includes having the hole being a stepped configuration that conforms to an exterior surface of a needle assembly intended for insertion in the hole, or which stepped portion is configured for capping a bottle or vial top.

An eighth aspect of the torque enhancement device of the first embodiment and any one of the first to sixth aspects includes having a surface defining a central body hole with the hole being one of a through-hole in the Z-axis direction or a hole not extending entirely though the body in the Z-axis direction.

A ninth aspect of the torque enhancement device of the eighth aspect includes a surface defining at least a portion of the hole having threading, with an embodiment including a through-hole threading as to have the torque enhancement device as a threaded nut.

A tenth aspect of the torque enhancement device of the first embodiment and any one of the first to ninth aspects includes having a base body of the torque enhancement device having the longer and shorter side walls and corner cut outs, and a tapering body portion extending in a Z-axis direction off of the base body, with a hole extending through each of the base body and tapering body portion.

An eleventh aspect of the torque enhancement device of the tenth aspect includes having threading in the hole portion provided in at least one of the base body and the tapering body portion.

A twelfth aspect of the invention according to the eleventh aspect includes having threading in the hole in the tapering body portion and a non-threaded region in the base body which is configured as a bowl or stepped recess.

A thirteenth aspect of the invention according to any one of the tenth to twelfth aspects includes having through-slots spaced circumferentially around the tapering body portion.

A fourteenth aspect of the invention according to the first embodiment or any one of the first to thirteenth embodiments wherein each of the longer sides has a circular or oblong depression formed therein.

A fifteenth aspect of the invention according to the first embodiment features the torque enhancement device having a thickness less than the length of the shorter side wall length.

A sixteenth aspect according to the fifteenth aspect wherein the torque enhancement device is a washer optionally having an arc shape along the Y-axis direction.

A seventeenth aspect of the invention according to the first embodiment wherein the torque enhancement device has a shaft extending away from the torque enhancement member in a Z-axis direction such that the torque enhancement member defines a shaft head, with that shaft being either solid or hollow, and with the shaft being either internally or externally threaded or both and/or graduated for at least a portion.

An eighteenth aspect of the invention according to the seventeenth embodiment wherein the shaft has a piston at an opposite end of the head end such that the torque enhancement device defines a piston plunger for a syringe, for example.

A nineteenth aspect of the invention according to the seventeenth aspect wherein the torque enhancement device is a bolt.

A twentieth aspect of the invention according to the first embodiment wherein the torque enhancement device is a tool having the torque enhancement member as one or both of a driver head and handle.

A twenty-first aspect of the invention according to the twentieth aspect of the invention has the tool as one selected from at least one of a ratchet tool, a hand tool, an air or hydraulic driven tool, and an L-shaped tool.

A second embodiment of the present invention includes a fastener assembly having at least one torque enhancement device of the first embodiment.

Another aspect of the invention according to the second embodiment includes multiple torque enhancement components assembled in the fastener assembly inclusive of one or more of the following torque enhancement components:

a) a tapered torque enhancement device with or without interior (and/or exterior) threading and slotted or not slotted;

b) a torque enhancement device in washer form with either a cup-shaped or flat shape and either with or without an inner portion projection or recess;

c) a bolt with one or both of interior and exterior threading;

d) a button or cap end with or without interior (and/or exterior) threading; and e) a gear with or without supporting central plating.

A third embodiment of the invention features a method of fastening a first structural member to a second structural member comprising driving a torque enhancement member of the fastener assembly of the second embodiment.

A fourth embodiment of the invention features a torque enhancement device comprising a driver such as a socket having at one of two ends the torque enhancement device of the first embodiment, and at an opposite end having a driving projection or recess that does not fall within the first embodiment.

An additional embodiment of the invention features the torque enhancement device of the first embodiment, wherein the corner recesses are configured as to have a torque level differentiation in one direction of rotation as compared to an opposite direction of rotation.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 38a and 38b show a first embodiment deeper positioning of a flanged hub of a needle, with FIG. 38b showing added radial grooves in the collar cavity providing added snap-in positional needle length capability; this relationship also provides for improved syringe-to-bottle flexing as when trying to get access to the last amount of medicament in the bottle.

FIG. 39 shows a syringe assembly that includes a first grasping collar at the plunger base, a second grasping configuration (molded or sleeve) along the syringe's cylinder, and a third grasping collar joined with the syringe's needle assembly and configured for insertion into the FIG. 3 torque enhancement collar with the needle not yet having punctured through the vial's top seal membrane.

FIG. 40 shows a similar view as that of FIG. 39 with the needle having been inserted through the vial's top seal membrane and into the vial.

FIG. 46 shows a bottle and FIG. 3 torque enhancement collar combination, but with the collar having a smaller aperture opening out at the smaller diameter collar end that is opposite to the larger diameter collar end with torque enhancement periphery in engagement with the threaded opening of the bottle (or a rimmed end); as in the prior embodiment, needle placement relative to the bottle is adjustable and there is also provided the ability to securely grasp and hold the bottle with a two finger off-center pinching operation, which is fixed enough for plunger activation, potentially followed by an easy torque twist off from the bottle or vial top (with or without threading featured).

FIG. 47 shows the same off-set two finger pinching relationship with a FIG. 3 torque enhancement collar, but with the through hole in the collar supporting a double-ended transfer needle with the user's pinching fingers well away from the needle.

FIG. 48 shows a single hand grasping of a FIG. 3 torque enhancement collar (open top version, with larger base aperture opening out at the bottom of the collar) and a grooved bulb head utensil.

FIG. 53 shows a full view of the combination of a syringe plunger shaft having an integrated FIG. 3 torque enhancement configured component at its base.

FIG. 54 shows a view of the torque enhancement component of FIG. 53 in bottom perspective.

FIG. 55 shows a view of the integrated elephant foot torque enhancement end of FIG. 53 in a bottom plan view showing a generally common configured central concavity extending down and inward from the exterior.

FIG. 56 shows the combination of FIG. 53 from a different orientation.

FIG. 57 also shows the combination of FIG. 53 from a different orientation

FIG. 65 showing a pinching holding of just the tool body; FIGS. 66 and 67 show different views of the combination of FIG. 64, while FIG. 68 shows a one hand holding of all components, but with the base collar removed. FIG. 69 shows a single hand support of the combination in ready for non-rotative use position, while FIG. 70 shows the combination of FIG. 64 with an added adapter component received by the removed base collar.

FIGS. 84a and 84b illustrate a longer or thicker version of the torque enhancement member in the collar configuration of FIG. 1 with the former showing a perspective view and the latter showing a central vertical cross-section and the stepped aperture configuration.

FIGS. 85a and 85b illustrate a longer or thicker version of the torque enhancement member in the collar configuration of FIG. 1 with the former showing a perspective view and the latter showing a central vertical cross-section and the stepped aperture configuration.

FIGS. 86a and 86b illustrate a longer or thicker version of the torque enhancement member in the collar configuration of FIG. 1 with the former showing a perspective view and the latter showing a central vertical cross-section and the aperture configuration.

FIGS. 87a and 87b illustrate a longer or thicker version of the torque enhancement member in the collar configuration of FIG. 1 with the former showing a perspective view and the latter showing a central vertical cross-section and the aperture configuration.

FIGS. 95a and 95b illustrate a closed top version of the torque enhancement member in the collar configuration of FIG. 3 with the former showing a perspective view and the latter showing a central vertical cross-section and the stepped aperture configuration.

FIGS. 96a and 96b illustrate a closed bottom version of the torque enhancement member in the collar configuration of FIG. 3 with the former showing a perspective view and the latter showing a central vertical cross-section and the aperture configuration.

FIGS. 97a and 97b illustrate a small diameter top aperture version of the torque enhancement member in the collar configuration of FIG. 3 with the former showing a perspective view and the latter showing a central vertical cross-section and the aperture configuration.

FIGS. 98a and 98b illustrate a version of the torque enhancement member in the collar configuration of FIG. 3 with the former showing a perspective view and the latter showing a central vertical cross-section and the stepped aperture configuration.

FIGS. 100a to 100j illustrate various views of an alternate combination of features of the invention featuring the torque enhancement member in the collar configuration of FIG. 1 with added side porting, with FIGS. 100a to 100d showing the turret combination comprising the FIG. 1 torque enhancement member collar ("collar") and an underlying spin platform (for torque application to the collar to create a twist action relative to the separate, spin platform below), and 100e to 100j showing the collar alone in various perspective and cut-away views.

FIG. 101b shows a front elevational view of that which is shown in FIGS. 101a, and 101c shows a cross-sectional view along cross-section A-A in FIG. 101b.

FIG. 102 shows a rotated view of the collar shown in FIG. 100a and with the inserted tool being at a shallower angle relative to the underlying surface of the collar such that it rests in the lower part of the illustrated oblong exit (or entry groove) that is detailed in the enlarged view shown in FIG. 102A, which shows an enlarged view of the circled section of FIG. 102.

FIG. 103 shows a rotated view of the collar shown in FIG. 100a and with the inserted tool being at a steeper angle relative to the underlying surface of the collar such that the tool (e.g., sheath) abuts the upper part of the illustrated oblong exit (or entry groove) that is detailed in the enlarged view shown in FIG. 103A which shows an enlarged view of the circled section of FIG. 103.

FIG. 104 also shows a rotated view of the collar shown in FIG. 100a and with the inserted tool being a combination sheath and interior wire, with the collar providing the desired angle of orientation.

FIG. 105 shows the collar of FIG. 104 with inserted sheath and wire tool received but from a different angle.

FIG. 106 shows a similar view as that of FIG. 105 but with a position retainer insert added.

FIGS. 106a to 106c show different variants of the position retainer insert designed to hold the tool at a desired orientation within the receiving oblong or oval shaped opening provided in the collar for tool positioning flexibility.

FIG. 110 illustrates the collar of FIG. 100a further comprising a plug member having a central aperture, which plug provides for hold down functioning of items received in the collar and/or alignment for needle insertion etc., relative to a central hole in the plug, and or deflecting a received thin instrument as to brake from further movement or stop flow in valve stop like fashion.

FIG. 110a shows the collar and plug arrangement shown in FIG. 110 but from a side view.

FIGS. 110b to 110d show different length plugs with integrated pin caps that can be inserted to seal off the plug itself received by the collar.

FIG. 111 shows the same collar as FIG. 110 but with the plug inserted into the collar and with the plug cap in place.

FIG. 111a shows that which is shown in FIG. 111 but in side view.

FIG. 121 shows a cross-section view of the torque enhancer of FIG. 117 taken along the Y-Y axis cross-section line thereof.

FIG. 122 shows a perspective view of an alternate embodiment of the torque enhancer of the present invention which is also shown in the form of a threaded nut.

FIG. 126 shows a cross-section view of the torque enhancer of FIG. 122 taken along the Y-Y axis cross-section line thereof.

FIG. 127 shows a perspective view of an alternate embodiment of the torque enhancer of the present invention which is also shown in the form of a threaded nut.

FIG. 131 shows a cross-section view of the torque enhancer of FIG. 127 taken along the Y-Y axis cross-section line thereof.

FIG. 132 shows a perspective view of an alternate embodiment of the torque enhancer of the present invention which is also shown in the form of a threaded nut (with each reference to threaded nut in this application also being suitable as a gear as in one threaded on a shaft).

FIG. 133 shows a top plan view of the torque enhancer of FIG. 132.

FIG. 134 shows a similar top plan view as that shown in FIG. 132, but with a considered "mechanical" contact point illustration.

Figure 132:
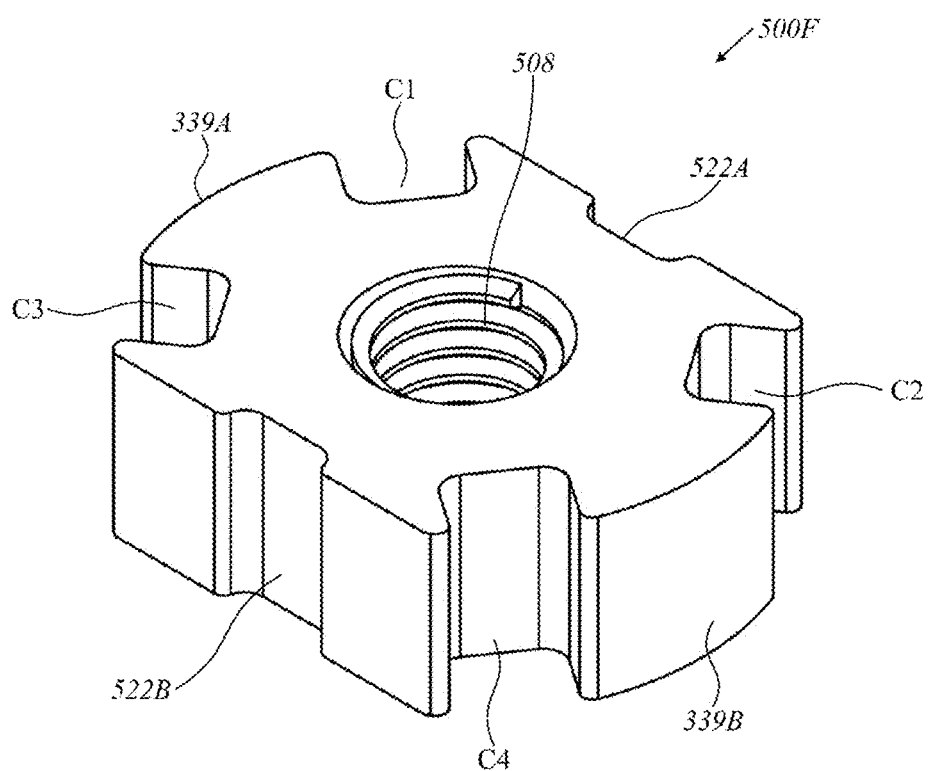
Figure 135:
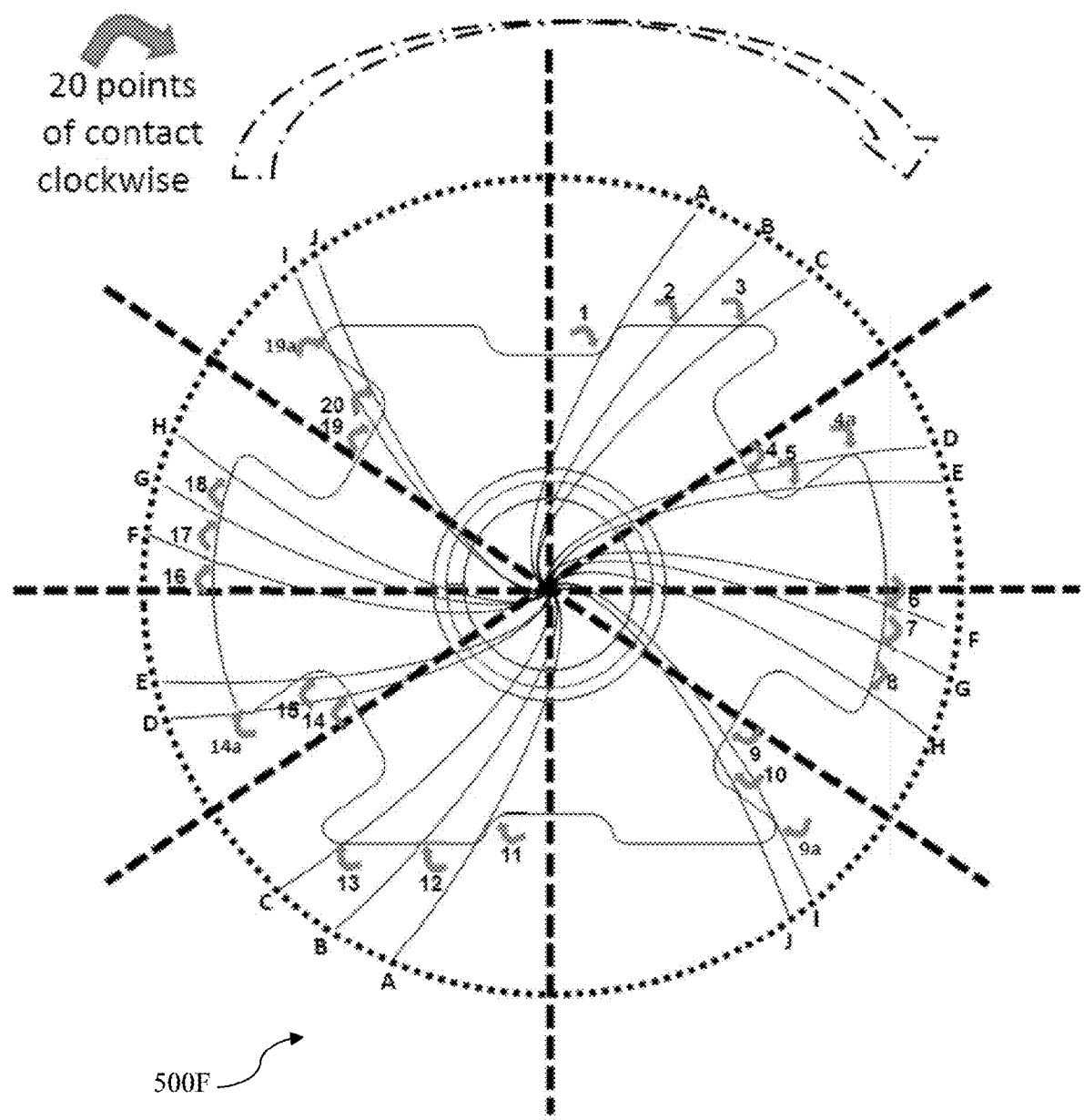

FIG. 135 also shows a top plan view of the torque enhancer of FIG. 132, but with a considered "spiral-centrifugal" contact point illustration.

Figure 136:
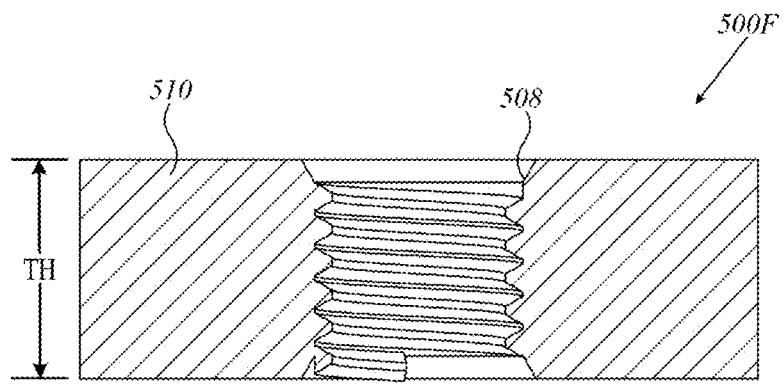

FIG. 136 shows a cross-section view of the torque enhancer of FIG. 132 taken along the Y-Y axis cross-section line thereof.

Figure 137:
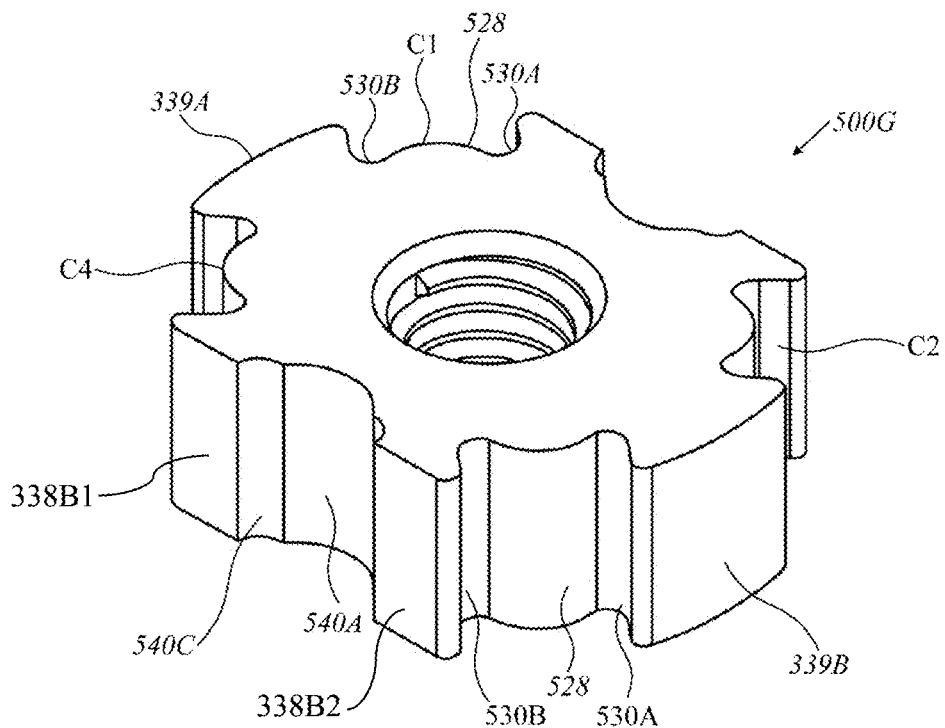

FIG. 137 shows a perspective view of an alternate embodiment of the torque enhancer of the present invention which is also shown in the form of a threaded nut (or gear with or without a support plate, which is true relative to any of the "500" series referenced torque enhancement components).

Figure 138:
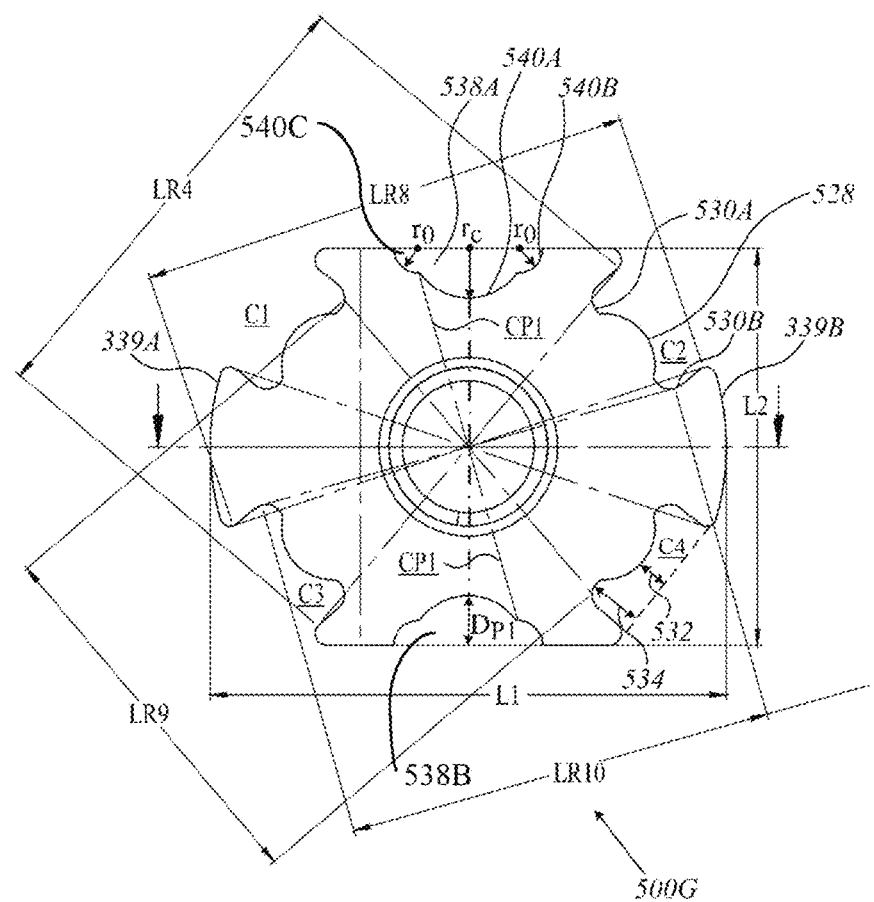

FIG. 138 shows a top plan view of the torque enhancer of FIG. 137.

Figure 139:
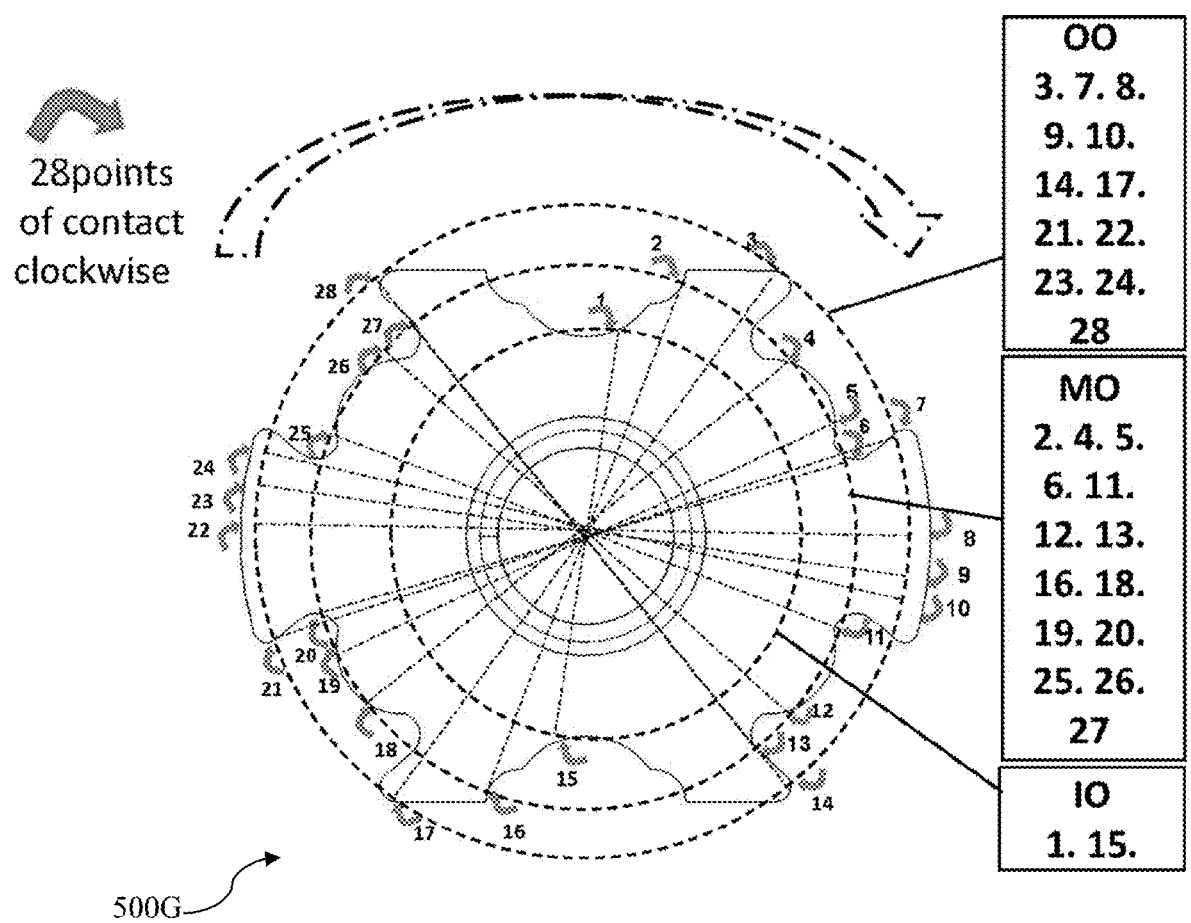

FIG. 139 shows a similar top plan view as that shown in FIG. 137, but with a considered "mechanical" contact point illustration.

Figure 140:
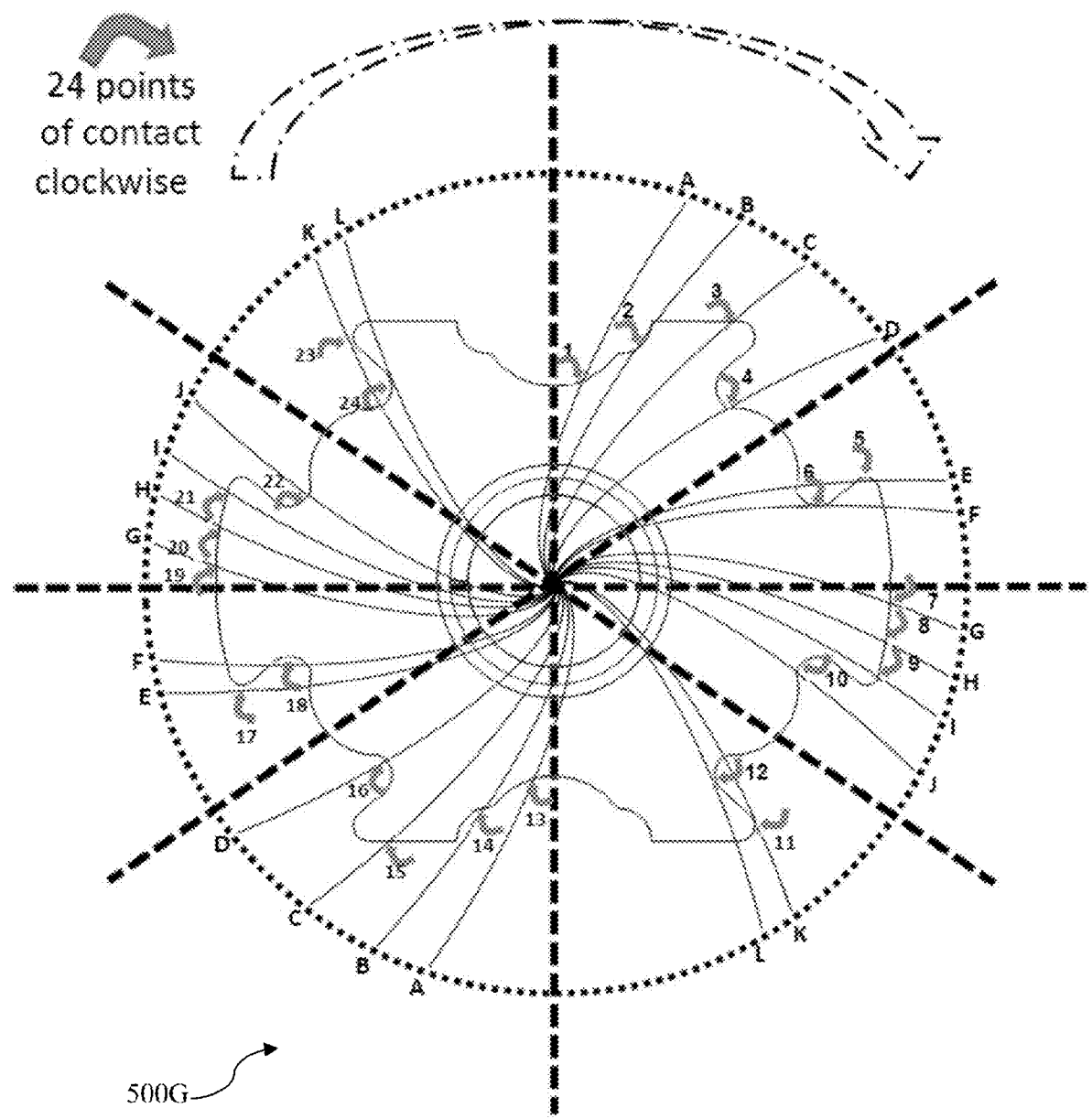

FIG. 140 also shows a top plan view of the torque enhancer of FIG. 137, but with a considered "spiral-centrifugal" contact point illustration.

Figure 141:
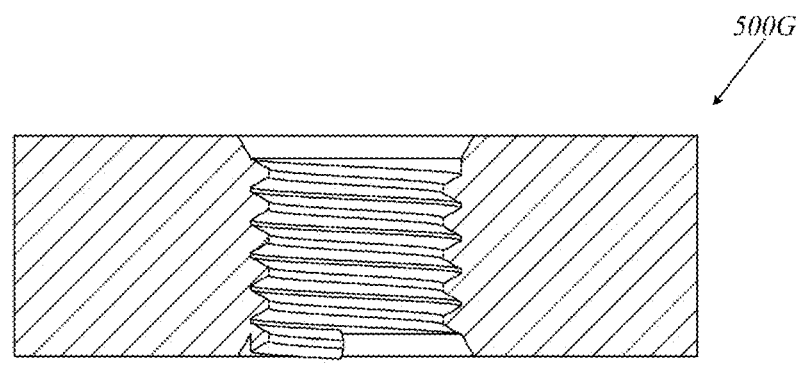

FIG. 141 shows a cross-section view of the torque enhancer of FIG. 137 taken along the Y-Y axis cross-section line thereof.

Figure 142:
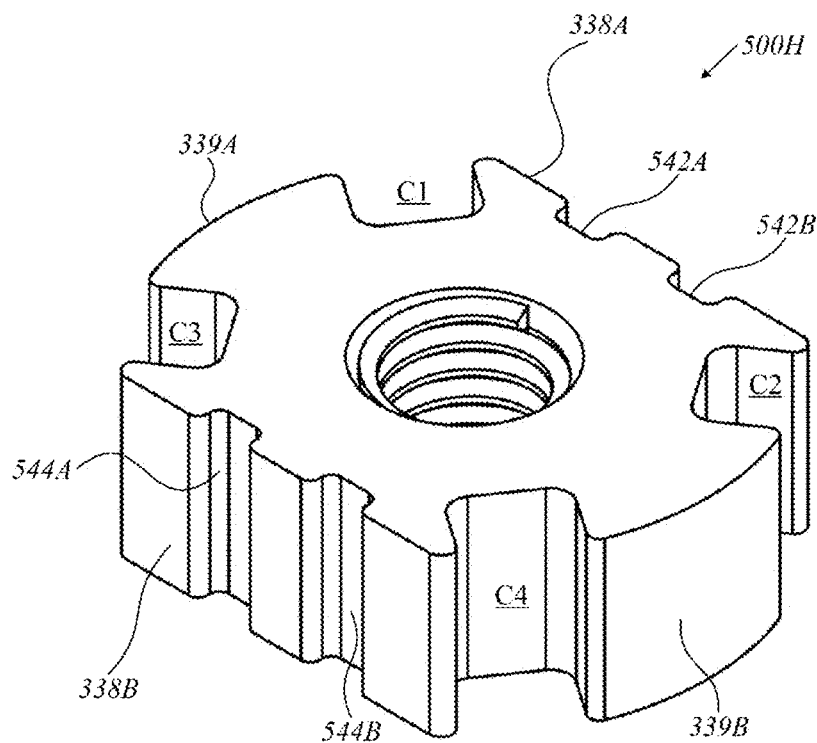

FIG. 142 shows a perspective view of an alternate embodiment of the torque enhancer of the present invention which is also shown in the form of a threaded nut.

Figure 143:
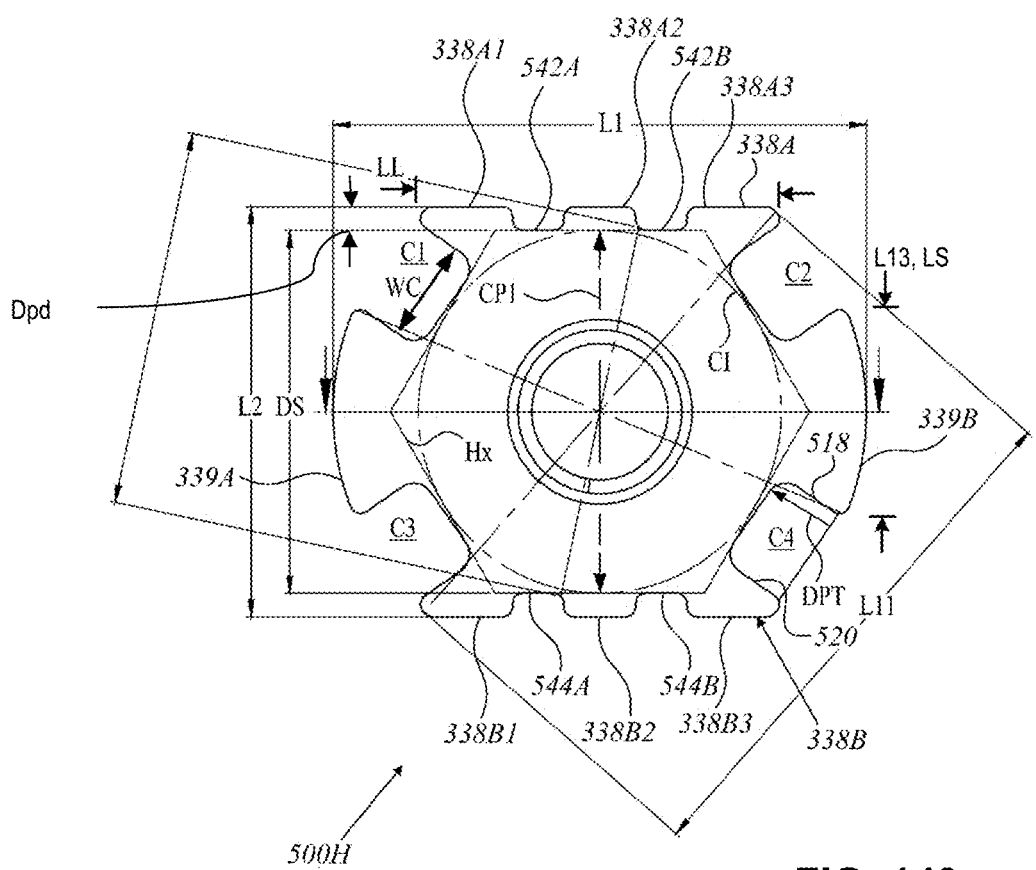

FIG. 143 shows a top plan view of the torque enhancer of FIG. 142.

Figure 144:
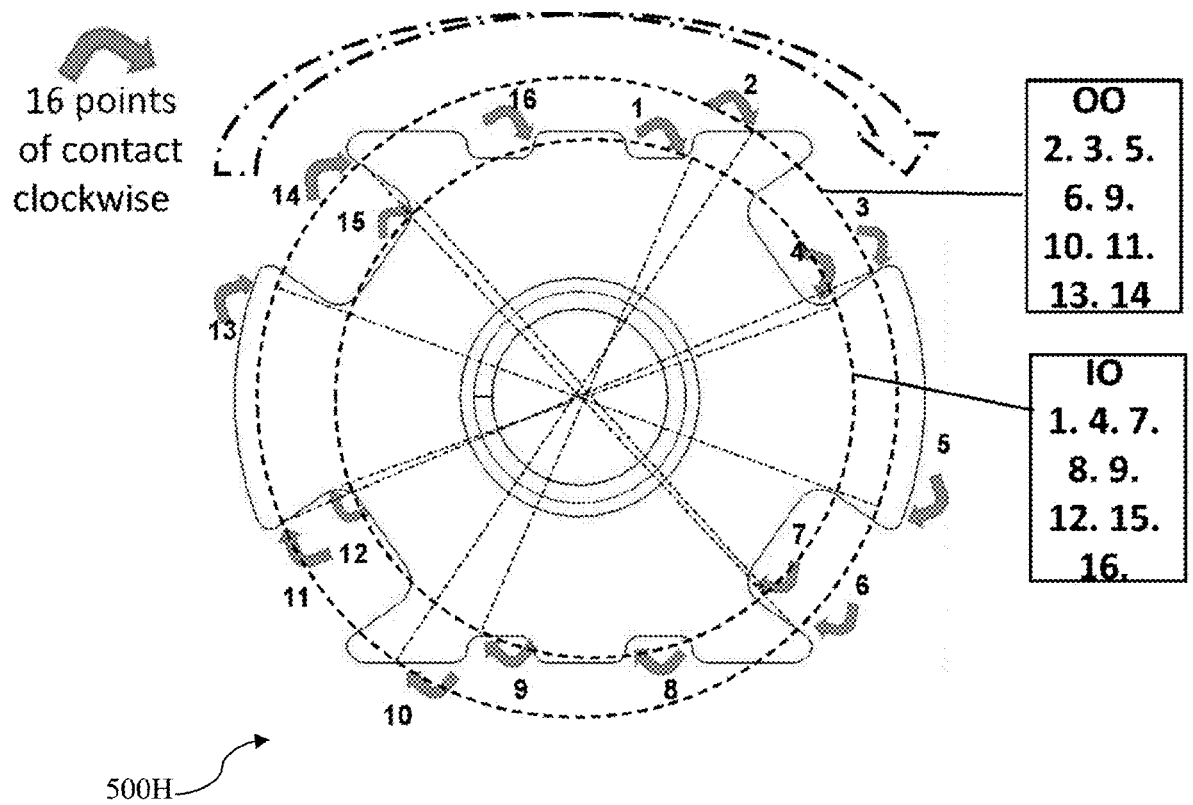

FIG. 144 shows a similar top plan view as that shown in FIG. 142, but with a considered "mechanical" contact point illustration.

Figure 145:
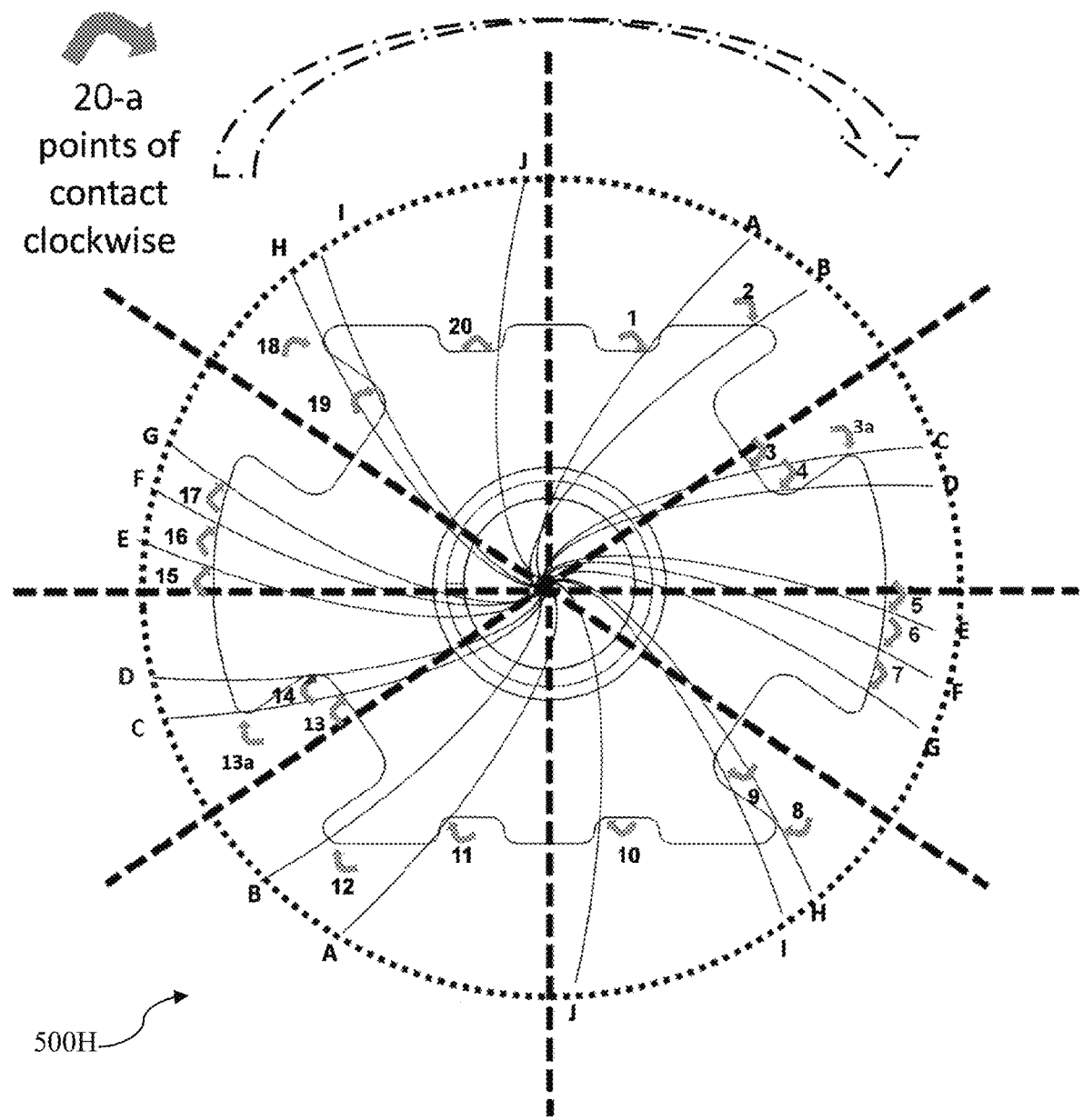

FIG. 145 also shows a top plan view of the torque enhancer of FIG. 142, but with a considered "spiral-centrifugal" contact point illustration.

Figure 146:
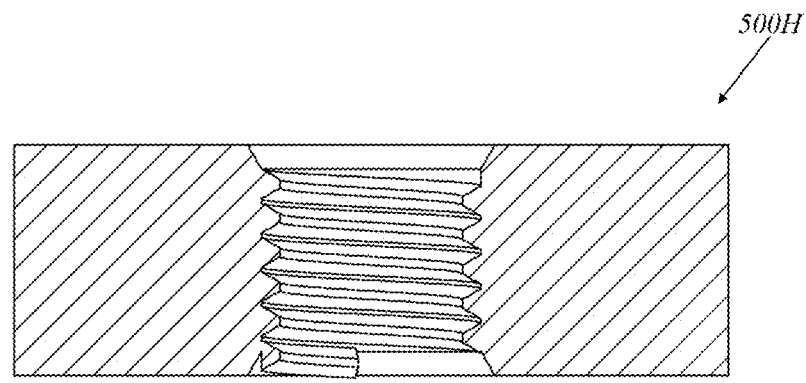

FIG. 146 shows a cross-section view of the torque enhancer of FIG. 142 taken along the Y-Y axis cross-section line thereof.

Figure 147:
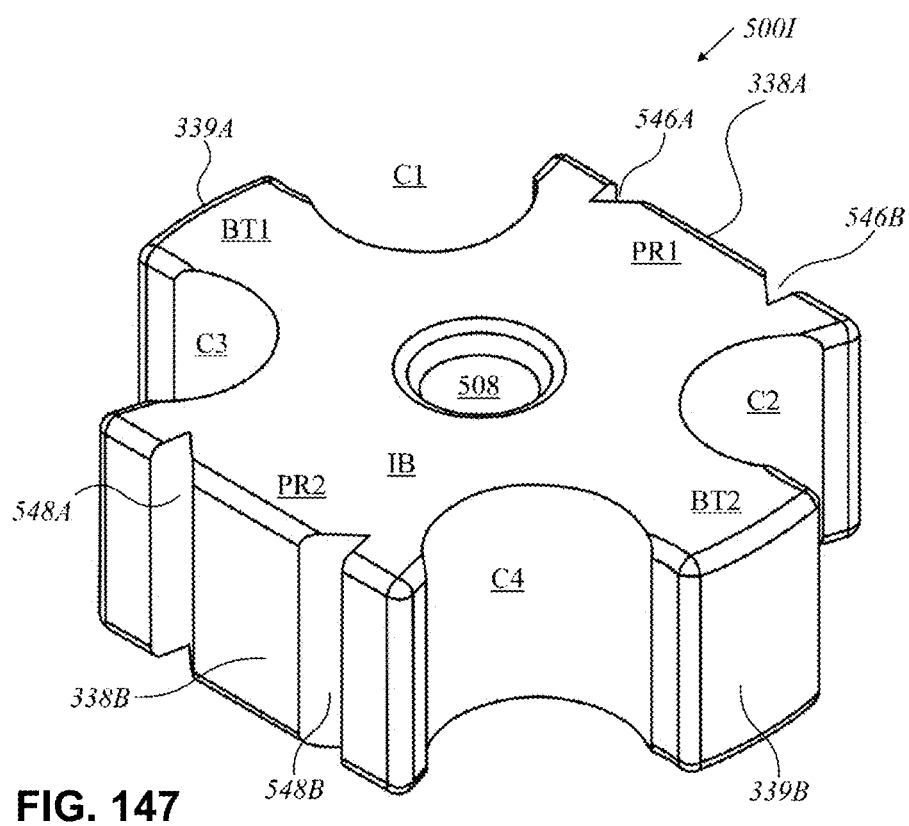

FIG. 147 shows a perspective view of an alternate embodiment of the torque enhancer of the present invention which is also shown in the form of a threaded nut.

Figure 148:
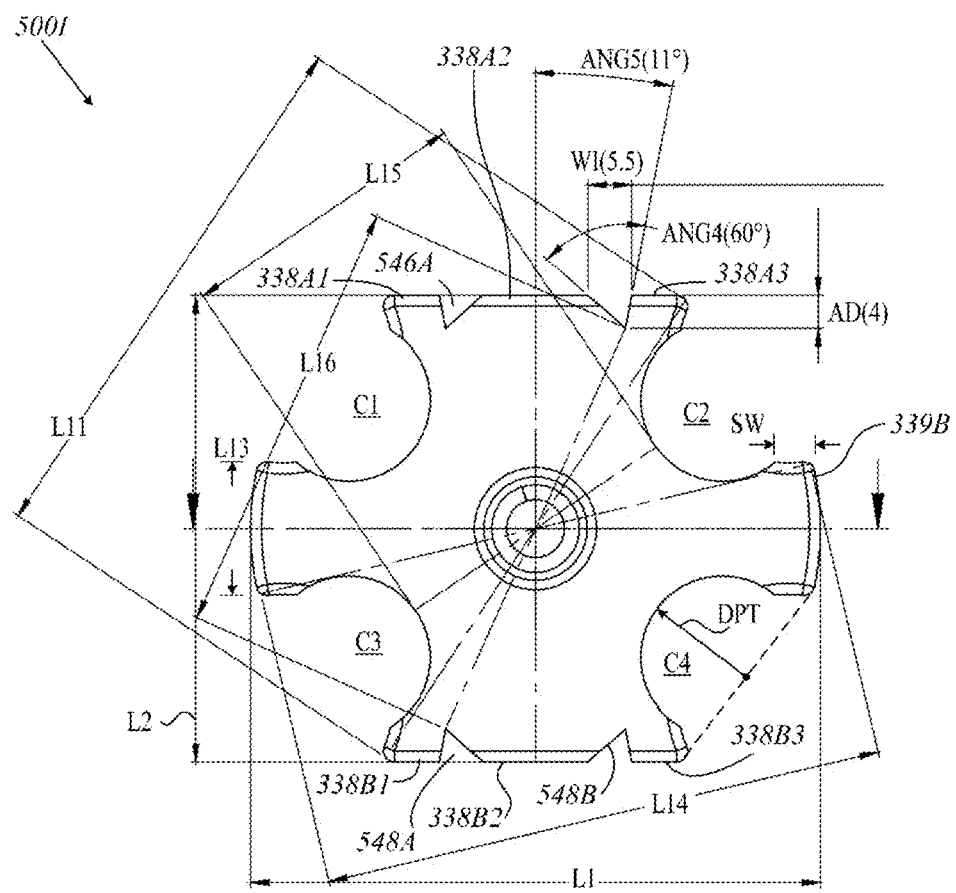

FIG. 148 shows a top plan view of the torque enhancer of FIG. 147.

Figure 149:
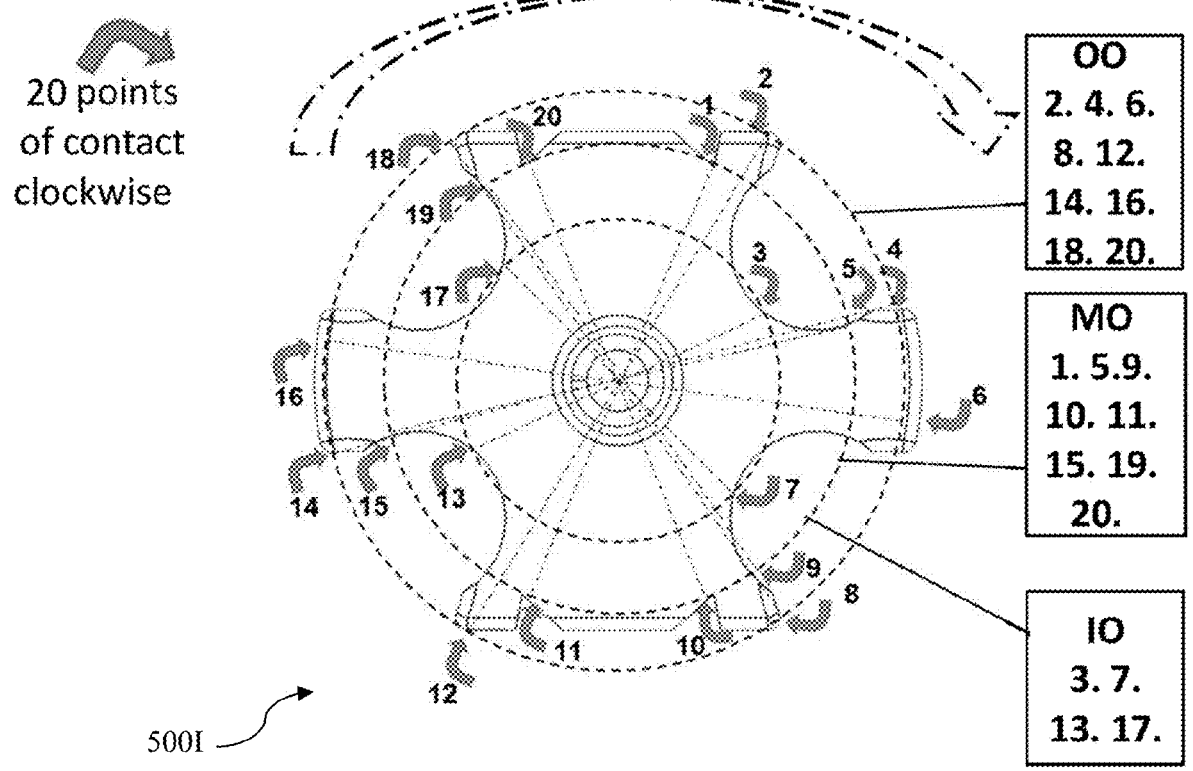

FIG. 149 shows a similar top plan view as that shown in FIG. 147, but with a considered "mechanical" contact point illustration.

Figure 150:
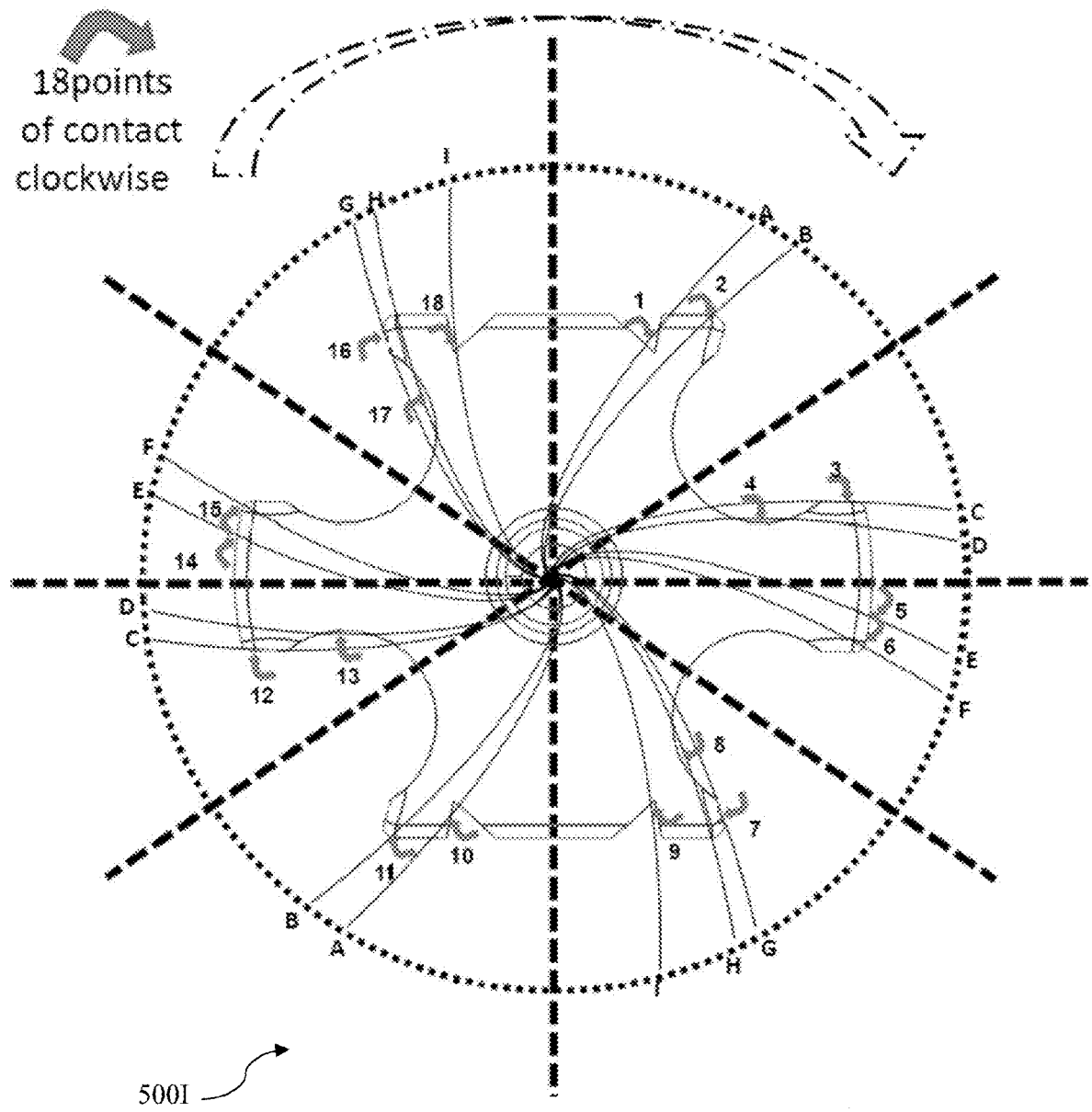

FIG. 150 also shows a top plan view of the torque enhancer of FIG. 147, but with a considered "spiral-centrifugal" contact point illustration.

Figure 151:
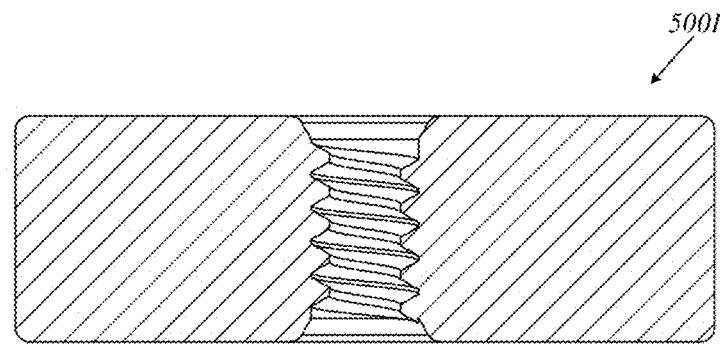

FIG. 151 shows a cross-section view of the torque enhancer of FIG. 147 taken along the Y-Y axis cross-section line thereof.

Figure 152:
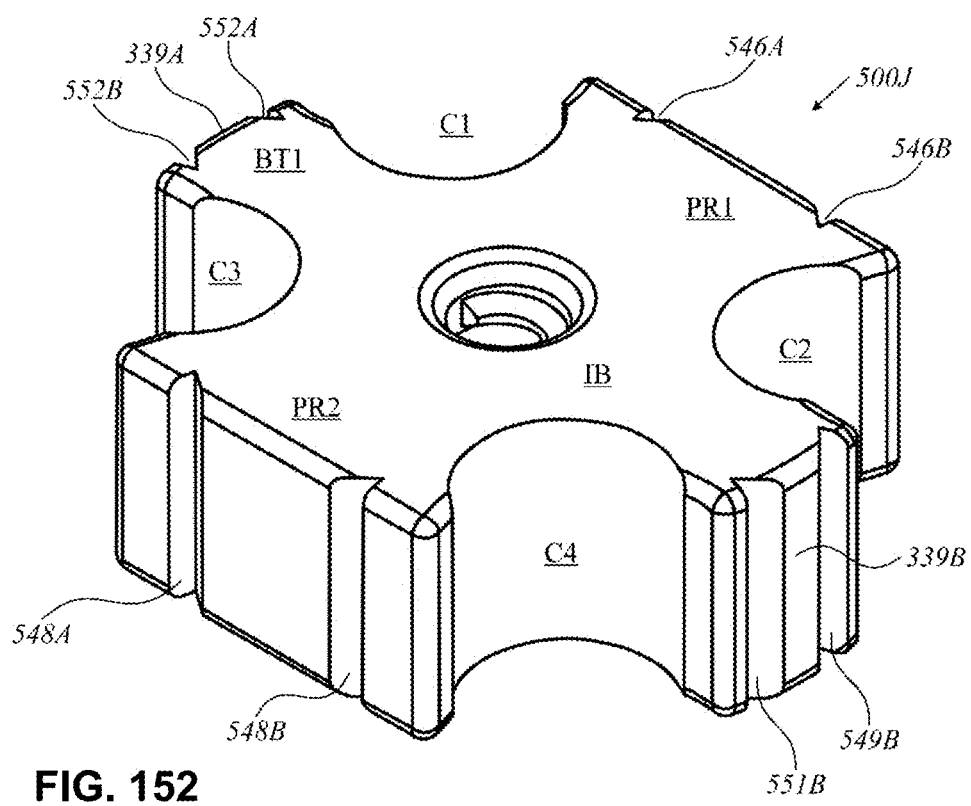

FIG. 152 shows a perspective view of an alternate embodiment of the torque enhancer of the present invention which is also shown in the form of a threaded nut.

Figure 153:
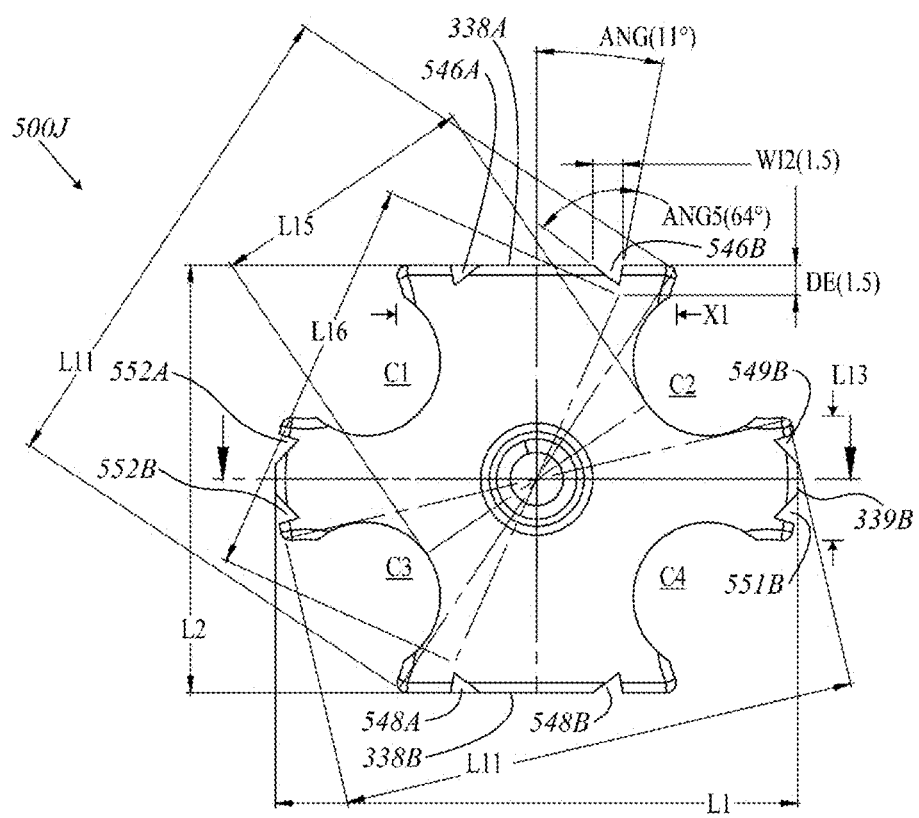

FIG. 153 shows a top plan view of the torque enhancer of FIG. 152.

Figure 154:
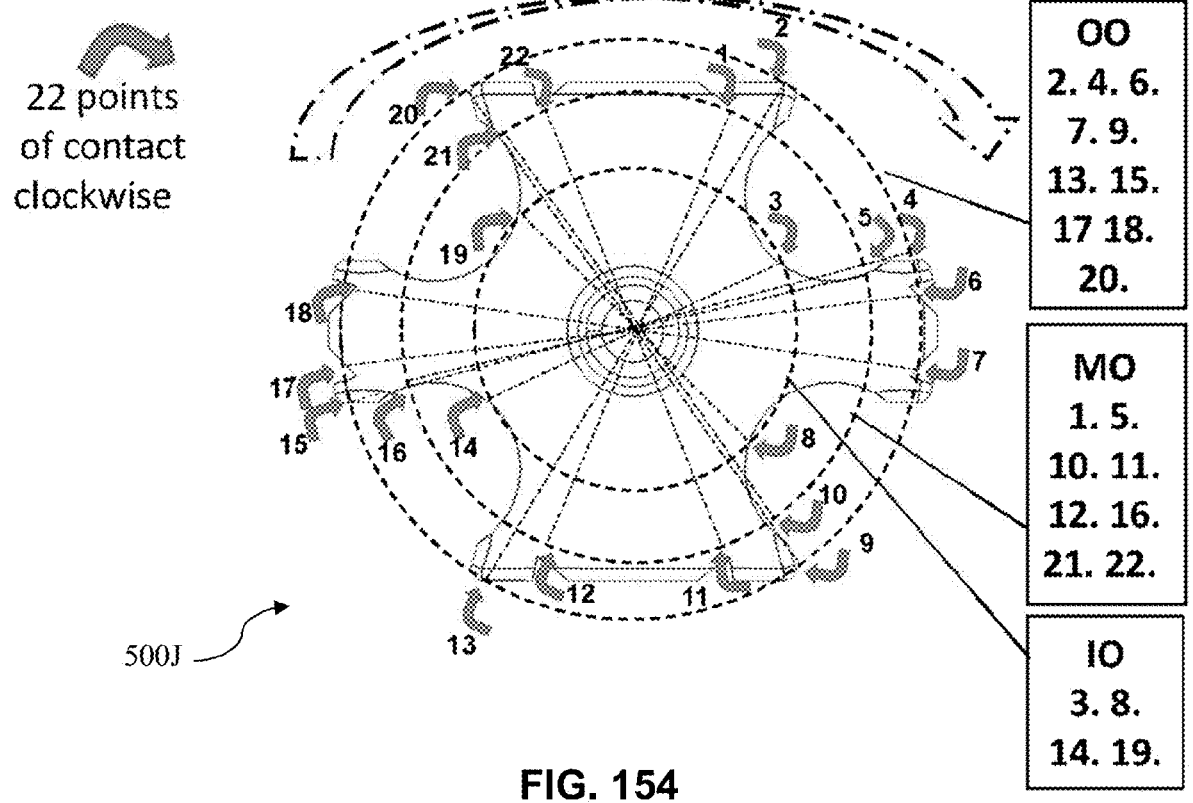

FIG. 154 shows a similar top plan view as that shown in FIG. 152, but with a considered "mechanical" contact point illustration.

Figure 155:
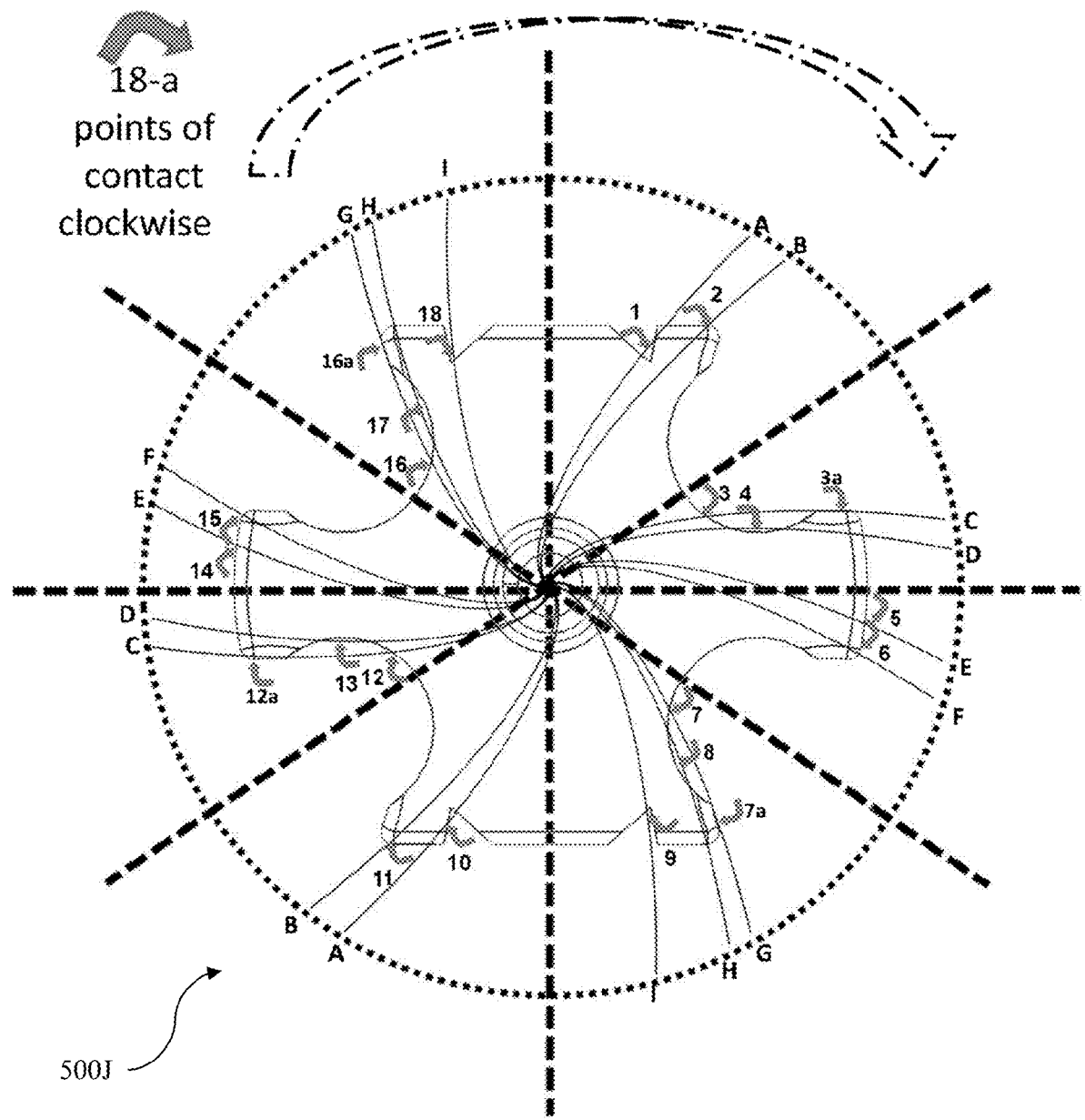

FIG. 155 also shows a top plan view of the torque enhancer of FIG. 152, but with a considered "spiral-centrifugal" contact point illustration.

Figure 156:
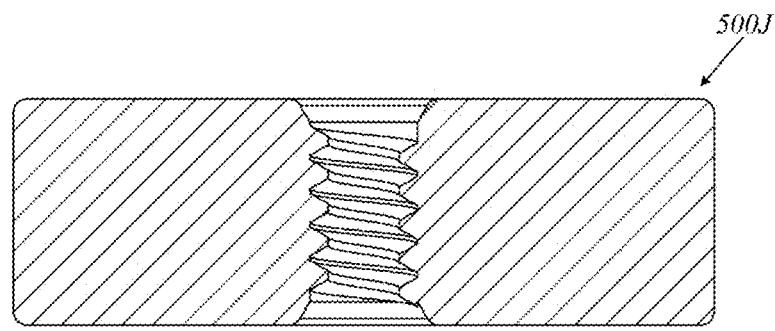

FIG. 156 shows a cross-section view of the torque enhancer of FIG. 152 taken along the Y-Y axis cross-section line thereof.

Figure 157:
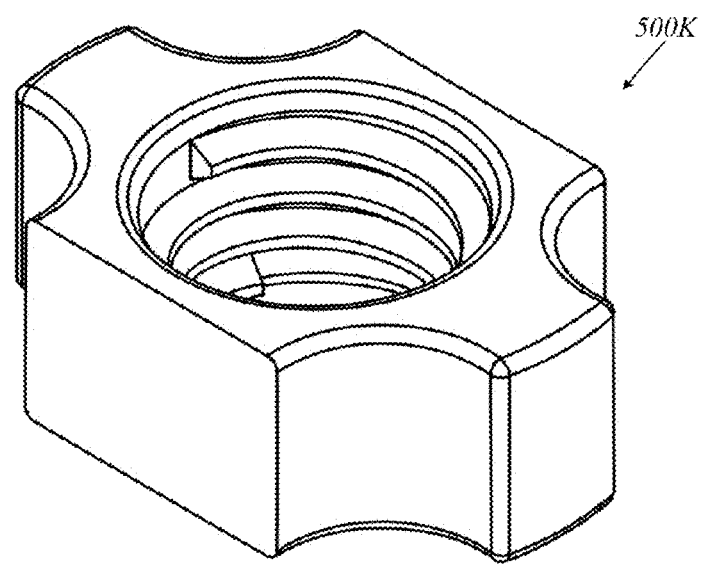

FIG. 157 shows a perspective view of an alternate embodiment of the torque enhancer of the present invention which is also shown in the form of a threaded nut.

Figure 158:
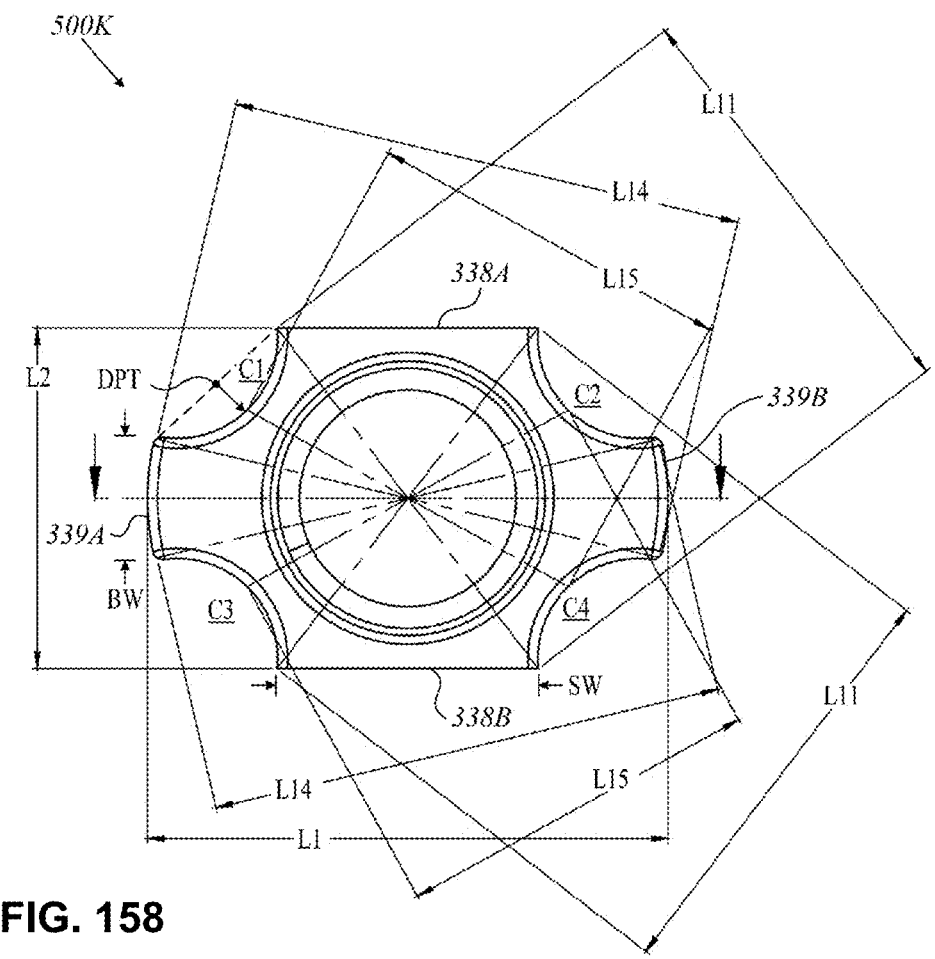

FIG. 158 shows a top plan view of the torque enhancer of FIG. 157.

Figure 159:
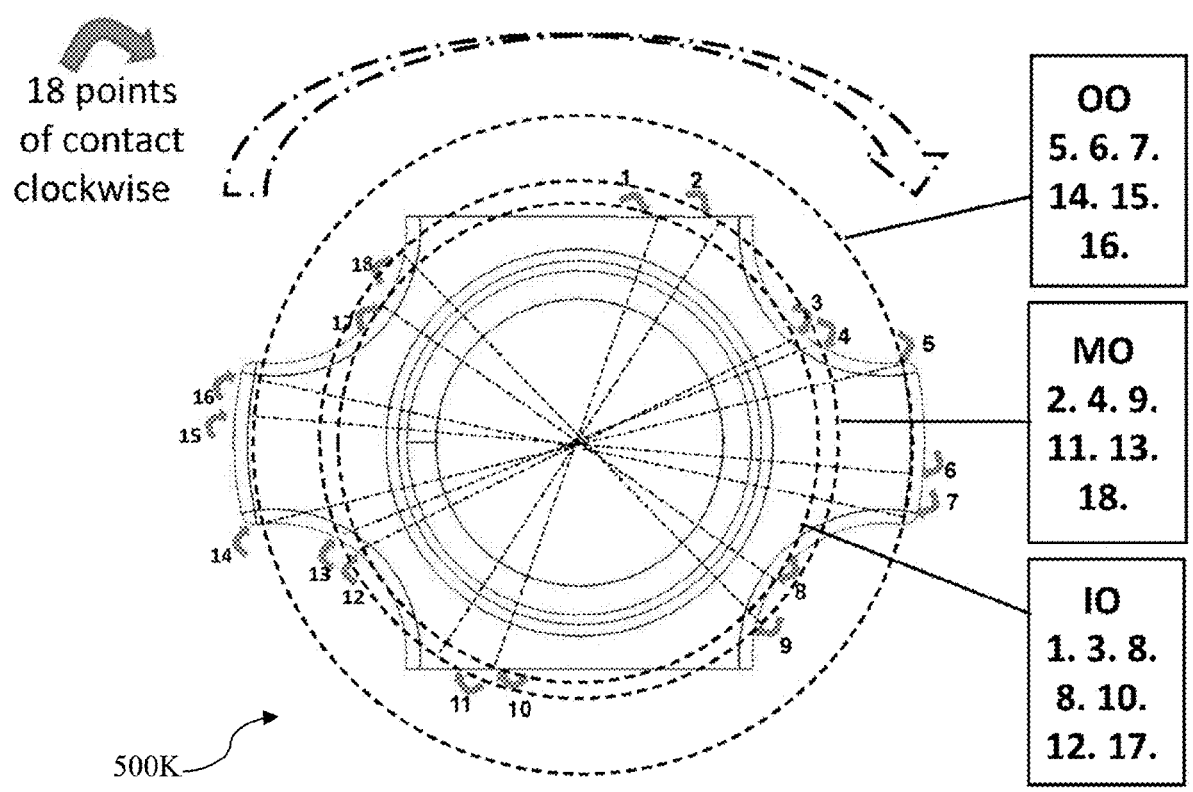

FIG. 159 shows a similar top plan view as that shown in FIG. 157, but with a considered "mechanical" contact point illustration.

Figure 160:
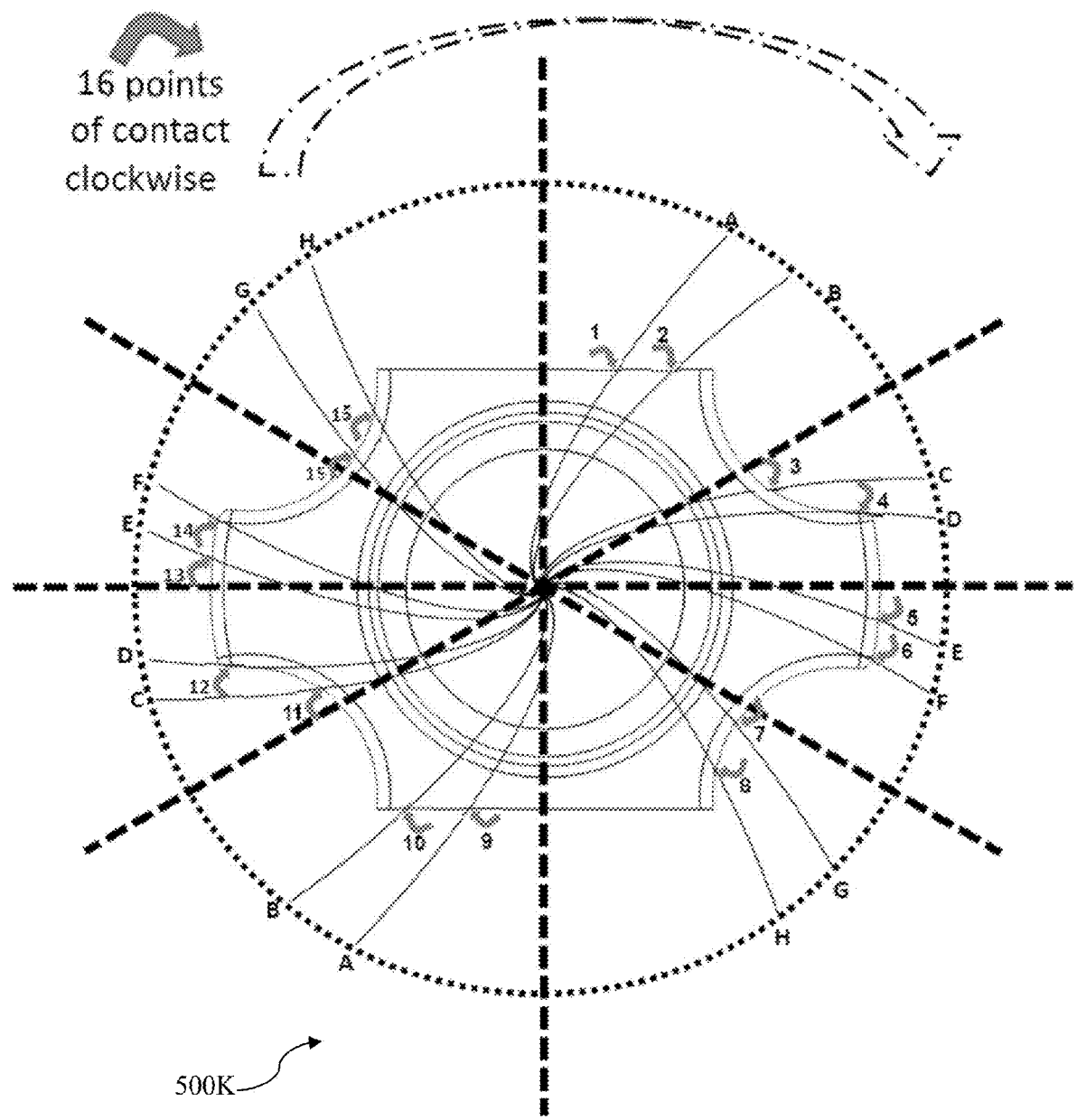

FIG. 160 also shows a top plan view of the torque enhancer of FIG. 157, but with a considered "spiral-centrifugal" contact point illustration.

Figure 161:
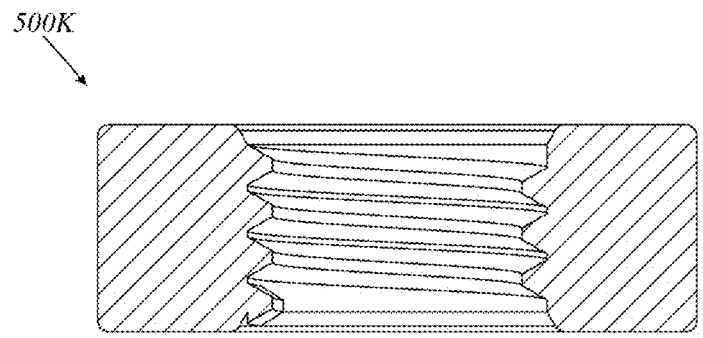

FIG. 161 shows a cross-section view of the torque enhancer of FIG. 157 taken along the Y-Y axis cross-section line thereof.

Figure 162:
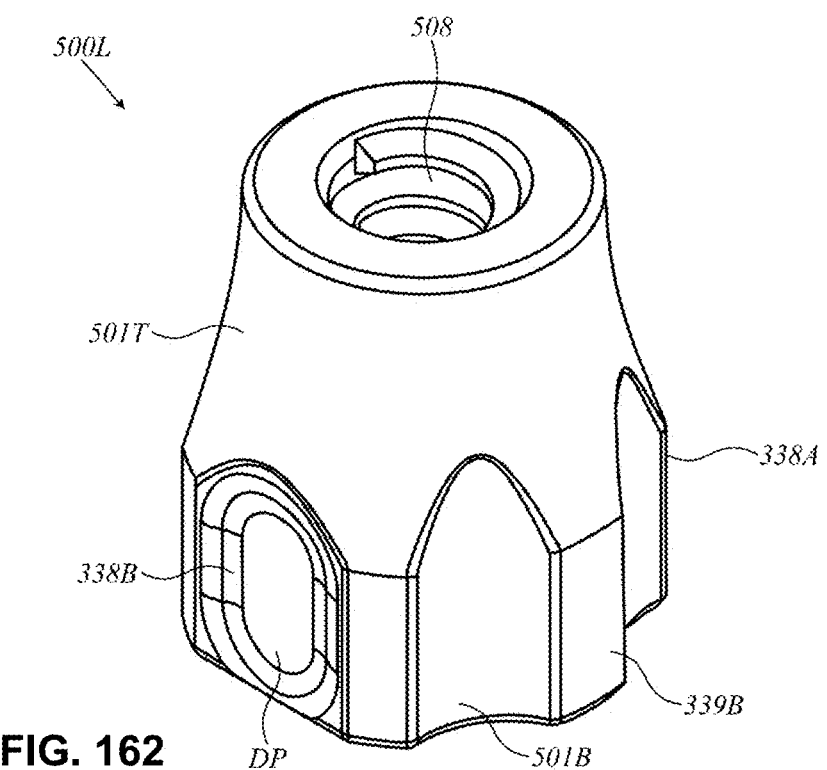

FIG. 162 shows a perspective view of an alternate "tapering" embodiment of the torque enhancer of the present invention which is also shown in the form of a base capped threaded nut.

Figure 163:
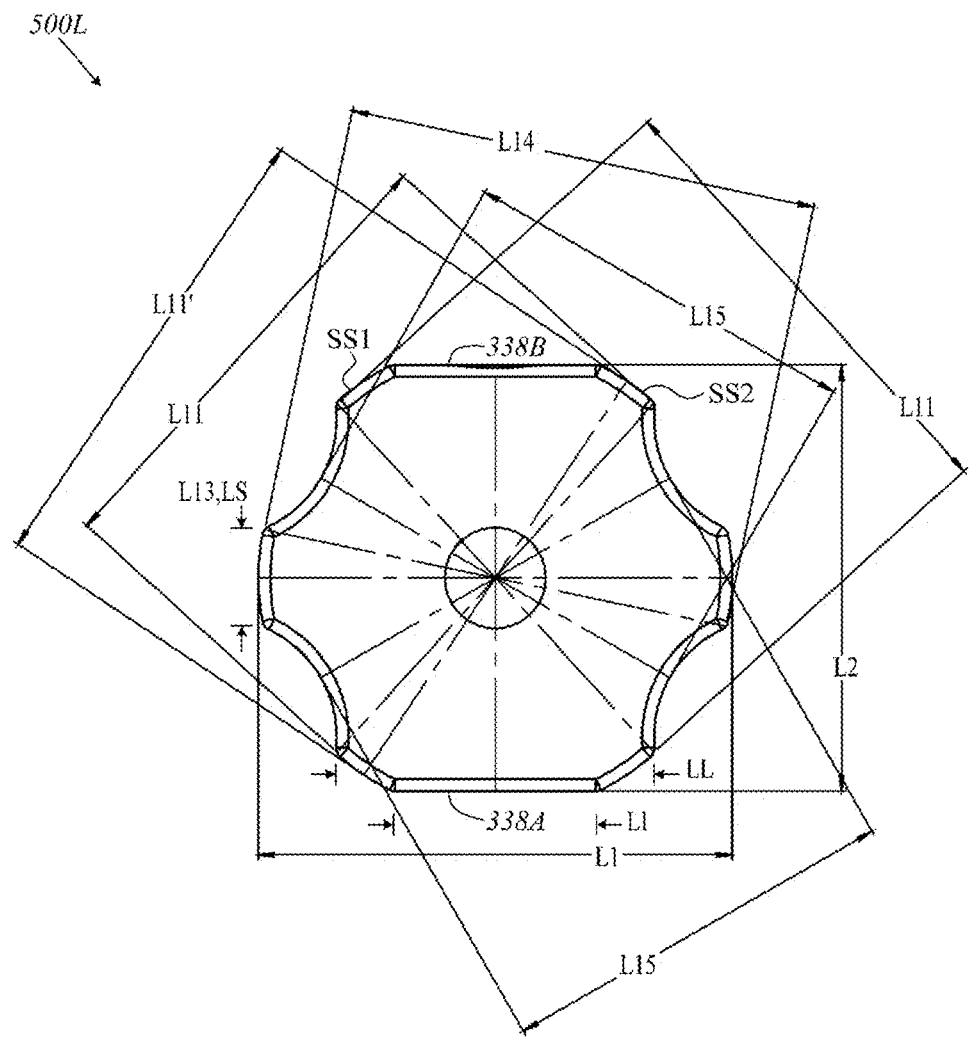

FIG. 163 shows a bottom plan view of the torque enhancer of FIG. 162.

Figure 164:
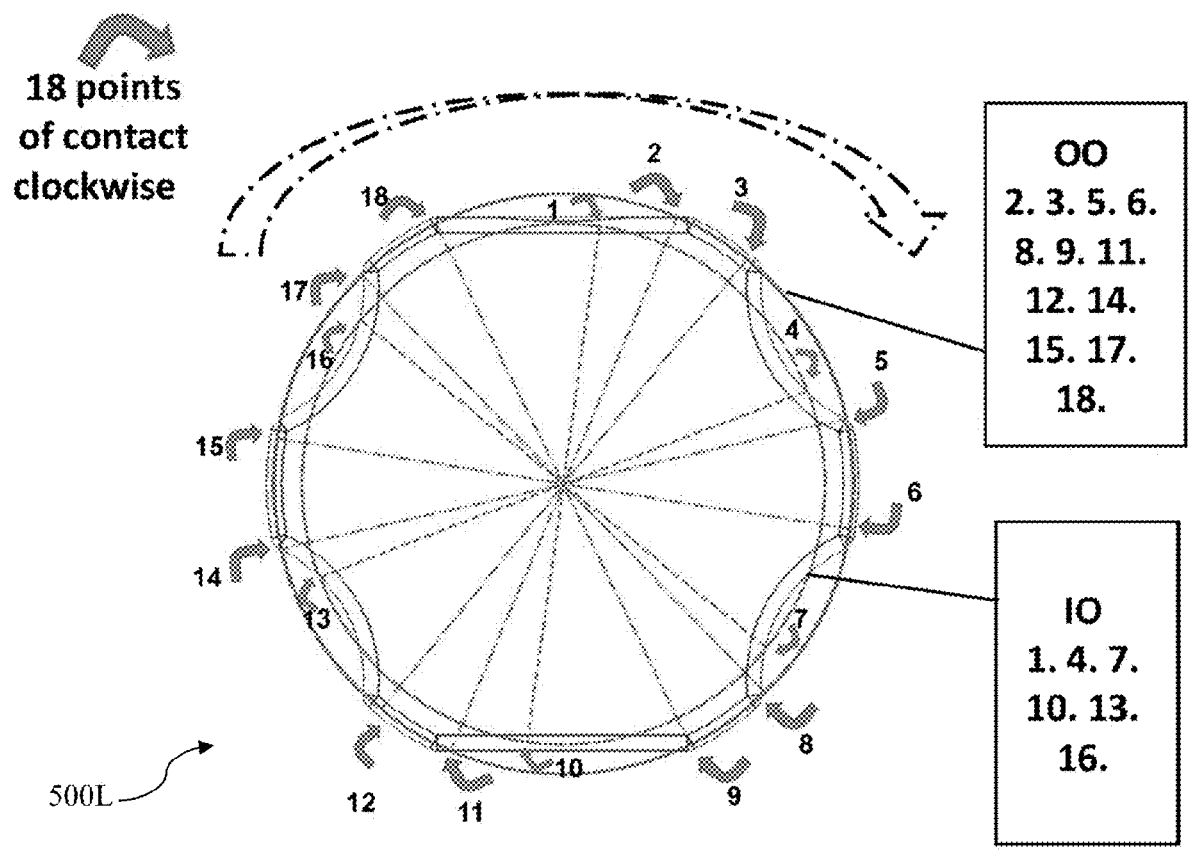

FIG. 164 shows a similar bottom plan view as that shown in FIG. 163, but with a considered "mechanical" contact point illustration.

Figure 165:
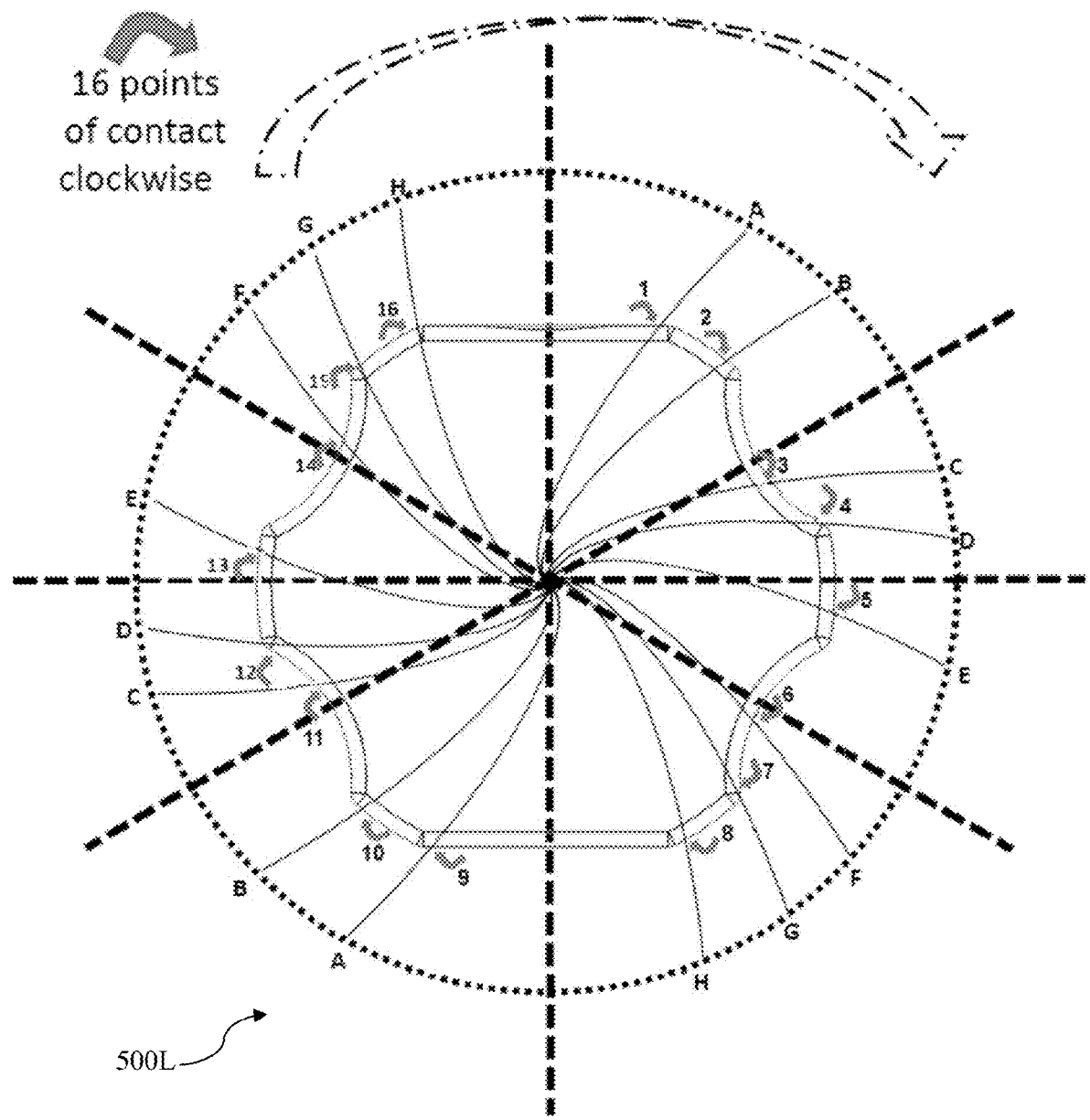

FIG. 165 also shows a bottom plan view of the torque enhancer of FIG. 163, but with a considered "spiral-centrifugal" contact point illustration.

Figure 166:
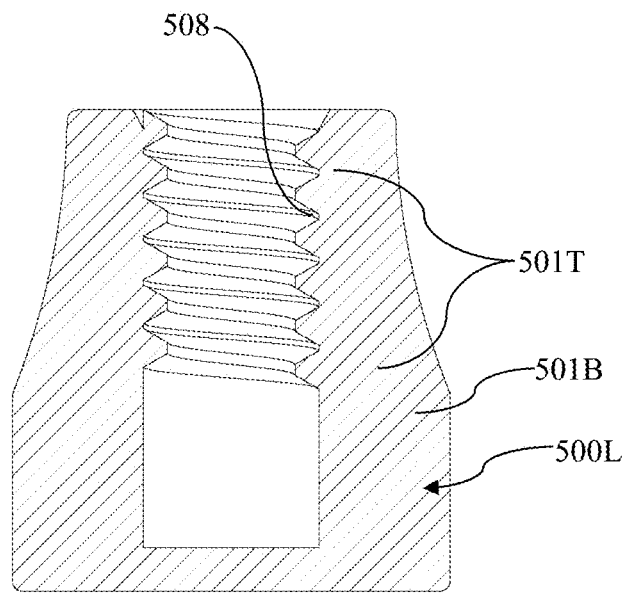

FIG. 166 shows a cross-section view of the torque enhancer of FIG. 162 taken along the elongated axis thereof.

Figure 167:
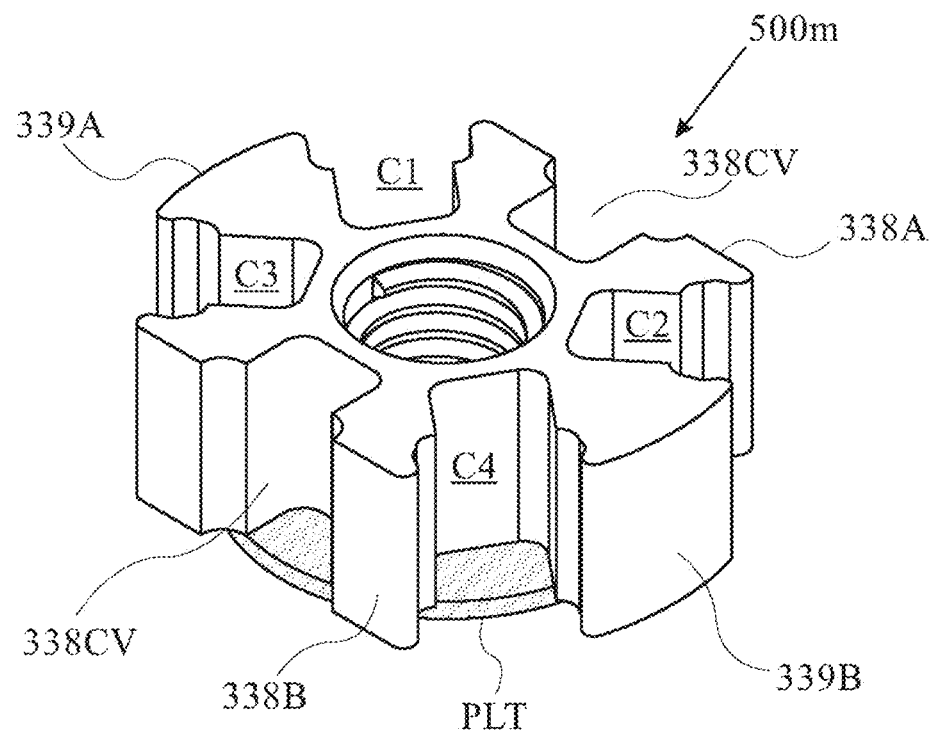

FIG. 167 shows a perspective view of an alternate embodiment of the torque enhancer of the present invention which is also shown in the form of a threaded nut or gear (as described above, any of the above referenced nut embodiments can also function as gearing with or without added support plating along an underside as shown in dashed lines in FIG. 167).

Figure 167A:
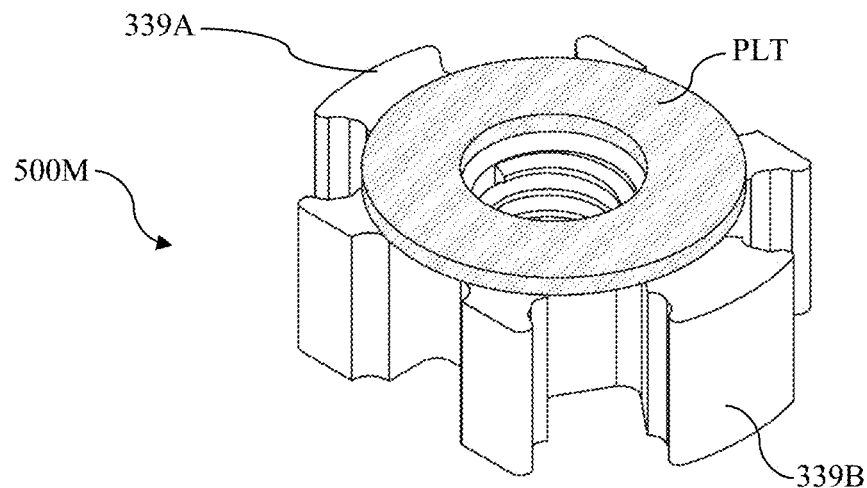

FIG. 167A shows a flipped over perspective view of the torque enhancer of FIG. 167.

FIG. 167B to 167G show additional embodiments of the torque enhancer shown in FIG. 167 which include double stacked base plating (with external and internal radial extensions) shown on one or both sides of the torque enhancement member with projections.

Figure 168:
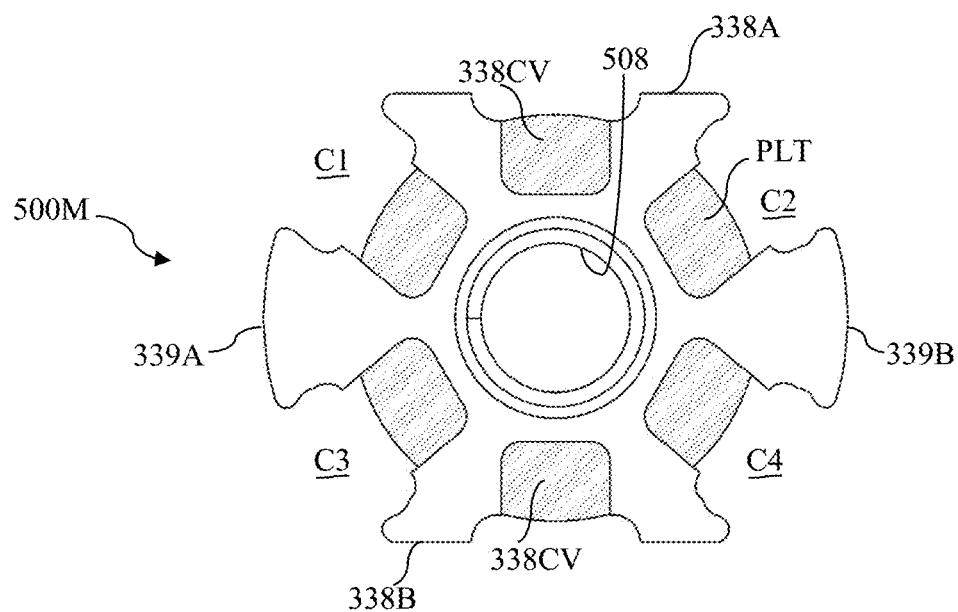

FIG. 168 shows a top plan view of the torque enhancer of FIG. 167 with alternate plate support embodiment shown in dash lines.

Figure 169:
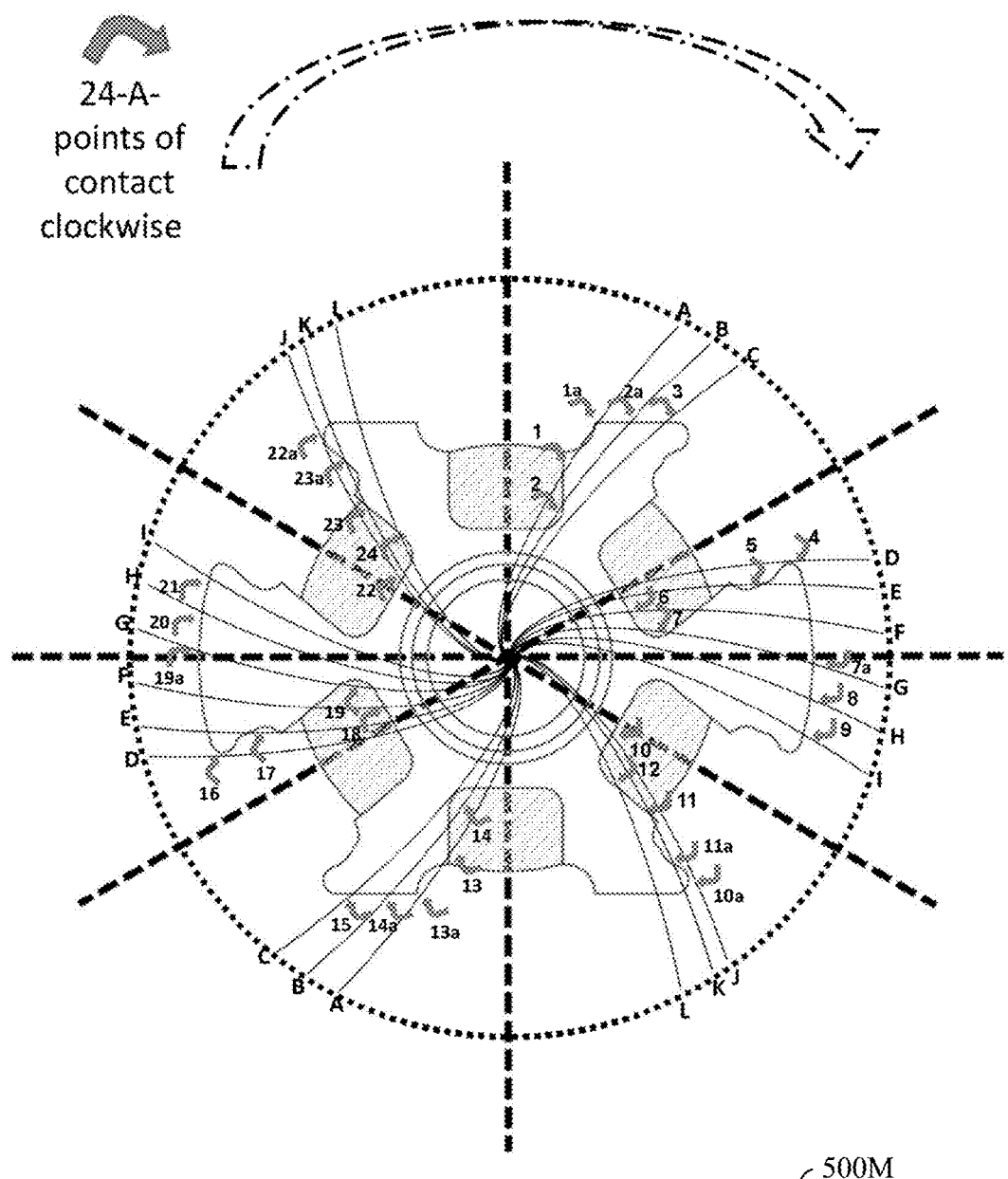

FIG. 169 shows a top plan view of the torque enhancer of FIG. 167, but with a considered initial "spiral-centrifugal" contact point illustration.

Figure 170:
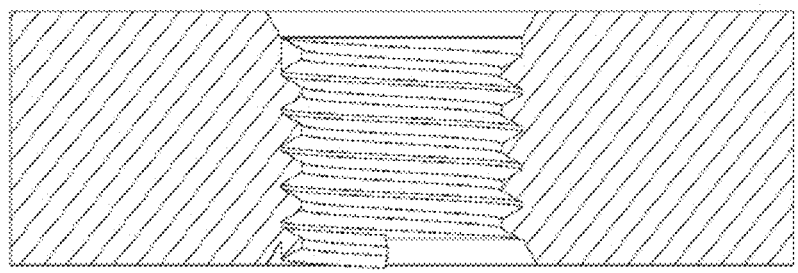

FIG. 170 shows a cross-section view of the torque enhancer of FIG. 167 taken along the longer Y-Y axis thereof.

Figure 171:
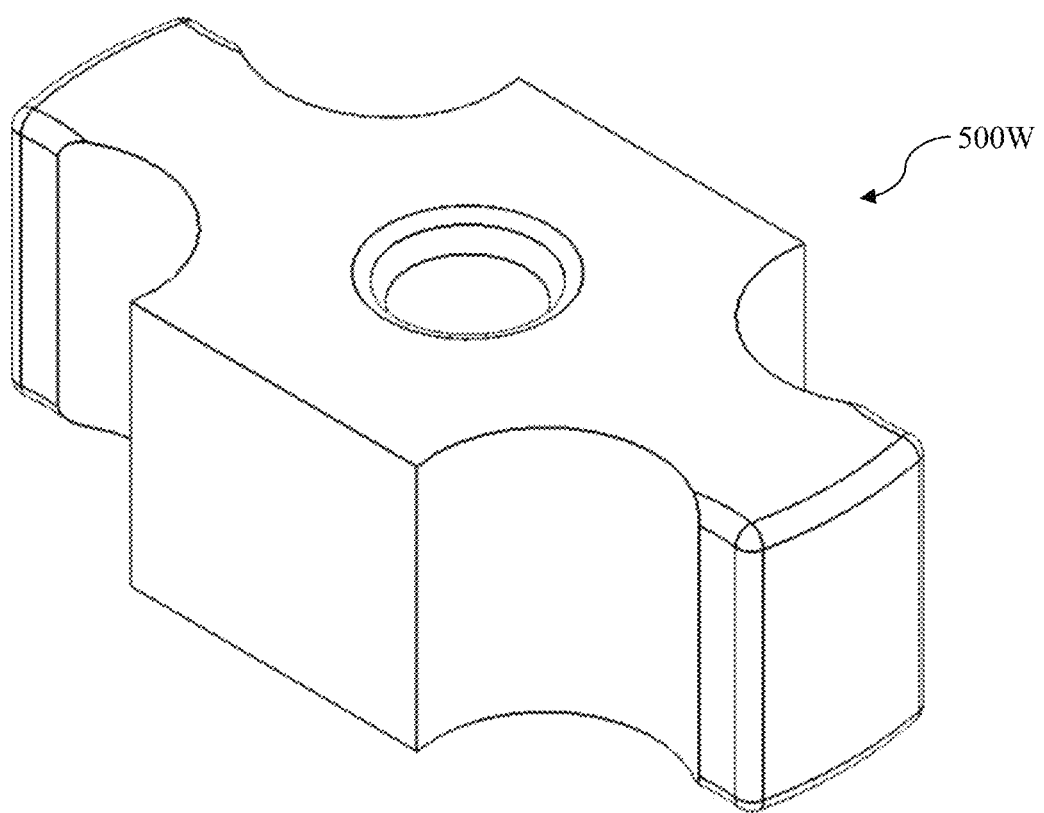

FIG. 171 shows a perspective view of an alternate embodiment of the torque enhancer of the present invention which is also shown in the form of a threaded nut and having large opposite Y-axis projections as to provide it with a relatively narrower rectangular configuration.

Figure 172:
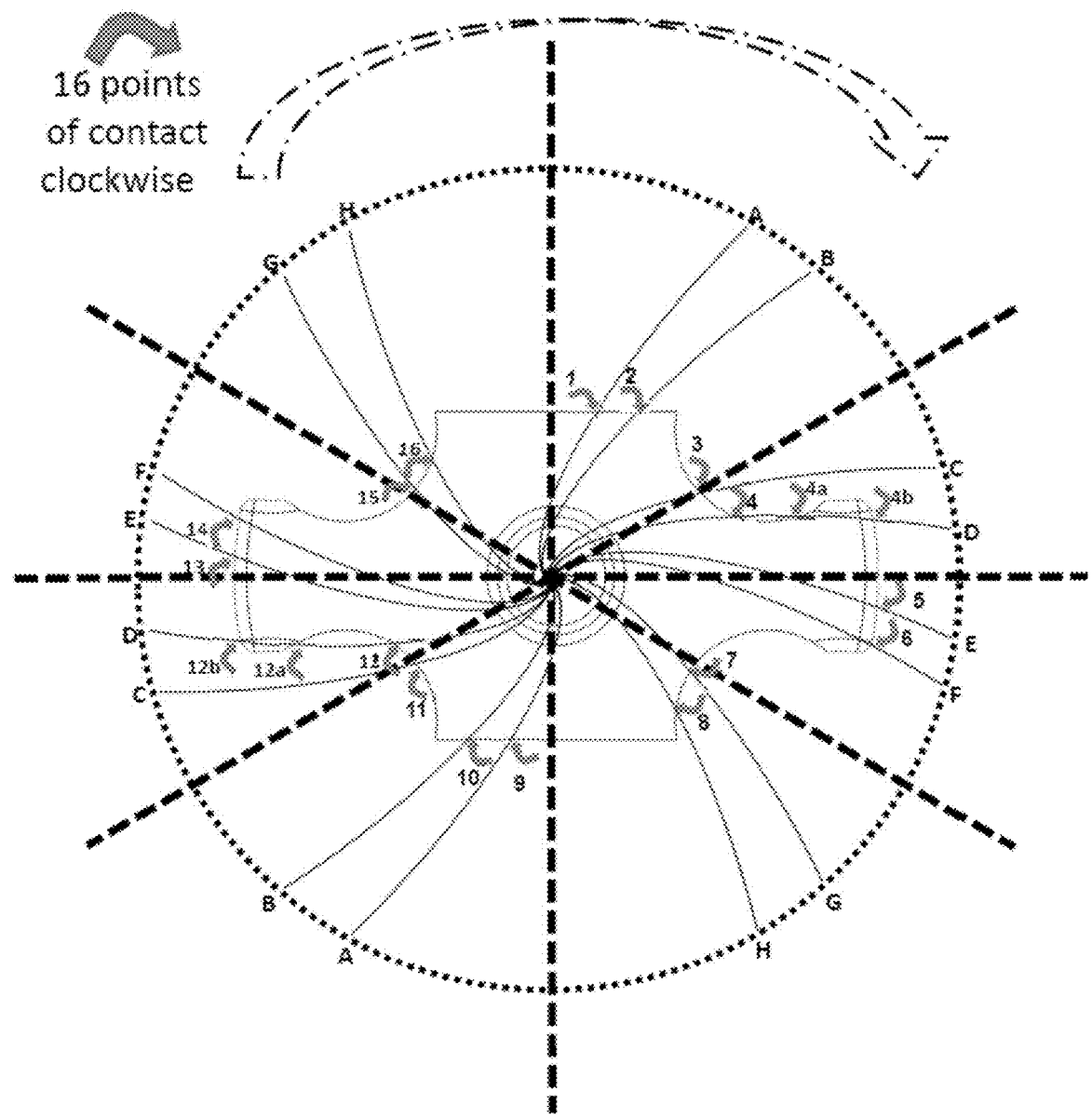

FIG. 172 shows a top plan view of the torque enhancer of FIG. 171, but with a considered "spiral-centrifugal" contact point illustration.

Figure 173:
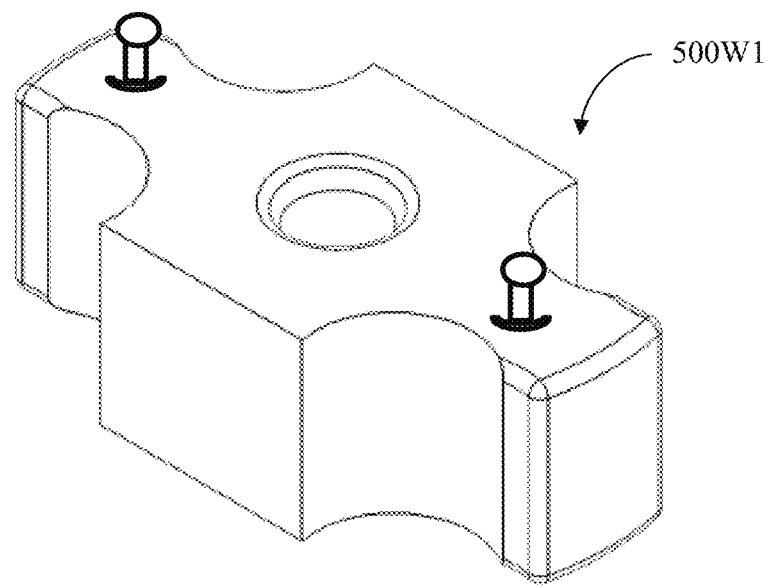

FIG. 173 shows a perspective view of an alternate embodiment of the torque enhancer of the present invention which is similar to the above narrow rectangle configuration, but further features added bow-tie projection fastener holes (and/or illustrative weight balance pockets or holes).

Figure 174:
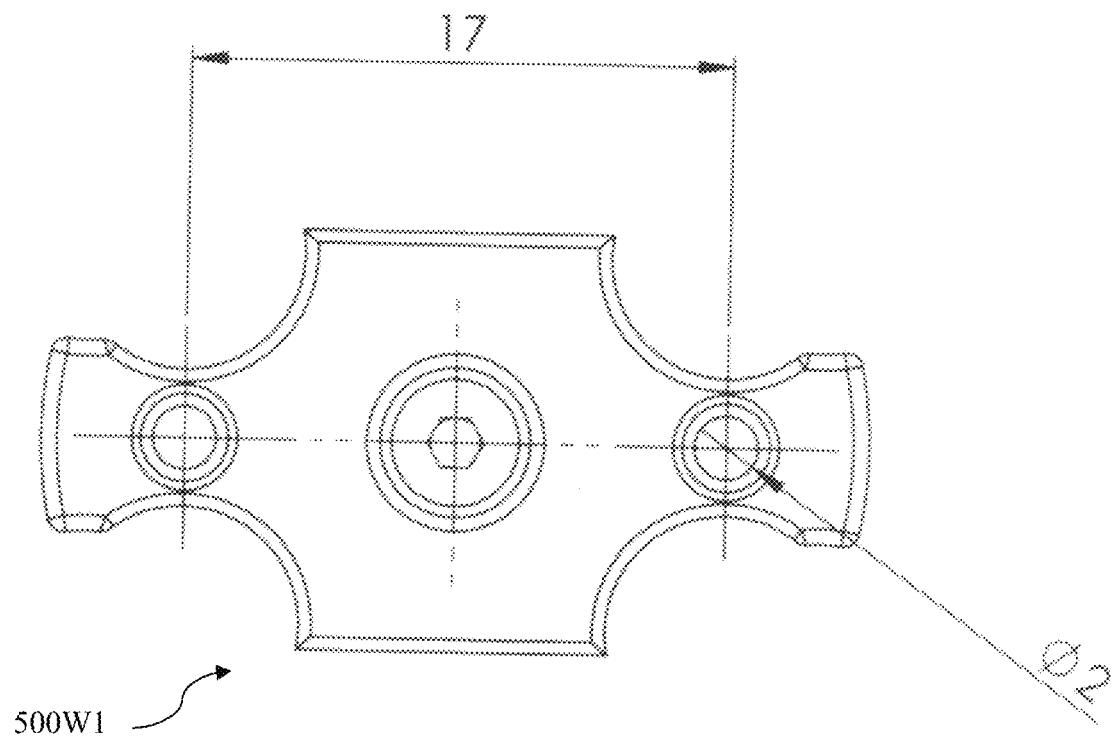

FIG. 174 shows a top plan view of the torque enhancer of FIG. 173.

Figure 175:
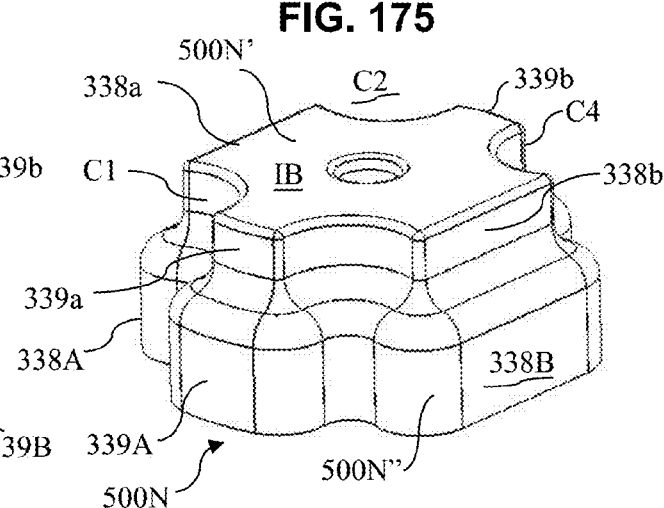

FIG. 175 shows a perspective view of an alternate embodiment of the torque enhancer of the present invention which is also shown in the form of a two level nut or cap.

Figure 176:
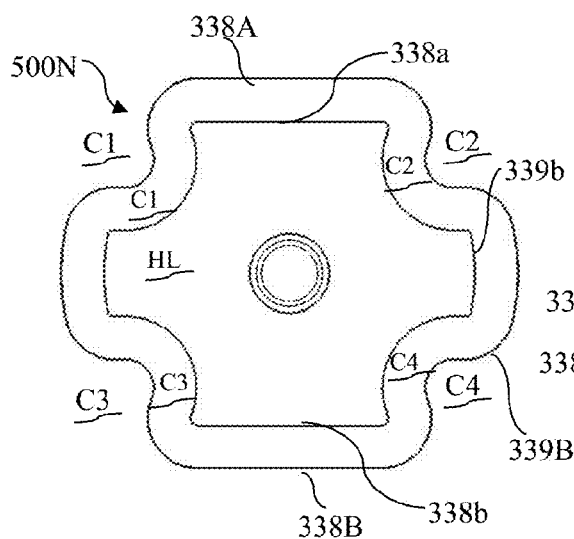

FIG. 176 shows a top plan view of the torque enhancer of FIG. 175.

Figure 177:
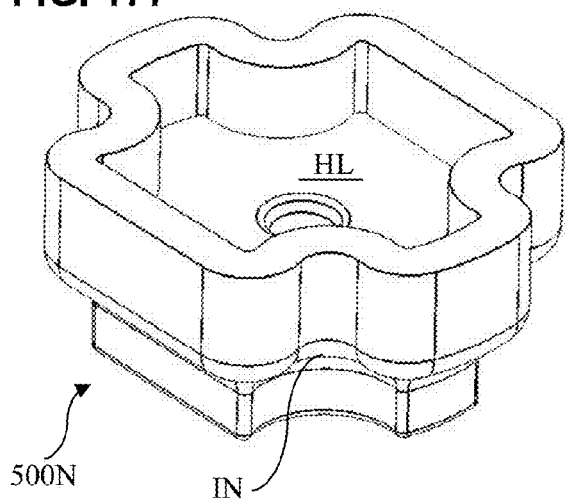

FIG. 177 shows a bottom perspective view of the torque enhancer of FIG. 175.

Figure 178:
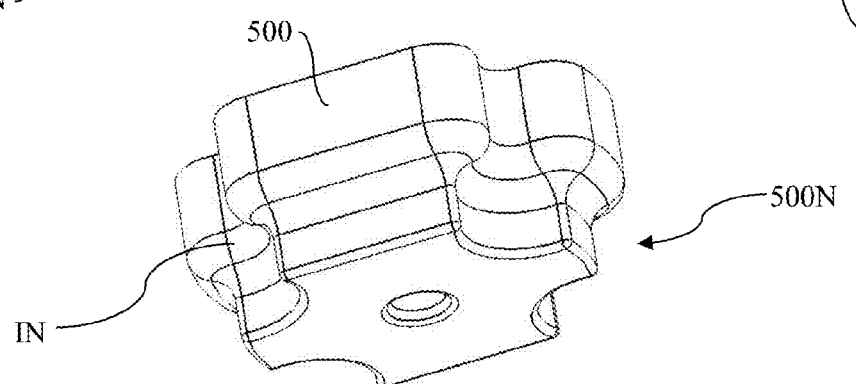

FIG. 178 shows another perspective view of the torque enhancer flipped over from the view of FIG. 175.

Figure 179:
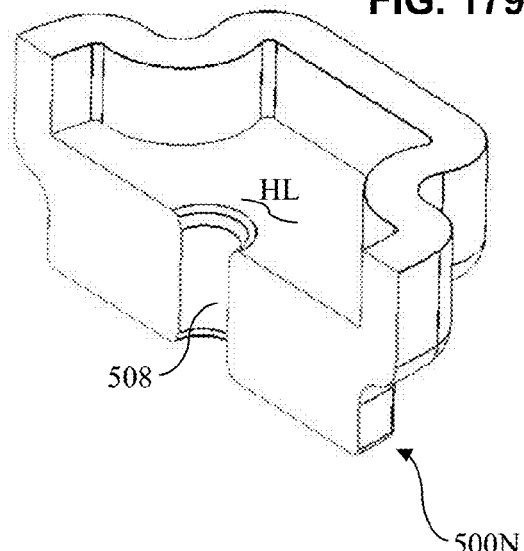

FIG. 179 shows a cross-sectional view of the torque enhancer as flipped over in FIG. 177.

Figure 180:
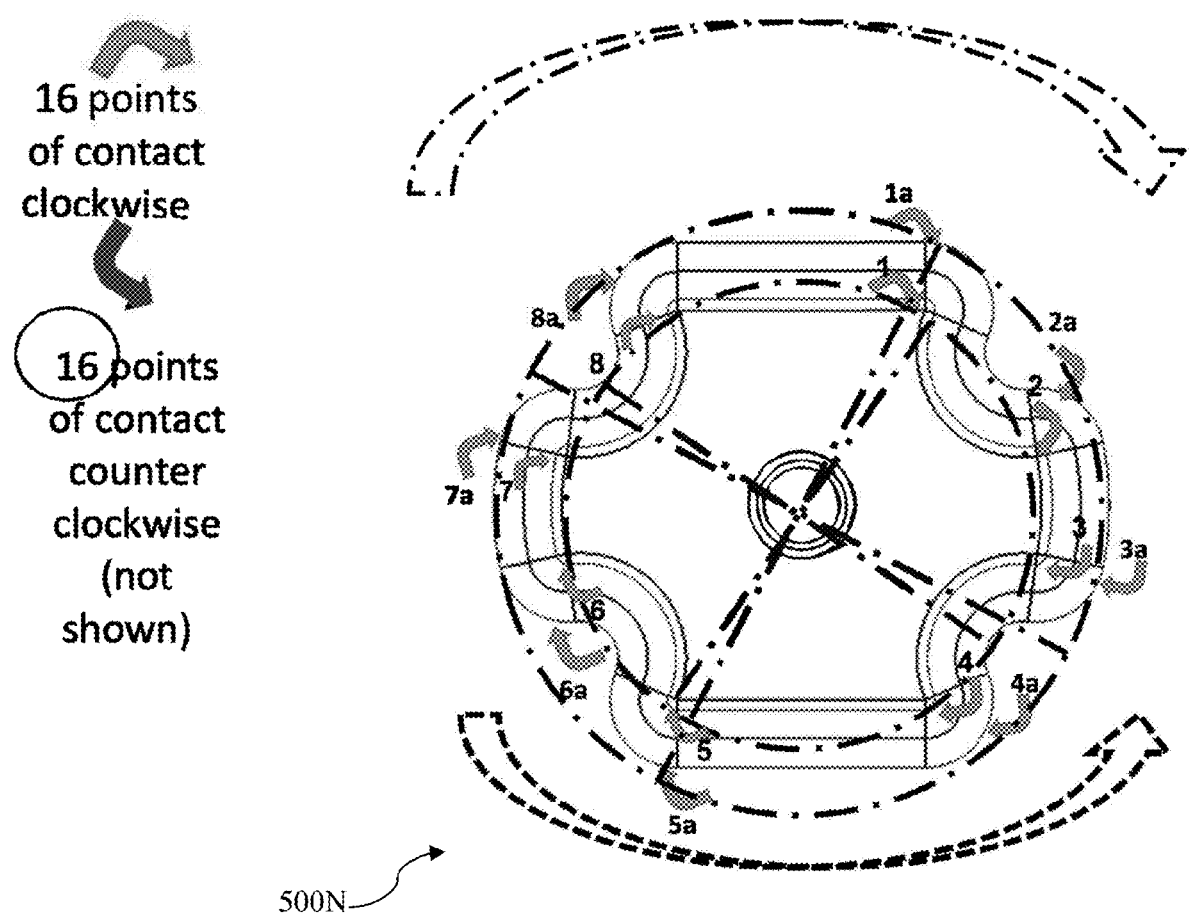

FIG. 180 shows a top plan view of the torque enhancer of FIG. 175 with considered "mechanical" contact point additions.

FIG. 181 shows a perspective view of a torque tool which is in the form of a wrench having opposite end torque enhancement capture recesses.

FIG. 182 shows a perspective view of a torque tool like that in FIG. 181 but with one of its torque enhancement capture recesses in a modified (more open) form.

FIG. 183 shows a perspective view of a torque enhancement component like that of the above described nuts, but having a non-threaded through-hole of hexagonal design, and which has an external periphery suited for receipt on one or both of capture recesses in the above referenced FIGS. 181 and 182 torque tools.

Figure 183A:
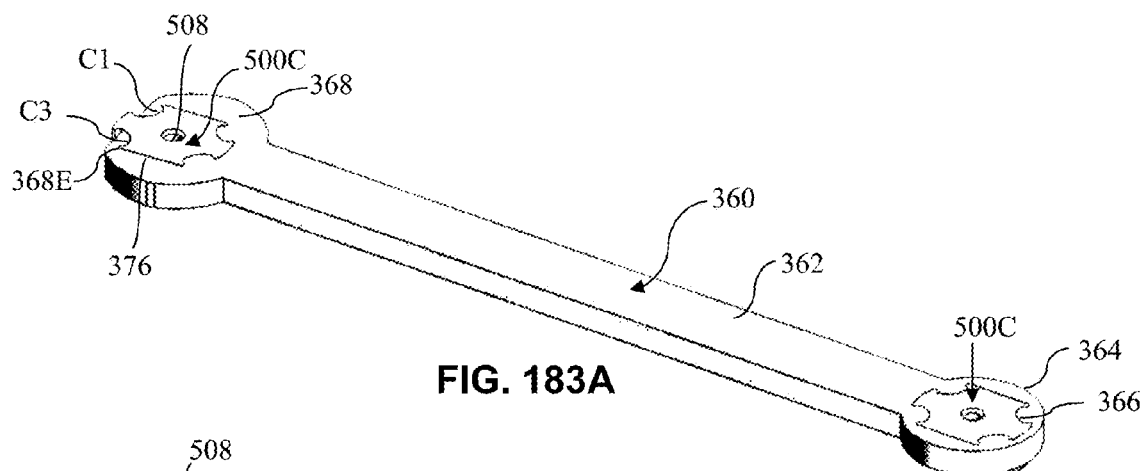

FIG. 183A shows a perspective view of the tool of FIG. 181 having within each of its recesses a torque enhancement component like that in FIG. 183 but with a central treaded aperture rather than the noted hexagonal core.

FIG. 184 shows a perspective view of a torque enhancement component like that of the above described nuts, but having a non-threaded through-hole of torque enhancement design, and which has an external periphery suited for receipt in one or both of capture recesses in the above referenced FIGS. 181 and 182 torque tools.

Figure 184A:
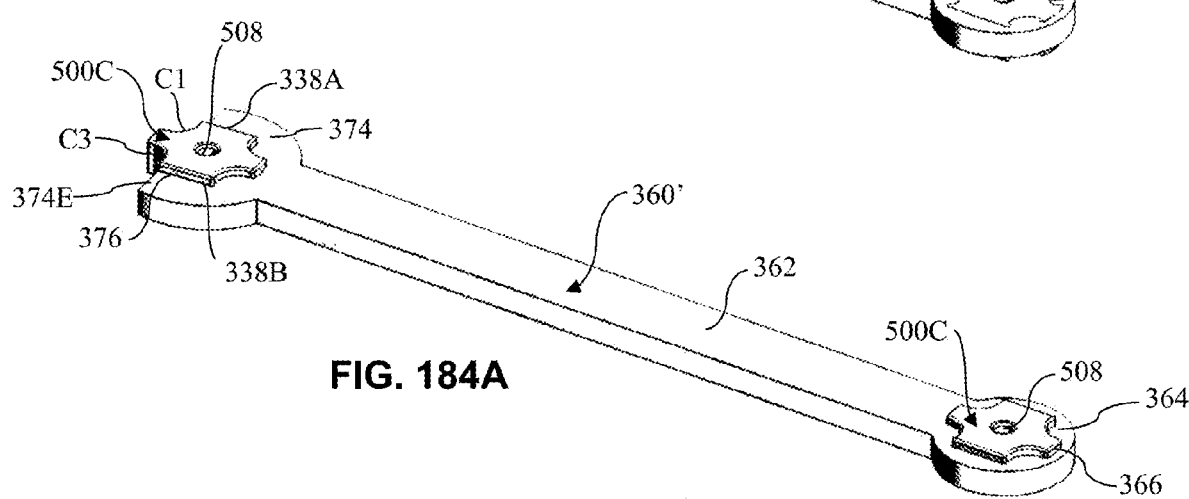

FIG. 184A shows a perspective view of the tool of FIG. 182 having within each of its recesses a torque enhancement component like that in FIG. 184 but with a central threaded aperture rather than the noted torque enhancement designed core.

Figure 185:
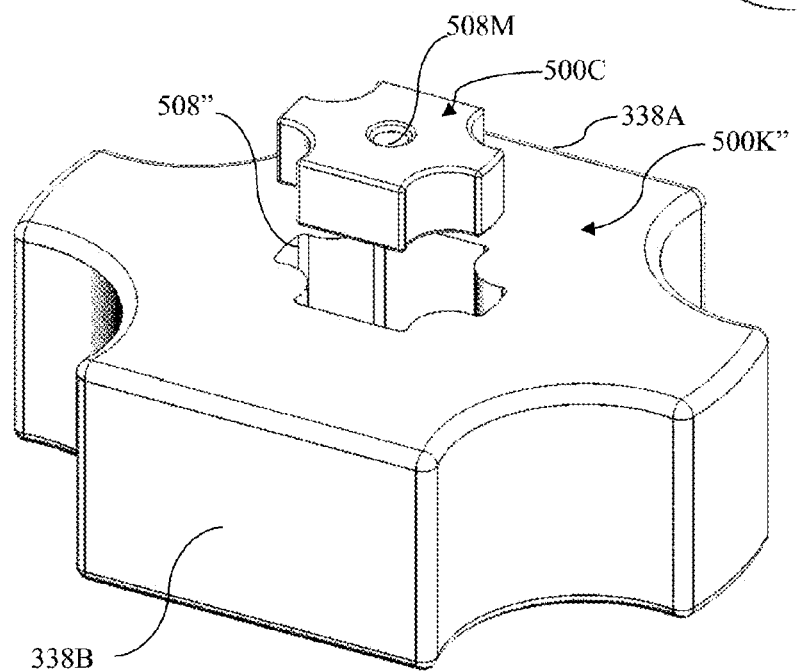

FIG. 185 shows in exploded view fashion a larger first (larger) torque enhancement component like that in FIG. 184 and a second (smaller) torque enhancement component configured for common configuration reception in the core of the first one, with the second one having a rivet opening as opposed to one of the above described cores.

Figure 185A:
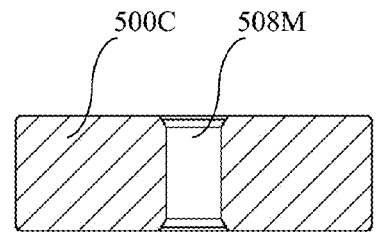

FIG. 185A shows a cross-sectional view of the second one with non-threaded, rivet shaped central core.

Figure 186:
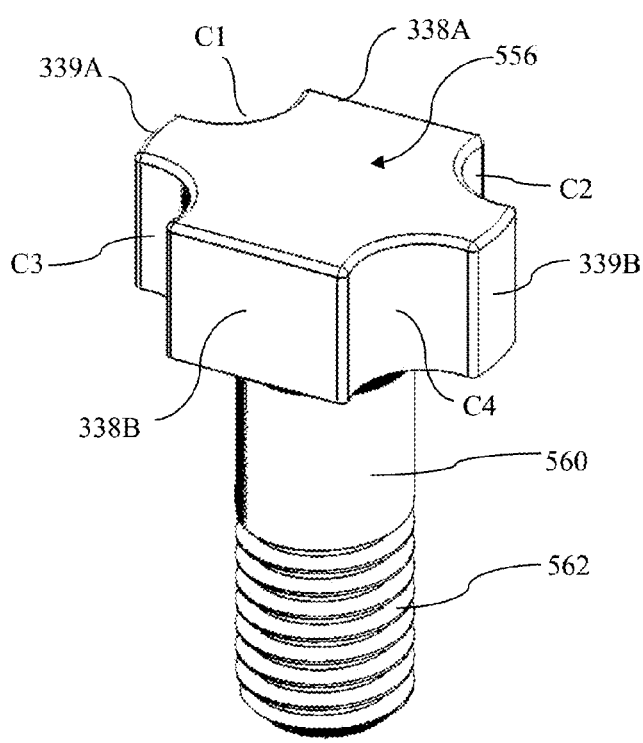

FIG. 186 shows a perspective view of another torque enhancement component of the present invention shown in the form of a partially threaded bolt.

Figure 186A:
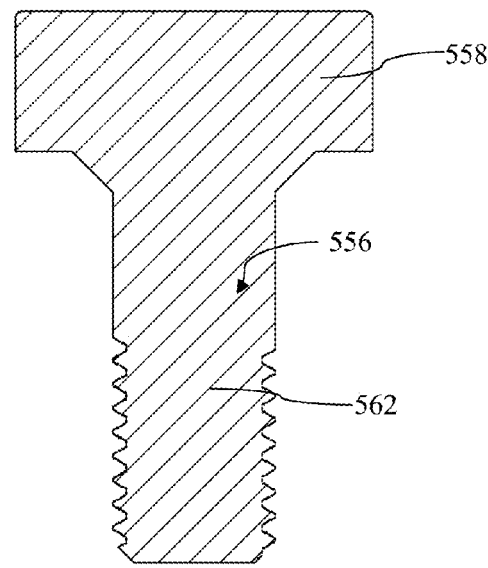

FIG. 186A shows a cross-sectional view of the bolt of FIG. 186.

Figure 187:
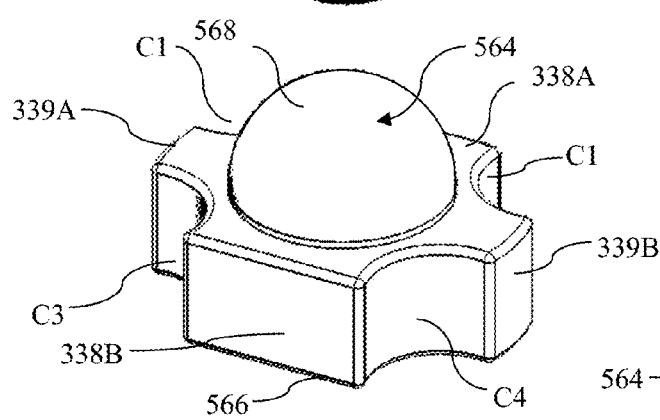

FIG. 187 shows a perspective view of another torque enhancement component of the present invention shown in the form of a semi-spherical domed nut or cap.

Figure 187A:
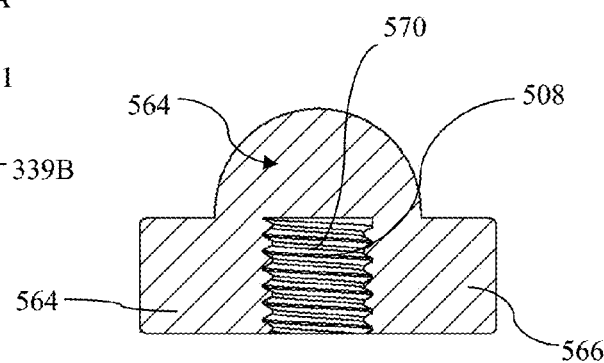

FIG. 187A shows a cross-sectional view of the domed nut of FIG. 187.

Figure 188A:
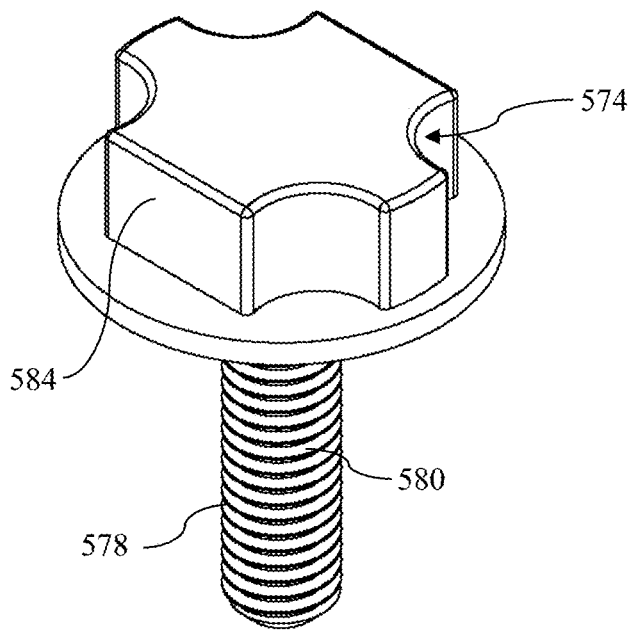

FIG. 188A shows a perspective view of a torque enhancement bolt similar to that of the bolt of FIG. 186 but with additional threading on its shaft and an integrated base head flange.

Figure 188B:
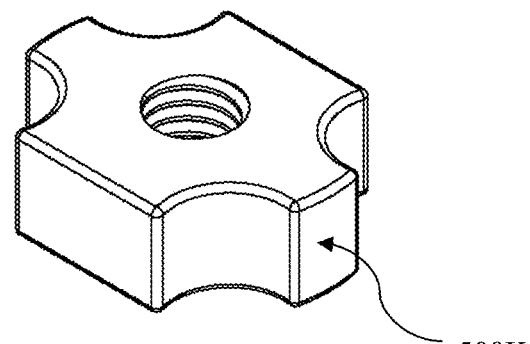

FIG. 188B shows a perspective view of another torque enhancement component in the form of a nut like that described above with a threaded interior core sized for FIG. 188A bolt receipt.

Figure 188C:
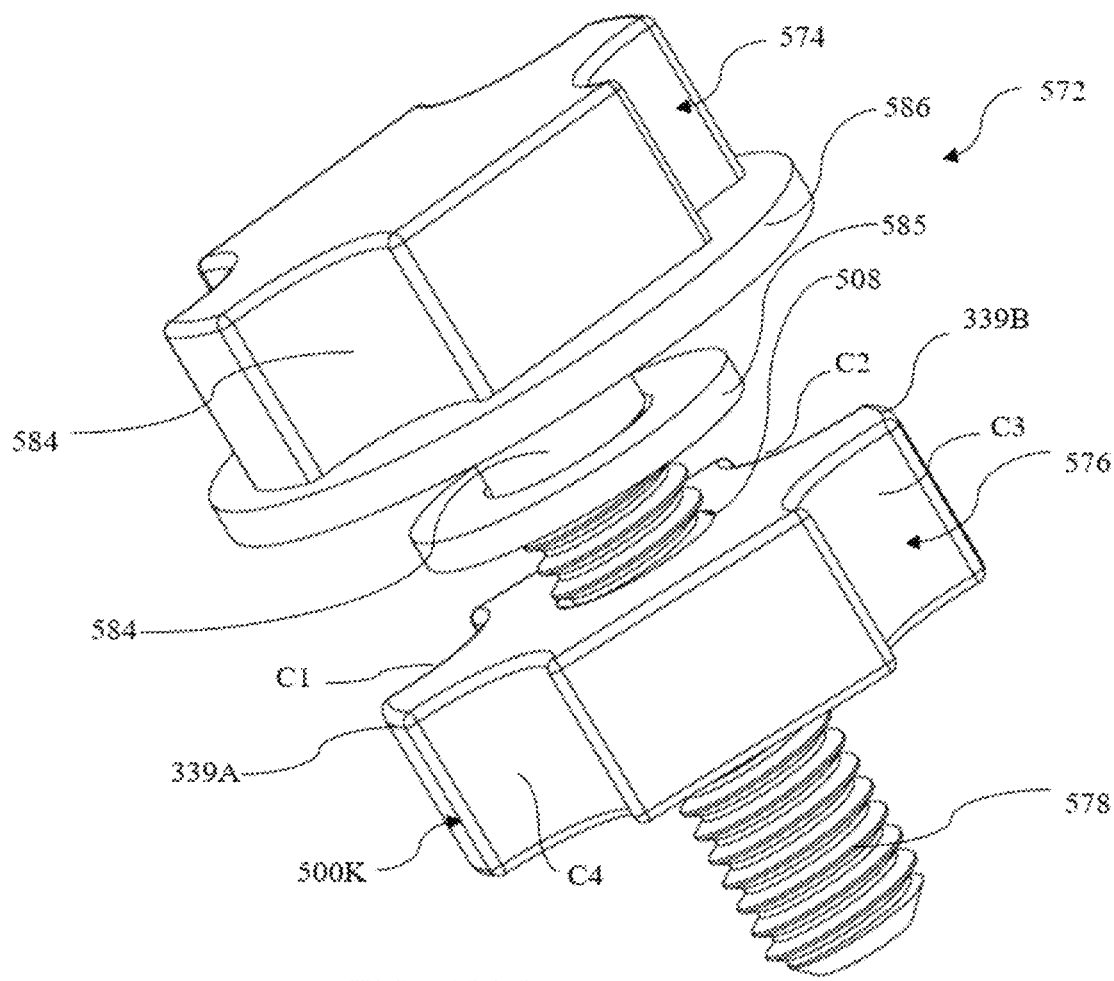

FIG. 188C shows a perspective view of a torque enhancement fastener assembly having the bolt and nut shown in FIGS. 188A and 188B together with a washer.

Figure 189:
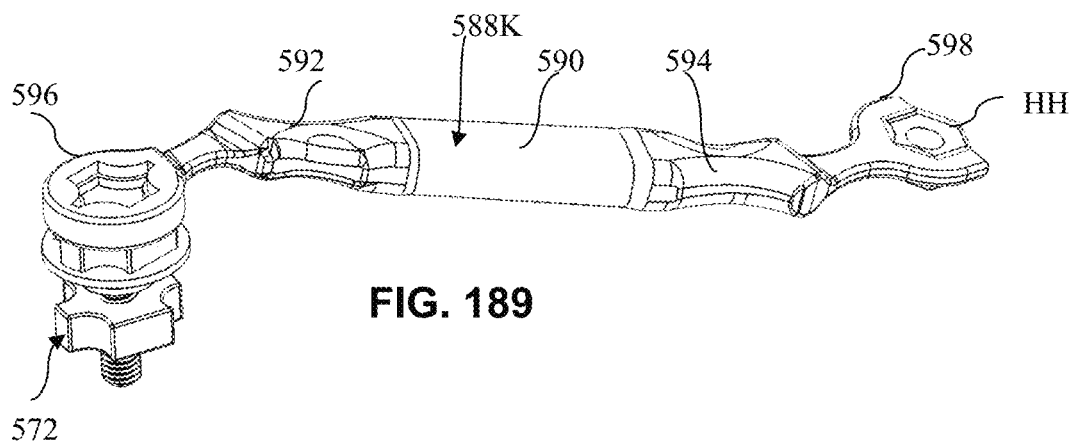

FIG. 189 shows a perspective view of a torque enhancement tool (wrench) in drive communication with torque enhancement fastener assembly of FIG. 188C and another torque enhancement component at the opposite (right) end of the tool.

Figure 189A:
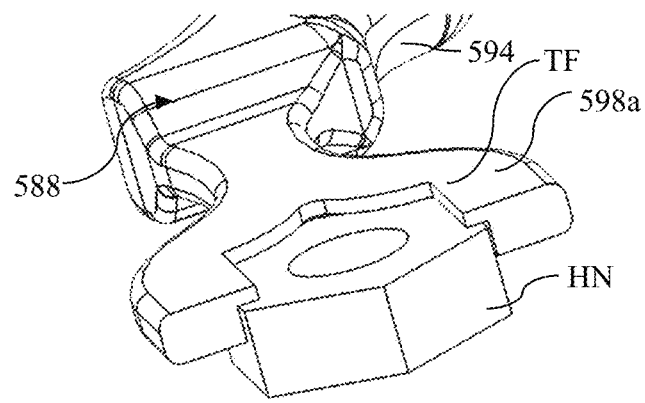

FIG. 189A shows a cut-away enlarged perspective view of the right end of FIG. 189 with an illustration of the wrench end having an internally directed flange shown in a bearing down association with the nut.

Figure 189B:
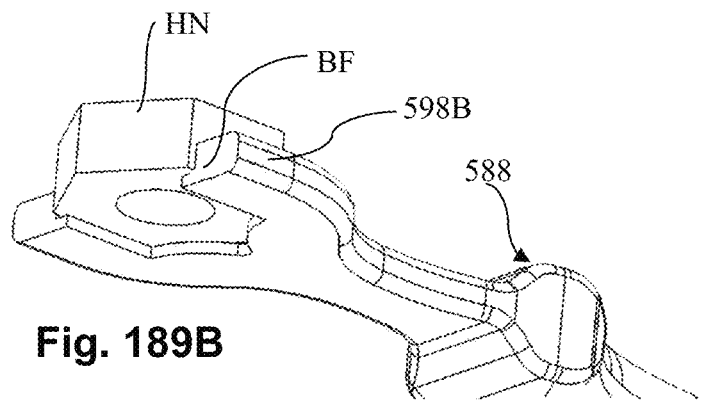

FIG. 189B shows another cut-away enlarged perspective view of the right end of FIG. 189 with an illustration of the wrench end having an internally directed flange shown in an upward retention association with the nut.

Figure 189C:
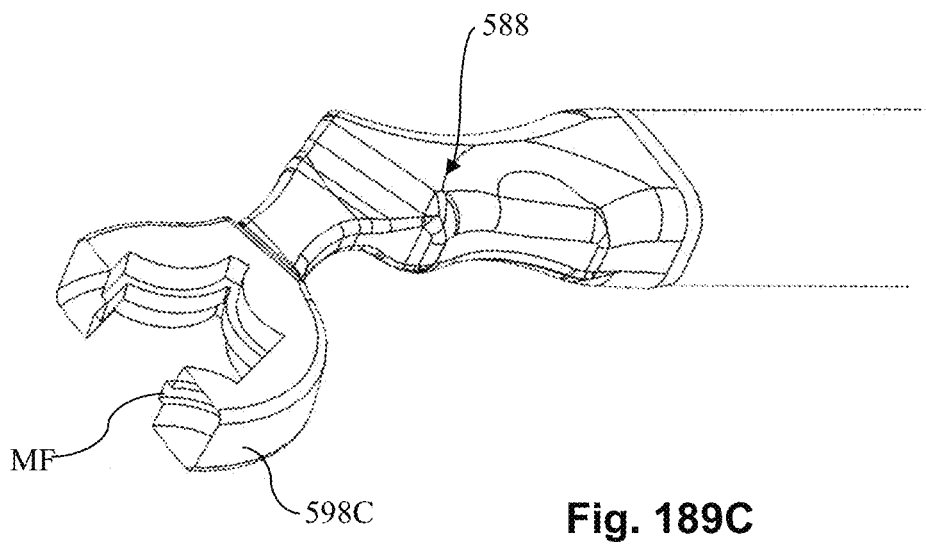

FIG. 189C shows another cut-away enlarged perspective view of the right end of FIG. 189 with an illustration of the wrench end having an internally directed intermediate height flange as to provide for a downward bearing relationship or an upper retention relationship without having to rotate the handle.

FIGS. 190A, 190B and 190C show some different viewpoints of torque enhancement recessed head bolt, with FIG. 190A showing a perspective view, FIG. 190B a front elevational view, and FIG. 190C showing a top plan view.

FIGS. 191A and 191B show an additional example of a torque tool featuring an L-shaped tool that has a torque enhancement cross-section configuration over the full length of the L-shaped tool.

FIGS. 192, 192A to 192D illustrate an additional example of a torque tool which has a general screw driver configuration, but features a torque enhancement driving head and also a torque enhancement finger grasp area. There is also shown a cut away section to designate potential length variation of the shaft as well as the notion that the left side can be a driving head device such as one suited for insertion in a chuck of a drill or air driven tool device.

Figure 193:
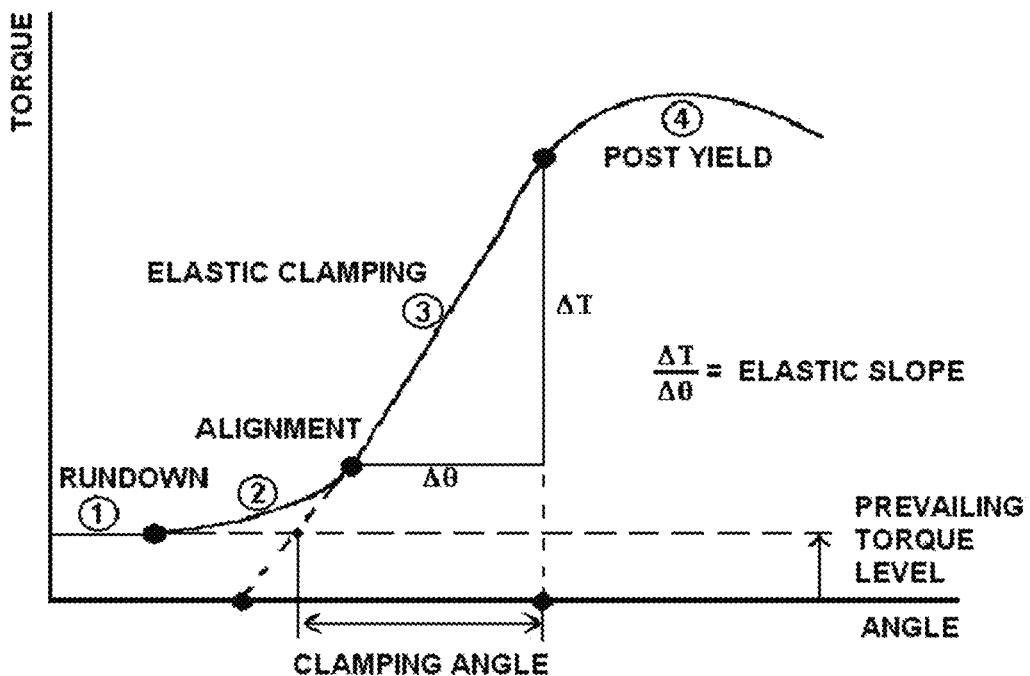

FIG. 193 shows the four zones associated with a fastener tightening process.

Figure 194:
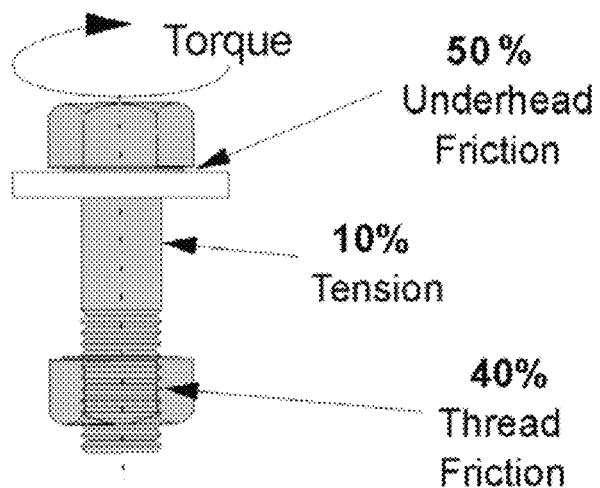

FIG. 194 shows a basic torque distribution for a fastener.

Figure 195:
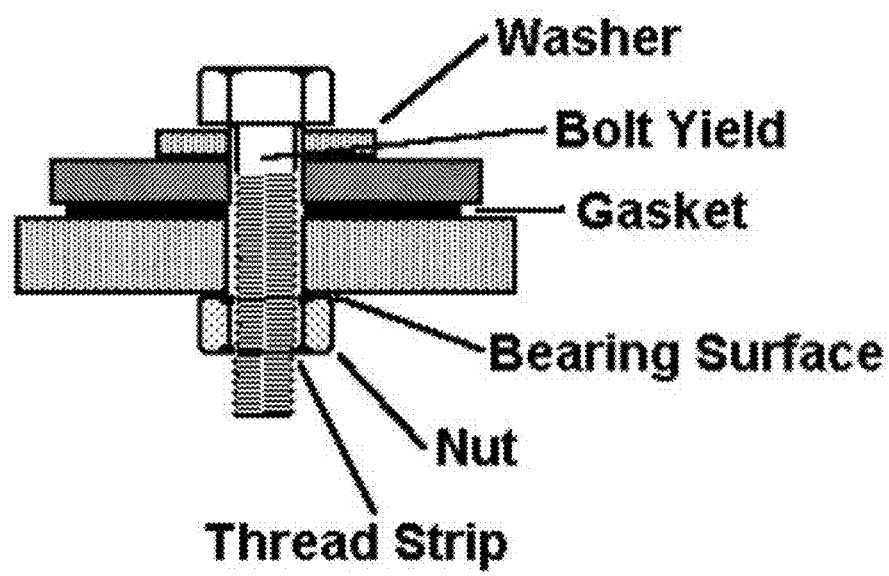

FIG. 195 shows an arrangement that includes additional components that can lead to a variation in the respective four zones.

Figures 196A, 196B:
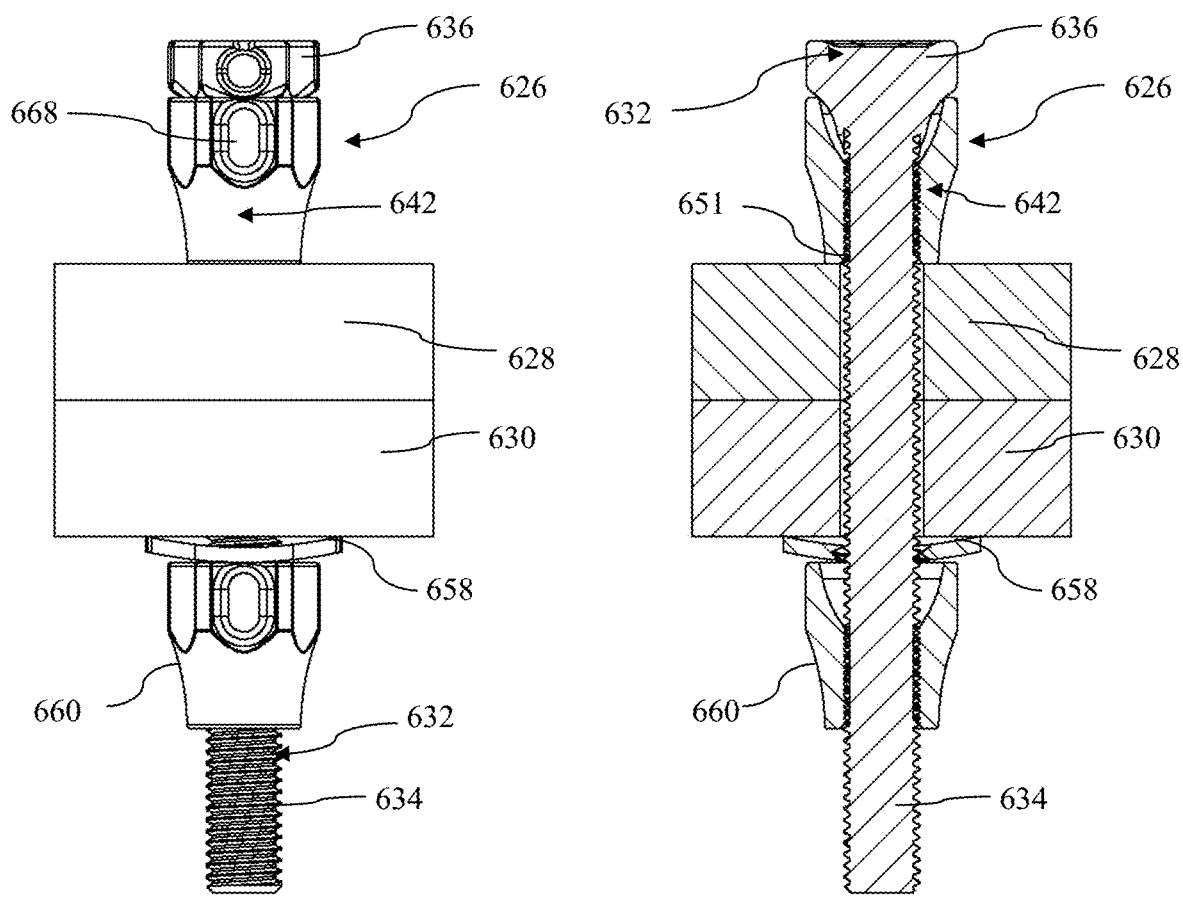

FIGS. 196A and 196B illustrate an example of a fastener assembly comprising multiple torque enhancement components featured under the present invention, with FIG. 196A showing the assembly in an initial assembly state and FIG. 196B showing the same assembly in cross-section.

FIG. 196C shows a perspective view of the "long" threaded bolt (with torque enhancement head) featured in the assembly of FIG. 196A.

FIG. 196D shows a front elevational view of the "long" threaded bolt (with torque enhancement head) shown in FIG. 196C.

FIG. 196E shows a front elevational of an alternate bolt configuration with head-shaft convergence threading.

Figure 197A:
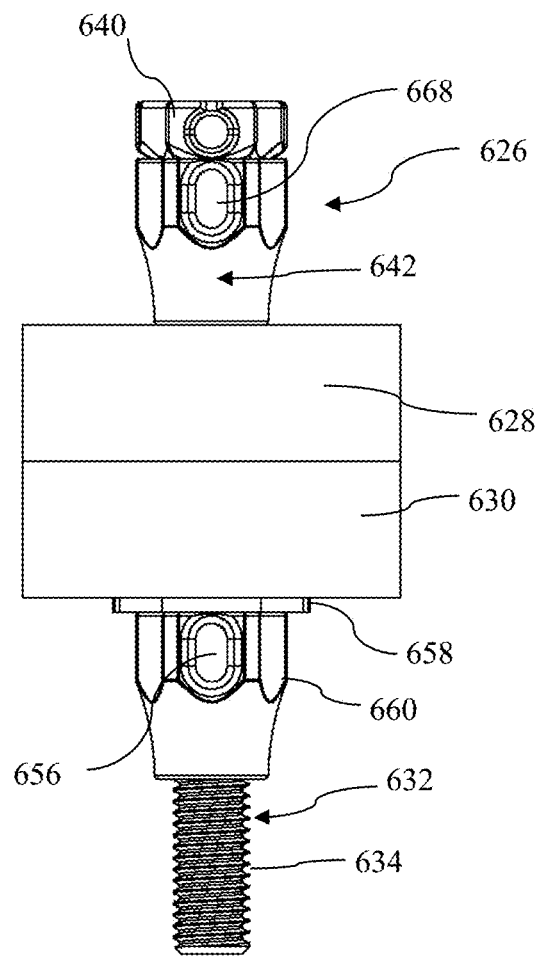
Figure 197B:
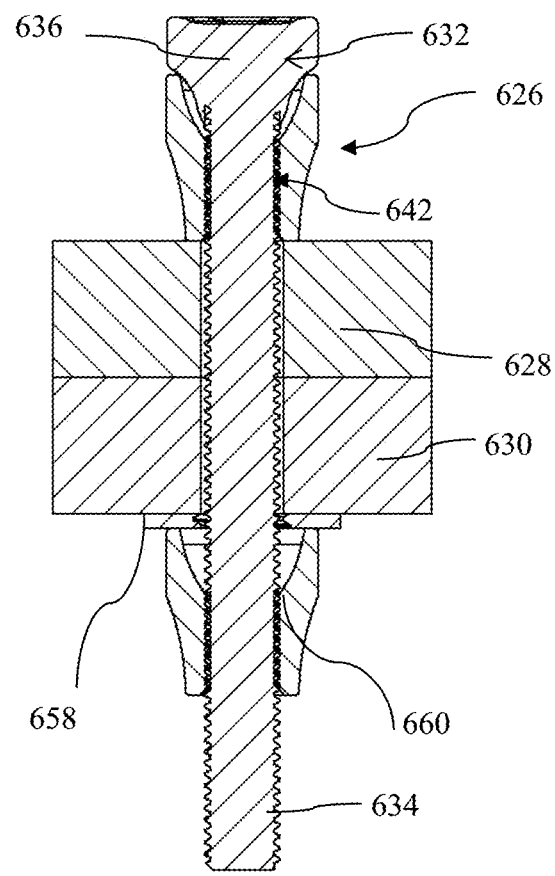

FIGS. 197A and 197B illustrate the same assembly featured in FIG. 196A, with FIG. 197A showing the assembly in a finalized state of assembly, and FIG. 197B showing the same assembly in cross-section.

Figure 198B:
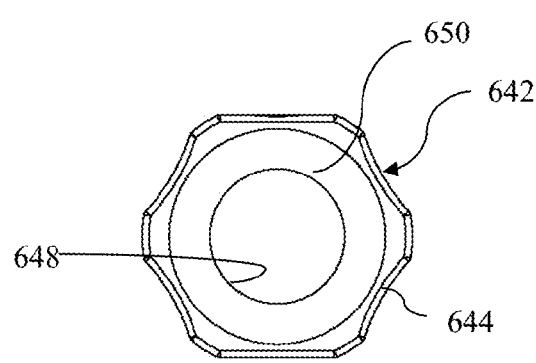
Figure 198A:
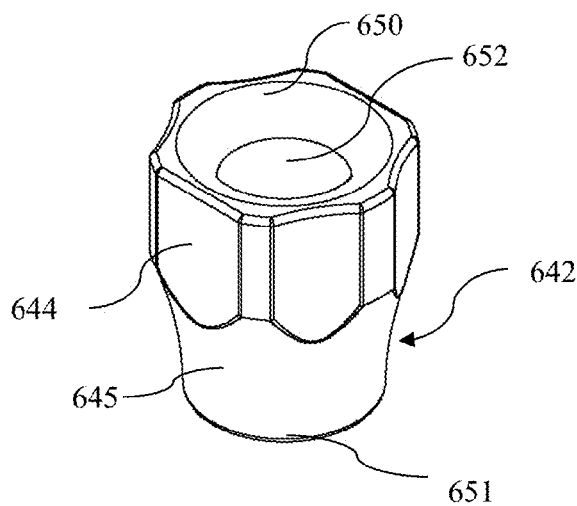
Figure 198C:
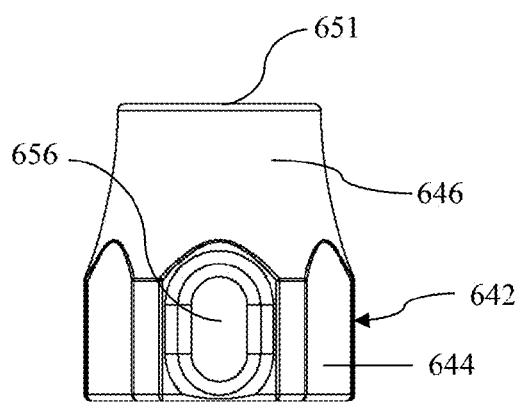
Figure 198D:
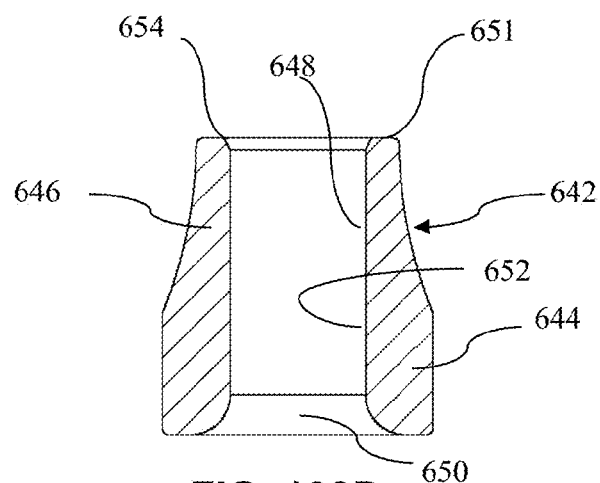
Figure 198E:
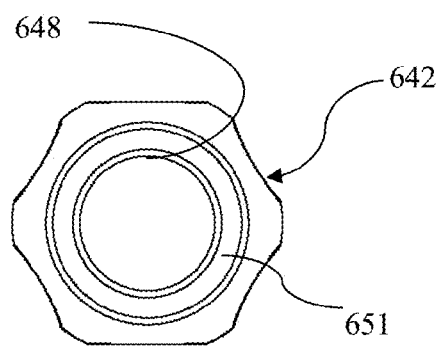
Figure 198F:
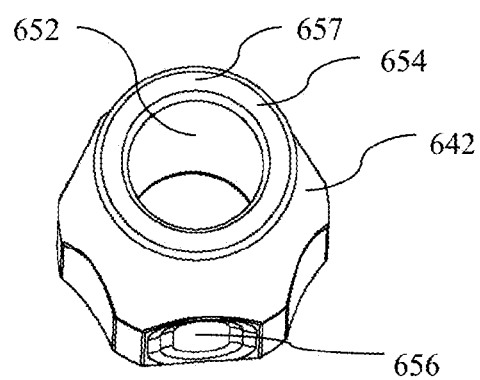

FIGS. 198A to 198F illustrate a first engagement member used in the assembly of FIG. 196A that has an exterior similar to that shown in FIG. 162, but with these figures showing an interior design different than that noted FIG. 162 (e.g., free of interior threading), with the first engagement member being illustrated, respectively, in: FIG. 198A as a top perspective view (as oriented for use in the assembly of FIG. 196A);

FIG. 198B a top plan view; FIG. 198C a flipped front elevational view; FIG. 198D a flipped cross-sectional view; FIG. 198E a bottom plan view; and FIG. 198F a bottom perspective.

FIGS. 199A to 199F show a washer utilized in the assembly of FIG. 196A which has an outer peripheral contour with the torque enhancement configuration, with the washer shown (relative to its in use orientation shown in FIG. 196A), respectively, in: FIG. 199A a top perspective view; FIG. 199B a flipped bottom perspective view; FIG. 199C a front elevational view; FIG. 199D a flipped front elevational view; FIG. 199E a top plan view; and FIG. 199F a flipped cross-sectional view.

FIGS. 200A to 200F show a second engagement component, which shares some similarities with the aforementioned first engagement component in FIG. 198A, but includes a threaded interior, with FIG. 200A showing the second engagement component in a flipped over (relative to the manner of use shown in FIG. 196A) such that its first (in use upper) end is in a below position for added visualization of the cup-shaped or truncated semi-spherical opening provided therein, with the remainder of the figures showing: in; FIG. 200B a front elevational view thereof; FIG. 200C a cross-sectional view thereof; FIG. 200D a bottom plan view thereof; FIG. 200E a top plan view thereof; FIG. 200F a top perspective view thereof.

FIGS. 200G to 200I show a sequenced insertion method wherein FIG. 200G shows an initial insertion of the fastener assembly bolt into the cup region of the second engagement component shown in 220F; FIG. 200H a centering and initial threading of the bolt into the second engagement component, and FIG. 200I shows the completely threaded state wherein the tapered region of the bolt head-shaft interface is nested within the non-threaded cavity of the second engagement component (as against an elastomeric seal or seal paste)

Figure 201:
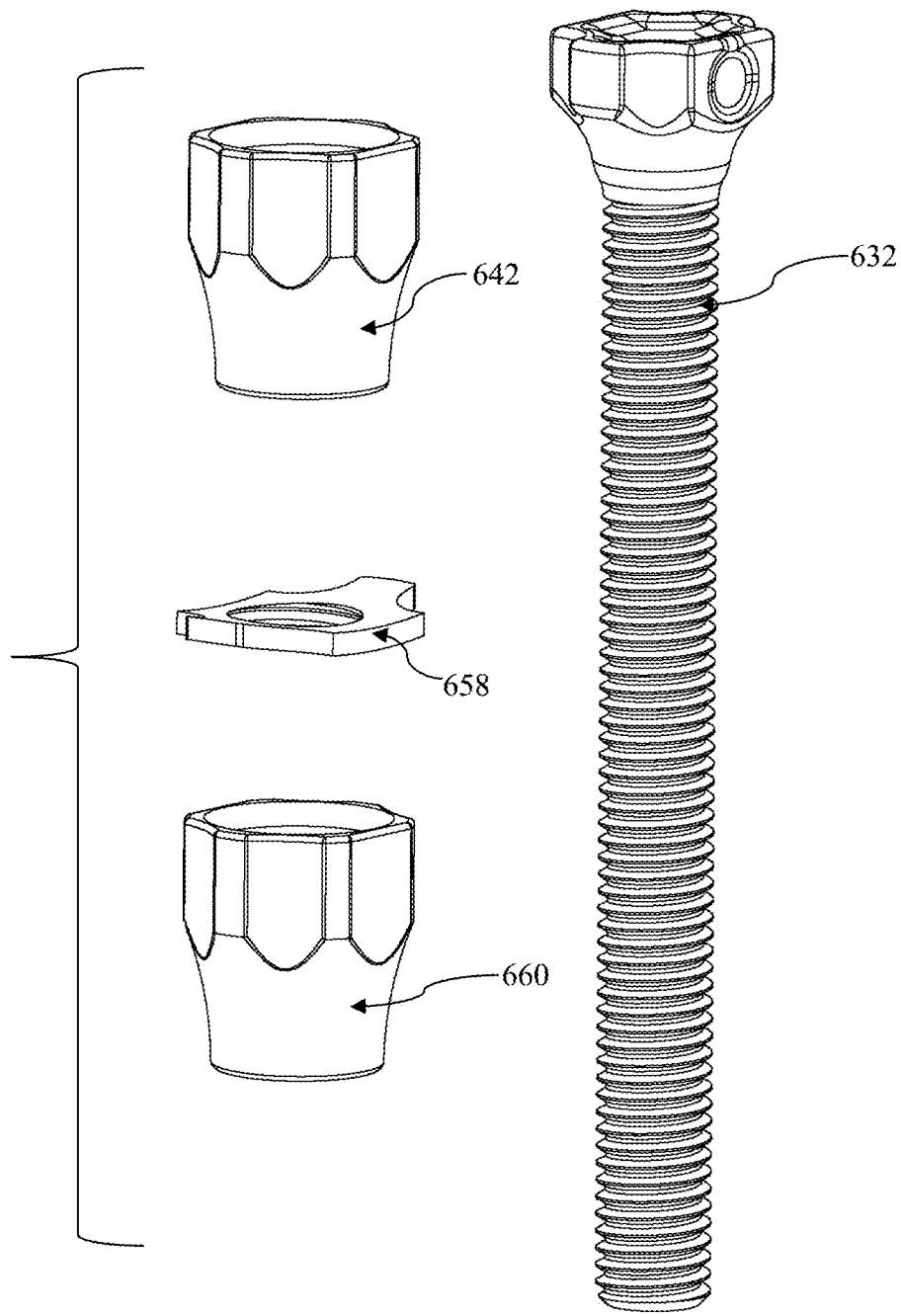

FIG. 201 shows a fastening assembly kit set of components suited for clamping structures, which kit includes the above referenced first and second engagement components and associated threaded bolt and washer.

FIGS. 202A to 202E show a hollow bolt configuration which includes torque enhancement features and is well suited for use in a fastener assembly combination, with FIG. 202A showing a perspective view of the torque enhancement hollow bolt, FIG. 202B showing a perspective cross-sectional view thereof, FIG. 202C showing a front elevational view thereof, FIG. 202D showing a front elevational cross-sectional view thereof, and FIG. 202E showing a top plan view thereof.

FIGS. 203A to 203D show a fastener assembly which is inclusive of the hollow bolt of FIG. 202A as a fastener component used in the fastening of stacked structural components relative to a bearing sleeve, with FIG. 203A showing the completed assembly in front elevational, FIG. 203B showing a cross-sectional view of thereof; FIG. 203C showing an exploded (initial assembly) view thereof, and FIG. 203D a cross-sectional view of FIG. 203C.

Figure 204A:
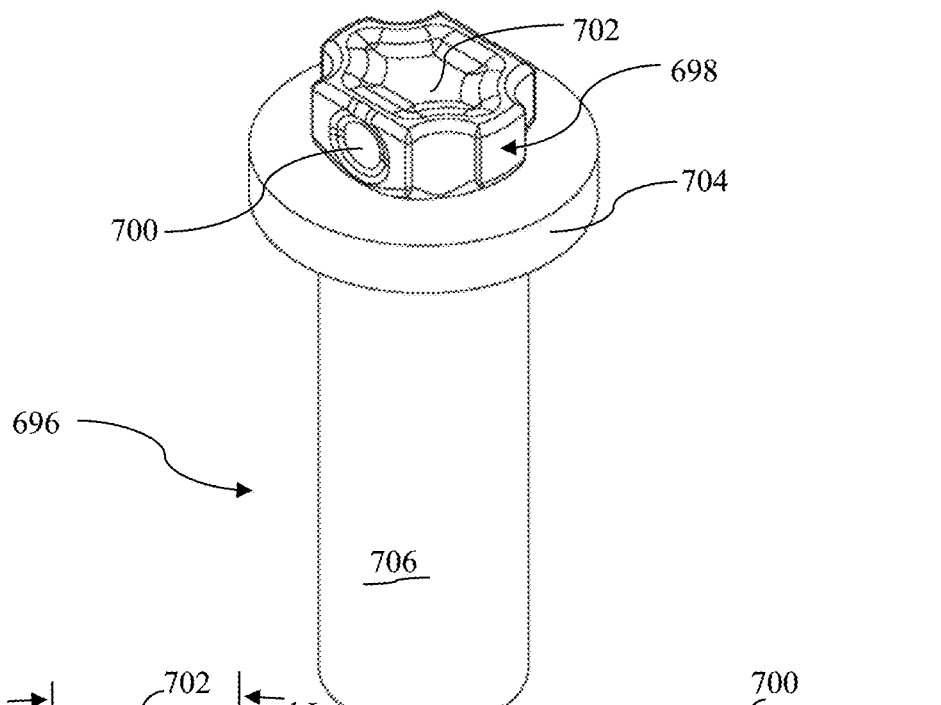
Figures 204B, 204C:
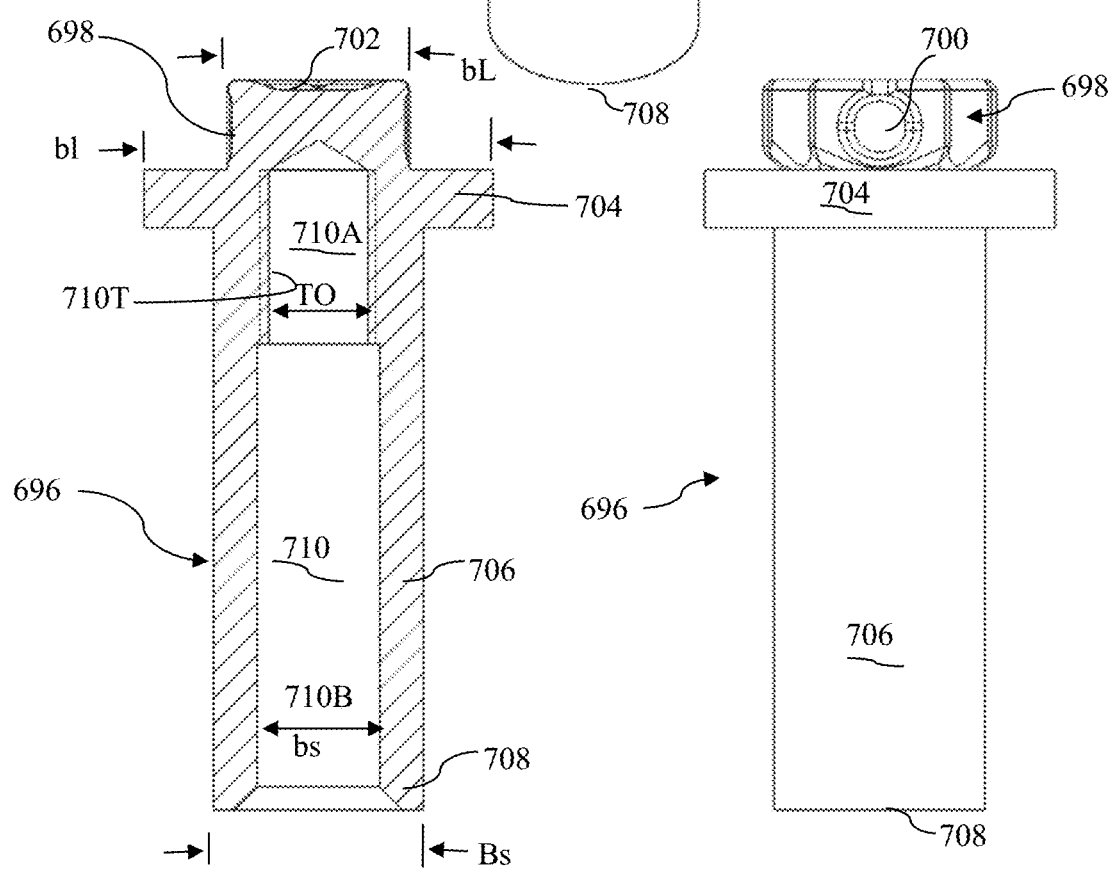

FIGS. 204A to 204C show views of the bearing sleeve noted for the assembly of FIG. 203A, with FIG. 204A showing a perspective view thereof; FIG. 204B a front elevational, and FIG. 203C a cross-sectional view of FIG. 204B.

Figures 205A, 205B, 205C:
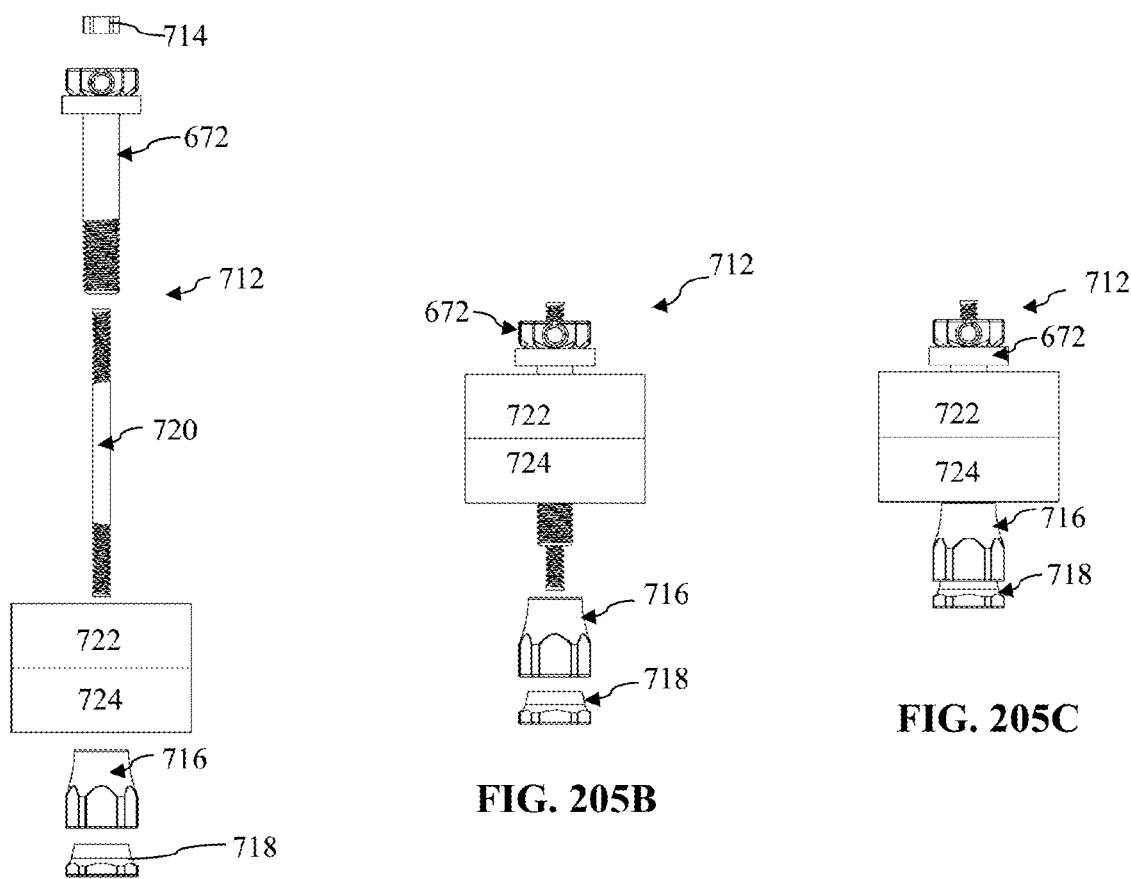

FIGS. 205A to 205C show: FIG. 205A a fully exploded view, FIG. 205B a partially exploded view, and FIG. 205C an assembled view, for an additional fastener assembly embodiment of the invention which includes some components previously described for the other fastener assembly arrangements, some new components (with both new and earlier described components including those having a torque enhancement configuration, inclusive of a beneficial stacked arrangement between two nesting torque enhancement components).

Figure 206A:
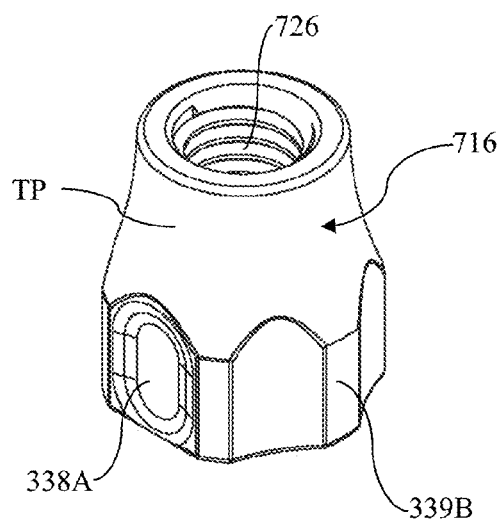
Figure 206B:
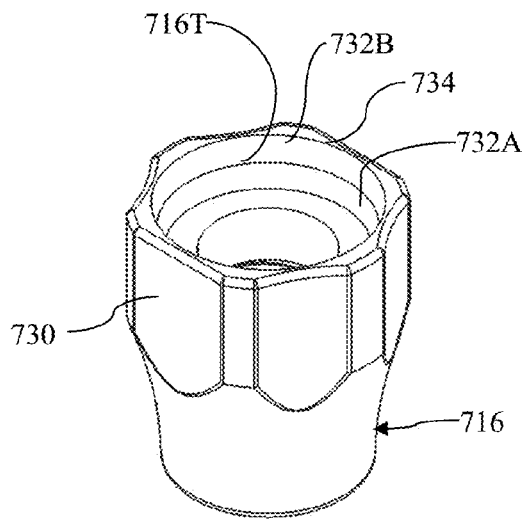

FIGS. 206A to 206D show another engagement component, which shares some similarities with the aforementioned engagement component in FIG. 200A, and thus includes a threaded interior, but also features a stepped recess rather than the bowl recess of FIG. 200A, with FIG. 206A showing a perspective in use (for the below described embodiment) orientation; FIG. 206B showing a flipped over perspective orientation showing the stepped recess thereof, FIG. 200C a cross-sectional view thereof; FIG. 200D a plan view looking down on the stepped recess.

Figure 207C:
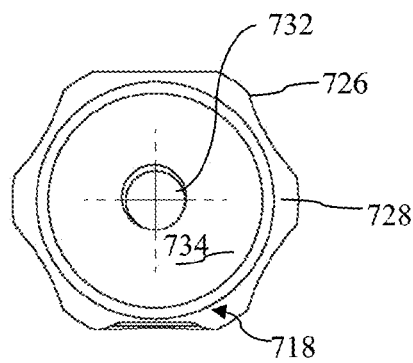
Figure 207D:
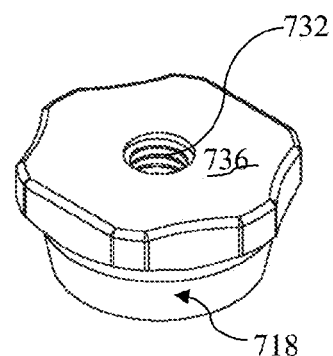
Figure 207E:
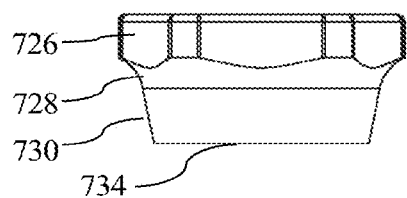
Figure 207B:
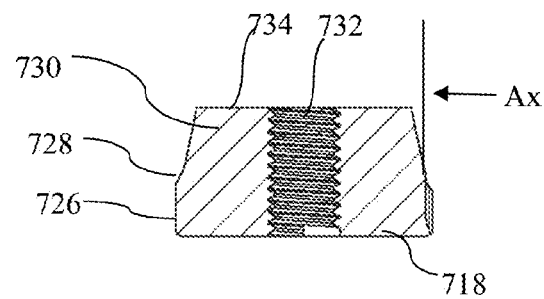
Figure 207F:
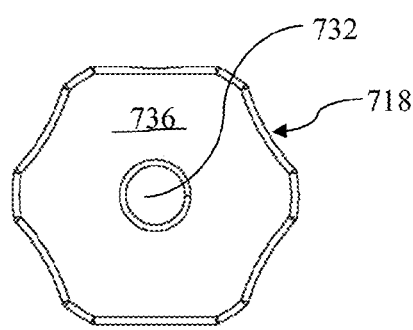
Figure 207A:
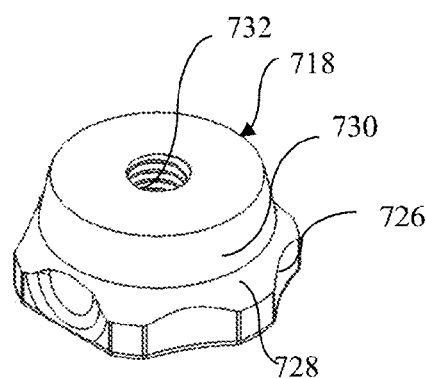

FIGS. 207A to 207F show a torque enhancement (internal thread only) button member embodiment in various views which are summarized as follows: FIG. 207A perspective view of the "in use" orientation shown in FIG. 205A, FIG. 207B a cross-sectional view thereof, FIG. 207C a top plan view thereof, FIG. 207D a flipped over perspective view; FIG. 207E a front elevational of the flipped over orientation, and FIG. 207F a plan view of the flipped over orientation.

Figures 208A, 208B:
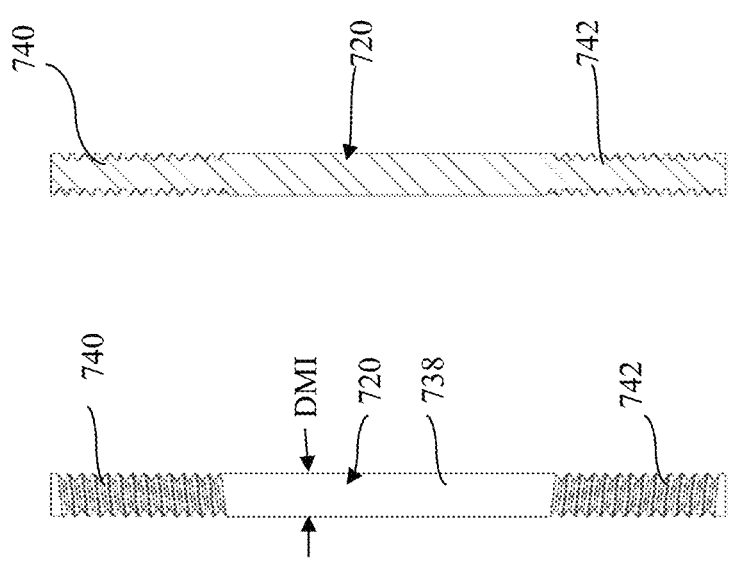

FIGS. 208A and 208B illustrate a threaded shaft having a central non-threaded region and end threaded sections for use as a relatively small diameter tensioning member in a fastener assembly.

Figures 209A, 209B, 209C:
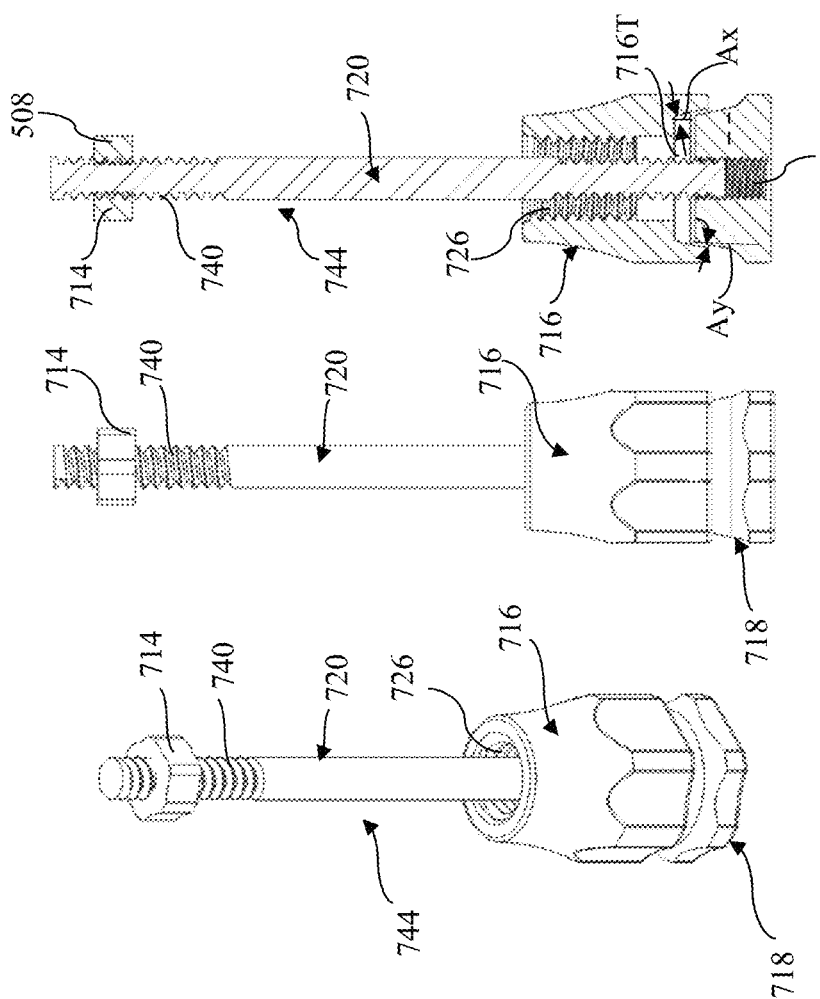

FIGS. 209A, 209B and 209C illustrate a sub-assembly of that which is shown as a full assembly in FIG. 207C (with the sub-assembly being devoid of a bolt and the stacked structural components in FIG. 207C), with FIG. 209A showing a perspective view, FIG. 209B a front elevational view and FIG. 209C a cross-section of FIG. 209B (again inclusive of torque enhancement members in a stacked and nesting relationship).

FIGS. 210A to 210C illustrate an additional fastener assembly sharing some similar components as in the other fastener assemblies, with FIG. 210A showing a fully exploded view, FIG. 210B showing a point still not fully assembled, but closer than FIG. 210A, and with FIG. 210C showing a full compression state and with cupped washer collapsed in similar fashion to the earlier described embodiments.

Figure 211:
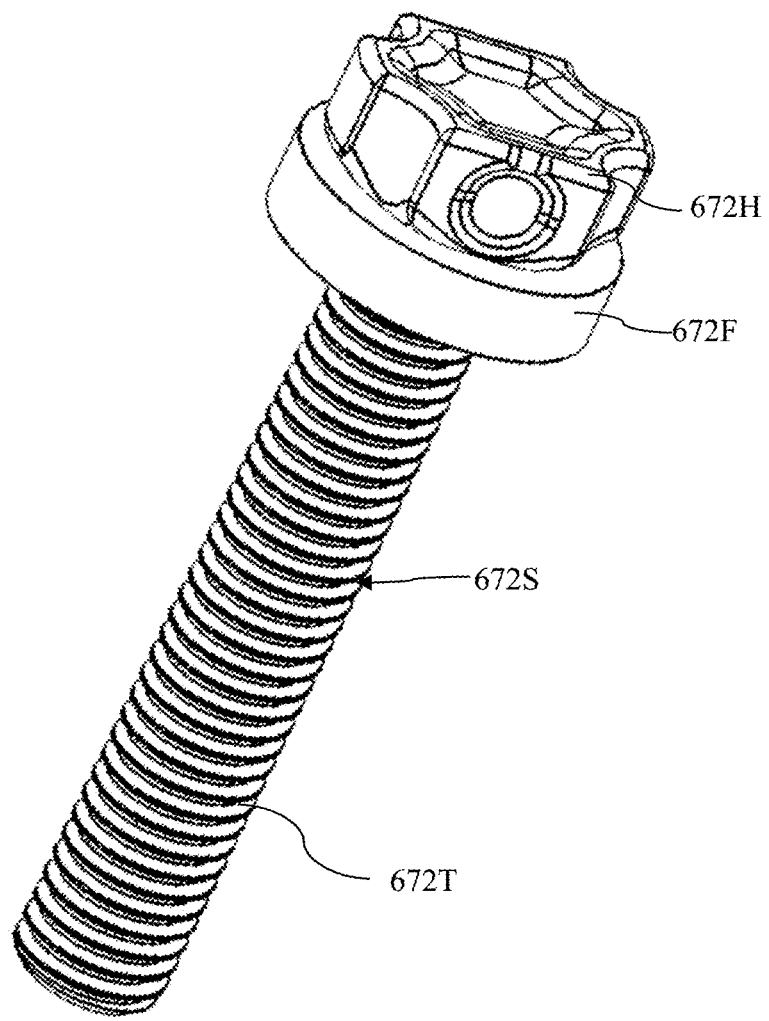

FIG. 211 shows a perspective view of a modified bolt which is a solid version of the earlier described hollow bolt of FIG. 202A (with added threading, but with a common flange washer and common bolt head as in the earlier described hollow bolt).

Figure 212:
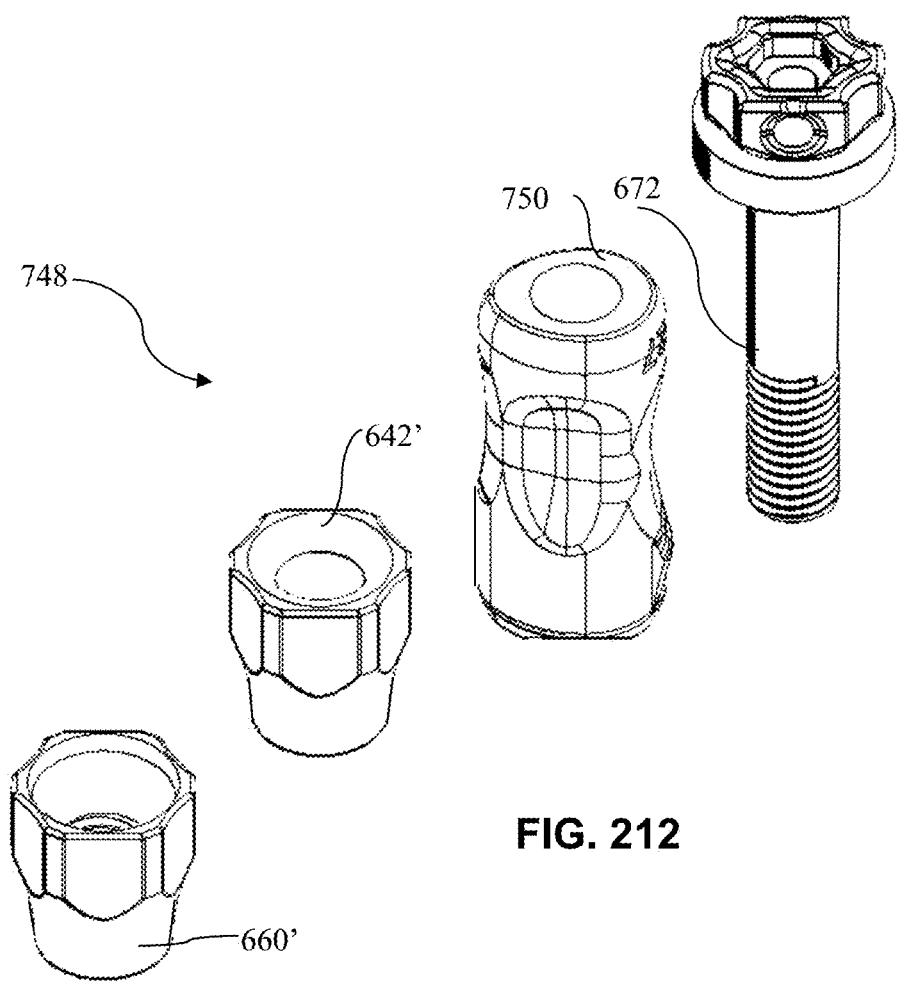

FIG. 212 illustrates an additional fastener assembly in pre-assembly or kit form sharing some similar components (although in a rearranged arrangement) as the previously described invention fastener assemblies as well as a newly introduced component.

FIGS. 213A to 213D show the fastener assembly of FIG. 212 in various states, with FIG. 213A showing the components in an aligned, but not yet assembled state, FIG. 213B shows both a compressible (e.g., elastomeric) insert and the hollow bolt of the kit of FIG. 212 having been inserted into aligned holes formed in each of a pair of stacked structural components as well as a pair of engagement members received on the threaded bolt, but not yet fully assembled; FIG. 213C shows a fully assembled state, and FIG. 213D shows a cross sectional view of that fully assembled state (inclusive of a beneficial nested, stack relationship among torque enhancement members).

Figure 214A:
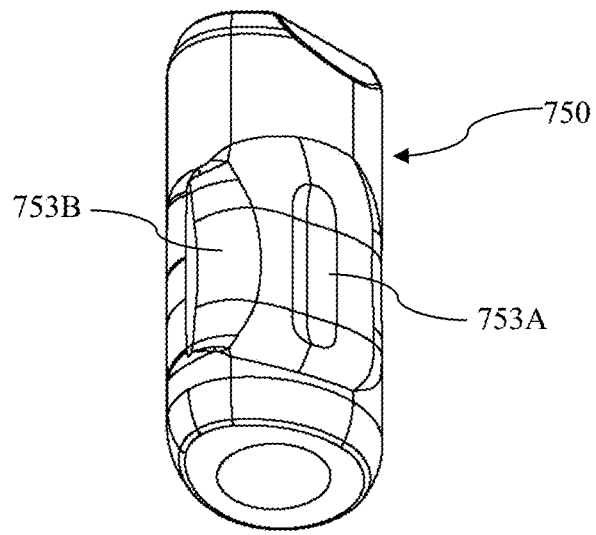
Figure 214B:
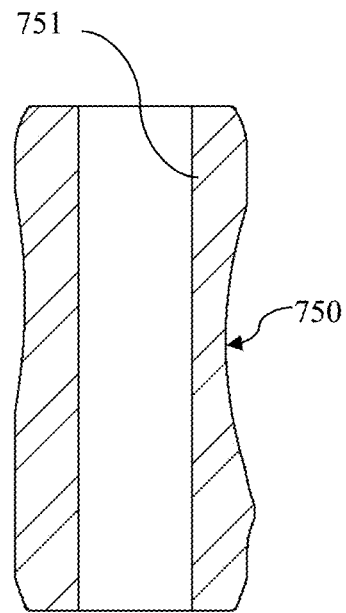

FIGS. 214A and 214B show an example of the insert of the kit in FIG. 212 in the form of a non-symmetrical sleeve (both axially and radially non-symmetric as provided by the various contouring shown).

Figure 1:
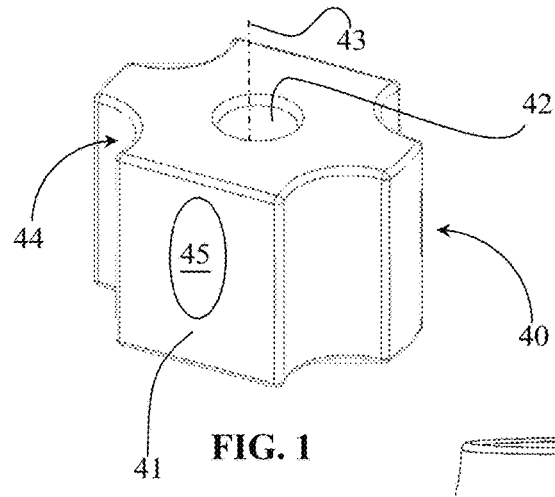
FIG. 1 shows detail of a torque enhancement device in a collar configuration according to a first embodiment of the invention.
Figure 215A:
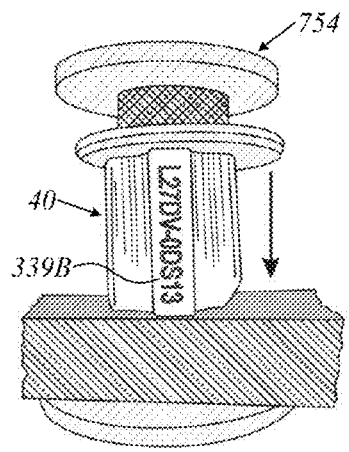
Figure 215B:
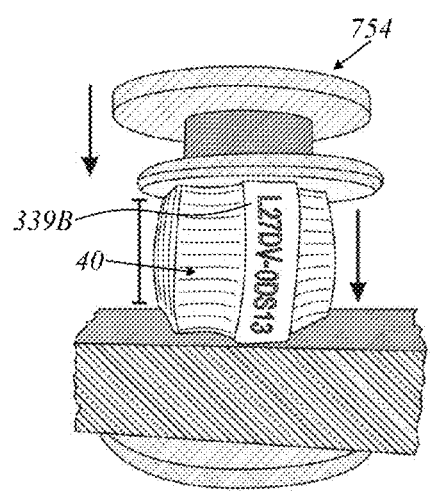
Figure 215C:
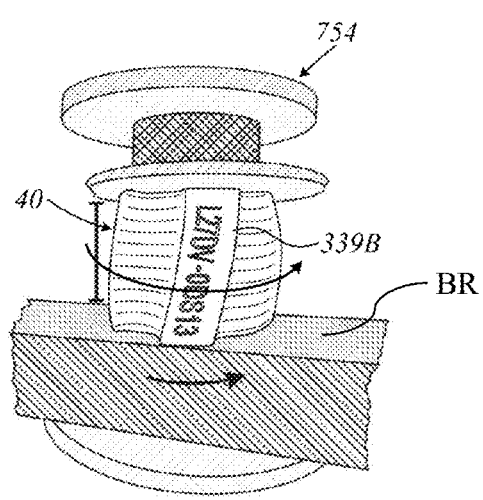

FIGS. 215A to 215D show the torque enhancement member of FIG. 1 in position relative to a combination compression and torsion generator test set up, with FIG. 215A showing the initial contact state (initial compression only), FIG. 215B a full-compression/pre-torsion state; FIG. 215C a full-compression, counterclockwise torsion state, and FIG. 215D a full-compression, clockwise torsion state.

FIGS. 216A to 216C show the torque enhancement member of FIG. 1 in position relative to a compression test set up, with FIG. 216A showing pre-initial contact state, FIG. 216B an initial compression contact state, and FIG. 216C a full compression state.

Figures 217A, 217B:
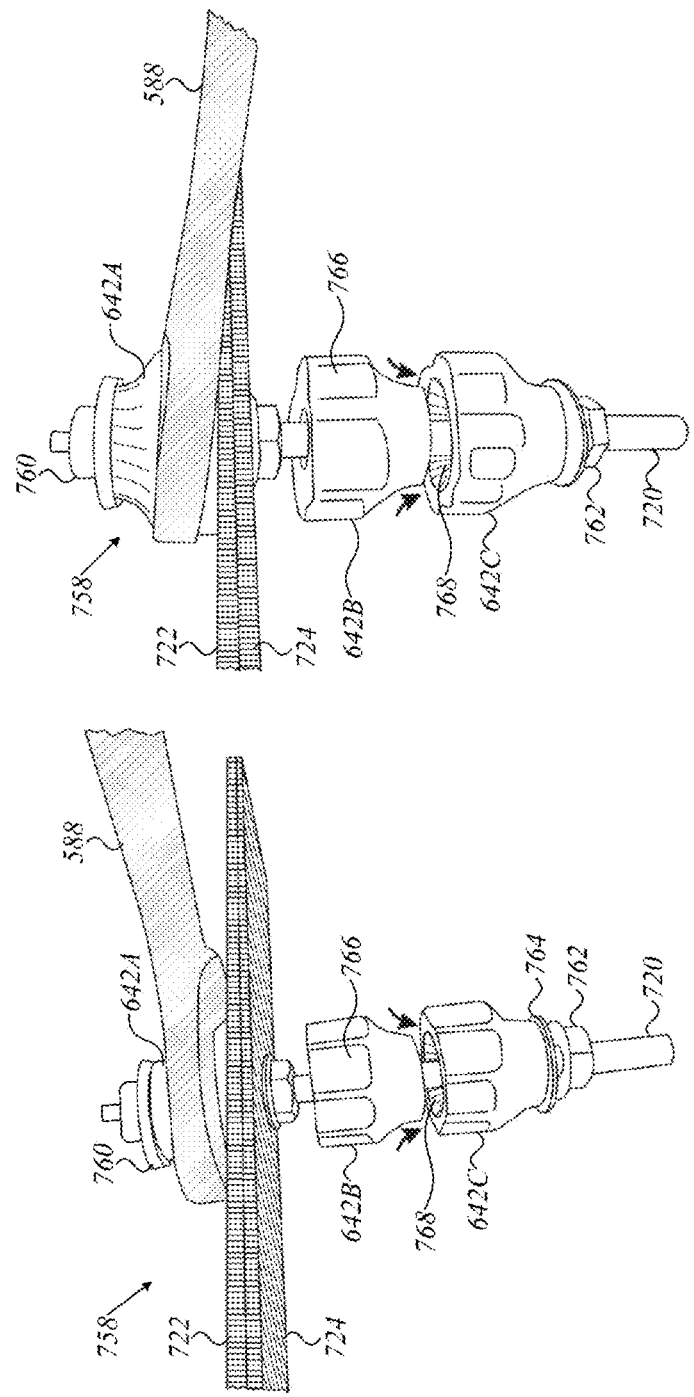

FIGS. 217A to 217B illustrate an additional fastener assembly involving torque enhancement components of the present invention in the same assembly state but from two different viewpoints.

Figure 218:
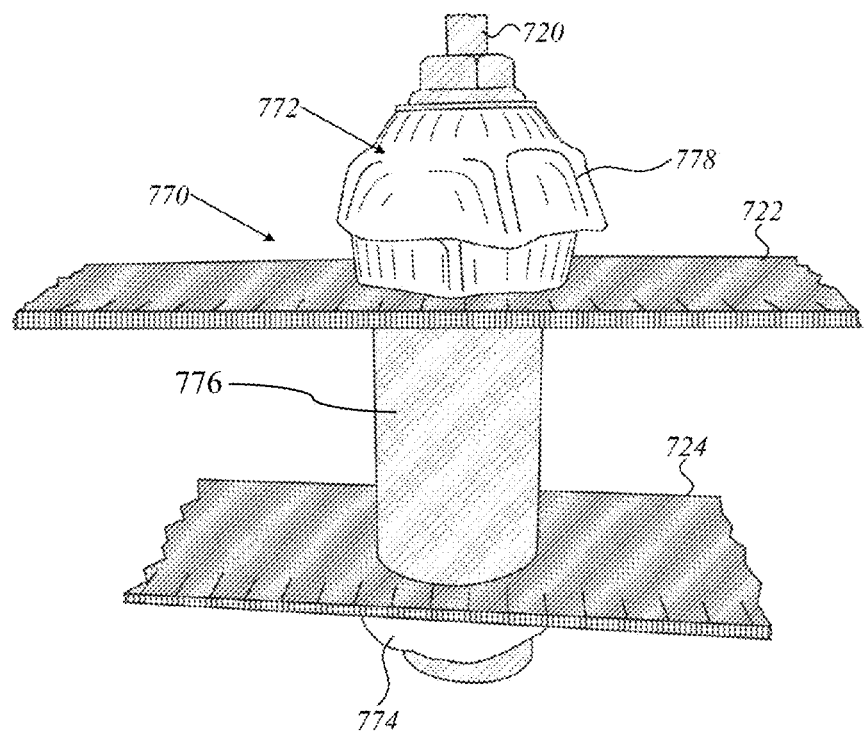

FIG. 218 shows an additional fastener assembly (in a completed assembly state) suited for connection of two structural components that are separated from one another by a cylindrical sleeve.

Figure 219A:
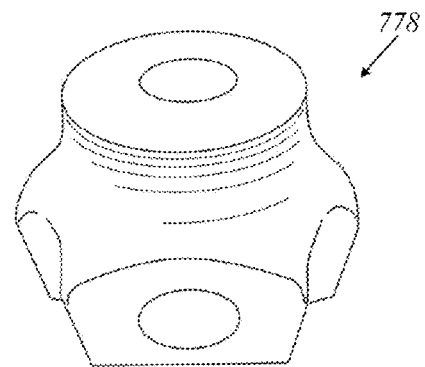
Figure 219B:
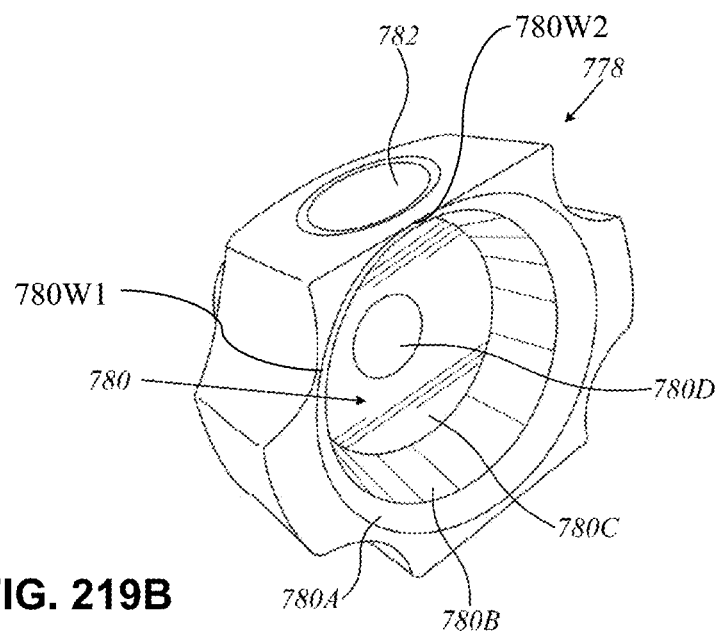

FIGS. 219A and 219B show different views of the engagement component shown in FIG. 218 in a compressed state relative to the exterior, upper surface of top separated structural component.

Figure 220A:
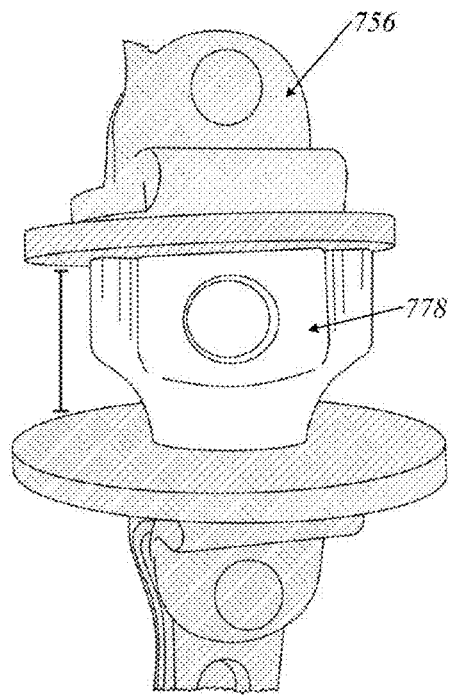
Figure 220B:
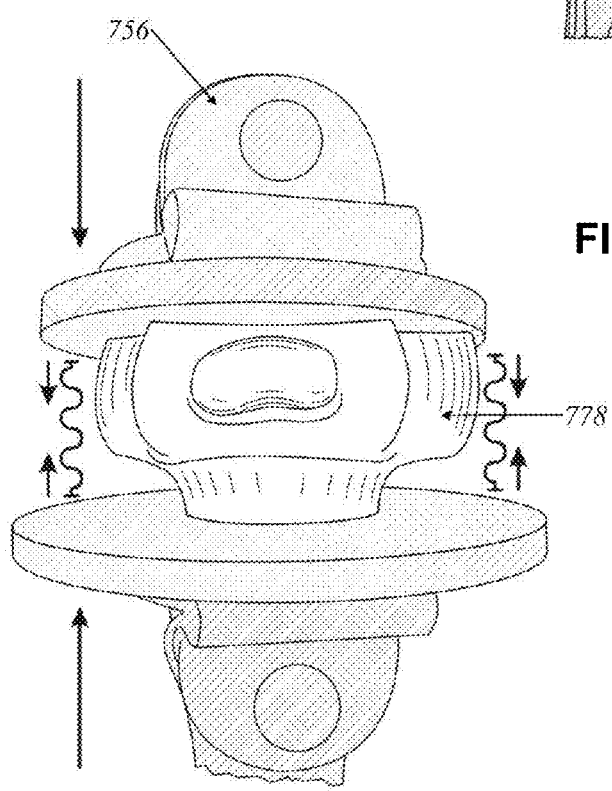

FIGS. 220A and 220B show the engagement component of FIG. 219A with FIG. 220A showing an initial contact state relative to a compression test assembly, and FIG. 220B a compressed (compression deformed) state following compression by the test assembly.

Figure 221A:
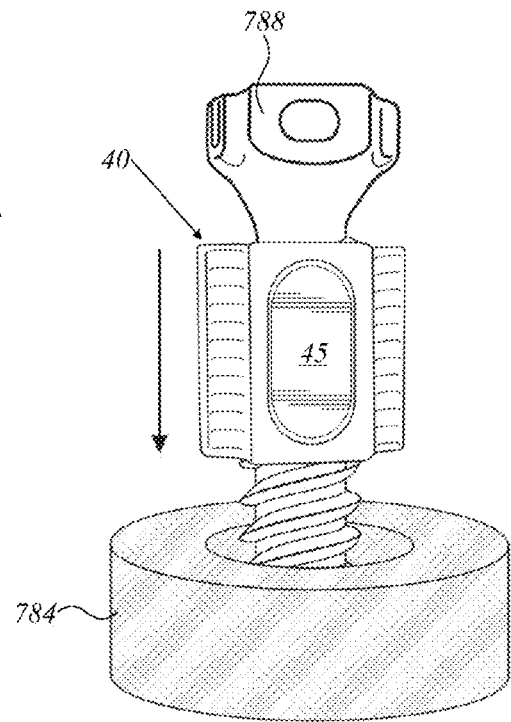
Figure 221B:
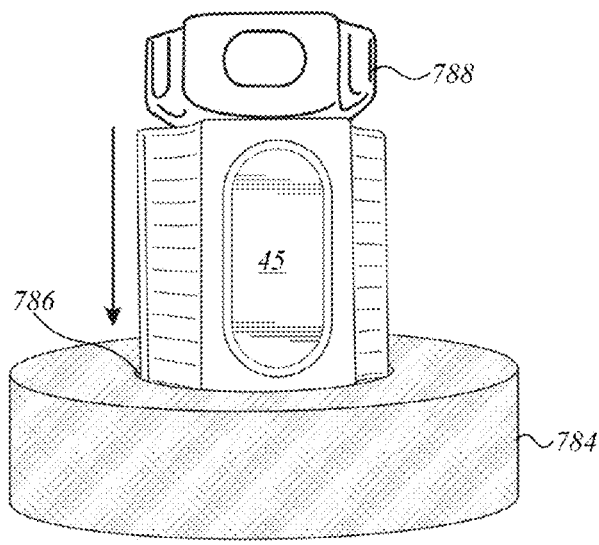

FIGS. 221A and 221B show a combination torque enhancement collar and bolt assembly that is shown prior to reception in a receiving hole of an annular ring in FIG. 221A, and having been received in FIG. 221B.

Figure 222C:
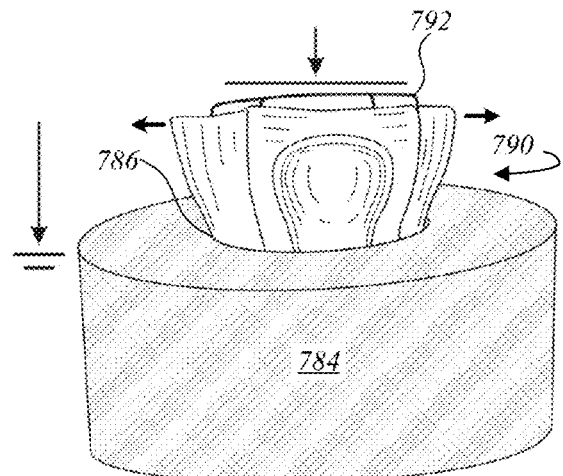
Figure 222B:
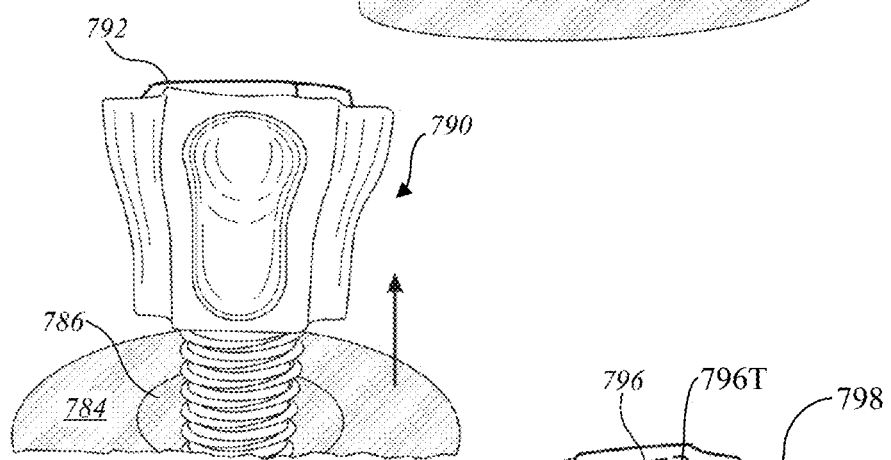
Figure 222A:
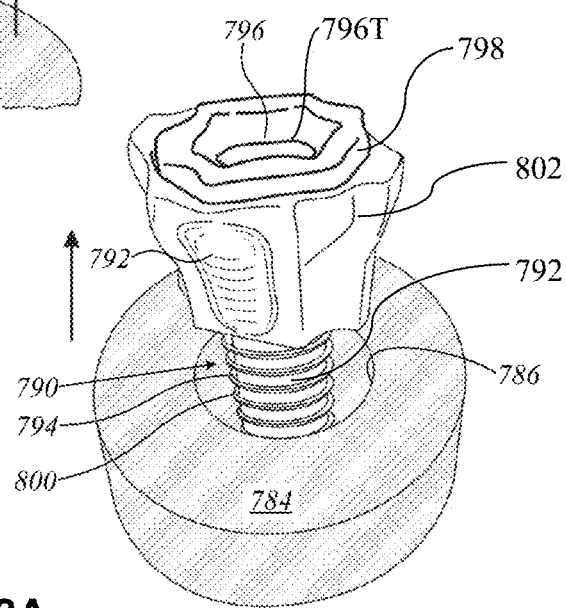

FIGS. 222A to 222C show a bolt or rod assembly having a modified torque enhancement "elephant foot" head comprised of the bolt shown in FIG. 221A received in a head sleeve also having a torque enhancement periphery (another example of a nested/stack combination of torque enhancement members), with the assembly designed for reception within a hole such as the hole presented by the illustrated receiving annular ring, with FIG. 222A showing a pre-full insertion state from a first view point; FIG. 222B also showing a pre-full insertion state from a different viewpoint, and FIG. 222C showing an insertion state between the noted components.

Figure 223:
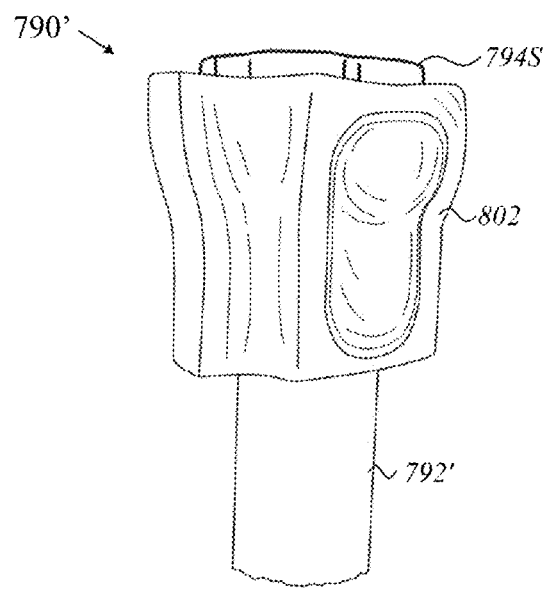

FIG. 223 shows a similar bolt or rod as that of FIG. 222A, but with a cut-away, non-threaded shaft (e.g., fully non-threaded).

Figure 224A:
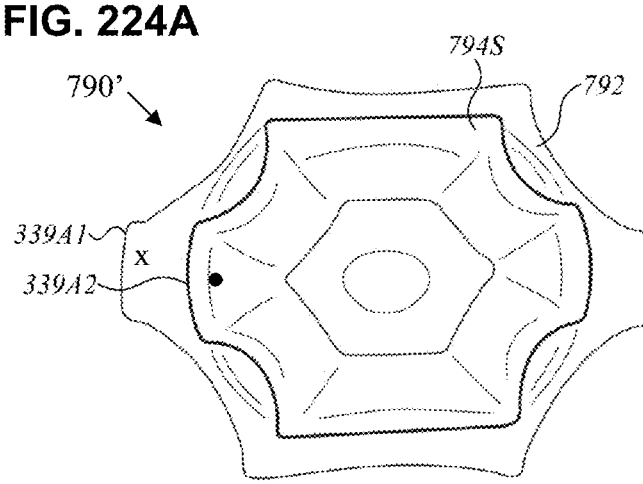
Figure 224C:
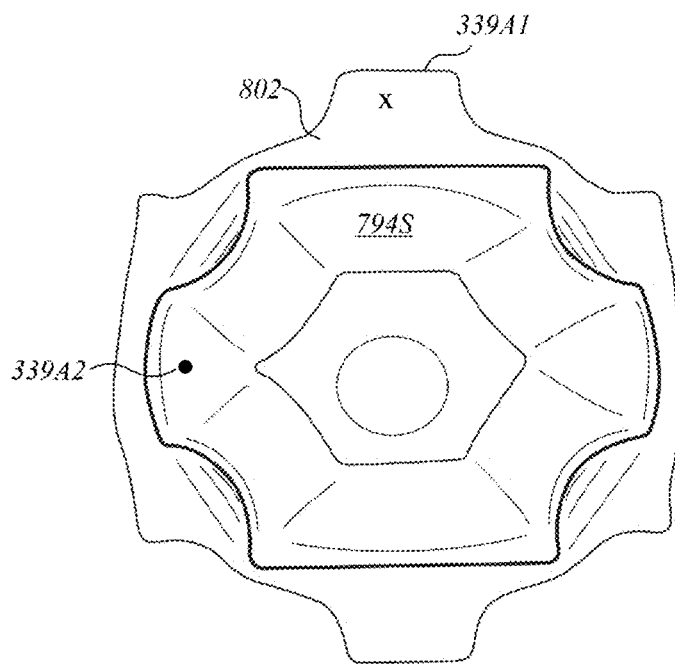
Figure 224B:
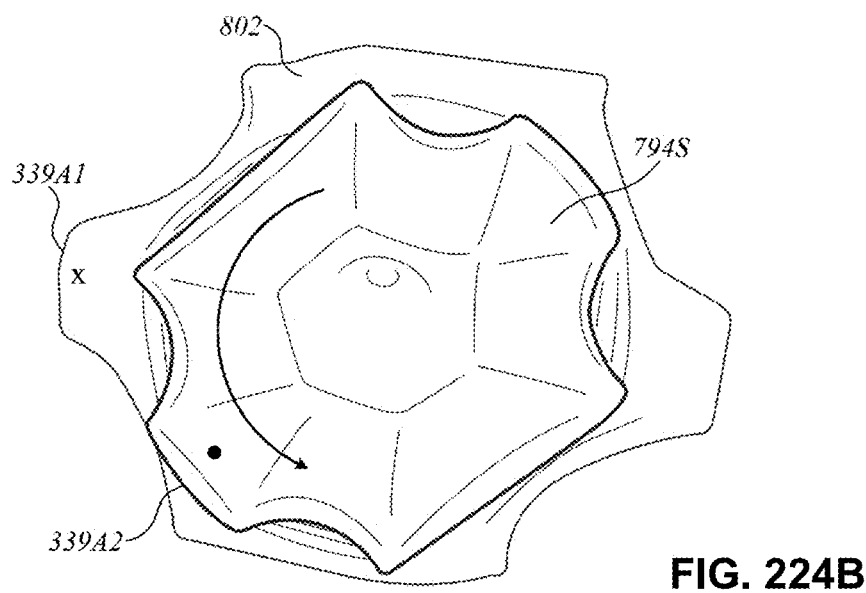

FIGS. 224A to 224C illustrate the same assembly as shown in FIG. 222A, but in different states of relative relationship between the bolt and sleeve, with FIG. 224A shown in a nested compression relationship in a hole (as shown in perspective in FIG. 222C), with FIG. 224B shown with the bolt further rotated and moved axially as by a thread drive as to assume a 45° offset relative to the state in FIG. 224A, and with FIG. 224C shown as having a relative rotation of a still further 45° (90° total).

Figure 225:
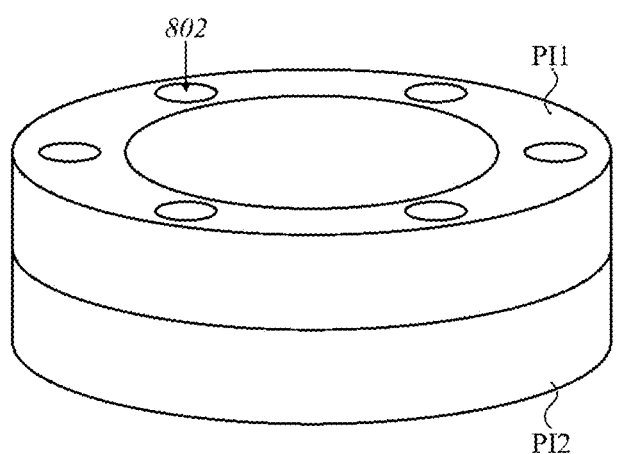

FIG. 225 shows a stacked ring set (as in a two end flanges of pipes to be adjoined) having a plurality of fastener assembly holes designed for receipt of fasteners like that shown in FIG. 224A, providing for the "biting" sleeves to be received in the respective circumferential holes and the bolts potentially oriented at different levels of fastening compression.

Figure 226C:
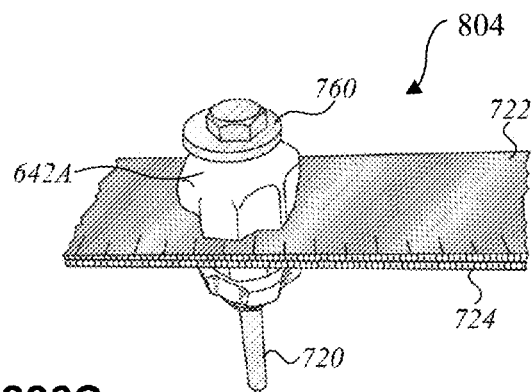
Figure 226B:
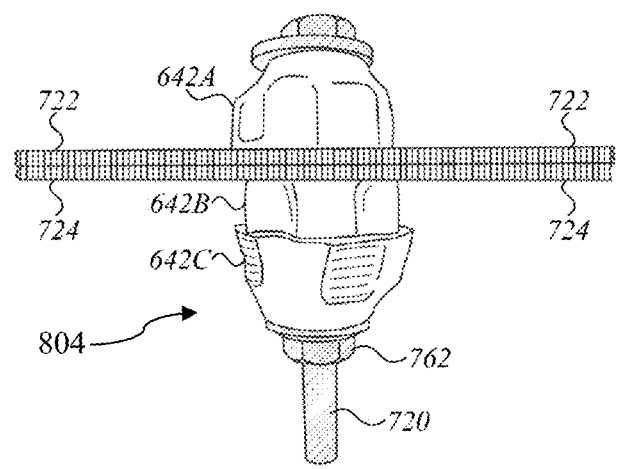
Figure 226A:
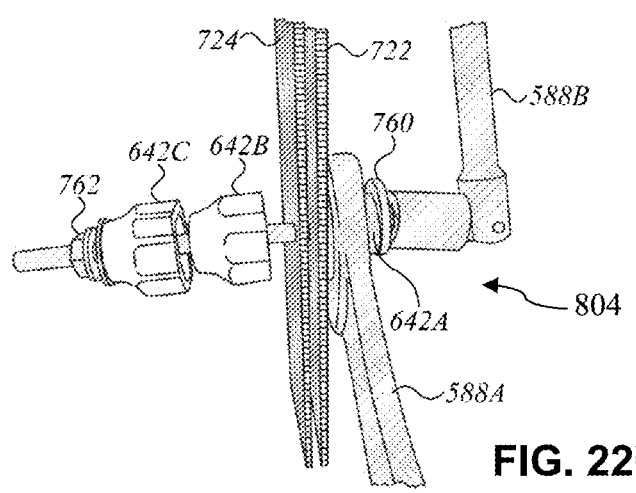

FIGS. 226A, 226B and 226C illustrate an additional fastener assembly, with FIG. 226A being in a pre-compression state of initial assembly (with the illustrated tooling), and with FIGS. 226B and 226C showing the fully assembled compression state from different viewpoints (again with a nested/stacked combination of torque enhancement members).

FIGS. 227A to 227F show a torque enhancement button member like that of FIG. 207A, but with both internal (partially through in this case) and external threading with the views summarized as follows: FIG. 227A perspective view with the base down, FIG. 227B a cross-sectional view thereof, FIG. 227C a top plan view thereof, FIG. 227D a flipped over perspective view, FIG. 227E a front elevational of the flipped over orientation, and FIG. 227F a plan view of the flipped over orientation.

Figure 228C:
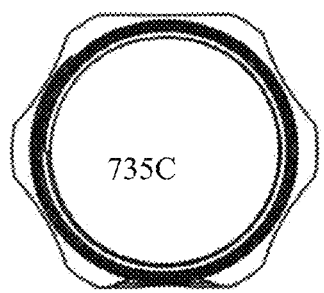
Figure 228D:
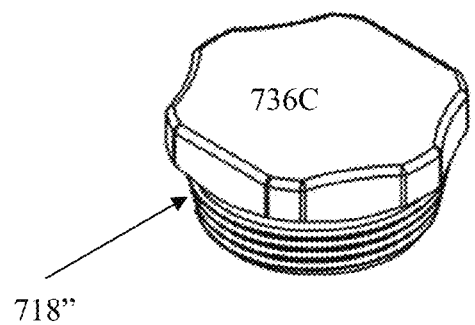
Figure 228E:
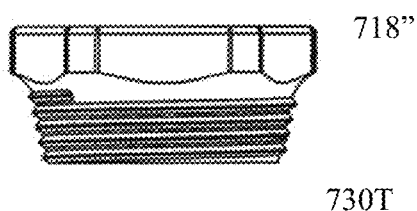
Figure 228B:
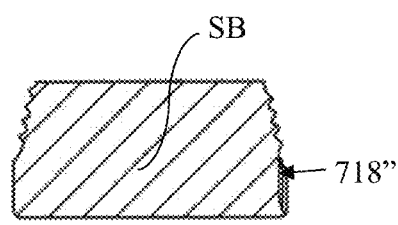
Figure 228F:
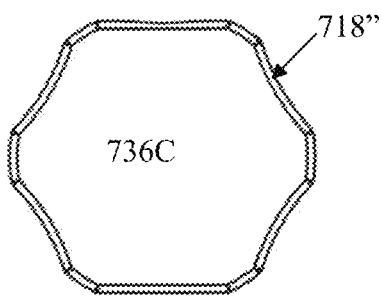
Figure 228A:
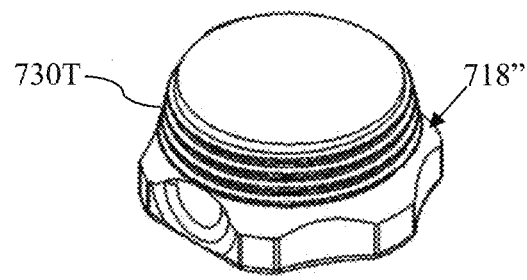

FIGS. 228A to 228F show a torque enhancement button member like that of FIG. 227A, but with a solid (non-threaded) interior body as to present a cap formation, with FIG. 228A providing a perspective view with the base down, FIG. 228B a cross-sectional view thereof, FIG. 228C a top plan view thereof, FIG. 228D a flipped over perspective view; FIG. 228E a front elevational of the flipped over orientation, and FIG. 228F a plan view of the flipped over orientation.

Figure 229F:
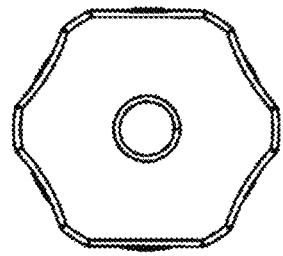
Figure 229A:
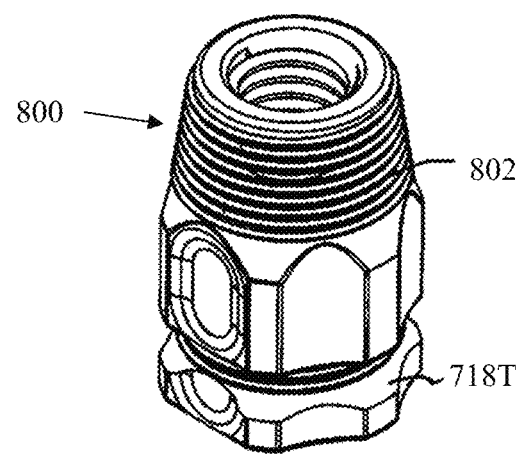
Figure 229C:
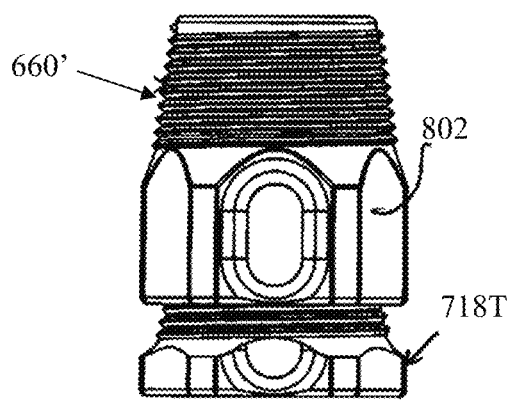
Figure 229B:
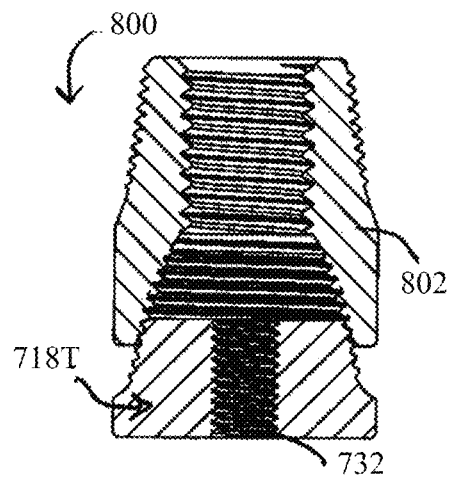
Figure 229D:
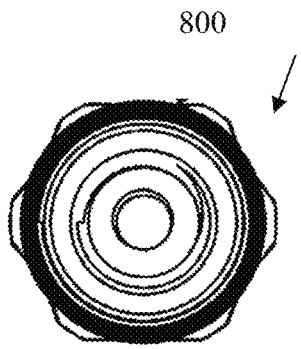
Figure 229E:
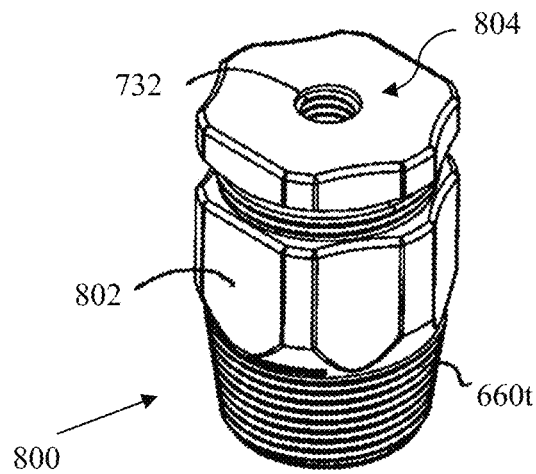

FIGS. 229A to 229F show a torque enhancement combination featuring a threaded button member and threaded tapered engagement member combination (another stacked/nested torque enhancement member combination), FIG. 229A providing a perspective view with the taper up, FIG. 229B a cross-sectional view thereof, FIG. 229C a front elevational thereof, FIG. 229D a top plan view thereof, FIG. 229E a flipped over perspective view; FIG. 229E a front elevational of the flipped over orientation, and FIG. 229F a plan view of the flipped over orientation.

Figure 230C:
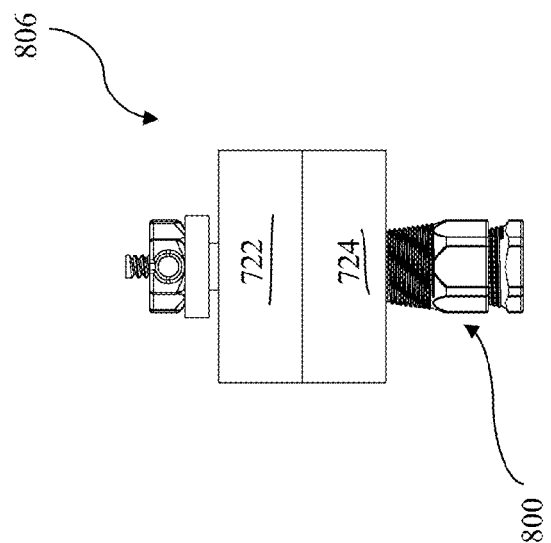
Figure 230B:
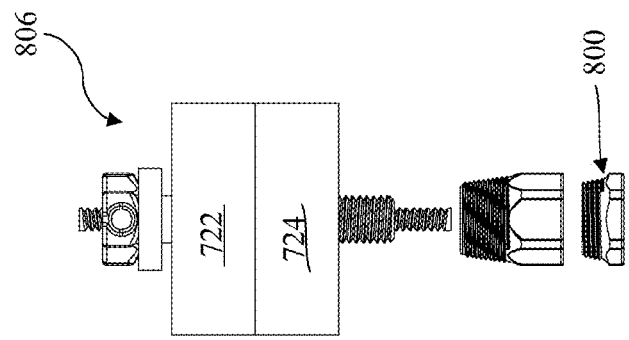
Figure 230A:
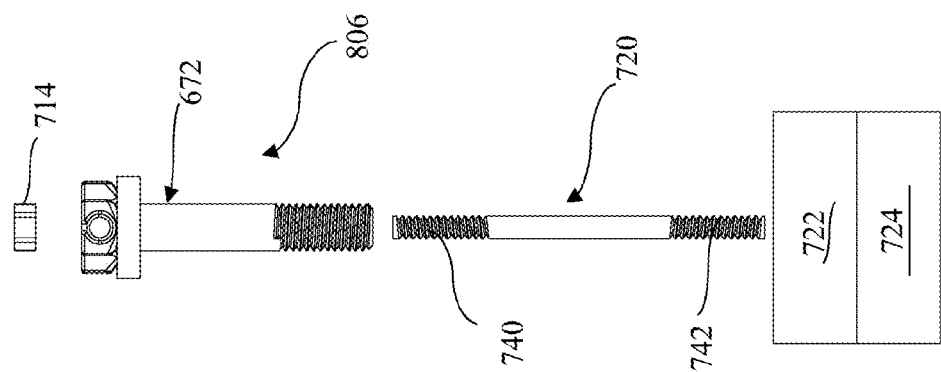

FIGS. 230A to 230C show an additional fastener assembly similar to that depicted in FIG. 205C, but with the externally threaded embodiment of the button of FIG. 227A (which is further modified to have a through-hole thread hole rather than a partial one), and a tapered engagement component configured as shown in FIG. 229A.

Figure 231A:
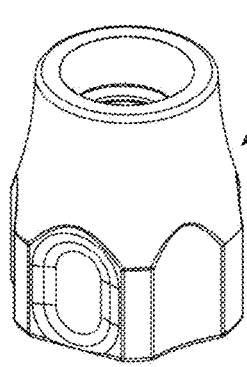
Figures 231B, 231C:
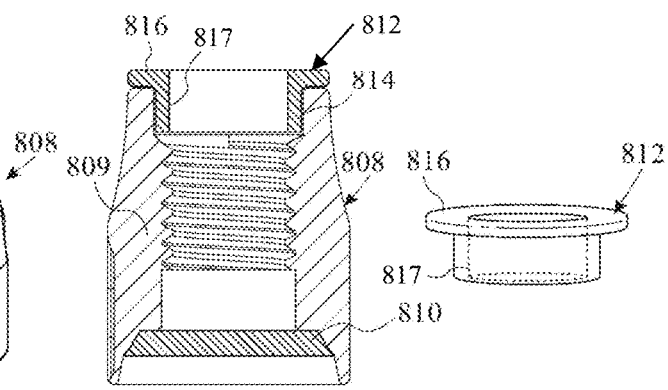
Figure 231D:
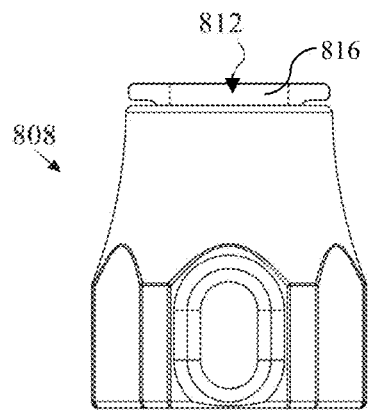
Figure 231E:
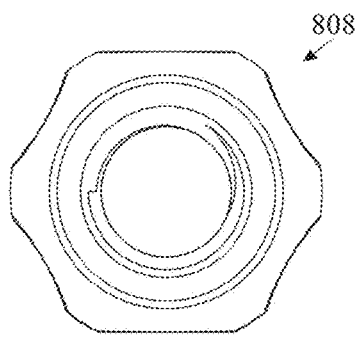
Figure 231F:
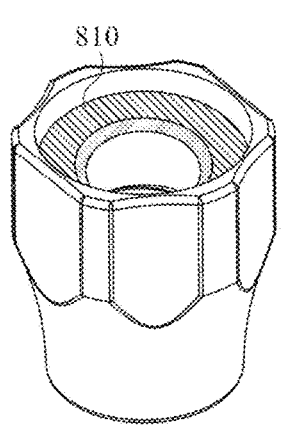
Figure 231G:
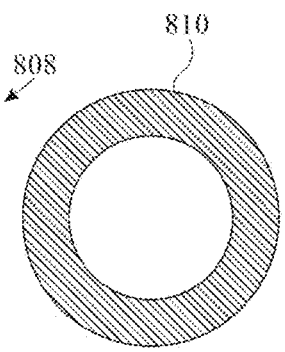

FIGS. 231A to 231H show an additional embodiment of a tapered engagement component, but with modifications directed at supporting seal members, with FIG. 231A providing a perspective view with the taper up and the flanged seal bushing nested, FIG. 231B a cross-sectional view thereof, FIG. 231C a view of the flanged seal bushing alone, FIG. 231D a front elevational thereof, FIG. 231E a top plan view thereof, FIG. 231F a flipped over perspective view; FIG. 231G a top plan view of the annular ring seal member designed for receipt in the top of the flipped over orientation, and FIG. 231H a top plan view of the annular ring seal member received within the flipped over orientation.

Figure 232D:
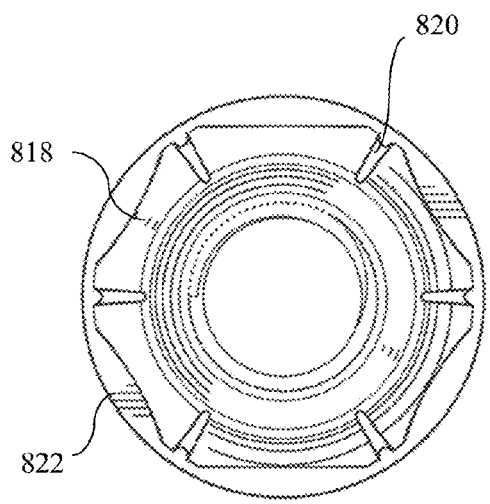
Figure 232A:
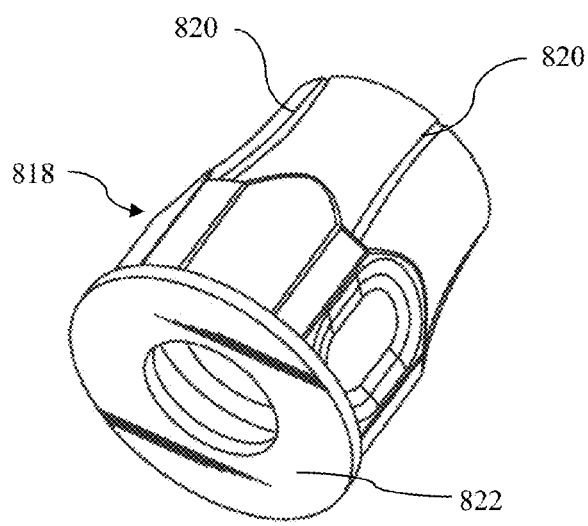
Figure 232C:
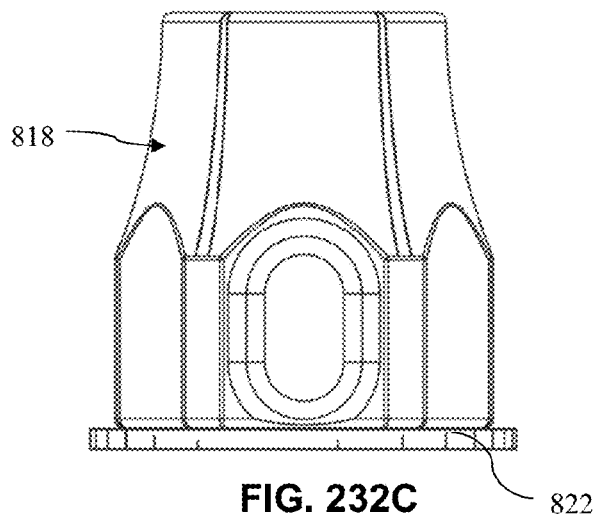
Figure 232B:
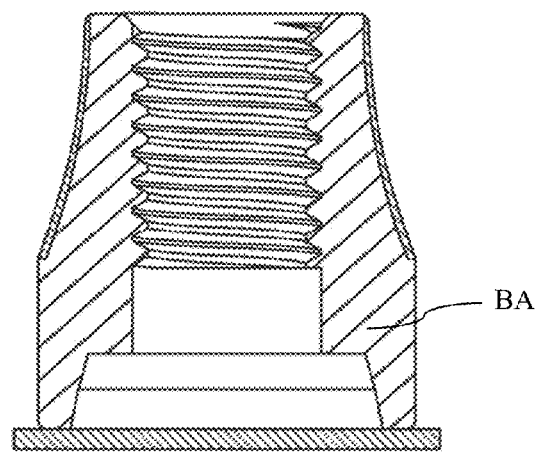
Figure 232E:
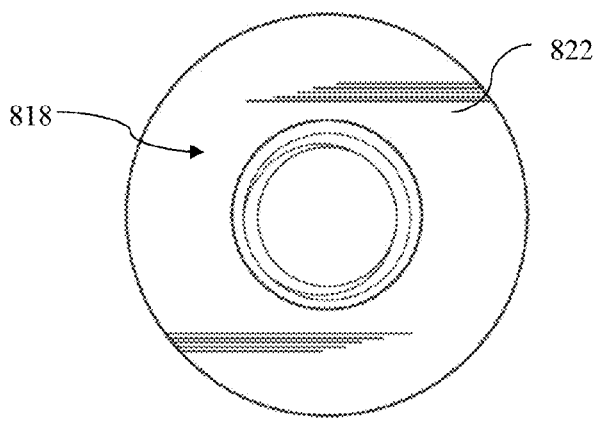

FIGS. 232A to 232E show an additional embodiment of a tapered engagement component, but with exterior grooving on the conical or tapered surface of the engagement component, with FIG. 232A providing a perspective view thereof with the flanged base portion shown, FIG. 232B a cross-sectional view thereof, FIG. 232C a front elevational thereof, FIG. 232D a top plan view thereof, and FIG. 232E a bottom plan view thereof.

Figure 233:
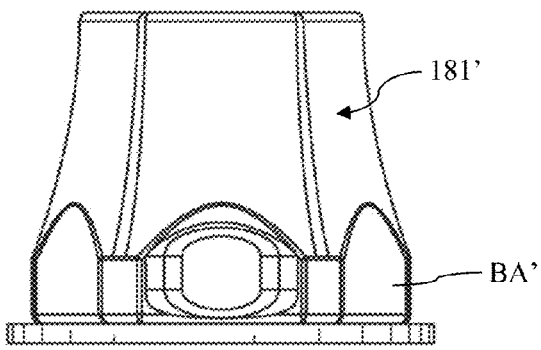

FIG. 233 shows an additional embodiment of a grooved, tapered engagement component, but with the base of less height.

Figure 234A:
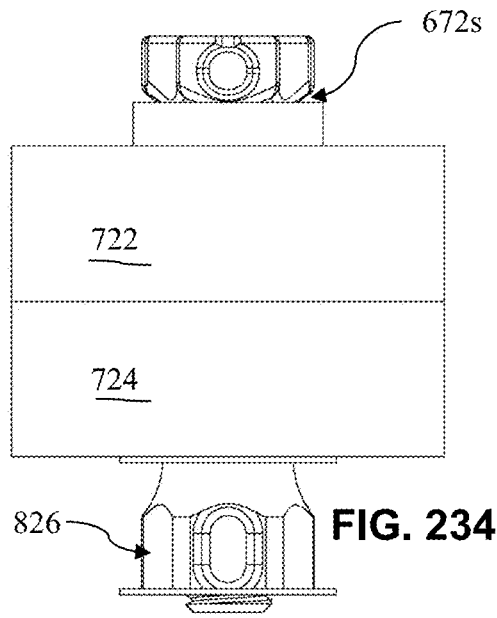
Figure 234B:
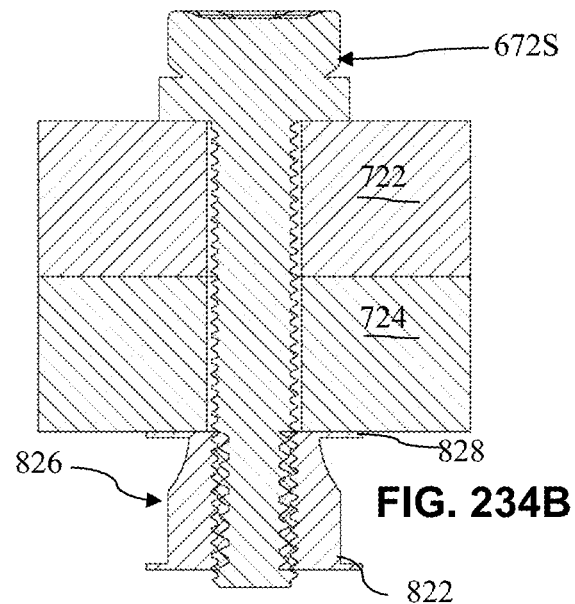
Figure 234C:
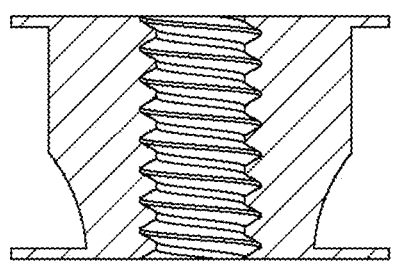

FIGS. 234A to 234C show an additional fastener assembly combination involving multiple torque enhancement components of the present invention, with FIG. 234A showing the combination in fully assembled mode, FIG. 234B showing a cross-sectional view thereof, and FIG. 234C showing a double flanged tapered engagement component used in the assembly.

Figure 235A:
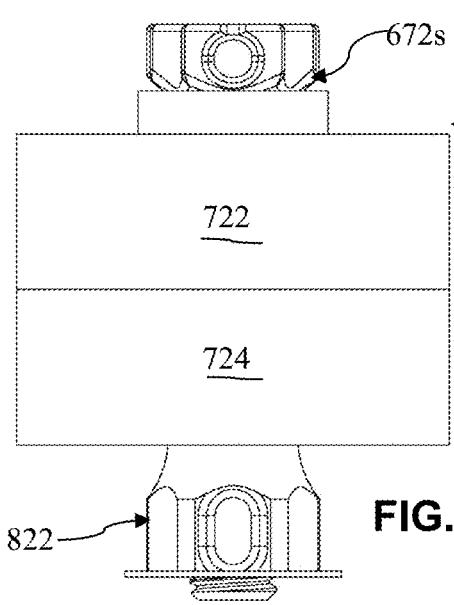
Figure 235B:
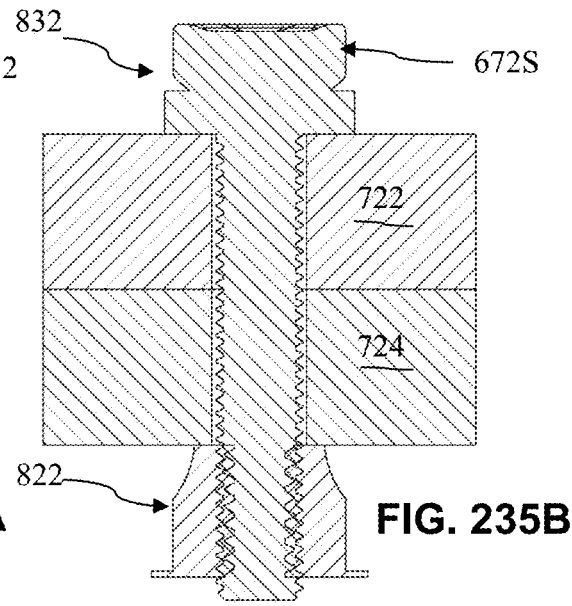
Figure 235C:
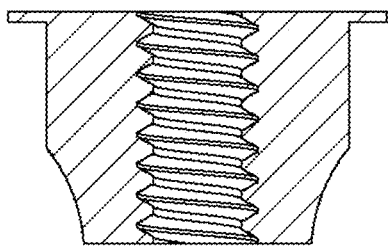

FIGS. 235A to 235C show an additional fastener assembly combination involving multiple torque enhancement components of the present invention, with FIG. 235A showing the combination in fully assembled mode, FIG. 235B showing a cross-sectional view thereof, and FIG. 235C showing a single flanged tapered engagement component used in the assembly.

Figure 236A:
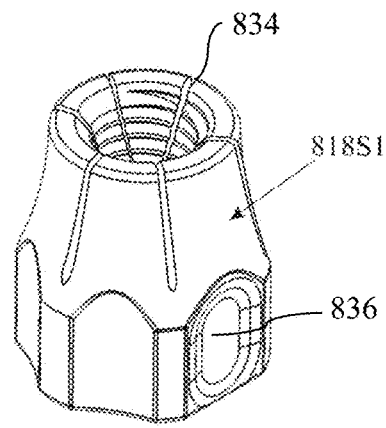
Figure 236B:
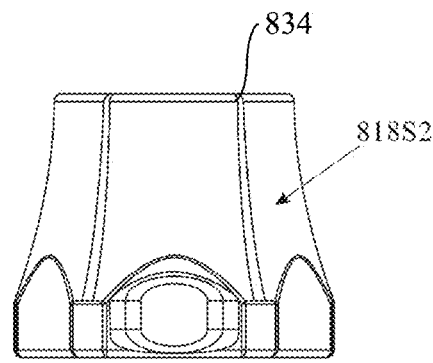
Figure 236C:
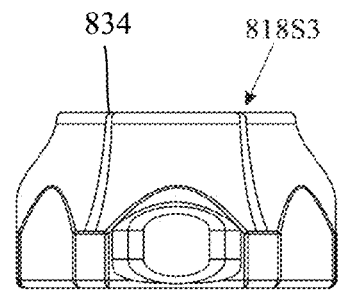

FIGS. 236A to 236C show additional embodiments of the tapered engagement component of the present invention, with FIG. 236A showing a perspective view of a first embodiment featuring in the conical region a plurality of compression through-slots shown extending entirely through the thickness into a threaded portion of the tapered end of the engagement component (as to present a plurality of wall sections therebetween), FIG. 236B showing the same arrangement but with a shorter height base region, and with FIG. 236C also showing a similar slotted tapered engagement component with the tapered region much shorter.

Figure 237A:
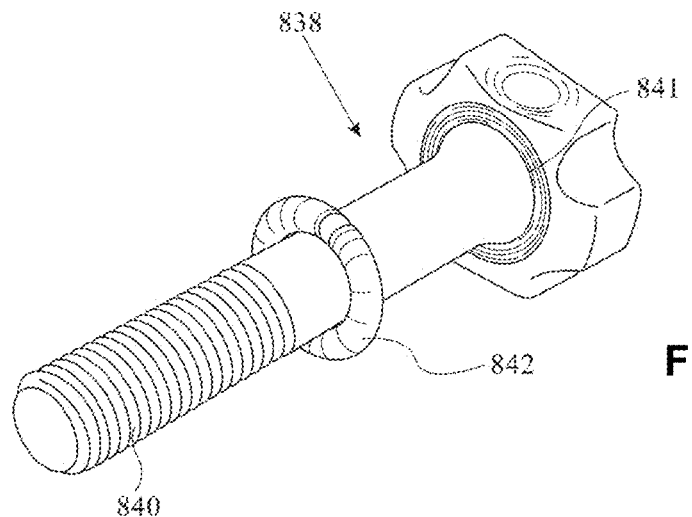
Figure 237B:
Figure 237C:
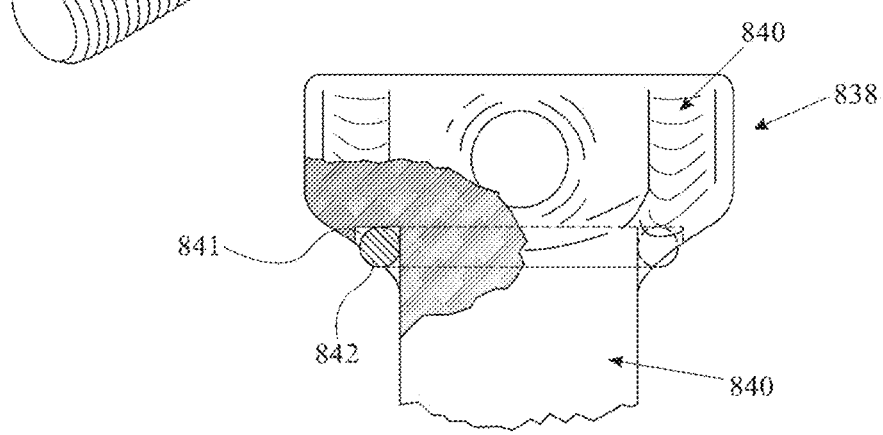

FIGS. 237A to 237C show an alternate embodiment of a torque enhancement bolt and seal assembly, with FIG. 237A showing the O-ring seal in a pre-final position state, FIG. 237B showing the O-ring seal in its reception groove provided in the region of bolt head and bolt shaft interface and FIG. 237C shows that interface region in greater detail via an enlarged cut-away and cross-sectional view.

Figure 238A:
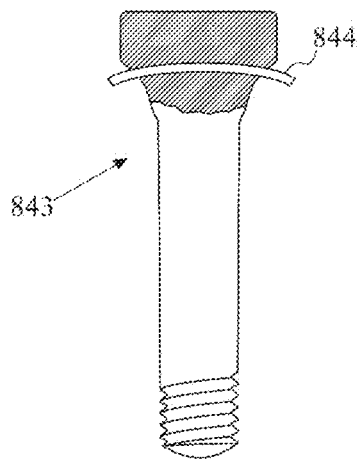
Figure 238B:
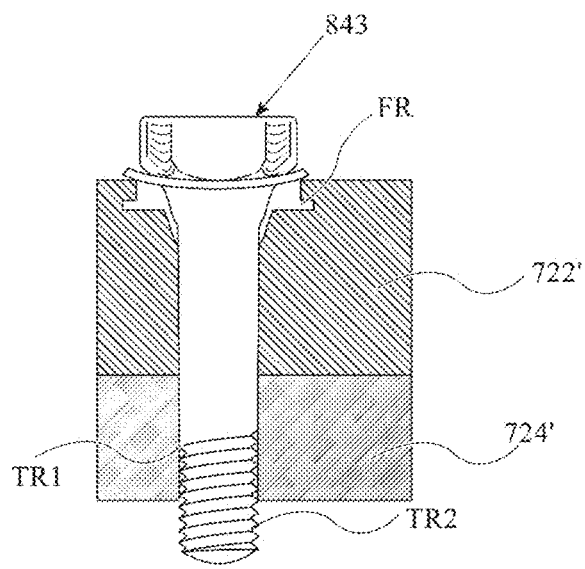
Figure 238C:
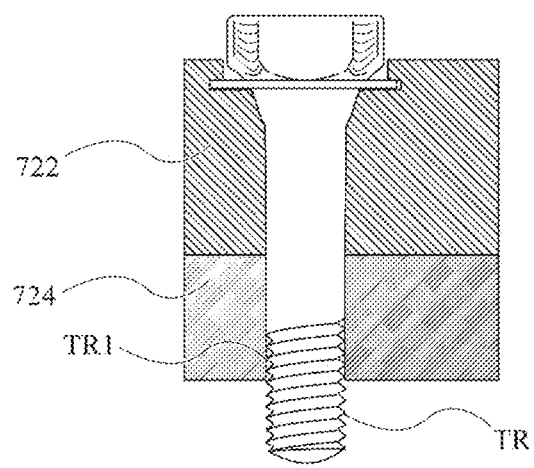

FIGS. 238A to 238C show an alternate embodiment of a torque enhancement bolt and flange (integrated washer) combination, with FIG. 238A showing the combination alone, FIG. 238B showing in partial cross-section the combination in an inserted, but pre-final insertion state relative to stacked structural components, and FIG. 238C showing the final insertion state thereof.

Figures 239A, 239B:
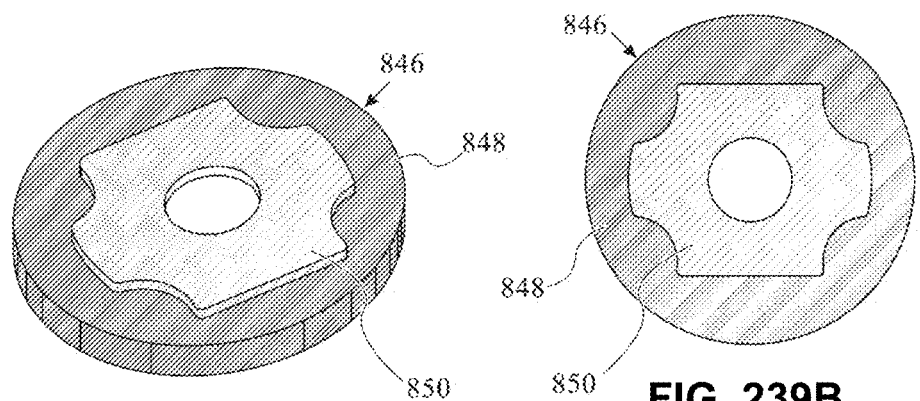

FIGS. 239A and 239B show an alternate torque enhancement component embodiment in the form of a projecting washer, with FIG. 239A showing a top perspective view thereof, and FIG. 239B a top plan view thereof (the underside being flat, for example, with the central through-hole or can be a recess corresponding to the projection as generated for example in a punch or stamping process).

Figures 240A, 240B:
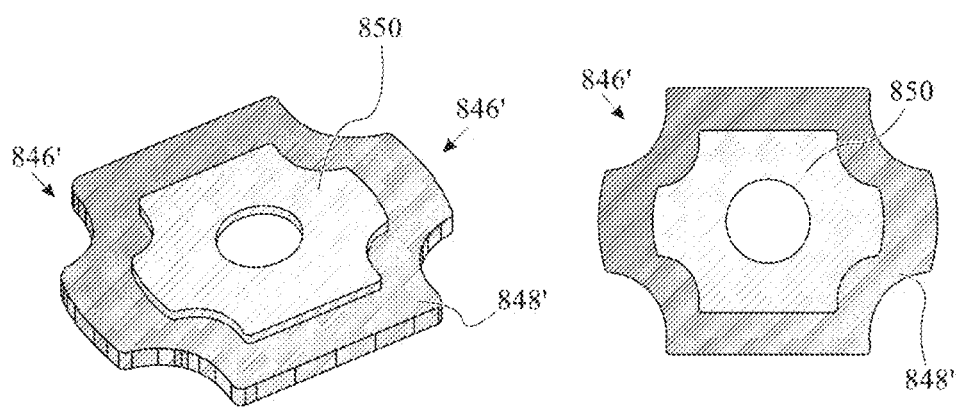

FIGS. 240A and 240B show an alternate torque enhancement component embodiment in the form of a projecting washer, with FIG. 240A showing a top perspective view thereof, and FIG. 240B a top plan view thereof (the underside being flat, for example, with the central through-hole or can be a recess corresponding to the projection as generated for example in a punch or stamping process).

Figures 241A, 241B:
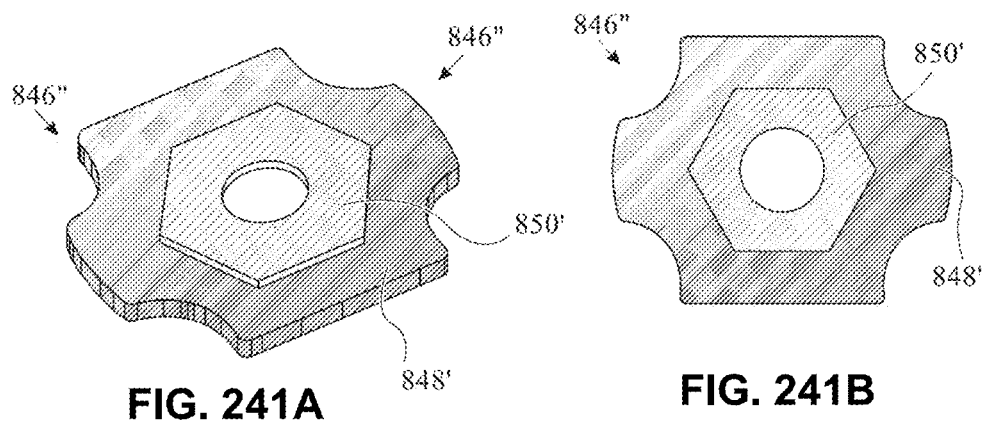

FIGS. 241A and 241B show an alternate torque enhancement component embodiment in the form of a projecting washer, with FIG. 241A showing a top perspective view thereof, and FIG. 241B a top plan view thereof (the underside being flat, for example, with the central through-hole or can be a recess corresponding to the projection as generated for example in a punch or stamping process).

Figures 242A, 242B:
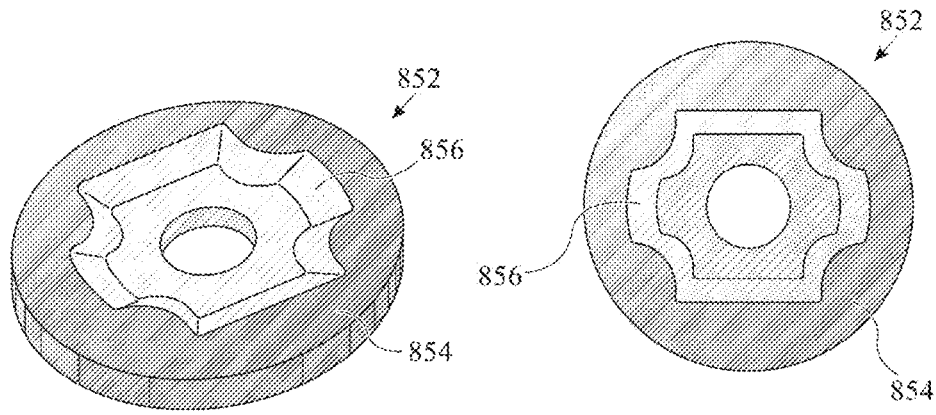

FIGS. 242A and 242B show an alternate torque enhancement component embodiment in the form of an internal area recessed washer, with FIG. 242A showing a top perspective view thereof and FIG. 242B a top plan view thereof (the underside being flat, for example, with the central through-hole or there can be a projection corresponding to the recess as generated for example in a punch or stamping process).

Figures 243A, 243B:
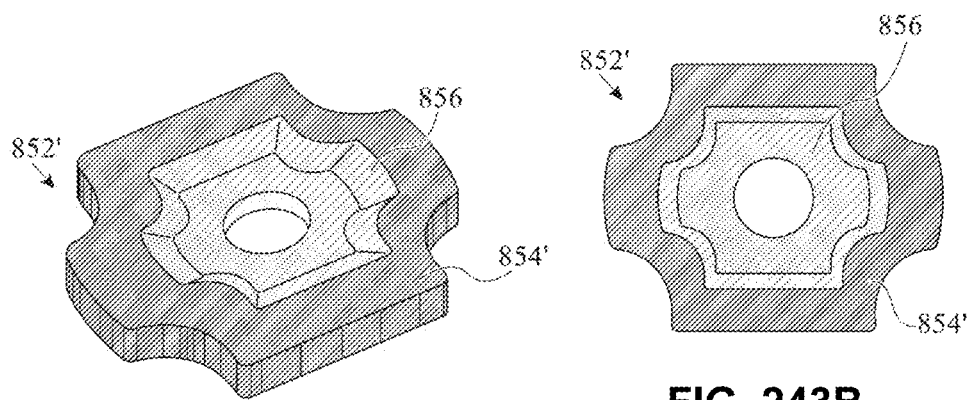

FIGS. 243A and 243B show an alternate torque enhancement component embodiment in the form of an internal area recessed washer, with FIG. 243A showing a top perspective view thereof, and FIG. 243B a top plan view thereof (the underside being flat, for example, with the central through-hole or there can be a projection corresponding to the recess as generated for example in a punch or stamping process).

Figures 244A, 244B:
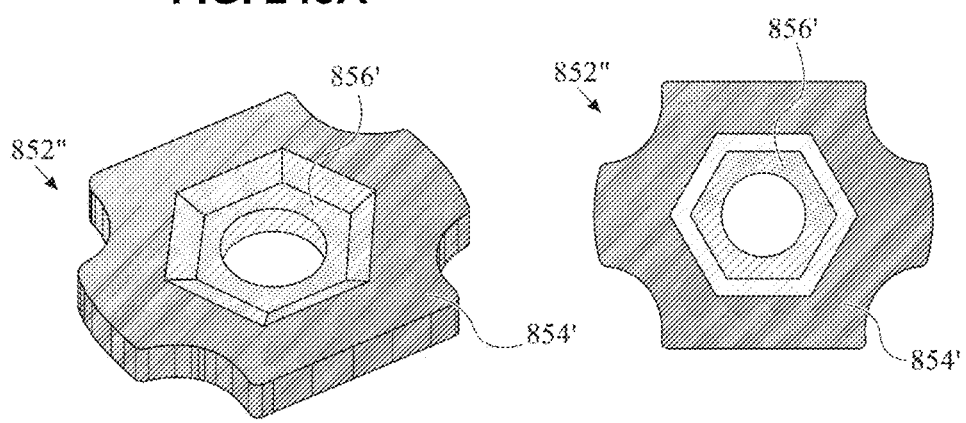

FIGS. 244A and 244B show an alternate torque enhancement component embodiment in the form of an internal area recessed washer, with FIG. 244A showing a top perspective view thereof, and FIG. 244B a top plan view thereof (the underside being flat, for example, with the central through-hole or there can be a projection corresponding to the recess as generated for example in a punch or stamping process).

Figure 245A:
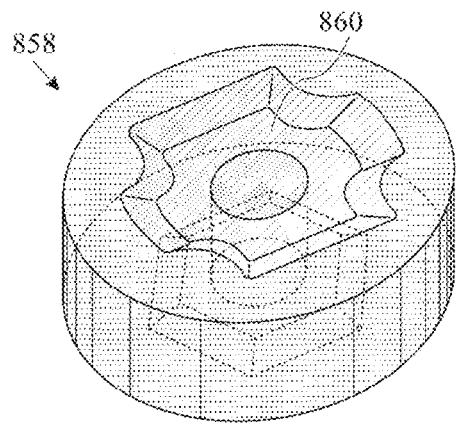
Figure 245B:
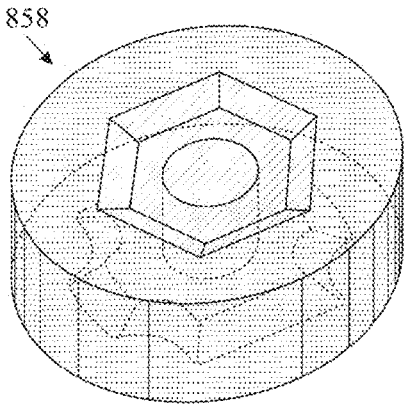
Figure 245C:
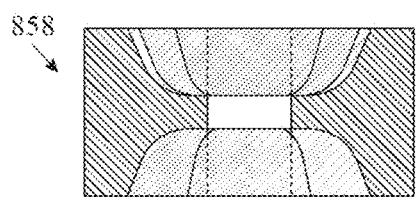
Figure 245D:
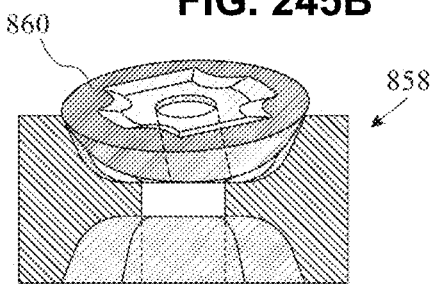
Figure 245E:
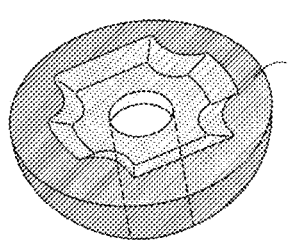
Figure 245G:
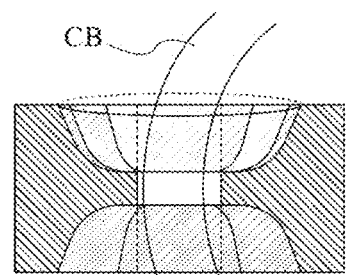
Figure 245F:
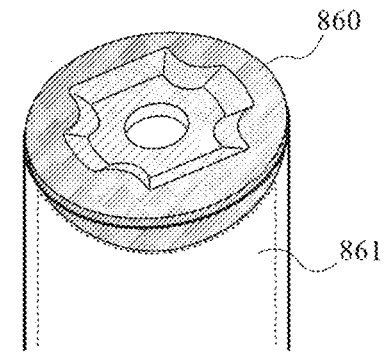
Figure 245H:
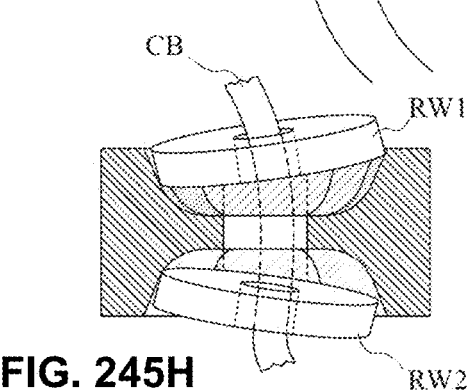

FIGS. 245A and 245H show additional torque enhancement component configurations, with FIG. 245A showing a grommet embodiment having a torque enhancement recess and through-hole, FIG. 245B showing the underside of FIG. 245A, FIG. 245C showing a bi-secting cross-section of FIG. 245A, FIG. 245D showing the grommet of FIG. 245A receiving in rotation potential fashion a torque enhancement component in the form of a bowl shaped receptor, FIG. 245E showing the bowl shaped receptor alone, FIG. 245F showing the bowl shaped receptor as a cylinder plug, FIG. 245G showing the grommet of FIG. 245A with a flexible conduit received therein, and FIG. 245H shows the grommet of FIG. 245A receiving upper and lower washers as well as a conduit (e.g., a solid cable) extending therethrough.

Figure 246A:
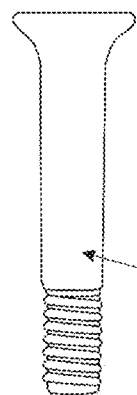
Figure 246B:
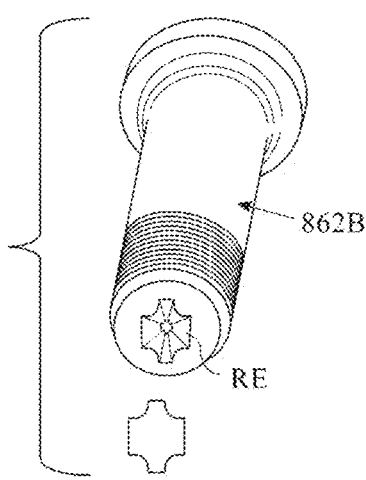
Figure 246C:
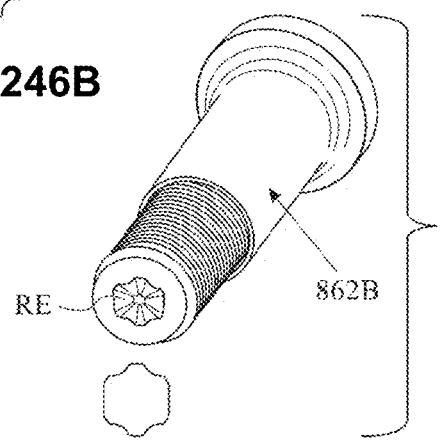
Figure 246D:
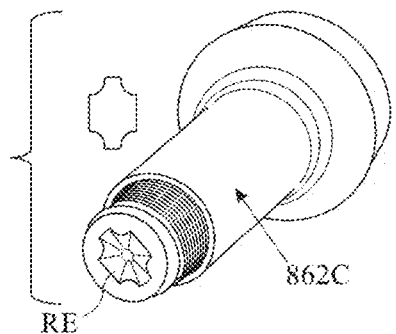
Figure 246E:
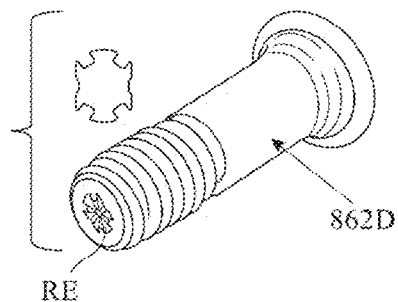
Figure 246F:
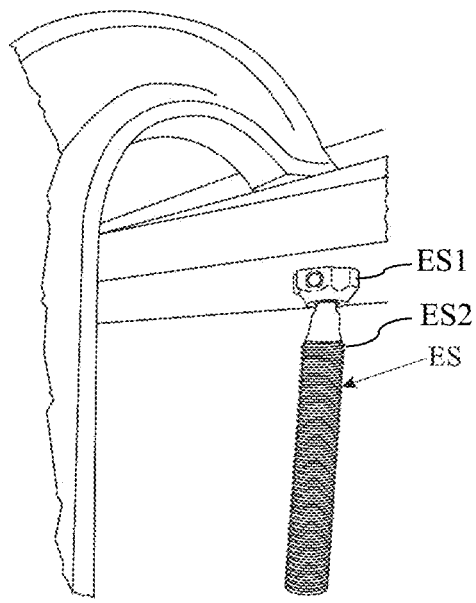
Figure 246G:
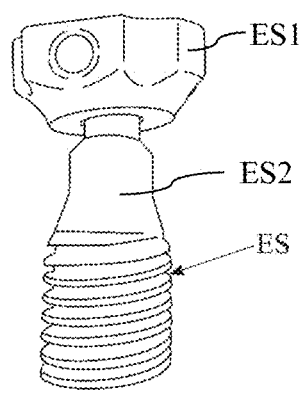

FIGS. 246A and 246G show additional embodiments of torque enhancement components under the present invention with FIG. 246A showing a front elevational view of a torque enhancement screw embodiment featuring a standard head (e.g., Phillips, Allen) and a torque enhancement shaft end recess, FIG. 246B showing the shaft end recess and a schematic plan view of the exterior configuration for that shaft end recess, FIG. 246C showing a different configured shaft end recess and a schematic plan view of the exterior configuration thereof, FIG. 246D showing a different configured shaft end recess and a schematic plan view of the exterior configuration thereof, and FIG. 246E showing a different configured shaft end recess and a schematic plan view of the exterior configuration thereof, FIG. 246F showing an elongated support shaft version having the torque enhancement shaft head end received in a corresponding (internal male projection not shown) cup member, FIG. 246G showing a closer view of the male/female end shaft and cup combination.

Figure 247A:
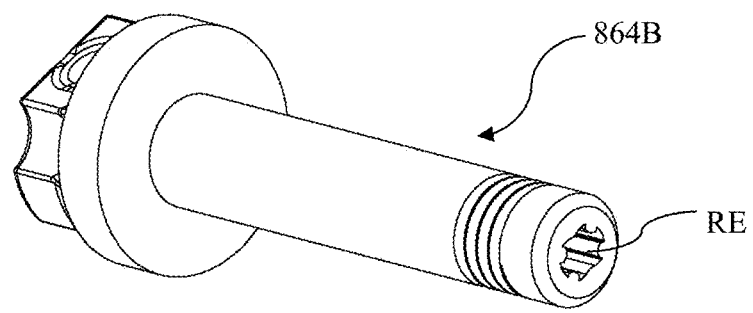
Figure 247B:
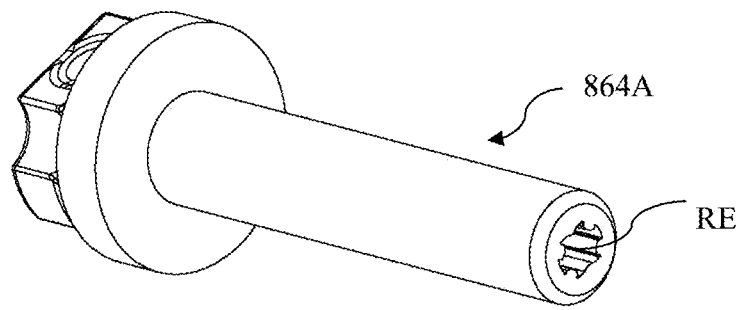

FIGS. 247A and 247B show two additional embodiments of torque enhancement components under the present invention with FIG. 247A showing a perspective view featuring a shaft end recess like that described above in FIG. 246A without threading and with a torque enhancement end with flange configuration, and FIG. 247B showing the same as that in FIG. 247A, but for a partial threading of its shaft.

Figure 248:
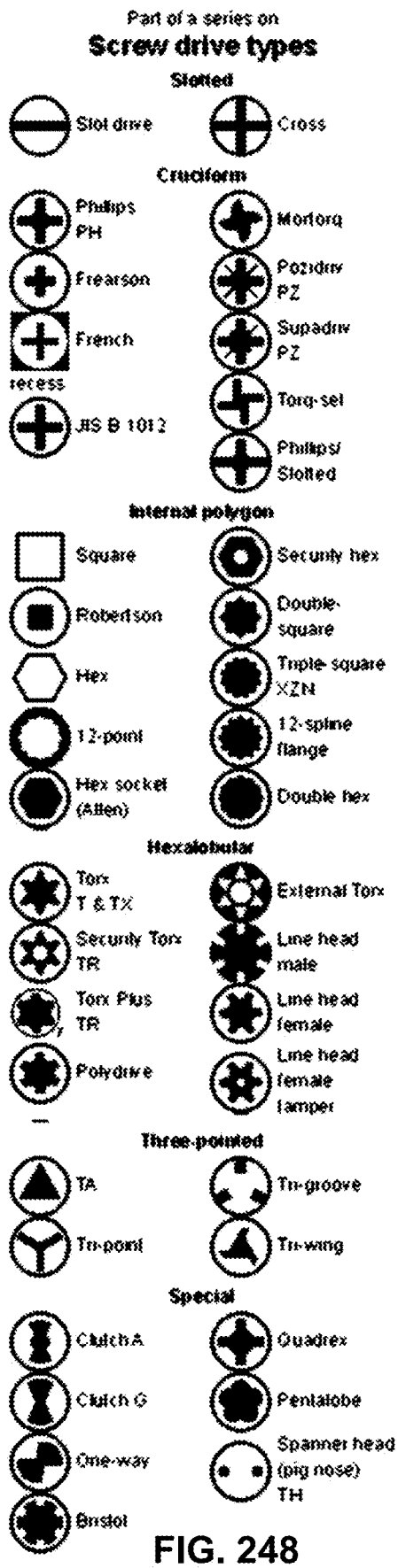

FIG. 248 shows a schematic presentation of a plurality of conventional drive configurations with associated labeling.

FIG. 249 shows an example of a conventional socket having a hexagonal drive hole (with associated standard square ratchet connector—not shown).

FIG. 250 shows a ratchet tool and associated socket combination with the combination having a male/female torque enhancement configured ratchet connection.

FIG. 250A presents an underside perspective showing the free end of the socket as having a torque enhancement configuration for driving at least a generally correspondingly shaped male component.

FIG. 250B shows a schematic line presentation of the interior cavity of the socket shown in FIG. 250A.

FIG. 250C shows an additional perspective view showing the free end of the socket shown in FIG. 250A.

Figure 250D:
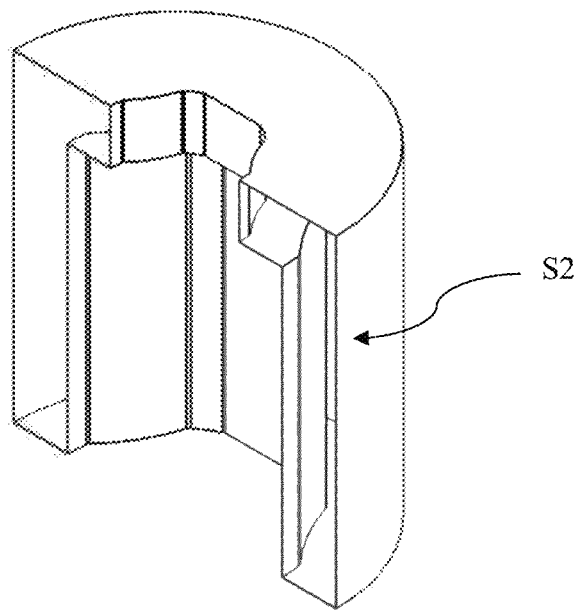

FIG. 250D shows a cross-sectional view of the socket shown in FIG. 250A.

Figure 250E:
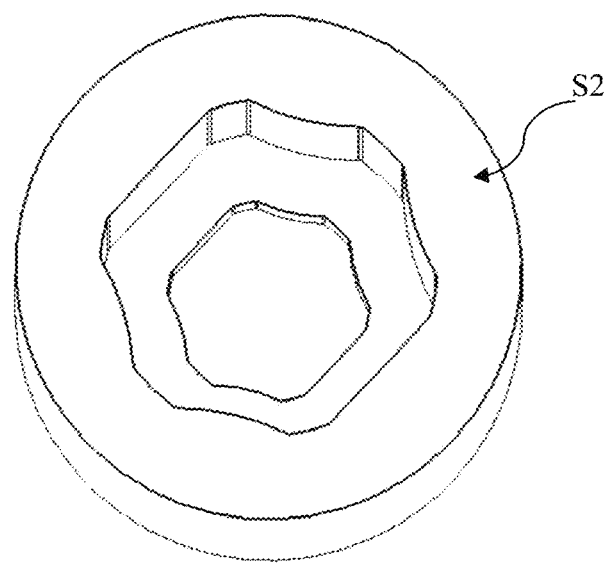

FIG. 250E shows another perspective view of the free end opening (as well as the ratchet engagement opening) of the socket shown in FIG. 250A.

FIG. 251 shows a ratchet tool and associated socket combination with the combination providing a standard male/female ratchet connection, but a socket with a torque enhancement free end for driving.

FIG. 251A shows a schematic line presentation of the interior cavity of the socket shown in FIG. 251.

FIG. 251B shows an additional perspective view showing the free end of the socket shown in FIG. 251.

Figure 251C:
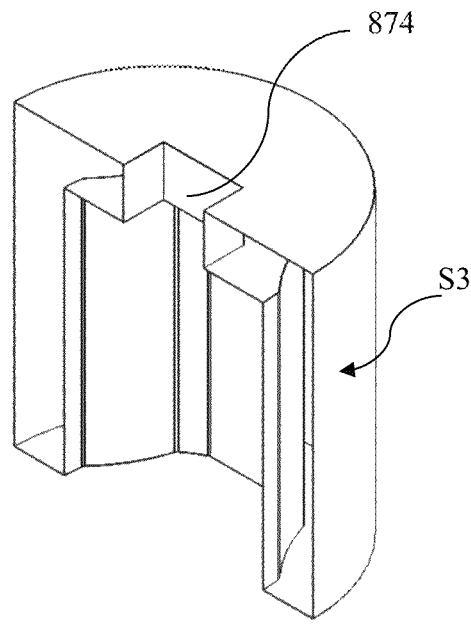

FIG. 251C shows a cross-sectional view of the socket shown in FIG. 251.

Figure 251D:
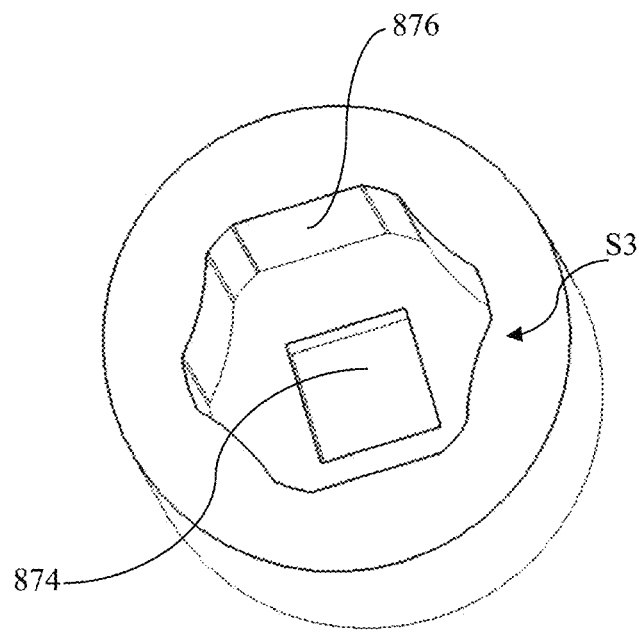

FIG. 251D shows another perspective view of the free end opening (as well as the ratchet engagement opening) of the socket shown in FIG. 251.

Figures 252A, 252B:
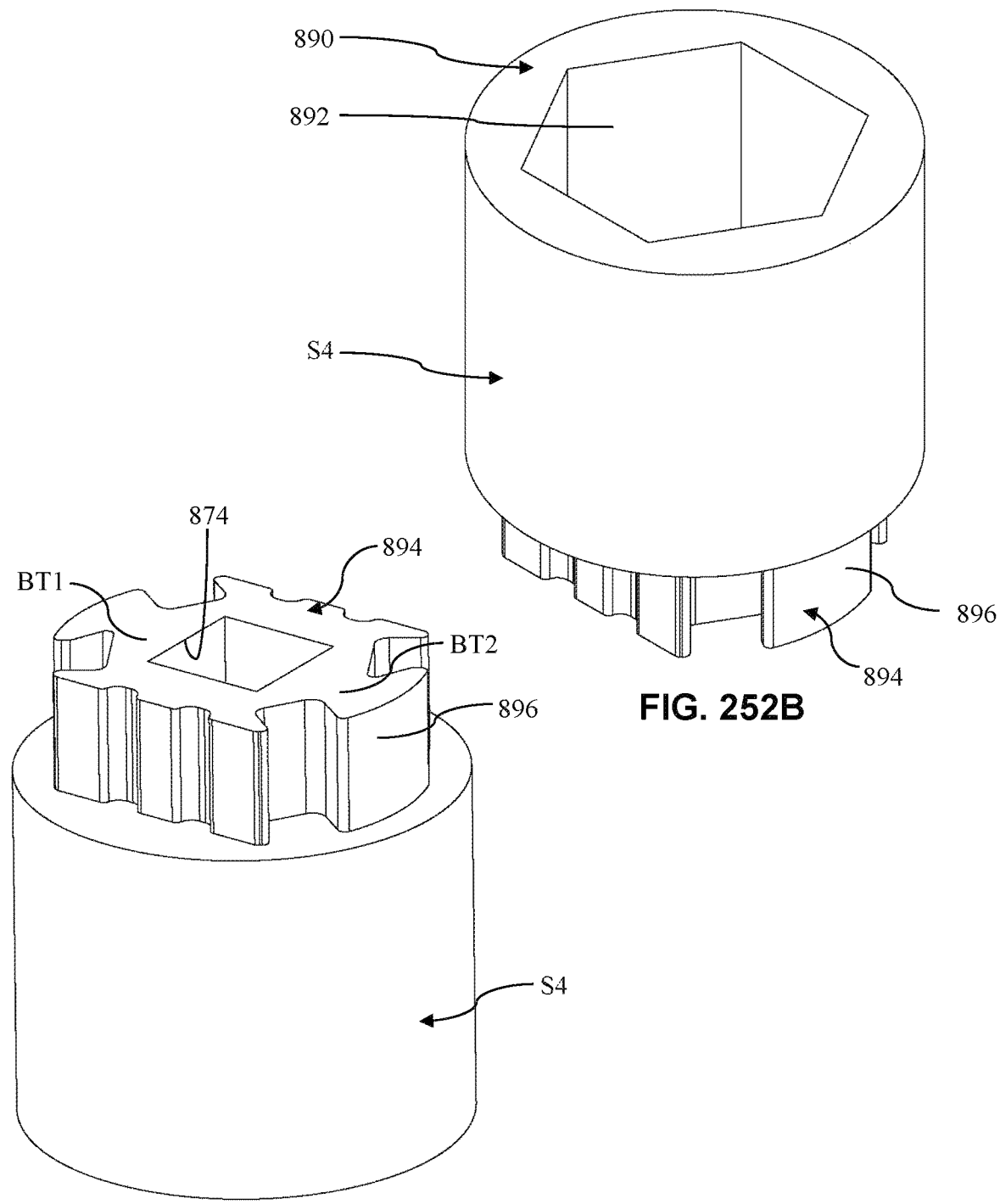

FIGS. 252A and 252B show views of a modified socket adapter assembly having a standard free end and a torque enhancement ratchet engagement head, with FIG. 252A showing a perspective view emphasizing the torque enhancement end, and FIG. 252B emphasizing the ratchet engagement end.

Figure 253A:
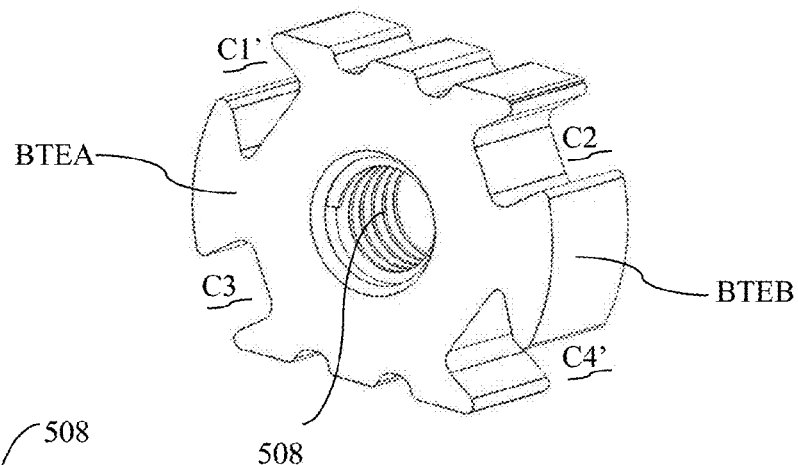
Figure 253B:
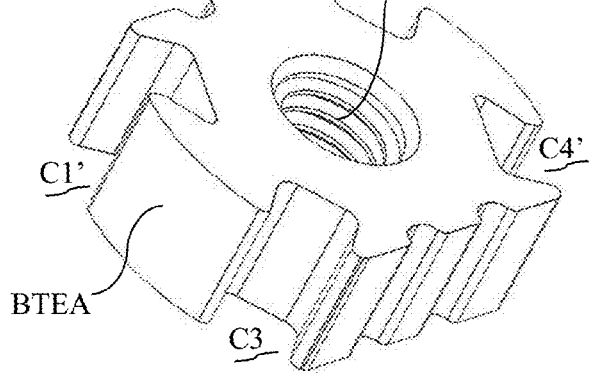
Figure 253C:
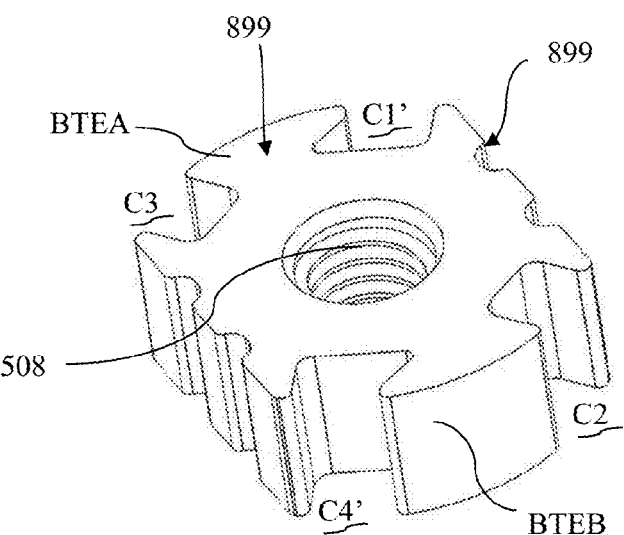
Figure 253D:
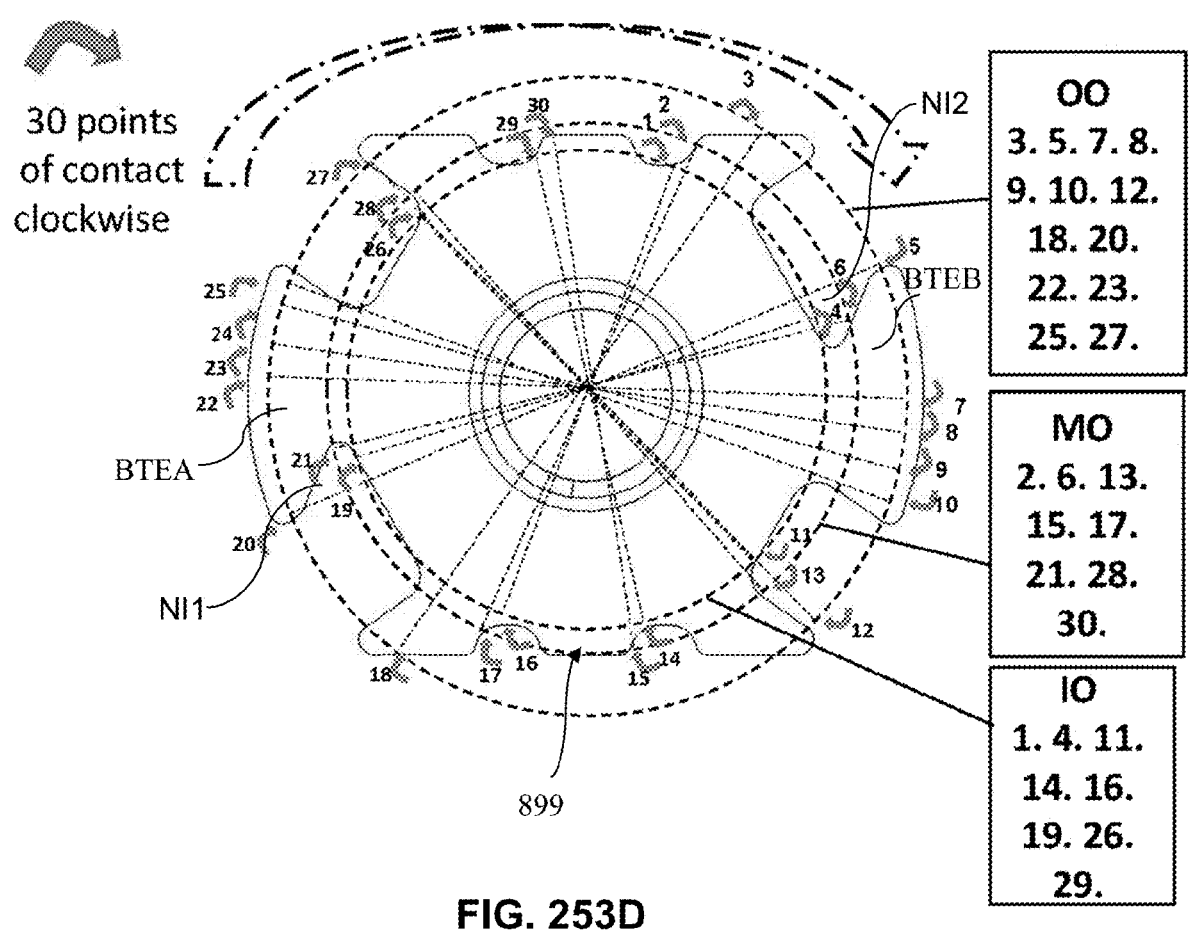
Figure 253E:
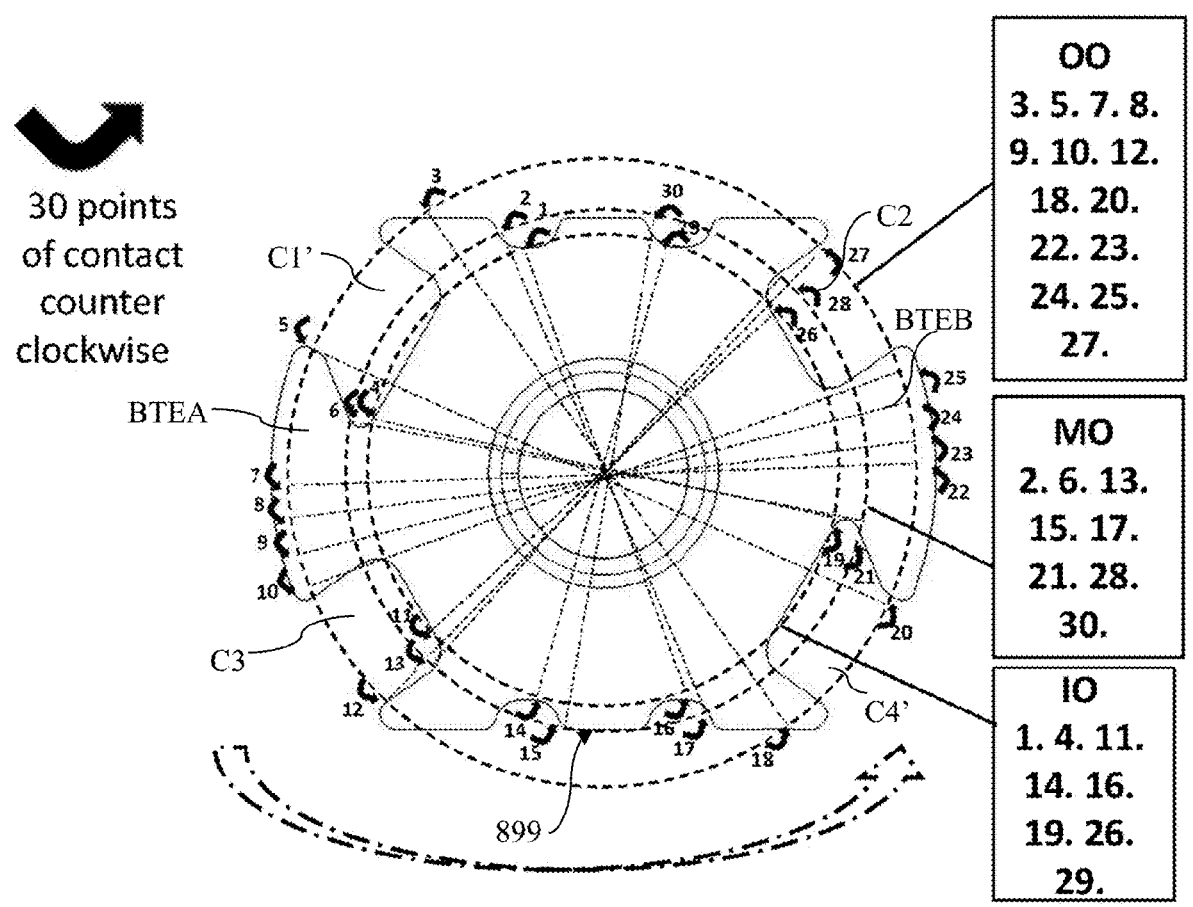
Figure 253F:
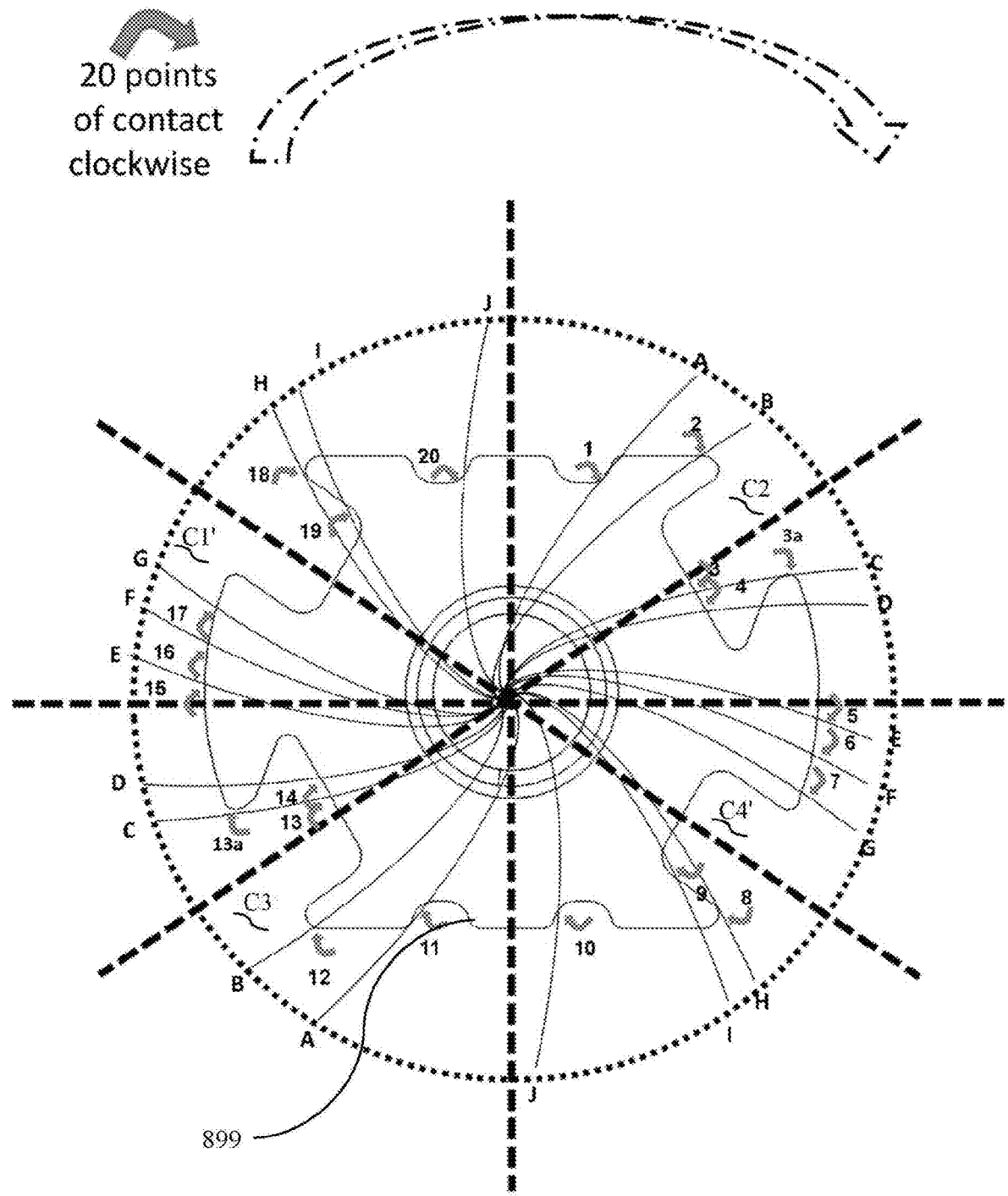
Figure 253G:
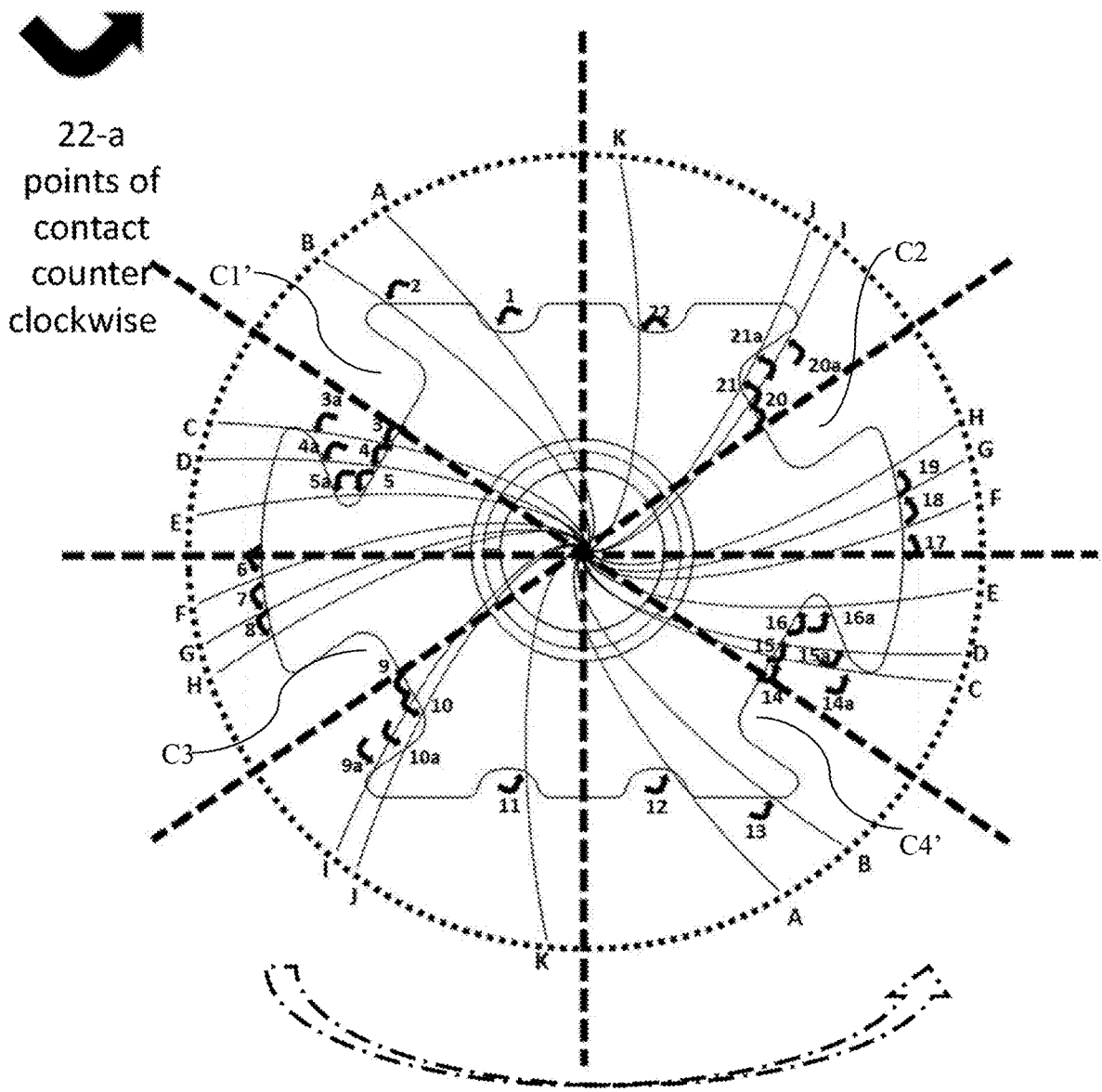

FIGS. 253A to 253G show various views of an additional embodiment of a torque enhancement component (solid version) that is generally bi-symmetric but includes different adjacent corner cut out configurations to promote a greater torque level in one direction as compared to the other; with FIG. 253A to 253C showing various perspective views thereof; FIG. 253D showing a considered mechanical contact point presentation for a clockwise rotation; FIG. 253E showing a considered mechanical contact point presentation for a counter-clockwise rotation; FIG. 253F showing a considered spiral-centrifugal contact point presentation for a clockwise rotation; FIG. 253G showing a considered spiral-centrifugal contact point presentation for a counter-clockwise rotation.

Figure 254A:
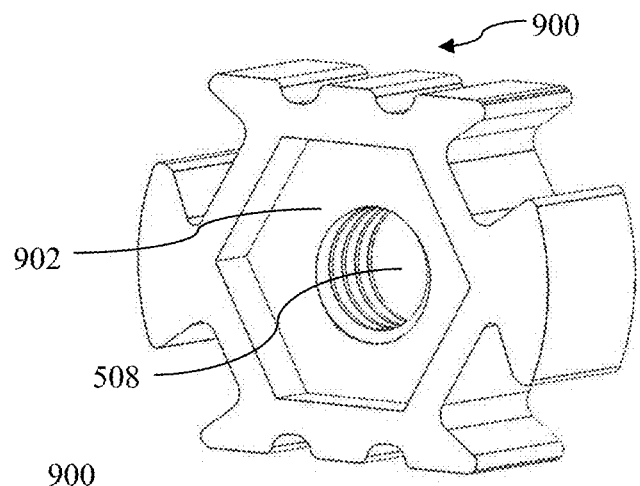
Figure 254B:
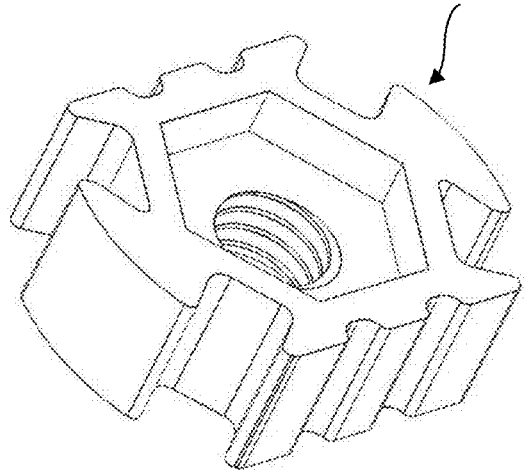
Figure 254C:
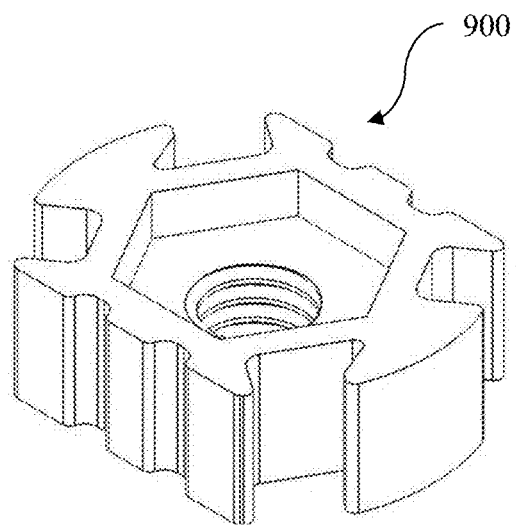
Figure 254D:
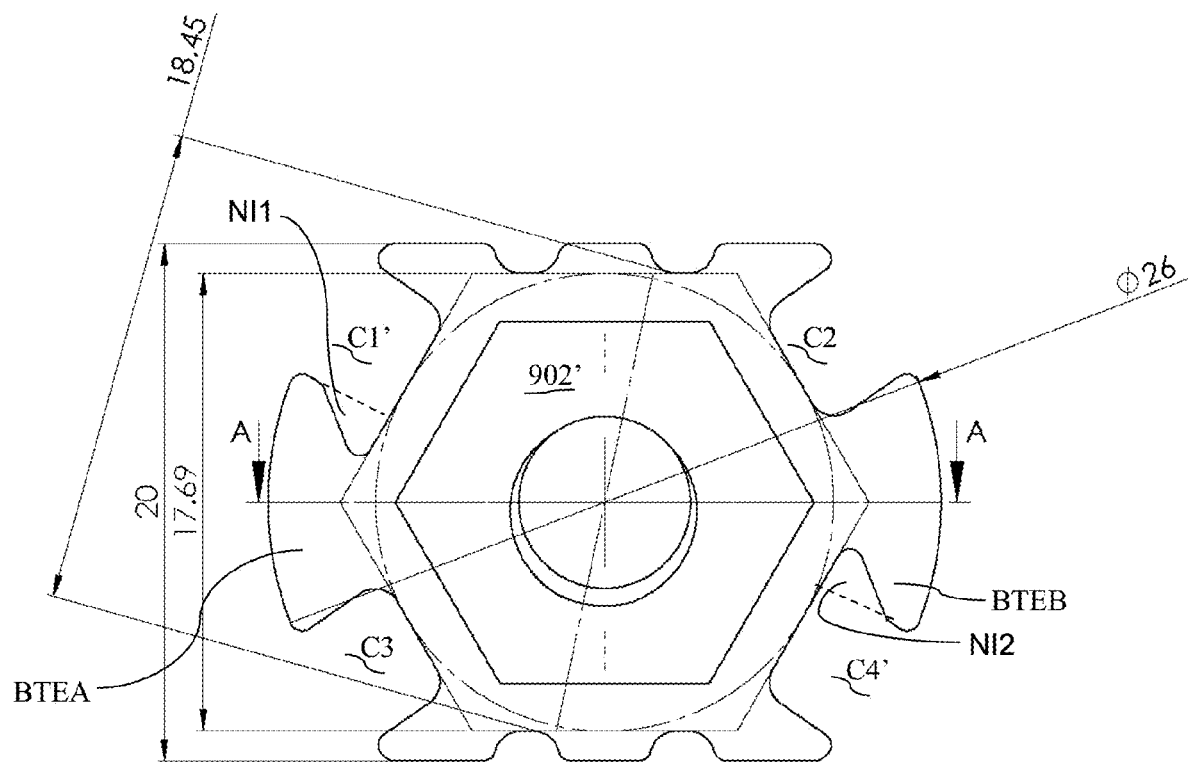
Figure 254E:
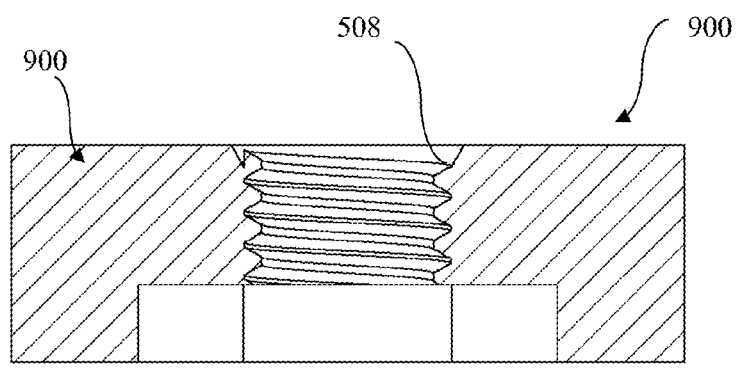

FIGS. 254A to 254E show various views of an additional embodiment of a torque enhancement component similar to that of FIG. 253A but in a pocket configuration, with FIG. 254A to 254C showing various perspective views featuring the hexagonal pocket interior and torque enhancement exterior configuration, FIG. 254D a plan view of the pocket size, and FIG. 254E showing a cross-sectional view thereof.

Figure 255A:
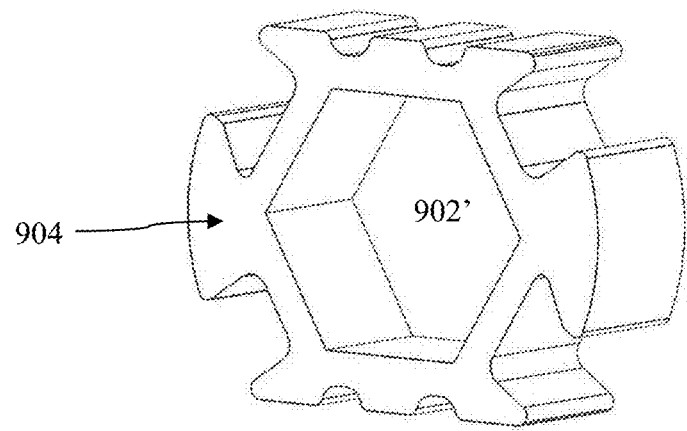
Figure 255B:
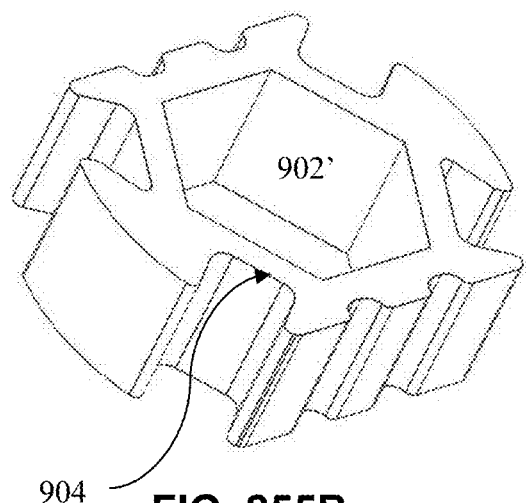
Figure 255C:
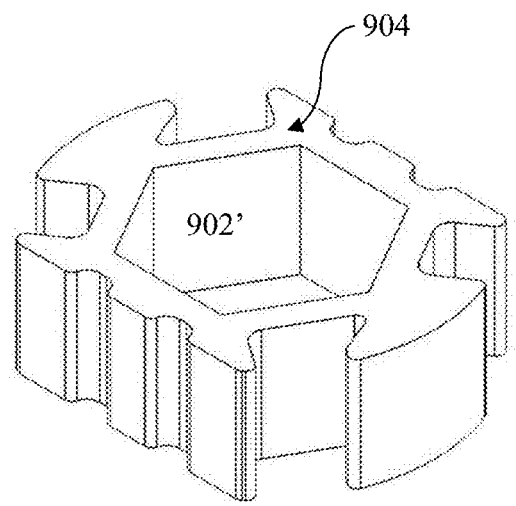
Figure 255D:
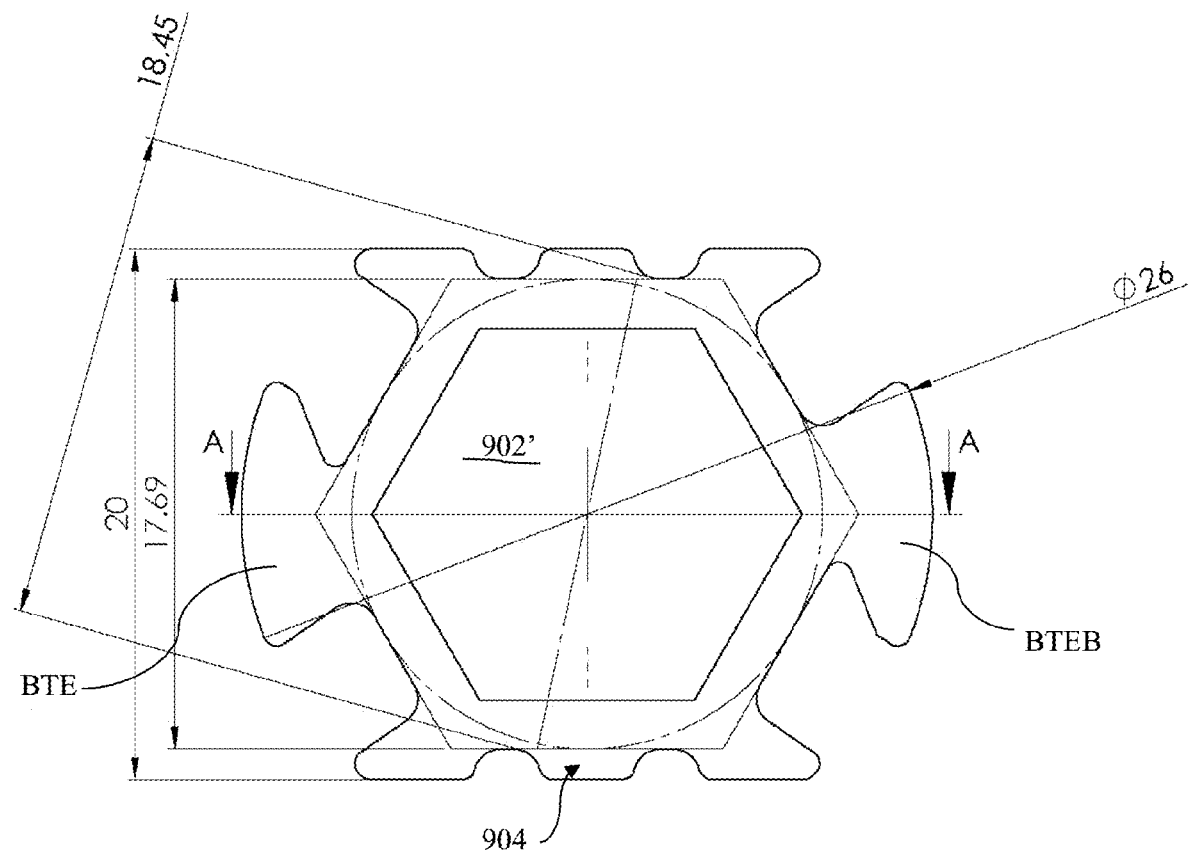
Figure 255E:
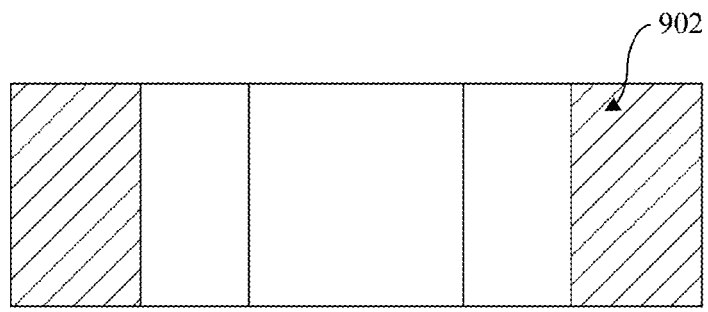
Figure 256:
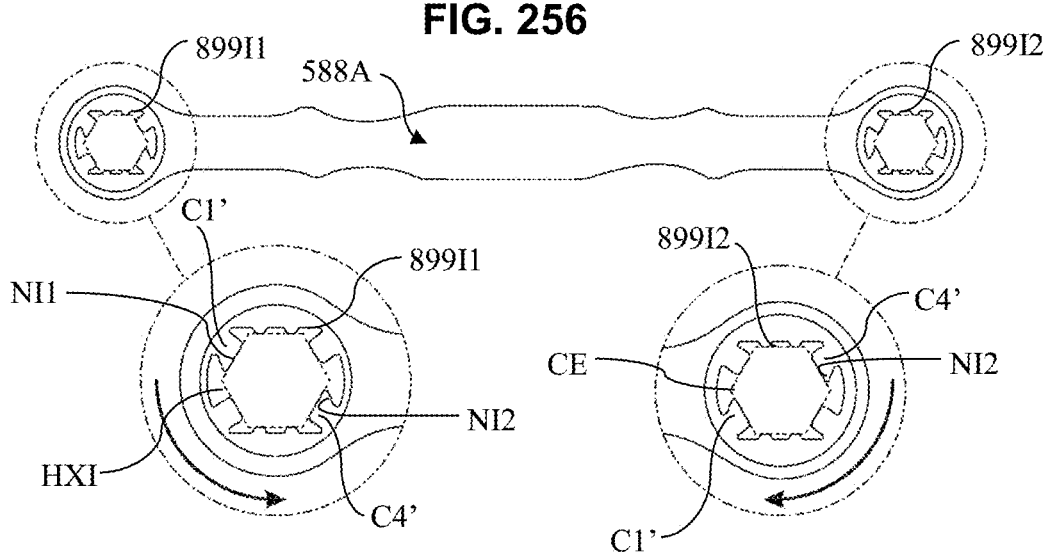

FIGS. 255A to 255E show various views of an additional embodiment of a torque enhancement component with FIG. 255A to 255C showing various perspective views showing the hexagonal through-hole interior and torque enhancement exterior configuration, FIG. 254D a plan view thereof, and FIG. 255E showing a cross-sectional view thereof.

FIGS. 256 to 259 show various wrench designs like that of FIG. 189 but having at least one end a torque enhancement configuration like that of FIG. 253 with different directional torque implications.

FIGS. 260 to 263 show various tool contact point with notches and corner cut outs in the torque enhancement configuration in both clockwise and counterclockwise directions.

DETAILED DESCRIPTION OF EMBODIMENTS

In the following description of some embodiments, identical components that appear in more than one figure or that share similar functionality are referenced in some instances by identical reference symbols or by new reference symbols with references back in the description.

Figure 2:
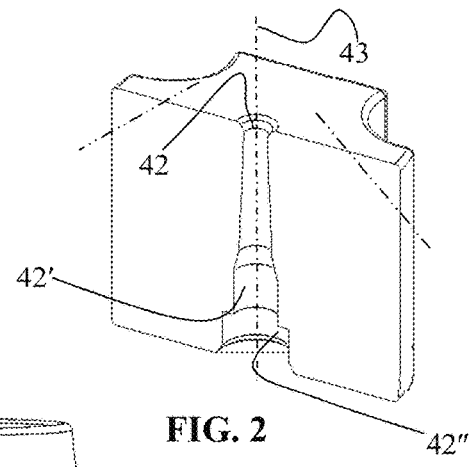
FIG. 2 shows a cross-sectional bisect view of an embodiment of the torque enhancement collar of FIG. 1.

FIGS. 1 and 2 show a first embodiment of the torque enhancement member in the form of a collar 40 (e.g., a bottle neck grasping collar) comprising a body portion 41 having an axial bore 42 for use in receiving an inserted component as in the neck of a utensil such as a bottle or shaft (e.g., a bolt shaft), and defining along at least a portion of an axis 43 (Z-axis) thereof a substantially quadrilateral cross-section having in each corner thereof a respective arcuate recess or corner "cut-out" 44, each for accommodating a user's thumb or finger or tool component. The axial bore 42 may be configured to accommodate, for example, an end of a hypodermic syringe; and, to this end, may include at least two mutually contiguous sections 42' and 42" of different cross-sectional areas so that the internal shape of the bore 42 is complementary to the external surface of the hypodermic syringe 36.

Under a needle hub reception use, the collar 40 may be formed of deformable material and dimensioned for axial compression or displacement of a predetermined distance that is adjusted to define a known protrusion of a hypodermic needle. This allows the collar 40 to be located at the end of the hypodermic needle, while concealing the tip of the needle, such that pushing the body of the syringe into the patient's skin causes the collar to compress and the needle to enter the skin. In an alternate embodiment, collar 40 is formed of a non-compressible plastic material that, in use, ensures the exposed end of a needle shaft extending away from the collar reaches the same depth of penetration upon collar-to-skin contact.

In the embodiment of FIG. 1 the torque enhancement component or body portion 41 is generally of rectangular cross-section and defines opposing pairs of first and second ridge side surfaces of different widths (and thus different lengths). In other embodiments, the body portion may be of square cross-section all of whose surfaces are of equal width, but the unequal length/width dimensioning featured in FIG. 1 presents an inherent torque enhancement configuration with features and benefits described below. At least one of the side wall surfaces may have an indent or depression 45 for accommodating the user's finger and for compression accommodation. By way of example, the indent may be provided on opposing side walls with each elongated with a major axis extending in the Z-axis direction on each opposing side wall. In some embodiments the top corners of the collar may be slanted as shown schematically by chain-dotted lines in FIG. 2 so that when the collar 40 is fitted to the operative end of a hypodermic syringe (or some other object) as described in more detail below, the resulting slanted edges may serve to guide the insertion of the needle at an angle determined by the degree of slant.

As a few non-limiting but illustrative dimensions for collar 40 embodiments, such as those in the examples described herein, a width (space between opposing longer length ridge walls representing peripheral, generally straight longer sides of the collar's periphery) of 18 mm is featured, while a length range (between opposing short length opposing ridge walls) of 25 mm is featured. As described in greater detail below, the height can vary greatly as in 2 mm heights up to 60 mm or more. As with all ranges discussed herein (unless otherwise indicated) all end points and points between the end points at the same unit dimension are intended for coverage herein. Additional non-limiting, but illustrative values for collar 40 includes a thickness height of 21 mm, a peripheral length of 6.5 mm in short ridge sides, and 13 mm peripheral length for the long ridge sides. The overall long length of collar 40 (from short ridge surface to short ridge surface) of 30 mm is illustrative. Some additional non-limiting, illustrative dimensions are provided below relative to, for example, FIG. 77a plus.

Figure 3:
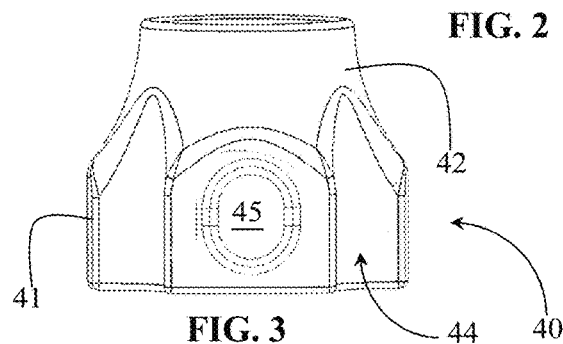
FIG. 3 shows a detail of a torque enhancement device according to a second embodiment.

FIG. 3 shows another embodiment of torque enhancement member in the collar configuration 40, having a body portion 41, an outer surface of which has a tapered portion 42 that projects axially upward opposite a torque enhancement periphery base portion of the collar. The body portion includes a lower portion of substantially quadrilateral cross-section, preferably rectangular for reasons described herein. The tapered portion 42 may be of smaller cross-sectional area than the base portion as shown in the figures so it that it tapers (converges) upward. Alternatively, it may be of larger cross-sectional area than the base portion so that it tapers (converges) downward. As in the first embodiment shown in FIG. 1, in each corner of the body portion 41 there is formed a respective arcuate recess 44 for accommodating a user's thumb or finger or tool. In some uses, it may be advantageous for the collar to be closed at one end to form a cap, or at the bottom to form a reception collar, or be formed entirely solid with reliance on the torque enhancement exterior periphery.

Figure 4:
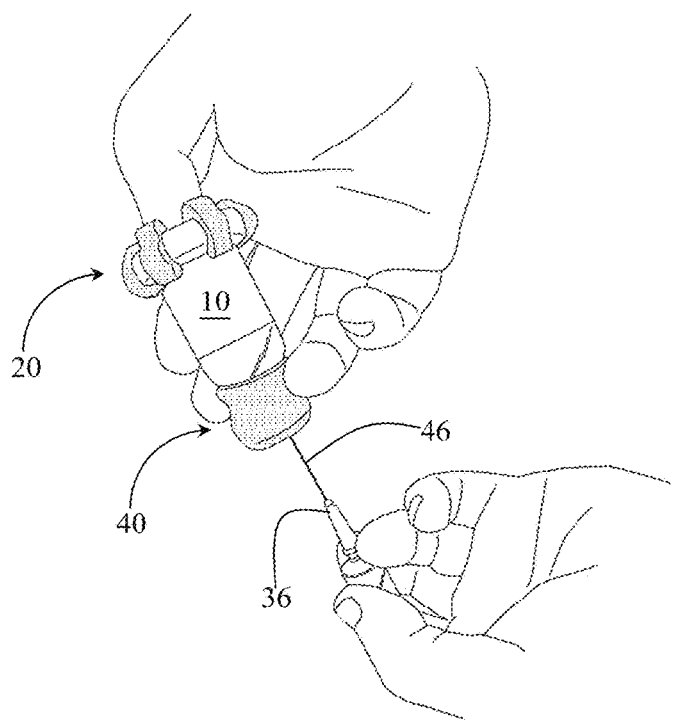
FIG. 4 shows finger rotation enhancement use of the torque enhancement device in collar form (collar only schematically shown without side wall detail) when transferring liquid between a bottle and a hypodermic syringe.

FIG. 4 shows use of the collar 40 (shown schematically without the detail of collar 40 shown in FIG. 1 for the same collar 40) when transferring liquid between the bottle 10 and a hypodermic syringe 36. Thus, the neck of the collar 40 defines a ribbed surface that is gripped between two fingers of one hand while the thumb of the same hand is held within, for example, a recess formed on the base or underside of the bottle 10. To this end, the collar may have a beveled indent (e.g., the version described above where the tapered portion diverges from its torque enhancement peripheral base) for better accommodating the fingers as best shown in FIG. 4. The user's other hand holds the hypodermic syringe 36 and aligns the needle 46 into the opening of the bottle. The ribbed surface of the collar 40 also provides some measure of shielding that reduces the risk of self-injection.

Figure 5:
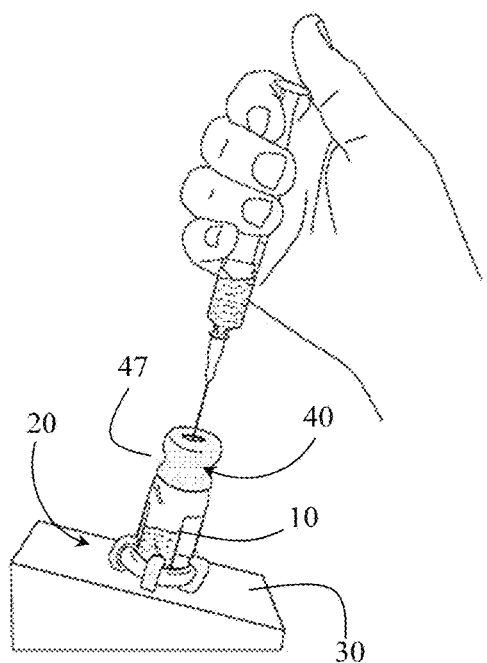
FIG. 5 shows use of the torque enhancement collar of FIG. 4 with its open or thinner material (sealing) top surface for use when transferring liquid between the bottle and a hypodermic syringe.

FIG. 5 shows one use of a ring-ribbed bottle support 20 to reduce the risk of self-injury by supporting the bottle or vial 10 in the bottle support 20 on a support surface 30 so as to obviate the need for the user to touch or hold the vial while aligning the hypodermic syringe therewith.

Figure 6:
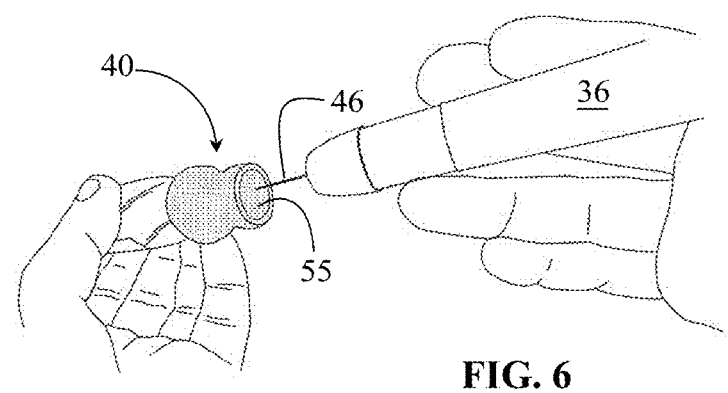
FIGS. 6 and 7 show use of the torque enhancement collar of FIG. 4 (again collar only schematically shown without side wall detail) to avoid the risk of self-injection or damage when transferring liquid between the bottle and a hypodermic syringe, and also to provide the possibility of a one handed suspended retention after connection.
Figure 7:
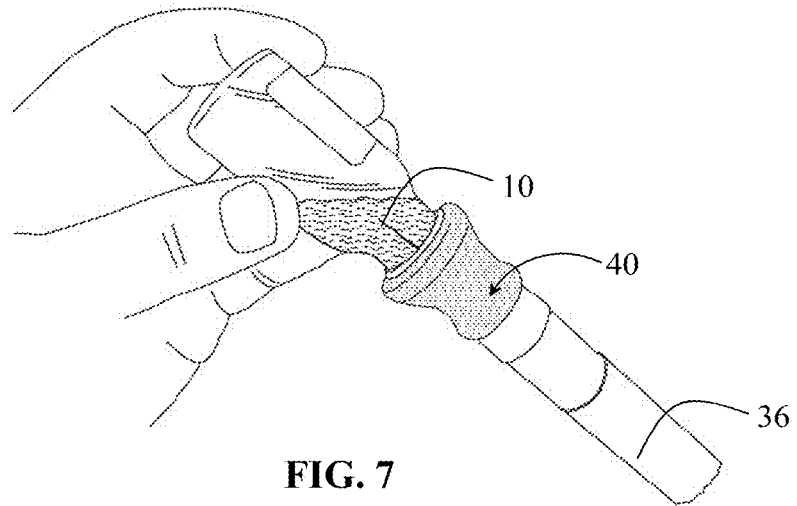

FIGS. 6 and 7 shows another embodiment where this risk is lowered by elongating the collar 40 and providing at its end an internal axial bore 55 configured to accommodate an end of the hypodermic syringe 36, thus allowing the neck of the bottle 10 to be coupled to the hypodermic syringe 36 as shown in FIG. 7. By such means, the collar 40 serves both as a grip and a sleeve or coupler for coupling to the mouth of another utensil as shown in FIG. 7.

Figure 8:
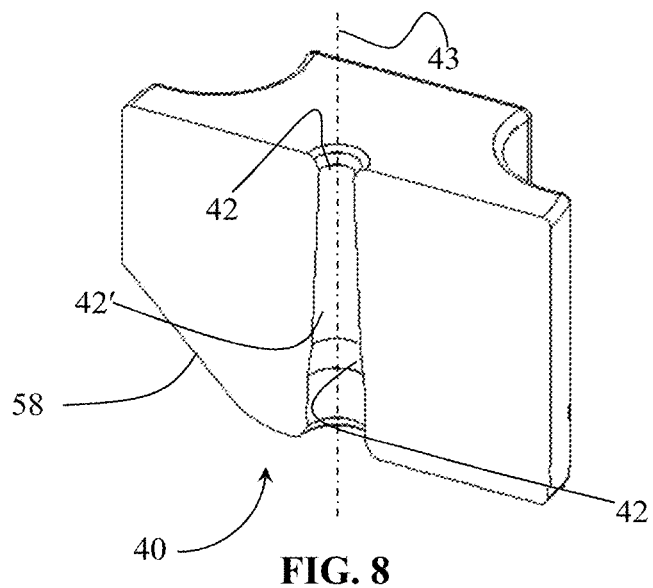
FIG. 8 shows, in cross-section, a torque enhancement device in collar "shield" form having a slanted surface for, for example, guiding a hypodermic syringe or fitting over a narrow vial at the bottom while a hypodermic needle syringe enters from the top.

FIG. 8 shows in cross-section a collar 40 having a bore 42 shaped for accommodating, for example, the end of a hypodermic syringe (not shown) as described above with reference to FIG. 2. One side face 58 of the collar is at least partially beveled or slanted at an angle of, for example, 15° (or some other angle such as one selected from the group of 15°, 20°, 40°, 60°) so that, in use, when this surface is guided along (or retained relative to) the surface of a patient's skin, the needle (not shown) will be maintained at an appropriate angle for venous injection without the need for manual support by the operator's finger. It should be noted that FIG. 8 shows the slanted edge at the hub reception side although a slant can also be formed on the opposite side where the needle extends out away from, or both sides (as represented by the double dot dashed lines in FIG. 2). This latter orientation is typical for sliding contact on skin with the needle at a pre-set desired angle for initial injection.

Figure 9:
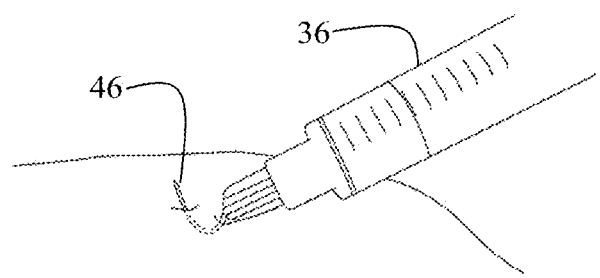
FIG. 9 shows bending of a hypodermic needle that may occur with conventional syringes resulting in extension under the skin in fish hook type fashion.

The extent to which the needle 46 protrudes in the default state directly impacts on its tendency to bend. Some hypodermic needles are very thin and easily deformed. If they are injected at the wrong angle and/or the patient moves, the needle can bend as shown in FIG. 9 and puncture the patient's skin in two locations. This is both painful and ineffective because the contents of the syringe are wasted and thus requires a further injection.

Figure 10:
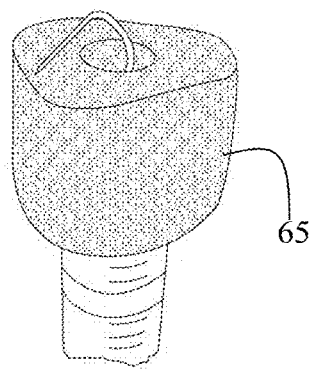
FIG. 10 shows a resilient torque enhancement collar (collar only schematically shown without side wall detail) that reduces the malfunction shown in FIG. 9.

FIG. 10 shows how this malfunction can at least be mitigated by use of a collar 40 such as that described above or one such as illustrated as collar 65 formed of deformable material such as foam and dimensioned for axial compression or displacement of a predetermined distance that is adjusted to define a known protrusion of a hypodermic needle. In this embodiment, the collar has a solid base portion that serves as a cap at the needle hub.

Figure 11:
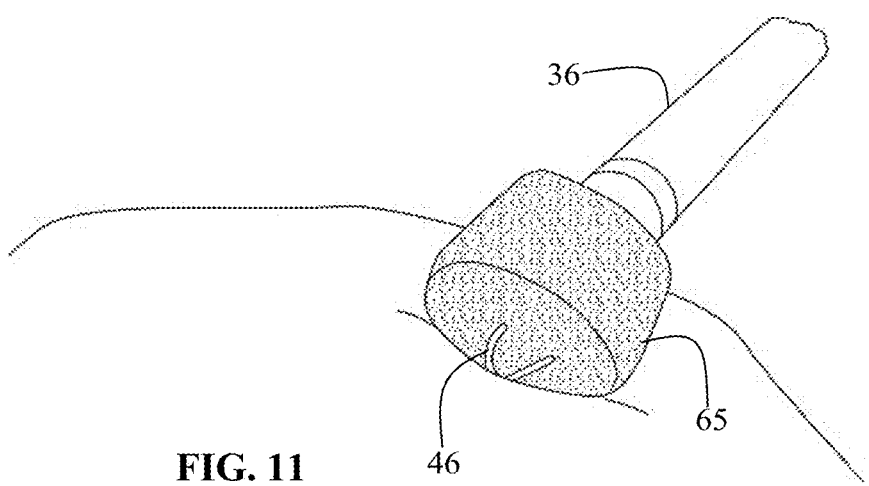
FIG. 11 shows how the resilient torque enhancement collar of FIG. 10 cushions the needle and prevents it from bending inside the patient's skin.
Figure 12:
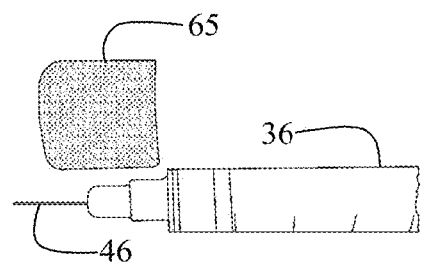
FIGS. 12 and 13 show, respectively, details of a hypodermic syringe before and after the collar of FIG. 10 is fitted over the needle.
Figure 13:
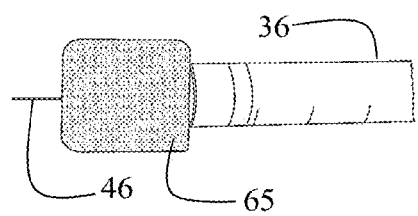
Figure 14:
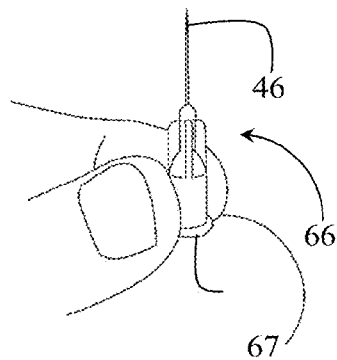
FIG. 14 shows a detail of a prior art needle assembly.
Figure 16:
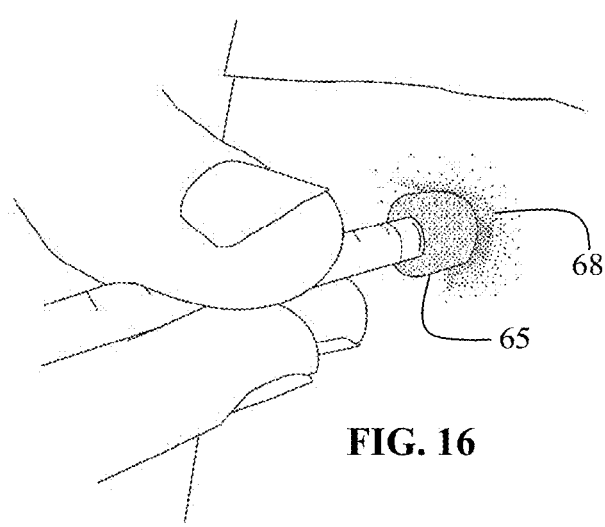
FIG. 16 shows the effect of using the collar to spread the pressure over a wider area.
Figure 15:
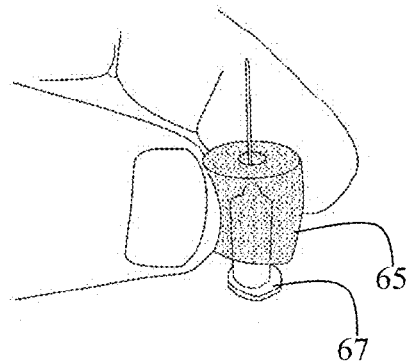
FIG. 15 shows how the collar of FIG. 10 is fitted on to such a needle assembly.

FIG. 11 shows use of the collar 65, which abuts the skin as the needle 46 is injected. Should the needle bend owing to slight misalignment, it is cushioned by the collar and will bend back on itself without penetrating the patient's skin. FIGS. 12 and 13 show respectively details of the hypodermic syringe before and after the collar 65 is fitted over the needle. The same relationship can also be obtained when collar 40 is used over a needle hub. FIG. 14 shows a detail of a needle assembly 66 having a base 67 supporting the needle 46. FIG. 15 shows the collar 65 as it is fitted on to the needle assembly 66 so as to be supported by a peripheral flange of the base with the needle protruding through the opposite end of the collar. FIG. 16 shows the effect of using the collar 65, which pushes against the surface of the patient's skin over an extended area 68 thereof, which spreads the pressure over a wider area thereby reducing pain and assists in distributing the contents of the syringe more quickly through the surrounding tissue.

Figure 17:
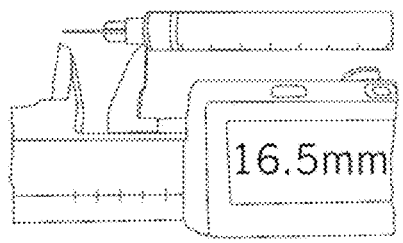
FIGS. 17, 18 and 19 show typical dimensions associated with the needle assembly with and without the collar in situ.
Figure 18:
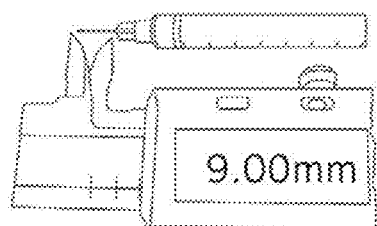
Figure 19:
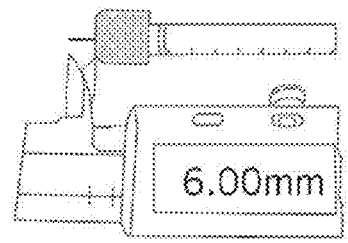

FIGS. 17, 18 and 19 show respectively some illustrative dimensions of the needle assembly 66 (16.5 mm), and the length of the protruding end of the needle 46 without (9 mm) and with (6 mm) the collar in situ. In an alternate embodiment the collar is designed to not be compressible upon skin contact but to keep a fixed length needle extension below the skin contact, as in the aforementioned collar 40 configurations.

In all embodiments, the collar may be integral with the object or utensil to which it is coupled. So, for example, it may be integral with the bottle allowing easy coupling to the hypodermic syringe, or vice versa.

Figure 20:
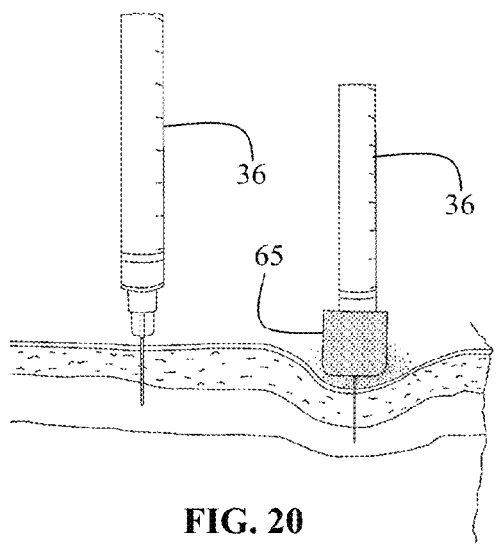
FIG. 20 shows a comparison of a prior art syringe with a syringe fitted with the collar of FIG. 10.
Figure 21:
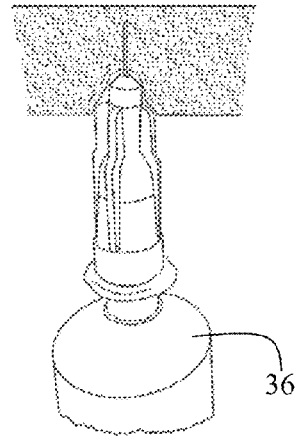
FIGS. 21 and 22 show prior art needle hub assemblies such as for use in FIG. 20.
Figure 22:
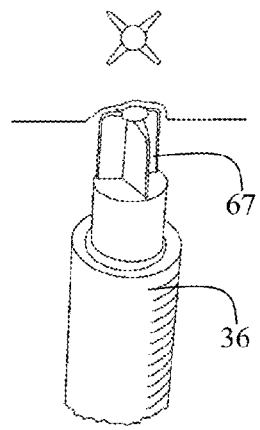

FIGS. 20, 21 and 22 show, pictorially, comparisons of prior art syringes with a syringe fitted with the collar of FIG. 21. Thus, as seen, the operative end of the hypodermic syringe has two intersecting ridges that press into the skin if pushed too deeply, causing significant pain to the patient. In contrast thereto, the resilient collar 65 cushions the impact and helps to distribute pressure and thereby reduces pain. Alternatively, the collar can be made rigid enough not to compress in use against skin contact as to control the puncture depth, while still helping to disperse (increase) the area of instrument to skin contact. Under either scenario there can be better achieved a desired needle tip positioning to ensure contact with a desired location (e.g., a desired skin layer depth) in a patient in comfortable fashion.

Figure 23:
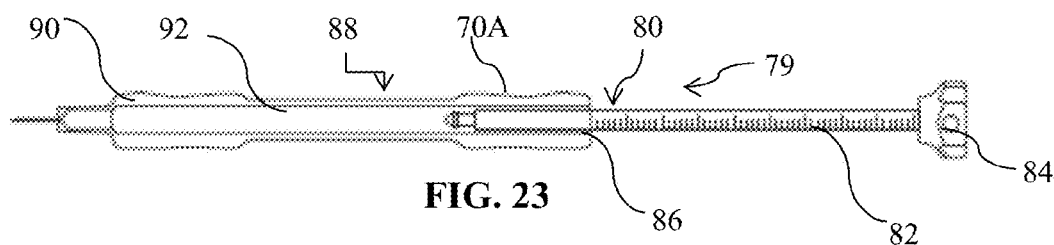
FIG. 23 shows a syringe with a modified torque enhancement plunger base featuring also a dumbbell shaped grasping feature in the syringe cylinder.

FIG. 23 shows syringe assembly 79 featuring syringe 80 with a modified plunger 82 featuring, at one end, an added torque enhancement (e.g., rotation) "elephant foot" shaped grasping head end member 84, which can represent a snap-on collar featuring a collar of, for example, the FIG. 3 configuration with open top rimmed end that is flexible enough to receive an inserted plunger flange (such as the circular flange located to the far right of the syringe of the below described FIG. 28). In an alternate embodiment, a one piece gripping torque enhancement collar is provided which forms a monolithic unit with the plunger 82 itself (in similar fashion to the integrated "elephant foot" plunger end shown in FIG. 31 as described below). FIG. 23 also shows, extending over the syringe cylinder 86, a grasping member 88 in the form of an elongated dumbbell shaped sleeve or molding comprised of a needle end enlarged portion 90, an intermediate extension portion 92, and an opposite enlarged portion 94 similar in configuration to that of the needle end enlarged portion 90. Grasping member 88 is provided with a central through-hole designed to receive in slide-on gripping fashion the cylinder 86 of syringe or collar 88 can be molded over cylinder 86, or be formed as a single unit as in common plastic molding of the cylinder and grasping member portion.

Each enlarged portion 90, 94 represents an adaptation of the gripping sleeve device for precision instruments described in U.S. Pat. No. 8,745,825 issued on Jun. 10, 2014 (US '825), and which patent is hereby incorporated by reference in its entirety for background purposes. That is, each enlarged portion has an outer surface with the finger contact regions described in US '825 that provides for enhanced finger manipulation, both with respect to longitudinal advancement or retraction in the direction of needle insertion, but as well as rotation of the syringe. The elongated dumbbell shape also facilitates handing off the utensil from one person to the next or one hand to the other, as the length of extension portion 92 is sufficient for finger grasping without contacting the two, opposite end enlarged portions 90 and 94 and also in a fashion that avoids interfering with extended plunges. In addition, the enlarged dumbbell ends 90 and 94 provides for lifting the needle away from a contaminated surface and ready pinch pick up due to the lifted off surface arrangement provided by enlargements 90 and 94. Further, the inclusion of the dumbbell shaped grasping member with enlarged portion 94 provides a grasping location that avoids the need for a syringe cylinder end flange. Also the inclusion of grasping member 84 removes the requirement for a free end plunger flange.

Figure 24:
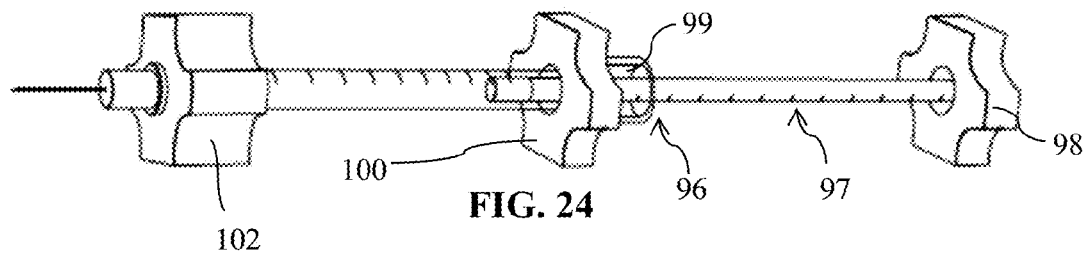
FIG. 24 shows another embodiment of the present invention featuring a set of different torque enhancement devices inclusive of a first smaller thickness grasping collar at the plunger base, a second, similar smaller thickness collar at the syringe's cylinder base, and a third, larger thickness collar at the needle support end of the syringe cylinder.

FIG. 24 shows another syringe assembly 96 embodiment of the present invention featuring a syringe 97 with a set of different collars inclusive of a first, smaller thickness torque enhancement member in the form of grasping collar 98 at the plunger base, a second, similar smaller thickness torque enhancement member shown as collar 100 at the syringe's cylinder base, and a third, larger thickness torque enhancement member in the form of collar 102 at the needle support end of the syringe cylinder. The smaller collars have interior apertures (through-holes) suited for stretch over (e.g., snap-on or just slide over) retention to their respective syringe sights (as in a sufficiently flexible material collar with an aperture that snaps over and engages the circular flange located to the far right of the syringe of the below described embodiment featuring an expansion over a plunger's flanged end, or simply slides over a flange-less plunger end). In addition, the same collar (collar 100) with its flexibility and suitably sized aperture can slide over and engage with the base of the cylinder of the syringe 97 of needle assembly 96.

As seen, each of the flexible grasping collars 98, 100 and 102 feature a torque enhancement peripheral configuration similar to that of FIGS. 1 and 2, inclusive of four concave recesses at corners of the grasping collar, two opposing longer length generally straight or slightly curving (e.g., a radius larger than that of a circumference contacting the outermost points of collar 98, 100 or 102), and two opposing also generally straight or slightly curving (see above) shorter length sides. Collars 98 and 100 can be of the same configuration. Also the thickness of the thinner collars 98 and 100 can be, for example, ½ of that of the thicker collar 102 (e.g., a thickness value of, for instance, 6 to 9 mm for the thinner collars 98 and 100 which is suitable for the small volume (e.g., a cylinder volume of, for example, 0.5 ml (or cc) to 10 ml) syringe 96 shown). Also, the concave (preferably equally configured and sized) recessed corners, and adjacent projections (resulting in the noted shorter and longer generally straight or slightly curved ridge sides) provide for ready finger pinching and twisting of the needle assembly external to the cylinder of the syringe and multiple finger grasp locations for a transfer (e.g., one person pinching and holding one of collars 98, 100 and 102 and the other person receiving the syringe with the needle in a safe location by grasping one of the remaining two collars not already grasped). The collars also are well suited to maintain the needle of the syringe suspended above an underlying potentially contaminated surface (and in non-rotation fashion relative to the supporting surface), and provide for ready torque application as in a twist off of a threaded needle hub received within a collar's confines once a torque application is applied.

Figure 25:
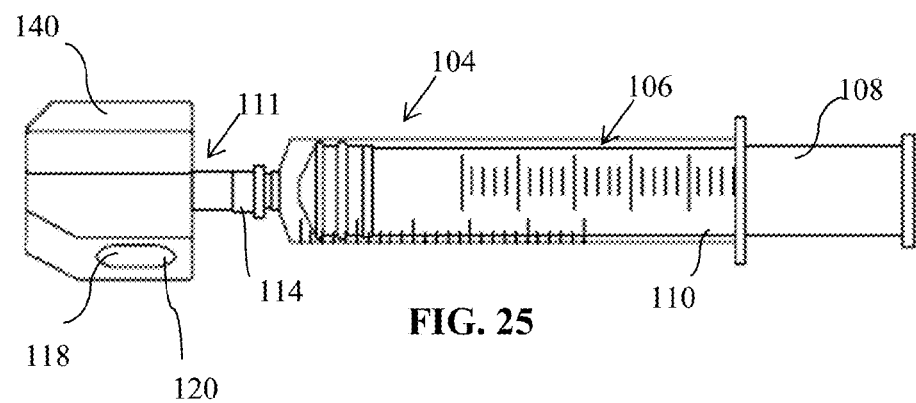
FIG. 25 shows the collar having a taper such as in FIG. 8 in an initial slide on position relative to the needle assembly of a syringe.
Figure 26:
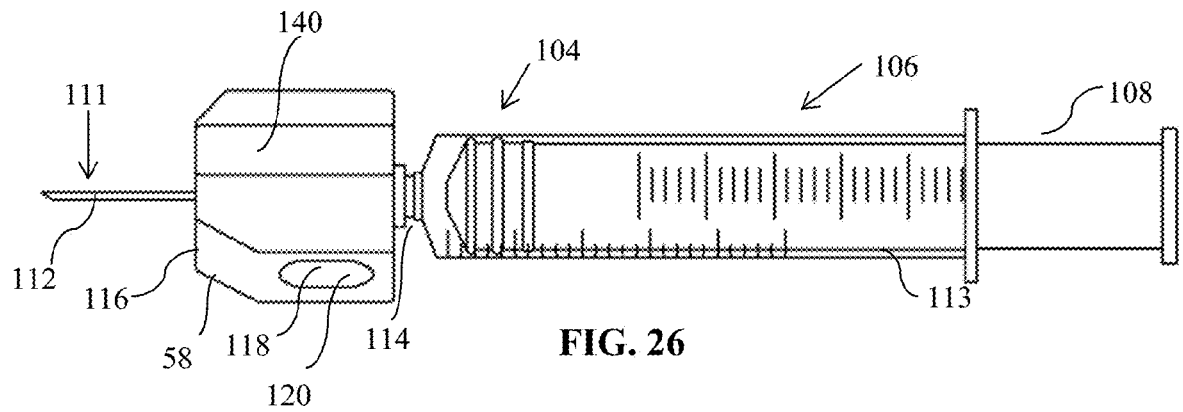
FIG. 26 shows the collar of FIG. 25 in a final resting position over the base of the needle assembly and with a predetermined length of needle extending outward away from the free end of the collar with slanted exterior surface.

FIG. 25 shows an additional syringe assembly 104 under the present invention featuring a syringe 106 comprised of a plunger portion 108, a cylinder portion 110 (e.g., a higher volume cylinder as in, for example, >10 ml to 400 ml), and a needle assembly 111, with the latter having a needle 112 and needle base hub 114. In FIG. 26, syringe assembly 104 is shown further comprising torque enhancement member (shown in the form of a collar 140—as in the collar shown in FIG. 8) having its aperture set (42, 42' and 42") in position for a slide on connection with the above described components of needle assembly 111 as in the needle associated with a 20 ml to 50 ml syringe. As seen, collar 140 in FIG. 25 has a similar external periphery as that of the above described collar 102 with its four corner positioned concave recesses and short and long sides extending between the corner concave recessed and in common opposing fashion (i.e., short-to-short generally straight ridge sides opposing, and long-to-long generally straight sides opposing and parallel to each other). Collar 140 in FIG. 25 is also shown with the above described sloped surface 58 (two options shown as in FIG. 27) which facilitates needle tip and needle orientation relative to the skin surface to receive the needle (this being in addition to the offset finger pinch grasping potential when holding, passing or receiving the needle assembly 104).

FIG. 26 shows the collar 140 of FIG. 25 in a final resting position over the base of the needle assembly 111 and with a predetermined length of needle 112 extending outward away from the free end 116 of the collar 140 with slanted exterior surface 58. FIG. 26 further shows the tapered surface 58 being formed on the longer opposing generally straight side which further includes a finger depression recess 118 (same as the oval recess depression 45 in FIG. 10a) along the non-slanted portion 120 that extends from an end of tapered surface 58. As also seen in FIG. 26, the outer circumference of the collar 140 has a larger diameter than that of the syringe cylinder (even the larger volume syringe cylinder) as to provide for offset grasping away from the needle, etc.

Figure 27:
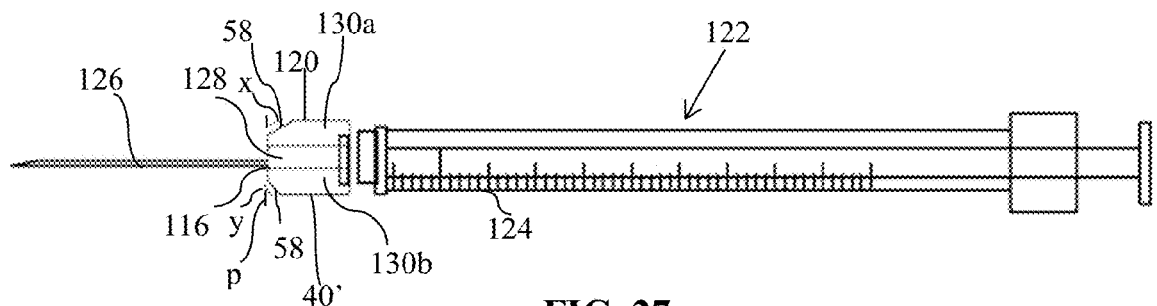
FIG. 27 shows a similar view as FIG. 26 but with a different, smaller volume cylinder syringe and with a longer needle extension out from the collar secured to the syringe's needle assembly, as well as a dual (different) angled sloped collar.

FIG. 27 shows a similar view as FIG. 26 but with needle assembly 122 featuring a different, smaller volume cylinder 124 and with a longer needle extension 126 out from the torque enhancement member configured as collar 40' secured to the syringe's needle assembly. FIG. 27 also provides a different viewpoint wherein there can be seen the short side ridge 128 of the opposing short sides ridges. Also, in this embodiment, collar 40' is similar to that of FIG. 8, but features a second, shorter length oblique surface 58' on the one side opposite the long or wider width ridge side in which oblique surface 58 extends. For example, concave (corner "cut-out") recesses 130a and 130b extend in longitudinal fashion for the full entire length of collar (longitudinal is perpendicular to plane P that extends flush on free end 116 of collar 40'). Suitable angle ranges for angles X and Y defined by plane P and the respective oblique side (58, 58') range from 10° to 80° with X preferably being equal to or greater than angle Y shown in FIG. 27.

Figure 28:
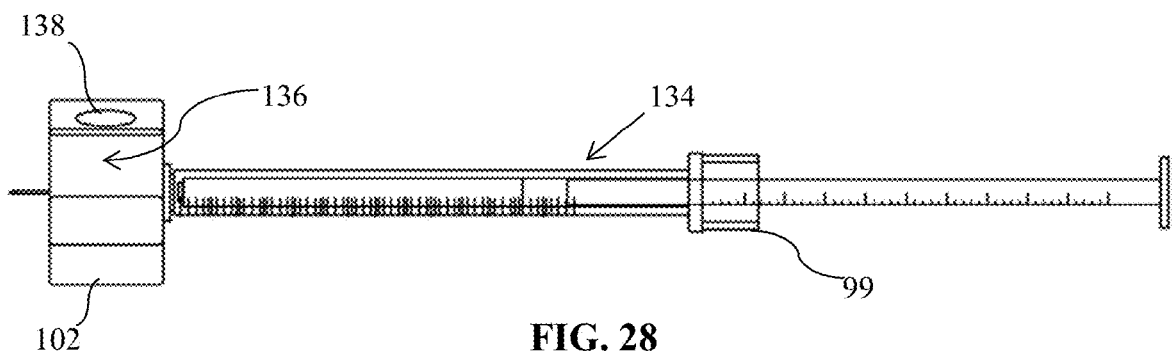
FIG. 28 shows an alternate arrangement featuring a similar volume cylinder syringe as in FIG. 27, but with a collar having the configuration shown in FIG. 2.

FIG. 28 shows an alternate needle assembly 134 arrangement featuring a similar volume cylinder syringe as in FIG. 27, but with a collar 136 having the configuration shown in FIG. 2. As further shown in FIG. 28, collar 136 comprises a finger depression recess 138 (in common with depression 45 shown in FIG. 1 and with an illustrative depression level of 0.5 mm). This finger recess can help a user control the desired tilt for insertion of the only partially visible needle shaft extending out from the collar (a second such depression can be provided on the opposite for symmetry and multi-position sourcing).

Figure 29:
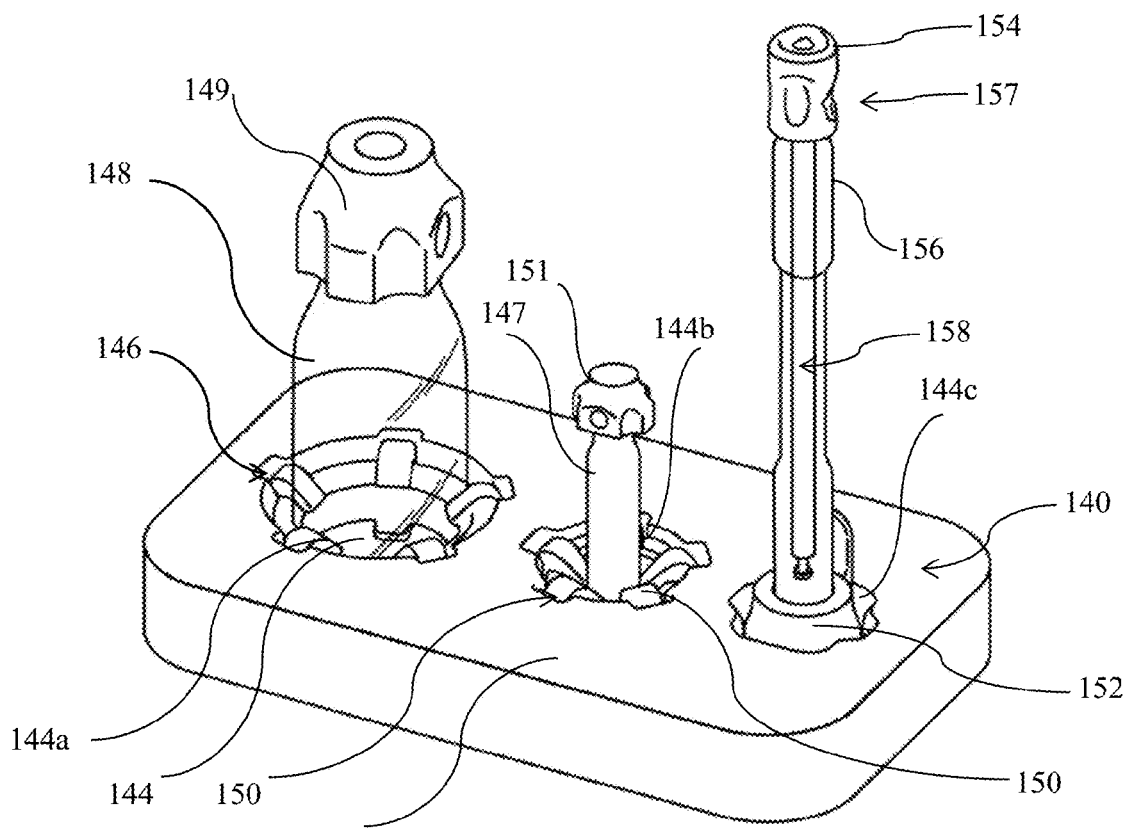
FIG. 29 shows a reception tray with the base mounts of two of the three utensils secured in the corresponding tray mount reception apertures, as well as an additional needle capping and crushing collar base component received in a corresponding collar tray reception aperture; and a grasping collar provided at the top of each utensil, including an open top torque enhancement collar for the far left utensil, a closed top torque enhancement cap configured collar for the interior utensil, and a grasping collar at the top end of the syringe shown received in the far right tray reception aperture.

FIG. 29 shows tray 140 comprising base body 142, having apertures 144, with a largest diameter aperture 144a, an intermediate aperture 144b, and a third, smallest aperture 144c. Aperture 144c represents an aperture configured for specific friction retention of the below described capping needle and crush collar (152 in FIGS. 35 and 36 and hereafter referenced just as "crush collar"), which crush collar generally has a FIG. 3 configuration. Aperture 144c thus has a unique shape designed to conform with the exterior periphery of collar 152 with its long and short ridge sides and in-between cavities.

FIG. 29 further shows a kit combination embodiment under the present invention involving tray 140 plus one or more additional components. While a kit combination is described for that which is shown in FIG. 29, the present invention described components can be provided in a variety of kit forms including combinations involving some or all of the component categories described herein; such as i) mounts (annular collar and ribs combination), ii) container collars (as in vial or bottle collar, with closed top or open top of various aperture sizes and configurations), iii) syringe collars (collars on a syringe plunger, syringe cylinder, and/or needle assembly) and iv) haptic collar(s) such as for catheter use, as a few examples, as well as other uses associated with the various torque enhancement member configurations described herein. In the FIG. 29 embodiment, the additional components include a larger sized (ribbed-ring) base mount 146 supporting the base of a larger sized bottle 148, with the mount and bottle nestled within conforming aperture 144a. In addition to base mount 146, the kit includes a FIG. 3 configured collar 149, which is shown as a torque enhancement member for a cap to bottle 148 and as having an open top (suitable for syringe insertion as described below). Collar 149 can also represent the cap itself as in an overmolding relationship with an interior threaded cap or the formation of threads on the interior of the collar or the collar can rely on flex-and-return frictional engagement. As a cap the top of collar 149 can be closed (e.g., a sealing membrane covering that can be punctured by the needle in a sterile manner).

The middle positioned aperture 144b also is configured to receive a corresponding sized base mount 150, which is supporting the base of a sample vial 147 having a smaller version FIG. 3 torque enhancement collar 151 which in this case has a closed top (e.g., a sealed membrane cover such as described above). Thus, the two larger apertures 144a and 144b have apertures designed specifically for receiving the flexible ribs of base mount 150 in extension recesses, while the smallest aperture 144c is configured differently, with an aperture configured to accommodate needle support-and-crush collar 152 received in the friction fit collar tray reception aperture 144c.

Additional components associated with the kit involving tray 140 include syringe assembly 157 comprising syringe 158 as well as plunger end grasping sleeve 154 (e.g., having a shape such as that described in the aforementioned US '825) and dumbbell shaped grasping member 156 provided along the cylinder of syringe 158 (provided by a slide fit over the cylinder or an overmolding integrated combination or as a single mold unit). The kit associated with tray 140 can be one that is functionally coordinated, as in a liquid bottle medicament supply 148, for drawing liquid medicament solvent therefrom, with syringe 158 (after pulling the syringe from collar 152 (in a not yet needle crush state) and inserting it into the open top of collar 149) and then passing the drawn liquid medicament to the powder storing vial supported in aperture 144b by puncturing the top seal of collar 151 whereupon the powder and medicament solvent can be mixed and drawn up for patient insertion and then, upon patient treatment completion, the syringe 158 is returned to collar 152 whereupon the enlarged lower end of the dumbbell grasping member (with associated enlarged "saddle horn" projection (described in US '825)) is rotated so as to avoid an interior projection in collar 152, whereupon a downward force is applied to move the syringe so as to crush the needle. The entire syringe collar and crush collar can then be discarded with a covered and crushed needle.

Figure 30:
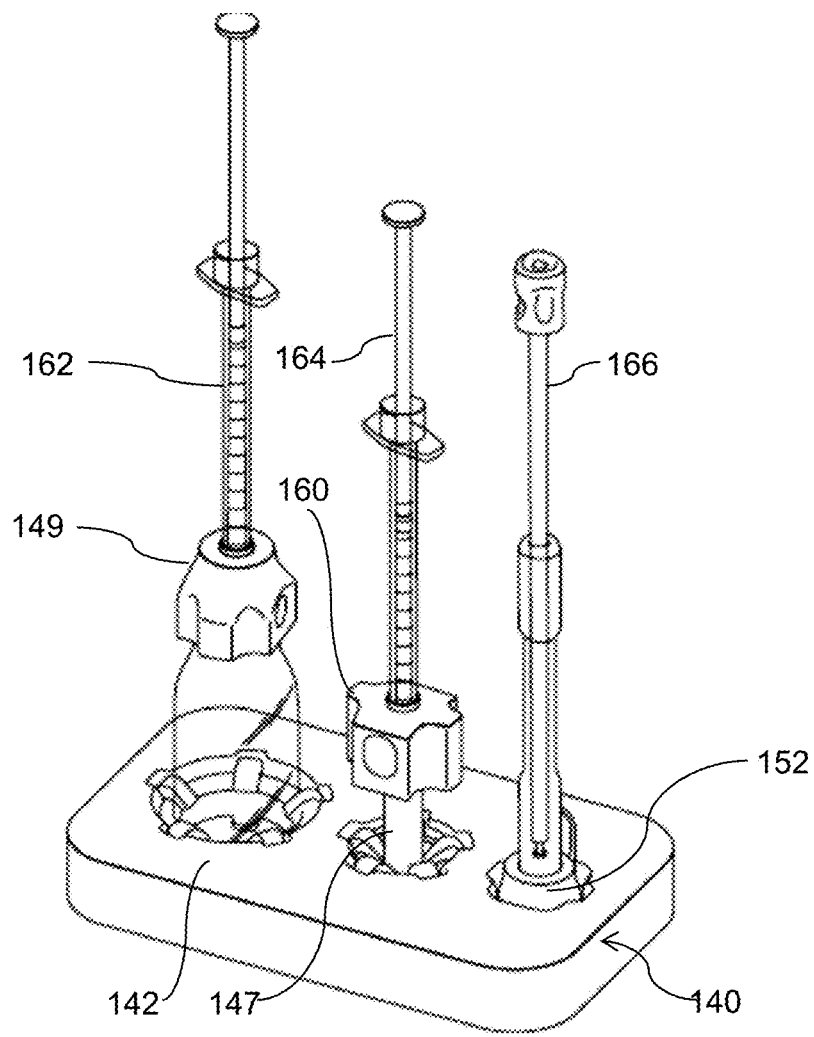
FIG. 30 shows a similar view as FIG. 29, but with a FIG. 1 collar embodiment for the intermediate utensil, and the added feature of the far left and intermediate collars showing syringe needle reception with the needle in each passing through and being supported by the receiving collar mounted on the utensil below.

FIG. 30 shows a similar view as FIG. 29, but in different kit form as it comprises, instead of collar 151, a FIG. 1 torque enhancement collar (160) embodiment is attached to the top of vial 147 as the intermediate utensil. There is also shown in FIG. 30, the added feature of the far left and intermediate syringes 162 and 164 with the needle of each of syringe 162 and 164 shown passing through and being supported by the receiving collar mounted on the utensil below. As above, the kit associated with FIG. 30 can be a functionally coordinated kit, with, for example, a pre-filled syringe 166, and the other two syringes (once liquid medicament is drawn from the associated utensil), being used in a desired sequence of application on a patient. Alternatively, there can be featured a single syringe as in the far left only for solvent draw and then subsequent supply to the vial (with another liquid or powder) for mixing and application, whereupon the crush collar can be utilized after application of the mix. Further, each component supported on the tray is designed for single hand removal or insertion.

Figure 31:
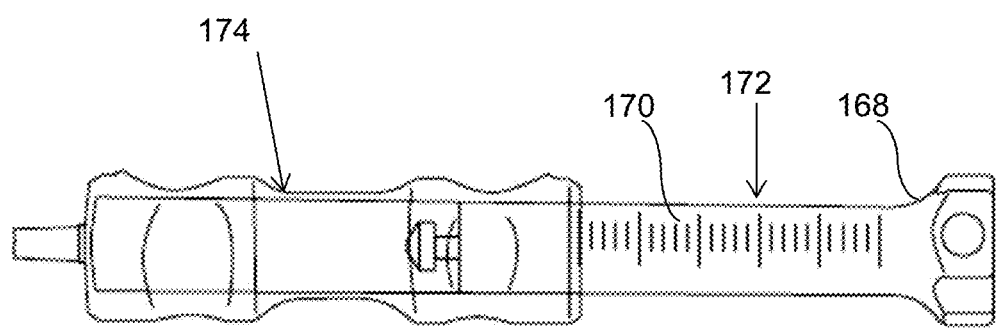
FIG. 31 shows an alternate embodiment of the invention featuring an integrated (unitary or monolithic) torque enhancement grasping body formed integrally (e.g., an "elephant foot" configuration) with a plunger of a syringe and of a common material as well as a non-monolithic grasping collar in a dumbbell shape provide along the cylinder of the syringe shown, and with volume demarcations or graduations provided on the shaft portion of the plunger body rather than the receiving cylinder with dumbbell grasping sleeve covering.

FIG. 31 shows an alternate embodiment of the invention featuring an integrated (unitary or monolithic) torque enhancement member (elephant foot configured grasping end) 168 formed integrally with shaft 170 in the form of a plunger for the illustrated syringe 172. That is, FIG. 31 shows a grasping member 168 that is formed as a monolithic component of the base end of a syringe plunger and preferably of a common material (e.g., a one polymer plastic molding of collar 168 and plunger body). Additionally, syringe 172 features a cylinder with a dumbbell grasping member 174 which is a single monolithic exterior of the syringe cylinder or a non-monolithic grasping sleeve in a dumbbell shape (and having the characteristics described above for grasping member 88 in FIG. 23) provided over or along the cylinder of the syringe shown. Also, rather than demarcations on the covering dumbbell collar, graduations showing volume demarcations are provided on the plunger itself. This arrangement is particularly suited for high viscosity liquids requiring a high plunger draw force and where visibility is impeded on the syringe barrel.

Figure 32:
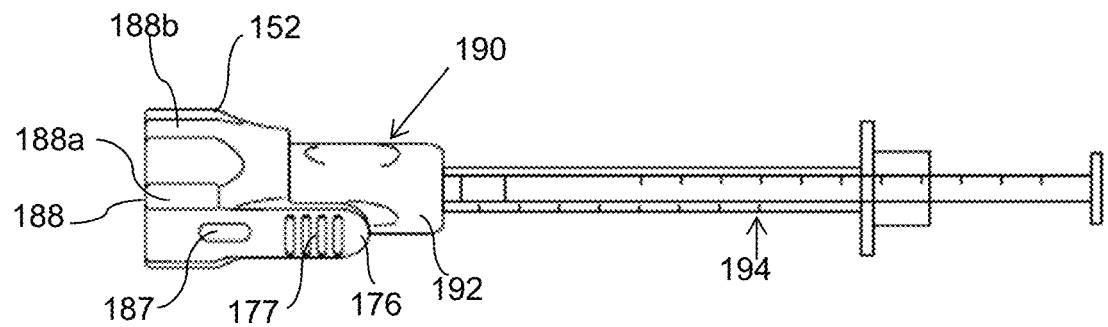
FIG. 32 shows an additional embodiment of the present invention featuring a torque enhancement device in the form of a capping and needle crush collar base component, noted in FIG. 29 above, working in combination with a needle assembly reception grasping collar that is received by the capping and crush collar ("crush collar" for shorthand reference).
Figure 33:
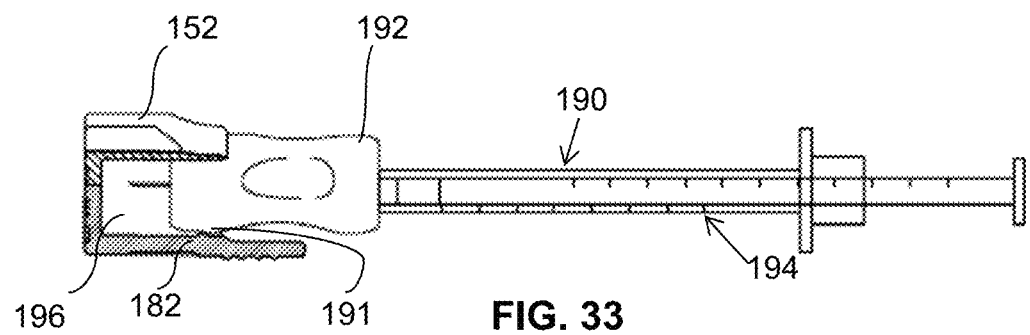
FIG. 33 shows a partially cut away view of that which is shown in FIG. 32 with the crush collar receiving the grasping collar at the distal end of the syringe and in a pre-needle crush state, and with abutting projection alignment for projections found on the crush collar interior and the grasping sleeve exterior.
Figure 34:
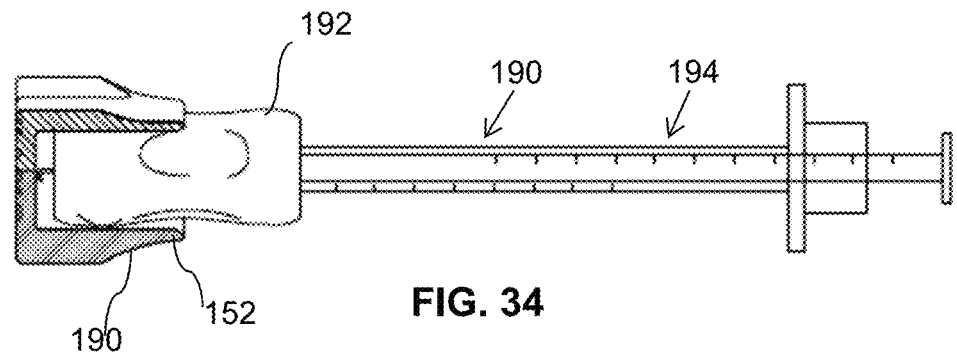
FIG. 34 shows the same view as FIG. 33 but with the syringe assembly and collar having been compressed together fully leading to the bending of the free portion of the needle extending out of the grasping collar on the syringe; in this state the entire assembly is suited for discarding in a needle collapsed, safe state.
Figure 35:
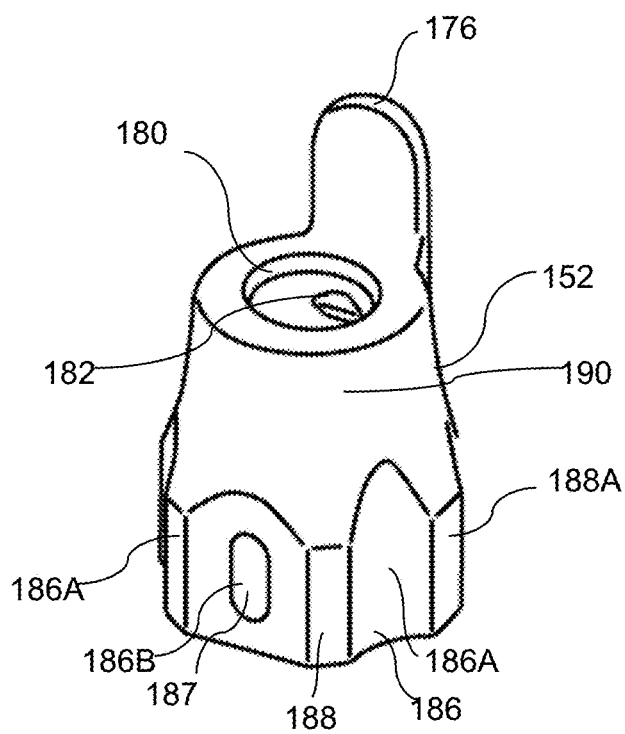
FIG. 35 shows a front perspective view of the crush collar with torque enhancement configuration shown in FIG. 34.
Figure 36:
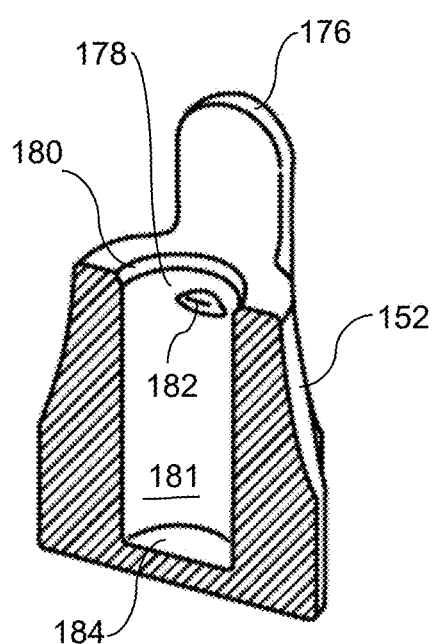
FIG. 36 shows a cross-sectional view of that which is shown in FIG. 35.

With reference to FIGS. 32 to 34 there is described the above referenced torque enhancement member in the form of syringe support/needle crush collar 152. With reference to FIGS. 35 and 36 there is shown collar 152 alone, with FIG. 35 showing a perspective view of collar 152 and FIG. 36 showing a cross-sectional view with the collar half removed with the removed portion being that opposite tab extension or clip 176.

As seen from FIG. 35, torque enhancement member 152 has the FIG. 3 configuration, but for the added tab extension or clip 176, as well as preferably added revisions with respect to providing a needle blockage base for facilitating needle crushing when so desired and an added interior projection 182. FIG. 35 further shows crush collar 152 with an open top 178 preferably having a slight conical alignment ledge 180 which tapers inward and downward from the top face of collar 152. In the interior cavity 181 shown in FIG. 36, there can be seen inward projection 182 that extends inwardly into cavity 181 away from tab extension 176 as to provide for pre-crush axial resistance during syringe support in collar 152 and provides a resistance factor for single handed removal. Floor 184 is preferable formed of a sufficiently hard plastic or is supplemented with a metal disc or the like that is supported by the circular face associated with floor 184. The harder plastic can be representative of the entire collar 152, but since having a flexible collar 152 that can be pliable to facilitate positioning of utensils in a support relationship is desirable, a dual plastic molding relationship can be implemented such that the floor is of a different, harder plastic or the aforementioned metal disc insert can be utilized (i.e., insertion of a thin metal, circular disc to conform to and cover floor 184). The collar 152 configuration and dimensions is suited for receiving grasping member 192 and thus is preferably similar to those featuring a "large mouth" reception aperture such as featured in FIG. 37 and FIGS. 96a and 96b described below.

FIG. 35 further illustrates in common fashion with FIG. 3 that the exterior side wall periphery of collar 152 is comprised of a series of concave depressions or corner "cut-outs" 186 separated by wall projections 188. As seen in FIGS. 3 and 35, the concave depressions can come in different length (Z-axis) and optionally as well different corner cut out width sizes (although embodiments also include common corner cut-out widths), with a plurality of narrower and higher extending depressions 186A (higher extension up into the conical top region 190 of collar 152), separated by shallower height concave depression 186B, with the latter also having finger depression recess 187 (on the side opposite the tab extension 176). The ridge line projections 188 include a similar shaped series of such ridge lines (188A, 188b . . . ) that provide for offset finger grasping with any two of such projections with finger nesting in the adjacent concave depressions.

FIG. 32 shows an additional embodiment of the present invention featuring needle crush collar 152 providing support to syringe assembly 190. As shown, syringe assembly 190 has grasping collar 192 formed at the needle assembly end of syringe 194 (of syringe assembly 190) working in combination with the receiving crush collar. Grasping collar 192 represents an adaptation of the gripping sleeve device for precision instruments described in the earlier noted U.S. Pat. No. 8,745,825 issued on Jun. 10, 2014. The adaptation in this case includes having the interior through-hole having a diameter or diameters to conform to the diameter(s) associated with the needle assembly of syringe 194. Due to the non-symmetrical configuration of collar 192 (e.g., saddle horn projection 191 in FIG. 33), the plateau of the sleeve or handle will engage inward projection 182 protrusion(s), which will block further penetration into the cap. When returning after use the syringe with the sleeve may be rotated such that protrusion 182 will meet a smooth surface of syringe assembly 190 and therefore be able to be depressed deeper into the crush collar and, after needle crushing, disposed, safely, as a unit (syringe and cap connected) into a disposal bin. Thus, a single hand needle de-capacitating safety system is provided.

With reference to FIGS. 32 and 33 (with FIG. 33 providing a cut-away view of syringe assembly 190 in a support (non-needle-crush) mode), there is shown needle 196 in a suspended state above floor 184 of collar 152. There can further be seen the syringe support function provided by collar 152. As further seen from FIGS. 32 and 33, tab extension 176 includes finger enhanced friction ridges 177 formed in the body of tab extension on the exterior side and above finger depression recess 187. This finger friction enhancement facilitates the ability to grasp collar 152 and the supported syringe either for movement to or from a support surface or for pulling out (or placement in) of collar 152 in a conforming tray aperture such as 144c in FIG. 29, or the final discard step described above. The needle crush conversion can be seen by a comparison of FIGS. 33 and 34 wherein the latter shows the crush state of the needle, and with floor 184 showing a partially harder material section via different cross-sectioning.

Figure 37:
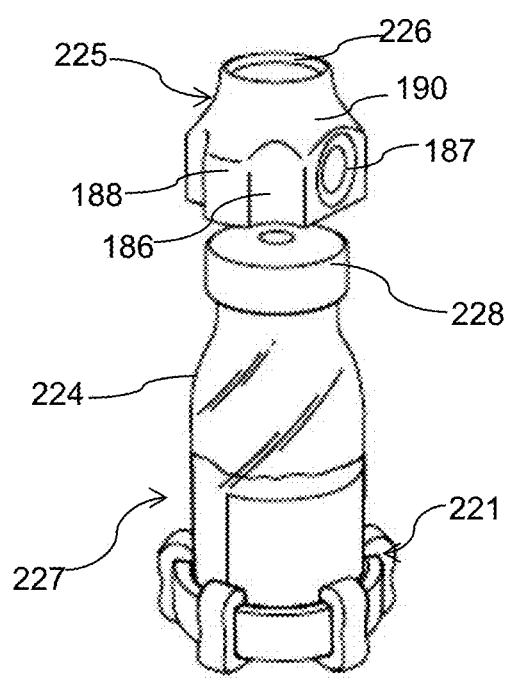
FIG. 37 shows a combination of present invention components, inclusive of the torque enhancement member with truncated conical top shown in FIG. 3 in collar form (just prior to vial top attachment), with the FIG. 3 grasping collar in this embodiment having a fully open, rimmed top for receipt of a syringe assembly or other interconnecting component.

FIG. 37 shows a kit combination 227 of the present invention components, inclusive of a base support mount 221, which supports fluid containing sealed vial 224, and torque enhancement member in the form of collar 225 of FIG. 3 configuration (just prior to vial top attachment), with the FIG. 3 collar 225 in this embodiment having a rimmed open top 226 for receipt of a syringe assembly or other interconnecting component. As seen from FIG. 37, collar 225 has the attributes earlier described for the FIG. 3 and FIG. 35 embodiments, but is absent the tab extension of FIG. 35. Thus, collar 225 has axially extending peripheral concave recesses 186 extending up to the conical top 190 as well as the circumferentially spaced ridges 188 and the finger depression recess 187.

Figure 38:
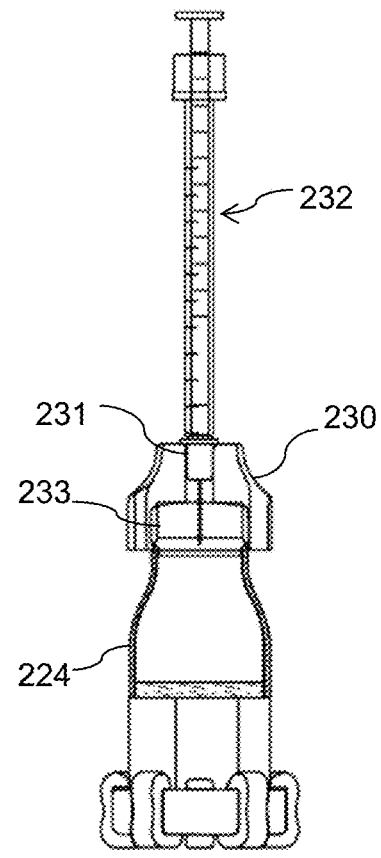
FIG. 38 shows a schematic line drawing showing the combination of the vial and a modified top collar of FIG. 37, and the associated positioning of the syringe assembly.

FIG. 38 shows a schematic line drawing showing a similar combination of vial 224 and a top collar such as shown in FIG. 37. As seen from a comparison of FIGS. 37 and 38, collar 230 has the same peripheral exterior as collar 225 in FIG. 37, but has a modified top region and interior cavity set up. That is, collar 230 has an upper smaller top aperture designed to receive directly syringe 232, which small top cavity 231 opens out in stepped fashion with enlarged diameter aperture 233 designed to provide a flex attachment (preferably non-threaded in this embodiment) to the vial top 228 (see FIG. 37) with central seal membrane extension (e.g., a seal membrane 228a supported in diaphragm fashion by an annular shaped metal vial top 228b). The combination of vial top collar and base mount shown in FIGS. 37 and 38 are representative of kit combinations within the above described potential kits based on the present invention described components (such kits can also include associated syringes, vials etc. in addition to the above described present invention component categories). Also, the combination of vial and syringe assembly in FIG. 38 can represent, for example, an insulin injection situation wherein after syringe 232 is engaged with collar 230, the syringe and vial may be single handedly tilted to receive the medicine. Also, as seen in FIGS. 38a and 38b flanged needle hub FH can have its upper flange sit on the top border of cavity 231 in collar 225. However, if there is desired to have the needle tip deeper in the bottle the flexible cavity wall can be expanded out to receive in a tighter squeeze fashion needle hub FH. This relationship also provides for controlled flexing and tilting of the needle within the bottle as when attempting to get remnants at the bottom of the bottle. Alternatively, as shown in FIG. 38b, cavity 231 can be provided with one or more radial grooves 231G, which provides for staged control of needle hub adjustment and needle tip extension in the bottle. The groove 231G and needle hub FH relationship also provides a good fulcrum location for needle tilting in the vial.

FIGS. 39 and 40 show the combination of top vial collar 225 of FIG. 37 and the receipt of an associated syringe assembly. In this embodiment, the syringe assembly is similar to that described above in FIG. 29. In other words, the syringe assembly of FIG. 39 that is being inserted into the open end of collar 225 features syringe assembly 157 comprising syringe 158 as well as plunger end grasping collar 154 and dumbbell shaped member 156 provided along the cylinder of syringe 158 (provided by a slide fit over the cylinder or an overmolding integrated combination or a single molding, and because of this volume measurements can be on the plunger). In addition, there is provided needle hub sleeve 192 like that described in FIG. 33. However, rather than needle hub sleeve 192 being inserted into a crush collar like in FIG. 33, in this case it is being inserted into the open topped collar 225 which provides for stable puncturing of vial 224 and removal of medicament therefrom in sterile fashion as when membrane 228*a* is featured. This stable puncture relationship between syringe assembly 157, collar 225 and vial 224 is illustrated in FIG. 40 wherein the syringe is in puncture mode with vial 224.

Figure 41:
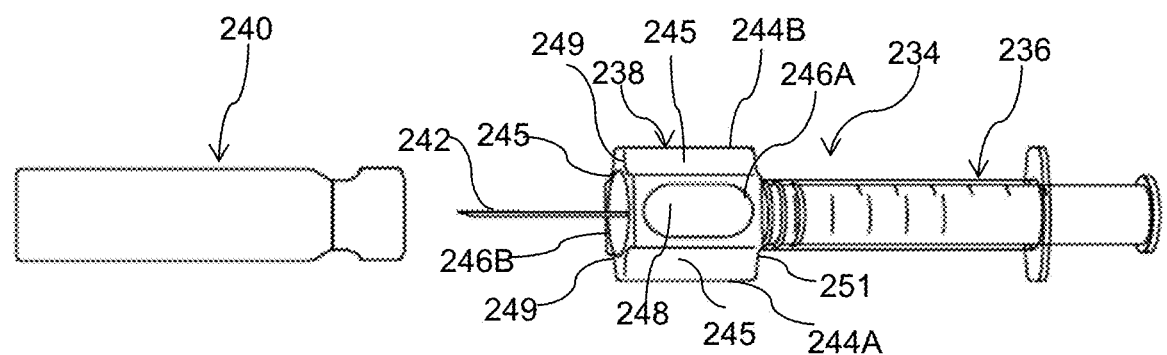
FIG. 41 shows a syringe having attached to it the torque enhancement member of FIG. 1 in the form of a collar just prior to supply vial puncturing with the needle of the syringe (with the collar having an interior suited for receipt of the needle assembly inclusive of a conical, guiding through-hole section as in a venturi shape (not shown in this Fig.)).

FIG. 41 shows syringe assembly 234 comprising syringe 236 as well as a torque enhancement member in the form of grasping collar 238 of FIG. 1 configuration. Syringe assembly 234 is shown just prior to supply vial 240 puncturing with the needle 242 of syringe 236. Collar 238 is shown as having elongation in the direction of needle extension and partially covering a portion of that needle. Further, as in the 1 embodiment, collar 238 is formed from a monolithic block of material that is, in this embodiment, preferably an elastomeric plastic and flexible as in medical grade silicone rubber. Further, collar 238 has a quadrilateral cross-section periphery that includes two opposing longer ridge walls (246A, 246B) that are circumferentially straight or only slightly curved about their periphery surface, two opposite opposing shorter ridge walls (244A, 244B), and finger depression recess 248. These walls are separated by concave depressions or corner "cut outs" 245 at locations that would otherwise have represented corners of the quadrilateral block. The side walls form gripping projections that are separated by the concave recesses that extend the full elongation length between forward surface 249 and rearward planar surface 251. The interior of collar 238 can have the needle assembly through-hole as described above, or some other configuration as in a tapered or conical interior surface used to help in centering the needle assembly as it is being inserted into the collar or one with an inherent angle tilt as toward a corner region of the base of the vial. With the arrangement of a generally confirming interior collar sleeve and the additional benefit of the seal membrane retaining the puncturing needle, there is provided a firm retention of a desired (predetermined) needle position (e.g., straight or tilt angled). The preferred flexible material in collar 238 for this embodiment also provides for a freedom to carry out controlled angling of the needle tip while in the vial and puncturing the membrane. The general range of height or thickness in this embodiment featuring collars having the FIG. 1 general configuration includes 2 mm to 60 mm with the embodiment of FIG. 41 being preferably about 20 mm to 50 mm, as in 40 mm long. The length can vary depending on the circumstances as in the length of the needle, the length of needle desired for exposure, the length of the needle hub assembly, the nature of the utensil involved at the collar engagement site at the cavity in the forward end 249 of collar 238.

Figure 42:
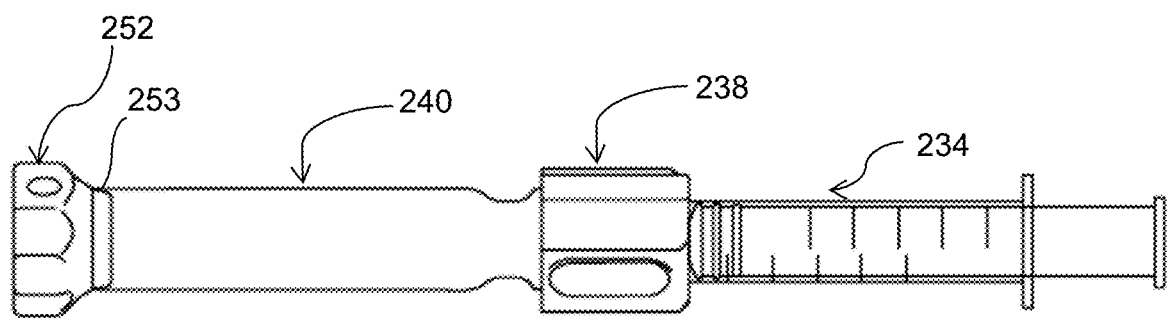
FIG. 42 shows a similar combination as FIG. 41, but with the combination of the FIG. 1 collar and syringe fully attached together, and with the supply (e.g., specimen or medicine source) vial having the collar of FIG. 3 as a means to better grasp the supply or specimen vial's base end and to help prevent rolling once attached; the sequence of collar attachment and utensil-syringe combination can be either collar first attached to syringe or collar first attached to vial before mutual connection (with the combination of the two torque enhancement configured components also shown as at a common level to work together to preclude rolling of the entire device shown).

FIG. 42 shows a similar combination as FIG. 41 but with collar 238 of syringe assembly 234 being fully attached to the sealed end of vial 240 in a puncture relationship, and with the supply (e.g., specimen or medicine source) vial 240 having collar 252 (of FIG. 3 configuration) mounted by flexure (or in an overmolding relationship) on the vial's base 253 as a means to facilitate better grasping of the vial as when separating the vial from the collar 238 following medicament draw from the vial or medicament insertion into the vial. Collar 252 also provides for a more stable base for plunger push down or just for support surface stand up. As noted, collar 252 can be supplied to the vial base by an overmolding plastic injection technique. Further, rather than attaching collar 238 to syringe before vial puncturing, collar 238 can be first mounted on the vial and the syringe then inserted. In addition, FIG. 42 is also representative of a potential horizontal orientation as when supported horizontally on a table or other supporting platform (not shown), and wherein the central axis of the needle assembly is retained in a parallel state with that horizontal supporting surface (and there is an anti-rotation feature even under environmental vibration situations).

Figure 43:
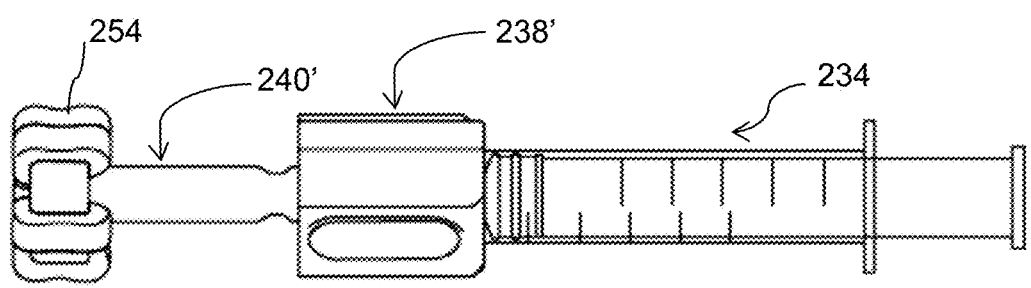
FIG. 43 shows a similar combination as that of FIG. 42, but with the vial having a ribbed ring base mount rather than the elephant foot end, and with a diameter size suited for horizontal orientation of the syringe assembly and rolling avoidance (in similar fashion to FIG. 42).

FIG. 43 shows a similar combination as that of FIG. 42, but with a small diameter vial 240' having a base mount 254 rather than the collar of FIG. 3 shown in FIG. 42. The smaller vial 240' is received in a corresponding smaller capture recess in the forward end of collar 238' (as compared to the larger capture recess in collar 238). The base mount also provides stable support during plunger down movement and while in stand-up state in general or may be rested horizontally with the central axis of the needle assembly parallel to the supporting surface and also precluded from easy rolling on the support surface even in situations of vibration as might be generated for anti-coagulation purposes or from other environmental vibration conditions.

Figure 44:
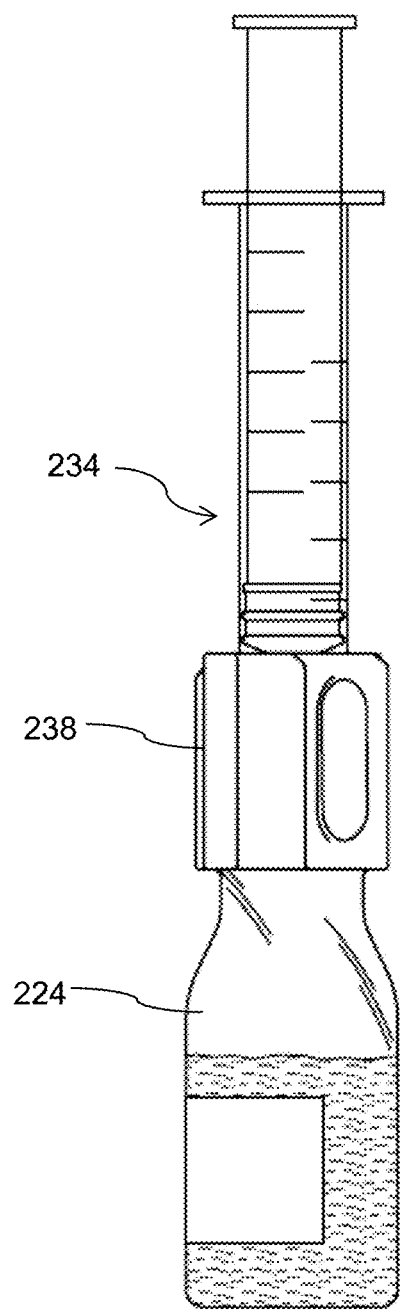
FIG. 44 shows the torque enhancement member collar of FIG. 1 (elongated or thicker in height version) attached to the syringe's needle assembly with the needle assembly's needle inserted in a medicine bottle.

FIG. 44 shows the same type collar 238 mounted on syringe assembly 234 in engagement with the upper rim of bottle 256. Again, the flexible nature of collar 238 and suitably dimensioned cavity at that end provides for a sealed engagement during needle puncturing or placement into the bottle. Alternatively, the collar 238 may be placed first over the vial (rather than first on the syringe) and the syringe inserted into the vial, allowing one handed fluid withdrawal procedures.

Figure 45:
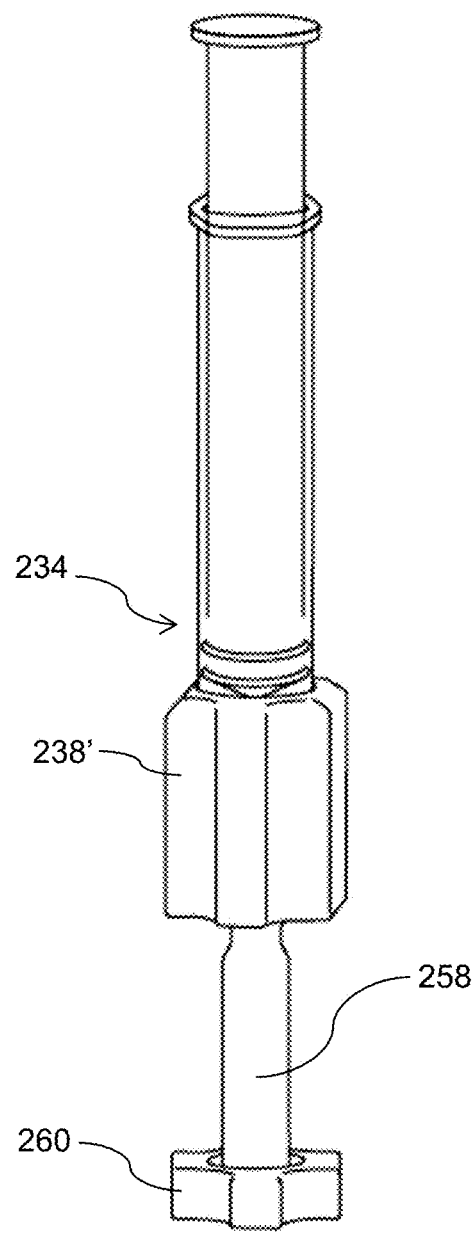
FIG. 45 shows the collar and syringe combination of FIG. 44 in fluid communication with a vial having at its base a FIG. 1 torque enhancement member collar (short or thinner in height version).

FIG. 45 shows the same type collar 238' mounted on syringe assembly 234 in sealed off engagement with the upper end of canister 258 having at its base collar 260 of FIG. 1 configuration (short or thinner version depicted). As depicted, the aperture in collar 260 is in friction engagement. The friction level can be increased upon a squeeze compression action on collar 238, such as when removing collar 238' from its engagement with canister 258. Collar 238' would have its vial capture end of a small diameter than collar 238 when the top rim of the bottle has a significantly greater diameter than that of the vial (e.g. a stepped relationship or a tapering, conical interior through-hole).

FIG. 46 shows combination 262 as represented by the FIG. 38 configuration. As further seen in FIG. 46, the projections of the FIG. 3 type torque enhancement member in the form of collar 230 (only schematically shown in FIG. 46, but understood to have the torque enhancement periphery as shown in FIG. 3) has a plurality of projections that provides the ability in a user to securely grasp and hold the bottle with a two finger off-center pinching operation, which is fixed enough for plunger activation with the opposite hand.

FIG. 47 shows the same off-set two finger pinching relationship with a FIG. 3 collar 230 but with the two stage through hole in the collar supporting hub 267 of the double-ended transfer needle assembly 268, with the user's pinching fingers well away from the needle. Further, with collar 230 in position, the combination may be rested on a surface in the middle collar 230, which will distance the two sided needle from being contaminated due to surface touching.

FIG. 48 shows a single hand grasping of a FIG. 3 type torque enhancement member shown in collar form (open top version, with larger base aperture opening out than the upper open top aperture such as collar 225 of FIG. 37) and a grooved bulb head utensil 269. FIG. 48 also shows the interior of collar 225 as having an upper diameter opening 270 for receipt (and relative flexible support and sealing) of, for example, a syringe assembly. The lower opening 272 in collar 225 is defined by the enlarged (smooth in this embodiment) diameter wall surface 274 designed to engage a bottle top as in FIG. 39, as well as different configured shaped utensils such as the bulbous head 276 of utensil 269, made possible by the flexibility and thinner relative nature of wall 227 defining wall surface 274. FIG. 48 also shows the freedom to hold collar 225 with two fingers, one on the periphery, and the other finger extending to (e.g., into) the top opening of collar 225 (or in some embodiments the top is closed off with a depressed or flexing membrane recession).

Figure 49:
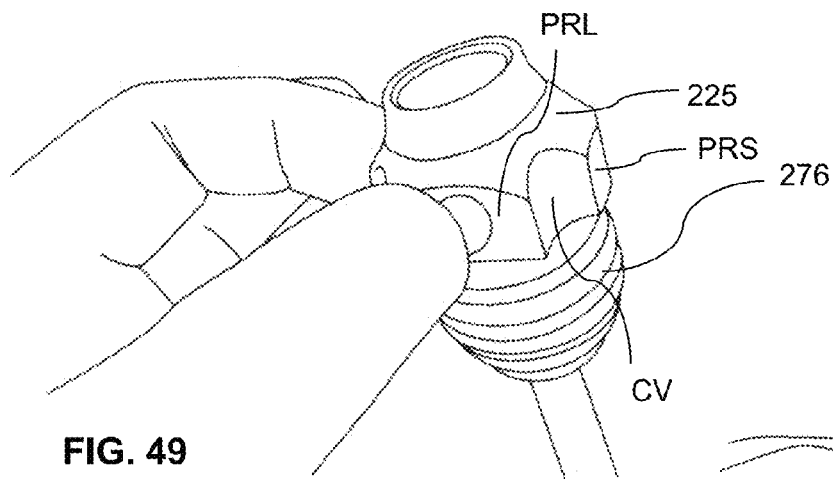
FIG. 49 shows the components of FIG. 48 in an engaged state and with the same offset, two finger grasping described above.

FIG. 49 shows the components of FIG. 48 in an engaged state and with the same offset, two finger grasping described above. Also, FIG. 49 illustrates that collar of FIG. 3 configuration also preferably, like the FIG. 1 general peripheral configuration, has a torque enhancement peripheral configuration with opposing long ridge sides PRL (one shown) and opposing short ridge sides PRS (one more visible) separated by corner cut outs or concavities CV as to provide for enhanced grasping as by two finger pinching and torque generation facilitation.

Figure 50:
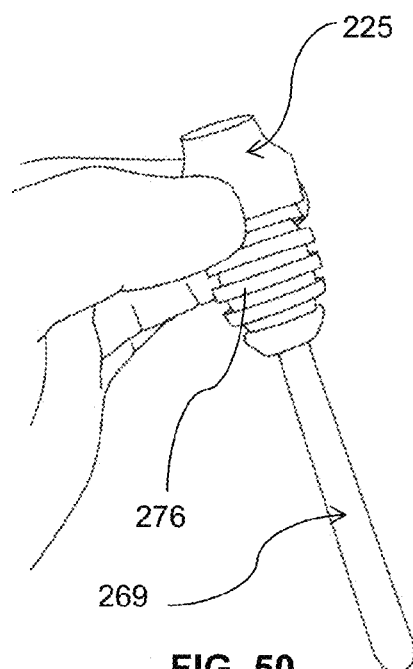
FIG. 50 shows the combined components of FIG. 49 and the ability for the pinch support to hold the combination in a suspended state with one hand.

FIG. 50 shows the combined components of FIG. 49 and the ability for a pinch support to hold the combination in a suspended state with one hand.

Figure 51:
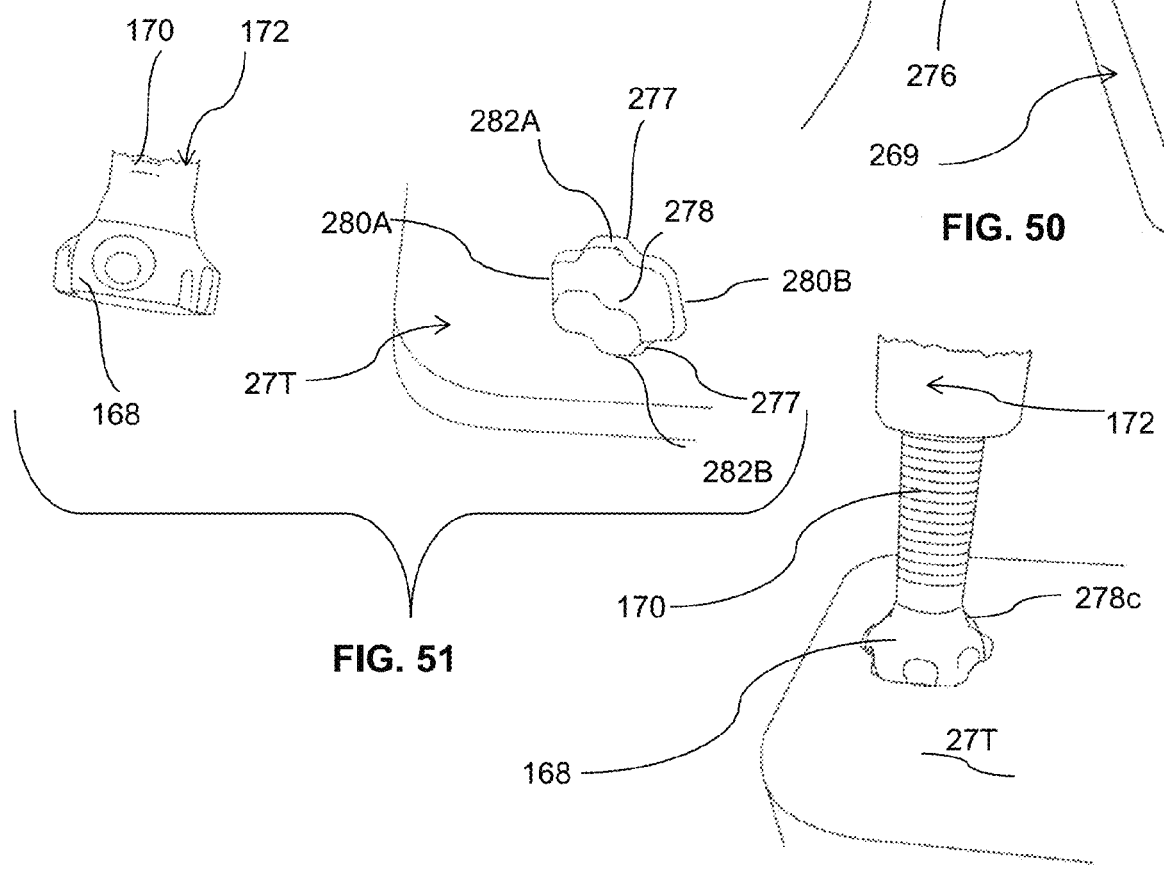
FIG. 51 shows a modified tray embodiment featuring a reception aperture that has a common surrounding configuration for snug receipt of the integrated "elephant foot" torque enhancement (e.g., palm or fingertip reception) end shown in the syringe plunger of FIG. 31.

FIG. 51 shows modified tray embodiment 27T which is shown in cut-away, but the remaining portion is in one embodiment represented by tray 140 in FIG. 29. In this embodiment, however, tray 27T has an end aperture 278 that has a configuration not designed specifically for a base mount, but has a generally quadrilateral outer periphery with inwardly extending convex walls, That is, as shown in FIG. 51, reception aperture 278 has a pair of opposing long sides 280A, 280B, a pair of opposing shorter sides 282A and 282B, and four corner projections 277 with curved exposed surfaces. Aperture 278 is designed to snugly receive a torque enhancement member such as the collar shown in FIG. 3, wherein there are long and short ridge sides opposing each other and recesses at the corners between the formed projections along the sides. Thus, tray 276 has aperture 278 that is well suited for support of components of the invention such as grasping body 168 formed integrally with plunger 170 of the illustrated syringe 172 in FIG. 31.

Figure 52:
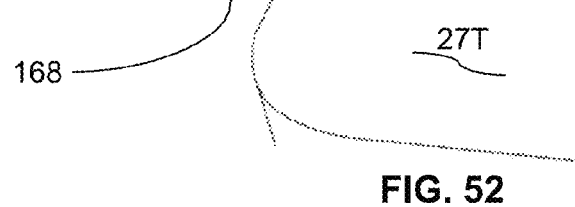
FIG. 52 shows the integrated elephant foot torque enhancement end and a threaded shaft extending therefrom in a snug reception state relative to a supporting/transfer tray.

FIG. 52 shows the snug interrelationship or integrated collar and plunger support relationship shown in FIG. 31. As seen in FIG. 52, the collar 168 end of plunger 170 is inserted into the conforming aperture 278c in a snug reception state relative to supporting/transfer tray 167. This snug relationship is also illustrative of the snug relationship formed between a torque enhancer driver and a torque enhancement recipient of such driving force as explained in greater detail below.

FIG. 53 shows plunger 170 (with rubber seal piston for mounting on the top plunger end not shown), having a shaft as its main body 171 (with graduations for liquid content) and the attached torque enhancement collar 168 of FIG. 3 general configuration (e.g., a flex attachment, overmolding or bonded relationship or a monolithic common molding with shaft 171). Also, as shown in FIGS. 54 and 55, collar 168 has opposing ridges with long (circumferential) sides PRL, opposing ridges with shorter (circumferential) sides PRS, and concavities CV separating the adjacent short and long ridges (PRL-PRS).

FIGS. 54 and 55 also illustrate the underlying depression UD formed at the base undersurface of collar 168 which features upwardly and inwardly extending wall sections WS that form the boundary for the interior depression area ID, which is centralized on the undersurface. In this way, the rim edging defined by wall surfaces WS and the outer periphery of the collar provide for a degree of flexure along the collar edging (when a sufficiently soft material is involved). Also, the interior depression depth is preferably less than the depth of the concavities CV on the periphery of the collar. The central elephant foot head end depression is also well suited for finger positioning and manipulation as when the plunger is being forced forward in a syringe barrel.

FIGS. 56 and 57 illustrate plunger 170 in a lying down state (rather than an upward or vertical support state shown in FIG. 53). As seen, the interior edging of the adjacent projections PRS and PRL can contact with the support surface, and since they are separated by bottom positioned concavity CVB, collar 168 acts to preclude rotation of plunger 170 once set on its side, which is helpful in a working environment where undesirable utensil roll offs can occur.

Figure 58:
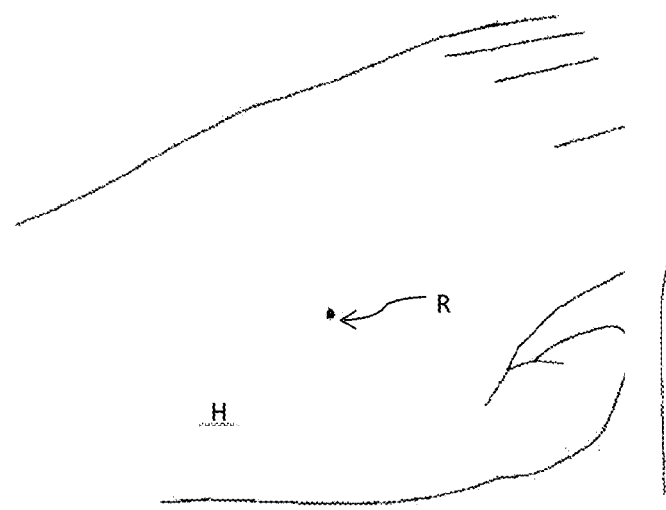
FIG. 58 shows a hand with a region intended for treatment.
Figure 59:
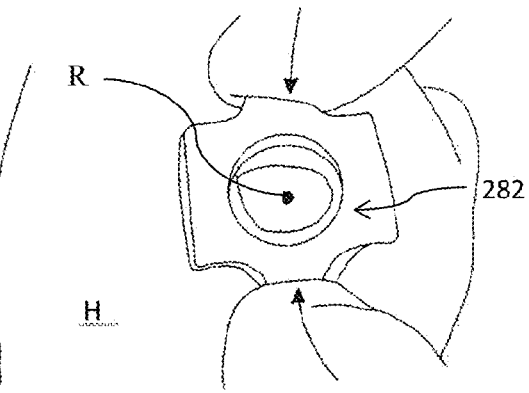
FIG. 59 shows the versatility of the torque enhancement collar, which is shown as a base mount in FIG. 45, but as a skin collector and positioner of the region intended for treatment in the present Figure, with this Figure showing initial placement of the thinner torque enhancement collar around the region intended for treatment.

With reference to FIGS. 58 to 63, there is described a treatment procedure using torque enhancement member in the form of grasping collar 282 of the FIG. 1 configuration, and of a thinner mode (e.g., 1.5 mm to 6 mm, and more preferably 2 mm to 4 mm). FIG. 58 shows hand H with region R intended for treatment, while FIG. 59 shows the versatility of torque enhancement member 282, which is shown as a base mount in FIG. 45, but as a skin collector and positioner of the region intended for treatment in the present FIG. 59, with FIG. 59 showing initial placement of the collar around the region R intended for treatment. Also, FIG. 59 shows the beneficial short ridge to short ridge compression orientation for this procedure.

Figure 60:
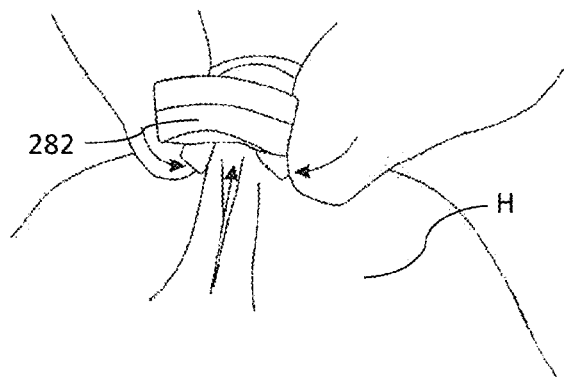
FIG. 60 shows the collar of FIG. 59 in a compression state (pressing together of two opposing shorter ridge side surfaces) that causes a simultaneous capture and lifting of skin such the region intended for treatment is presented within an intermediate, upper region, (or above) the aperture of the collar with the skin assuming a mushroom configuration due to the lower edging of the collars recess bending inward and upward.

FIG. 60 shows torque enhancement member 282 in the peripheral compression state that causes a simultaneous capture and lifting of skin such the region R intended for treatment is presented within an intermediate, upper region, or above the aperture of the collar 282 and the underlying skin is compressed by the collar there below. Further, as seen from FIG. 60 the lift up is achieved by having the collar flex in a bowed up state that results in the lower interior cavity edging achieving an automatic skin pile lift up while compression is ongoing which helps isolate the region R without pain in the patient, and with the lower edging of the collars cavity being closest together to form a mushroom configuration in the skin pile. Further the buckling activity provided by torque enhancement member on the skin under this technique is relatively painless particularly when considering the typical alternate techniques involving metal forceps or plier skin pinching.

Figure 61:
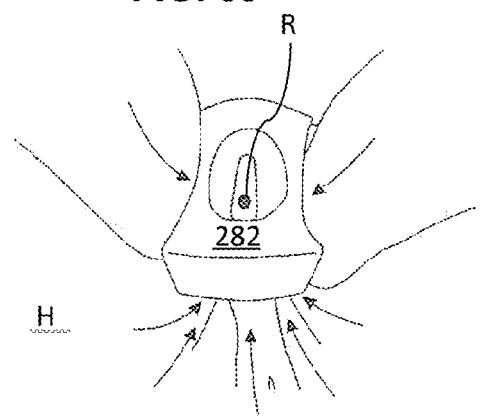
FIG. 61 shows another view of the relationship shown in FIG. 60.

FIG. 61 shows a more top oriented view of the pinched pile of skin.

Figure 62:
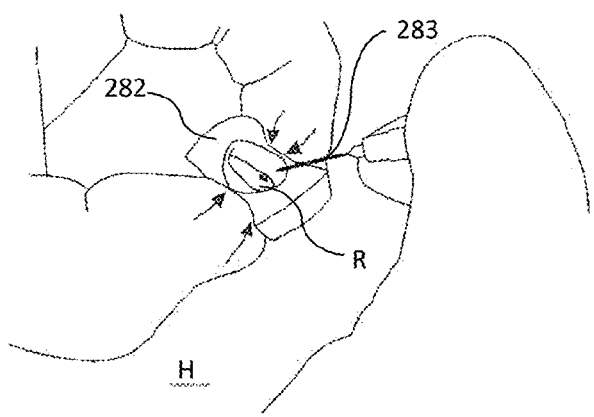
FIG. 62 shows the insertion of a needle in the exposed, desired area in the region intended for treatment.

FIG. 62 shows the insertion of a needle 283 in the exposed, desired area in the region R intended for treatment.

Figure 63:
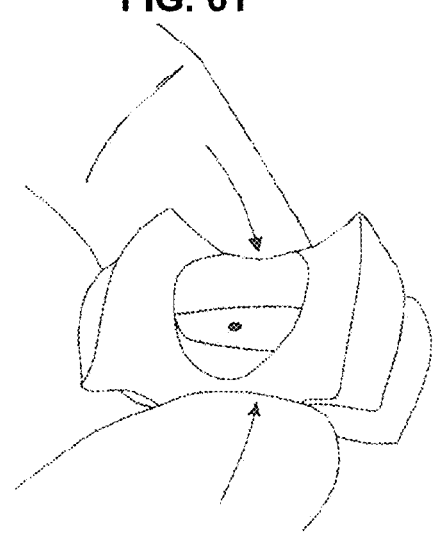
FIG. 63 shows the collar of FIG. 59 in a similar compression, lift state relative to a different object (film material), and how the lower edging of the collar moves inward and upward simultaneously.

FIG. 63 shows collar 282 of FIG. 59 in a similar compression, lift state, but relative to an object O other than skin.

Figure 64:
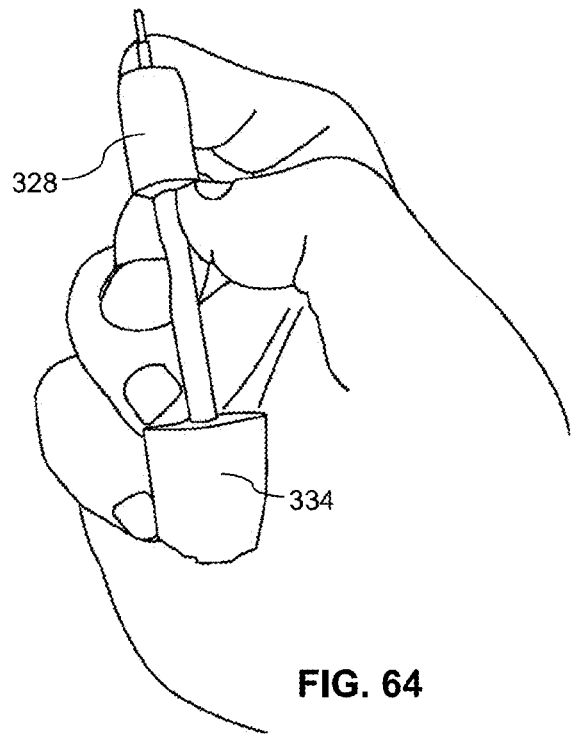
FIGS. 64 and 65 and FIGS. 66 to 70 show various views of a combination set of the torque enhancement members shown in FIGS. 1 and 8 (or 27) in the form of collars featuring a first collar for securement to a distal end of an object such as the illustrated push, pull and/or torque (e.g., dental) tool and a second collar of FIG. 1 configuration for attachment to the base of the tool, with FIG. 64 showing the combination being held with one hand contact on each of the collars and the tool.
Figure 66:
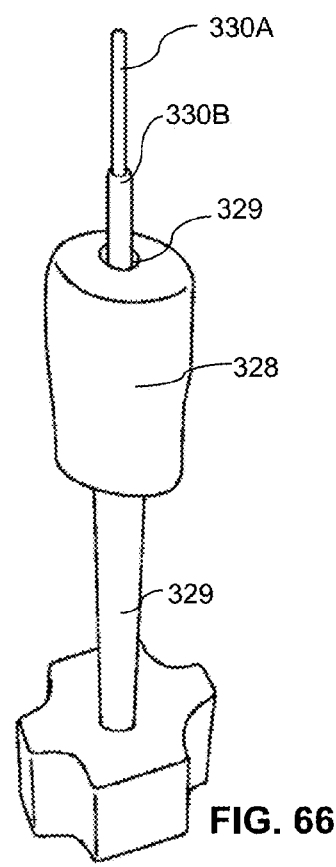
Figure 65:
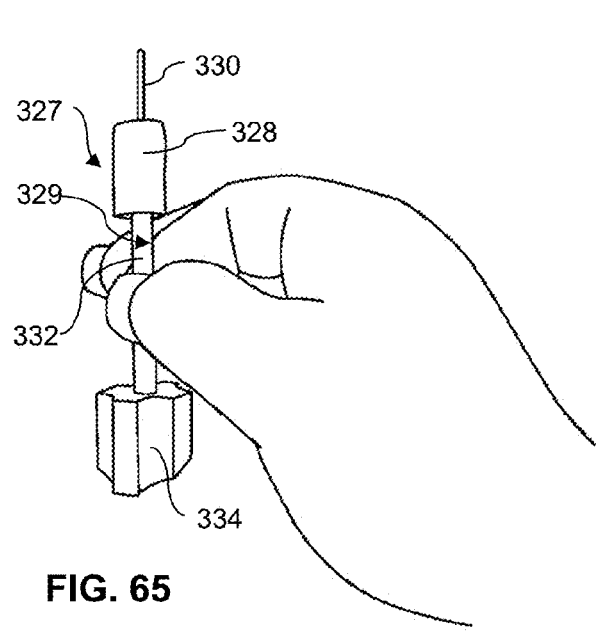
Figure 67:
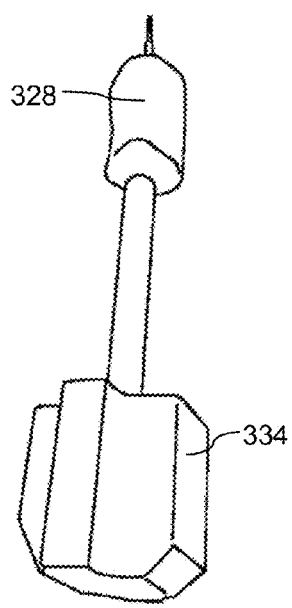
Figure 68:
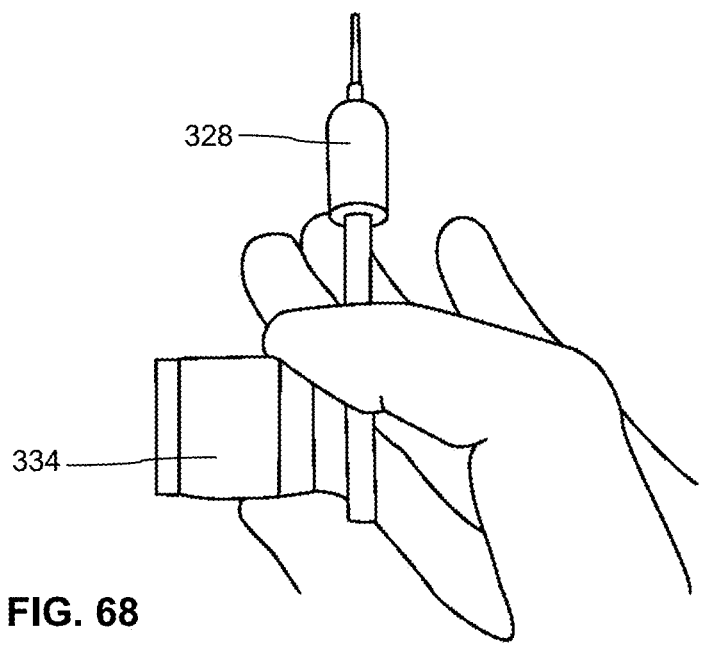
Figure 69:
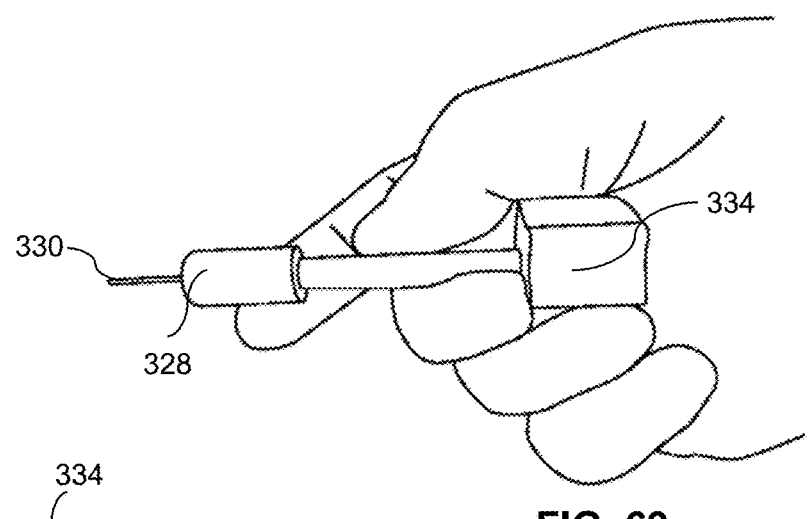

Collar 328 is also suited for other object grasping purposes such as a "pushed puncture" tool (e.g., dental and other medical and non-medical uses) instrument, and as part of a kit associated with such tool or instrument manipulation. As seen in FIGS. 64 to 70, collar 328 forms part of a two component kit suited for single hand securement of such an instrument 329 and desired no-rotation or rotation states, through single handed manipulation. Instrument 329 in this embodiment has a narrow shafted end 330 (two stage 330A, 330B) extending from a (e.g., knurled) handle 332. The second part of the kit is shown as torque enhancement member 334 shown in the form of a base collar 334 of the FIG. 8 configuration that includes one or more slanted long sided projections as best shown in FIGS. 64 and 65. The kit combination 327, comprised of base collar 334 and distal end collar 328, provides for a secure but readily adjustable grasping arrangement on the object (tool or instrument) shown. That is, the combination provides for smooth rotation of the instrument within the one common holding hand by twisting fingers pinching collar 328 while discontinuing compression at the palm and collar 334 interface. Also since the slanted projection of collar 334 sets against the thicker part of the palm (extending out and to the thumb of a hand) upon compression of the instrument there against the corner cut outs and side edging of the projections helps lock the tool in place against the skin being compressed and thus the sleeve portion can be locked into place on the noted palm region with minimum effort, until a torsion rotation of the instrument or forward projection is desired. Also, the FIG. 69 grasping configuration with the projections separated by elongated concavities enables the holder to push the fingers holding collar 328 forward (or retract the fingers back in the opposite direction), while base collar 334 is sufficiently released from compression and allowed to slide along the palm in controlled manner due to the "sliding runners" associated with the projection edges of the collar periphery (FIG. 8 configuration) resting in the palm of the hand. This creates a controlled positive reaction force and limits excessive, uncontrolled forward movement. The central cavity of each of the collars can be a straight smooth circular cylindrical cavity that holds on to the body of the instrument (or any desired object for the present combination kit) with sufficient friction retention or can be a different diameter stepped portion matching 330A and 330B diameters in collar 328. The materials for this kit can be similar to those described above for other collars.

Figure 70:
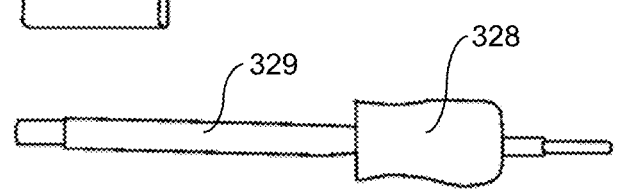

FIG. 70 shows a modified kit arrangement with added interface or adapter component 336 that facilitates the connection between the base end of instrument 329 and base collar 334. This adapter 336 can be relied upon to bridge the gap when the cavity of the collar 334 is too large for the instrument intended. Also, the central cavity of collar 328 is preferably designed to preclude passage of the base of the instrument out through the non-receiving end of collar 334. A central cavity having either a common diameter cylindrical shape or one with varying diameter either in stepped and/or continuous fashion is applicable. Thus for finger holding collar 328, a sufficiently retaining smooth circular cylinder cavity can be utilized or a stepped arrangement that coordinates with a step down (330A and 330B) in the instrument's body as represented by the step down 336 shown in FIG. 70. If the adapter 336 has a non-circular interior that matches that of the tool shaft's base there can be provided an arrangement designed not to have relative spinning between the tool base and adapter/collar combination. On the other hand the adapter 336 can provide a free spin hub, with the fingertip collar 328 providing spin control.

With reference to FIGS. 71 to 75 an illustration of the versatility and benefits of the kit combination 227 shown in FIG. 38 is provided. That is, the combination of base mount 221 and collar 225 provides for one handed removal as well as the ability for a person to take a variety of grasping approaches including approaches made available to a person with arthritis that would otherwise be unable to open the bottle.

Figure 71:
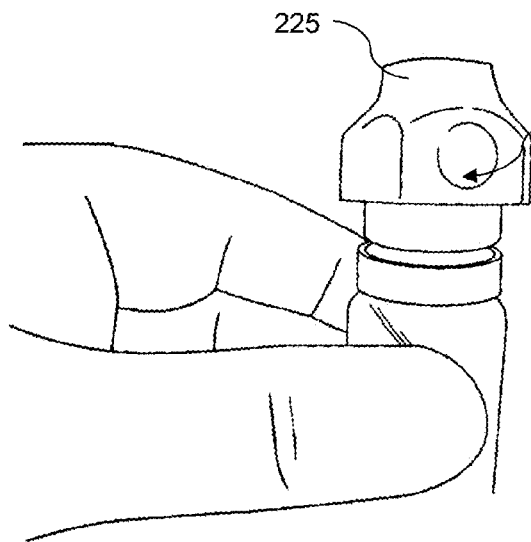
FIGS. 71 to 75 illustrate various views relative to a combination of the torque enhancement member in the form of a collar of FIG. 3 in use with a bottle mount and some of the various hand positions and component positions utilized for bottle cap removal through use of a torque enhancement collar attachment.

For example, FIG. 71 shows a grasp that a person with two free hands could take as with one hand holding the bottle and pushing down into the mount 221, while the other hand can readily grasping and compressing collar 225 (e.g., fingers within the recesses to compress against the underlying threaded cap) and then rotate off. There is an enhanced torque capability here with two components spaced apart (collar and mount) and each able to provide friction resistance in appropriate direction.

Figure 72:
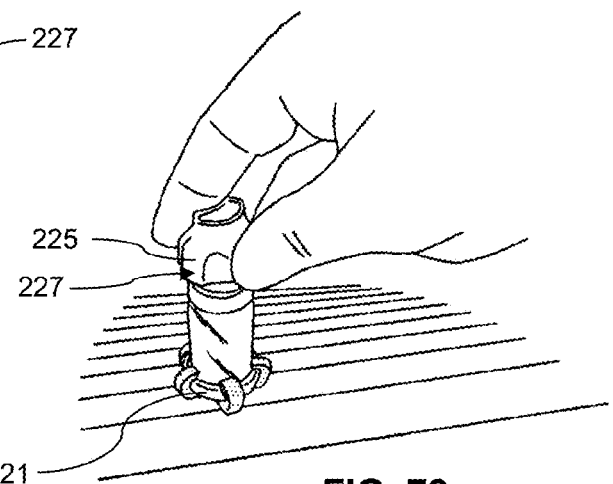
Figure 73:
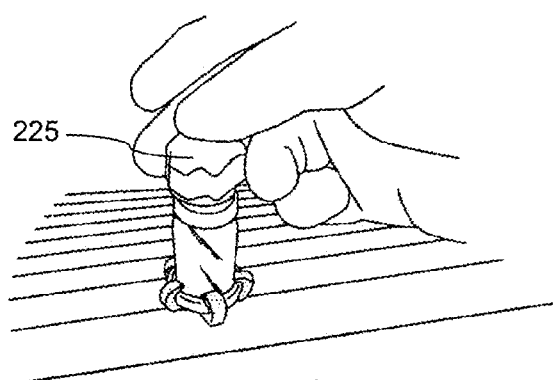
Figure 74:
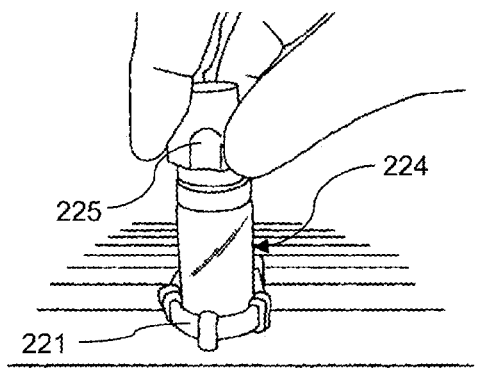

For situations or for personnel not having a second hand free, the present combination 227 allows for one hand cap removal. For example, each of FIGS. 72, 73 and 74 illustrate single hand bottle removal capability (either relative to a pre-set up combination kit or one where a single hand free user carries out both collar and base mount 221 (with annular ring 221A and flexible ribs 221R) installation before cap removal). In the situation where the person does all stages in entirety, a suitable sized mount is set on a surface whereupon the bottle is slipped into the ribs 221R for friction retention. Once the bottle is mounted, the collar 225 can be readily flexed and inserted onto the bottle cover (in similar fashion to collar attachment to the bulbous head in FIG. 49). Following collar 225 attachment, the bottle cap can be readily removed due to the added grasping power provided by collar 225. That is, as shown in FIG. 72 the user can place one finger (e.g., the thumb) within one of the elongated grooves while a pair of fingers (e.g., the index finger and adjacent long finger) is placed upon the cone portion 190 with at least one finger compressing the free rim defining the open top or extending into the open top. In this way, there is sufficient friction retention as to initiate cap removal of the bottle while the bottle base is pressed down on mount 221 which frictionally precludes bottle rotation in favor of cap rotation. Further, the configuration of the torsion enhancement member 225 provides for enhanced torque generation with minimized effort and thus allows for rapid torsion generation and cap removable.

FIG. 73 shows an alternate gripping approach that a person with arthritis might favor. As seen, the thumb is placed on the top opening with top rim contact and the two interior long fingers form a V-compression relationship on collar 225 with the combination being suitable for vertical press down and circumferential spin off without the need for thumb and adjacent most long finger pinching which can be difficult for some. The configuration of the torsion enhancement member 225 provides for enhanced torque generation with minimized effort and thus allows for rapid torsion generation and cap removable alleviating some of the associated pain and difficulty which a person with arthritis might otherwise be subject.

FIG. 74 shows yet another approach, where there is a three finger general vertical extension combination (thumb and adjacent most two long fingers) around collar 225, with each of the three fingers nested within a respective one of the concave recesses so that they are abutting a respective adjacent ridge. With the nestled fingers (and their abutment with a ridge that is ahead in the direction of spin off) coupled with an inward radial compression of the three fingers as well as a vertical mount compression force, the cap can be readily spun off. That is, the configuration of the torsion enhancement member 225 provides for enhanced torque generation with minimized effort and thus allows for rapid torsion generation and cap removal.

Figure 75:
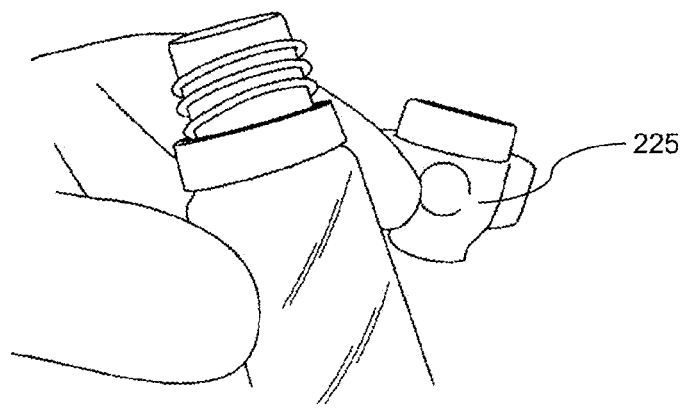

The referenced concave recesses and associated projections further provide for facilitated retention of the cap 225 with two fingers of a hand with the thumb and a remaining finger or fingers securing the bottle for one hand holding of both the cap and bottle as show in FIG. 75.

Figure 76:
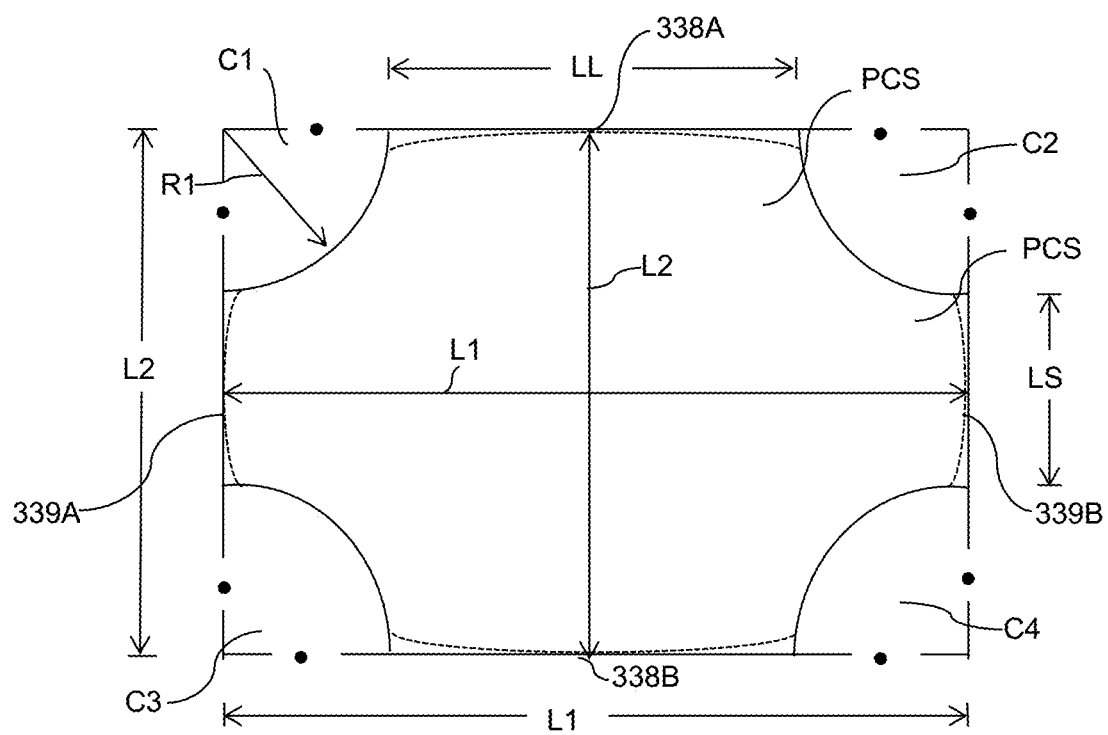
FIG. 76 shows a schematic depiction of a top plan view of a torque enhancement member of FIG. 1 with some of the lengths and corner cut out cavity depths demarcated.

FIG. 76 provides a schematic depiction of the torque enhancement component or collar 500A configuration of FIG. 1 (with central cavity removed for illustrating the general configuration) and shows a top plan view of the torque enhancement member or collar of FIG. 1 with a long length L1 and a width length L2, together with corner "cut outs" (actually preferably molded in or otherwise formed concavities) C1 to C4 each being concave with a general radius value R1 (that is shown as common configured and sized for each of the four). The corner concavity open areas C1 to C4 result in projection surfaces PCS on each of the long length projections (having parallel surfaces 338A and 338B each of peripheral length $L_L$), as well as short length projections (having surfaces 339A and 339B each of peripheral length $L_S$). Also, a slight curvature can also be provided in each of the long and short sides as demarcated with dashed lines in FIG. 76 with the dot-dash lines reflecting the concavities where no material is present. For some of the intended uses of the present invention FIG. 1 configured collar, the length L1 ranges from, for example, 20 to 40 mm (e.g., 30 mm), the length L2 ranges from 10 mm to 30 mm (e.g., 18 mm), resulting in $L_L$ ranges from 8 mm to 18 mm (e.g., 13 mm), $L_S$ ranges from 4 mm to 10 mm (e.g. 6.5 mm) and radius R1 sufficient to enable finger reception with sufficient ridge interior wall friction contact, with suitable concave edge-to-edge distancing of 5 to 15 mm as in 8 mm (sufficient for enough insertion in most finger sizes), coupled with a radius of 8 mm to 12 mm as in 10.5 mm. Various other dimensions are also presented elsewhere in the present application. Further as seen a circle contacting the outer ends of each of the longer length sides 338A and 338B extends inward of the maximum extension of the other pair of projection surfaces 339A and 339B. This relationship provides a geometric form that provides for a multitude of beneficial uses (e.g., some of which are described above and some of which are described below).

Figure 77A:
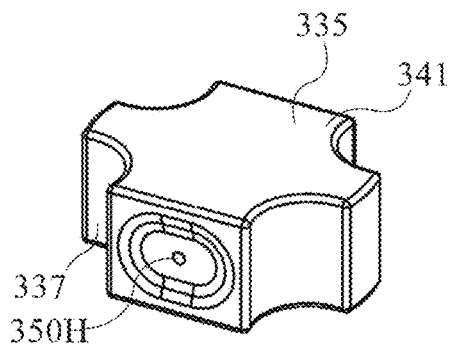
FIGS. 77*a* to 77*n* show a variety of different embodiments of thinner version collars of the FIG. 1 configuration.
Figure 77B:
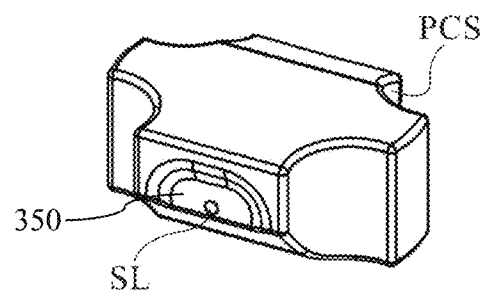

Figure set 77A to 77N illustrates a variety of examples of the torque enhancement member or collar configuration of FIG. 1, with some of the features of this set being generally thin "height" lengths from forward to rearward planar ends 335, 337 (in which planes the central cavity intersects). For example, the Z=axis "thinner" versions of the FIG. 1 collar feature lengths of, for example 2 to 13 mm, and more preferably about 6 mm to about 13 mm (the invention includes each value within this range and the end points; with the figure set of 77A to 77N including examples of thickness values of 6, 9 and 11 mm). Also, examples of different apertures are shown in the figure set of 77A to 77N with some of the apertures being through-holes and others being partial thickness apertures (extending for greater than a majority of the thickness). The apertures AP, at the boundary region with the above and/or below surfaces of the sleeves, preferably have downwardly sloping reception rims 339 to facilitate attachment to an object when so utilized. For example, FIGS. 77A and 77B, include capped tops 341 (FIG. 77A) and 343 (FIG. 77B) with the apertures extending therebelow to the lower end. FIGS. 77A and 77B illustrate side to side cavities as in a horizontal aperture (350 opening with similar on other side or just on one side), with the cavity having, for example, the above described needle reception cavity with larger inlet opening (not shown). A tapered orientation in the central cavity is also featured. FIG. 77B also shows a sloped surface SL for fixed needle insertion incline purposes (e.g. 20°, 40°, 60° angle insertion).

The remainder of collars shown includes ones with smaller diameter apertures AP (e.g., 3.8 mm), medium diameter apertures AP (e.g., 6.2 mm to 10 mm) and larger relative diameter apertures AP (>10 to 13 mm) relative to the peripheral overall sizes featured in FIGS. 77C to 77N.

Figure 77C:
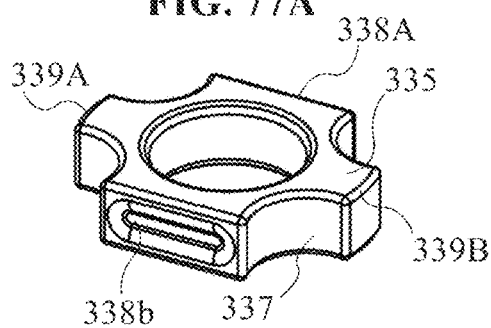
Figure 77D:
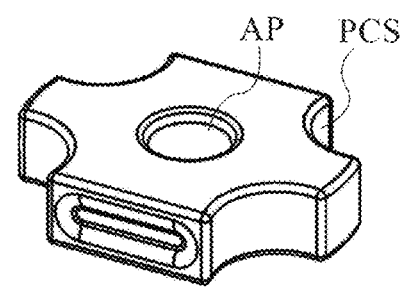
Figure 77E:
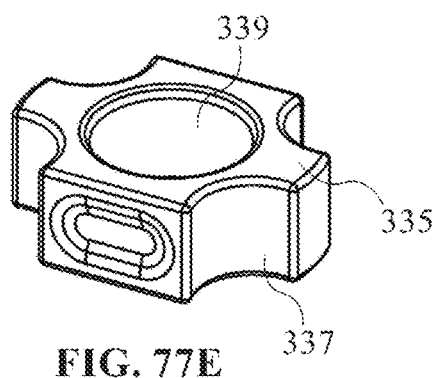
Figure 77F:
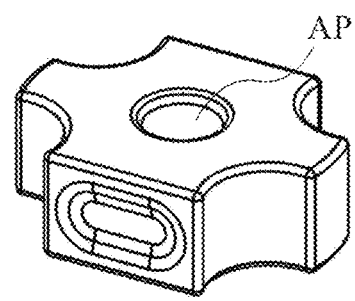
Figure 77G:
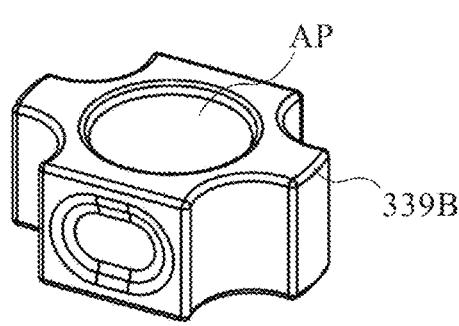
Figure 77H:
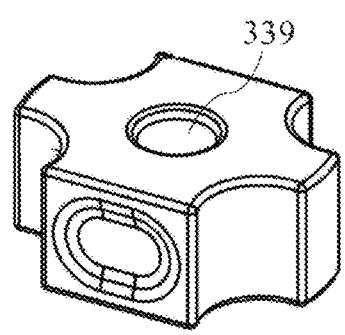

As shown in FIG. 77C the radius R1 of each concavity, which is generally in the form of a semi-circle, is set at, for example, 8 mm to 15 mm for the collars shown in FIGS. 77A to 77N. In alternate embodiments different radius concavities can be featured, with an object being to provide suitable grasping surfaces PCS wherein fingers can be inserted in the concavities and compression forces applied to the ridges having PCS surfaces to each side (e.g., by way of finger generated forces or conforming tool generating forces). Further, the collar embodiments shown in FIGS. 77A to 77N of the thinner height type, feature apertures of one diameter through the thickness, although alternate embodiments feature varying diameter values along the length of an aperture AP, such as the different stepped and sloped configurations described below for the FIG. 1 type collars of the longer height mode, with either no threading or threading.

Fig. sets 78A and 78B; 79A and 79B; 80A and 80B; 81A and 81B; 82A and 82B; 83A and 83B; 84A and 84B; 85A and 85B; 86A and 86B; 87A and 87B; and 88A and 88B show examples of the FIG. 1 torque enhancement member with thicker or long heights as well as a variety of aperture AP variations. The plan view for collars of FIG. 1 type configuration and associated lengths and widths provided in FIG. 77 embodiments are applicable for the above thicker embodiments referenced in this paragraph. The "thicker" embodiments of the present invention are generally greater than 13 mm as in 14 mm to 50 mm in thickness, with examples presented in the figure set of this paragraph including values of 14 mm, 14.5 mm, 17 mm, 22 mm, 27 mm, 31 mm, 40 mm and 48 mm.

Figure 78A:
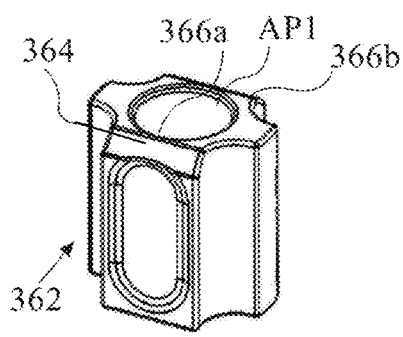
FIGS. 78*a* and 78*b* illustrate a longer or thicker version of the torque enhancement member in the collar configuration of FIG. 1 with the former showing a perspective view and the latter showing a central vertical cross-section and the tapered aperture configuration.
Figure 79A:
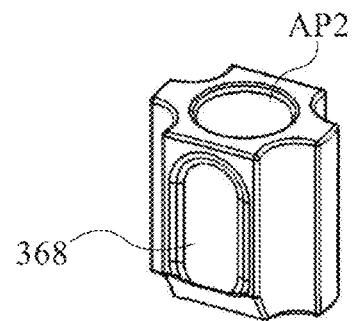
FIGS. 79*a* and 79*b* illustrate a longer or thicker version of the torque enhancement member in the collar configuration of FIG. 1 with the former showing a perspective view and the latter showing a central vertical cross-section and the tapered aperture configuration.
Figure 78B:
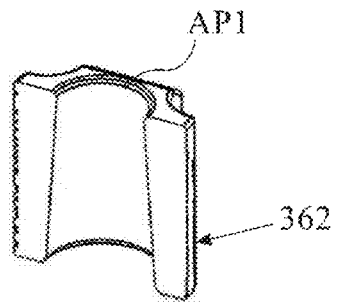

In Fig. set 78A and 78B, torque enhancement member 362 in the form of a collar represents a collar well suited as a connecting collar between a vial and a syringe, with a collar thickness or height of 27 mm. As shown in the cross-section view of FIG. 78B, aperture AP1 has a frusto-conical shape that features a diverging top to bottom shape having an uppermost diameter of 13 mm and a lowermost diameter of 16.5 mm, which makes the top well suited for syringe insertion, and the bottom well suited for vial attachment. FIG. 78A also shows sloping shelf 364 at the top end of each of the long length ridges 366A and 366B.

Figure 79B:
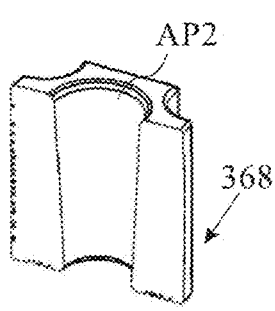

In Fig. set 79A and 79B collar 368 represents a collar well suited as a connecting collar between a vial and a syringe, with a collar thickness or height of 27 mm. As shown in the cross-section view of FIG. 79B, aperture AP2 has a frusto-conical shape that features a converging top to bottom shape having an uppermost diameter of 13 mm and a lowermost diameter of 10 mm, which makes the top well suited for syringe insertion, and the bottom well suited for a smaller sized vial attachment.

Figure 80A:
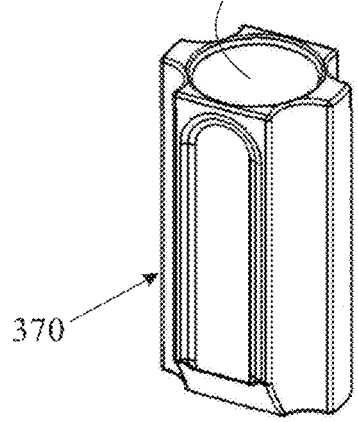
FIGS. 80*a* and 80*b* illustrate a much longer or thicker version of the torque enhancement member in the collar configuration of FIG. 1 with the former showing a perspective view and the latter showing a central vertical cross-section and the tapered aperture configuration.
Figure 80B:
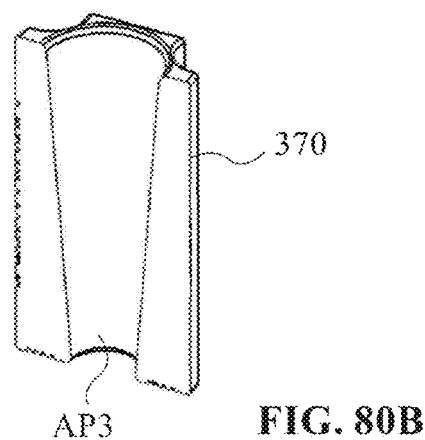
Figure 82A:
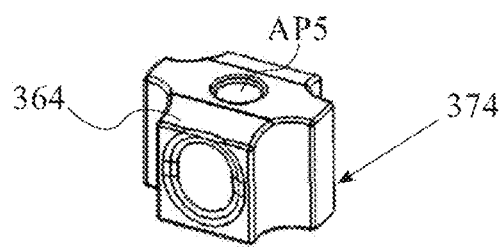
FIGS. 82*a* and 82*b* illustrate an intermediate (tapered) hole length version of the torque enhancement member in the collar configuration of FIG. 1 with the former showing a perspective view and the latter showing a central vertical cross-section and the aperture configuration.

In Fig. set 80A and 80B collar presents two cross sectional views of collar 370. Collar 370 represents a collar well suited as a connecting collar between a vial and a syringe, with a collar thickness or height of 48 mm. As shown in the cross-section views of FIGS. 80A and 80B, aperture AP3 has a frusto-conical shape that features a converging top to bottom shape having an uppermost diameter of 17 mm and a lowermost diameter of 9.5 mm which makes the top well suited for syringe insertion, and the bottom well suited for smaller vial attachment, with the needle assembly also being automatically centered upon insertion (while still providing for needle point flexing relative to a vial seal membrane).

In Fig. set 81A and 81B collar 372 represents a collar well suited as a connecting collar between a vial and a smaller diameter syringe, with a collar thickness or height of 17 mm.

Figure 81A:
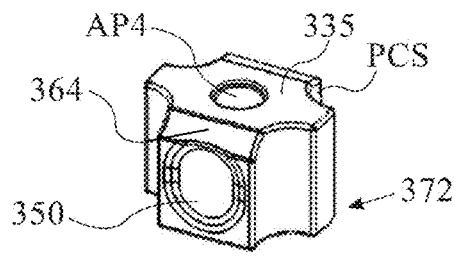
FIGS. 81*a* and 81*b* illustrate a shorter or thinner version of the torque enhancement member in the collar configuration of FIG. 1 (FIG. 8 as well) with the former showing a perspective view and the latter showing a central vertical cross-section and the tapered aperture configuration.
Figure 81B:
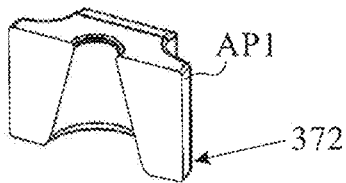

As shown in the cross-section view of FIG. 81B, aperture AP4 has a frusto-conical shape that features a diverging top to bottom shape having an uppermost diameter of 6 mm and a lowermost diameter of 14.5 mm which makes the top well suited for small diameter syringe insertion, and the bottom well suited for vial attachment.

Figure 82B:
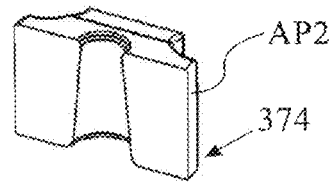

In Fig. set 82A and 82B collar 374 represents another torque enhancement member configuration in the form of a collar well suited for use, for example, as a connecting collar between a vial and a smaller diameter syringe, with a collar thickness or height of 17 mm. As shown in the cross-section view of FIG. 82B, aperture AP5 has a frusto-conical shape that features a diverging top to bottom shape having an uppermost diameter of 6 mm and a lowermost diameter of 9 mm, which makes the top well suited for small diameter syringe insertion, and the bottom well suited for smaller vial attachment.

Figure 83A:
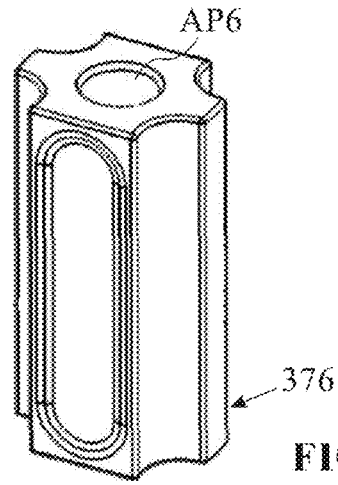
FIGS. 83a and 83b illustrate a much longer or thicker version of the torque enhancement member in the collar configuration of FIG. 1 with the former showing a perspective view and the latter showing a central vertical cross-section and the aperture configuration inclusive of a through-hole.
Figure 83B:
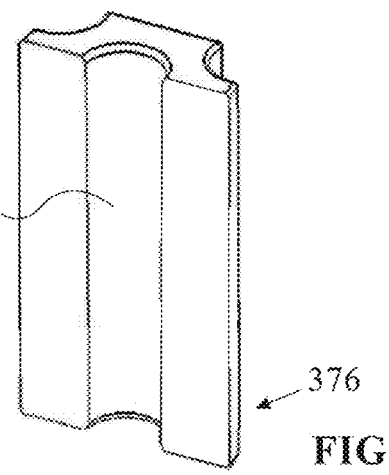

In Fig. set 83A and 83B collar 376 represents another torque enhancement member configuration in the form of a collar well suited as a connecting collar between a vial and a smaller diameter syringe, with a collar thickness or height of 48 mm. As shown in the cross-section view of FIG. 83B, aperture AP6 has a frusto-conical shape bore that features a converging top to bottom shape having an uppermost diameter of 15.5 mm and a lowermost diameter of 9.5 mm which makes the top well suited for an intermediate diameter syringe insertion, and the bottom well suited for vial attachment.

In Fig. set 84A and 84B there is shown another torque enhancement component or member configuration in the form of a collar 378 represents a collar well suited as a connecting collar between a vial and a syringe, with a collar thickness or height of 40 mm. As shown in the cross-section view of FIG. 84B, aperture AP7 is made up of a smaller diameter circular cylindrical bore AP7A that opens out into a larger diameter circular cylindrical bore AP7B. Upper bore AP7A has a 10 mm diameter in the illustrated embodiment, and lower bore AP7B has an 18 mm diameter in this embodiment, which makes the top well suited for small diameter syringe insertion, and the bottom well suited for larger vial attachment. Also the axial length of the top bore is preferably longer than the axial length of the lower bore as in 80% length in the top bore and 20% length in the lower bore or 75% length in the top bore and 25% length in the lower bore and points therebetween these two ranges. This embodiment as well as other suitably sized collar embodiments can also function as a catheter holding device wherein the catheter is inserted as to abut the narrower region for holding purposes and also to help the user with long period holding requirements as to help against muscle spasms and fatigue as well as tendon over usage.

In Fig. set 85A and 85B another torque enhancement member configuration in the form of a collar 380 represents a collar well suited as a connecting collar between a vial and a syringe, with a collar thickness or height of 40 mm. As shown in the cross-section view of FIG. 117, aperture AP8 is made up of a smaller diameter circular cylindrical bore AP8A that opens out into a larger diameter circular cylindrical bore AP8B. Upper bore AP8A has a 13 mm diameter in the illustrated embodiment, and lower bore AP8B has an 18 mm diameter in this embodiment, which makes the top well suited for intermediate diameter syringe insertion, and the bottom well suited for larger vial attachment. The same bore length ratio ranges as discussed above for FIG. 116 is applicable here.

In Fig. set 86A and 86B there is shown another torque enhancement member configuration in the form of a collar 382 which is well suited as a connecting collar between a vial and a syringe, with a collar thickness or height of 40 mm. As shown in the cross-section view of FIG. 86B, aperture AP9 is made up of a smaller diameter circular cylindrical bore AP9A that opens out into a larger diameter circular cylindrical bore AP9B. Upper bore AP9A has a 15.5 mm diameter in the illustrated embodiment, and lower bore AP9B has an 18 mm diameter in this embodiment, which makes the top well suited for intermediate to larger sized diameter syringe insertion, and the bottom well suited for larger vial attachment inclusive of threaded connections for direct thread mounting under either scenario. The same bore length ratio ranges as discussed above for FIG. 84B is applicable here.

In Fig. set 87A and 87B there is shown another torque enhancement member configuration in the form of a collar 384 which is well suited as a connecting collar between a vial and a syringe, with a collar thickness or height of 31 mm. As shown in the cross-section view of FIG. 87B, aperture AP10 is made up of a smaller diameter circular cylindrical bore AP10A that opens out into a larger diameter circular cylindrical bore AP10B. Upper bore AP10A has a 13 mm diameter in the illustrated embodiment, and lower bore AP10B has an 18 mm diameter in this embodiment, which makes the top well suited for intermediate to larger sized diameter syringe insertion, and the bottom well suited for larger vial attachment. An additional feature of upper bore AP10A is that it has equally circumferentially spaced grooves 6R providing a plurality of individual bore pads BP extending radially inward and which provided an added degree of flexing and accommodation for an object insertion as in the referenced syringe (which also are illustrative of a threading configuration). In the embodiment described here and above featuring a syringe/vial combination, the collars are also adaptable to connecting different lower and upper components rather than the exemplified syringe and collar combination for connection. Also, the same bore length ratio ranges as discussed above for FIG. 84b is applicable here.

Also, the aforementioned collars having through-holes also present catheter or wiring organization collars which avoids having to tape or otherwise attach a bundle of wire(s) and/or catheter(s) and/or other conduit types together. An additional advantage of such collars, particularly when formed of flexible material as in soft silicone is that they can be held and slid into a new position through use of finger pressure without crimping the flow of liquid or inner catheter cable.

In Fig. set 88A and 88B collar 386 represents a collar well suited as a connecting collar for a syringe's needle assembly, with a collar thickness or height of 22 mm. As shown in the cross-section view of FIG. 88B, aperture A11 is made up of a series of different diameter regions including a smaller diameter circular cylindrical bore AP11A that opens out into a larger diameter circular stacked frusto-conical bore arrangement AP11B (similar to that described above for collar 314), followed by an intermediate diameter bore AP11C which in turn opens out into a larger diameter needle reception/insertion bore AP11D.

Fig. set 89A and 89B shows collar 388 as being similar to that described above for Fig. set 88A and 88B, but having a smaller diameter upper bore as for a finer diameter needle shaft. The aperture sections AP12A, AP12B, and AP 12D share a common shape with that of FIG. 88B, but are designed for smaller needle assembly reception. Also, sloped wall SL provides for a controlled needle insertion angle as in 40° to 60° needle insertion.

Figure 88A:
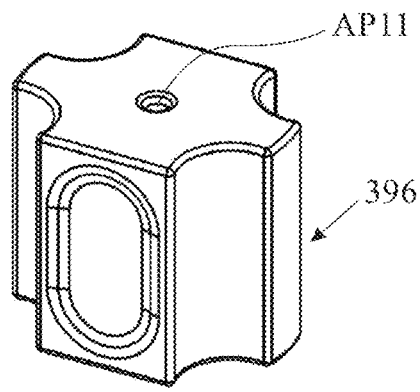
FIGS. 88a and 88b illustrate a longer or thicker version of the torque enhancement member in the collar configuration of FIG. 1 with the former showing a perspective view and the latter showing a central vertical cross-section and the aperture configuration.
Figure 89A:
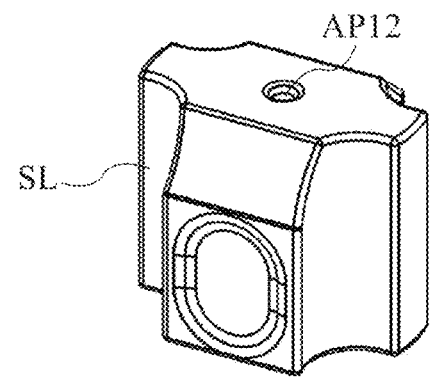
FIGS. 89a and 89b illustrate another embodiment of the torque enhancement member in the collar configuration of FIG. 8 (but with slope on needle exit side) with the former showing a perspective view and the latter showing a central vertical cross-section and the aperture configuration.
Figure 88B:
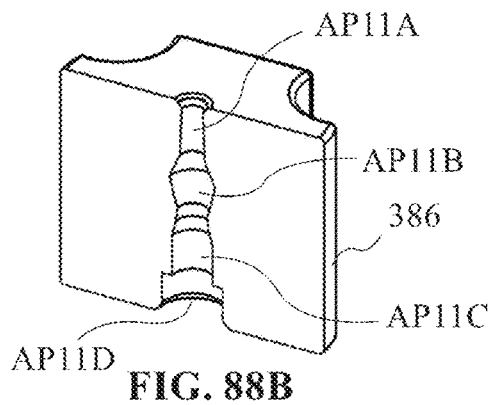
Figure 89B:
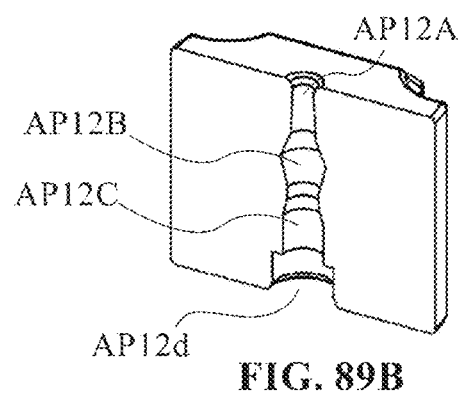
Figure 90A:
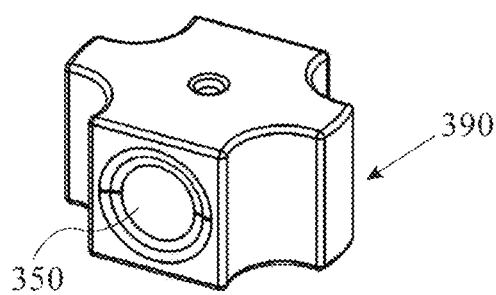
FIGS. 90a and 90b illustrate another embodiment of the torque enhancement member in the collar configuration of FIG. 1 with the former showing a perspective view and the latter showing a central vertical cross-section and the aperture configuration.
Figure 91A:
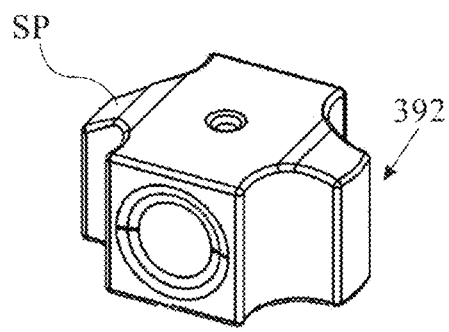
FIGS. 91a and 91b illustrate another embodiment of the torque enhancement member in the collar configuration of FIG. 27 with the former showing a perspective view and the latter showing a central vertical cross-section and the aperture configuration.
Figure 90B:
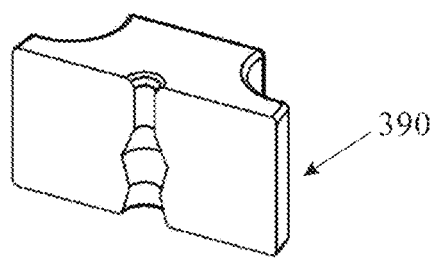
Figure 91B:
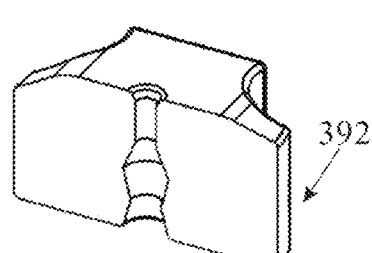

Fig. sets 90A and 90B as well as 91A and 91B (featuring torque enhancement members 390 and 392 in the form of collars), closely conform, respectively, to the above described collars in FIGS. 88A and 89A, but have a thinner body (14 mm rather than 22 mm). Also, sloped surface SP provides for a controlled needle insertion angle as in 15°-30°.

Figures 92A, 92B:
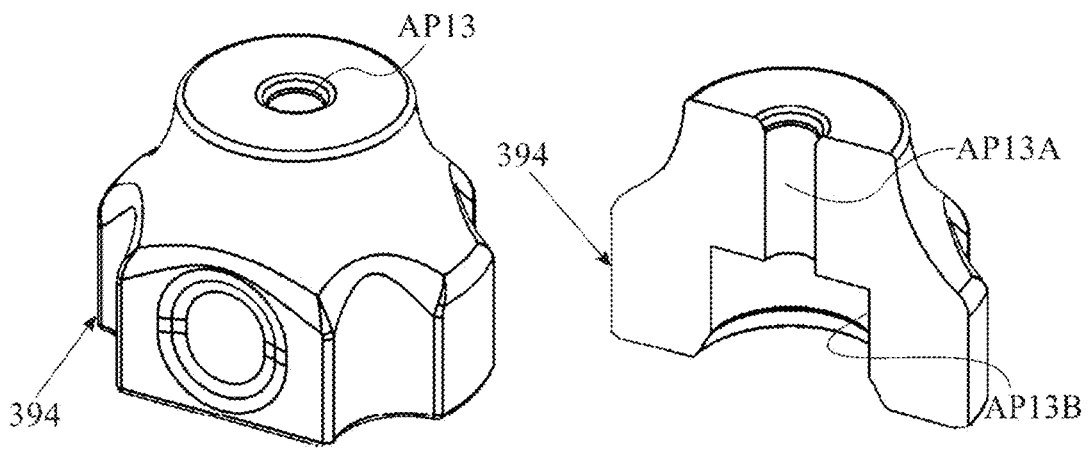
FIGS. 92a and 92b illustrate a version of the torque enhancement member in the collar configuration of FIG. 3 with the former showing a perspective view and the latter showing a central vertical cross-section and the stepped aperture configuration.

In Fig. set 92A and 92B show another torque enhancement member 394 in the form of a collar having the FIG. 3 configuration (and thus has the attributes described above for collars of the FIG. 3 configuration) and represents another torque enhancement member configuration in the form of a collar well suited as a connecting device between a vial and a syringe, with a vertical collar thickness or height of, for example, 10 to 30 mm (e.g., 20 mm). As shown in the cross-section view of FIG. 92B, aperture AP13 is made up of a smaller diameter circular cylindrical bore AP13A (e.g., 3 to 6 mm) that opens out into a larger diameter circular cylindrical bore AP13B (e.g., 8 to 20 mm). In this embodiment, upper bore AP13A has a 6 mm diameter, and lower bore AP13B has an 18.5 mm diameter, which makes the top well suited for syringe insertion, and the bottom well suited for vial (canister or bottle type) attachment. The bore length for each of the upper and lower bore sections is about equal as in 50/50 or (60/40 to 40/60 as representative relative bore length ratios for bores AP13A and AP13B).

Figures 93A, 93B:
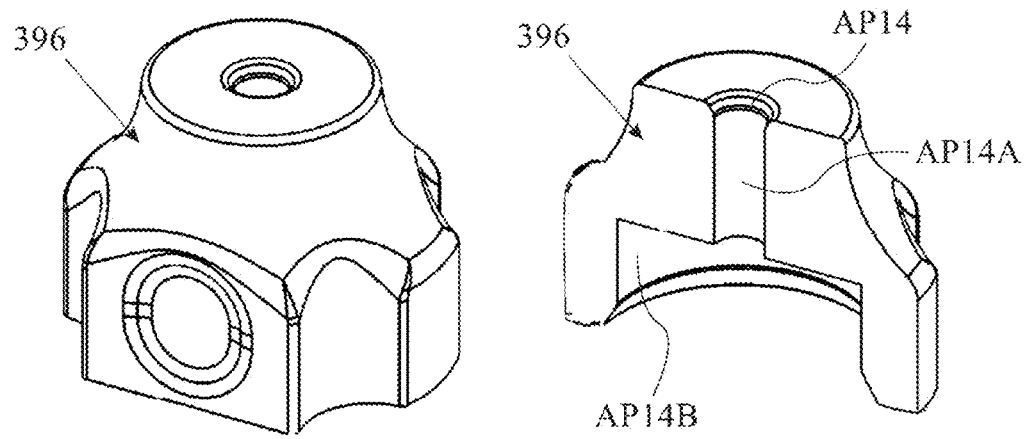
FIGS. 93a and 93b illustrate a version of the torque enhancement member in the collar configuration of FIG. 3 that is similar to that of FIG. 92a but for a greater step differentiation, and with FIG. 93a showing a perspective view and FIG. 93b showing a central vertical cross-section and the stepped aperture configuration.

In Fig. set 93A and 93B show another torque enhancement member 396 in the form of a collar having the FIG. 3 configuration (and thus has the attributes described above for collars of the FIG. 3 configuration) and represents a collar well suited as a connecting collar between a vial and a syringe, with a collar thickness or height of about 20 mm. As shown in the cross-section view of FIG. 93B, aperture AP14 is made up of a smaller diameter circular cylindrical bore AP14A that opens out into a larger diameter circular cylindrical bore AP14B. Upper bore AP14A has, for example, a 6 mm diameter in the illustrated embodiment, and lower bore AP14B has an 10 mm diameter (smaller vial than FIG. 92a) in this embodiment, which makes the top well suited for syringe insertion, and the bottom well suited for vial (canister or bottle type) attachment. The bore length ratios here conform with that described in FIG. 92A.

Figures 94A, 94B:
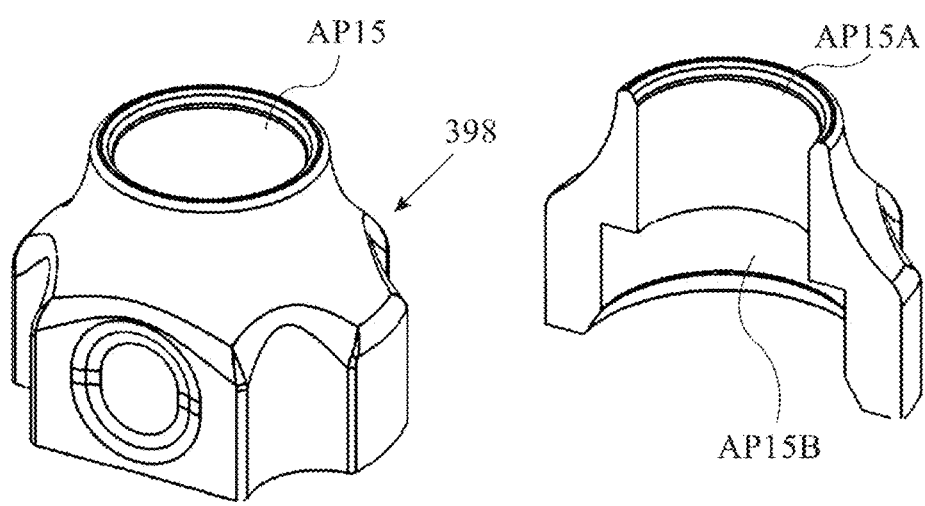
FIGS. 94a and 94b illustrate another version of the torque enhancement member in the collar configuration of FIG. 3 with the former showing a perspective view and the latter showing a central vertical cross-section and the stepped aperture configuration.

In Fig. set 94A and 94B show another torque enhancement member 398 in the form of a collar having the FIG. 3 configuration collar 398 represents a collar of the FIG. 3 configuration (and thus has the attributes described above for collars of the FIG. 3 configuration) and represents a collar well suited as a connecting collar between a vial and a syringe, with a collar thickness or height of about 20 mm. As shown in the cross-section view of FIG. 94B, aperture AP15 is made up of a smaller diameter circular cylindrical bore AP15A that opens out into a larger diameter circular cylindrical bore AP15B. Upper bore AP15A has a "large mouth" 13 mm diameter well suited for syringe with grasping collar as described, for example, in the disclosure for FIGS. 59, 61 and 62 illustrated embodiment, and lower bore AP15B has an 18.7 mm diameter in this embodiment, which makes the top well suited for syringe insertion, and the bottom well suited for vial (canister or bottle type) attachment. The bore length for each of the upper and lower bore sections is about equal as in 50/50 or (60/40 to 40/60 as representative relative bore length ratios for bores AP15A and AP15B).

In Fig. set 95A and 95B show another torque enhancement member 400 in the form of a collar having the FIG. 3 configuration with a closed top (and thus has the attributes described above for collars of the FIG. 3 configuration) and represents a collar well suited as a connecting collar between a vial and a syringe, with a collar thickness or height of about 20 mm. As shown in the cross-section view of FIG. 95B, aperture AP16 is in the bottom half only while the upper half is solid with the elastomeric material forming the collar of FIG. 3 configuration. This closed top is of a thickness that is suitable for needle puncture when access to the vial is desired and as a liquid seal cap relative to the material in the bottle or vial. The vial is connected to collar 400 by way of aperture AP16 which in this embodiment has an 8 mm diameter. The FIG. 95A embodiment is well suited for smaller vial containers and thus has an upper solid puncture area of 8 mm and a larger exterior as in 11.8 mm, with 8.5 mm vial capture recess diameter and a height of 7.5 mm.

In Fig. set 96A and 96B show another torque enhancement member 402 in the form of a collar having the FIG. 3 configuration with collar 402 representing an open top/closed bottom collar (and thus has the attributes described above for collars of the FIG. 3 configuration) and represents a collar well suited as an insertion location for the base of an object as in the plunger flange of a syringe, such as shown in FIG. 33. As shown in the cross-section view of FIG. 96B, aperture AP17 is in the upper half only while the lower half is solid (e.g., 2 mm thickness for a 7.5 mm height collar) with the elastomeric material forming the collar of FIG. 3 configuration. The open top has a diameter of, for example, 6 mm.

In Fig. set 97A and 97B show another torque enhancement member 404 in the form of a collar having the FIG. 3 configuration (and thus has the attributes described above for collars of the FIG. 3 configuration) and represents a collar well suited as a connecting collar between a vial and a syringe, with a collar thickness or height of about 18 mm. As shown in the cross-section view of FIG. 97B, aperture AP18 is made up of a smaller diameter circular cylindrical bore AP18A that opens out into a larger diameter circular cylindrical bore AP18B. Upper bore AP18A has a relatively small 2 mm diameter in the illustrated embodiment, and lower bore AP18B has an 18.5 mm diameter in this embodiment, which makes the top well suited for needle insertion, and the bottom well suited for vial (canister or bottle type) attachment. The bore length for each of the upper and lower bore sections is about equal as in 50/50 or (60/40 to 40/60 as representative relative bore length rations for bores AP18A and AP18B).

In Fig. set 98A and 98B show another torque enhancement member 406 in the form of a collar having the FIG. 3 configuration (and thus has the attributes described above for collars of the FIG. 3 configuration) and represents a collar well suited as a connecting collar between a vial and a syringe, with a collar thickness or overall height of 18 mm. As shown in the cross-section view of FIG. 98B, aperture AP19 is made up of a relatively smaller diameter circular cylindrical bore AP19A that opens out into a larger diameter circular cylindrical bore AP19B. Upper bore AP19A has a 10 mm syringe reception diameter in the illustrated embodiment, and lower bore AP19B has an 18.5 mm diameter in this embodiment, which makes the top well suited for syringe insertion, and the bottom well suited for vial (canister or bottle type) attachment. The bore length for each of the upper and lower bore sections is about equal as in 50/50 or (60/40 to 40/60 as representative relative bore length rations for bores AP19A and AP19B).

Figure 99A:
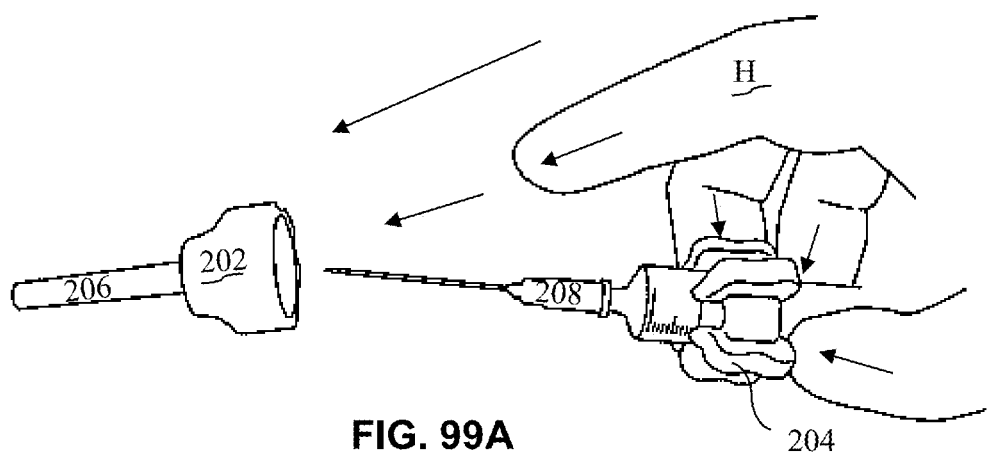
FIGS. 99a to 99c, provide an example of a combination the torque enhancement member in the collar configuration of FIG. 3 and a ribbed ring mount being used to hold a needle cover in position for safe insertion of the needle into the needle cover and to snap on with one hand the needle cover through use of the combination, with FIG. 99b also showing an alternative initial stage of separation of the two with one hand.
Figure 99B:
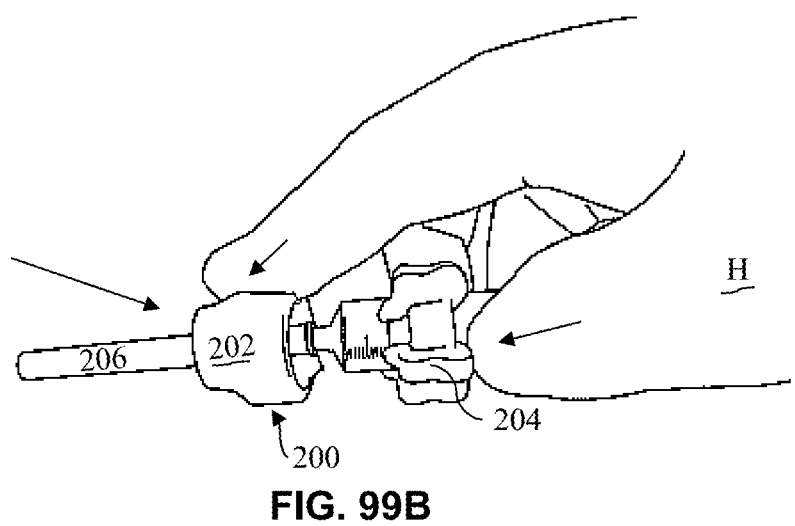
Figure 99C:
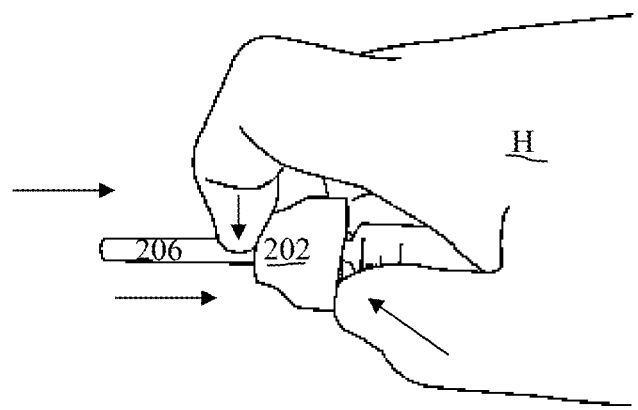

FIGS. 99A to 99C, provide an example of a combination 200 comprised of torque enhancement member or collar 202 (of FIG. 3 configuration) and mount 204 being used to hold a needle cover 206 (following its insertion into the enlarged open end of collar 202 until becoming trapped in the smaller diameter portion of the collar cavity such as the cavity arrangement shown in FIG. 97B). With the needle cover 206 in position as shown in FIG. 99a and the collar frictionally retained on the support surface in a tilted up direction, the user can insert with one hand H the needle assembly 208, as shown in FIG. 99b, such that the needle shaft enters into the enlarged open end of collar 202. Once sufficiently inserted the user, with the same single hand, can then grasp the top end of collar 202, with needle casing extending there-away, and pull it toward the base mount 204 (or simultaneous toward each other or hold the collar and move the mount forward) to achieve a snapped engagement of the needle in the needle cover (as depicted in FIG. 99c).

The FIG. 99b embodiment also illustrates how, with the same single finger downward compression used to enter the needle, there can be achieved separation. That is, with collar 202 pinned to the surface with a single finger, the user can retract the vial with other fingers of that same hand to achieve separation of the needle assembly and collar 207.

FIGS. 100a to 100d illustrate various views of turret collar combination 234 comprised of torque enhancement member 236 in the form of a turret collar, and an underlying platform 238 (preferably a spin and lock platform to provide a turret rotation function support to collar 236). That is, FIG. 135a shows turret collar combination 234 comprised of a modified collar 236 (generally of the FIG. 1 configuration) that is combined/retained (frictional reception contact holding relationship with rotation possible until a desired lock position is reached) by underlying platform 238. As seen, platform 238 has a saucer like configuration with a disc main body 240 having a circular periphery with smooth, upper contoured outer edging 242. Main body 240 further includes a planar upper surface 244 having at its center a raised mound that is generally semi-spherical turret mound 246. As seen in FIG. 100b, turret mound 246 is designed for extension into a conforming recess 250 conveniently provided as part of a through-hole aperture APT that extends through the thickness of the collar. Platform 238 further includes a preferably channeled reception area (preferably a plurality of concentric channels formed in the undersurface of platform 238 as represented by channels 252 shown in cross-section). Also, platform 238 is preferably a soft, pliable material such as silicone rubber as to provide for frictional position retainment as to provide a stable turret support and also for accommodating variations in body surface when used as a medical instrument. Mounting of the platform can also be made even more position secure via use of temporary adhesive as used in EKG pads such as those with removable non-adhesive cover sheeting). Suitable dimensions for platforms 238 includes a diameter of 15 to 30 mm as in 20 mm, a thickness plate of 1 mm to 4 mm as in 1.7 mm, a bulb 246 height of 3 to 7 mm (as in 4 mm) and a bulb diameter of 4 to 8 mm as in 6.3 mm.

Torque enhancement member 236 is preferably provided with a sloped (long collar ridge side to opposing long collar ride side) through-hole 254 that is conical in shape and shown as slanting downward from its larger insertion end 254A to its narrower exit end 254B lying at the lower extremity of finger depression recess 256. Also, through-hole 254 also is bisected by aperture AP such that it opens at two interior points into aperture APT. In this way, porting is provided vertically in aperture APT and also through the long length of collar 236 with aperture APT in communication with the through-hole. Some non-limiting illustrative dimensions for components of collar 236 include a thickness height of 10 to 15 mm as in 11 mm, an aperture 258 oval of 2 mm height, 5 mm length, and a maximum length (short ridge to short ridge) of about 20 to 30 mm (e.g., 26.2 mm).

Torque enhancement member 236 is provided with additional porting via an oblong (e.g., oval) passageway 258 with open end 258A shown in FIG. 100a (and a full cross-sectional view provided in FIG. 101c which is described below). Passageway 258 extends the full length from short-ridge side to short-ridge side of the main body of collar 236 (see PR as short ridge example in FIG. 100d) and also bisects with the aperture APT such that each extension opens into the central aperture APT as also depicted in FIG. 101a. Passageway 258 is preferably arranged to pass in the lower portion of the main body of collar 236 (the lower quarter relative to the height of the collar), but is preferably not blocked off by the bulbous turret mound 246. In this way the smooth contour of the top of mound 246 can help in the feeding of elongated instruments through the desired porting including passageway 258 which opens into aperture APT in that region.

Figures 100E, 100F:
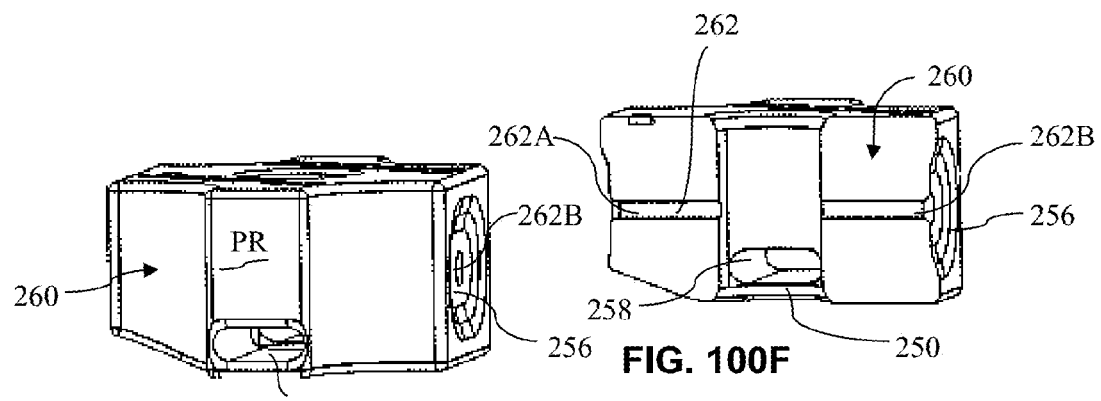
Figure 101A:
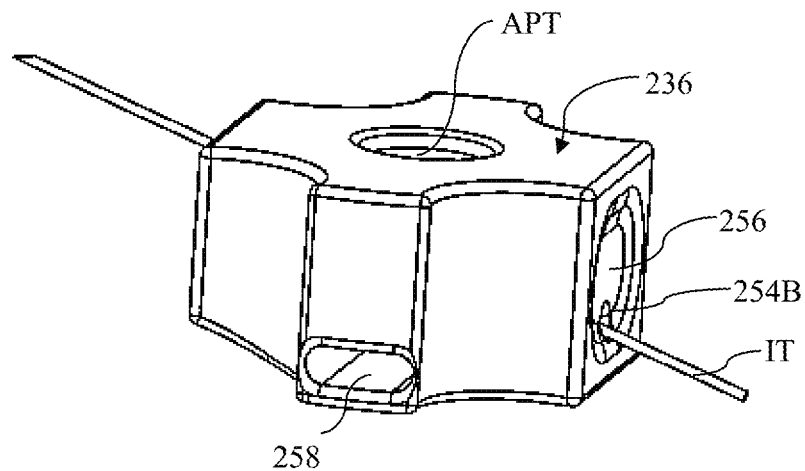
FIGS. 101a to 101c illustrate the collar of FIG. 101a removed from its mount, with FIG. 101a showing a perspective view of the collar with an angled thin tool inserted as in a needle insertion, catheter sheath, wire, fluid tube, etc. insertion.

FIGS. 100e and 100f illustrate a modified turret collar 260 having similar features as described above for turret collar 236, but rather than a conical through-hole that is tilted, there is provided through-hole 262 that has a common diameter along its entire length (each extension thereof extending to opposite sides of aperture APT which is in communication with through hole 262) and is arranged in horizontal fashion. That is, opening 262A is at the same height level as opening 262B, with the latter opening out at the center of finger depression recess 256 rather than at its lower edge in the earlier embodiment. FIG. 100f also illustrates the turret recess 250 lying just below and in communication with passageway 258.

Figures 100G, 100H:
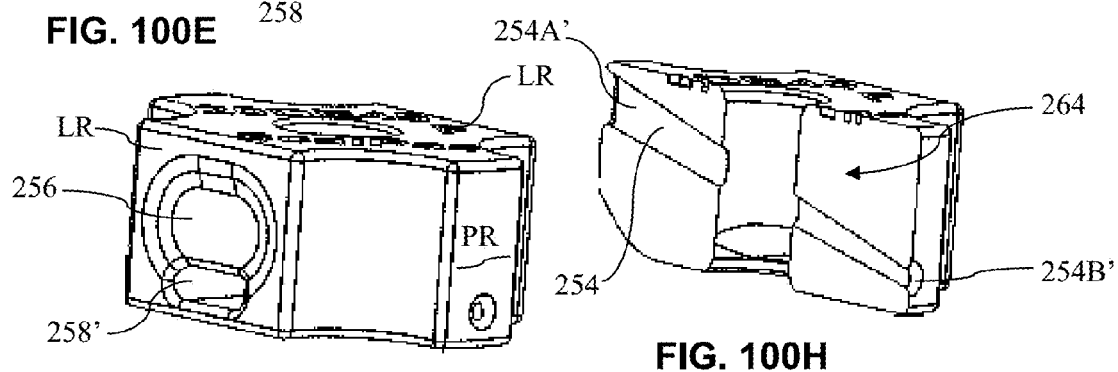

FIGS. 100g and 100h show a modified embodiment of the turret collar described above. In this embodiment turret collar 264 includes generally the same collar configuration but features the lower passageway 258' as passing not between the opposing short length ridges PR but between the opposing long side ridges LR. Thus, the oblong opening of passageway 258 opens out at the lower region of finger depression recess 256. Also, through-hole 254' is similar to through-hole 254 described above (sloped and conical), but instead extends through the collar body and aperture APT from short side ridge PR to its opposing ridge (PR). As seen from FIG. 100h, the slope results in opening 354B' being in the lower quarter of collar body height and the enlarged opening 254' in the upper quarter of height of collar 264.

Figures 100I, 100J:
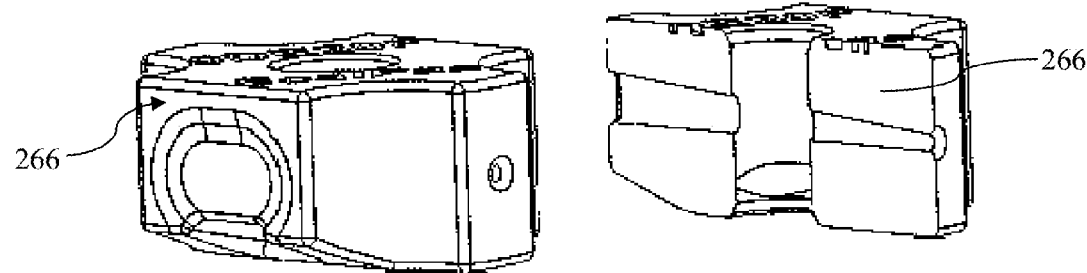

FIGS. 100i and 100j show turret collar 266 which has the same configuration as that of turret collar 264 but for rather than a tilting through-hole such as through-hole 254' in FIG. 100h it has a horizontal through-hole 268 (while also retaining the conical configuration featured in through-hole 254', however).

Figure 101B:
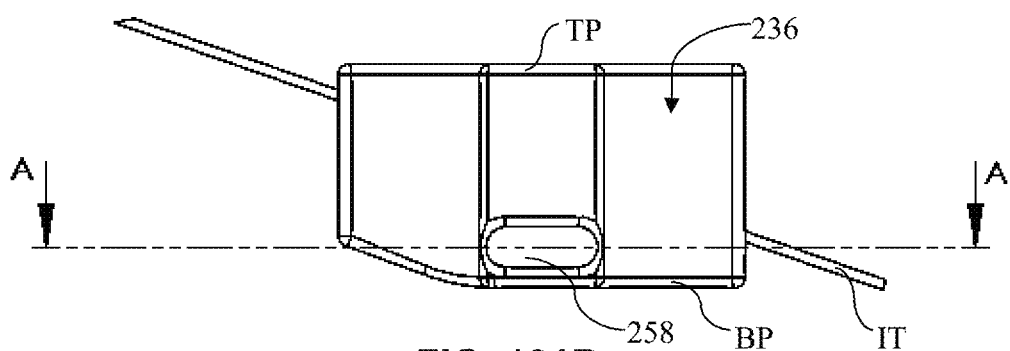
Figure 101C:
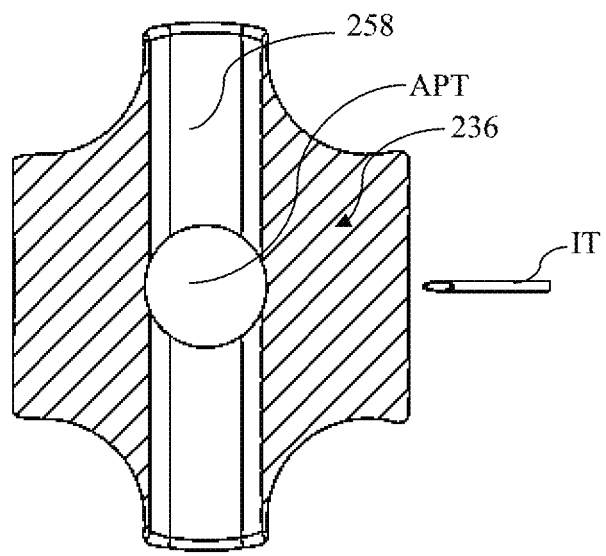

FIGS. 101a to 101c illustrate yet another torque enhancement member 236 which is shown as a collar of FIG. 100a that is removed from its mount, with FIG. 101a showing a perspective view of the collar with an angled thin tool (e.g., a flexible or non-flexible tool as in one <3 mm in diameter and preferably less than 1 mm) inserted into through-hole 254, as in through opening 254A and down through to the opposite opening 254B whereupon the tool extends to both sides of collar 235 (e.g., a tool as in a needle, a sheath (e.g., a catheter sheath), a wire, a fluid tube, etc.). While turret collar 236 is mentioned for receipt of insert tooling or utensils, depending on the circumstances, any of the other above described turret collars can be utilized for insertion(s) of such tools or utensils.

FIG. 101b shows a front elevational view of that which is shown in FIGS. 101a, and 101c shows a cross-sectional view along cross-section A-A in FIG. 101b (which represents a horizontal bisect of passageway 258). As further seen from FIG. 101b inserted tool IT can extend above and below the respective top plane and bottom planes TP and BP of collar 236 (with the lower one potentially illustrating a below skin entry point).

FIG. 102 shows another embodiment of a torque enhancement member which is in the form of turret collar 270 which is similar to collar 236 but for a different through-hole 272 that replaces through-hole 254 in collar 236. That is, through-hole 272 has an oval or oblong shape like passageway 258, but has its major diameter extending vertically rather than horizontally like for passageway 258 (e.g., 1 mm minor diameter and 3 mm major diameter). There is still retained a downward slope as seen by the IT ends being at different height in FIG. 101a. As shown in the enlarged detail in FIG. 102A, through-hole opening 272A has a smooth lead in edge 274 which defines the IT insertion hole 276. The minor axis diameter for this insertion hole can be sized as to provide some frictional resistance from upward or downward adjustment in the IT relative to the maximum diameter direction for the oval shaped opening. In FIGS. 102 and 102A there is shown the tool IT in a shallow angle orientation wherein the IT tool contacts the bottom of the insertion opening 272 border.

FIGS. 103 and 103A depict the same turret collar 270 as in FIG. 102, but has the IT tool adjusted up to a maximum angle such that tool IT abuts the upper extremity of the border defining through-hole opening 272A.

FIG. 104 shows the same view as FIG. 101a, but show the utensil as being a combination utensil ITC, having IT as described above as a hollow sheath initially inserted through the collar plus a feed though instrument ITI. Such an arrangement can represent a useful relationship in a variety of fields both medical and non-medical, but is particularly useful in the medical field as once the turret collar is mounted on its platform after the platform is placed in position (or a simultaneous mounting) and the ITC placed, it can be held in place or rotated to a different desired orientation in turret fashion. Additionally, sheath IT will retain its position while the interior instrument ITI can be threaded in one direction or the other. Examples include sheathed wiring assemblies, catheter sheath and insert combinations, fiber optics and line-up sheathing, etc.

FIG. 105 shows the arrangement of FIG. 104 rotated so that the inlet side of opening 272A is more visible rather than the outlet side 272B of FIG. 104.

FIG. 106 shows a similar view as that of FIG. 105, but with a position retainer insert 278 added. In this way there is added assurance of the desired upward positioned tool IT is retained relative to collar 272. FIGS. 106a to 106c show different variants of the position retainer insert 278 designed to hold the tool at a desired orientation within the receiving oblong or oval shaped opening provided in the collar for tool positioning flexibility. Also, the base of insert 278 is provided with a hole for insertion of a tool facilitating removal.

Figure 107:
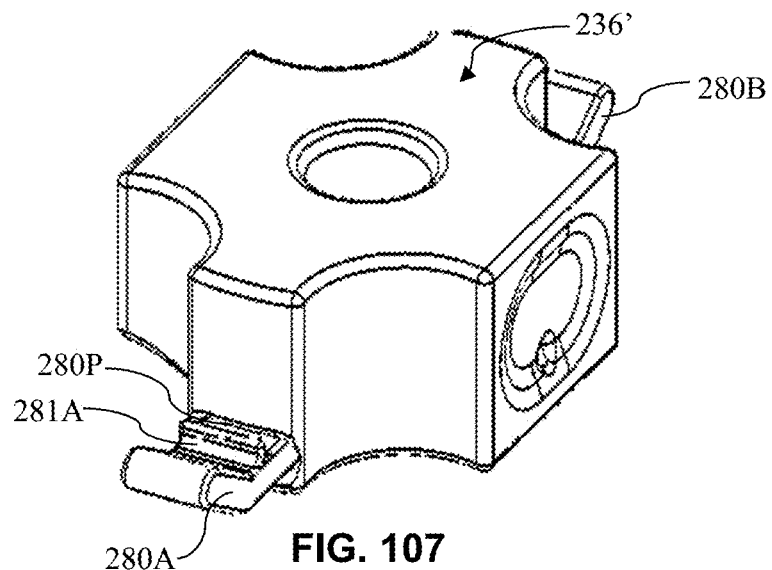
FIGS. 107 and 108 show different views of a swivel mounted collar similar to FIG. 100a, but with a pair of clamp down wings extending out from the collar main body (e.g., after insertion into respective passageway sections of the turret collar).
Figure 108:
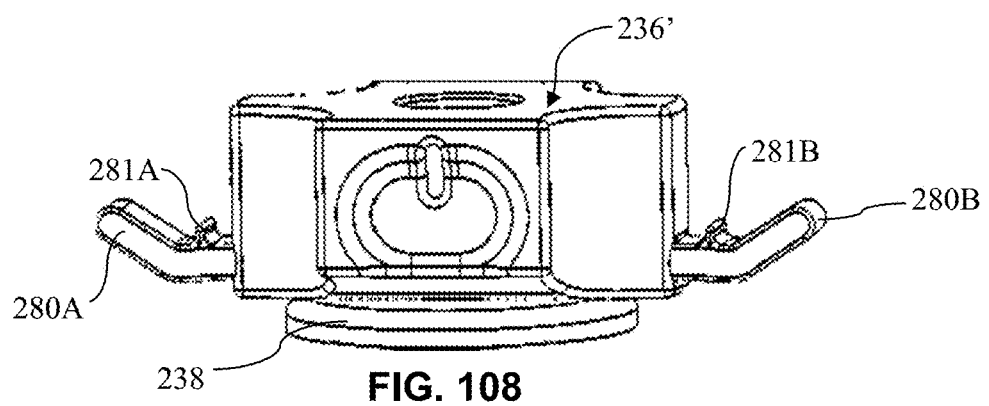

FIGS. 107 and 108 show different views of the combination 234 comprising a turret collar and swivel mount as shown in FIG. 101a, but with a modified turret collar (236') featuring a pair of clamp down wings 280A and 280B with wing platforms extending out of short side ridges PR at their base and supporting clamps 282A and 282B within reception grooves/ridging 281A and 281B. Clamp down wings provide a useful location for securement of the turret collar in place once the rotation position of the turret collar relative to the base represented by spin platform 238 is chosen. For example, clamp down wings can be, for example, stapled in position to the recipient support surface such as a patient. Also, clamp down wings can be threaded into an existing aperture such as 258.

Figure 109:
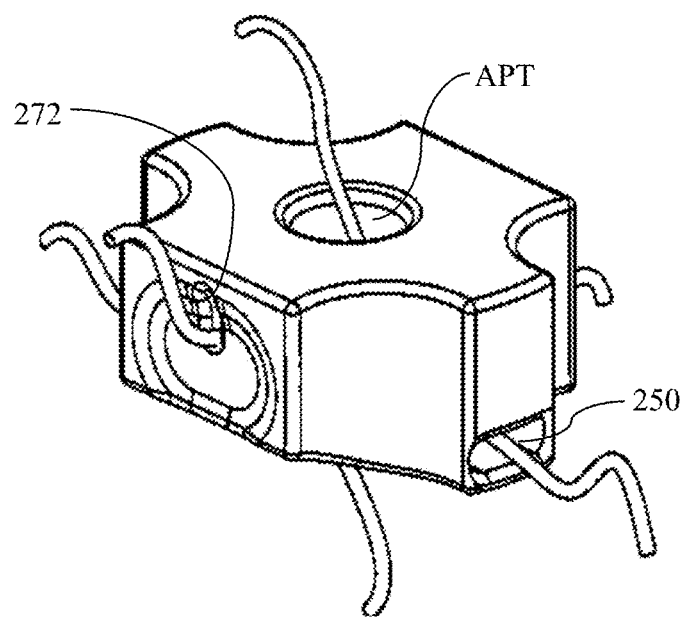
FIG. 109 shows a swivel mounted collar similar to FIG. 100a with a plurality of different utensils or one utensil having a plurality of different offshoots (e.g., instrument wiring or tubing) received therein and coming out of the different porting.

FIG. 109 shows a swivel mounted collar 270 similar to FIG. 102 with an illustration of the numerous porting provided by passageways 258 and through-hole 272 and aperture APT communicating with all porting. Hence, a plurality of different utensils or one utensil having a plurality of different offshoots (e.g., instrument wiring or tubing) can be received therein and directed in a desired direction and slope (up or down) or horizontally. In FIG. 107 a series of wires are showing with five different exit points illustrated.

FIGS. 110 and 110a illustrate collar 270 of FIG. 102 further comprising plug device 284 just prior to insertion, with the plug device comprised of a base body 286 with a central aperture, a pin top 288 that is retained secured to base body 286 via tether 290. As shown, insertion of pin portion 287 of pin top 288 places its cap 289 in a closed state relative to the central aperture in the base body 286. As further shown in FIG. 110, pin top 288 has a central aperture CA, which can provide an insertion opening for a smaller instrument (a though-hole through the entire plug, for example) or a threading guide for an item retained in collar 270. The plug 284 also can close off and pin, if desired, instruments or tooling placed in aperture APT or though the various portings described above. FIG. 110a shows the collar and plug arrangement shown in FIG. 110 but from a side view. FIG. 110a also shows porting IP in the base body of the plug that can be used for threading of a thin instrument such as a flexible sheath, whereupon plug downward movement and/or rotation results in a crimping or braking function and/or a fluid blockage mode if fluid is passing through instrument IT.

FIGS. 110b to 110d show different length plug devices 284 (284' and 284") each with integrated pin caps that can be inserted to seal off the plug itself received by the collar. As shown, the base body can be adjusted in height so as to extend into aperture APT to a greater or lesser extent.

FIGS. 111 and 111a show the same collar 270 and plug device 284 featured in FIG. 110, but with the plug device 184 inserted into the aperture APT of collar 270 in sealing fashion. FIG. 111 also shows optional segregated porting XX that can be added if additional instruments are to be supported (e.g., those extending in generally common direction at least initially).

With reference again to FIG. 76, there can be seen a reference framework provided relative to the torque enhancer therein shown (i.e., a plan view of the torque enhancement collar shown in FIG. 1 with added reference framework). In the discussion to follow, regarding different aspects of the present invention's torque enhancer, there is similarly referenced a long length L1 and a width length L2, together with corner "cut outs" (actually preferably "formed-in" concavities as in molded-in or die press formed cavities) C1 to C4. Each of cavities C1 to C4 is shown in FIG. 76 to be concave with or without side edge extensions. The below discussion also references the corner concavity open areas C1 to C4 that result in projection surfaces PCS on each of the long length projections (having surfaces 338A and 338B, each of peripheral length $L_L$), as well as short length projections (having surfaces 339A and 339B, each of peripheral length $L_S$). The concave cut-outs can also be formed in other shapes as in stepped side walls and generally more rectangular than semi-circular configurations, with some examples of each presented below.

Also, the below discussion also uses the frame-of-reference rectangular RE shown in FIG. 76 which is in co-linear contact with the straight edge(s) of the 338A and 333B side and extends into tangent contact with the slight curvature sides 339A and 339B (or along straight edge versions of the same). As further described below the co-linear relationship is made whether there exists or not, intermediate side wall notches between the linear extension ends. The same is also true relative to the long sides which can be notch inclusive or notch-less (e.g., each of the long and short sides as demarcated with dashed lines in FIG. 76 with the dot-dash lines reflecting the concavities where no material is present). Also, side walls 338A and 338B can be perpendicular to the top plane frame of reference in three dimension, or can be sloped inward or outward (either in linear or curved or both linear and curved) relative to the top plane, and can also be smooth walled or have one or more recessions in the wall region (with examples of the same being described for other examples of the invention, inclusive of oval shaped recesses provided on walls such as 338A and 338B which can provide both compression benefits and also a finger reception recess).

Figure 112:
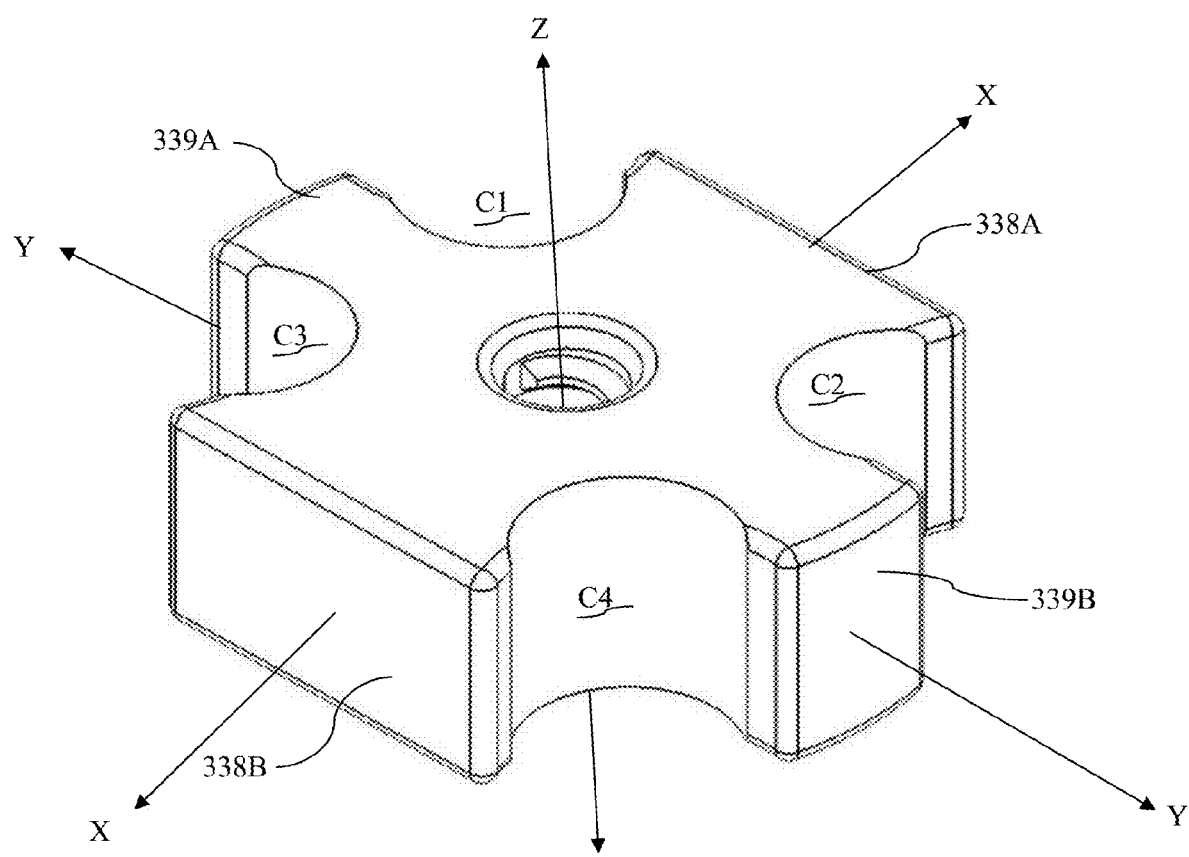
FIG. 112 shows a perspective view of an alternate embodiment of the torque enhancer of the present invention which in this embodiment has the same general bi-symmetry configuration as shown in FIG. 76 and is in the form of a threaded nut (e.g., bolt nut) with the longer length surfaces extending in the Y-axis direction, the shorter length surfaces extending in the X-axis direction, and the Z-axis extending perpendicular to the horizontal plane defined by the X-Y axes combination.

FIG. 112 shows a perspective view of an alternate embodiment of a torque enhancement device of the present invention comprising torque enhancement member 500B which in this embodiment has the same general bi-symmetry configuration as shown in FIG. 76 and is in the form of a threaded nut (e.g., bolt nut, with the central threaded hole represented by hole 508) with the longer length surfaces 338A and 338B extending in the illustrated Y-axis direction, the shorter length surfaces 339A and 339B extending in the X-axis direction, and the Z-axis extending perpendicular to the horizontal plane defined by the X-Y axes combination).

Figures 113A, 113B:
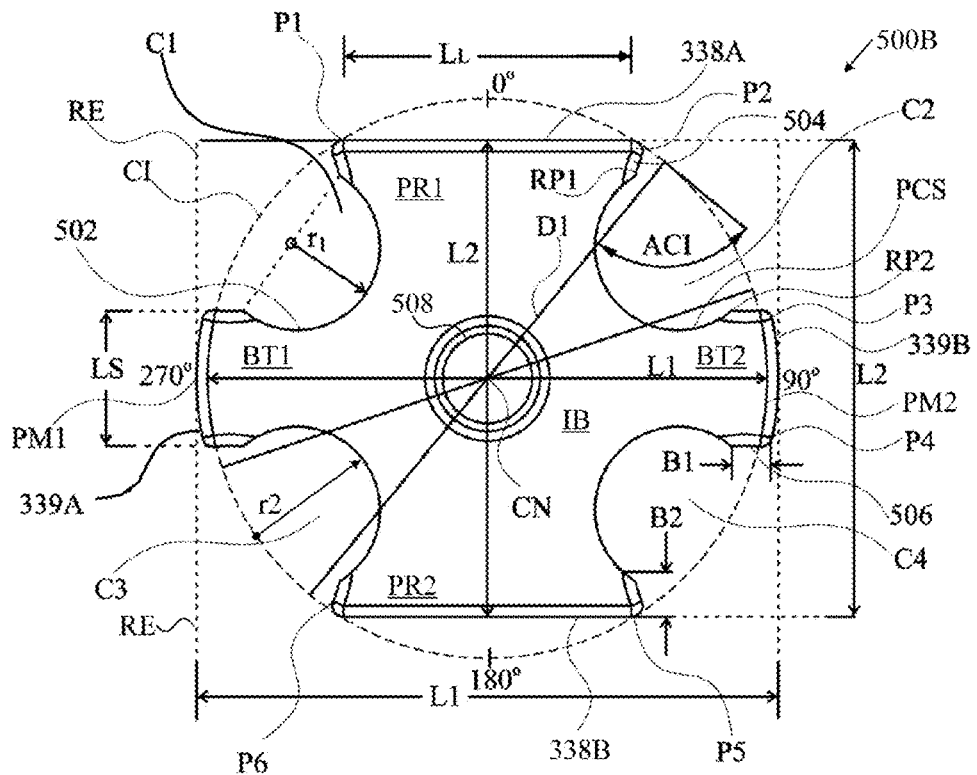
FIGS. 113A and 113B show, respectively, a top plan view and bottom plan view the torque enhancer member shown in FIG. 112.

FIG. 113A shows a top plan view of that shown in FIG. 112, while FIG. 113B shows a bottom plan view thereof. As seen from a comparison of FIGS. 113A and 113B, the side walls of torque enhancement member 500B are generally non-sloped between the area defined by the top plan view and bottom plan view is shown equal (although tapering matching side wall set(s) are also featured under the present invention as well as the inclusion of the aforementioned finger depressions as well).

FIG. 113A also shows an overlay reference plane RE like that shown in FIG. 76, as well as an added reference circle CI. As seen in 113A (and 113B) torque enhancer 500B includes two elongated surfaces 338A and 338B (which can be of similar length as the earlier referenced same reference numbers, or of different length, and are preferably of equal length relative to each other relative to a preferred bi-symmetry configuration). Also, like reference numbers and letters used throughout the application relative to the referenced information (e.g., reference plane illustration, reference circle illustration, various lengths, radius values, angles, etc.), can vary in value or attribute from one embodiment to the next despite the commonly used reference number or letter (with a few examples of such potential variety, despite common reference number or letter set, being described below). For example, a corner cut out C1 in FIG. 113A may be referenced again in another figure set despite having a specific configuration different than that in FIG. 113A.

An aspect of the present invention includes an advantageous geometric form that provides for a multi-purpose torque enhancement device with enhanced torque generation potential. In this regard reference is made to the reference circle CI shown as extending through the end points (P1 and P2 in FIG. 113A) of the side walls 338A and 338B of projections PR1 and PR2 extending out along the X-axis from interior body portion IB. As also seen in FIG. 113A, the reference circle CI extends radially inward of at least the outer points (PM1 and PM2 relative to the Y-axis) of the exterior surfaces 339A and 339B formed at the end of the "bow-tie" projections BT1 and B2T extending in the Y-axis direction out from interior body portion IB. FIG. 113A also shows that, for this embodiment, the entirety of the exterior surfaces 339A and 339B fall outward of reference circle CI. As will be explained in greater detail below, this geometry provides points of leverage extending beyond the reference circle CI and thus is illustrative of a longer torque generating moment arm as to provide increased rotation force (while also avoiding instability due to the differential, as through centrifugal force generation countering control as explained in greater detail below as well). This differential is also represented by the spacing differential between the maximum thickness of the torque enhancement body in the X-axis direction and the maximum thickness of the torque enhancement body in the Y-axis direction (i.e., L2 and L1 are different).

In the embodiment shown in Fig. set 112 to 116 there is featured solid or uninterrupted (e.g., notch-less) sides 338A and 338B of common length $L_L$, although the illustrated example in FIG. 112 can have one or multiple features varied from that which is depicted (e.g., the inclusion of notched or interrupted side walls 338A and 338B in place of the notch-less side walls 338A and 338B shown, with examples of some of the suitable notch types being described below).

Torque enhancement member 500B further includes shorter length side walls defining surfaces 339A and 339B (which are also preferably equal in length relative to each other in accordance with the noted bi-symmetry). Walls 339A and 339B are shown having a minor curvature (notch-less) with the reference rectangular RE having short side walls extending tangentially from the mid-point or maximum outer curvature points PM1 and PM2 of walls 339A and 339B. In alternate aspects of the invention, the short side walls 339A and 339B can be straight walls as to continue on a common line with the short length reference rectangle's walls. Also, as shown in FIGS. 113A (and 113B), there is featured solid or uninterrupted (e.g., notch-less) slightly curved side walls defining surfaces 339A and 339B of length LS.

FIGS. 113A and 113B further illustrate that, from a three dimensional perspective, the side walls 339A and 339B are perpendicular to the top plane frame of reference. Alternate embodiments feature long and/or short side oblique (to the top plan view plane) walls that slope inward or outward (either in linear or curved or both linear and curved fashion) relative to that top plane reference plane; and in addition to the embodiment shown in FIG. 112 with all walls 338A, 338B, 339A and 339B being smooth walled sides, embodiments of the invention include having different designs for the side wall pairs as in having one or more recesses in the internal wall surface region and/or the border region of those side walls (as in, for example, an embodiment having inward sloping long and short side walls of equal or different angle value such that the area on the top surface periphery is larger and the periphery of the bottom surface of the torque enhancer is smaller). The slope angle of the short sides 339A and 339B can be the same as those of the long sides 338A and 338B or can be different (e.g., a different slope angle in or out for a wall 338A and 338B can be the same or different as compared to a 339A and 339B), or different recesses provided in the interior region of the side walls.

The ratio of long versus short can be varied in accordance with intended needs, as in situations where low stress (e.g., low torque speeds and low torsion stress concerns) can provide for a lower percentage value representing the L2/L1 ratio (less square like configuration) versus situations wherein there is high stress and torsion (e.g., I-beam girder bolts) wherein a higher percentage value (closer to square configuration) may be desirable (L2/L1 less than 100% but greater than 75%). Under embodiments of the present invention (some of which are shown in this application) L2/L1 ratios are from 60% (farthest removed from reference frame RE being a square) to 95% (closer to reference frame RE being a square), and more preferably 65% to 90%. Under further embodiments of the present invention the L2/L1 ratio is from 75% to 90%, as in ratios of 76% to 81%.

Also, while not having 360 degree symmetry, preferred embodiments of the invention feature an opposing symmetry or bi-symmetry configuration with respect to a common X-Y axes plane (e.g., a horizontal top plan plane or horizontal cross-sectional plane), as in a first symmetrical relationship for opposing sides/areas to opposite sides of the X-axis and a second (different than first) symmetry to opposite sides of the Y-axis. Thus, with reference to FIG. 113A there can be seen a first symmetry to opposite sides to a line extending along the X-axis between the 0° and 180° compass points, and a second (different) symmetry to opposite sides to a line extending along the Y axis between the 270° and 90° compass points and thus also through the maximum extension points PM1 and PM2 for the bow-tie projections BT1 and BT2.

As with the FIG. 76 embodiment, in the embodiment featured in FIGS. 112 to 116 there are provided four corner recessed regions C1 to C4 (inward with respect to each of the four corners of reference rectangle RE). The surface portions of torque enhancement member 500B that define the radially interior-most portion of the corner notch regions C1 to C4 are each of the same configuration and length, and are shown as each being a semi-circular surface 502, with each of radius r1 (each being the same in this embodiment although variations in the shape and/or relative size for the interior-most portion are also featured herein). Also, there is shown in FIG. 113A that each of recesses C1 to C4, in addition to the semi-cylindrical portions represented by radius line r1, have less curved and somewhat outwardly tapered sections as represented by length dimensions B1 and B2 for projection sets BT1, BT2 and PR1, PR2, respectively. Accordingly the full depth for each of corner notches is shown as being of radius r2 relative to the reference circle CI, with r2 thus being greater than r1.

Figure 116:
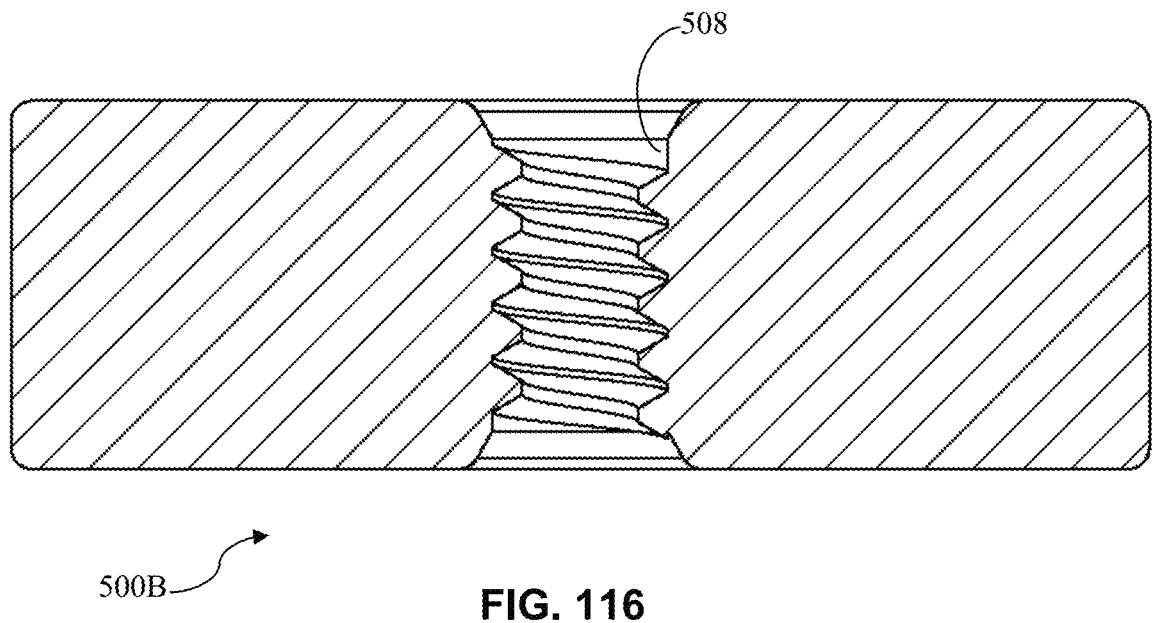
FIG. 116 shows a cross-section view of the torque enhancer of FIG. 112 taken along the Y-Y axis cross-section line thereof.

The FIG. 112 embodiment of torque enhancer member 500B is shown as having a central point CN from which the reference diameter lines D1 for reference circle CI are shown. Aperture 508 formed in inner body IB is also shown as being centered on point CN. Thus member 500B is well suited for use as a nut (or gear), and when featured as a nut, is shown in FIG. 116 in cross section as having threading extending along the Z-axis for the full thickness of the member 500B.

Torque enhancer embodiment 500B can come in a variety of sizes with preferably relative relationships retained such that the presented view is merely a zoomed in or out presentation of that which is shown. Thus, there is no intention to be limited to a particular size as that would be dictated by the intended use. In the torque enhancement member shown in FIG. 112 there is an L2/L1 percentage ratio of 80%. Also, to help illustrate the relative relationships in the different components, the following dimensions are provided (which are generally on a larger size parameter as might be well suited for industrial structures requiring relatively large bolt and nut sizes such as those involved with I-beam girders and the like): L1=75 mm; L2=60 mm; L2/L1=0.8 or 80%; $L_L$=40 mm; $L_S$=18 mm; r1=11 mm; B2=6 mm.

Also, the central aperture can also be sized for intended use and in consideration of the overall size of the torque enhancement member, with a suitable range for the FIG. 112 embodiment being 6 to 26 mm, with 16 mm being a value featured in conjunction with the dimensions described in the paragraph above. The thickness TH is use dependent as well, with standard nut thickness being applicable depending on the overall nut size and intended use.

Figure 114:
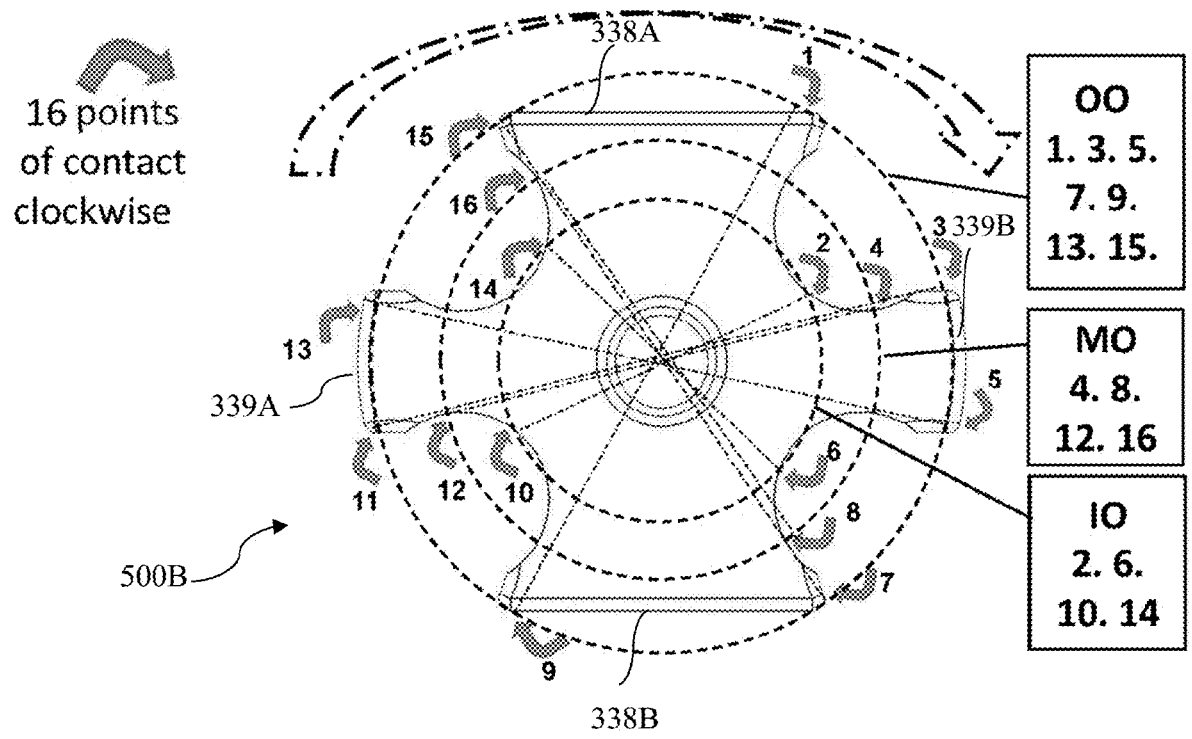
FIG. 114 shows a similar top plan view as that shown in FIG. 113, but with a "mechanical" contact point illustration (without consideration of centrifugal force impact).

With reference to FIG. 114 there is provided the same top plan view as in FIG. 113A, but with an added overlay of initial (without centrifugal rotation forces considered) contact points. These contact points are representative of the contact points that would arise as when there is utilized a hand wrench having a common configured torque enhancement interior recess designed for insertion around the exterior periphery of the nut shown in FIG. 113A (an example of suitable wrenches for such purpose is described below, with wrench 360 in FIG. 181 being illustrative). For purposes of the present invention, this initial contact mode showing (as in a hand wrench) will be referenced here and below as a "mechanical contact" mode presentation as to differentiate over the also below described initial rotation consideration which involves consideration of centrifugal force impact etc. (levels of which can be incurred with, for example, an air or hydraulic wrench that can travel at high RPM's as to generate higher centrifugal forces in the nut).

As seen from FIG. 114, the illustrated torque enhancement member 500B features relatively deep corner cut-outs C1 to C4 and therefore is marked as providing for three orbital contact circles relative to, for example, a conforming torque generating tool such as torque wrench 360 shown in FIG. 181. The three orbitals are denoted as inner orbit IO, middle orbit MO and outer orbit OO in FIG. 114. Further, as shown in FIG. 114, each of the illustrated mechanical contact point presentations is depicted as having a common diameter opposite contact point (differently numbered) on a common orbital. Thus there is shown IO contact point sets 2-10 and 6-14 representing contact points at the base of the corner-cut outs along inner orbit IO in the common side (right side) as the clockwise progression shown for torque tool rotation (an opposite rotation would put the contact points on the opposite side of the common configured surface in similar diametrically opposed relationships). There is further shown in FIG. 114 contact point sets such as 4-12 and 8-16 that fall on middle orbit MO and are shown as falling on the same contact side as the earlier described IO contact points, but at a location farther up so as to land on the upper side portion of the respective cut-out corners.

FIG. 114 still further shows additional contact points generally pertaining to the OO outer orbital. Shown are projection contact points, both relative to the exposed surface and corners of projections defining straight edges 338A and 338B and the exposed arc surface and corners of the bow-tie projections 339A and 339B. Thus, there is shown contact point 1 on the far right upper surface of straight edge 338A and, based on the bi-symmetric configuration for torque enhancer, a far left surface contact point 9 in surface 338B (contact point set 1-9); as well as contact point 3 at the corner cut-out upper (straightened) edging just before formation of the arc surface of 339B and a similar arrangement, but for being on the lower rather than upper side and on the bow-tie projection 339A as to define contact point set 3-11. Contact point set 5-13 is shown as being contact points on the clockwise end of the arc surface defining bow-tie projections 339B and 339A, respectively. Additionally, mechanical contact point set 7-15 are contact points still within the corner cut outs C1 and C3, but on the far ends just before the periphery of torque enhancer goes into the straight side walls 338A and 338B. Thus, as shown in FIG. 114, there are three contact points in each cut-corner zone with the outer most being in the corner region where the corner cut out straightens and just before the torque enhancer periphery extends into the straight wall edges 338A and 338B.

There would also be featured 16 mechanical contact points going in the counterclockwise direction (not shown), but they would conform to the bi-symmetry nature of the torque enhancer (e.g. the points 14, 16 and 15 shown all hitting their respective inner, middle and outer orbits would instead by hitting the opposite side of corner cut out C1 (the left side wall of corner cut out C1 shown in FIG. 114)). In similar fashion the outer surface contact points 5 and 13 would shift to the opposite lower/upper side as the side presently shown in FIG. 114.

Figure 115:
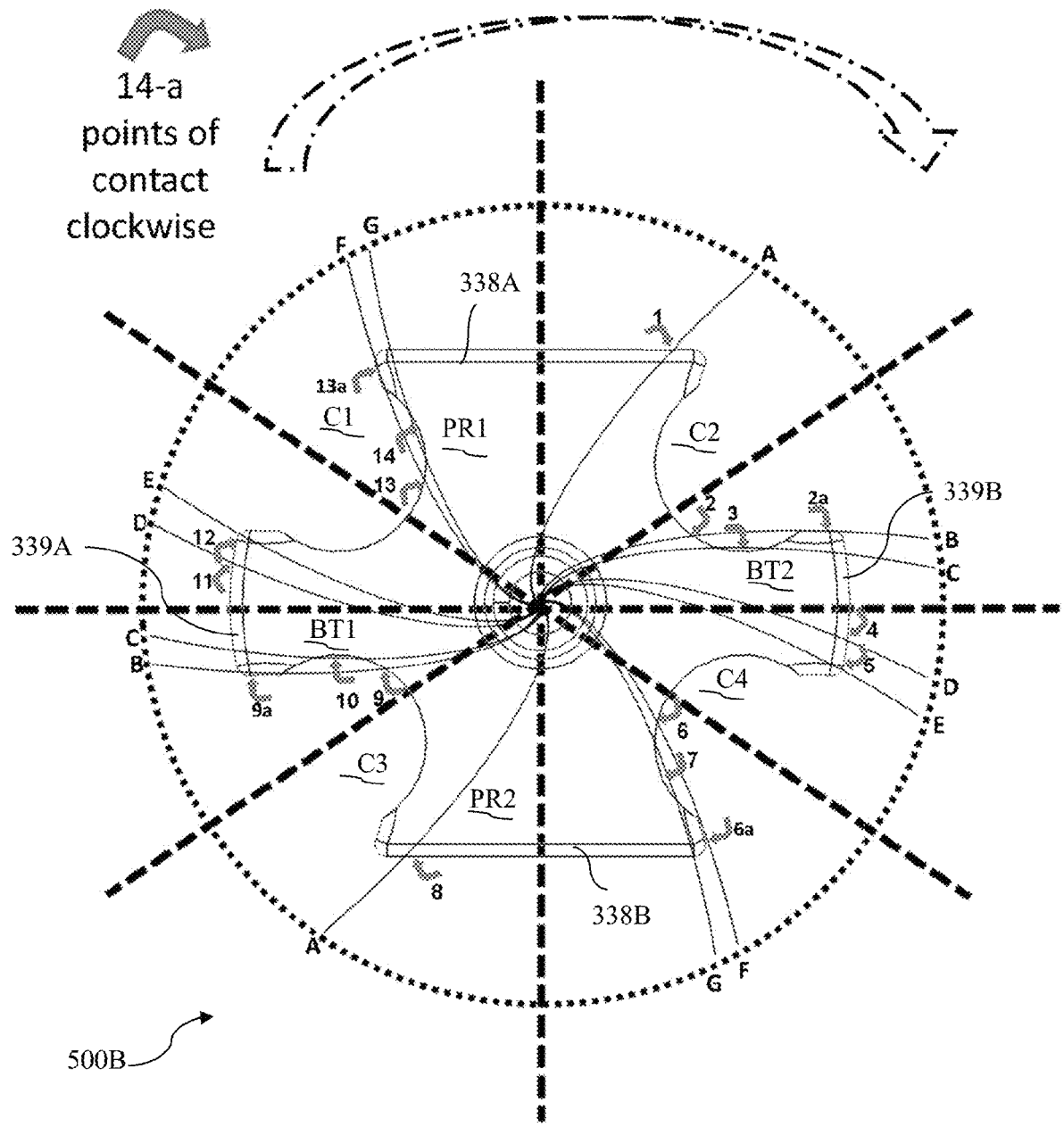
FIG. 115 also shows a top plan view of the torque enhancer of FIG. 112, but with a "spiral-centrifugal" contact point illustration (representative of an initial spin rotation status with consideration of initial centrifugal force development).

With reference to FIG. 115 there is shown a presentation of potential contact points relative to the "spiral-centrifugal" mode described above. While not being bound by any theories, it is Applicant's belief that the geometry of the present invention provides the beneficial force interrelationships described above, herein and below, with reference to the generated force contact points presentations being utilized to help illustrate these concepts. Further, in light of the additional forces that would be generated in a spinning nut, there is utilized curved (spiral segments) to help illustrate what is considered to be the potential contact points on the nut as it is being spun as described. That is, FIG. 115 depicts spiral segments A to G (two sets with one to each side of the vertical line shown in view of the bi-symmetry) relative to the 14 (spiral segments) point contact presentation for this mode (shown with rotation in the clockwise direction with 7 spiral segments to each side of the vertical). Further shown in FIG. 115 is the single or multiple contact points considered present on the respective spiral segments, with the below description directed at the force developments thereat.

For example, contact point 1 is found on spiral segment A, and is shown on the right side end region of surface 338A with a contact force out and down on that surface; contact points 2 and 2a are found on spiral segment B with the more radial outward contact point 2a shown as being both well aligned (essentially parallel with the tangent of the rotation orbit) and relatively far away from the inner body IB center point CN as to represent a strong torque generation point. Contact point 3 is found on spiral segment C and has a generally aligned force direction with that of contact point 2a, but is a bit closer to the center point CN (and thus while having a relatively high tightening (or loosening) force value, is lower than contact point 2a). Point 2 deeper in the corner cut out C2 which not only is lessened in torque generation due to its closer position to the center but also can be seen as contacting a curved surface tending to generate some force direction back towards the center (again considered to help compensate for the forces developed at contact points such as 2a (higher region of rotation force provided by the longer length projection availability could generate some instability as there is a differential in length in the noted projection sets (PR1, PR2 and BT1, BT2)). However, the overall geometry of the present invention is considered to help avoid such instability brought about by the differential. In this regard, reference is also made to contact points 4 and 5 shown falling on spiral segments D and E, respectively. There can further be seen that, while providing some rotation assistance forces, they also can be seen as being positioned as to generate some radially inward component back toward the center CN (which is considered to provide some outer centrifugal damping aspects). Accordingly, while contact points 4 and 5 are below in torque generation value as that of the two earlier noted contact points of 2a and 3, they are considered to counteract some of the forces generated due to rapid spinning of a not entirely symmetric body as to help avoid instability as might be otherwise generated due to the lack of full symmetry.

Reference is further made to the depicted contact points 6, 6a and 7 falling on segments F and G, respectively, with points 6a and to a lesser extent point 7 considered to present relatively higher torque generation as they are arranged in common with the rotation direction for the most part. Again, with reference to contact point 8 on the left side of side wall 338B, there is considered to be again some force direction directed back toward the center point to help offset any differential developed and centrifugal forces by providing a degree of counteracting forces. Also due to the bi-symmetry, a similar situation is considered to exist relative to the earlier mentioned contact point 1, and the similar (to 6, 6a and 7) forces 13, 13a and 14 found on segments F and G. In addition, the description presented for contact points 2, 2a, 3 and 4, 5 is considered to be applicable to the bi-symmetry contact points 9, 9a, 10 and 11, 12 working on projection BT1 and falling respectively on spiral segments B to E on the left side.

Figure 117:
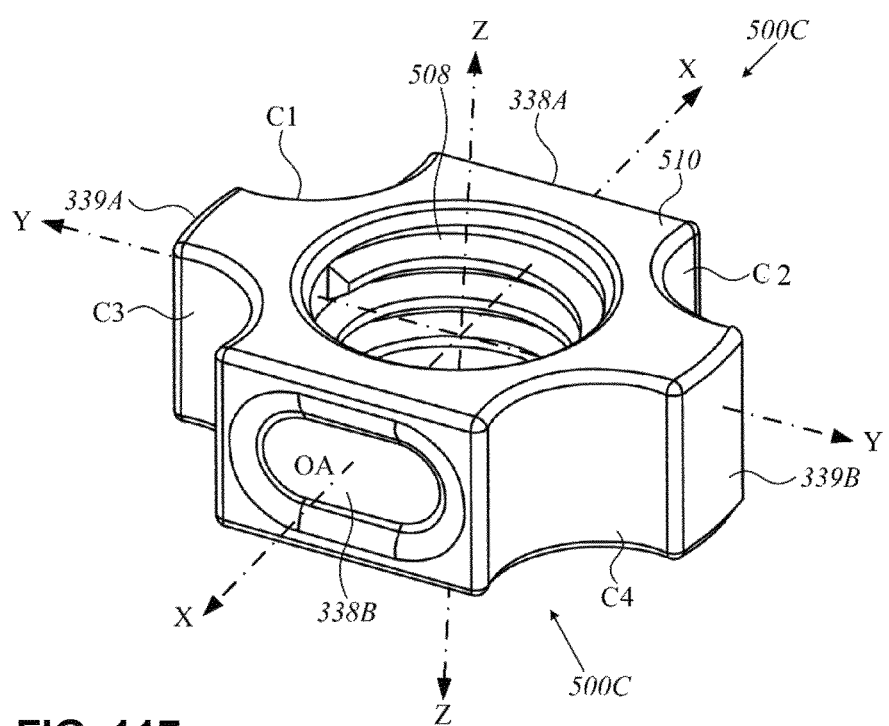
FIG. 117 shows a perspective view of an alternate embodiment of the torque enhancer of the present invention which is also shown in the form of a threaded nut.
Figure 118:
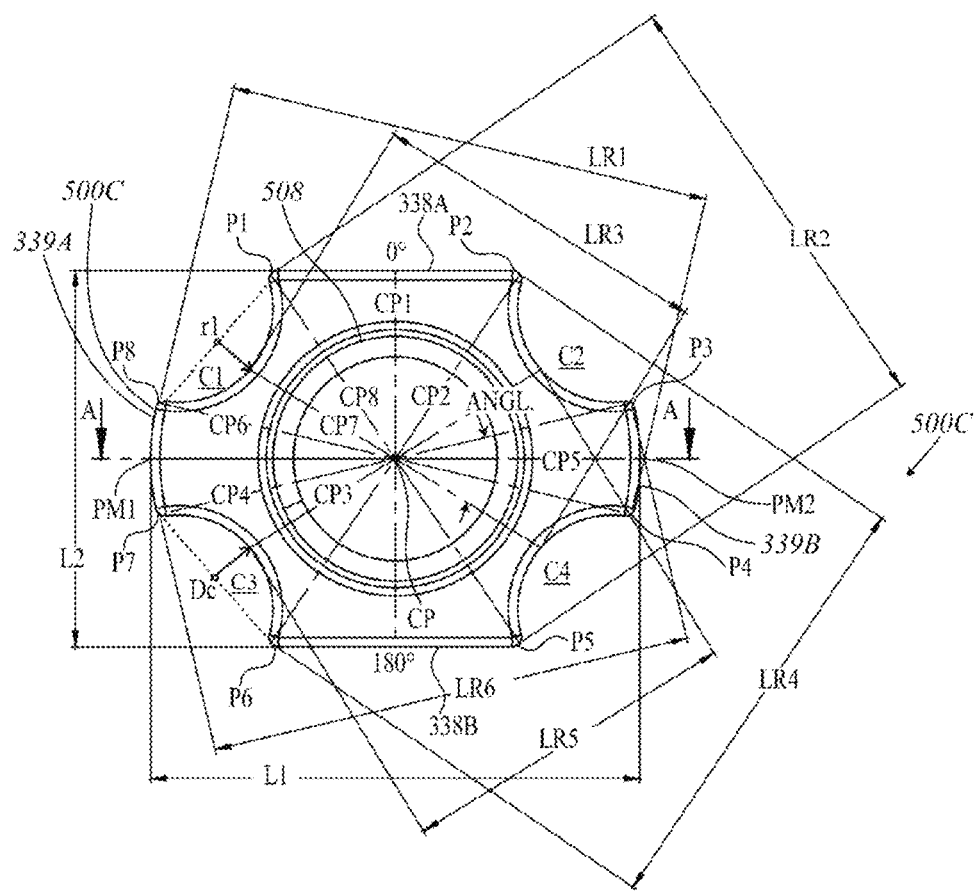
FIG. 118 shows a top plan view of the torque enhancer of FIG. 117.

FIGS. 117 to 121 show an additional torque enhancer embodiment enhancer 500C which is also shown in the form of a threaded nut or gear (e.g., bolt nut) having the above described bi-symmetry with longer and shorter length characteristics, although a bit different than the embodiment of 500B. With reference to FIG. 118 for torque enhancer 500C there can be seen that length L1 corresponds to the long length between the outermost points PM1 and PM2 in the respective short sides 339A and 339B. That is, rather than reliance on reference rectangle RE, a different reference approach is taken in this figure set to depict the long length which is carried out through use of length depiction L1 free of an overlying reference rectangle. In FIG. 118 there is illustrated compass point diameters (CP1, CP2, ... CP8) all passing through center point CP (which is also the centerpoint for the thread ring 508 formed in the interior of nut body 510). Threads 508 can take on any suitable form for a nut as the present invention works well with a variety of binding means (e.g., threads, key slots, expansion mechanisms, etc.).

As shown in FIG. 118:

compass point diameter CP1 runs between the center point of the long side edges 338A and 338B, which in this embodiment is represented by compass point diameter running from 0 degree to 180 degrees;

compass point diameter CP2 runs between opposite end points P2 and P6 of long sides 338A and 338B (representing counter-clockwise potential torque generating force contact points as described below);

compass point diameter CP3 runs between opposite end points representing the deepest concavity points of the surfaces 502 of corner notch regions C2 and C3, with CP3;

compass point diameter CP4 runs between opposite end points P3 and P7 of short sides 339A and 339B (representing clockwise potential torque generating force contact points as described below);

compass point diameter CP5 runs between the center point of the short side edges 339A and 339B, which in this embodiment is represented by compass point diameter running from 90 degree to 270 degrees. As such, CP5 also runs between the maximum points PM1 and PM2 of the illustrated slight curvatures as to define length L2;

compass point diameter CP6 runs between opposite end points P4 and P8 of short sides 339A and 339B (representing counterclockwise potential torque generating force contact points as described below);

compass point diameter CP7 runs between opposite end points representing the deepest concavity points of the surfaces 502 of corner notch regions C1 and C4; and compass point diameter CP8 runs between opposite end points P1 and P5 of long sides 338A and 338B (representing clockwise potential torque generating force contact points as described below).

As also seen from FIGS. 117 and 118, the end walls represented by side walls 339A and 339B, while slightly curved, are also smooth in surface configuration. Torque enhancer 500C is also shown as having a top planar surface 510T and a bottom planar surface 510B; although, at least in this embodiment with a bolt form of torque enhancer, the reference to top and bottom is for references purposes only as the final orientation of the nut 500C is controlled by the threaded component to which it is threaded. There is also illustrated that for side walls 338A and/or 338B there can be provided therein side wall contouring as in an oval depression OA featured in FIG. 117 with smooth sloping inwardly walls to provide easy finger pinch grasping.

With further reference to FIG. 118, there is seen additional reference length values LR1 to LR5 (in addition to the aforementioned short rectangle RE length L2 and long reference rectangle length L1). LR1 is directed at the length of CP6 running between points P4 and P8; LR2 represents the length of CP8 running between P1 and P7. LR3 represents the length of CP7 running between the maximum depression points in respective surface portions 502 of corner-notch regions C1 and C4; LR4 represents the length of CP2 running between points P2 and P6; LR5 represents the length of CP3 running between the maximum depression points in respective surface portions 502 of corner-notch regions C2 and C3; LR6 is directed at the length of CP4 running between points P3 and P7; LR2 represents the length of CP8 running between P1 and P7. Length L1 is longer than length L2, with an example of suitable ratio "RA" values for the L2 (shorter)/L1 (longer) ratios being as described above for the embodiment 500B.

For instance in the embodiment shown in FIG. 118 there can be provided a long length L1 of 26 mm and a short length of 20 mm, leading to a L2/L1 ratio RA of 0.76. With such dimensions suitable LR1 to LR6 values are 25.74 mm; 23.64 mm; 18.11 mm; 23.64 mm; 18.11 mm; 25.74 mm, respectively, with the matching values showing the bi-symmetry nature of the present invention as described above.

As an additional "larger bolt" example for the embodiment featured in FIG. 117 (and also showing the general common relationship scaling up of the above described "smaller" bolt non-limiting illustrative dimensions), there is LR1 to LR6 of about 73 mm; 68 mm; 52 mm; 68 mm; 52 mm; 73 mm, respectively, with Dc at 8 mm. Also, for this embodiment L2 and L1 are 57 mm and 75 mm as to represent the same L2/L1 ratio of 57/75 or 76%.

Also, as shown in FIG. 121, there is a relatively large threading diameter of TD, although the preferred size is dependent on intended usage as in a bolt size to be accommodated. For the FIG. 117 embodiment illustrated a preferred diameter for threaded hole 508 is 6 to 40 mm.

Figure 119:
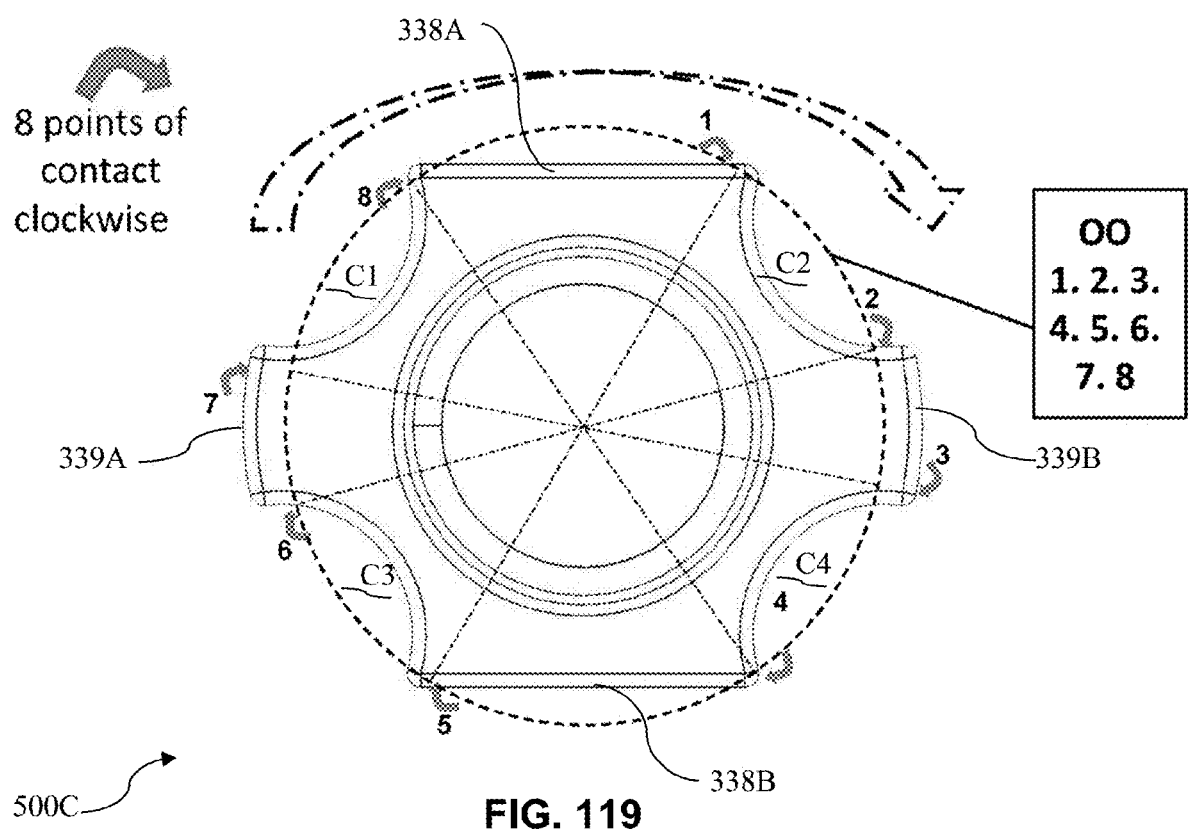
FIG. 119 shows a similar top plan view as that shown in FIG. 113, but with a considered "mechanical" contact point illustration.
Figure 120:
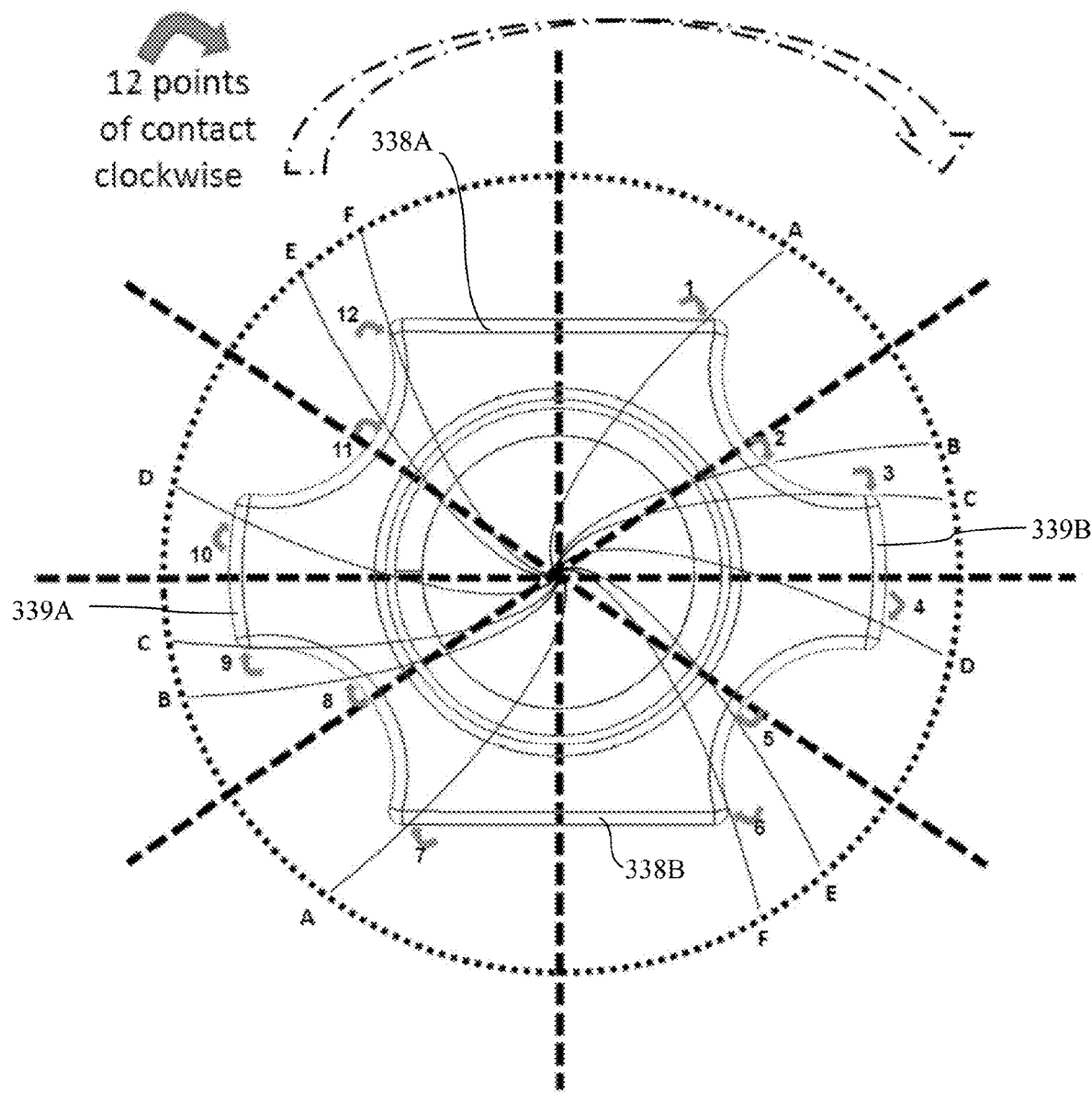
FIG. 120 also shows a top plan view of the torque enhancer of FIG. 117, but with a considered "spiral-centrifugal" contact point illustration.

FIGS. 119 and 120 provide a mechanical and spiral-centrifugal overlay for torque enhancer 500C, with the former shown as having 8 contact points or 4 pairs of diametrically opposite contact points. That is, in view of the relatively shallow corner cut-outs C1 to C4, there is illustrated just one orbit circle corresponding to CI. Thus, FIG. 117 shows the 8 contact points in clockwise rotation by a torque tool sharing a common configuration (slightly larger (e.g., 0.5 mm or less) in peripheral configuration as to allow for slide retention over the conforming configuration of the torque enhancer so as to come in contact at the eight noted points. Starting at contact point 1 there is seen that a conforming tool hits to the far right end of straight wall 338A just before the depression starts for cut-out corner C2. The next point of contact (contact point 2) falls on the noted circle CI on the clockwise side of the surface defining cut-out corner C2. The next point of contact (contact point 3) falls outside the circle CI and on the clockwise far end of the exposed arc surface of projection BT2 with surface 339B. This is followed by contact point 4 falling at the outer tip of the border region between cut-out corner C4 and the far right end of straight edge 338B. This is still followed by contact point 5 falling on a point diametrically opposite to point 1 and on the left end of straight edge 338B at the circle CI intersection therewith. Contact point 6 is shown inward within cut-out C3 on the circle CI in similar fashion to the diametrically opposite contact point 2. The next point of contact (contact point 7) falls outside the circle CI and on the clockwise far end of the exposed arc surface of projection 339A, which is then followed by contact point 8 which is diametrically opposite contact point 4 and falls at the outer extremity of cut-out corner C1 where it borders on the far left side of straight edge 338A (i.e., at the point where circle CI intersects that border region).

The diametrically opposite contact point pairs achieved by the tool during a clockwise torque application by a tool such as wrench 360 in FIG. 181 is further represented by the diametric contact point pairs of 1-5; 2-6; 3-7; 4-8.

The counterclockwise direction leads to different contact points (similar contact point arrangements, but on opposite contact locations relative to the bi-symmetrical configuration). For example, the contact point 1 for the clockwise direction is shown at the right side end of side edge 338A, while a counter-clockwise direction would place it on the equivalent left side of side edge 338A in the opposite direction of rotation.

With reference to FIG. 120 there is shown a presentation of potential contact points relative to the "spiral-centrifugal" mode for the torque enhancer shown in FIG. 117. Again, while not being bound by any theories, it is Applicant's belief that the geometry of the present invention provides the beneficial force interrelationships described above, herein and below, with reference to the generated force contact points presentations being utilized to help illustrate these concepts. As in the above, in light of the additional forces that would be generated in a spinning nut, there is utilized curved (spiral segments) to help illustrate what is considered to be the potential contact points on the nut as it is being spun as described. That is, FIG. 120 depicts 12 spiral segments for enhancer 500C (labeled A to F for each bi-symmetric side opposite the vertical bifurcation line shown—shown with rotation in the clockwise direction). Further shown in FIG. 120 is the one contact point per respective spiral segment, with the below description directed at the force developments thereat.

For example, contact point 1 is found on spiral segment A, and is shown on the right side end region of surface 338A with a contact force out and down on that surface; contact point 2 is found on spiral segment B positioned on the clockwise side of smooth concave corner cut out C2 (and thus has a similar inward stabilization orientation as contact point 3 in the enhancer 500B). Contact point 3 in FIG. 120 is shown being both well aligned (essentially parallel with the tangent of the rotation orbit) and relatively far away from the center point CN of the inner body IB. This higher region of rotation force at contact point 3 is provided by the longer length projection availability, which, on the other hand, would normally generate some instability as there is a differential in length in the noted projection sets (PR1, PR2 and BT1, BT2). However, the geometry of the present invention is considered to help avoid such instability brought about by the differential. In this regard, reference is made to made to the contact point 2 discussion above, and contact point 4 (shown falling on spiral segment D), while providing some rotation assistance forces, is also positioned as to generate some radially inward component back toward the center CN (which is considered to provide some outer centrifugal damping aspects). Accordingly, contact point 4 is below in torque generation value as that of contact point 3, and is considered to counteract some of the forces generated due to rapid spinning of a not entirely symmetric body as to help avoid instability as might be otherwise generated due to the lack of full symmetry.

Reference is further made to contact point 5 which like 2 is found within a clockwise side of a smoothly contoured and relatively shallow corner cut out (C4) on spiral segment E. Like the similarly situated contact point, the associated torque force generated is has less of a moment arm as compared to contact point 3 and is also in contact with a smooth wall with some return to center force vectors. There is also depicted contact point 6 which is also considered to present relatively higher torque generation as it is arranged in common with the rotation direction for the most part (but is not as far removed from the center point as point 3 due to the L1 and L2 length differential). With reference to contact point 7 on the left side of side wall 338B, there is considered to be again some force direction directed back toward the center point to help offset any differential developed and centrifugal forces by providing a degree of counteracting forces (in similar fashion to point 1, just to the opposite of the vertical). Hence, the description presented for contact points 1 to 6 is considered to be applicable to the bi-symmetry diametrically corresponding contact points 7 to 12 working on the left side of the vertical line shown in FIG. 120.

Figure 123:
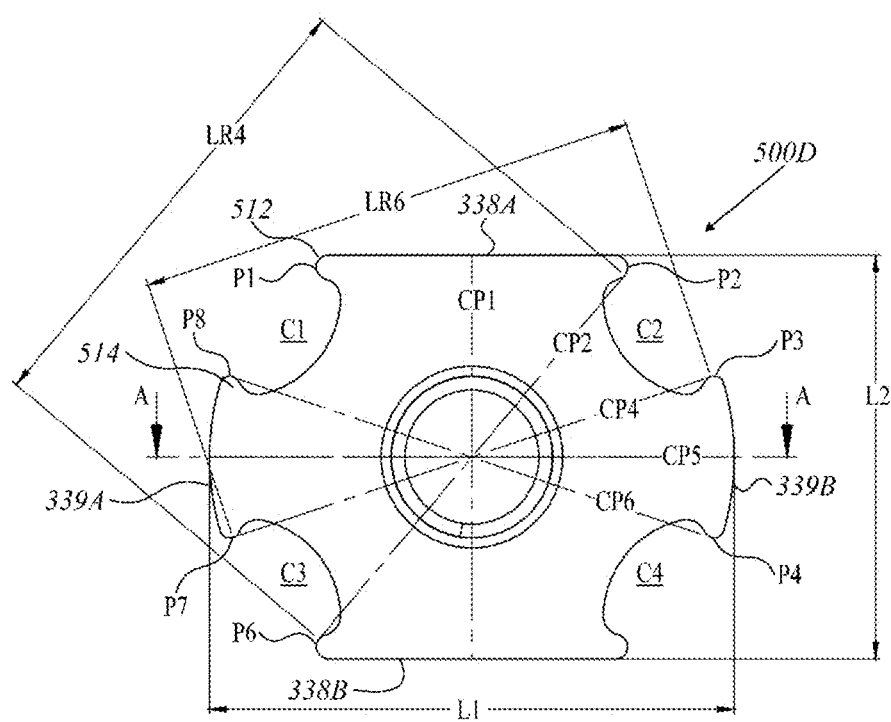
FIG. 123 shows a top plan view of the torque enhancer of FIG. 122.

FIGS. 122 to 126 show torque enhancer 500D which is also in a nut configuration as to feature central threads 508 as in the prior embodiment. An additional similarity between this enhancer 500D and the prior described enhancer 500C is that the relative shorter to longer length ratio RA is the same (for example, an L2 length of 20 mm and an L1 length of 26 mm as to provide a 76% value). A variation found in enhancer 500D lies in the shape of the corner notch regions C1 to C4. That is, corner notch regions C1 to C4 in FIG. 123 shows a "c-shaped" concavity which results in a bowing back inward of the outer extremities as to form ridge extension such as ridge 512 at end point P1 of long side 338A, and ridge 514 at end point P8 of short side 339A relative to corner cut out C1. These ridge lines with bowed in corner notch regions adjust the potential torque force contact location, with examples being found in the length designations LR4 and LR6, with LR4 representing the length of compass point diameter CP2 running between points P2 (right end of long side 338A) and P6 (left end of long side 338B) as in the earlier embodiment; and LR6 representing the length of compass point diameter CP4 running between points P3 (top of short side 339B) and P7 (bottom of short side 339A); and with CP6 being the above/below symmetrical equivalent of CP4 across cross-section line A-A or CP5 with respect to the first of the two bi-symmetry halves (the other being represented by the two opposite sides of the bow-shaped area formed by CP4 and CP6 about center point CN and to opposite sides of the left/right bi-section line CP1 representing the dividing line of the other bi-symmetry halves).

As seen by the contact points represented by, for example, P2 and P6 of CP2, the bowing in of the concavities such as C2 and C3 and respective contact point ridges leads to a relative lesser length since the contact points are drawn radially in from the outer extremity at the linear end of, for example, long side 338A (e.g., even with common L1 and L2 values between enhancers 500C and 500D, the CP2 length drops from 23.64 mm to 23.55 mm, and the CP4 length drops from 25.78 mm to 24.98 mm Thus, the concavity configuration provides further structural configuration sources for providing the longer/shorter relationship without too much differentiation in that long/short relationship to take advantage of the increased torque moment without too much deviations in the relative bi-symmetry.

As an additional "larger bolt" example for the embodiment featured in FIG. 122 (and also showing the general common relationship scaling up of the above described "smaller" bolt non-limiting illustrative dimensions), there is shown LR4 and LR6 of about 68 mm and 72 mm, respectively, (which is also representative of slightly different moment arms with respect to the below described contact points on the different length projections (e.g., 339A versus 338A)). Also, for this embodiment L2 and L1 are about 57 mm and 75 mm as to represent the same L2/L1 ratio of 57/75 or 76%.

Furthermore, while torque enhancer 500D is shown as having a threaded nut configuration, the exterior surface having the noted side walls and cut-outs can represent a variety of torque enhancement products as in drivers, shaft collars, reception collars (e.g., having interior and exterior surfaces with the same general configuration). This versatile product concept is also applicable to other embodiments described above and below when non-conflicting.

Figure 124:
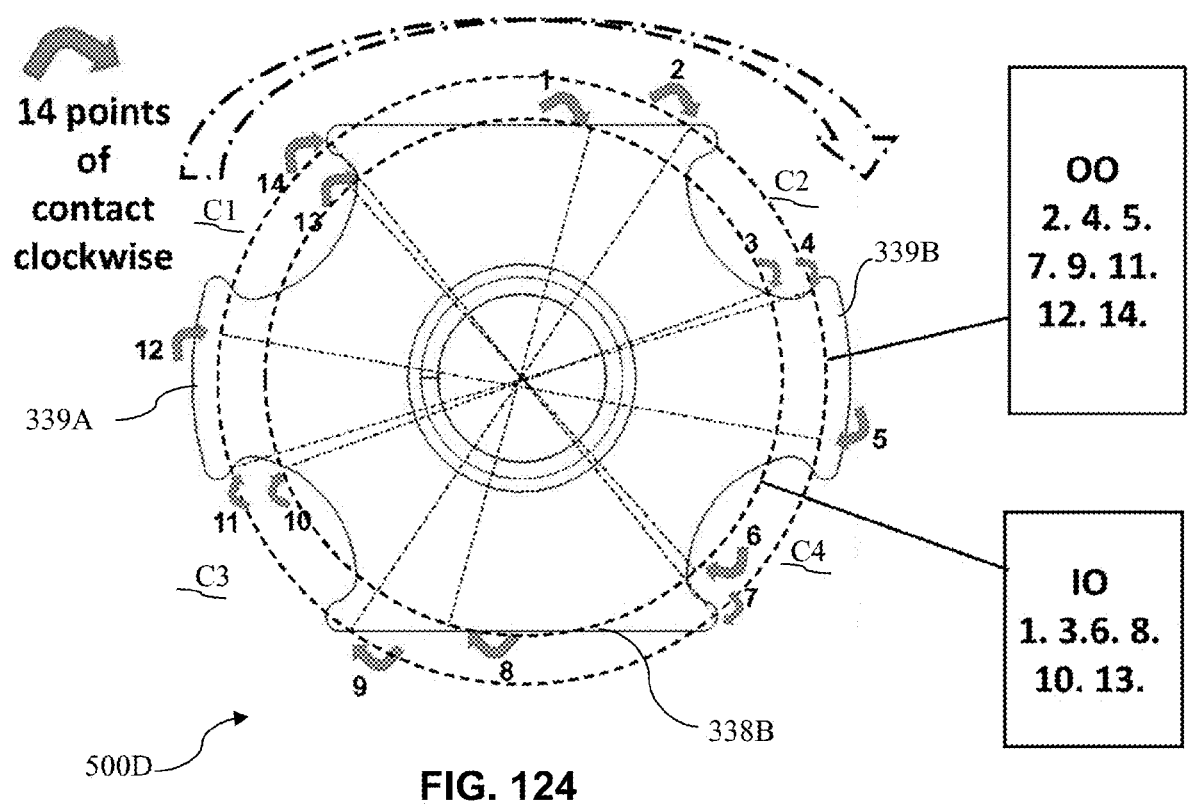
FIG. 124 shows a similar top plan view as that shown in FIG. 122, but with a considered "mechanical" contact point presentation.
Figure 125:
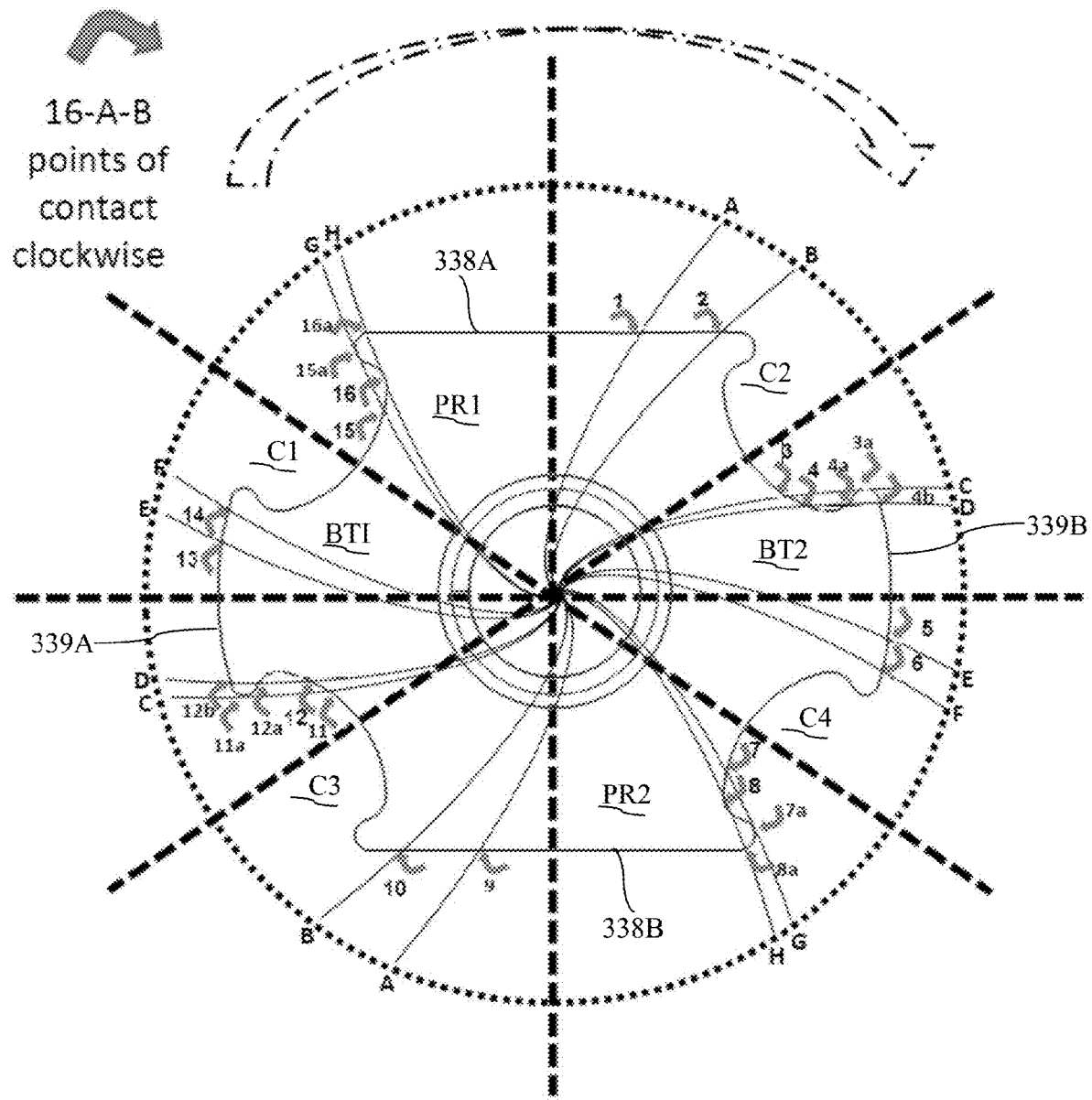
FIG. 125 also shows a top plan view of the torque enhancer of FIG. 122, but with a considered "spiral-centrifugal" contact point presentation.

FIGS. 124 and 125 provide a mechanical and spiral-centrifugal overlay for torque enhancer 500D, with the former shown as having 14 contact points. That is, while having relatively shallow corner cut-outs C1 to C4, there is also provided the aforementioned corner cut out inwardly directed projection points that can be seen to be directly contacted as by contact points 7 and 14. The contact points 7 and 14 are shown as falling on an outer orbital OO as well as the contact points such as 2 and 5 following on or outward of outer orbital OO. On the other hand there is featured an interior orbit IO occupied by points in the interior of the corner cut-outs (e.g., point 3) as well as points falling more in the middle region of the side walls 338A and 338B (e.g., points 1 and 8). Thus, FIG. 124 shows a total of 14 contact points in clockwise rotation by a torque tool sharing a common configuration (slightly larger (e.g., 0.5 mm or less)

in peripheral configuration as to allow for slide retention over the conforming configuration of the torque enhancer with the points following on both the inner orbit IO and outer orbit OO.

A review of the relative contact points falling on the inner and outer orbits reveals those falling on the outer orbit and hitting surfaces confronting the direction of rotation (e.g., the projection in the C-shaped corner cut outs represent points in the way of the tool in the intended direction of rotation) are more torque generating than outer orbital counterparts such as contact point 5 presenting a surface in a less obstructive orientation and having more of a degree of return to center characteristic. The interior orbit points are also inclusive of torque generation, but with also a force vector component back to center as in the above described contact point 1. Again, this different torque force presentation in the contact points is considered to help in stabilizing the potential for destabilization normally present when different length projections are involved about a common center.

With reference to FIG. 125 there is shown a presentation of potential contact points relative to the "spiral-centrifugal" mode for the torque enhancer shown in FIG. 122. Again, while not being bound by any theories, it is Applicant's belief that the geometry of the present invention provides the beneficial force interrelationships described above, herein and below, with reference to the generated force contact points presentations being utilized to help illustrate these concepts. As in the above, in light of the additional forces that would be generated in a rotating nut, there is utilized curved (spiral segments) to help illustrate what is considered to be the potential contact points on the nut as it is being spun as described. That is, FIG. 122 depicts spiral segments A to H for each bi-symmetric side opposite the vertical bifurcation line shown relative to the 26 point contact presentation for this mode (shown with rotation in the clockwise direction). Further shown in FIG. 125 is the one or multiple contact points per respective spiral segment, with the below description directed at the force developments thereat.

For example, contact points 1 and 2 are found on spiral segments A and B, and are shown on the intermediate and far right side end regions of surface 338A with a contact force out and down on that surface; contact point 3 and 3a are found on spiral segment C both deep within the clockwise side of corner cut out C2 and at the inward edge of the upper inward projection at the top of the C-shaped corner cut out (thus contact point 3a presents a strong torque generation as it is in the general direction of rotation and far out on the longer projection 339B). Contact points 4 and 4a are both found on segment D and within the side wall of the corner cut out C2 as that cut-out has a generally shallow rise and then a sharp turn in. On that same spiral segment D, there is found contact point 4b representing a centrifugal dampening contact point as it has a relatively large force back toward the center point of the inner body. Similarly, contact points 5 and 6 provide a combination of rotation torque assistance with some degree of centrifugal dampening and are found on spiral segments E and F. For the shorter projection there is shown contact point sets 7, 7a and 8, 8a with 7 deepest in corner cut out C4 and 7a hitting the inward return projection defining the corner cut-out. Points 8 and 8a fall to opposite radial sides of 7a in the curved region just below the returning projection and on the exterior surface 339B (again the relative difference in length between the projections such as BT2 and PR2 shown result in the 3 versus 2 contact points for a similarly situated spiral segment relative to the return corner projection for the cut-outs, and contact point 8a is representative of another partial force back toward center dampening orientation). Again, in view of the bi-symmetrical nature, a corresponding set of contact points are shown to the left of the vertical line in FIG. 125.

Figure 129:
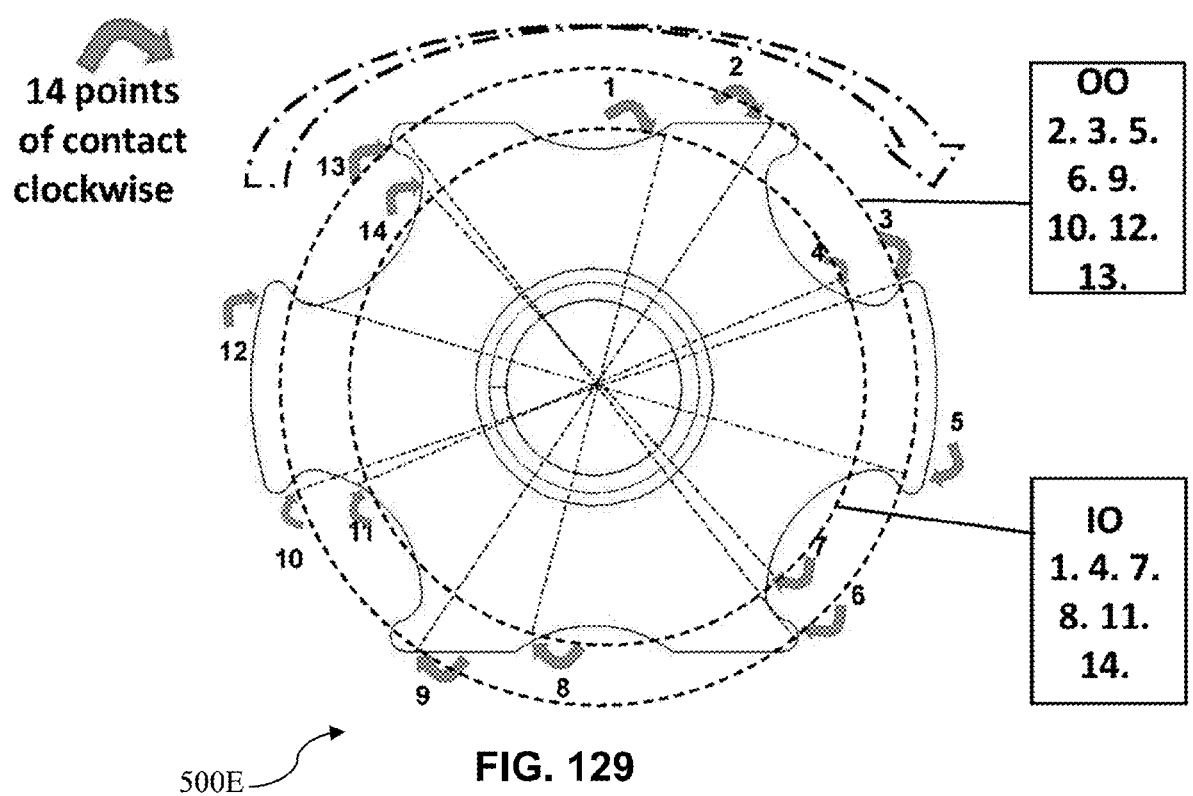
FIG. 129 shows a similar top plan view as that shown in FIG. 127, but with a considered "mechanical" contact point presentation.
Figure 130:
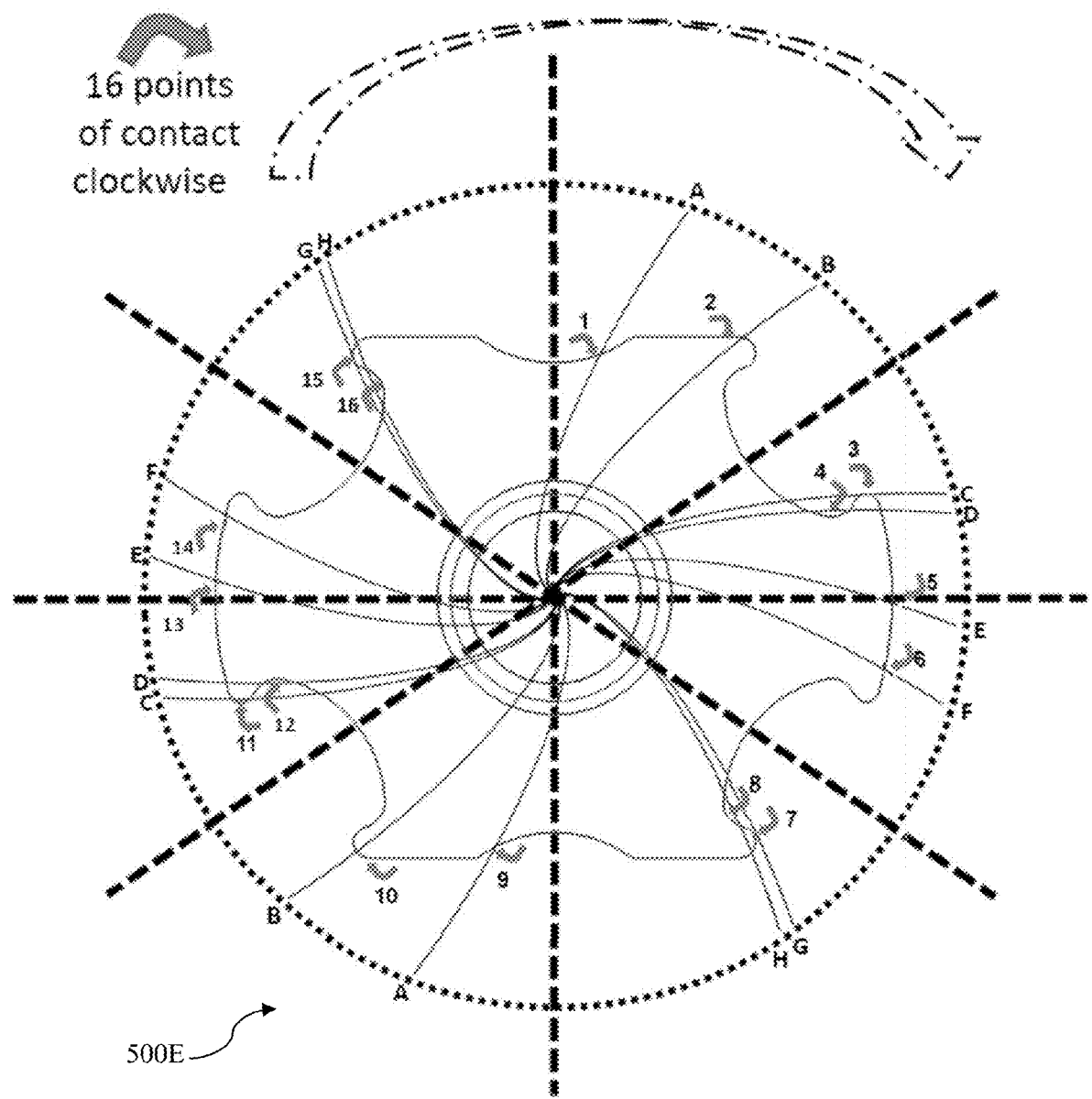
FIG. 130 also shows a top plan view of the torque enhancer of FIG. 127, but with a considered "spiral-centrifugal" contact point presentation.
Figure 131:
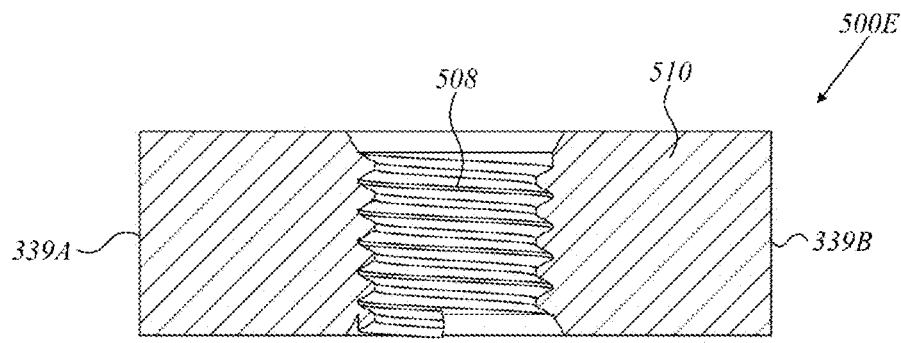

With reference to FIGS. 127 to 131 there is shown torque enhancer 500E which is also in a nut (e.g., bolt nut) or gear configuration as to feature central hole 508 (threaded in this embodiment as shown in FIG. 131). An additional similarity between this enhancer 500E and the prior described enhancer 500D is that the shorter to longer length ratio RA is the same at 76% (for example, an L2 length of 20 mm and an L1 length of 26 mm or an L2 of 57 mm and an L1 of 75 mm for a larger version thereof). Like enhancer 500D, enhancer 500E also has the c-shaped or bowed corner notch regions C1 to C4. One differentiating feature between the similar enhancers 500D and 500E is that enhancer 500E features a non-continuous, notched side wall configuration in each of its long side walls 338A and 338B. In this embodiment each of the long side walls 338A and 338B features a crescent shaped cavity and which concavities 512A and 512B are centered at the 0 degree and 180 degree compass points and form about 30 to 40% of the overall Y-axis length of the long sides 338A and 338B, and are relatively shallow as compared to the depth of the corner cut-outs (based on the different projection lengths since both the shallow concavity in sides 338A and 338B and the corner cut-outs have a maximum depth falling on the illustrated inner circle reference IC in FIG. 128).

Figure 128:
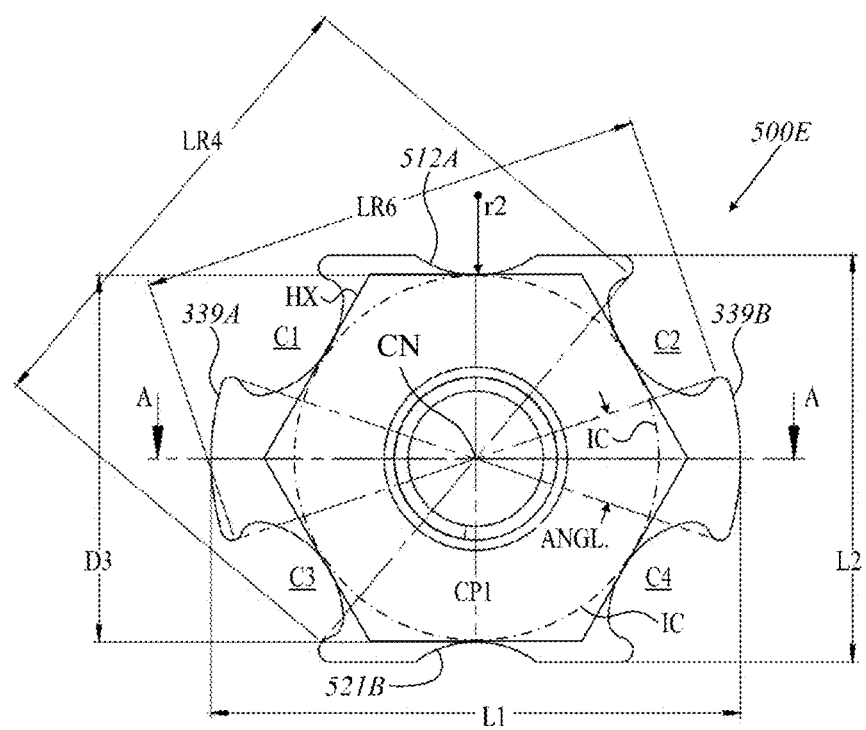
FIG. 128 shows a top plan view of the torque enhancer of FIG. 127.

That is, to further appreciate some of the differences in enhancer 500E, there is added interior circle IC and hexagonal reference frame HX, with each centered about center axis CN. As seen, despite the difference in relative length between the center points PM1 and PM2 of the two short sides 339A and 339B, and the spacing of the parallel linear lines that run on the respective linear long length sides (side walls) 338A and 338B, the referenced interior circle makes contact with each of the radially minimum contact points in each of the corner notch regions C1 to C4 as well as the radially interior most portion, or deepest portion, of concavities 512A and 512B. In addition the shapes of the added concavities 512A and 512B are the same, such that in this embodiment there is no disruption relative to either of the two bi-symmetry halves of torque enhancer 500E. The hexagonal shaped frame of reference HX further illustrates how the deepest (radially inwardmost) portions of each of corner notch sections C1 to C4 and also concavities 512A and 512B fall on tangent lines representing the hexagonal sides. As seen by the relationship between the hexagonal shaped frame of reference HX and the various concavities and corner notch sections, they generally have their deepest point falling on a central or highly intermediate location of the respective linear segments of the hexagonal frame of reference HX. In FIG. 128 the diameter of interior reference circle IC is represented as D3 which is also the distance between the central, deepest regions of concavities 512A and 512B (as well as the distance between opposing sides of the hexagonal reference HX). Accordingly, the length L2 (between the parallel, linear long sides 338A and 338B) minus D3=2DP, with DP representing the depth of each concavity amongst 512A and 512B. Suitable (and non-limiting as exemplary only) values for the arrangement shown in FIG. 128 has D3 at 18.02 mm and L2 at 20 mm and L1 at 26 mm (so there is a common RA value of 0.76). The depth value is thus 20-18.02/2=DP or about 1 mm. For a non-limiting additional example of a larger bolt size dimension, there can be values of L1 of 75 mm and L2 at about 57 mm (for a common 76% ratio) example, with a suitable diameter for circle IC being 52 mm and a value of LR4 of 67.5 mm. As with the other embodiments a suitable range for threaded hole 508 is 6 to 40 mm (e.g., a range well associated with some standard threaded bolt dimensions as well as for non-threaded versions of hole 508).

The added crescent shaped concavities 512A and 512B thus each present a surface with an intermediate maximum depression point and rising curved side surface sections. These side sections provide for additional torque contact force potential depending on the force applier. In this way, there is an added contact surface section to the left of the concavity 512A and right of concavity 512B in FIG. 128 when rotating counter-clockwise and the opposite arrangement when rotating in a clockwise, direction. Also, with the inclusion of one additional concavity on each long surface there is provided the additional contact points strategically as the long sections provide the greatest potential for added concavities without degrading performance, although in alternate embodiments added concavities can be provided in the short side walls (although preferably in conjunction with added concavities in the long sides inclusive of multiple concavities on each long wall surface).

As noted, the inclusion of the notched regions or concavities 512A and 512B in the respective sides 338A and 338B provide added potential contact points which are described below in reference to both the mechanical contact point presentation of FIG. 129 and the spiral-centrifugal contact point presentation in FIG. 130.

With reference to FIG. 129 there is shown an inner orbital IO and an outer orbital OO for contact point illustration. Based on the above discussion describing the beneficial geometry and applicable contact point orientations for the prior embodiments, a detailed explanation is not provided for all points. As in the earlier embodiment, contact points such as contact point 3 on the outer orbit provide a high torque generation point in view of the location on the longer projection BT2, while points such as point 5, while falling far out (radial out past the outer orbit), have a contact location on the surface 339B that generates some added torque rotation force, but also a degree of force back toward the center point in the above noted damping and stabilizing fashion. There is also seen that the newly featured side wall cavities 512A and 512B provide inner orbit contact points that are generally intermediate in force presentation as the forces are generally split as to help with the nut tightening (or loosening) while also providing a degree of inward stabilization (although that stabilization is to a lesser degree to that of points such as contact point 5 working on a downwardly sloping surface relative to the direction of rotation and point 1 is working on an upward (obstructing) sloped presentation wall of notch 512A).

The spiral segment contact point configuration shown in FIG. 130 shares some similarities with earlier described spiral-centrifugal presentation, and thus only contact point differences brought about due to the different configuration (e.g., the noted concavities or notches 512A and 512B) is discussed below. That is, the inclusion of notches 512A and 512B add two contact points (1 and 9 shown on common labeled spiral segments A) which fall on opposite sides of the vertical bifurcation line. As noted above, these added contact points are intermediate in force generation due to their positioning within the driven side wall of the tool receiving notch (e.g., the contact 1 torque generation forces fall below the torque generation potential found in the contact points that are radially outward and better aligned with the rotation direction circle as represented by contact point 3 for example).

With reference to FIGS. 132 to 136 there is shown an additional embodiment of a torque enhancement member or torque enhancer 500F that is shown in a nut configuration with central threads 508 (shown in the cross-sectional view of FIG. 136) as in the prior embodiments. FIG. 132 also illustrates straight side walls for this embodiment (see the discussion above about potential different contouring and/or angles and/or side wall recessing which is also applicable here). An additional similarity between this enhancer 500F and some of the prior embodiments is that the shorter to longer length ratio RA is the same (for example, an L2 length of 20 mm and an L1 length of 26 mm with a RA % of 76%; or as another "larger" version with an L2/L1 ratio of 57 mm/75 mm or 76%).

A further variation found in enhancer 500F lies in the shape of the corner notch regions C1 to C4. That is, corner notch regions C1 to C4 in FIG. 133 feature a linear base 516 from whose opposite ends there extend corner notch side surfaces 518 and 520. Accordingly, in this embodiment the deepest portion of the corner notch regions features a linear section leading into curved corner regions and then into the straight side walls (rather than an entirely curved deepest recession surface for the corner cut out as in prior embodiments). Also, a further variation can be seen in that the long sides (338A and 338B) each feature a linear floored notch region in notches 522A and 522B, respectively. Each of side wall notches 522A and 522B are centrally positioned relative to reference line/diameter CP1 and feature a depth less than the depth of the corner cut-outs (although again the geometry of enhancer 500F places the floor of the notches and the corner cut outs all on the common reference circle CI as well as in contact with the linear sides of the reference hexagonal HE). Further as shown each depression or notch 522A and 522B includes a linear trough 524 with curved, concave corners expanding outward to the adjacent straight edge section pairs. The depth of each notch 522A and 522B is the same in this embodiment (as to achieve the preferred bi-symmetry).

Figure 133:
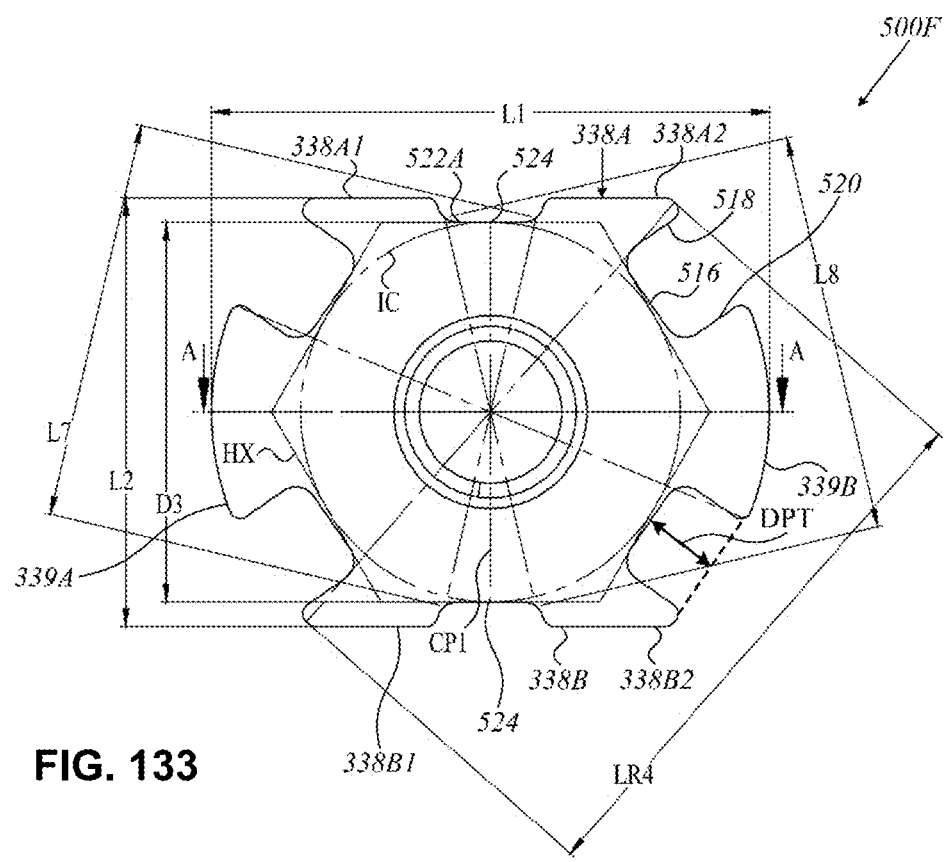

As noted and as seen from FIG. 133, a 360° rotation of CP1 scribes a circle IC that hits the center of each base surface 516 as well as the center point of each of the side walls of the reference hexagonal depiction HX (having a corner point falling within each of the two straight edge sections broken up by depressions DT (338A1; 338A2; 338B1 and 338B2) as well as the two bow-tie extensions extending radially out from circle CI for a distance of [(L1–CP1)/2]). The relative linear distances for each of sections 338A1/522A/338A2 (the 338A "set") along the straight edge co-linear with edge 338A1 is about (25 to 40%)/(20 to 50%)/(25 to 40%), respectively, with 338A1 and 338A2 sections preferably being of a common length. In view of the bi-symmetrical relationship to opposite sides of CP1 (left to right in the figure) in FIG. 133; and cross-section line A-A in FIG. 133 (above/below in the figure), the relationships described above for the 338A set is equally applicable to the 338B set. For example, in a larger nut version, there is featured a length along the Y-axis for side 338A of 40 mm and a centralized notch of 15 mm leaving 12.5 mm to each side.

Figure 134:
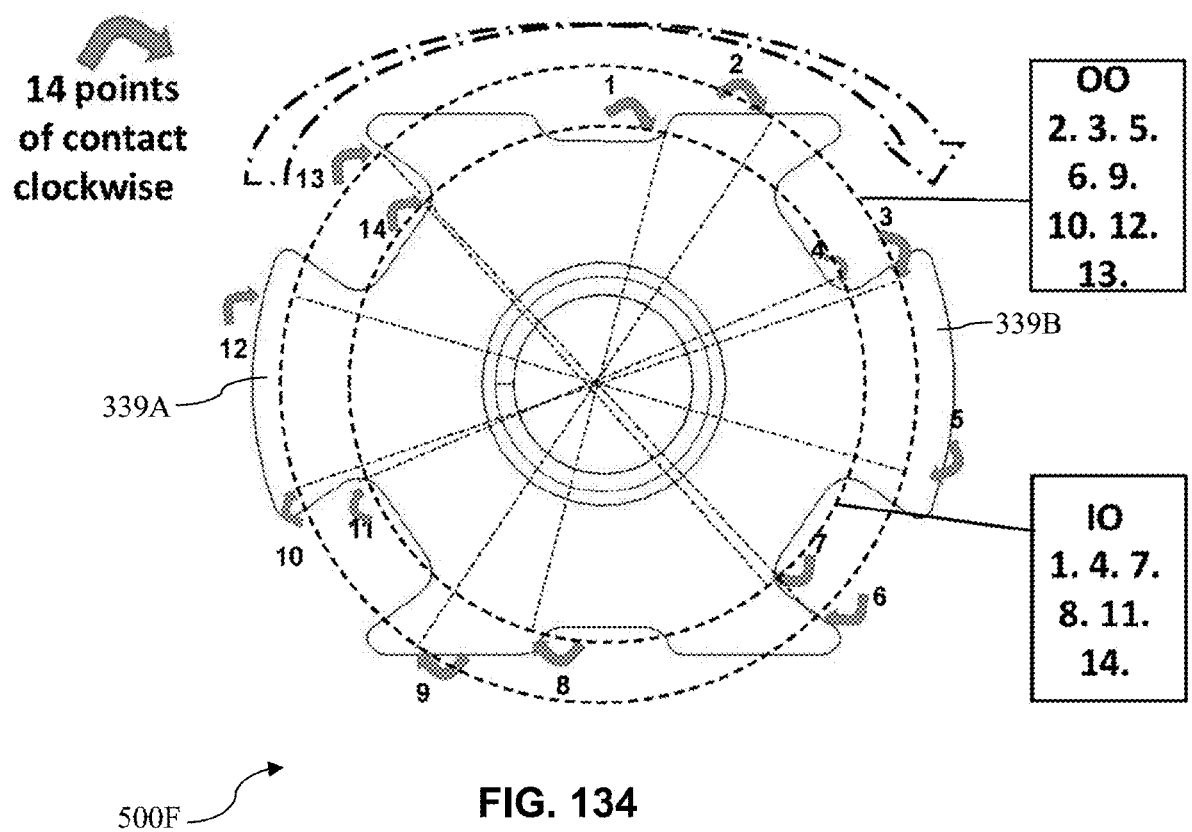

FIG. 134 illustrates the 14 total point mechanical contact point overlay which includes contact points lying on the illustrated inner orbit IO and outer orbit OO. Reference is made to the earlier discussion as to the nature of the various contact points including those pertaining to the added central notches on the side walls 338A and 338B (shown as contact points 1 and 8 of the total 14 contact points in the set shown in FIG. 134). A difference in contact point configuration as compared to that of torque enhancer 500E can be seen in the contact points positioning at the base of the corner cut-outs C1 to C3 which are deeper due to the relative depth of the corner cut outs between enhancers 500E and 500F and also the contact points such as 4 are directed at a smaller radius curvature (i.e., the difference between a tight corner between two linear sides (enhancer 500F) and a smooth contoured wall (enhancer 500E). This is considered to lead to a more focused force application in the direction of rotation at these corners as compared to a smoother curve due to the difference in obstruction configuration.

This difference in corner cut-out configuration is also represented in the spiral-centrifugal contact point presentation in FIG. 135 showing 20 spiral segments having one or more contact points. Again reference is made to the earlier described spiral-centrifugal contact point presentations for the other embodiments for an appreciation of what is shown in FIG. 135. One difference presented in FIG. 135 is in the contact points associated with the linear base wall and linear side wall (in the direction of rotation side wall) wherein the contact point such as 5 is hitting in more of a transverse fashion than an embodiment where the wall has a curved side wall as to provide a stronger torque force. The contact point 4 is shown on the other hand as hitting the base of the corner cut out and thus has a more inward toward the center and less transversely oriented force (as to provide both a force enhancer and a stabilizing component in combination). Also, like in the last embodiment the notches add to the contact potential in the correspondingly torque enhancement configured driving tool.

FIGS. 137 to 141 show torque enhancer 500G which is also in a nut configuration with central threads 508 as in the prior embodiments and has threading as shown in cross-section FIG. 141. A similarity between this enhancer 500G and prior embodiments is that the relative shorter to longer length ratio RA is the same (for example, an L2 length of 20 mm and an L1 length of 26 mm with a RA % of 76%; or relative to a larger nut embodiment 57 mm/75 mm or 76%).

A variation found in enhancer 500G lies in the shape of the corner notch regions C1 to C4. That is, corner notch regions C1 to C4 in FIG. 138 feature a central bulbous base extension 528, and, to each side thereof, corner edge depressions 530A and 530B that are concave in configuration and each of a common size and shape. As is true for the above and below configurations, the shape of the corner cut-outs has an impact on the location of a torque driver's points of contact.

The bulbous extension thus, while representing a depression relative to the reference frame rectangular RE (shown in FIG. 113, but not shown here for convenience) has a center point with a minimal depth as compared to the deeper and adjacent corner edge depressions 530A and 530B. Accordingly, in this embodiment the deepest portion of the corner notch regions is at the most interior points of the depressions 530A and 530B. Also, in this embodiment, the depth 532 to the tip of the convex extension in the corner cut out is less than the depth Dp1 to the bottom of the 338B (and 338A) side wall notch 540. The notch 540 can be seen as having similar corner concave depressions as found in the corner cut outs; but, rather than the central area being convex relative to the two adjacent side concavities, it is concave as to extend even deeper (Dp1) into the interior body of the torque enhancer.

Thus, long sides (338A and 338B) each feature a depression 538A and 538B, respectively. Each of depressions 538A and 538B is centrally positioned relative to reference line/diameter CP1. Further, each depression 538A and 538B includes a central concave trough 540A, with adjacent side troughs 540B and 540C which are also concave. Central trough 540A is shown as having radius $r_c$, with side troughs 540B and 540C having radius $r_o$ (e.g., in the example shown $r_c > r_o$).

FIG. 138 further shows that the troughs or notches 538A and 538B each have a Y-axis linear length (represented by the combination of central trough 540A and side troughs 540B and 540C) with trough 540A centrally positioned between the solid side edges (e.g. 338B1 and 338B2) to the left and right of the trough (e.g., 538B)) along the long sides 338A and 338B. The relative linear distances for each of sections 338B1/538B/338B2 (the 338B "set") along the Y-axis extending straight edge co-linear with edge 338B1 is set up so that 538> than either of 338B1 and 338B2, but < than the sum of (338B1 and 338B2), with the 338B1 and 338B2 sections preferably being of a common length in view of the bi-symmetrical relationship to opposite sides of CP1 (left to right in the figure) in FIG. 138; and above and below cross-section line A-A in FIG. 138, the relationships described above for the 338B set is equally applicable to the 338A set.

FIG. 138 also shows the relative lengths (in addition to the LR1 and LR2 lengths described above) LR4, which as in the prior embodiments shows opposing contact points at the upper ends of the respective corner cut-out side walls. Length LR9 shows the distance between opposing contact points relative to opposing corner edge depressions 530A and 530B. This length LR9 is shown as being less than side length L2 in this embodiment (e.g., LR9 at 19.33 mm and LR2 at 20 mm). Also, LR8 is longer than LR4 with the illustrated embodiment being LR4=23.55 mm and LR8=24.98 mm. As an additional non-limiting example (but informative relative to geometrical relationships) for a larger nut size there is (in mm): L1=57.5; L2=75; LR4=67.5; LR9=55.5; LR8=72; LR10=62 and with associated corner cut out depths of 4.5 mm and 7.0 mm for depths 532 and 534, respectively.

As noted, the inclusion of the notched regions or concavities 512A and 512B in the respective sides 338A and 338B provided added potential contact points which are described below in reference to both the mechanical contact point presentation of FIG. 139 and the spiral-centrifugal contact point presentation in FIG. 140.

With reference to FIG. 139 there is shown an inner orbital IO, an intermediate orbit MO and an outer orbital OO for the relatively high 28 contact point illustration in enhancer 500G. Based on the above discussion describing the beneficial geometry and applicable contact point orientations for the prior embodiments, a detailed explanation is not provided for all points. It is noted that the different level concavities in the side wall notches 538A and 538B contribute to the higher contact number (with the relatively deep depth of the side wall notches 538A and 538B also contributing in that the contact points on the curved concave deep bases for notches 540A and 540B represent additional contact points on their own inner orbital). As in the earlier embodiment, contact points such as contact point 7 on the outer orbit provide a high torque generation point in view of the location on the longer projection BT2, while points such as point 9, while falling far out (radial out past the outer orbit), have a contact location on the surface 339B that generates some added torque rotation force, but also a degree of force back toward the center point in the above noted damping and stabilizing fashion. There is also seen that the newly featured side wall cavities 538A and 538B in addition to providing the noted deep depth inner orbit contact points 1 and 15 also present middle orbit contact points on the concave regions 540B adjacent the deep central concavity 540A. In addition the added convex projection 528 in the corner cut outs present an added obstacle and the adjacent cavities such as cavity 530B also present a region for added contact point contact. As seen by these newly added contact points brought about by the different geometries in the notches an corner cut outs there is both added different levels of torque force enhancement and correspondingly different levels of stabilizing force contact points.

FIG. 140 illustrates a 24 spiral-centrifugal segments with associated contact point(s) for the torque enhancer 500G shown. In view of the earlier explanations provided for the spiral-centrifugal contact points for other embodiments, a detailed explanation of the various relationships is not repeated. However, as seen the above described modifications made in the regions of the corner cut outs and notches on the Y-axis extending side walls results in some different contact point locations and orientations. For example, as seen from contact point 4 on spiral segment D, the bulbous convex rise in the corner cut-out presents an obstruction wall point (positioned to the left of the center point of the corner cut out) relative to the torque generation. As with enhancer 500F there is also provided a tight corner region where there is shown contact points such as contact point 6 hitting a corner region of depression 530B.

FIGS. 142 to 146 show torque enhancer 500H which is also in a nut configuration as to feature central threads 508 as shown in the cross-section view of FIG. 146. FIG. 142 also illustrates straight side walls (i.e., side walls extending perpendicular into the paper from the top surface shown in FIG. 143) for the embodiment shown (the discussion above about different contouring and/or angles and/or side wall recessing is also applicable here). An additional similarity between this enhancer 500H and the prior embodiments such as torque enhancer 500F is that the relative shorter to longer length ratio RA is the same (for example, an L2 length of 20 mm and an L1 length of 26 mm with a RA % of 76% or for a larger nut version about 57 (e.g., 57.5) mm/75 mm or 76%).

A comparison of torque enhancer 500H with the previously described torque enhancer 500F reveals some further similarities as in the nature of the corner cut-outs of depth DP1 and the previously described reference circle CI and reference hexagonal HX being similarly set up in this embodiment (e.g., scribed circle CI of diameter CP1 of length D3 extends into contact with the center of each trough bottom defining the cut-outs C1 to C4 and on a Y-axis direction line extending from the base of each below described non-centered notches). As with the prior torque enhancer 500F, enhancer 500H has corner notch regions C1 to C4 having a linear base 516 from whose opposite ends there extends corner notch side surfaces 518 and 520. Accordingly, in this embodiment the deepest portion of the corner notch regions features a linear region with end curve regions rather than an entirely curved deepest recession surface as in prior embodiments.

A variation between enhancer 500F and 500H can be seen in that, rather than one side wall notch or depression as shown in FIG. 500F, there are featured two side wall depressions 542A and 542B for long side 338A and side wall depressions 544A and 544b for long side 338B. Each of the sets of depressions 542 and 544 are the same configuration (again relative to the above described preferred bi-symmetrical relationship), and feature a matching shape (albeit smaller) than that of the corner sections in that they have linear bottoms (running parallel to the straight sides of 538A and 538B) and are provided on opposite sides of a central positioned projection 338A2 such that depression 542A falls between central projection 338A2 and projection 338A1 on the left side, and depression 542B falls between central projection 338A2 and projection 338A3 on the right side (the same being true relative to the bi-symmetric equivalent set of depressions 544A and 544B and the adjacent projections 338B1, 338B2 and 338B3).

In the embodiment shown in FIGS. 142 to 146 the long wall depressions, such as 542A, have a depth DPd less than the depth of the corner cut-outs (as represented by depth DPT shown in FIG. 143). Further as shown each depression such as depressions 542A and 544A are shaped the same and include a linear trough with curved, concave corners expanding outward to the adjacent straight edge section pairs. The depth of each depression is the same in this embodiment As further seen from FIG. 143, a 360° rotation of CP1 scribes a circle CI that hits the center of each of each base surface of the central projections 338A2 and 338B2 as well as the center point of each of corner cut-outs C1 to C4, As further shown in FIG. 143, there is a reference hexagonal depiction HX having a corner point falling within each of the two straight edge sections broken up by depressions (338A1; 542A; 338A2; 542B and 338A3) as well as the two bow-tie extensions 339A and 339B extending radially out from circle CI for a distance of [(L1−CP1)/2]. The relative linear distances for each of sections 338A1/542A/338A2/542B/338A3 (the 338A "set") along the straight edge collinear with edge 338A1 is preferably about (20 to 30%)/(10 to 15%)/(20 to 30%)/(10 to 15%)/(20 to 30%), respectively, with 338A1, 338A1 and 338A2 sections preferably being of a common length as well as 542A and 542B. As a non-limiting example, relative to a larger nut configuration, there is featured a side wall 338A length of 50 mm with each of 338A1, 338A1 and 338A2 being 12.33 mm and each of notches 542A and 542B being 6.5 mm). In view of the bi-symmetrical relationship to opposite sides of CP1 (left to right in the figure) in FIG. 143; and cross-section line A-A in FIG. 143 (above/below in the figure), the relationships described above for the 338A set is equally applicable to the 338B set.

FIG. 143 also shows that length L1 between the outermost points of the bow-tie shaped projections 339A and 339B (e.g., 26 mm, or 75 mm for a larger nut) is the same as length L11 extending between outer contact regions of oppositely exterior projections 338B1 and 338A3. Also line L12 is shown extending between the innermost corners of diametrically opposing cavities 544A and 542B, and is shown as being greater than CI diameter distance D3, but less than L2 (e.g., L12 at 18.39 mm with L2 at 20 mm). Also, relative to FIG. 146 the threaded screw nut of this embodiment is shown as having a common thickness as with the prior embodiments (although other nut thicknesses are featured under the present invention and lesser thicknesses are also contemplated for other uses of the present invention's torque enhancer as in non-threaded thinner washer embodiments having the torque enhancement peripheral edging shown).

FIG. 144 shows the 16 point mechanical contact point overlay for the torque enhancer of FIG. 142. Reference is made to the above discussion as to the geometrical configuration of the torque enhancer embodiments and contact point presentations based on that geometry. Torque enhancer thus has some similar contact point parameters with the above described embodiments. For example, as seen, the illustrated torque enhancer 500H, with its deep corner cut-outs C1 to C4, there is two orbital contact circles (IO and OO), and thus it has similar contact points as the above described deep corner cut out embodiment 500F. However, since torque enhancer 500H has the two pairs of notches on side walls 338A and 338B (as opposed to just a single notch for each side wall such as shown for 500F), there is further shown contact points based on side wall depressions 542A and 542B formed in long side edge 338A and side wall depressions 544A and 544*b* formed in long side 338B. The spaced apart notch contact points and the deep depth corner cut out contact points are all shown as falling only on the inner orbital IO. Thus, upon engagement with a conforming torque generating tool such as torque wrench 360 shown in FIG. 181 there is achieved a multi-point contact arrangement with a high torque capability (e.g., the 16 contact point arrangement—both clockwise and counterclockwise).

FIG. 145 shows the 20 spiral segment spiral-centrifugal contact point presentation for the torque enhancer 500H. In view of the earlier discussions concerning spiral-centrifugal contact parameters in the earlier embodiments, particularly that of similarly constructed torque enhancer 500F, an in-depth discussion for these contact points in not presented. However, the aforementioned difference of having two notches on each side wall 338A and 338B leads also to a different spiral-centrifugal contact presentment as seen by, for example, contact point pair 20 and 1 in the two notches in side wall 338A as well as contact point pair 10 and 11, which present an added torque development, particularly point 1 which is past center relative to clockwise rotation and its corresponding contact point 11 (also on spiral segment A) which is past center beyond the vertical bi-furcation line shown. The other notch contact points 10 and 20 on common spiral segment J, that are not past center relative to the illustrated rotation direction (noting the differentiation in projection length), are considered to provide a greater force back toward the center, and hence an added stabilization component to the projection size differentiated nut 500H.

FIGS. 147 to 151 show torque enhancer 500I which is also in a nut configuration with central threading 508 (shown in cross-section in FIG. 161), with FIG. 147 also illustrating straight side walls (i.e., side walls extending perpendicular into the paper from the top surface shown in FIG. 148) for the embodiment shown (the discussion above about different contouring and/or angles and/or side wall recessing is also applicable here). A difference between this enhancer 500I and the prior embodiments is that the relative shorter to longer length ratio RA is not the same as that in the earlier embodiments. The embodiment shown in FIGS. 147 to 151 feature a lesser length to width differential than the prior described embodiments, and thus a ratio that is greater than the earlier described 76% and more preferably a ratio greater than 80% and below 100% (with 100% representing a square or no length to width differential). For example, rather than the previously described L2 length of 20 mm and an L1 length of 26 mm with a RA % of 76%, a larger length to width percentage ratio is presented that exceeds 80%, as in one featuring a length L1 (the length between maximum outer ends of the bow tie projections 339A and 339B) of 26 mm, as in above, but a relatively longer distance for the length L2 of 21.3 so as to give the ratio of 21.3 mm/26.0 mm or 81%. As an additional non-limiting example for a larger sized bolt, L2 is 61 mm and L1 is 75 so as to provide the L2/L1 81% value. Accordingly, the FIG. FIG. 147 embodiment depicts an enhancer that more closely approaches a square presentation (in overall length to width ratio) as compared to, for example, enhancer 500H, but still includes some longer length to shorter side attributes as to provide the above noted increased potential torque contact length component, but to a lesser extent with associated attributes as in greater torsion stability, etc.

A comparison of torque enhancer 500I with the previously described torque enhancer 500B reveals a return to having generally semi-cylindrical corner cut-outs, although variations are also possible inclusive of switching one corner cut-out design with another and/or switching out one side wall notch arrangement with another (true throughout the examples).

Enhancer 500I also has straight wall regions 338A and 338B having similar characteristics as those described above, but having different "angled" catch indentations or notches as represented by angled catch regions 546A and 546B defining therebetween straight section portion 338A2, and to respective outer sides thereto, straight section portions 338A1 and 338A3. Due to the bi-symmetry corresponding angled catch indentations 548A and 548B are formed on the straight wall region 338B, together with corresponding straight wall sections 338B1, B2 and B3.

The acute angled catch indentations are shown as shallower than the corner cut outs (e.g., a depth that represents 10 to 40% of the depth of a corner cut-out). Enhancer 500I represents one embodiment illustrating indentations or notches having different sloped opposing walls for each indentation with the steeper or closer to vertical wall being that in the contact direction of torque (e.g., with reference to FIG. 148 there is seen that notch 546B on wall 338A and to the right side of the vertical line features a steeper wall surface on its right side as compared to the opposing left side wall notch 546A. The other notch 546A (which is also on wall 338A, but to the left side of the vertical line) is shown as having its less steep wall surface as being on the right side. The impact of such a differential in the present invention's bi-symmetric with different projection length configuration is described relative to the contact point description below. An illustrative notch acute angle is 60°, with preferred angles being 60°=/−10°.

Again with reference to FIG. 148 some illustrative relationships between the relative sides of the more closely approximating a square nut 500I includes the aforementioned side walls L1 and L2 defining an L2/L1 ratio of 81% in the illustrated embodiment, and also having an extended tip to tip length L11 (e.g., 24.95 mm) that is less than length L1 (e.g., 26 mm) and L11 (e.g., 25.74 mm), but more than lengths such as L15 (the minimal length between opposing bases of cut-out portions with C2 and C4 featured in FIG. 148) and L16 (the distance between opposing angle indentation bottoms, with the illustrated embodiment being 20.05 mm in distance for L11). For a larger nut embodiment there can be, for example, values (all in mm) of L1=75; L2=61.5; L11=72; L12=50; L13=29; L14=74; L15=38; L16=58; and notch width of 5.5 along Y-axis; a notch depth of 4 mm in X-axis direction; a notch angle ANG4 of 60°; a semi-cylindrical corner cut out depth of 10; a full corner cut out full depth of 15; a wing extension SW for corner cut out of 6.

With reference to FIG. 149 there is shown an inner orbital JO, an intermediate orbit MO and an outer orbital OO for the 20 point mechanical contact point illustration in enhancer 500I. Based on the above discussion describing the beneficial geometry and applicable contact point orientations for the prior embodiments, a detailed explanation is not provided for all points. It is noted that the different level concavities in the side wall notches 546A and 546B (and 548A and 548B) contribute to the higher contact number (with the relatively deep depth of the side wall corner cut-outs C1 to C4 also contributing in the development of three orbitals instead of two as in some earlier embodiments). As in the earlier embodiment, contact points such as contact point 4 on the outer orbit provide a high torque generation point in view of the location on the longer projection BT2, while points such as point 6, while falling far out (radial out past the outer orbit), have a contact location on the surface 339B that generates some added torque rotation force, but also a degree of force back toward the center point in the above noted damping and stabilizing fashion. There is also seen that the newly featured side wall cavities such as notches or cavities 548A and 548B present middle orbit contact points such as contact points 1 and 20 which thus provide an intermediary force generation together with some back to center stabilization. That is, as seen by these newly added contact points brought about by the different geometries in the notches and corner cut outs there is both added different levels of torque force enhancement and correspondingly different levels of stabilizing force contact points.

FIG. 150 shows a spiral-centrifugal contact point for torque enhancer 500I with an illustrated 18 spiral segments with point(s) of contact in the clockwise direction. In view of the earlier discussions concerning spiral-centrifugal contact parameters in the earlier embodiments, an in-depth discussion for these contact points in not presented. However, the aforementioned difference of having two acute angle notches on each side wall 338A and 338B leads also to a different spiral-centrifugal contact presentment as seen by, for example, contact point pair 18 and 1 in the two notches in side wall 338A, as well as contact point pair 9 and 10, which present an added torque development, particularly point 1 which is past center relative to clockwise rotation and its corresponding contact point 10 (also on a spiral segment A) which is past center beyond the vertical bifurcation line shown and are hitting the steeper side of the notches. The other notch contact points 9 and 18 on common spiral segment I, that are not past center relative to the illustrated rotation direction, provide a greater force back toward the center and hence an added stabilization component to the project size differentiated nut 500H (noting as well the differential in length of the projections supporting the notches). The different slopes in the walls also lead to a differentiation in contact, with the above noted more direct torque force relative to the direction of rotation achieved on the steeper confronting walls at contact points 1 and 10 as compared to the less steep walls which however are considered to provide a degree of stabilizing effect with the more centrally directed forces developed. It is noted that there is a recognition in the art that it is often more difficult to remove a bolt than to put it on originally (e.g., due to thread forces that develop due to environmental forces, thread degradation and/or rusting and other environment corrosion). There thus can be utilized an essentially bi-symmetric configuration with minor non-bi-symmetrical orientation revisions that are directed at providing a greater retraction force (e.g., changing the corner cut out design to increase reverse torque and/or changing the angles of corner cut outs so all angles favor retraction (threading-off) as opposed to threading-on: an example of such an enhanced removal force application is presented below in FIGS. 254A and 255A).

FIGS. 152 to 156 show torque enhancer 500J which is a similar embodiment as that described above for torque enhancer 500I (i.e., same dimensioning inclusive of an 81% L2/L1 ratio). The noted differences between enhancers 500I and 500J include the presence of notches on bow-tie projections BT1 and BT2 as well as a variation in the notch configuration (shallower depth for the side wall notches in side walls 338A and 338B as compared to those in 500I). The same notch design is featured in all 8 of the total notches shown in FIG. 153. Thus, torque enhancer 500J includes bow-tie projections 339A, 339B, each with the addition of two acute angle indentations in the bow-tie projections (see bow-tie projection notches 550A, 552A and 549B, 551B). The shape of the 8 illustrated acute angle notches is the same as is preferably the size. The size is also preferably smaller than that featured in enhancer 500I which is in part facilitated by the increased number of indentations overall as compared to enhancer 500I. As an illustration of such the somewhat smaller configuration for the acute angle side wall notches featured in enhancer 500J (again not meant to be limiting to a particular size but helpful in better understanding, for example, relative geometrical relationships) there is provided sizes for a larger nut version. These sizes include a Y-axis length opening of 4 mm for each notch, a maximum depth of 4.5 mm, and a less acute angle of 64° as compared to the aforementioned 60° in enhancer 500I.

Accordingly, with the addition of two pairs of indentation angles on the exposed surface of the bow-tie projections 339A and 339B there is provided additional torque generating contact points relative to a torque generating tool. For example, for this embodiment and the earlier described threaded nut embodiments, there is preferably provided a corresponding tool (e.g., a wrench) having either an opened grasping wrench end component or a closed cavity wrench end component that has a surface configuration that conforms with the exterior surface of the torque enhancer threaded nut. The wrench end with conforming grasping surface is preferably designed with little play between the exterior surface of the threaded nut and the intended interior surface of the grasping component of the wrench end. A few examples of such wrenches or torque generating tools for use with the nut embodiments described herein are provided below.

A comparison between, for example, the nut in enhancer 500J and that 500C also shows different interior thread diameters (respectively, small diameter interior threading and relatively larger interior threading). The torque enhancing nuts of the present invention can have formed therein a variety of interior thread dimensions (e.g., ranging from very small to very large in conformance with the overall nut dimensions) depending on intended use. As it is the torque surface configuration of primary interest in the present invention, and threads of a variety of sizes are suited for use in the present invention, further detail is not provided as to the thread types, sizes, etc. suited for use under the present invention (other than the aforementioned typical range of diameter for nut threading of, for example, 6 to 40 mm).

With reference to FIG. 154 there is shown an inner orbital JO, an intermediate orbit MO and an outer orbital OO for the 22 mechanical contact point illustration in enhancer 500I. Based on the above discussion describing the beneficial geometry and applicable contact point orientations for the prior embodiments, particularly that of the similarly configured enhancer 5501, a detailed explanation is not provided for all points. It is noted that the different level concavities in the side wall notches 546A and 546B (and 548A and 548B) contribute to the higher contact number (with the relatively deep depth of the side wall corner cut-outs C1 to C4 also contributing in the development of three orbitals instead of two as in some earlier embodiments). As in the earlier embodiment, contact points such as contact points 6 and 7, which actually fall within the bow tie notches, fall outside the outer orbit as to provide a high torque generation point from that standpoint, but because of the force focus in the bow-tie notches also considered to provide stabilization via to center force presentment. There is also seen that the newly featured side wall cavities such as notches or cavities such as 548A and 548B present middle orbit contact points such as contact points 1 and 22 while the notches on the bow tie have external to outer orbital contact. Thus these newly added contact points brought about by the different geometries in the notches are considered to present added different levels of torque force enhancement and correspondingly different levels of stabilizing force contact points.

FIG. 155 shows the 18 spiral segment spiral-centrifugal contact point presentation for enhancer 500J which is similar to that of enhancer 500I and thus only the differences therewith are emphasized. These differences are found in the contact points associated with the notches formed at the free ends of the bow tie projections which are presented as a few of the total contact points shown and include contact points 5, 6 of spiral segments E and F (and their opposite side counterparts 14 and 15). Contact points such as 6 and 15 provide a strong torque generation assistance as they are on the outer ends of the longer bow-tie projections and abut the steeper side walls of the respective notches in the illustrated clockwise direction while contact points 5 and 14 provide a more inward force stabilization on the less steep side wall of the respective notches.

FIGS. 157 to 161 show torque enhancer 500K which is also in a nut configuration as to feature central threads 508 as in the prior embodiments. A difference between this enhancer 500K and the prior embodiments is that the relative shorter to longer length ratio RA is not the same as that in the earlier embodiments. The embodiment shown in FIGS. 157 to 161 has a greater length to width differential than the prior described embodiments, and thus a ratio % that is lower than the earlier described 76% and 81% values. For example, rather than the previously described L2 length of 20 mm and an L1 length of 26 mm with a RA % of 76%, a smaller percentage length to width ratio is presented that falls below 76%, as in one featuring a length L1 (the length between maximum outer ends of the bow tie projections 339A and 339B) of (still) 26 mm as in above, but a relatively shorter distance for the length L2 of 17.02 so as to give the ratio of 17.02 mm/26.0 mm or 65%. Accordingly, the FIG. 157 embodiment depicts an enhancer that is more rectangular (narrower rectangle) in overall dimension as it moves farther away for a square presentation (in overall length to width ratio), and thus includes a longer length to shorter side attribute as to provide the above noted increased potential torque contact length component, but avoids moving too far into an over elongated rectangular overall configuration and such a configuration's associated attributes (as in less torsion stability, etc.). A further non-limiting example as to dimensions providing a 65% ratio in a larger nut include an L2=49 mm and an L1 of 76 mm (L2/L1=49/75=65%). Additional values for the "larger" nut noted immediately above includes (in mm) L11=62; L14=74; L15=52.5.

A comparison of torque enhancer 500K with the previously described torque enhancer 500J reveals some further differences as in the avoidance of cut outs or indentations in both the straight edges and the bow-tie projection exterior edges. Torque enhancer 500K is also shown with smoother contoured corner cut-out configuration for its cut-outs C1 to C4 nature of the corner cut-outs featuring in enhancer 500K shallower depth cut outs (e.g., with respect to the larger bolt dimensions noted above a maximum depth for the crescent shaped corner cut out of 5 mm).

FIG. 159 shows an 18 point mechanical contact point presentation for enhancer 500K. As seen, while the corner cut outs are relatively shallow, the long Y-axis length is shown as presenting 3 orbitals (IO, MO, OO). There is included the earlier featured high torque contact points as in point 5 hitting the upper surface of the bow-tie projection as its far end, as well as a pair of more inward contact points (points 3 and 4) in each corner cut-out at different height levels within those corner cut outs and thus different torque generation and stabilization tendencies. Additional points include a pair shown on each of the clockwise sides of the longer surface 338A and 338B, as well as a pair on the clockwise side of each bow-tie projection so as to present various degrees of centralized force parameters.

FIG. 160 shows a spiral-centrifugal contact point presentation for torque enhancer 500K. The illustrated 16 points of contact include locations and geometries that were generally described above and thus the focus is on some of the differences. For example, in view of the lower percentage RA of 65% for this embodiment, the overall configuration and the shallower corner cut-outs, there is presented a variation in the spiral-centrifugal contact point relationships. For example, the longer bow-tie projections brought about by the more rectangular 65% ratio means that there is a very large torque generation as at contact points 4. However, in recognition of the greater instability potential brought about when the ratio percentage goes smaller, the other contact points in the corner cut outs are more diffused (due to the shallow depth and large radius curvature) and thus have a greater central vector focus and are considered to provide a degree of centrifugal force generation control.

FIGS. 162 to 166 show torque enhancer 500L which is also in a nut configuration as to feature central threads 508 as in the prior embodiments and is also shown to have a different exterior configuration relative to the earlier described nuts, in that it has a conical upper surface 501T extending from its torque enhancement base 501B (with the base presenting the exterior configuration as seen by the bottom view depicted in FIG. 163). The shape of torque enhancer is thus similar to that earlier described for FIG. 3 of the present application. Further, as with the earlier described nut embodiments, enhancer 500L has a threaded interior 508 extending fully therethrough.

With reference to FIG. 162, there is further seen that, like the FIG. 3 counterpart, one of the longer side walls has a bowl shaped minor depression DP as to facilitate finger grasp in collusion with the combination of any one of the cut-outs C1 to C4 and the adjacent edge at the outer border region of that cut-out (e.g., see FIG. 49) and, as explained below, also plays a roll in compression deflection stabilization considering the different thicknesses presented in the different length projections PR1, PR2, BT1, BT2). Also, FIG. 163 shows that there is a different length/width ratio RA as presented in the earlier embodiments. That is, torque enhancer 500L features a closer to square relationship (RA of 90%) than the earlier described torque enhancer embodiments. For example, an illustrate ratio range of 50 to 95% (and more preferably 60 to 90%) is featured in the present invention, with the above described enhancer 500K with its 65% value approaching the lower end of the range, and the present 500L approaches the other end of the range with its 90% value. For high speed tooling as in high rpm air or hydraulic drivers the higher end of the range is preferable (e.g., 75% to 95% is preferred).

With reference to the bottom view in FIG. 163 there can be seen values L1 and L2 with one ratio example being L2=18 mm and L1=20 mm for a ratio L2/L1 value of 18/20 or 90%.

Also, FIG. 163 shows a central aperture 508, but unlike the earlier embodiments is not a through-hole but extends for a majority but not all the way through as depicted in cross-section FIG. 166 (as seen below alternate embodiments do feature both threaded and non-threaded through-holes in enhancer 500L).

An additional difference is seen in FIG. 163 in the Y-axis extending oblique (added short base straight wall outer segments SS1 and SS2) provided at opposite ends of the non-oblique, portion of straight side walls 338A, 338B. These added short straight wall segments SS1 and SS2 are optional as the side wall 338A and 338B can extend for the same Y-axis length along an entirely linear line for the same Y-axis length as provided by the illustrated SS1 and SS2 end additions.

The inclusion of the noted walls SS1 and SS2 does present a variation in both the mechanical and the spiral-centrifugal contact point presentments as illustrated in FIGS. 164 and 165. This differential is represented by contact points such as contact point 3 on spiral segment C (one of 18 spiral segment presentation) which is shown as having a larger return to center force direction as compared to the situation where the segment did not slope inward and down. There can also be seen such a higher percentage of return to center force contact point arrangements (e.g., the very shallow corner cut outs result is a higher percentage of return to center stabilizing forces than is found in the earlier embodiments with a) deeper or less smoothly curving cut outs, and/or b) a closer to square and thus less relative differential in the respective projections (as in PR2 and BT2). The enhancer 500L is considered to present a very stable embodiment, but one without the same torque generation potential provided by a lower RA % value as is provided in some of the other embodiments.

Some non-limiting dimensions provided to help appreciate some of the geometrical relationships include (for the L2/L1 smaller embodiment featuring lengths of L2=18 mm and L1=20 mm) are as follows (all in mm): L11=19.9; L11'=20; L15=16.97). A larger scaled up embodiment features (all in mm) L1=72; L2=65; L11=71.5; L11'=72; L15=61; LI=31; LL=48; LS=15 and the maximum depth of the corner cut-outs 4.5.

FIGS. 167 to 170 all are directed at embodiments of enhancer 500M and show an example of a high torque generation embodiment via its RA % being an intermediate value as in 76% and a series of very deep and non-sloping (non-curved) walls for the corner cut outs and the centered 338A and 338B side wall cavities 338CV. Thus, torque enhancer 500M, while representing a nut embodiment is also well suited for gear formation, with preferably an added support plate PLT due to the deep notches and thinner projection base areas (also influenced by hole 508—shown relatively large for the inner body size in this embodiment). FIG. 167 shows the familiar surfaces 338A, 338B and 339A, 339B and corner cut-outs C1 to C4. Additionally shown is side wall notches (each labeled 338CV) in FIG. 167. These notches are shown as being deeper than prior embodiments and also as having a stepped side wall arrangement. As also best seen from FIG. 168 the stepped side walls defining both the corner cut outs and the notches feature straight base walls, that have at opposite ends rounded corners that lead into straight radially extending side walls, which then open out into concave surfaces on opposing sides of the notches (and in similar fashion in the corner cut-outs).

Figure 167B:
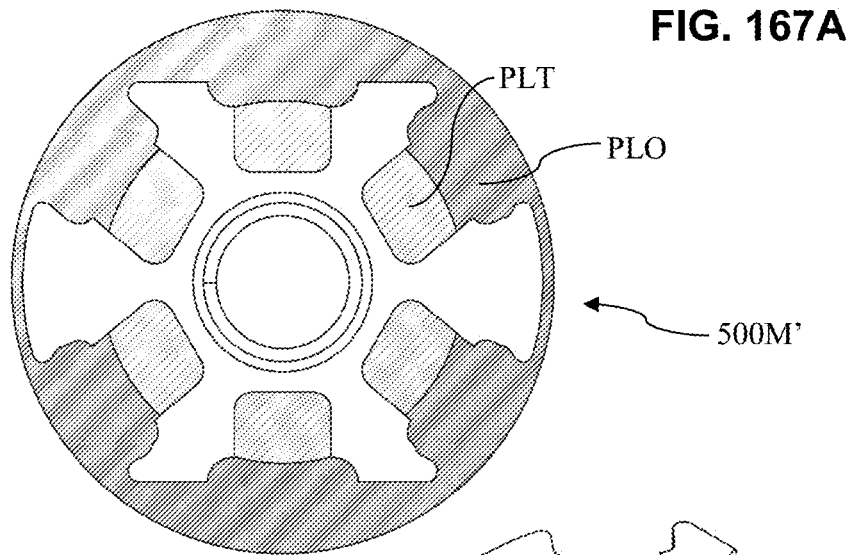
Figure 167C:
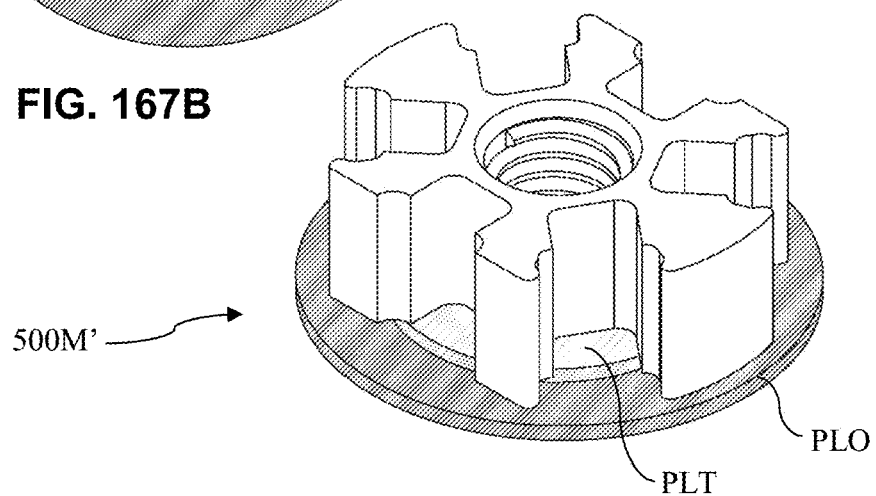
Figure 167D:
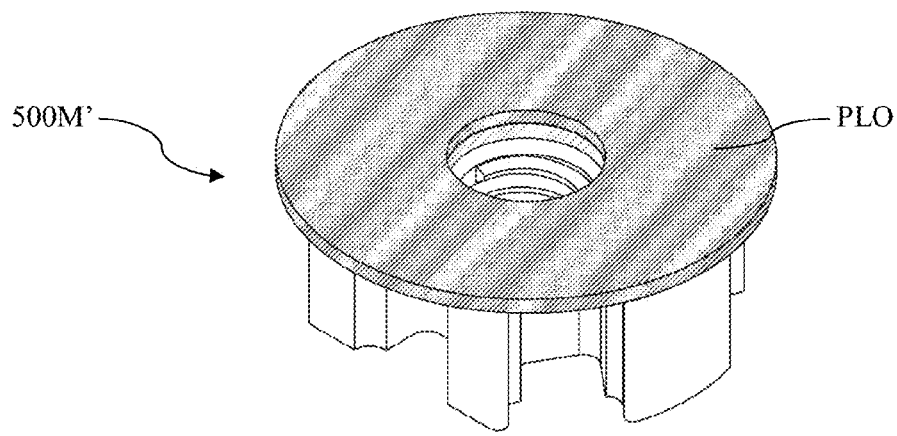

FIGS. 167, 167A and 168 show an embodiment of enhancer 500M that has base plate PLT (integrated flange of a bolt or gear base plating for added strength and/or contact with a corresponding torque enhancer socket mesh gear contact). Plate PLT is shown circular in configuration and in this embodiment has a diameter less than each of lengths L1 and L2 and includes a central aperture aligned with hole 508. FIGS. 167B to 167D shows an alternate embodiment enhancer 500M' that is similar in all ways as enhancer 500M but for having an added outer plate PLO that is shown having a diameter larger than each of L1 and L2 while still having a corresponding central aperture.

Figure 167E:
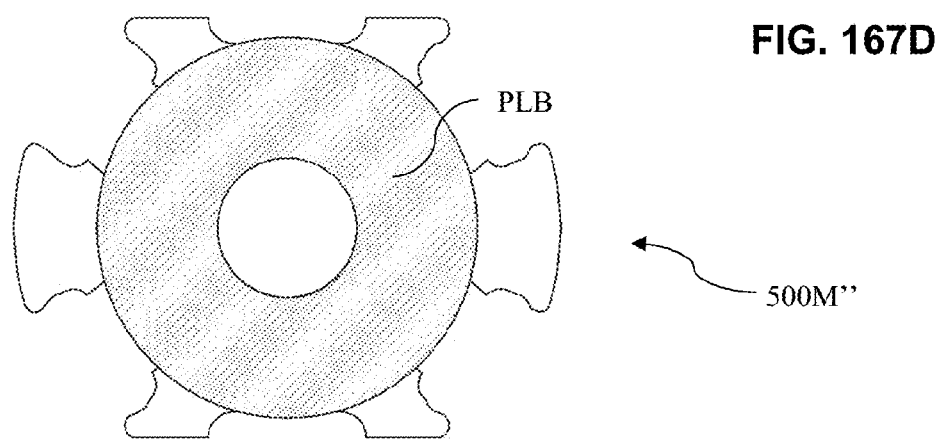
Figure 167F:
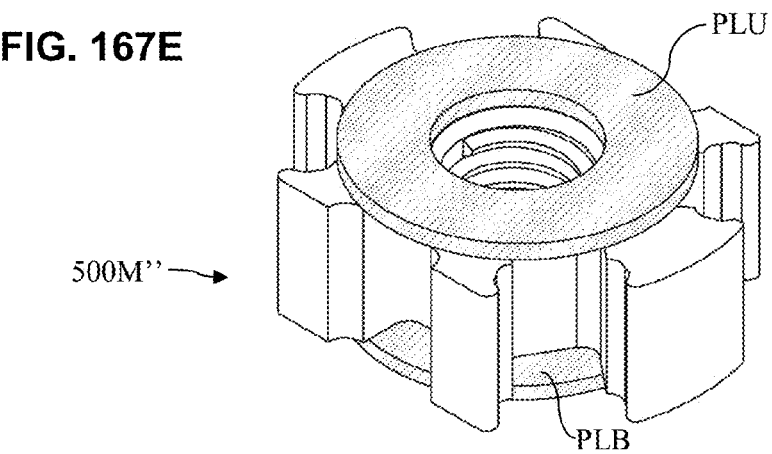

FIGS. 167E and 167F show a further enhancer 500M" that is similar to that shown as enhancer 500M but includes base plates PLU and PLB on the upper and lower sides of the illustrated torque enhancer configuration shown in FIG. 167.

Figure 167G:
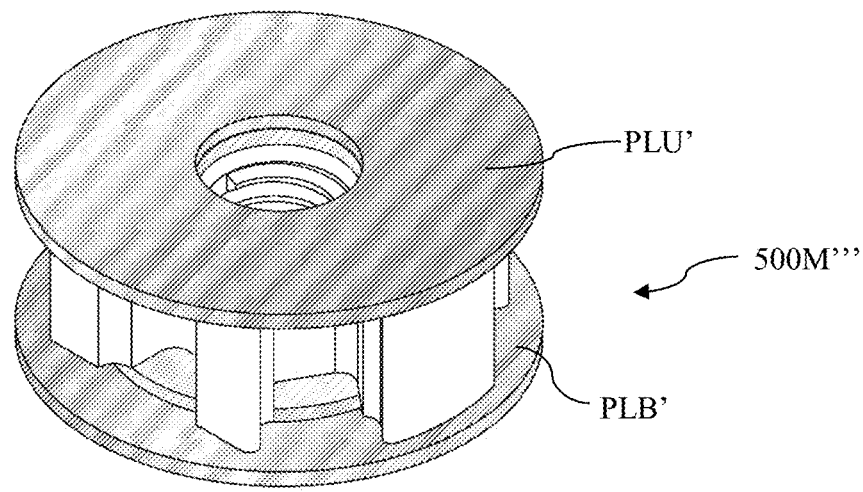

FIG. 167G shows a similar upper and lower plate stack to opposite sides of the side walls of the projections, but with a large plate such as shown in FIG. 167D on both sides (plates PLU' and PLB") of the planar walls of the projection and inner body of enhancer 500M'". Also, while a plate has been shown in each of the above 500M series enhancer, embodiments include an enhancer like that in 500M without any plates.

As some additional variations on the aforementioned "plated" 500M series" enhancers described above, enhancer 500 shown in FIGS. 167 and 168 as a gear, the branched projections with bases that when assembled form the interior body can be independent and assembled together on the plate as by fasteners through the plate or the entire assembly formed as a monolithic unit as by milling. An alternate embodiment relative to enhancer 500M' shown in FIG. 167E is to have either the plate PLT rigidly attached to the enhancement inner body and the combination sliding received in a corresponding bearing aperture in outer plate PLO, optionally the PLO plate and inner plate PLT can be rigidly attached and the inner plate slidingly received in a corresponding aperture formed in the interior body IB of the enhancer. In situations as when there is a vertical orientation, a complimentary plate arrangement can be provided on the opposite side as in a trunnion support for the intermediate inner body of the enhancer (in similar fashion to the opposite side plate set up in FIG. 167G—with such an arrangement providing outer protection to a threading 508 interior and Z-axis wrench slippage preclusion). As an additional embodiment example, reference is again made to FIG. 167G, wherein the outer plate PLO can have a central aperture for receiving the inner plate as to be aligned along a common plane with the addition of a bearing ring (e.g. ball bearing ring cage with ball bearings) between the aligned plates (e.g., a bearing ring arrangement provided on each side) as to enable the inner body and plate (or shaft bearing equivalent) to rotate relative to the opposite sided bearing ring and outer plate having an inner surface surrounding the outer surface of the bearing ring). Also, a suitable gear relationship is one where the pivot axis coincides as in a socket type gear with projections conforming to the recesses of the gear for relative drive rotation between the meshed driver and driven torque enhancer member.

FIG. 169 shows a 24 spiral segments spiral-centrifugal contact point presentation for torque enhancer 500M. As shown, with the deep and stepped notches and corner cut outs, the number of contact points increases as seen by the 24 spiral segments with one or more contact points illustrated. Further, the upper end convex side walls in the upper regions of each of the notches and the corner cut outs provide some degree of return to center, but the forces generated are numerous and strong as there are numerous presented contact points many of which are oriented general transverse to tangent lines on the orbits or circumferential reference lines (not shown). In this regard, reference is made to the multiple contact points 10, 10a, 11, 11a, 12 all falling in the stepped side wall region of corner cut out C4 as well as the three contact points 1, 1a and 2 provided just in the notch on side wall 338A.

FIGS. 171 and 172 illustrate torque enhancer 500W which features the lowest RA % value presented relative to the embodiments shown of 50% and thus is consider well suited for hand manipulation as the torque applicator (although higher speed applications including air and hydraulic rapid RPM socket tooling is envisioned as well). FIG. 172 illustrates the spiral-centrifugal contact presentation for enhancer 500W with the 16 contact points shown. Reference is made to the above described spiral-centrifugal contact points presentation discussions and thus only some of the highlights are presented based on this familiarity. That is, due to the low RA % of 50%, the torque arm presented by bow-tie projections BT1 and BT2 provides high torque application points such as represented by the group of contact points 4a and 4b on spiral segment D (and the opposite counterpart group of 12a and 12b). The points contacting the downstream side of corner cut out C2 and the upstream side of bow-tie projection BT2 are relatively high in number in view of the RA % of 50% so as to represent an elongated, narrow rectangle RE frame of reference (not shown in this embodiment). Accordingly the contact points acting on the obstructing side of the elongated bow tie projection generate high torque values (particularly the outer orbital positioned ones in the respective groups as they take advantage of a long moment arm). There is however also provided some degree of centrifugal force diffusion as through the relatively shallow and smooth contoured cut-outs which facilitate contact point force return toward the center as shown by contact point 7, for example.

FIGS. 173 and 174 show torque enhancer 500W1, which has the same exterior configuration as presented for torque enhancer 500W, but also includes outer apertures as in threaded through-holes which can accommodate screws or bolts at the bow-tie projection's base region (as well as the central bolt or screw shown or in place thereof). The outer apertures are also illustrative of potential weight balance regions as in the removal of some of the material to help alleviate the rotation wobbling produced by the lack of weight balance. In similar fashion to tire weight balancing, rather than core balancing, a weighting approach can be taken as in providing appropriately positioned weight inserts or general material weight equalization differentiation during mold formation or the like.

With further reference to FIGS. 175 to 180 there is illustrated torque enhancer 500N with its two tier configuration (500N' top and 500N'') designed for a suitably configured torque tool as in a two tier socket or wrench head (or a single tier wrench or socket head for engagement just one of the two tiers or two different tools having advantages as described below). FIG. 175 shows a top perspective view, while FIG. 176 shows a top plan view. As seen from these two figures, there is an inner body area IB at the very top having a central hole 508. Central hole 508 can be threaded as a nut or can be non-threaded (as shown) for usage as a cap or fastener element having an additional fastener element to lock it in place (this thread or non-thread option is also available in each of the above described "500" series of illustrated torque enhancers). Inner body IB is shown having opposite elongated side walls 338a and 338b and bow-tie projection surfaces 339a and 339b, which, together with corner cut outs c1 to c4 define the upper tier 500N' of enhancer 500N. The bottom of the top tier borders with an intermediary portion IN that diverges outward and in a shallow concave manner to provide a smooth transition between the top tier 500N' and base tier 500N''. FIGS. 175 and 176 further illustrate that in addition to the smooth wall transition in the Z-axis direction, the lower tier 500N'' has a periphery devoid of sharp angled corners in that all surfaces are either concave or convex. This provides for example, a torque enhancement component that provides a non-sharp edge surface at its base for finger manipulation where counter forces are low enough (e.g., a run up of a threaded nut to a point where compression and axial tension of the bolt makes further finger tightening difficult). Once the point of difficult finger manipulation is reached the enhancer's top tier with its sharper edge transitioning provides for tool attachment as in a wrench whereupon final tightening can take place (with the reverse order being applicable for loosening of the capping nut 500N).

FIGS. 177 to 179 illustrate the enhancer shown in FIG. 175 flipped over such that there can be seen that enhancer 500N has a hollow chamber HL formed below the under surface of interior body IB. FIG. 179 shows that the top tier and intermediate portion IN are solid with the base tier 500N'' being open as to form the hollow chamber HL. This enables enhancer to be utilized, for example, both as a covering cap and a potential nut engagement device. For example in a non-thread mode of enhancer 500N it can be slipped down a bolt shaft until contacting a smaller sized nut having a configuration generally conforming with that of the interior surface defining the hollow chamber HL. Accordingly, enhancer 500N can be used as a protective cap as in of a plastic material (non-rusting) over a metal (potentially rusting) or can be used as a size increaser to help remove a stuck cap by providing greater leverage relative to the interior conforming shaped smaller nut). For example, some estimates suggest a 2.5 increase in torque requirements in an initial removal mode as compared to an initial insertion mode for a nut, with mutual thread engagement degradation or locking up often being a component of that additional force required for releasing a threaded attachment. The torque enhancement configuration can help in removing such a bound nut.

With reference to FIG. 180 there is seen a mechanical contact point presentation wherein there is shown 8 contact point per tier level for a total of 16 contact points. Enhancer 500N is shown having relatively shallow contour cut outs C1 to C4 in the base tier level and c1 to c4 in the top tier level. Thus, the illustrated torque enhancer 500H has a lower tier orbital contact point set and an upper tier orbital contact point set each or either (as in one designed for finger manipulation as described above) designed for use with a conforming torque generating tool such as torque wrench 360 shown in FIG. 181 for one or the other tier sizes, or a specially modified torque generating tool having two tier conformance capability (not shown)). In FIG. 180 the top tier orbital set is shown as having contact point set 1 to 8, while the lower, larger tier contact point set is shown as 1a to 8a. As seen, the focus of the contact points is shown to be based on projection surface contact and single corner cut out contact, rather than the earlier embodiment's emphasis on multi-contact corner cut out contact and projection surface contact.

There are also featured 16 contact points (1 to 8 and 1a to 8a) going in the counterclockwise direction (not shown) but they would be switched on relative sides in conformance with the illustrated bi-symmetry nature of the torque enhancer.

FIG. 181 shows an example of a torque tool 360 as in one having wrench characteristics and thus includes a main shaft (hand grip) section 362; and, at one end, closed retainer 364 having an interior torque enhancement cavity 366 (which is designed to conform to the exterior surface of an associated nut as in torque enhancer 500C). The length of the shaft 362 can conform to those traditionally used for wrench applications with the larger length typically being associated with larger nut removal. The opposite end of shaft 362 can be a free end without any retainer component or, as shown, can include a second retainer 368 as in one having a difference relative to the first retainer 364 (e.g., a different sized common torque enhancer designed shape or a different torque enhancer designed shape). In the illustrated embodiment the closed, first retainer is shaped to conform to torque enhancer in closed fashion, while the opposite end illustrates a common configuration (suited for torque enhancer 500C) but with one open end gap 370.

FIG. 182 shows a second torque tool 372 similar to that shown in FIG. 181 but with a modified second retainer end 374 which is shown as having only one half (roughly) of the conforming torque enhancer profile for placement around a nut having a conforming configuration 376 (again a configuration suited for retention (partially) around the periphery of torque enhancer 500C). Each of the torque tools discussed above and below can also take on other configurations (preferably having the fully conforming or at least partly confirming internal peripheral matching configuration) as in a socket set with socket and ratchet handle, for example.

As shown in FIG. 183, torque enhancer 500K' represents a common design as enhancer 500C, but is modified as to have a non-threaded through-hole 508' rather than a threaded interior 508. In the modified torque enhancer 500K' there is shown a multi-sided (as to preclude free rotation) non-threaded interior recess 508' that is smooth walled but, in this embodiment, is shown with a hexagonal configuration and thus can readily slide over and along a hexagonal exterior configured rod to a desired axial location on that rod.

FIG. 184 shows torque enhancer 500K" represents the earlier described enhancer 500C modified from its threaded interior 508 as to have a non-threaded interior recess. In the modified torque enhancer 500K" there is shown a multi-sided (as to preclude free rotation) non-threaded interior recess 508" that is smooth walled but, in this embodiment, is shown with the same shaped torque enhancement configuration that the exterior surface of nut 500K", only smaller in dimension as to be able to be centrally positioned within the interior of the body forming nut 500K". In this way a rod or the like can readily slide within the interior of nut 500K" while being strongly prevented from free rotation within the interior of nut 500K".

Reference is made to FIG. 183A for an illustration of the slide on relationship between common peripheral (exterior of torque enhancer 500C nut) and interior (interior surface of torque tool 360 wrench) configurations, with a slight slide on size differentiation between the corresponding exterior periphery and interior conforming surfaces. In FIG. 183A, the interior surface 366 of first retainer 364 is shown as fully encompassing nut 500C with the noted slide on gapping. At the opposite end of tool 360 there can be seen the partially open configuration (opening in only a part of the exterior most end 368E of second retainer 368) shown as having free ends extending into respective corner cut-outs C1 and C3, while the free end of bow-tie projection 339A extends out past the exterior most end 368E.

Reference is made to FIG. 184A for an illustration of the slide on relationship between common peripheral (exterior of torque enhancer 500C nut) and interior (interior surface of torque tool 360' wrench) configurations, with a slight slide on size differentiation (between the corresponding exterior periphery and interior conforming surfaces. In FIG. 184A, the interior surface 366 of first retainer 364 is shown as fully encompassing nut 500C with the noted slide on gapping. At the opposite end of tool 360 there can be seen the one side fully open configuration (full opening at the free end part of the exterior most end 374E of second retainer 374) shown as having free ends extending short of corner cut-outs C1 and C3 as to terminate on the respective straight side edges 338A and 338B, while the free end of bow-tie projection 339A extends out past the exterior most end 374E.

FIG. 185 illustrates an example of the flexibility in types of torque enhancer configurations available under the present invention by illustrating the torque enhancer 500K" (see FIG. 184) having the common configured inner core 508". There is further featured in FIG. 185, in exploded view fashion, a suitable insert as in smaller, but common shaped insert 500C that is received in the core 508" so as to be precluded from rotation, but enabling a smaller sized rod or the like (as in an elongated cylindrical rod suited to slide though a rivet like central bore 508M as seen in the cross-sectional view of torque enhancer 500M shown in FIG. 185A).

FIG. 186 shows an additional embodiment of a torque enhancer 556, which is in the form of a partially threaded bolt having a torque enhancement configuration at the bolt head end 558 of the bolt. Extending off from the solid bolt head end 558 is shaft 560 which in this embodiment is shown with a partial threading 562 leaving the base of the shaft unthreaded. This is but one form of bolt configuration with other configurations including different versions of shafts and heads as in tapered shafts (threaded screw shaft configurations), fully threaded bolt shafts and other fastener means having anyone of the above described torque enhancement peripheral configurations depending on the needed fastener function. FIG. 186A shows a cross-sectional view of torque enhancer 556 with the solid bolt head 558 and shaft with partially threaded section 562.

FIG. 187 shows an additional embodiment of a torque enhancer 564, which is in the form of a capped nut featuring a torque enhancement configuration base 566 of the nut. Extending off from the base 566 is a semi-spherical cap 568. This is but yet another form of nut configuration having any one of the above described torque enhancement peripheral configurations (with FIG. 187 showing one similar to nut 500C, but for there not being a threaded through-hole). As seen from FIG. 187A, nut 564 instead has it's center hole 508 as an interior thread section 570 that terminates inside the main body of torque enhancer 564 and over which is formed semi-spherical cap 568.

FIGS. 188A, 188B and 188C show a torque enhancer fastener assembly combination 572 having torque enhancement threaded bolt 574 to which is attached torque enhancement threaded nut 576. In the embodiment shown threaded nut 576 has the form of torque enhancement nut 500C with its 76% ratio. Threaded nut 576 is readily adaptable to torque tool connection. As further seen from FIGS. 188A and 188C, torque enhancement threaded bolt 574 of torque enhancer combination 572 has shaft 578 with threading 580 extending for more than a majority of the length of the shaft 578 (from the free end of the shaft to non-threaded border region 582 leading into the solid head 584 of the nut). At the border region 582 is located a ring washer 585 which is slidable along the shaft until placed into abutment with an intermediate object or the unitary washer flange 586 formed in monolithic fashion at that base of solid head 584 of the bolt having the same or a different torque enhancement peripheral configuration as that of nut 576.

A further example of a torque tool for use in adjustment of, for example, threaded bolt 574 via torque tool engagement with solid head 584 is seen in FIG. 189 showing a perspective viewpoint relative to the engagement of torque tool 588 to torque enhancer combination 572. As seen in FIG. 189, torque tool 588 has a central non-recessed section 590 as well as left and right contoured sections 592 and 594 each shown as having enhanced ergonomic finger grip configuration as explained in U.S. Pat. No. 8,850,662 to the present Applicant, which patent is incorporated herein by reference. The left contoured grip section 592 is shown as having an encircling wrench tool retention end 596 shown in slide over engagement on torque enhancement bolt head 584 (the opposite retention end with the open faced wrench end 598 is also shown in engagement with a standard hex nut HH for illustrating suitable wrench meshing). The wrench end 598 is also suited for contact with enhancers of the present invention with the contact points preferably directed at the parallel walls 338A and 338B thereof.

FIGS. 189A, 189B and 189C show close-up views of different versions (598A, 598B and 598C) of the open wrench head shown generally in FIG. 189. As shown in FIG. 189A, the open head of wrench 588 features a top flange TF (as applied to hex nut HN) that forms a stepped region in the open head of the wrench which facilitates the capability of applying a downward force on the threads to help break up bonds. FIG. 189B shows a bottom flange BF (which could be a flipped version of that which is shown in FIG. 189A, but is shown as being a pre-formed bottom flange as seen by the different contouring of the wrench handle sections in FIGS. 189A and 189B). FIG. 189C shows a modified open wrench head 598C having an intermediate flange MF (which enables below support as featured in FIG. 189B as well as downward force application as depicted in FIG. 189A).

FIGS. 190A, 190B and 190C show some different viewpoints of recessed head bolt 600, with FIG. 190A showing a side view, FIG. 190B a top plan view and FIG. 190C showing a perspective, top view. As seen, bolt 600 has a threaded shaft 601 and a bolt head 602 that has a centered torque enhancement configured recess 604 which can take on any of the above described torque enhancement configurations described above, but relative to an exterior surface rather than an interior recess defining surface (e.g., torque enhancer 500C is illustrative of a suitable torque enhancement configuration for the recess shape shown in FIGS. 190B and 190C).

FIGS. 191A, 191B show an additional example of a torque tool 606; which, rather than having a wrench configuration like that described above, features an L-shaped tool that has a general "allen" wrench design, but has a torque enhancement cross-section configuration at least at one free end and preferably at both of the free ends (key ends 608 and 610) of the L-shaped tool. In addition to preferably having a torque enhancement configuration at opposite ends, tool 606 is shown as having its torque enhancement contour continuous from one free end to the other. FIGS. 191A, 191B further illustrate oblique inwardly tapered end most regions 609 and 611 provided, respectively, in key ends 608 and 610, which tapered or chamfered end most regions facilitates initial slippage into the generally conforming (just slightly larger—see gap dimensions described above) torque enhancement recess 604 in bolt head 602 having the same shape as the key end of tool 606. In alternate embodiments a non-chamfered or right angled end is featured.

As shown, each of key ends 608 and 610 is designed to be received in the conformingly configured recess of a bolt head with FIG. 192 illustrating such an engaged relationship relative to key end 608. With such a mutual connection of torque enhancement configured male/female ends of the bolt and tool combination, there is provided for enhanced tightening and loosening once tightened capability based on the above described torque enhancement extended length to width ratio relationship.

FIGS. 192A, 192B, 192C, 192D illustrate an additional example of a torque enhancement member shown as torque tool 612 having a torque enhancement configuration at its drive head in accord with that which is described above (e.g., any one of the above described 500 series of torque enhancement configurations described for the nut and/or bolt exteriors described above as in 500C as well as those described below). Torque tool 612 is shown as having two independent torque enhancement areas having different general functioning purposes. That is, while wrench tool 588 is described above as having two, opposite end different torque tool engagement ends 596, 598, each has the generally same functioning purpose of engaging a correspondingly shaped object as in a bolt head or nut. FIGS. 192A, 192B, 192C, 192D show the torque enhancement configuration provided both on driving head end 614 as well as on the handle region 616, providing tool 612 with a general screw drive configuration, but with the noted torque enhancement differentiation at both the drive head end and at the finger grasp handle regions.

A comparison of FIGS. 192A, 192B shows the length/width interplay relative to both driving head end 614 and handle region 616. That is, FIG. 192A shows the shorter length portion of the above described torque enhancement configurations (e.g., any one of the 500 series described above for the torque enhancement nut configurations as in 500C as well as those described below), with each of the handle and driving end region having a common torque enhancement configuration (as shown) or one having a different torque enhancement configuration as compared to the other, noting that one configuration may be more suited for a palm and finger wrap around and another for the driving function at the driving head end. As seen from the noted comparison, the shorter length LG1 for handle region 616 (having the familiar projection surface labeling involving reference numbers 538 and 539 similar to that used in the 500 series torque enhancement shapes described above but referenced as 338 and 339) is found in FIG. 192A, while the longer length LG2 is shown in FIG. 192B, with the length of each of LG1 and LG2, while different, being well configured for a universal palm/finger wrap grip. The noted FIGS. 192A, 192B also shows a coinciding shorter length LE1 for the driving head end shown in FIG. 192A and a longer length driving head end length LE2 for the FIG. 192B view. Tool 612 is also shown as having a same view coinciding short length orientation for each of the handle region and driving head end region LE1 and LG1, although in alternate embodiments they can be skewed relative to each other including shorter length handle in the FIG. 192A view and longer length driving head end in the same FIG. 192A view and a coinciding 180 degree offset relationship in the FIG. 192B.

Also, to help bridge the different size handle and driving head relationship for tool 612 there is provided a conical step down 618 leading to shaft extension 620 which ends in driving head 614. Handle region 616 is shown as having an interior cylindrical core 622 (unitary with the conical step down 618) as well as an exterior gripping region 624 forming the grasp part of handle 616 and having the noted torque enhancement configuration, with the potential of a softer material used in the grip portion as compared to the core although a monolithic combination is also contemplated.

While FIG. 192A shows a hand manipulated driving tool, additional embodiments include similar shaft driving head combinations that can be used on standard driving power source devices as in air guns, etc. For example, FIG. 192B illustrates a break away section with is illustrative of either A) that the length of the shaft can be of varied length, or B) that the left side can be an independent tool shaft with the same driving head 614 but a back end that is contoured (e.g., four sided) and thus well suited for insertion into a chuck or the like, inclusive of a chuck for an electric or fluid driven tool driver as in a drill with a multi-prong chuck head designed to receive torque enhancement component CP.

With reference back to FIG. 188C there can be seen a fastener assembly combination with a combination washer 585, bolt 578 and nut 576, with the washer and bolt head having the torque enhancement configuration. As explained in greater detail below, the washer outer periphery can also be provided with a torque enhancement peripheral configuration such as any of the aforementioned 500 series exterior shapes.

A discussion below follows relative to some additional threaded fastener assembly combinations that incorporate torque enhancement features of the present invention, which assemblies are well suited for alleviating issues that arise under prior art threaded fasteners as in bolt head shear off, thread degradation, improper loading, loss of proper compression levels due to relaxation in the assembly, etc. The avoidance of such issues being particularly important relative to critical bolted joints where proper level pre-tensioning, but not over tensioning is of high importance, as might be present in building, bridge, and other structures where proper bolting is critical for safety and structural integrity. For additional background in this regard, reference is made to "*Engineering Fundamentals of Threaded Fastener Design and Analysis*" by Ralf S. Shoberg, P. E., Director of Technology, PCB (date not indicated) which describes four distinct zones of a fastener tightening process that are illustrated in FIG. 193.

The most general model of the torque turn signature for the fastener tightening process can be construed as having four distinct zones as illustrated in FIG. 193. The first zone is the rundown or prevailing torque zone that occurs before the fastener head or nut contacts the bearing surface (e.g., see the discussion above relative to the base tier in nut 500N being well suited for finger start of threading). The second zone is the alignment or snugging zone wherein the fastener and joint mating surfaces are drawn into alignment to achieve a "snug" condition. The third zone is the elastic clamping range, wherein the slope of the torque-angle curve is essentially constant. The fourth zone is the post-yield zone, which begins with an inflection point at the end of the elastic range. Occasionally, this fourth zone can be due to yielding in the joint or gasket, or due to yield of the threads in the nut or clamped components or nut, rather than to yield of the fastener.

The basic torque distribution for a fastener is illustrated in FIG. 194. The torque applied to a fastener is absorbed in three main areas. First, there is underhead friction, which may absorb 50 percent or more of the total torque. Thread friction absorbs as much as 40 percent of the applied torque. The final 10 percent of the applied torque develops the clamping force that holds the components together. Thus an increase in either friction component of 5% can reduce tension significantly.

The proper pre-tensioning requirement in such threaded fastener assemblies has also led to a variety of direct-tensioner-indicators as in flexible silicone embedded in bolt heads that squirt out a certain extent at pre-calibrated tightening levels (e.g., see "SQUIRTER DTIs" from Applied Bolting Technology). However, such indicators add a great deal of complexity to manufacture and have some indicator limitations.

FIG. 195 shows an arrangement that includes additional components that can lead to a variation in the respective four zones due to for example absorption of forces by a washer or the like.

The below described fastener assemblies of the present invention are directed at helping dissipate the forces that develop during torque turning of a fastener assembly while providing good and consisting clamping of the structures being fastened (inclusive of "compression/peripheral catch" bound stacked torque enhancement member). For example, as explained in greater detail below the torque enhancement configuration is helpful in providing a biting surface when one torque enhancement component compresses into another structure (either another torque enhancement component or a different type structure) as well as torsion absorption that is promoted with the noted digging in feature of the abutting structures as well as the torque enhancement shaped periphery). A nesting arrangement between the two stacked components can facilitate this beneficial arrangement. As explained herein, a stacking relationship between torque enhancement components under the present invention is particularly helpful in diffusing forces that arise such as bolt tension or bolt head shear off forces, etc. A few examples of such stacked relationships are referenced above and will become apparent below in the below described various fastener assemblies wherein there is involved stacked torque enhancement components.

FIG. 196A and FIG. 196B illustrate an example of a fastener assembly that is inclusive of the torque enhancement advantages described above, as well as additional structural attributes that help in alleviating some of the above described issues with prior art fastener assemblies. Also there is seen a stacked arrangement both above and below the structural components 628 and 630 being clamped together. Fastener assembly 626 is shown in FIG. 196A and FIG. 196B as being in an initial assembly state relative to the two structural components 628 and 630 being clamped. With reference to FIG. 196C and FIG. 196D, threaded bolt 632 of fastener assembly 626 is shown having threaded shaft 634 and bolt head 636. Bolt head 636 features an upper region 637 featuring a torque enhancement peripheral configuration (such as 500C described above). In this embodiment, bolt 632 has a shaft that is essentially a full thread length. The perspective view of bolt 632 in FIG. 196C illustrates a center top depression 638 as well as at least one side wall depression 640 (one or a pair, for example, with the pair preferably opposing as in opposing on sides 338A and 338B), each depression 640 facilitates hand manipulation in providing further grasping surfaces in addition to those provided by the corner cut outs and associated projections. Further, the side wall depression(s) 640 provides a demarcation or indicia that is helpful to monitor the in use turn location of the bolt head. As best shown in FIG. 196C and FIG. 196D, bolt head 636, in addition to upper region 637, has tapering configuration 639 (converging in a downward direction and also having a rippled or non-continuous surface which promotes sealing as described below), which leads into the upper end of the threaded portion of bolt shaft 634 and is non-threaded (in this embodiment). FIG. 196E illustrates an alternate bolt configuration which is shown as having the same components as that in FIG. 196D, but for extended threading up into the tapering configuration to the border with the upper region 637. This provides for a washer (e.g., an unthreaded one or a threaded one such as those described below in FIGS. 199A to 199F) to situate high near the bolt head and lock in place the bolt relative to the associated fastener assembly.

As further shown in FIG. 196A and FIG. 196B, fastener assembly 626 includes an "upper" (with "upper" only being in reference to the manner the fastener assembly is shown oriented in FIG. 196A) or first engagement member 642, which is further illustrated in FIG. 198A to 198F (which illustrate, respectively, a top perspective view; a top plan view; a flipped front elevational view; a flipped cross-sectional view; a bottom plan view and a bottom perspective). As shown in these figures, first engagement member 642 features a base (upper as shown) torque enhancement section 644 shown in this embodiment with a torque enhancement configuration similar to that of 500L in FIG. 162. At the opposite end of first engagement member 642 there is found a converging section (converging down in shown use) that is shown as being a smooth walled tapered exterior surface 645; and, as seen by FIG. 198D that convergence is facilitated by way of thinning wall 646.

FIG. 198D also illustrates there is a through-hole 648 extending axially through the first engagement member that has at its top end curved transition section 650 that leads into a cylindrical opening 652 which in turn leads into a second, but smaller length sloped transition section 654. With reference to FIG. 198C there is illustrated elongated depression 656 (shown formed in one of the elongated sides such as 338A described above, with the opposite counterpart not shown) which is shown as being elongated with an oval configuration. As explained in greater detail below the elongated depression 656, through-hole 648 (with curved reception ends 650 and 654) facilitate an equalization of compression forces in conjunction with the torque enhancement outer configuration with its outer surface corner cut outs and different length and designed projections (e.g., as in the above noted longer length bow-tie projections 339A and shorter projections such as 338A).

With reference back to fastener assembly 626 in FIG. 196A and FIG. 196B, there is shown that the "lower" free edge 651 (shown as generally flat and annular) is designed for contact with an upper surface of structural component 628. Further, the structural components 628 and 630 are shown as having axially aligned apertures that are devoid of threading such that the threaded bolt shaft 634 extends therethough without threading.

Moving down the component arrangement in FIG. 196A and FIG. 196B, there is shown the aforementioned washer 658 which, as noted, has an outer peripheral contour with the torque enhancement configuration such as the 500 series described above, and is also a cupped washer with an arc (shown extending upward in this use) such that the edges of washer 658 (discontinuous edges because of the torque enhancement edging with corner cut outs) are placed in contact ("bite" with compression) with the underside of structural component 630. FIGS. 199A to 199F show washer 658 alone in, respectively, a top perspective view; a flipped bottom perspective view; a front elevational view; a flipped front elevational view; a top plan view; and a flipped cross-sectional view.

Washer 658 is shown as a non-flat, cupped washer for purposes described below. Washer 658 has a torque enhancement external periphery having a configuration either the same or different than that of the above described first engagement member, as in a more elongated rectangular configuration in washer 658. In view of the common torque enhancement periphery, similar edging demarcations as that featured in, for example, nut 500C are referenced in FIGS. 199A to 199F including straight edge walls 338A and 338B; bow-tie projection free arched edges 339A and 339B, and corner cut-outs or recesses C1 to C4. Washer 658 further includes central through-hole 508W which is either threaded (e.g., a single thread projection 500T as shown in FIG. 199F which is a thread well suited for engagement with threading such as shown at the convergence section 639 in the aforementioned FIG. 196E) or thread-less (as per FIG. 199E showing a different embodiment of washer 658); and in any event is sized for pass through of threaded bolt shaft 634. FIG. 199C illustrates cup radius Rw which is pre-designed (e.g., having an arch designed relative to the material utilized for washer 658 to reach a "biting" flattened state upon reaching a predetermined bolt tension in the fastening assembly). FIGS. 199A and 199C further illustrate upper corner edge CE which is the edge that is placed in contact in the initial bolt tension contact state shown in FIG. 199A (i.e., prior to the collapse of the cupped washer 658 into a horizontal state).

Below washer 658 is found second engagement component 660, which shares some similarities with the aforementioned first engagement components 642, although, has some differences, as can be gleaned from the description below. Second engagement component 660 is shown in greater detail in FIG. 200A to 200E. Second engagement component 660 is in a flipped over state (relative to the orientation of first engagement component 642) such that its larger area first end 662 is that which contacts the washer 658. FIG. 200A illustrates in perspective view the larger diameter bowl (cup-shaped) or truncated semi-spherical opening 664 provided therein. Second engagement component has a second end 666 (in-use lower). Second engagement component 660 has a similar outer configuration as that of the first engagement component 642 in that is has a torque enhancement peripheral section 664 having, for example, a close to square length/width ratio in similar fashion to 500L (although depending on the intended usage alternated torque enhancement peripheries can be utilized such as any one of the aforementioned 500 series, with the configuration for the first and second engagement components being either the same or different). Also in similar fashion to the first engagement component, second engagement component includes elongated depression 668 having in this embodiment an oval configuration with a depth less than the adjacent corner cut-outs C1 to C4 (with the 500 series side wall and bow-tie projection arches being similarly identified for reference). As with the first engagement component, there is the smooth wall, tapered section 668, that extends out away from torque enhancement peripheral section 664 to free end 666. Further, since the base of second engagement component 660 has torque enhancement peripheral edging the stacked relationship with washer 658 produced a similar biting in relationship therebetween upon compression.

With reference to the cross-sectional view in FIG. 200C, there is seen that tapered section 668 converges as it moves away from torque enhancement peripheral section 664. Thus, the opposite free end 662, which surrounds the bowl-shaped concavity 664, is larger in outer circumferential coverage than free end 666. FIG. 200C also shows that, unlike the first engagement component, the second engagement component 660 has a threaded section 670 that initiates at the inward most end of cup-shaped cavity 664 and opens out at free end 666 and has a thread diameter that is less than the median and maximum diameter of cup-shaped cavity 664. Threaded section 670 thus extends in the thicker wall region of second engagement component 660.

With reference to FIGS. 200C and 200D, it can be seen that the cup or bowl-shaped cavity 664 increases in diameter away from its border region with the threaded section such that the side wall of the torque enhancement peripheral section 664 decreases in thickness in response to the increase in diameter of the bowl-shaped cavity 664, with the wall approaching, but not reaching the maximum depression of the corner cut outs C1 to C4. In similar fashion, the wall thickness is of the same reduced thickness between the cavity 664 maximum extension and the parallel sidewalls 338A and 338B (which have less of a width separation than the arc surfaces of the bow-tie projections 339A and 339B). This reduction in thickness provides for controlled Z-axis compression flexing in the second engagement component which controlled compression deformation has advantages as described below.

An additional advantage in the bowl-to-thread arrangement featured in second engagement component 660 is shown in FIGS. 200F to 200I. FIG. 200F shows another bowl-end perspective view wherein there can be seen the bowl-shaped section 664 leading to the threaded section 670. FIG. 200G shows an initial stage in bolt 632 being joined with second engagement component 660 (initial insertion of the bolt such that the free end of the bolt is in contact with the guiding surface of the smooth bowl-shaped section 664 and at a stage before any threading). FIG. 200H shows a thread engagement stage wherein the bolt, after being properly centered with the assistance of the guiding bowl surface, has been threaded fully through the thread section 670, but the bolt has not been fully threaded to its component compression position. It is noted that this guidance helps avoid a problem associated with damage to threads that has a high risk of occurrence in the initial attempt to start threading, as any such deviation can lead to binding and/or thread damage in either the free end of the bolt, the receiving nut threads or both. The guidance provided is considered to help avoid such issues of improper initial thread start. FIG. 200I shows the bolt in a fully threaded state wherein the transition section 639 is fully received within the confines of the bowl 664 and the bolt head is positioned such that the bolt head's lower end is Z-axis aligned or more preferably in an initial bite down relationship with the upper region of receiving bowl 664. The shape of the bowl and the tapered shape region 639 is shown as leaving a clearance region CL which is an area well suited for receiving an elastomeric seal as represented by a generally conical seal 6443 filling in a portion of the bowl to receive in compression contact the aforementioned rippled side wall of the bolt's tapering portion 639 (or in an alternate embodiment a softer washer seal shown at 658 can be utilized).

Thus, upon assemblage of the assembly shown in FIG. 200G, conical seal member 664S is received in the clearance region CL formed between the different angled bowl side wall 664 and bolt transition section 639, whereas upon the nesting of transition section with clearance region CL it compresses against seal member 664S as to generate a biting seal relationship which helps avoid relative rotation while maintaining a tight seal, with seal 664S also preferably having a bowl shape interior conforming with that of bowl 666 for bolt guidance.

FIG. 201 shows a fastening assembly kit set of components suited for clamping structures such as structures 628 and 630 in FIG. 196A, which kit includes threaded bolt 632, first engagement component 642, cupped-shaped washer 658 and second engagement component 660. With reference again made to FIGS. 196A and 196B there is described the clamping characteristics of the kit shown in FIG. 201 in operation. FIG. 196A illustrates the assembly as having undergone some initial threading (threaded second engagement component 660 is threaded along threaded shaft 634 until initial contact with the still cup-shaped washer). At this point the fastener assembly 626 has reached a stage of completion of run-down and the initiation of the alignment stage; but, as seen, the inclusion of the cup-shaped washer and the below further described concavities in each of the first and second engagement members have not been fully positioned.

FIGS. 197A and 197B reveals the extension of the torque application to completion such that there is reached the final two stages shown in FIG. 193, with the result being the collapse of the cup-shaped washer into a horizontal configuration wherein the washer has converted from its cup-shape to a flat profile which is indicative of a proper-tensioned state and, because of the corner cut outs there is a compression grip formation as the edging of the washer embeds in the surface and vice versa such that the further rotation is prevented once that state is reached.

FIG. 197B further shows a bite-in nesting arrangement that comes after the initial contact state and is achieved as the non-continuous peripheral edge of washer 658 goes from its initial contact state in FIG. 197A into a dug-in relationship with the structural component 630. The final biting engagement is thus achieved as the washer collapses and the corner cut outs and projections of the torque configuration portion of the bolt head 636 digs in to the upper (larger) free end (inner edge) defining the top end curved section 650. Further, on the opposite side of washer 658 (i.e., the lower side in FIG. 53B) there is also a flexing relationship (as in a slight buckling) as the larger circumference end of second engagement component 660 compresses on the bottom of washer 658 as to flatten it out. This enlarged end is also the torque enhancement periphery end such that wrench or tool engagement is carried out close to the washer surface and there is seen that the cup-shaped opening or concavity 664 defines the thinner walled end of second engagement component 660. The opposite end of second engagement component 660 features the smooth walled and higher to lower converging portion 668 (the portion surrounding the threaded section and thicker in thickness due to the lack of the concavity 664). Thus upon torque rotation of the second converging component, the forces are diffused outwardly in the bottom to top direction relative to second engagement component's interfacing with washer 658, which again, once sufficiently embedded in the bottom surface of second structural component discontinuous free slide rotation). In other words, between washer 658 and the underlying second engagement component 660, there is an additional dig-in relationship together with a degree of radial deflection as the thinner bowl shaped (with torque enhancement peripheral configuration) end is forced into a compression state with the inner body portion of washer 658.

At the opposite end of the stacked structural components there is also a dig-in plus radial deflection relationship between the torque enhancement bolt head 636 and the receiving thinner walled bowl section of first engagement component 642. That is, the thinner walled region defining the curved section 650 flexes to some degree outward and is considered to both help dissipate some of the bolt thread tension and also dampen some of the shearing torque on the bolt head. The lack of threads at first engagement member 642, allows for threaded adjustment at just the second engagement member 660 (e.g., one wrench or holder at the bolt head and another wrench or holder at the opposite ends allows for torque of just one of the bolt head or second engagement member at the time of tightening; noting the dig in relationship provides some added avoidance of undesirable spinning of one end while another end is tightened up to a certain level of torque application). Accordingly, the nested relationships described for this assembly provide some diffusion of the stress generated during torque application and also some dampening relative to potential bolt head shear off (as to the torque enhancement configuration's considered ability to help diffuse shear potential due to torsion diffusion and/or compression control, reference is made to the discussion below concerning FIGS. 215A and 220A).

FIGS. 202A to 202E illustrate a hollow bolt configuration of the present invention which includes torque enhancement features in accordance with the present invention and provides for a variety of advantageous fastener assembly combinations some of which are detailed below. FIG. 202A shows hollow bolt 672 which is comprised of a torque enhancer bolt head 674 (e.g., one having any one of the 500 series described above and with the one depicted in FIG. 202A having a peripheral configuration of 500C, etc.). To facilitate an appreciation of the bolt heads 500 series peripheral configuration, there is provided in this figure set the previously relied upon corner cut outs (C1 to C4), side walls 338A and 338B, and bow tie projection surface 339A and 339B referencing utilized previously. Positioned below bolt head 674 is integrated washer flange 676 which is shown as being a monolithic (common material) body with respect to both the bolt head 674 and bolt shaft 678. Bolt shaft 678 is shown as having both a threaded end section 680 and a non-threaded intermediate section 682. Also, while a variety of bolt sizes are featured under the present invention (at least those suited for the hollow nature), the preferred diameter differential for the torque enhancement bolt head maximum width BL, flange washer diameter; and bolt shaft diameter BS has the following correlation BS<BL<B1.

Bolt 672 is formed with a central through-hole 684 that has an first (upper) portion 684A formed in the confines of bolt head 674 and a second portion 684B that extends from communication with first portion 684A to the free end 686 of the bolt (the free end of the threaded end). As seen by the cross-sectional views in FIGS. 202B and 202D, first through-hole portion 684A is a multi-walled cavity having a torque enhancement configuration which can be the same as the exterior or different as in a less rectangular configuration, and with the first portion cavity 684A extending, preferably, at least a majority of the Z-axis height of bolt head 674. Second portion 684B is a cylindrical shaped through-hole extending the full length from its communication border with first portion 684A. The multi-sided first portion 684A is useful for providing an insertion location for a similarly shaped nut or the like which is precluded from rotation once inserted (see the example described below). As with the earlier described embodiments bolt head 674 also includes a pair of side wall depressions 688 (circular shaped in this embodiment and only one of two opposing shown).

With reference to FIGS. 203A to 203D there is featured fastener assembly 690 which is shown as including the aforementioned hollow bolt 672 as a fastener component used in the fastening of structural components 692 and 694 (which in the illustrated embodiment structural members 692 and 694 are not placed in a mutual compression setting by fastener assembly 690, rather fastener assembly 690 is shown with bolt flange 676 positioned away from structural member 692 as to represent some degree of axial adjustment potential, as in mutually sliding components as might be found in mutually rotating legs in a folding chair for example (usually with a bushing to fill in the space); although alternate embodiments can include the length of the fastener assembly 690 being designed for a non-rotation compression relationship relative to structural components 692 and 694). Thus, fastener assembly 690 is illustrative of a sleeve bearing assembly with the below described fastener component 696 providing a suitable outer bearing contact portion thereof.

That is, FIGS. 204A to 204C show a second fastener component 696 of fastener assembly 690. Second fastener component includes a bolt head 698 which shares a common torque enhancement peripheral configuration (e.g., one having, for example, any one of the 500 series described above and with the one depicted in FIG. 204A having a peripheral configuration of 500C). Bolt head 698 includes as well a circular minor depression 700 in a side wall 338A (one of the pair). Also, while having a depression 702 at the top end of bolt head 698, unlike the top end of bolt 672, depression is a minor depression and not designed for receipt of a torque tool or a torque enhancement nut or the like as in cavity 684A for fastener component 672. Rather it provides a good finger depression location to facilitate the assembly process. Fastener component 696 includes flange washer 704 which is integrally formed with bolt head 698. An additional monolithic part of second fastener component 696 is the casing shell 706 extending away from the lower side of flange washer 704 to free end 708. Also, while a variety of fastener component 696 sizes are featured under the present invention (at least those suited for the hollow, shell nature), the preferred diameter differential for the torque enhancement bolt head 698 maximum width bL, flange washer diameter bl; and shell 706 diameter Bs has the following correlation bL<bs<bl (with bl>Bl and Bs>BS relative to the first and second fastener components 672 and 696). Further the interior cavity 710 of fastener component 696 has two sections that include an upper (as oriented in FIG. 204C) threaded section 710A of diameter TO; and a lower, larger diameter non-threaded section 710B of diameter bs. The diameter bs of the interior surface of the non-threaded portion 710B of shell 710 is sized larger than each of threaded end section 680 and a non-threaded intermediate section 682 of bolt 672 with the diameter BS thereof suited for a thread connection between sections 710A and 680 while some circumferential clearance is provided between the interior section 710B of shell 710 and the exterior surface 682 of bolt 678. In an alternate embodiment (bolt configuration not shown) the free end of the bolt that is threaded is stepped in fashion such that the non-threaded section of the hollow bolt is received in the interior of the shaft (with spacing or in slide friction contact) while the threaded free end of the bolt is threaded for thread engagement with threads 710T of sleeve 706.

With reference again to FIGS. 203A to 203D there is seen fastener assembly 690 in both an assembled and exploded view (both cross-sectional and front planar). As seen from FIG. 203B exterior shell diameter Bs is sized for reception in sliding fashion within the mutual reception holes 692H and 694H in structural components 692 and 694, respectively. In this way, the fastener assembly 690 in FIG. 203B can function as well as a bearing unit as in roller bearing shaft assembly. Thus, in assembling fastener assembly 690, first fastener component 672 and second fastener component 696 are arranged as to have their respective flange washers opposing different surfaces of the stacked structural components, with FIG. 203A showing the underside of flange washer 676 opposing top surface 692T of structural component 692, and the top of flange washer 704 opposing the bottom surface 694B of structural component 694. Further as seen from the exploded view in FIG. 203C, the bolt or first engagement component is inserted from the top and the second engagement component 696 is extended up from the bottom, with both being nested while being inserted into each of the holes 692H and 694H such that the first and second components are in a telescoping relationship that provides for threading initiation between the threads 680 of bolt 672 and the threads 710T of second engagement component 696. Upon further threading at least one or both of bolt heads 674 and 698 are torqued with a suitable torque tool until the free end 708 of shell 706 is brought into a compressive relationship with the underside of the flange washer 676 of bolt 672). This arrangement provides for a rapidly torqued into place assembly and also one that holds firmly until a desired release (again using the torque enhancement configuration of the bolt heads).

FIGS. 205A to 205C show a fully exploded view, a partially exploded view and an assembled view, respectively, for an additional fastener assembly 712 embodiment of the invention which includes some components previously described for the other fastener assembly arrangements, some new components described below with both new and earlier described components including those having a torque enhancement configuration. With reference to the fully exploded view in FIG. 205A, there can be seen previously described components: bolt 672; and nut 714 (e.g., nut 714 is the same as nut 500C described earlier; and which is also designed to nest in non-rotation fashion within the commonly configured cavity 684A of bolt 672). There is also featured in assembly 712 an additional fastener component 716 sharing similarities with nut 500L in FIG. 162 and FIG. 163 as well as with second engagement component 660 (but with some interior cavity configuration differentiation). FIG. 205A to 205C also show an additional (new engagement component) interior threaded member or "button member" 718 and another new component in the form of opposite ends threaded shaft 720. All of these former described and newly described components are shown in a preliminary stage of assembly in 205B and a fully assembled state in 205C relative to stacked structural components 722 and 724.

Figure 206C:
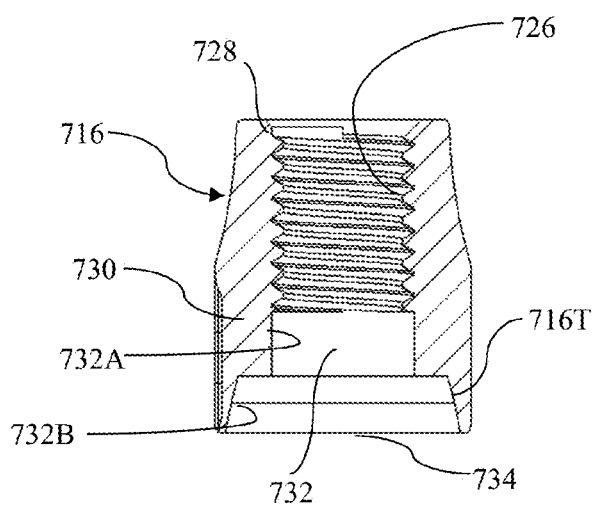
Figure 206D:
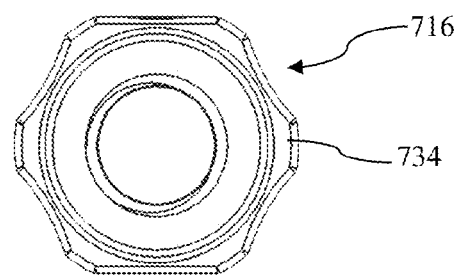

Reference is made to 205A which illustrate some of the differences between engagement component 716 of fastener assembly 712 and the earlier described engagement component 660 (although in view of the exterior similarities reference is made to the disclosure for engagement component 660 which is applicable as well to fastener assembly 712). As seen in FIGS. 206A to 206C, engagement component 716 includes the familiar central threaded section 726 that extends from the free (smaller diameter) annular end 728, through the entire smooth walled tapered section and partially into the torque enhancement base 730. Torque enhancement base 730 features a stepped cavity arrangement generally referenced at 732 that includes a cylindrical (smooth walled) section 732A that has a diameter in common with the base groove end of the threaded section and extends for about ½ of the distance between the thread end to the other free end 734 of engagement component 716. Stepped cavity arrangement 732 further includes a truncated cone cavity section 732B that extends in diverging (essentially smooth walled or rippled) fashion the remaining distance to the free end 734. The divergence is at an acute angle to the vertical which is sufficient to provide a suitable wall thickness adjustment for purposes described below. In this regard the free end 734 features the thinnest walled section of engagement component 716 with the opposite end 728 featuring the next thinnest section with the smooth walled section and the lower end portion of the threaded section 726 being in the thickest part of engagement component 716.

FIGS. 207A to 207F show button member 718 in various views, with FIG. 207A providing a perspective view of the in use orientation shown in FIG. 205A. As seen, button member has a torque enhancement configuration having the less rectangular configuration shape of 500L as a preferred configuration, although alternate torque enhancement configurations, such as those others shown in the 500 series can be utilized. Also, button member 718 features a shorter height as compared to engagement component 716 as in ⅓ to ½ of the height thereof.

Torque enhancement configured base 726 of button member 718 is shown as having an exterior wall region 728 extending inwardly and upwardly as to merge into button section 730 having a truncated conical configuration that converges as it moves away from base 728 and has a smooth walled surface for facilitation of the below described contacting nesting relationship with engagement member 716. Further button member 718 includes a central threaded through-hole 732 (relatively smaller diameter as compared to the interior threaded diameter 726 of engagement member 716) that extends between the planar surfaces 734 and 736 of button member 718.

FIGS. 208A and 208B illustrate threaded shaft 720 having a central non-threaded region 738 and end threaded sections (shown upper) 740 and (shown lower) 742. The diameter of the central region 738 (and outer thread diameter as well for end threaded sections 740 and 742 is referenced at DM1 which is smaller than the internal wall diameter DM1 for bolt 672 and hence also even smaller than the diameter BS for the exterior surface of bolt 672).

FIGS. 209A to 209C illustrate sub-assembly 744 which is shown as part of the full assembly 712 shown in FIG. 205C (with sub-assembly 744 being devoid of bolt 672 and the stacked structural components 722 and 724 seen in the full assembly in FIG. 205C). Sub-assembly 744 helps illustrate the aforementioned nesting arrangement between the button member 718 and engagement component 716, and particularly between the different angled (Ax, Ay) sloped surfaces defining truncated cone cavity section 732A in engagement component 716 and surface 730B in button member 718. As seen, FIG. 205C shows a stage where all components are assembled (e.g., the nesting, rotation lock relationship between nut 714 and open cavity 684A of bolt 672 with correspondence torque enhancement configuration not being shown, but structurally present upon full assembly like that shown in FIG. 205C). Under this assembly upon rotation of bolt head 674 (in unison with the nested nut 714) there is achieved a drawing up of button member 718 within the engagement component 716 (which is also in threaded engagement with bolt 672 so that it too is drawn up against the undersurface of structural component 724). With the drawing up of button member 718 within the truncated conical reception area 732A in the (shown) bottom of engagement component 716, there is an outward deflection of the thinner walled region 716T (See FIGS. 206A to 206C) such that (in similar fashion to the other nesting arrangements) there is a diffusion of tension generated in the fastener assembly as well as the potential for a dampening of shearing forces generated.

FIGS. 210A to 210C illustrate an additional fastener assembly 746 sharing some similar components as in the other fastener assembly (and thus they are commonly referenced relative to the earlier described assembly). FIG. 210A shows a fully exploded view, while FIG. 210B shows a point still not fully assembled, but closer than FIG. 210A, with FIG. 210C showing a full compression state and with cupped washer 658 collapsed in similar fashion to the earlier described embodiments. Further, FIG. 211 shows a perspective view of a modified bolt designated as bolt 672S with "S" designating a solid version of the earlier described hollow bolt 672 (with common flange washer 672F and common bolt head 672H with the earlier described hollow bolt 672). An additional distinction lies in the fully threaded shaft 672T (as opposed to the partially threaded shaft of bolt 672). A single, previously described engagement component 660 completes the threaded arrangement in that the previously described interior threading for engagement component is threaded up on the bolt 672S until the thinner walled cup region of engagement component 660 comes in compression contact with the underside of (e.g., an axial and radial force deflection due to the relative thin walled construction having a minor degree of buckling).

FIG. 212 illustrates an additional fastener assembly in kit form sharing some similar components (although in a rearranged arrangement) as the previously described invention fastener assemblies as well as a newly introduced component. FIG. 212 shows fastener assembly 748 in kit fashion with its component parts shown individually (the present invention also inclusive of kits relative to the earlier described fastener assemblies) with the earlier described engagement components 660 (but with an outer exterior and an interior threading modification described below—660') and 642 (but with an outer exterior threading modification described below—642') and hollow bolt 672 featured. The specifics as to the kit components are described below in FIGS. 213A to 213D relative to the fastener assembly usage and in associated FIGS. 214A and 214B for insert 750.

FIGS. 213A to 213D show fastener assembly 748 is various stages of assembly as well as with modified forms (660' and 642') of the earlier described engagement components 660 and 642. The respective differences include added threading (660T in the cup region and threading 660t in the exterior conical region of the enhancement member 660 earlier shown; and exterior conical surface threading 642t in torque enhancement member 642 earlier shown). The hollow bolt 672 featured in the earlier embodiments is also utilized in the assembly 748. FIGS. 213A to 213D show these components in various stages of alignment and assembly. FIG. 213A shows an axial alignment in fully exploded view fashion. FIG. 213B shows both insert 750 and hollow bolt 672 having been inserted into aligned holes formed in each of structural components 722 and 724. Further, bolt 672 is shown inserted into insert 750 so that its shaft is in friction contact with the below described hollow interior of insert 750, while the exterior of insert 750 is placed in a compression relationship relative to the walls defining the axially aligned (or essentially axially aligned) holes for structural components 722 and 724.

FIGS. 214A and 214B show an example of insert 750 in the form of a non-symmetrical sleeve (both axially and radially non-symmetric as provided by the various contouring shown). Preferably insert 750 is made up of a softer (having more resiliency and compressibility potential for a given force as compared to the bolt and at least threaded engagement component 660 (e.g., a silicone insert)). As a suitable example of such a non-symmetrical component reference is made to U.S. Pat. No. 8,745,825 to the present Applicant, which patent is incorporated herein by reference as an example of a suitable insert 750. Thus insert 750 has a sleeve configuration with a central through-hole 751 (FIG. 214B cross-sectional view) suitably sized to receive the shaft of bolt 672 as well as a variety of different concavities formed in various locations in the outer surface of insert 750 a few of which are labeled as 753 (e.g., 753A and 753B) in FIG. 214A.

With reference to FIGS. 213C and 213D there is shown an assembled state for fastener assembly 748. As seen therein the compression force on insert 750 causes it to contact the interior regions of each of the structural components with a different degree of force which facilitates a catching relationship that is well suited for accommodating a variety of different vibration levels. Further a portion of the compressible material lower end of insert 750 flows into the through-hole in engagement component 642 through which the threaded shaft already extends in its extension into the threaded reception area in engagement component 660, (to which the bolt is threaded to achieve the fastening attachment). Furthermore the converging (lower shown) threaded end of 642t of engagement component 642 is received in partially nested fashion with the bowl shaped cavity in the (upper shown) end of engagement component 660. Furthermore, particularly with reference to FIG. 213D, there can be seen that there is both a relative compression and threading relationship between the interior "bowl" threads 660T and the exterior "cone" threads 642t as to provide a good thread locking arrangement in the assembly 748. For example, the threading direction in the interlocking threads 642t and 660T can be different than that formed between the bolt and interior threads 670 within second engagement component 660' for added safety from loosening.

To better appreciate the dampening and/or diffusion of torsion and axial tensioning provided by the torque enhancement members particularly when in a biting and/or nested interrelationship, reference is made to FIGS. 215A to 215D, wherein a torque enhancement member (such as torque enhancement member 40 shown in FIG. 1 as but one example) is shown in position relative to a torsion generator test set up 754. Set up 754 is shown as having a compression function (see compression arrows in FIGS. 215A and 215B, relative to the torque enhancement member 40 (with one of the bow-tie projections 339B referenced for appreciation of the orientation within the test equipment)). Thus, upon maximum compression there is seen a deformation in the vertical direction or shortening in height of member 40. Rather than an expected non-equal change in height over the area or periphery of member 40 due to the different thickness the bow tie and longer sided projections, there is actually experienced a generally equal overall change in height believed likely due to the peripheral configuration with the corner cut-outs absorbing and dissipating the anticipated more difficult thicker wall section compression as compared to the thinner bow-tie projections. The ability to more evenly deform in an X-Y axes plane as compression lessens the overall height of the torque enhancement direction in the Z-axis is also believed to be enhanced by the above described depressions such as the illustrated oval depression 45 (one of two opposing ones shown).

Figure 215D:
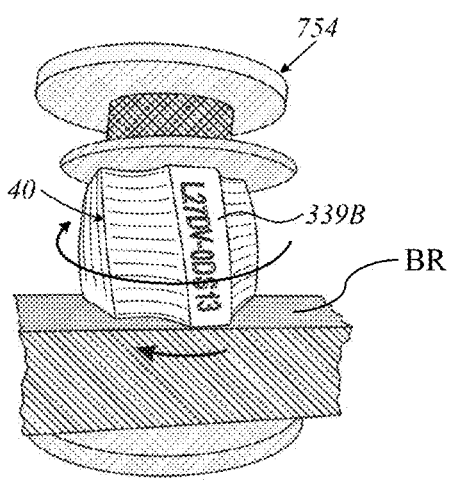

There is further shown in FIGS. 215C and 215D relative twisting within test set up 754 while in the state of compression shown in FIG. 215B. FIG. 215C shows bar BR subjected to a counter-clockwise rotation between the clamp ends, which in turn twists torque enhancement member 40 in a counter-clockwise rotation. As seen enhancement member 40 with its corner recesses and relative projections of different peripheral lengths is well suited for absorption and dissipation of those torsion forces and dampening of movement (e.g., a dampening of lower structural component movement such as 724 in the above examples) while limiting the stress on the bolt head or the like which only receives dissipated torsion forces after enhancement member absorption. Thus, torque enhancement member 40 with its design (as well as the other embodiments having the peripheral configuration such as the 500 series described above) provides an advantageous damping function relative to two structural components that may shift or rotate with respect to each other (one or both relatively rotating or shifting with respect to each other). Further, this ability to dampen elastically the torsion forces generated during torqueing of a fastener assembly through use of the torque enhancement member 40 inclusion also helps in avoiding loosening of threads in addition to avoidance of bolt head shear off. Further, the deflections shown in FIGS. 215C and 215D can represent exaggerations of deflections that a high strength, not readily compressible material (e.g., tool steel) or can represent less exaggerated or actual deflection for material such as an elastomeric torque enhancement member 40 such as one of silicone or other elastomeric material. FIG. 215D shows the same as FIG. 215C, but with bar BR moving in a clockwise direction and with a same result only in the opposite direction relative to torsion deflection and dissipation via torque enhancement member 40.

With reference to FIGS. 216A to 216C there is shown a compression only test set up 756, with FIG. 216A showing introduction of torque enhancement member 40 between the upper and lower compression plates of test set up 756; FIG. 216A showing initial set up of the compression plates relative to the upper and lower ends of torque enhancement member 40; and FIG. 216B showing an initial compressions state and FIG. 216C showing a full compression mode of the noted plates (with added lines to show the change in height and the spring like nature of the member 40). Again, depending on the material featured for member 40 what is shown in FIG. 216C is either an exaggeration or a more realistic depiction. One feature of the member 40 is the presence of a depression (as in the oval depression 45 shown elongated in the vertical direction) that is formed in the more elongated walls 338A and 338B (see the 500 series discussion above for additional examples). Relative to compression dampening and level compression without skewing of the member 40 due to different compression resistance as might be expected, it has been determined that there is a highly uniform Z-axis collapse over the entire area of member 40. Although such a collapse nature is considered unexpected due to the different lengths of the relative components and different thicknesses, in addition to the aforementioned leveling provided by the corner cut-out and projection relationship, there is believed to be additional skew force absorption relative to the collapsing depression 45. In this regard, note the reconfiguration of the side wall depression 45 as it goes from an oval configuration before full compression to a more circular configuration in a state of maximum deflection (see FIG. 216C). This being in addition to the handling benefit provided by such side wall depressions 45.

FIGS. 217A to 217B illustrate an additional fastener assembly 758 in the same assembly state but from two different viewpoints. The assembly state shown for fastener assembly 758 shows a central threaded rod 720 threadingly receiving an upper nut with associated large flange washer 760 and a lower nut 762 with associated (smaller diameter as compared to the above noted large flange washer) also being in threaded engagement with threaded rod 720. Alternatively, the above referenced threaded rod 720 can be a threaded bolt with its head comprised of the noted upper nut with associated flange washer. Assembly 758 further includes a set of three engagement components 642A, 642B and 642C (all three shown as the aforementioned engagement components 642; and, thus, in the illustrated embodiment are all the same, although alternate embodiments include variable engagement components having the noted generally common exterior configuration). Assembly 758 is shown as having a primary fastening sub-set and a back-up fastening sub-set, with the former comprising the aforementioned nuts with flange washers (shown as standard hexagonal nuts in the illustrated embodiment, although torque enhancement nuts are also possible), and the latter having threaded second component 642C as potentially also threaded up into its own compression relationship with an unthreaded intermediate and generally similarly configured component 642B (with the final nut 762 further being secured after that). The two washer nuts are tightened or held relative to the stacked arrangement of the two structural components 722 and 724 and the first noted (top shown) engagement component 642A; and, once tightened down, place the structural components 722 and 724 in a primary state of compression. FIGS. 217A to 217B there is shown torque tool 588 (such as that shown in FIG. 186).

The aforementioned fastening sub-set includes the bottom nut with flanged washer 762 which is placed in contact with an optional larger washer 764 which abuts against the narrower end of another engagement component 642C. The opposite bowl shaped recess end of engagement component 642C is aligned with another (intermediate) engagement component 642B, which has its narrow end designed for nested reception with the larger diametered cavity end of engagement component 642C. Although not shown in FIGS. 217A to 217B, upon full completion of the back-up fastening sub-set tightening, the narrower end of intermediate component 642B (preferably inclusive of the beginning region of the torque enhancement periphery 766) enters and abuts against the reception cavity 768 presented at the top of component 642C, with the corner cut-out and projections of the torque enhancement periphery 766 acting to both radial stretch out the thinner walled region of component 642C defining cavity 768 and also to dig into the sides as to provide a radial lock (that still provides for the FIG. 215D type torsion absorption feature) and thus helps in assuring that various forces are absorbed as to not loosen the prime fastening sub-set (which even if loosened) as the secondary securement provided by the back-up fastening sub-set.

FIG. 218 shows an additional fastener assembly 770 suited for connection of two structural components that are separated from one another by spacer 776. In the embodiment shown the arrangement is similar to that shown in FIG. 217A on the top region, but features the aforementioned spacer, plus an underside fastening assembly which can mirror the top configuration. To provide a desired spacing between structural components 722 and 724 there is provided hollow cylindrical spacer 776 though which threaded rod 720 extends. There is thus provided a stable and secure (less chance of thread disengagement as compared to prior art embodiments) arrangement with the fastening sub-sets as in the illustrated top one 772 comprising the aforementioned threaded rod 720, flanged washer nut 760 threaded on rod 720 and engagement component 778 which shares some similarities with the earlier described engagement component 716 (See FIG. 206C), but is free of threads (thus having the stepped recess set, but with the thinner recess not being a threaded recess). In this regard, reference is made to FIGS. 219A to 219B showing different views of engagement component 778, which has the same exterior configuration as earlier described engagement components (e.g., torque enhancement configured base and converging, smooth walled extension away from the base, a circular side wall depression) and thus further detail is not provided. As shown in FIG. 219B, the interior cavity 780 in engagement component 778 features a sloped, annular interior rim 780A (representing the thinnest wall region such as wall region 780W1 shown at one of the four corner cut-outs and similarly thin wall region 780W2 shown on the side wall in which minor circle side wall depression 782 is also formed).

The interior cavity 780 is further shown as comprising a circular wall defined cylindrical section 780B extending which is bordered by undersurface 780C that extends to the smaller diameter recess 780D extending through to the top surface of engagement component 778. This structural configuration is well suited for providing damping and dissipation of compression forces that develop and thus the potential for less strain on threaded rod 720. FIGS. 220A to 220B illustrate the smooth and even compression deformation provided in engagement component 778 despite having the different thickness sections generated by the corner cut out and projection configuration in the torque enhancement base of engagement component 778 (which configuration also provides the benefit of cutting into material being compressed as to help avoid relative slippage between the engagement component and the contacted material of, for example, structural component 722, which allows for better torsion absorption in the engagement component as illustrated in FIGS. 215C to 215D for a similar engagement component). Further, the thickness of wall 780B can be adjusted as in thicker if more support is deemed desirable (i.e., less flexibility in radial expansion out with Z-axis compression).

Further as presented in FIGS. 220A to 220B (showing a similar compression test set-up 756 like that described above for FIG. 216A for the non-converging torque enhancement component 40 tested therein), there is shown engagement component 778 in an initial support, but not yet fully compressed by the test set-up; and a fuller compression setting, respectively. As seen by FIG. 220B under high compression (again shown exaggerated for some material or closer to actual deflection if more elastomeric material is relied upon) there is a generally equal compression lessening in height across the whole area defined by engagement component 778 despite the different projection thicknesses, etc. This generally equal deformation across the area of the engagement component is facilitated by the interior cavity wall configuration (with the minor 338A,B side wall depressions 45 also helping in avoid some of the stresses generated as seen by the conversion of its circular shape to one that is more horizontally oblong).

As noted above for the stacked and telescoping engagement components 642B and 642C there are benefits in the torque enhancement configuration relationship in such instances, including facilitating a rotational lock to enhance torsion damping within the torque enhancement portion of the body of the engagement component involved. In this regard, reference is made to FIGS. 221A to 221B featuring a torque enhancement member 40 receiving a threaded bolt 788 having an "elephant foot" torque enhancement head end with extending shaft as in that illustrated in FIGS. 51 and 52 and similar as well to the earlier described threaded bolts such as bolt 632 in FIG. 196D. FIG. 221A further shows a reception ring 784 with interior hole 786 which preferably has a diameter sized slightly smaller than the exterior maximum circumference of torque enhancement member 40 (e.g., the full length between the arches of the bow tie projections or non-arched linear versions of the same such as shown in FIG. 1). The relationship between the exterior circumference for torque enhancement member 40 and the diameter of hole 786 provides for reception of member 40, but only after some degree of deformation in one or both of member 40 and ring 784 (e.g., the ring can be formed of aluminum and torque enhancement member 40 of tool steel). Also, preferably there is a downwardly converging taper configuration in the interior hole in torque enhancement member as in the configuration depicted in FIG. 79B as to provide for ease of initial contact and then a ramping up of radial relative compression. Although not shown, the threaded end of bolt 788 is either threaded into a threaded body below ring (e.g., bushing) 784 or a nut is provided for clamping the arrangement such in the various manners described above. Upon reception in the manner illustrated in FIG. 221B, there can be seen a digging engagement between the interior surface defining hole 786 and the multi-faceted exterior surface of the torque enhancement shaped periphery of member 40. Accordingly, there can be achieved the torsion dampening associated with the illustrated torsion dampening deformation in member 40 like that illustrated in FIGS. 215C and 215D.

FIGS. 222A to 222D and FIG. 223 show an additional embodiment of a torque enhancement assembly 790 that has a torque enhancement bolt 792 with a threaded shaft 794 and an open headed top 796 (with an interior torque enhancement configured cavity 796T) and an exterior torque enhancement head periphery 798. The exterior torque enhancement periphery 798 is further received in a torque enhancement sleeve 802 that has a central cavity for such reception (e.g., a bowl or tapered configuration as earlier described). Also the torque enhancement sleeve 802 has an exterior torque enhancement configuration for its full Z-axis height, but that full height includes a first (lower shown) section that is linear or less tapered as compared to its tapered second (upper shown) section. Thus, upon a thread tightening function on bolt 792 (insertion of a torque tool within cavity 796 as in a ratchet projection of common non-rotation shape or one of the driving heads such as those in the tools illustrated in FIG. 192), there is achieved the aforementioned biting engagement between the sleeve 802 and the surface defining ring hole 784 (with the linear or less tapered arrangement at the bottom region providing for easier initial insertion until the more tapered surface is brought into contact with the surface defining ring hole 786).

Again, once in the position shown in FIG. 222C there is both a radial expansion with the noted biting action to provide a good fastening relationship that can readily absorb and dampen torque induced torsion or twisting or misalignment actions on the fastened structural component(s). While annular ring 784 is represented as having a hole 786, alternate structural members with receiving holes are also contemplated including girder beam, floor and wall panels, etc.

FIGS. 223, 224A to 224C show a torque enhancement assembly 790' that is similar to assembly 790 described above in all respects, but for the head of bolt 792' being solid head 794S such that tool torque generation is carried out on the torque enhancement periphery surface of head 794S which is also partially nested in the interior of sleeve 802. As seen by the top planar view shown in FIG. 224A there can be aligned the relative corresponding-in-shape, but different in size torque enhancement peripheries (with FIG. 224B showing common projections 339A1 and 339A2 for the bolt head 794S and sleeve 802). This relationship is referenced as a 0 degree relationship and there is some outward compression as the bow-tie ends are compressed against corresponding contacting surface of the receiving sleeve 802. FIG. 224B shows a 45 degree offset, while FIG. 224C shows a full 90 degree offset between bolt head 794S and sleeve 802. It is noted that when in the 90 degree orientation, wherein the bow-tie projections are compressed against the interior of sleeve 802 that forms the configuration of the side walls such as 338A, there is the greatest amount of relative compression and thus a high lock relationship. This arrangement helps an operator (e.g., an operator applying either a manual or automated driver to the head 794S to gauge the relative torsion levels based on the easily visualized angle relationship between head 794S and sleeve 802 as the threaded component is torqued. This can also provide for varied pre-tension or varied final tension (following relaxation) relative to two structural components such as two meshed pipe end flanges (schematically shown in FIG. 225 with just the flanges PI1 and PI2 shown) wherein there are a plurality of fastener holes 786 like those described above for assembly 790' insertion around the circumference of the meshed flanged pipe ends, and an operator can set the same for each or a variety of different tension levels by usage of, for example, the above noted 0 degree, 45 degree and 90 degree offsets—as in an equal number in series about the noted meshing circumference of the pipe flanges with anti-vibration absorption.

FIGS. 226A to 226C illustrate an additional fastener assembly 804 that is similar in many respects to that described above FIGS. 217A to 217C, but has some differences as described below. That is, the embodiment of FIGS. 226A to 226C features the (alternate) threaded bolt 720 arrangement described above with flanged bolt head 760 as well as the aforementioned first, second and third torque enhancement engagement components 642A, 642B and 642C. One difference is that there is not featured a nut between structural component 724 and component 642B as in the earlier described embodiment, but reliance is placed on a similar bottom flanged washer nut 762 (or separate nut and washer assembly).

FIG. 226A shows the structural components 722 and 734 not yet fully placed in the desired level of compression, while FIGS. 226B and 226C do show the various components in the full compression state (including the aforementioned benefits associated with the nested torque enhancement arrangement between components 642A and 642C and the deformation arrangement of the thinner walled region of 642A on the structural component 722). FIG. 226A shows as well a suitable socket torque generation tool 588B for engagement with the bolt head 760 and an additional torque tool 588A for stabilizing via engagement with the torque enhancement periphery of component 642A.

FIGS. 227A to 227F show button 718' which is a modified version of button 718 shown in FIGS. 207A to 207F with similar components between the two not described, but with the below discussion as to differences. Button 718' is shown as having a partial central thread 732P in essentially the tapered portion only of the button 718' (unlike the through-hole in button 718). An additional distinction is in the exterior threading 730T provided on the exterior of the cone shaped portion of the button. These modifications present an alternate torque enhancement member that is more cap like in structure in that the base planar surface 736C shown for button 718' is devoid of any holes. Thus for attachment there is the option of a threaded shaft reception in the partial hole thread 732P and/or reliance on the cone threads 730T.

FIGS. 228A to 228F show button 718" which is a modified version of button 718' shown FIGS. 227A to 227F (and thus also that in FIGS. 207A to 207F) with similar components between the two not described, but with the below discussion as to a difference. Button 718" is shown as being devoid of any hole (threaded or otherwise) in its solid body SB, and thus not designed for internal threading as with a threaded shaft rod such as shown in FIG. 208A. As button 718" does have exterior threading 730T as in the earlier embodiment, it has a true cap configuration making it well suited for a variety of uses as in a gas tank cap, a drain cap a structural fastener assembly end, etc.

FIGS. 229A to 229F show an alternate fastener assembly 800 combination comprised of two different (nested) torque enhancement members which is similar in some respects to the combination featured in FIG. 213D at the bottom region. Assembly 800 features engagement component 802 which is the same as that represented by 660' in FIG. 213D plus a further modified button 804 that is like button 718 (FIG. 207A) in that it has a threaded though-hole 732, but is different in that is has an exterior cone thread 730T (FIG. 228A). The exterior cone thread 730T of button 804 is shown being in threaded engagement with the threads 660T of engagement component 802 which provides for the threaded locking connection between the two components. Further as in the earlier described FIG. 213 embodiment, there can be a reverse thread relationship in the assembly 800 that is opposite the thread direction of another component attached to assembly 800 by threading, as in a central bolt or threaded shaft rod (not shown) threaded within through-hole 732. Such an arrangement thus provides for an assembly well suited to avoid vibration separation or loosening.

FIGS. 230A to 230C show an additional fastener assembly 806 with fastener assembly 800 as a sub-component. Assembly 806 is similar to fastener assembly 712 in FIG. 205A (and thus includes like reference numbering) and thus the discussion focuses on the differences which concern the usage of sub-assembly 800 in place of the components 716 and 718 shown in FIG. 205A. This includes the ability to have the noted reverse threading at sub-assembly 800 (which in this embodiment and the assembly 712 can also include a reverse threading relationship relative to the opposite end threading regions in threaded shaft 720 shown in FIG. 205A and FIG. 230A).

Figure 231H:
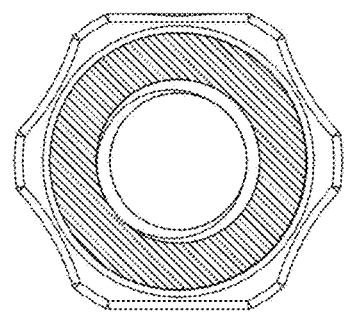

FIGS. 231A to 231H show an additional embodiment of a tapered engagement member (referenced as member 808). Engagement member 808 has the same general configuration of that which is shown in FIG. 206C, but includes some differences directed at the below described sealing members reception. That is, as shown in cross-sectional view FIG. 231B, there is featured first seal member 810 and second seal member 812. First seal member 810 is shown by itself in FIG. 231G and in its nested location in the stepped region of member 808 as shown in FIG. 231F and FIG. 231H. As seen in the cross-sectional view of FIG. 231B, first seal member 810 has a tapered side edge conforming to the tapered side wall of the larger, stepped region of engagement member 808 with main body 809. This provides a good location for a combination biting in and sealing relationship between two torque enhancement members of the present invention. At the opposite end of main body 809 there is provided a cylindrical cavity 814 that receives flanged seal member 812 having a conforming sized cylindrical section 817 and an upper flange 816 designed to rest on the free end (most tapered end) of engagement member main body 809 and to be placed into compression contact with a structural member for example. Seal members 810 and 812 are thus well suited for sealing off both ends (e.g., are formed of a suitable elastomeric material or cold flow material) upon deformation as when member 808 is in a compressed state in a fastener assembly.

FIGS. 232A to 232E show an additional embodiment of a tapered engagement component (referenced as 818). Engagement member 818 has the same general configuration of that which is shown in FIG. 206C, but includes some differences directed at the below described. These differences include exterior grooving 820 extending in Z-axis elongation along the smooth tapered exterior conical wall of member 818. Exterior grooving 820 on the conical or tapered surface of the engagement component is shown as being equally spaced circumferentially around the tapered portion. This grooving also provides for a biting action upon nested compaction of enhancement members as well as a tendency to radial compress easier than if no grooving provided. The grooving can be provided to a desired depth depending on intended usage.

An additional feature in component 818 is found in the flanged base platform 822 which provides an integrated washer feature as well as the ability to better centralize a rod or the like passing through the centralized hole 824 (threaded or non-threaded options).

FIG. 233 shows an additional embodiment of a grooved, tapered engagement component (referenced as 818'), but with the torque enhancement base of less Z-axis height than the above described member 818.

FIGS. 234A to 234C show an additional fastener assembly combination involving multiple torque enhancement components of the present invention, with FIG. 234A showing the combination in fully assembled mode. FIG. 234B showing a cross-sectional view thereof, and FIG. 234C shows a double flanged tapered torque enhancement engagement member 826 used in the assembly. Member 826 is similar to the above described member 818, but is devoid of the stepped recess region in place of a solid body region receiving the central threading. An additional difference is found in the addition of an opposite integrated flange 828. One further difference is that the Z-axis height of the tapered portion is less than that in member 818 as to reduce overall axial length of the fastener assembly shown in FIGS. 234A to 234B. With reference to FIGS. 234A to 234B there can be seen a fully assembled state wherein structural members 722 and 724 are under compression by the aforementioned solid bolt 672S and the engagement member with the flanged region 828 generally aligning in compression location with the integrated flange of the solid bolt 672S.

FIGS. 235A to 235C show a similar combination of features as depicted in FIGS. 234A to 234C, but with engagement member 830 only having one flange (flange 822). As shown in FIGS. 235A and 235B the resultant fastener assembly 832 has a more focused contact abutment relationship via the non-flanged, tapered free end of engagement member 830 being placed in compression contact with the underside of structural component 724.

FIGS. 236A to 236C show additional embodiments of tapered engagement members of the present invention which are similar to those described above, but for the main difference of rather than conical wall exterior grooving there is through-slots 834 in the locations of such grooving 820. The differences between engagement members 818S1, 818S2 and 818S3 shown in perspective lies in the relative Z-axis height of the base and conical or tapered regions of each (as well as a change in the side wall depression 836 configuration in FIG. 236A from a vertical oriented oval to a major axis in horizontal direction orientation). Each of members 818S1, 818S2 and 818S3 include the noted slots with the length conforming to the length of the conical portion, and for members 818S2 and 818S3 the slots extend partially into the torque enhancement configured base portion in each. The aforementioned through-slots provide for a flexing function in the engagement members as when a threaded bolt is threaded through and/or in conjunction with one of the above described nested compression relationships such as shown in FIG. 213A wherein the tab (between slots) body portions of the tapered section of the engagement members can more easily flex in and out upon radial force contact (in or out). The natural thread diameter can thus be made slightly smaller in diameter than the bolt thread diameter resulting in a flexing out of the tabs in the threading process.

FIGS. 237A to 237C show an alternate embodiment of a torque enhancement bolt and seal assembly 838. Bolt 840 is shown to be similar to bolt 632 in FIG. 196D, but with some differences. That is, bolt 840 has only a partially threaded shaft as well as more transverse border region where that shaft contacts the bolt head. In this border region there is provided an O-ring reception cavity 841 (FIG. 237C) for receipt of O-ring 842, with FIG. 237A showing the O-ring seal in a pre-final position state, FIG. 237B showing the O-ring seal in its reception groove provided in the region of bolt head and bolt shaft interface, and FIG. 237C shows that interface region in greater detail via an enlarged cut-away and cross-sectional view. Additionally, a preferred embodiment has the O-ring and cavity 841 are dimensioned such that the O-ring is sufficiently received in the cavity as to enable the bottom surface of the bolt head to come in direct contact with a washer (e.g., washer 658 described above) or a structural component as in a metal-to-metal contact relationship therebetween.

FIGS. 238A to 238C show an alternate embodiment of a torque enhancement bolt and flange (integrated washer) combination 843 which includes a bolt like that described for assembly 838 described immediately above (referenced here as 840'), which rather than having the O-ring cavity has a recess receiving an engaged arched washer 844 so as to be fully integrated with the tapered base of the bolt below its head. FIG. 238A shows the combination alone, FIG. 238B shows in partial cross-section the combination in an inserted, but pre-final insertion state relative to stacked structural components, and FIG. 238C showing the final insertion state thereof. The upper shown structural component has a strategic flange shaped recess in its upper surface and the lower structural component is compressed against the upper structural member upon applying a fastener to the threaded free end of bolt 840' (or there can be featured a threaded region TR for threading with a corresponding threaded portion of a bolt as in bolt 838. A comparison between FIGS. 238B and 238C shows the initial compression contact state between the arched washer (having been adjusted from its bow down configuration in its free state to a bow up state in the illustrated pre-final state of compression). Upon additional compression of the stacked components via further tension generating threading of the bolt, the washer eventually snaps into place within the noted recess FR. This arrangement provides a highly stable threaded engagement despite extensive environment vibration as well as an indicator of bolt tension levels needed to achieve the snap in location.

FIGS. 239A and 239B show an alternate torque enhancement component member 846 in the form of a projecting washer, with FIG. 239A showing a top perspective view thereof, and FIG. 239B a top plan view thereof (the underside being flat, for example, with the central through-hole or can be a recess conforming to the projection on the opposite side as might occur in a stamping or pressing operation). As seen, member 846 includes a larger diameter cylindrical base 848 out from which projects a torque enhancement peripherally configured projection 850 (thus providing the above noted biting in action due to the edge shape). The projection with underlying cavity as per the above described stamping technique is further beneficial in that the projection 850 is placed in a compression state against a structural member or the bolt head as to provide an elastic spring like compression quality.

Figure set 240A and 240B shows an alternate embodiment washer 846' having a modified base 848' with a common torque configuration periphery configuration as that of projection 850. Figure set 241A and 241B show another embodiment with washer 846" featuring a common base as that of FIG. 240A, but a standard hexagonal periphery projection 850'.

FIGS. 242A and 242B show an alternate torque enhancement component member 852 in the form of a recessed washer, with FIG. 242A showing a top perspective view thereof, and FIG. 242B a top plan view thereof (the underside being flat, for example, with the central through-hole or a projection as from the above noted stamping or punching process formation). As seen member 852 includes a larger diameter cylindrical base 854 in which is formed a torque enhancement peripherally configured recess 856 (thus providing the above noted biting in action upon receipt of a component therein). Figure set 243A and 243B shows an alternate embodiment washer 852' having a modified base 854' with a common torque configuration periphery configuration as that of recess 856. Figure set 244A and 244B show another embodiment with washer 852" featuring a common base as that of FIG. 243A, but a standard hexagonal recess 856'.

FIGS. 245A and 245H show additional torque enhancement component configurations, with FIG. 245A showing a grommet embodiment 858 having a torque enhancement recess 860 and a central through-hole, FIG. 245B shows the underside of FIG. 245A, FIG. 245C shows a bi-secting cross-section of FIG. 245A, and FIG. 245D shows the grommet of FIG. 245A receiving, in rotation potential fashion, a bowl shaped torque enhancement component 860. FIG. 245E shows bowl shaped receptor 860 alone, FIG. 245F shows bowl shaped receptor 860 as a plug for cylinder 861, FIG. 245G shows the grommet of FIG. 245A with a flexible conduit or cable CB received therein, and FIG. 245H shows the grommet of FIG. 245A receiving upper and lower washers RW1 and RW2 as well as a conduit CB (e.g., a solid cable) extending therethrough, while the washers are captured at a naturally assumed angle relative to the receiving recess regions of the grommet.

FIGS. 246A and 246G show additional embodiments of torque enhancement components under the present invention with FIG. 246A showing a front elevational view of a torque enhancement screw 862 featuring a standard head (e.g., Phillips, Allen, or a non-standard torque enhancement recess—not shown) and a torque enhancement shaft end recess RE. FIG. 246B shows an illustrative first embodiment 862A with shaft end recess and with a schematic plan view of the exterior configuration for that shaft end recess of the first embodiment. FIG. 246C shows a different screw embodiment 862B and its configured shaft end recess and a schematic plan view of the exterior configuration thereof. FIG. 246D shows a different screw or bolt embodiment 862C configured shaft end recess and a schematic plan view of the exterior configuration thereof. FIG. 246E shows another screw or bolt embodiment 862D featuring a different configured shaft end recess and a schematic plan view of the exterior configuration thereof. FIG. 246F shows an elongated support shaft ES assembly having a similar male/female relationship featuring a shaft ES2 (with a recessed end as in the bolt 862) that is received in a corresponding cup member ES1 with internal male projection centered within the cup member which further includes an external torque enhancement shape. Thus the torque enhancement shaft head end of shaft ES2 is received in a corresponding (internal male projection not shown) cup member within cup ES1. FIG. 246G shows a closer view of the male/female end shaft and cup combination. As shown in FIG. 246G, by rotating cup member relative to the exterior torque enhancement peripheral surface there can be rotated the shaft ES2 such that it is further threaded (telescoping length adjustment) within an opposite end thread receiving member (not shown). Examples of such an arrangement can be seen in temporary or permanent structural supports such as shown in FIG. 246F (a building structural component) or in other items such as shower curtain rods or (e.g., washing machine) adjustable leg supports, etc.).

FIGS. 247A and 247B show two additional embodiments of torque enhancement components (864A and 864B) under the present invention with FIG. 247B showing a perspective view featuring a shaft end recess like that described above in FIG. 246A without threading and with a torque enhancement end with flange configuration, and FIG. 247A showing the same as that in FIG. 247B but for a partial threading of its shaft.

FIG. 248 shows a schematic presentation of a plurality of conventional "screw drive type" configurations with associated labeling.

FIG. 249 shows an example of a conventional socket 51 having a hexagonal drive hole (with associated standard square ratchet connector—not shown).

FIG. 250 shows a ratchet tool RT and associated socket combination of the present invention with the combination having a male/female torque enhancement configured ratchet connection. Ratchet RT is shown as having a drive head 870 with a torque enhancement configuration such as any one of the above described "500 series" (or any of the other additional designs described below). FIG. 250 also shows that the combination includes socket S2 having ratchet head reception recess 872 with a conforming torque enhancement configuration.

FIG. 250A shows an underside perspective showing the free end of the socket S2 as having a torque enhancement configuration for driving at least a generally correspondingly shaped male component (e.g., socket S2 has both ends provided with a torque enhancement configuration such as a common 500 series configuration or different ones as described herein).

FIG. 250B shows a schematic line presentation of the interior cavity of the socket shown in FIG. 250A.

FIG. 250C shows an additional perspective view showing the free end of the socket shown in FIG. 250A.

FIG. 250D shows a cross-sectional view of the socket shown in FIG. 250A.

FIG. 250E shows another perspective view of the free end opening (as well as the ratchet engagement opening) of the socket shown in FIG. 250A.

FIG. 251 shows a standard ratchet tool RS and associated socket S3 combination with the combination providing a standard male/female ratchet connection, but a socket with a torque enhancement free end for driving. That is, as shown in FIG. 251 the ratchet engagement end of socket S3 has a standard square ratchet engagement slot 874, but a modified torque enhancement drive cavity 876 (having, for example, any one of the aforementioned 500 series wall surface configurations or any of the others described herein). This arrangement thus illustrates a beneficial attribute made possible under embodiments of the invention in that standard tooling such as a prior ratchet RS can still be used with embodiments of the invention, as in socket S3, which has a torque enhancement drive opening on the opposite side of the standard engagement side such that the above described torque enhancement benefits of the present invention can still be achieved.

FIG. 251A shows a schematic line presentation of the interior cavity of the socket S3 shown in FIG. 251.

FIG. 251B shows an additional perspective view showing the free end of the socket S3 shown in FIG. 251.

FIG. 251C shows a cross-sectional view of the socket S3 shown in FIG. 251.

FIG. 251D shows another perspective view of the free end opening (as well as the ratchet engagement opening) of the socket S3 shown in FIG. 251.

FIGS. 252A and 252B show views of a modified socket adapter assembly S4 having a free end with standard walled socket hole 892 (a hexagonal shape hole shown but any standard engagement hole can be featured such as one chosen from the standard set depicted in FIG. 248). The opposite end of socket adapter assembly S4 includes a torque enhancement ratchet engagement head 894, with FIG. 252A showing a perspective view emphasizing the torque enhancement end, and FIG. 252B emphasizing the standard socket walled opening end. As shown in FIG. 252A, torque enhancement engagement end includes a torque enhancement peripheral surface 896 having a configuration similar to the above described 500 series (the one illustrated approaching that of 500H), but has an alternate variation wherein the peripheral configuration is essentially bi-symmetric but for a modified corner cut out arrangement (C1' and C4' rather than the earlier featured C1 and C4 corner cut-outs) to one side of each of the bow-tie projections BT1 and BT2. As described in greater detail below, the altered corner cut outs provide a differential or stronger torque impact in one direction of rotation as compared to the other, which makes the configuration particularly well suited for helping break a bound nut or the like via socket S4 with the torque multiplication provided by the enhancement configuration of surface 896. For example, the standard socket end can be placed over an hex-nut and a wrench or the like applied to the torque enhancement surface 896 can be added to help initially break the bond with standard ratchet engagement at hole 874 being used to remove the loosened nut (the same can be featured with a reversed direction wherein, if the corner cut outs C1. and C4' are oriented for improved torque levels in the tightening direction, the standard socket approach can be used until there is achieved a first compression level and then the wrench/enhanced torque configuration surface 896 can be used for a final tightening down at a high torque level).

Stated differently, the additional feature shown in FIG. 254A of having a standard ratchet engagement square 874 (as earlier described for socket S3 in FIG. 251) plus the torque enhancement head 894 of socket S4 presents a beneficial configuration. For instance, the inclusion of standard engagement square 874 is in line with the above described beneficial ability of embodiments of the present invention being adapted for use with standard tooling as in standard ratchets, while still providing for the benefit of use of the torque enhancement benefit of the present invention. For example, with reference to the combination shown in engagement head 894 in FIG. 253A, there can be utilized a standard ratchet for initial compression which is then followed, for example, with a wrench application at the torque enhancement exterior surface wherein there is the potential to increase the torque for final compression (or in reverse wherein a difficult thread engagement can be broken with a hand wrench or the like on the torque enhancement region and there can then be removed the wrench and the ratchet used to rapidly remove the friction bond broken by the torque enhancement wrench). For example, as noted above, the torque required for an initial breakage of a threaded connection in a bolt or the like can be much higher than that involved with the initial application of that bolt. Thus, under the torque enhancement member 254A, there can be utilized the torque enhancement head at a time when extra torque power is required as compared to that generated by a standard drive as in a hexagonal bolt head and associated socket engagement.

FIG. 253A to 253G show various views of an additional embodiment of a torque enhancement member 899 having the altered corner cut outs C1' and C4' referenced above for torque enhancement surface 896 in the ratchet engagement head 894 of socket S4. FIGS. 243A to 253C show various perspective view of torque enhancement member 899 shown in the form of a nut with threaded center 508. As torque enhancement member 899 has the same general shape as the earlier described enhancer 500H (and head 894 surface 896), the focus of the discussion below is on the differences relative thereto.

As seen in FIGS. 253A to 253C, there is presented (as compared to the 500 series) modified bow-tie projections BTEA and BTEB with modified outer surfaces 339A' and 339B' which is brought about by a corner recess differential between opposite side corner recesses C1' and C3 relative to projection BTEA and opposite side corner recesses C2 and C4'. With reference to the planar view of enhancer 899 provided in the mechanical contact point presentation in FIG. 253D, there can be seen that rather than the vertical, radial walls to each side of corner cut outs C1' and C4' there is an added "additional cut-out" or notched areas NI1 and NI2, respectively. Notched areas NI1 and NI2 are shown as extending deeper into the interior of the bow-tie projections profile and farther under outer surfaces 339A and 339B. The impact of these modified corner recesses on one side only of each of the bow-tie projections is discussed relative to the mechanical contact and spiral-centrifugal contact point presentations in FIGS. 253D to 253G.

FIGS. 253D and 253E show mechanical contact point presentations in clockwise and counter-clockwise directions, respectively. Also, FIGS. 254F and 254G show spiral-centrifugal contact point presentations in clockwise and counter-clockwise directions, respectively. As seen under each of the mechanical contact directions there is generally the same number of contact points in either direction (although a high number of 30 for this embodiment inclusive of added contact points in the notched regions), with the different cut-out corner configurations shown as having different contact point presentations as compared to non-asymmetric corner cut out embodiments described above. A comparison between FIGS. 253F and 253G shows a spiral-centrifugal differentiation between the clockwise and counter-clockwise, with the clockwise presentation shown as having 20 and the counter-clockwise with 22, with the distinction located in the modified corner cut out shape differential (added notch areas NI1 and NI2) with the counter-clockwise (typically loosening) direction contact points 14, 14a; 15, 15a, 16, and 16a in corner cut out C4'(and the corresponding set 3, 3a, 4, 4a, 5, and 5a for corner cut C1') shown as presenting an added torque generation focus (spiral momentum focusing) in that area that enhances torque generation more so in the illustrated counter-clockwise direction than in the clockwise direction. This differential can be utilized as per the discussion above for socket S4, to more readily loosen bound nuts as they would be subject to the enhanced torque generation in the loosening thread direction in the counter-clockwise direction.

FIGS. 254A to 254E show various views of an additional embodiment of a torque enhancement component 900 having the altered corner cut outs C1' and C4' also referenced for torque enhancement surface 896 in the ratchet engagement head 894 of socket S4 and in enhancer 899 described above. As torque enhancement member 900 has the same general shape as the earlier described enhancer 500H (and enhancer 899 and socket head 894), the focus of the discussion below is on the differences relative thereto.

FIGS. 254A to 254C show various perspective views of enhancer 900 inclusive of a showing of the hexagonal pocket interior 902 (as one example of a standard adapter configuration with alternate standard shapes also being possible for the pocket interior 902) used together with the aforementioned torque enhancement exterior configuration provided by modified corner cut outs C1' and C4'. In this regard, FIG. 254D provides a plan view of the standard hexagonal shape walled pocket 902 as well as the referenced added (momentum focusing) notch regions NI1 and NI2. FIG. 254E shows a cross-sectional view thereof.

As the plan view for torque enhancer 899 is the same as that shown for enhancer 900 in FIG. 254A reference is made to the earlier mechanical contact and spiral-centrifugal contact point presentations for enhancer 899 which are equally applicable here and thus not further illustrated.

Enhancer 900 is particularly well suited for handling the more difficult release of a bolt or the like following initial application and the potential for degrading environmental effects or the like having been incurred. As torque enhancement member 900 is similar in many respects as enhancer 899 only differences are emphasized below. That is, rather than a solid nut as in enhancer 899, enhancer 900 features a hexagonal capture recess 902 formed on one side of its interior body. As with the earlier embodiments there remains a central hole as in a threaded hole 508 that opens into the capture recess 902. Also, like in the above described embodiment, there are modified corner cut-outs C1 and C4 and thus they are referenced as C1' and C4'. In view of this, there is not a strict bi-symmetry relationship (thus reference being made to "essentially bi-symmetric" as all other sections but for the below described added removal torque enhancement feature in two of the cut-outs is retained). The reason for the differential in C1' and C4' relative to the remaining corner cut-outs C2 and C3 is that the new configuration for C1' and C4' provides an increased torque potential with respect to one direction of rotation as compared to the opposite direction of rotation. With reference back to the contact point (mechanical and spiral-centrifugal) discussion for prior embodiments, it can be seen that the deeper extension in the corner cut outs C1' and C4' results in a greater torque potential in the counter clock wise direction as compared to the clockwise direction. This differential thus is beneficial as it conforms to the differential described above between initially screwing on a bolt or nut or the like and then efforts to remove it (e.g., removal being two and half times more difficult in many situations), particularly after a period of time has elapsed. Further the lower torque corner cut out orientation relative to tightening can help avoid the potential for over torqueing when initially tightening a bolt or the like.

The design of the enhancer is thus also well suited for helping to remove stuck standard bolts or nuts, in that the capture recess 902 can be placed over a standard configured nut or the like (hexagonal shown as an example) and the increased torque application provided by the torque enhancement feature of the present invention in general, and with the catalyst provided by the optionally added torque removal differential (e.g., provided by the corner cut out C1' and C4' configurations), further facilitates removal of stuck bolts and the like. Thus, with an example of a stuck nut on a bolt shaft, the opening 508 can be appropriately sized for a slide over arrangement such that the exterior of the stuck hex nut is received in capture recess 902 and then a suitable torque wrench or the like is placed about the larger sized periphery surface of torque enhancer 900 which can facilitate removal of the nut in situations where a normal hex wrench engagement might not achieve the required degree of torque to loosen the bound nut. This is but one example of the benefits of torque enhancement member 900. An additional advantage can be found in a capping arrangement that comes about with the inclusion of member 900 over preexisting nuts that are for example subject to a harsh environment and prone to bind up, with that cap being retained for eventual removal (inclusive of retrofit situations).

FIGS. 255A to 255C show various perspective views of an additional torque enhancement member 904 having the same general features as that of enhancer 900 but for the below described differences. That is, enhancer 904, like enhancer 900, has the above described directional torque generation differentiation means provided by the noted corner cut out differential. FIG. 255A shows a perspective view showing that rather than the hexagonal compartment in enhancer 900, there is provided a hexagonal through-hole 902' (or alternate standard) interior together with the torque enhancement exterior configuration. FIG. 255D shows a plan view thereof, and FIG. 255E shows a cross-sectional view thereof.

Like enhancer 900, enhancer 904 is particularly well suited for handling the more difficult release of a bolt or the like following initial application and the potential for degrading environmental effects or the like having been incurred. Rather than a solid nut as in enhancer 899, enhancer 904 features a hexagonal capture through-hole 902' formed on one side of its interior body. Also, like in the above described embodiment, there are modified corner cut-outs C1 and C4 and thus they are referenced as C1' and C4'. In view of this, there is not a strict bi-symmetry relationship (thus reference being made to "essentially bi-symmetric as all other sections but for the below described added removal torque enhancement feature in two of the cut-outs is retained). The reason for the differential in C1' and C4' relative to the remaining corner cut-outs C2 and C3 is that the new configuration for C1' and C4' provides an increased torque potential with respect to one direction of rotation as compared to the opposite direction of rotation. With reference back to the contact point (mechanical and spiral-centrifugal) discussion for prior embodiments, it can be seen that the deeper extension in the corner cut outs C1' and C4' results in a greater torque potential in the counter clock wise direction as compared to the clockwise direction. This differential thus is beneficial as it conforms to the differential described above between initially screwing on a bolt or nut or the like and then efforts to remove it (e.g., removal being two and half times more difficult in many situations), particularly after a period of time has elapsed. Further the lower torque corner cut out orientation relative to tightening can help avoid the potential for over torqueing when initially tightening a bolt or the like.

The design of the enhancer it thus also well suited for helping to remove stuck standard bolts or nuts, in that the capture recess 902' can be placed over a standard configured nut or the like (hexagonal shown as an example) and the increased torque application provided by the torque enhancement feature of the present invention in general, and with the catalyst provided by the optionally added torque removal differential (e.g., provided by the corner cut out C1' and C4' configurations), further facilitates removal of stuck bolts and the like. Thus, with an example of a stuck nut on a bolt shaft, the opening 902' can be appropriately sized for a slide over arrangement such that the exterior of the stuck hex nut is received in capture recess 902' and then a suitable torque wrench or the like is placed about the larger sized periphery surface of torque enhancer 904 which can facilitate removal of the nut in situations where a normal hex wrench engagement might not achieve the required degree of torque to loosen the bound nut. Further, the central region having a capture recess 902' that extends all the way through the inner body as to represent the central cavity provides even added versatility in use as an adapter either to tighten or loosen a stuck nut or the like as it can readily be put in place with the desired orientation (e.g., the corner cut outs C1' and C4' being arranged for utilization of the added torque power provided by the deeper outs represented by corner cut outs C1' and C4').

FIGS. 256 to 259 show various wrench designs like that of FIG. 189 but having at least one end a differential torque enhancement configuration like that described above for enhancers 899, 900 and 904. A comparison of the wrench torque tool 588 shown in FIG. 189 and the wrench tools shown in FIGS. 256 to 259 show that there is an equivalent ergo-dynamic handle configuration in each and thus the focus is on the torque heads provided at the opposite ends of the handles in each. Thus, handle 588A in FIG. 256 features wrench tool retention end 899I1 at one end (left end shown) and wrench tool retention end 899I2 at the opposite end. A review of the enlarged view for the left end shows that the modified corner cut outs such as C1', C4' have the notched area NI1 and NI2 orientated as to favor higher torque generation in the counterclockwise direction (see FIG. 253D). The opposite end 899I2 features a different orientation with the corner cut outs such as C1', C4' have the notched area NI1 and NI2 orientated as to favor higher torque generation in the clockwise direction. This provides the user with a versatile tool wherein an initial run can be used under the weaker mode, and upon reaching completion of the first stage, the tool can be used in a stronger mode application to achieve a stage 2 final tightening. The reverse order is also available whereupon a difficult to release fastener or the like can be worked on using the stronger rotation position end (see the counterclockwise rotation arrow in end 899I1 which is the stronger mode) at least to achieve initial release (bond breakage).

An additional advantage provided in the retention head configuration such as featured in end 899I1 is that it is well suited to accommodate standard hex-shaped bolts. For example, with reference to the hexagonal outline referenced by dashed line HXI in the enlarged ends of FIG. 256 (at each end), there can be seen that the interior of each of end recesses 899I1 and 899I2 is also configured to receive a hex-shaped bolt head or the like. This also provides for the aforementioned torque enhancement. For instance, there can be seen that the extended surfaces (represented by the base floor of the corner cut-outs C1' and C4' featuring the extra length provided by the extension of notch areas NI1 and NI2) at around the 10 o'clock and 4 o'clock locations in recess 899I1 are positioned for contact with a side wall of an inserted hex bolt or nut. Thus upon rotation the noted extended surfaces provide a strong torque application to the received nut or bolt. An additional advantage provided by the torque enhancement configuration such as the 500 series or the configuration like that in torque enhancement member 899 is found in the ability of a wrench or the like having the noted HXI interior recess to place its notches (part of recess 899I1) at the locations where the corners of the hex-nut or bolt are positioned. For example, in reference to the enlarged view on the right end of the wrench in FIG. 256 there can be seen the corner CE of a hex configuration extending into a corner cut-out. Thus, in situations where a hex nut or bolt has its corners stripped and the material pushed in one direction or the other, the end 899I2 is still able to accommodate the bolt head whereas an appropriate sized hexagonal socket recess would have difficulty fitting over the stripped nut or bolt due to the edge misconfiguration. As seen each of the 6 corner edges of the hex shaped nut or bolt head is received in a corresponding cavity of the torque enhancement configuration (in the 500 series as well as the illustrated 899 series configuration). This relationship for the 500 series is also schematically presented in FIG. 133 (but requires a transposing of an exterior surface torque enhancement member shown in FIG. 133 to one with an interior recess of the same peripheral configuration in similar fashion to recess 899I2) where it can be seen that the hexagonal reference outline has each of its corners in a recess depression (that is a depression formed upon the noted interior/exterior surface transposition).

Figure 257:
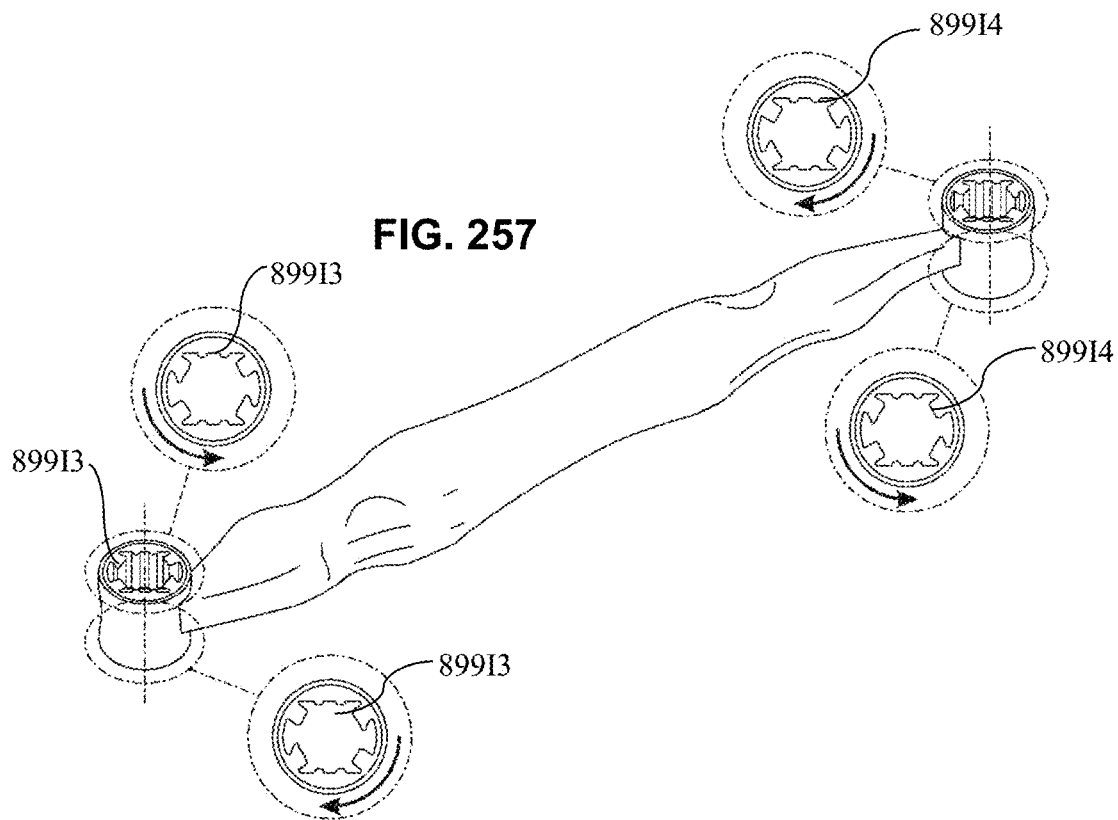

FIG. 257 illustrates a wrench tool 588B that is similar to that of 256 but features dual configured engagement configurations at each of ends 899I3 and 899I4. For example end, 899I3 is shown in the enlarged upper view end 899I3 having a stronger counter-clockwise torque enhancer orientation, and in the enlarged bottom view at the same end a weaker counter-clockwise torque enhancer orientation. The opposite end 899I4 has the reverse with the enlarged upper view showing a stronger clockwise torque enhancer orientation; and, in the enlarged bottom view at the same end, a weaker clockwise torque enhancer orientation. Which arrangement again provides the user with the above described versatility in release and tightening modes at different torque levels or stages, and the FIG. 257 also provides the benefit of allowing the user to more simply rotate about an axis of rotation extending as to coincide with the axis of elongation of the handle rather than having to rotate the entire handle about an axis parallel to the axis of handle elongation.

Figure 258:
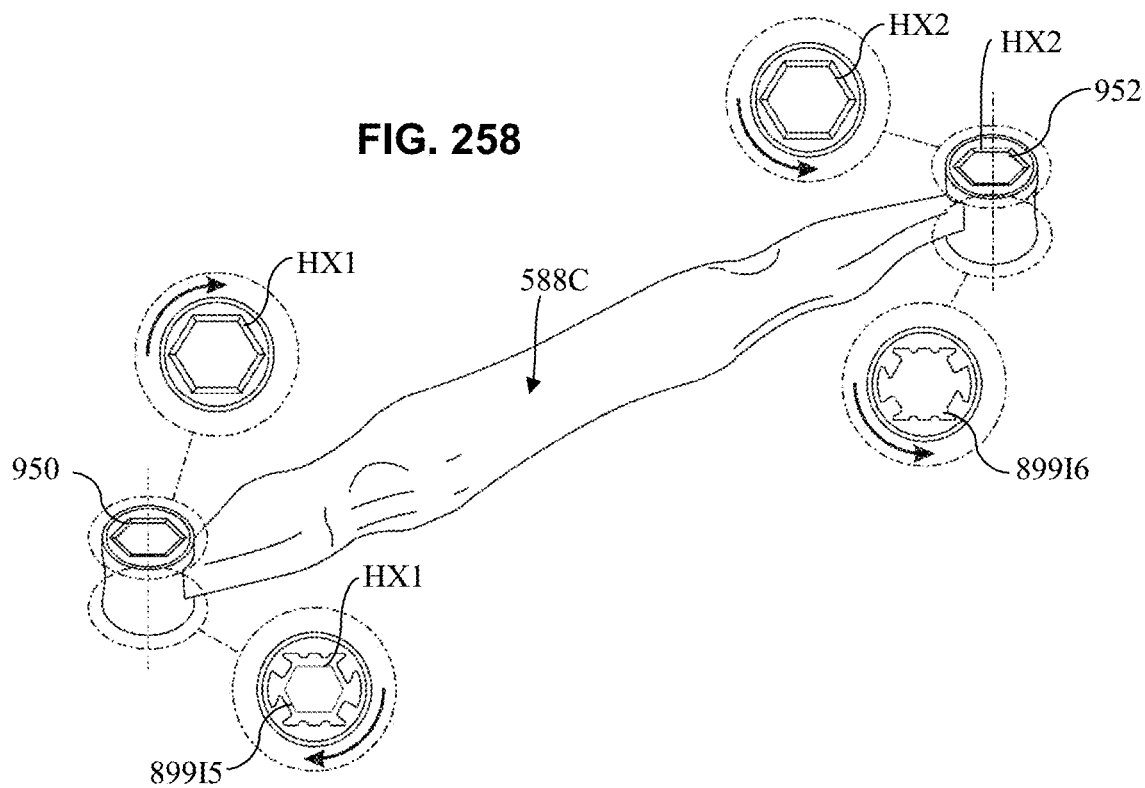
Figure 259:
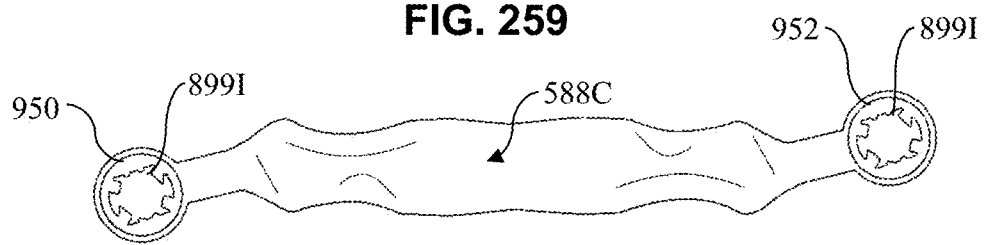
Figure 260:
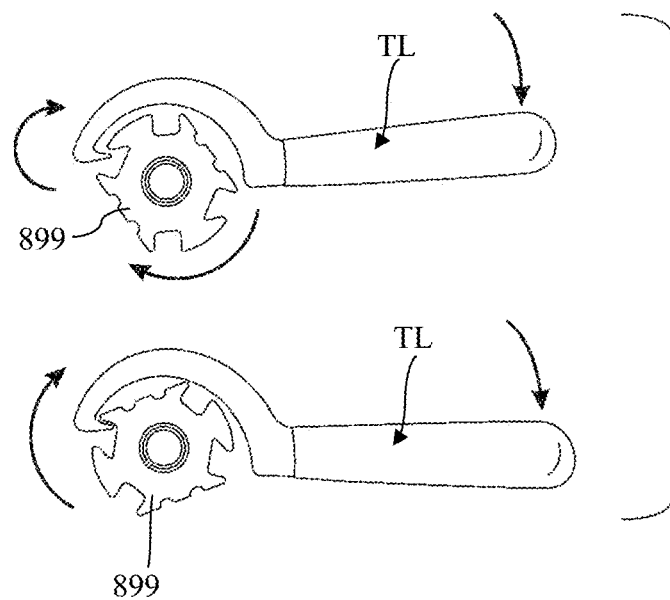
Figure 261:
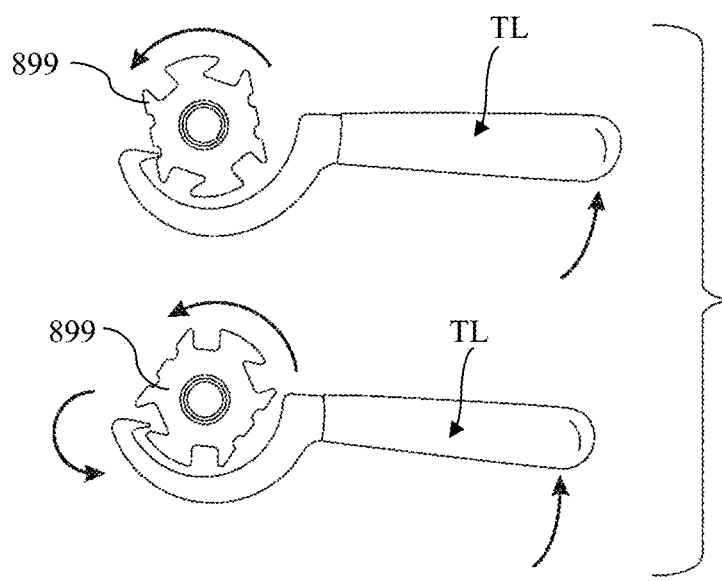

FIGS. 258 and 259 show a perspective and a plan view of an additional embodiment of the present invention featuring a wrench 588C having a similar handle as above, but modified capture ends referenced as 899I5 and 899I6. As seen, end 899I5 provides a versatile standard/non-standard torque enhancement combination at each end as to be in line with the above described versatility and bridging notion important when there is a conversion of an earlier fastener or tool configuration to a newer different line. As seen, first (left shown) end 952 features (shown upper) a standard hexagonal socket type engagement opening HX1, and on the lower side of the left end 952 features a torque enhancement configured engagement recess 899I5. Recess 899I5 is shown as having its weaker mode in the illustrated clockwise direction. Further, there is shown a hexagonal profile HXI in recess 899I5 to illustrate that although 899I5 is best designed for removal of a similarly configured fastener, it is also versatile in that it can be utilized on a standard hex shape (see, for example, the hexagonal reference HX configuration in FIG. 133 which illustrates an appropriate nesting arrangement is provided within the recess 899I5 configuration (as would be true for the 500 series configurations as well) features a standard hex socket type end plus on the reverse side the enhancement configuration. The opposite end 952 features the same (or different sized) hex recess HX2, but a re-oriented torque enhancement recess having the stronger mode in the counter-clockwise direction which unless a fastener is reverse threaded is a loosing mode.

Figure 262:
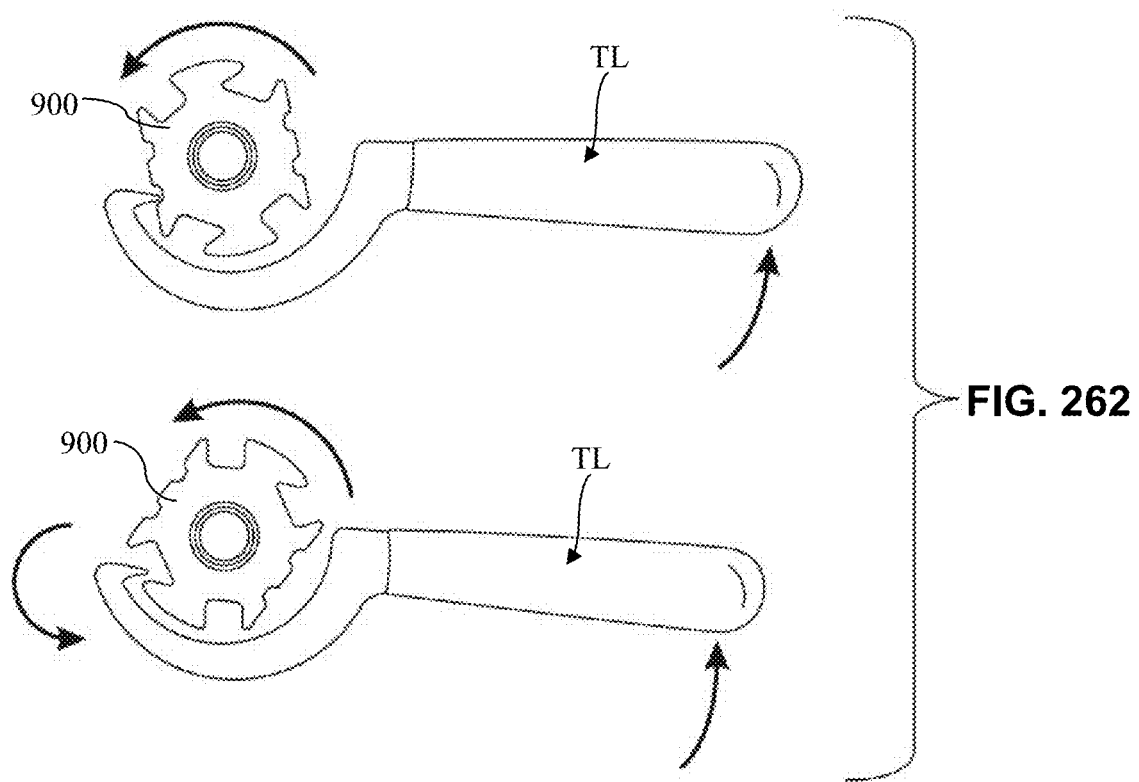

FIGS. 260 to 263 show various standard hook tool TL contact points with notches and corner cut outs in the torque enhancement configuration as in found in torque enhancement member 900 (in both clockwise and counterclockwise directions). FIG. 262 shows in the upper region the tip end of tool TL received in one of the notches in the side walls such as 338A (and the interrelationship between the curving outer walls such as surface 339A and the curved component of tool) relative to a counter-clockwise rotation using the relatively long torque arm of tool TL. The lower region in FIG. 262 shows the same tool tip, but received in one of the modified corner cut outs relative to the same counterclockwise rotation direction. As seen this orientation provides for a strong torque generation with various points involved including those on at least one end point on a side wall such as 338A.

Figure 263:
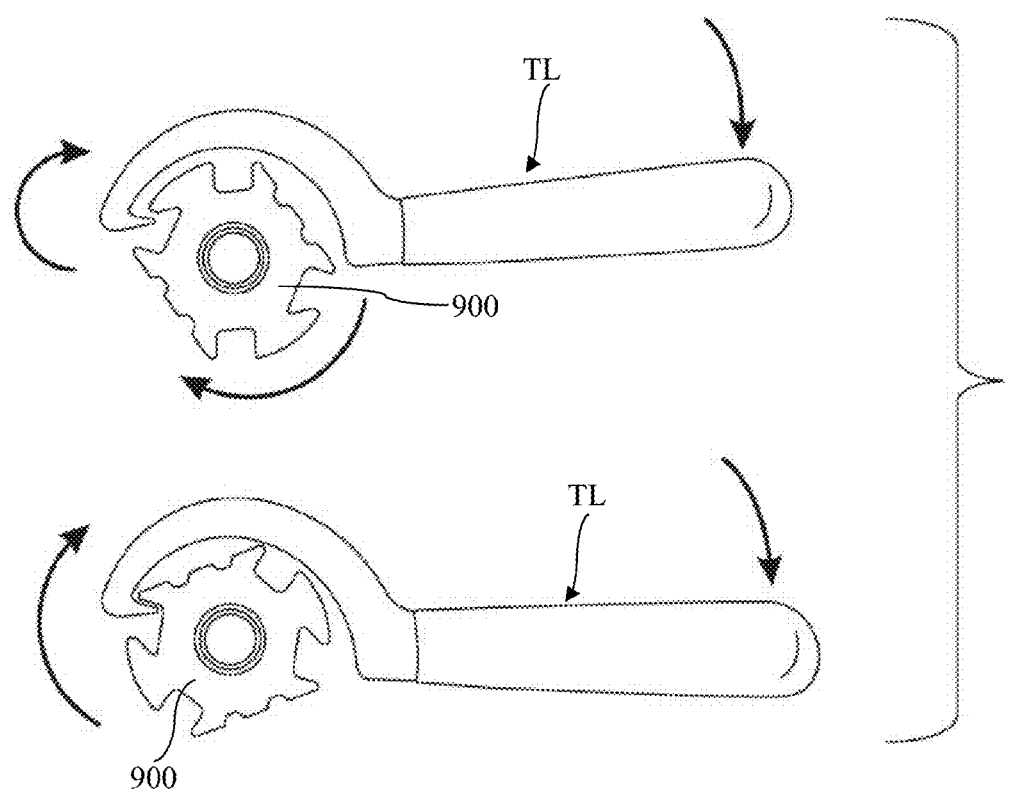

FIG. 263 shows a reverse or clockwise (e.g., tightening mode) with a strong mode torque relationship provided by the tool tip reception in one of the modified corner cut outs as in C1'. Further rotation can also be achieved in the same direction using the opposing corner side wall (similar to that in some of the 500 series described earlier). Thus the degree of torque application can be controlled by the user by choosing which notch or corner cut out wall to contact with the tool TL such that an initial degree of torque down can be carried out at a less strong mode with the final tightening at the strong mode, with the reverse being applicable in the reverse loosen/remove stages in the typical counterclockwise direction.

All ranges disclosed in this application, unless stated otherwise, are inclusive and combinable e.g., ranges set forth in the present description include endpoints and all intermediate values of the ranges (e.g., a range of 65% to 90% for the L2/L1 ratio is inclusive of end points 65% and 90% as well as each intermediate common unit value as in 66%, 67% . . . ).

It should be noted that features that are described with reference to one or more embodiments are described by way of example rather than by way of limitation to those embodiments. Thus, unless stated otherwise or unless particular combinations are clearly inadmissible, optional features that are described with reference to only some embodiments are assumed to be likewise applicable to all other embodiments also.

What is claimed is:

1. A torque enhancement device comprising a torque enhancement member that has a Z-axis rotation torque generation tool contact surface configuration defined by longer torque generation tool contact side walls, each extending in a Y-axis direction and separated apart by an X-axis length (L2), and shorter torque generation tool contact side walls, each extending in an X-axis direction and separated apart by a Y-axis length (L1), and four corner recesses positioned between ends of adjacent longer and shorter side walls, the four corner recesses each being positioned radially inward of sections of the surface configuration defining the longer and shorter side walls, and wherein a ratio L2/L1 is at least 50% and less than 100%, and wherein the tool contact surface configuration is configured to be operated by a torque generation tool or is configured to operate as a torque generation tool, and wherein an X-Y axes plane extending through a central region, relative to Z-axis extension, of torque generation surfaces of the longer side walls also extends through a central region, relative to Z-axis extension, of torque generation surfaces of the shorter side walls.

2. The torque enhancement device of claim 1, wherein each of the four corner recesses represent the only recess formed between the ends of adjacent longer and shorter side walls.

3. The torque enhancement device of claim 1, wherein the torque enhancement member has bi-symmetry or essentially bi-symmetry about an X-axis and a Y-axis and the surface configuration is one of an interior surface or an external peripheral surface.

4. The torque enhancement device of claim 1, wherein the L2/L1 ratio is from 60% to less than 100%.

5. The torque enhancement device of claim 1, wherein the L2/L1 ratio is from 65% to 95%.

6. A fastener assembly comprising at least one torque enhancement device of claim 1.

7. The torque enhancement device of claim 1, wherein the torque enhancement device is one of a fastener with a fastener head having the tool contact surface configuration or a driving tool having the tool contact surface configuration.

8. The torque enhancement device of claim 1, wherein at least one diametrically opposing pair of the corner recesses features each corner recess in that pair having shape symmetry to opposite sides of a bisecting Z-axis extending plane.

9. The torque enhancement device of claim 8, wherein each of the longer side walls and each of the shorter side walls are positioned, and individually of a sufficient length, as to extend and cross to opposite sides of a Z-axis relative to a plane perpendicular to the Z-axis.

10. The fastener assembly of claim 6, comprising the at least one torque enhancement device, which is represented by at least one of the following: a) a tapered torque enhancement device with or without interior (and/or exterior) threading and is slotted or not slotted; b) a torque enhancement device in washer form with either a cup shape or flat shape and either with or without an inner portion projection or recess; c) a bolt with one or both of interior and exterior threading; d) a button or cap end with or without interior (and/or exterior) threading; and e) a gear with or without supporting central plating.

11. The fastener assembly of claim 6, comprising first and second torque enhancement devices with the first torque enhancement device having a tapered portion for receipt within a receiving aperture formed in the second torque enhancement member to define a nested torque enhancement combination, with the tapered region radially pushing out on an interior surface defining the receiving aperture of the second torque enhancement member.

12. The fastener assembly of claim 6, comprising:
a shaft;
a first compression member and a second compression member spaced apart along the shaft as to provide for sandwiching of a structural component through which the shaft extends, with the first compression member representing the at least one torque enhancement device.

13. The fastener assembly of claim 12, wherein the shaft is a threaded shaft, and the torque enhancement device, through which the threaded shaft extends, has a base region end and an opposite tapered end, and the base region end has a greater peripheral area than the tapered region, and wherein the greater peripheral area is more closely positioned to the structural component than the tapered region as to diffuse compression forces radially outward relative to the sandwiched structural component.

14. The fastener assembly of claim 12, wherein the fastener assembly is used for sandwiching first and second structural components having sufficiently aligned holes through which the shaft extends, and wherein the fastener assembly further comprises an elastomeric sleeve that surrounds the shaft and extends axially along the shaft as to bridge opposing interior surface edges of the structural components and wherein the elastomeric sleeve is compressed axially by the torque enhancing device that extends around the shaft and is fixed in axial position relative to the shaft.

15. The fastener assembly of claim 6, comprising: a bolt having a proximal head region, the proximal head region includes a converging section, and the bolt further including a shank extending distally away from the converging section, and wherein at least a portion of the bolt head region comprises a first torque enhancement device of the at least one torque enhancement device, and a receiving component having an interior surface defining an aperture for receiving the portion of the bolt head region representing the first torque enhancement device as to have external surfacing of the first torque enhancement device portion radially outward as to form a bite-in relationship with said interior surface defining the aperture.

16. The fastener assembly of claim 12, wherein the shaft is a threaded shaft and there are first and second sandwiched structural components having sufficiently aligned holes through which the threaded shaft extends, and the fastener assembly further comprises a sleeve that either extends through the holes in the first and second sandwiched structural components or is sandwiched between the first and second structural components, and wherein the interior of the sleeve extends about the threaded shaft as to define an annular space around the threaded shaft.

17. The fastener assembly of claim 16, wherein the sleeve is arranged as to be sandwiched between the first and second structural components, and the sleeve is further arranged relative to the threaded shaft such that a shearing force acting on the fastener assembly is diffused by way of the first compression device, representing the torque enhancement device, adjusting relative to a surface of a closest structural component while the threaded shaft shifts within the annular spacing defined by the sleeve.

18. The fastener assembly of claim 6, comprising: a bolt having a proximal head region, the proximal head region includes a converging section, and the bolt further including a shank extending distally away from the converging section; and wherein the at least one torque enhancement device includes a first torque enhancement device with an aperture that receives the converging section of the bolt head region such that the first torque enhancement device is pressed radially outward by the converging section.

19. The fastener assembly of claim 18, wherein the first torque enhancement device has a base end and a tapering or conical extension extending away from said base end.

20. The fastener assembly of claim 19, wherein the base end has a converging aperture that extends inwardly starting from a free edge of the base end, and which converging aperture is configured for receipt of at least a portion of the converging section of the proximal head region.

21. The fastener assembly of claim 19, wherein the tapering or conical extension has interior threading for threading engagement with a threaded portion of the shank of the bolt, and the base end has a tapered aperture that extends inwardly starting from a free edge of the base end.

22. The fastener assembly of claim 19, wherein the at least one torque enhancement device includes a second torque enhancement device that also has a base end and a tapering or conical extension extending away from the base end, and wherein the first and second torque enhancement devices are spaced apart along an axis of elongation of the shank such that the second torque enhancement device is positioned more distal than the first torque enhancement device relative to the proximal head region of the bolt, and the first and second torque enhancement devices are arranged such that the base ends of the first and second torque enhancement devices are each positioned more proximal than are the corresponding tapering or conical extensions of the first and second torque enhancement devices.

23. The fastener assembly of claim 22, wherein the second torque enhancement device has interior threading while the first torque enhancement device is free of any interior threading.

24. A fastener assembly, comprising:
a fastener member having a shaft sufficiently elongated in an axial direction as to extend through a pair of holes in a pair of structural components to be fastened, wherein a diameter of an exterior surface of the shaft is smaller than a diameter of the holes receiving the shaft;
a first abutment member forming part of, or attached to, the shaft of the fastener member for contacting a first side of the pair of structural components and having a diameter larger than the diameter of a most adjacent one of the holes as to enable compression contact with the first side of the structural components;

a second abutment member having an aperture into, or through, which the fastener member extends, the second abutment member being in compression contact with a second side of the pair of structural components; and at least one of the first and second abutment members has a torque enhancement configuration that features a Z-axis rotation torque generation tool contact surface configuration defined by longer torque generation tool contact side walls, each extending in a Y-axis direction and separated apart by an X-axis length (L2), and shorter torque generation tool contact side walls, each extending in an X-axis direction and separated apart by a Y-axis length (L1), and four corner recesses positioned between ends of adjacent longer and shorter side walls, the four corner recesses each being positioned radially inward of sections of the surface configuration defining the longer and shorter side walls, and wherein a ratio L2/L1 is at least 50% and less than 100%, and wherein the tool contact surface configuration defines an X-Y axes rectangular configuration falling on a common X-Y axes plane and comprised of linear, or essentially linear, extensions in each of said longer side walls and shorter side walls, and wherein the surface configuration is configured to be operated by a torque generation tool or is configured to operate as a torque generation tool.

25. The fastener assembly of claim 24, further comprising a sleeve that axially extends through the pair of holes in the pair of structural components or is sandwiched between the structural components, and wherein the sleeve has an interior surface that has a diameter larger than an exterior surface of the shaft.

26. The fastener assembly of claim 24, wherein an X-Y axes plane extending through an intermediate region, relative to Z-axis extension, of the longer side walls also extends through an intermediate region of the shorter side walls.

27. A torque enhancement device comprising a torque enhancement member that has a Z-axis rotation torque generation tool contact surface configuration defined by Y-axis longer torque generation tool contact side walls, each extending in a Y-axis direction and separated apart by an X-axis length (L2), and X-axis shorter torque generation tool contact side walls, each extending in an X-axis direction and separated apart by a Y-axis length (L1), and four corner recesses positioned between ends of adjacent longer and shorter side walls, the four corner recesses each being positioned radially inward of sections of the surface configuration defining the longer and shorter side walls, and wherein a ratio L2/L1 is at least 50% and less than 100%, and wherein the tool contact surface configuration defines an X-Y axes rectangular configuration that falls on a common X-Y axes plane and that is comprised of linear, or essentially linear, extensions in each of said longer side walls and shorter side walls, and wherein the surface configuration is configured to be operated by a torque generation tool or is configured to operate as a torque generation tool.

28. The fastener assembly of claim 27, wherein an X-Y axes plane extending through an intermediate region, relative to Z-axis extension, of torque generation surfaces of the longer side walls also extends through an intermediate region, relative to Z-axis extension, of torque generation surfaces of the shorter side walls.

* * * * *